(12) United States Patent
Burke et al.

(10) Patent No.: US 8,343,747 B2
(45) Date of Patent: Jan. 1, 2013

(54) AMYLASES AND GLUCOAMYLASES, NUCLEIC ACIDS ENCODING THEM AND METHODS FOR MAKING AND USING THEM

(75) Inventors: Ellen G. Burke, San Diego, CA (US); Michelle H. Cayouette, San Diego, CA (US); Cathy Chang, San Marcos, CA (US); Majid Ghassemian, Carlsbad, CA (US); Uvini Gunavardena, San Diego, CA (US); Geoff Hazlewood, Newbury (GB); Peter Luginbuhl, San Diego, CA (US); Aron Silverston, Durham, NC (US); Malgorzata Slupska, San Diego, CA (US); Yan Zhang, Apex, NC (US)

(73) Assignee: Verenium Corporation, San Diego, CA (US)

( * ) Notice: Subject to any disclaimer, the term of this patent is extended or adjusted under 35 U.S.C. 154(b) by 377 days.

(21) Appl. No.: 12/520,523

(22) PCT Filed: Dec. 21, 2007

(86) PCT No.: PCT/US2007/088631
§ 371 (c)(1),
(2), (4) Date: Apr. 27, 2010

(87) PCT Pub. No.: WO2008/080093
PCT Pub. Date: Jul. 3, 2008

(65) Prior Publication Data
US 2011/0039308 A1 Feb. 17, 2011

Related U.S. Application Data

(60) Provisional application No. 60/877,068, filed on Dec. 21, 2006, provisional application No. 60/892,823, filed on Mar. 2, 2007.

(51) Int. Cl.
*C12N 9/34* (2006.01)
*C12N 9/26* (2006.01)
*C12N 15/00* (2006.01)
*C12N 1/20* (2006.01)
*C12N 15/82* (2006.01)
*C12P 21/06* (2006.01)
*C12P 19/34* (2006.01)
*C07H 21/04* (2006.01)
*C07K 1/00* (2006.01)

(52) U.S. Cl. ...... 435/205; 435/201; 435/69.1; 435/91.1; 435/320.1; 435/252.3; 536/23.1; 536/23.2; 530/350; 800/278; 800/284

(58) Field of Classification Search .................. 435/205, 435/201, 69.1, 91.1, 320.1, 252.3; 536/23.1, 536/23.2; 530/350; 800/278, 284
See application file for complete search history.

(56) References Cited

U.S. PATENT DOCUMENTS

| 3,847,740 | A | 11/1974 | Heady |
| 4,521,252 | A | 6/1985 | Miyake |
| 4,557,927 | A | 12/1985 | Miyake |
| 5,789,228 | A | 8/1998 | Lam |
| 5,939,250 | A | 8/1999 | Short |
| 6,479,258 | B1 | 11/2002 | Short |
| 2001/0053519 | A1 | 12/2001 | Fodor |
| 2003/0135885 | A1 | 7/2003 | Lanahan |
| 2004/0018607 | A1 | 1/2004 | Callen |
| 2004/0259222 | A1 | 12/2004 | Breves et al. |
| 2005/0176000 | A1 | 8/2005 | Callen |
| 2007/0157329 | A1 | 7/2007 | Callen |

FOREIGN PATENT DOCUMENTS

| CN | 1222938 A | 7/1999 |
| EP | 0606753 A2 | 12/1993 |
| EP | 0628630 A2 | 12/1994 |
| EP | 0648843 A1 | 4/1995 |
| FR | 2778412 | 11/1999 |
| GB | 2106912 A | 4/1983 |
| JP | 62-104580 A2 | 5/1987 |
| JP | 09173077 A | 7/1997 |
| WO | 93/00426 A1 | 1/1993 |
| WO | 9638469 A1 | 12/1996 |
| WO | 9639528 A2 | 12/1996 |
| WO | 9744361 A1 | 11/1997 |
| WO | 9845417 A1 | 10/1998 |
| WO | 99/67406 A1 | 12/1999 |
| WO | 0058508 A3 | 10/2000 |
| WO | 0190338 | 11/2001 |
| WO | 0268589 A2 | 6/2002 |
| WO | 02068597 A2 | 9/2002 |

(Continued)

OTHER PUBLICATIONS

Devos et al., Practical limits of function prediction. Proteins: Structure, Function, and Genetics. 2000, vol. 41: 98-107.*
Wishart et al., A single mutation converts a novel phosphotyrosine binding domain into a dual-specificity phosphatase. J. Biol. Chem., 1995, vol. 270(45): 26782-26785.*
USPTO—Oct. 12, 2011—Office Action—U.S. Appl. No. 12/822,413.
EPO—Jan. 21, 2011—Office Action—EP09171688.6.
USPTO—Nov. 16, 2011—Final Office Action—U.S. Appl. No. 12/567,550.
CIPO—Nov. 14, 2011—Office Action—CA2515340.
EPO—Dec. 13, 2011—Office Action—EP07869797.9.
CIPO—Jan. 9, 2012—Office Action—CA2438205.

(Continued)

Primary Examiner — Ganapathirama Raghu
(74) Attorney, Agent, or Firm — Justin H. Cross, Esq.

(57) ABSTRACT

In one aspect, the invention is directed to polypeptides having an amylase and/or glucoamylase activity, polynucleotides encoding the polypeptides, and methods for making and using these polynucleotides and polypeptides. In one aspect, the polypeptides of the invention can be used as amylases, for example, alpha amylases, to catalyze the hydrolysis of polysaccharide, oligosaccharide or starch into sugars. In one aspect, the invention provides delayed release compositions comprising an desired ingredient coated by a latex polymer coating. In alternative embodiments, enzymes are used to make biofuels, e.g., ethanol, butanol, propanol, or a gasoline-ethanol mix, including a bioethanol, biopropanol, biobutanol, or a biodiesel, or for any form of fuel or biomass processing.

6 Claims, 36 Drawing Sheets

FOREIGN PATENT DOCUMENTS

| WO | 03/012071 A2 | 2/2003 |
|---|---|---|
| WO | WO03012071 | 2/2003 |
| WO | 2004091544 A2 | 10/2004 |

OTHER PUBLICATIONS

ROBYT—Enzymes and Their Action on Starch in Starch: Chemistry and Technology (2009) 3rd ed.—237-292.
Atichokudomchai—Carbohydrate Polymers (2006) 64:582-588.
Bork—Genome Research (2000) 10:348-400.
Broun—Science (1998) 282:1315-1317.
Chica—Curr. Opin. Biotechnol. (2005)—4-378-384.
CIPO—Feb. 25, 2011—Office Action—CA2438884.
Dong—App. and Environ. Microbiol. (1997) 63(9):3569-3576.
Examiner's Second Report—AUIP—2004229313—mailed Jul. 2, 2010.
Fox—Anal. Biochem. (1991) 195(1):93-96.
GenBank Accession No. U96622 Jorgensen (1997).
GenBank Accession No. AF017454 Jones (2001).
GenBank Accession No. AF068255, Leveque (2000).
GenBank Accession No. D83793, Tachibana (2000).
GenBank Accession No. E13334, Imanaka (1997).
GeneSeq Accession No. AAR72603, Asada (1995).
GeneSeq Accession No. AAW26131, Imanaka (1997).
GeneSeq Accession No. AAW34998, Lam (1998).
GeneSeq Accession No. AAW70536, Dong (1999).
GeneSeq Accession No. AAY53917, Leveque (2000).
GenPept Accession No. AAB87860, Jones (2001).
GenPept Accession No. ACC97877, Herlemann (2008).
Giver—Current Opinion in Chemical Biology (1998) 2:335-338.
Guo—PNAS USA (2004) 101(25):9205-9210.
Jones—Journal of Applied Microbiology (1999) 86(1):93-107.
Jorgensen—J. of Biol. Chem. (1997) 272(26):16335-16342.
JPO—Feb. 15, 2010—Office Action—JP2006-506966.
JPO—Jul. 12, 2010—Office Action—JP2006-506966.
JPO—Feb. 7, 2011—Final Office Action—JP2006-506966.
Kim—FEMS Microbiol. Lett. (1996)—138(2-3):147-152.
Laderman—J. of Biol. Chem. (1993)—268(32):24394-24401.
Leveque—FEMS Microbiology Letters (2000)—186-67-71.
Malhotra—Lett. Appl. Microbiol. (2000) 31:378-384.
Narang—Lett. Appl. Microbiol. (2001) 32: 31-35.
NCBI Accession No. BAA21130, Tachibana, (2000).
NCBI Accession No. Y13601—Streptomyces lividans (1998).
Nigam—Enzyme Microbial Technology (1995) 17:770-778.
O'Neill—Mol. Gen. Genet. (1990) 221:235-244.
Office Action—AUIPO—2006207843—mailed on Sep. 8, 2008.
Office Action—CIPO—2438205—mailed Jan. 19, 2010.
Office Action—CIPO—2438205—mailed on Jan. 30, 2009.
Office Action—CIPO—2438884—mailed on Apr. 24, 2009.
Office Action—EPO—027231927, mailed on Jul. 24, 2008.
Office Action—JPO—2002-568685, Jun. 1, 2009.
Office Action—USPTO—U.S. Appl. No. 10/385,305—mailed on Jun. 25, 2008.
Office Action—USPTO—U.S. Appl. No. 10/489,510—mailed on Oct. 16, 2007.
Office Action—USPTO—U.S. Appl. No. 10/489,510—Mailed on Nov. 13, 2008.
Office Action—USPTO—U.S. Appl. No. 11/400,030—Mailed on May 28, 2008.
Office Action—USPTO—U.S. Appl. No. 11/400,030—Mailed on Feb. 9, 2009.
Office Action—USPO—U.S. Appl. No. 11/621,534—mailed on May 13, 2009.
Office Action—USPTO—U.S. Appl. No. 11/621,534—Mailed on Sep. 17, 2009.
Rubingh—Current Opinion in Biotechnology (1997) 8:417-422.
Search Report—EP 02723192.7—Supplementary Partial European Search Report mailed on Mar. 11, 2005.
Search Report—EP02706401—Supplementary EP Search Report—Sep. 6, 2004.
Search Report—EP09171688.2—Partial EP Search Report—Feb. 26, 2010.
Search Report—EP09180956.6—Jul. 27, 2010.
Search Report—EP09180956.6—Nov. 29, 2010.
Search Report—PCT/US2004/07096, mailed on Jul. 16, 2008.
Seffernick—J. of Bacteriol. (2001) 183(8):2405-2410.
Sen—Appl. Biochem. Biotechnol (2007)—2-212-223.
Tachibana—J. Ferment. Bioeng. (1996)—82-224-232.
UniProt—Swiss-Prot Protein Knowledgebase, Swiss Institute of Bioinformatics (SIB) et al., Glycosyl hydrolase families: classification and list of entries <http://www.expasy.ch/cgi-bin/lists?glycosid.txt> Release 55.5, Jun. 10, 2008.
UniProt Accession No. Q8RNJ6—(2002)- MA.
UniProtkb Accession No. Q9P9LO, Wang (2000).
Van De Loo—Proc. Natl. Acad. Sci. (1995) 92(15):6743-6747.
Whisstock—Biophysics. (2003) 36 (3): 307-340.
Witkowski—Biochemistry (1999) 38:11643-11650.
Wong—J. Agric. Food Chem. (2000) 48(10):4540-4543.
GeneSeq Accession No. ABU03143—(2003)—Callen.
EPO—EP02723192.7—Supplementary Partial European Search Report—Mar. 11, 2005.
EPO—EP02706401—Supplementary EP Search Report—Sep. 6, 2004.
EPO—EP09171688.2—Partial EP Search Report—Feb. 26, 2010.
EPO—EP09180956.6—Search Report—Jul. 27, 2010.
EPO—EP09180956.6—Search Report—Nov. 29, 2010.
WIPO—PCT/US2004/07096—Search Report—Jul. 16, 2008.
UniProt Accession No. Q8RNJ6—(2002)—MA.
UniProtkb Accession No. Q9P9LO, Wang (2000.
USPTO—U.S. Appl. No. 10/547,957—Notice of Allowance—Mar. 11, 2010.
USPTO—U.S. Appl. No. 11/621,543—Office Action—May 13, 2009.
EPO—EP10184478.5—EP Partial Search Report—Apr. 6, 2011.
EP10184415.7—Partial EP Search Report—Apr. 6, 2011.
EP10 184 381—Partial EP Search Report—May 24, 2011.
UniProt Accession No. Q59222—LIN—1996.
GenBank Accession No. U22045—LIN—1995.
LIN—Journal of Applied Microbiology—(1997)—82-325-334.
LIN—Letters in Applied Microbiology—(1997)—24-365-368.
JP2008-136876—Office Action—Jun. 2, 2011.
USPTO—Jun. 10, 2011—Final Office Action—U.S. Appl. No. 12/567,550.
UniProt Accession No. Q52413—Kim—1996.
AUIP—2010246342—Examiner's First Report—mailed Jun. 8, 2011.
AUIP—2009222426—Examiner's First Report—mailed Jul. 4, 2011.
EPO—10184415.7—Extended EP Search Report—Aug. 9, 2011.
EPO—10184478.5—Extended EP Search Report—Aug. 9, 2011.
AUIP—2010246342—Examiner's Second Report—mailed Aug. 18, 2011.
GenBank Accession No. CAB88152 (Apr. 19, 2000).
AUIP—2009222426—Examiner's Second Report—Aug. 22, 2011.
EPO—10182375.5—Extended EP Search Report May 19, 2011.
SIPO—Aug. 15, 2011—Decision of Rejection—CN200480012052.5.
SIPO—Aug. 23, 2011—First Office Action and Translation—CN200910224585.4.
EPO—Mar. 15, 2012—94(3) Communication—EP09180956.6.
HU—Journal of General Microbiology (1992)—138-1647-1655.
EPO—Feb. 7, 2012—94(3) Communication—EP09171688.6.
EPO—May 2, 2012—94(3) Communication—EP10184415.7.
EPO—May 2, 2012—94(3) Communication—EP10184478.5.
EPO—Mar. 7, 2012—94(3) Communication—EP10182375.5.
JPO—May 14, 2012—Office Action—JP2010-135846.
INPO—Jun. 7, 2012—First Examination Report—3819/KOLNP/2008.
EPO—May 29, 2012—Extended EP Search Report—EP12152662.8.
EPO—May 29, 2012—Extended EP Search Report—EP12152656.0.
UniProt Accession No. QOCPK9—Birren—2006.
NCBI Accession No. EAU34822—*Aspergillus terreus* NIH2624 glucoamylase precursor—2006.

UniProt Accession No. Q0C881—Birren—2006.
EBI Accession No. EAU29552—*Aspergillus terreus* NIH2624—2006.
EBI Accession No. ABB80178—Jiang—2003.
GeneSeq Accession No. ABQ80348—Jiang—2003.
EP07869797.6—Supplementary EP Search Report—Sep. 29, 2009.
EP04718513.7—Supplementary EP Search Report—Oct. 5, 2009.
Uniprot Database Accession No. Q4WIT7—Aspergillus fumigatus Jul. 5, 2005.
Geneseq Accession No. ABU03040—Alpha Amylase—Jan. 21, 2003.
Uniprot Accession No. Q8JZK3—Alpha Amylase—Oct. 1, 2002.
Geneseq Accession No. ABQ80354 (2003)—Jiang.
Geneseq Accession No. ABB80181 (2003)—Jiang.
EMBL Accession No. AR941925 (2006)—Lanahan.
Richardson—Journal of Biological Chemistry (2002)—277-26501-26507.
JPO—Aug. 16, 2012—Office Action—JP2010-132602.
Gray—Journal of Bacteriology—(1986)—166-2-635-643.

* cited by examiner

Figure 22

Trypsin digested LC MS\MS peptide identification

>SEQ ID NO:52 66kD pH1.3 pepsin cut
MKWTFSLLLLLSVFGQATHALTPAEWRSQSIYFLLTDRFGRTQNSTAACDTTDRVYCGGSWQGIINHLDYIQGMGFTAI
WITPVTGQFYENTGDGTSYHGYWQQDIYDLNYNYGTAQDLKNLASALHERGMYLMVDVVANHMGYDGAGNTVDYSVF
NPFSSSSYFHPYCLISNYDNQTNVEDCWLGDTTVSLPDLDTTSAVRDIWYDWVADLVANYSIDGLRVDTVKHVEKDFW\
PDYNSAAGVYCVGEVFSGDPAYTCPYQNYMDGVLNYPIYYQLLYAFESSSGSISDLYNMISSVASSCKDPTLLGNFIENH
DNPRFASYTSDYSQAKNVITFIFLSDGIPIVYAGQEQHYSGGSDPANREATWLSGYSTSATLYTWIASTNQIRSLAISKDAG
YVQAKNNPFYSDSNTIAMRKGTTAGAQVITVLSNKGASGSSYTLSLSGTGYSAGATLVETYTCTTVTVDSSGNLPVPMTS
GLPRVFVPSSWVNGSALCNTECTAATSLPVLEEELVTTTYGENIYLSGSISQLGSWNTASAVALSASQYTSSNPKWYVSV
TLPVGTSFQYKFIKKGSDGSVVWESDPNRSYTVPAGCEGATVTVADTWR → 5095 Da NRSY → N-linked Glycosylation site

| | | |
|---|---|---|
| 3938.8977 | 571-607 | 0 | IKKGSDGSVVWESDPNRSYT VPAGCEGATVTVADTWR |
| 3212.4483 | 40-69 | 0 | GRTDNSTAACDTTDRVYCG GSWQGIINHL |
| 3118.4500 | 341-369 | 0 | SDGIPIVYAGQEQHYSGGSD PANREATWL |
| 2525.0528 | 90-110 | 0 | YENTGDGTSYHGYWQQDIYD L |
| 2461.0798 | 135-157 | 0 | MVDVVANHMGYDGAGNTVDY SVF |
| 2397.2442 | 408-430 | 0 | YSDSNTIAMRKGTTAGAQVI TVL |

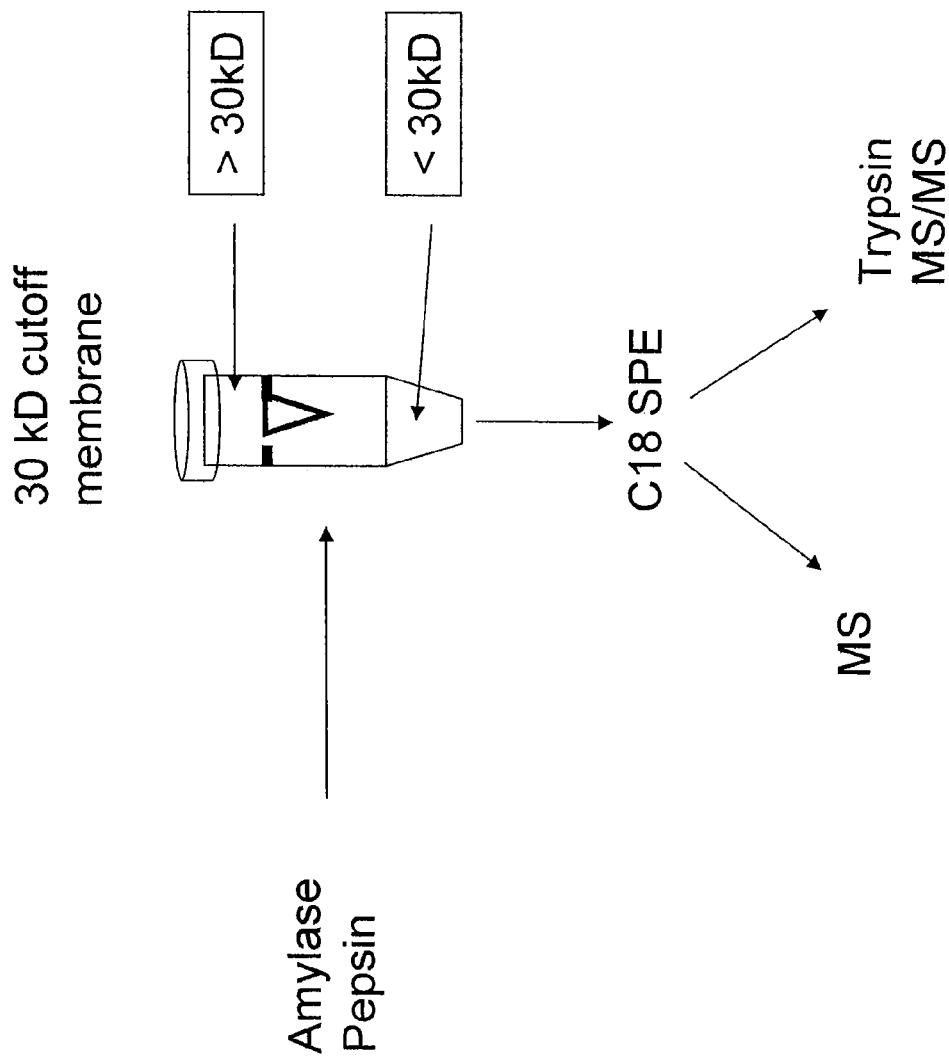

1) Pepsin
2) Amylase SEQ ID NO:52
3) SEQ ID NO:52 Pepsin
4) 30kd cut off top
5) 30kd flow through
6) C18 RP captured

Figure 23D

>SEQ ID NO:52 66kD pH1.3 pepsin cut
MKWTFSLLLLSVFGQATHALTPAEWRSQSIYFLLTDRFGRTDNSTTAACDTTDRVYCGGSWQGIINHLDYIQGMGFTAI
WITPVTGQFYENTGDGTSYHGYWQQDIYDLNYNYGTAQDLKNLASALHERGMYLMVDVVANHMGYDGAGNTVDYSVF
NPFSSSSYFHPYCLISNYDNQTNVEDCWLGDTTVSLPDLDTTSTAVRDIWYDWWADLVANYSIDGLRVDTVKHVEKDFWA
PDYNSAAGVVYCVCGEVFSGDPAYTCPYQNYMDGVLNYPIYYQLLYAFESSSGSISDLYNMISSVASSCKDPTLLGNFIENH
DNPRFASYTSDYSQAKNVITFIFLSDGIPIVYAGQEEQHYSGGSDPANREATWLSGYSTSATLYTWIASTNQIRSLAISKDAG
YVQAKNNPFYSDSNTIAMRKGTTAGAQVITVLSNKGASGSSYTLSLSGTGYSAGATLVETYTCTTVTVDSSGNLPVPMTS
GLPRVFVPSSWVNGSALCNTECTAATSLPVLFEELVTTYGENIYLSGSISQLGSWNTASAVALSASQYTSSNPKWYVSV
TLPVGTSFQYKFIKKGSDGSVVWESDPNRSYTVPAGCEGATVADTWR

| | | |
|---|---|---|
| 3938.8977 | 571-607 | 0 | IKKGSDGSVVWESDPNRSYT VPAGCEGATVTVADTWR |
| 3212.4483 | 40-69 | 0 | GRTDNSTTAACDTTDRVYCG GSWQGIINHL |
| 3118.4500 | 341-369 | 0 | SDGIPIVYA*GQEQHYSGGSD PANREATWL* |
| 2525.0528 | 90-110 | 0 | YENTGDGTSYHGYWQQDIYD L |
| 2461.0798 | 135-157 | 0 | MVDVVANHMGYDGAGNTVDY SVF |
| 2397.2442 | 408-430 | 0 | YSDSNTIAMRKGTTAGAQVI TVL |

Figure 23E

Asn-Xaa-Ser/Thr sequons in the sequence output below are highlighted in blue.
Asparagines predicted to be N-glycosylated are highlighted in red.

putative glycosylated site

SEQ ID NO:52

Output for 'Sequence'

Name: Sequence    Length: 607

MKWTFSLLLLLSVFGQATHALTPAEWRSQSIYFLLTDRFGRTDNSTTAACDTTDRVYCGGSWQGIIMHLDYIQGMGFTAI
WITPVTGQFYENTGDGTSYHGYWQQDIYDLNPMYGTAQDLKMLASALHERGMYLMVDVVANHMGYDGAGNTVDYSVFNPF
SSSSYEHPYCLISNYDHQTMVEDCWLGDTTVSLPDLDTTSTAVRDIWYDWVADLVAHYSIDGLRVDTVKHVEKDEWPDYR
SAAGVYCVGEVFSGDPAYTCPYQMYMDGV NYP IYYQLLYAFESSSGSISDLYNMISSVASSCKDPTLLGNPIEMHDNPR
FASTISDYSQARIVITFIFLSDGIFIVIAGQEQHYSGGSDPANREATWLSGYSTSATLYTWLASTNQIRSLAISKDAGYV
QAKMNPFYSDSNTIAMRKGTTAGAQVITVLSMKGASGSSYTLSLSGTCYSAGATLVETYTCTFVTVDSSGNLPVPMTSGL
PRVFVPSSWVNGSALCWTECTAATSLPVLFEELVTTTYGENIYLSGSISQLGSWNTASAVALSASQYTSSNPKWTYSVTL
PVGTSFQYKFIKKGSDGSVVWESDPNRSYTVPAGCEGATVTVADTWR

Figure 23F

SEQ ID NO:52

```
Name:  Sequence    Length:   607

MKWTFSLLLLSVFGQATHALTPAEWRSQSIYFLLTDRFGRTDMSTTAACDTTDRVYCGGSWQGIINHLDYIQGMGFTAI
WITPVTGQFYENTGDGTSYAGYWQQDIYDLNYNYGTAQDLKNLASALHERGMYLMVDVVANHMGYDGAGNTVDYSVFNPF
SSSSYFHPYCLISWYDNQTNVEDCWLGDTTVSLPDLDTTSTAVRDIWYDWVADLVANYSIDGLRVDTTVKHVEKDFWPDYM
SAAGVYCVGEVFSGDPAYTCPYONYMDGVLNYPIYYQLLYAFESSSGSISDLYNMISSVASSCKDPTLLGNFIENHDNPR
FASYTSDYSQAKNVITFIFLSDGIPIVYAGQEQHYSGGSDPAWREATMLSGYSTSATLYTWIASTMQIRSLAISKDAGYV
QAKMNPFYSDSNTIAMRKGTTAGAQVITVLSMKGASGSSYTLSLSGTGYSAGATLVETYTCTTVTVDSSGNLPVPMTSGL
PRVFVPSSWVNGSALCNTECTAATSLPVLFEELVTTTYGENIYLSGISQLGSWNTASAVALSASQYTSSNPKWTVSVTL
PVGTSFQYKFIKKGSDGSVVWESDPNRSYTVPAGCEGATVTVADTWR
```

Figure 24

| Enzyme | Initial rate* ±SD Granular starch | Initial rate* ±SD Soluble starch |
|---|---|---|
| SEQ ID NO:48 | 35.6 ± 3.8 | 60.7 ± 5.1 |
| SEQ ID NO:26 | 28.8 ± 3.4 | 51.8 ± 7.4 |
| SEQ ID NO:74 | 25.1 ± 2.5 | 84.3 ± 3.5 |
| SEQ ID NO:18 | 24.3 ± 4.3 | 58.3 ± 3.0 |
| SEQ ID NO:28 | 17.8 ± 4.3 | 33.8 ± 4.0 |
| SEQ ID NO:14 | 6.6 ± 1.2 | 53.9 ± 4.1 |
| SEQ ID NO:20 | 0 | 59.3 ± 8.5 |
| A.niger | 11.3 ± 2.7 | 43.3 ± 7.4 |

Figure 26

Summary of Purity

|  | Before Purification | | After Purification | |
|---|---|---|---|---|
|  | A260/A280 | Expression Ratio | A260/A280 | Expression Ratio |
| SEQ ID NO:18 | 0.52 | 91% | 0.59 | 92% |
| SEQ ID NO:26 | 0.56 | 85% | 0.65 | 86% |
| SEQ ID NO:4 | 0.67 | 91% | 0.73 | 85% |

Summary of Activity

|  | Raw Starch | | Soluble | |
|---|---|---|---|---|
|  | Purified | Unpurified | Purified | Unpurified |
| SEQ ID NO:18 | 10.7228 ±0.7925 | 6.4828 ± 0.5681 | 40.6725 ± 1.7016 | 24.7354 ± 3.821 |
| SEQ ID NO:26 | 5.7837 ± 0.2271 | 4.0691 ± 0.2864 | 17.4833 ± 0.7831 | 14.1849 ± 0.3761 |
| SEQ ID NO:4 | 6.47 ± 0.34 | 4.074 ± 0.35 | 127.37 ± 1.78 | 116.52 ± 1.27 |

Fig. 28A

Temperature Profile of Glucoamylases on Granular Starch – Initial Rate (ug glucose/min/ug glucoamylase)

| Temperature (°C) | SEQ ID NO:74 | SEQ ID NO:28 | SEQ ID NO:26 | Benchmark | SEQ ID NO:14 | SEQ ID NO:18 | SEQ ID NO:48 | SEQ ID NO:20 |
|---|---|---|---|---|---|---|---|---|
| 30 | 3.04 | 1.64 | 3.12 | 1.4 | 0.96 | 3.92 | 4.6 | inactive |
| 34 | 3.92 | 2.24 | 4.36 | 1.56 | 1.08 | 5.2 | 5.64 | inactive |
| 37 | 4.36 | 2.76 | 5.16 | 1.84 | 1.36 | 5.24 | 6.84 | inactive |
| 40 | 5.12 | 3.32 | 5.92 | 1.84 | 1.44 | 5.72 | 7.84 | inactive |

Fig. 28B

Temperature Profile of Glucoamylases on Soluble Starch (Dextrin) – Initial Rate (ug glucose/min/ug glucoamylase)

| Temperature (°C) | SEQ ID NO:20 | Benchmark |
|---|---|---|
| 30 | 6.840 | 4.380 |
| 34 | 9.920 | 6.980 |
| 37 | 11.080 | 8.600 |
| 40 | 15.040 | 10.380 |

Figure 29

Fig. 29A pH Profile of Glucoamylases on Granular Starch – Percent Relative Activity

| pH | SEQ ID NO:26 | SEQ ID NO:74 | SEQ ID NO:18 | SEQ ID NO:28 | SEQ ID NO:14 | SEQ ID NO:48 | Benchmark | SEQ ID NO:20 |
|---|---|---|---|---|---|---|---|---|
| 3.5 | 100.0000 | 78.6207 | 98.1308 | 88.1720 | 60.6061 | 99.3151 | 100.0000 | inactive |
| 4.0 | 88.1081 | 100.0000 | 100.0000 | 100.0000 | 66.6667 | 99.3151 | 100.0000 | inactive |
| 5.0 | 67.0270 | 91.0345 | 87.8505 | 91.3978 | 66.6667 | 100.0000 | 100.0000 | inactive |
| 6.0 | 43.2432 | 84.8276 | 79.4393 | 88.1720 | 100.0000 | 78.0822 | 40.0000 | inactive |
| 7.0 | 16.2162 | 37.2414 | 38.3178 | 61.2903 | 45.4545 | 34.2466 | 18.6667 | inactive |

Fig. 29B pH Profile of Glucoamylases on Soluble Starch (Dextrin) – Percent Relative Activity

| pH | SEQ ID NO:74 | SEQ ID NO:14 | SEQ ID NO:18 | SEQ ID NO:28 | SEQ ID NO:20 | SEQ ID NO:26 | SEQ ID NO:48 | Benchmark |
|---|---|---|---|---|---|---|---|---|
| 3.5 | 83.4997 | 72.1981 | 81.9000 | 79.4340 | 91.6548 | 98.2773 | 91.3527 | 91.3255 |
| 4.0 | 85.6287 | 76.7159 | 88.3000 | 91.1321 | 98.7874 | 100.0000 | 89.8116 | 100.0000 |
| 5.0 | 90.3526 | 83.0582 | 100.0000 | 100.0000 | 100.0000 | 85.4799 | 100.0000 | 80.8967 |
| 6.0 | 100.0000 | 100.0000 | 80.9000 | 98.6792 | 72.9672 | 46.4315 | 78.5103 | 67.9337 |
| 7.0 | 75.5156 | 81.2337 | 60.6922 | 68.8679 | 29.8859 | 11.8130 | 29.1952 | 18.3236 |

Figure 30

Temperature Profile of Amylases on Granular Starch – Percent Relative Activity

| Temp. (°C) | SEQ ID NO:56 | SEQ ID NO:70 | SEQ ID NO:62 | SEQ ID NO:66 | SEQ ID NO:2 | SEQ ID NO:52 | SEQ ID NO:78 | SEQ ID NO:76 | Sigma-A6211 | Megazyme E-ANAAM |
|---|---|---|---|---|---|---|---|---|---|---|
| 30 | 6.44 | 0.82 | 2.24 | 0.26 | 6.05 | 8.99 | 0.14 | 1.26 | 0.42 | 0.167432 |
| 34 | 10.98 | 1.29 | 3.26 | 0.47 | 6.97 | 11.21 | 0.27 | 2.20 | 0.49 | 0.229423 |
| 37 | 14.61 | 1.88 | 3.25 | 0.75 | 7.46 | 11.53 | 0.36 | 2.85 | 0.55 | 0.307667 |
| 40 | 17.66 | 2.36 | 3.11 | 1.27 | 6.93 | 11.40 | 0.51 | 3.26 | 0.54 | 0.29692 |

Figure 31

Fig. 31A pH Profile of Amylases on Granular Starch – Percent Relative Activity

| pH | SEQ ID NO:56 | SEQ ID NO:70 | SEQ ID NO:62 | SEQ ID NO:66 | SEQ ID NO:2 | SEQ ID NO:52 | SEQ ID NO:78 | SEQ ID NO:76 | Sigma-A6211 | Megazyme E-ANAAM |
|---|---|---|---|---|---|---|---|---|---|---|
| 3.5 | 0.00 | 3.69 | 0.00 | 24.31 | 31.59 | 89.70 | 6.89 | 6.87 | 72.06 | 51.25 |
| 4.0 | 0.00 | 3.88 | 0.00 | 70.83 | 86.95 | 100.00 | 9.85 | 9.33 | 94.34 | 74.69 |
| 5.0 | 93.07 | 45.60 | 50.20 | 100.00 | 100.00 | 96.97 | 87.70 | 72.80 | 100.00 | 100.00 |
| 6.0 | 100.00 | 100.00 | 100.00 | 97.10 | 95.08 | 76.59 | 100.00 | 100.00 | 78.16 | 62.43 |
| 7.0 | 92.52 | 99.12 | 85.70 | 64.29 | 79.10 | 43.67 | 61.30 | 71.84 | 71.04 | 47.70 |

Fig. 31B pH Profile of Amylases on Soluble Starch – Percent Relative Activity

| pH | SEQ ID NO:86 | SEQ ID NO:70 | SEQ ID NO:62 | SEQ ID NO:66 | SEQ ID NO:2 | SEQ ID NO:52 | SEQ ID NO:78 | SEQ ID NO:76 | Sigma-A6211 | Megazyme E-ANAAM |
|---|---|---|---|---|---|---|---|---|---|---|
| 3.5 | 0.00 | 2.23 | 0.00 | 11.00 | 51.35 | 100.00 | 1.22 | 1.25 | 38.55 | 46.04 |
| 4.0 | 6.94 | 2.57 | 0.00 | 47.94 | 89.60 | 96.63 | 18.89 | 3.62 | 63.72 | 60.97 |
| 5.0 | 74.57 | 37.01 | 35.90 | 100.00 | 100.00 | 83.16 | 84.63 | 83.03 | 100.00 | 100.00 |
| 6.0 | 97.83 | 65.88 | 93.03 | 86.33 | 94.27 | 60.31 | 100.00 | 100.00 | 57.80 | 50.62 |
| 7.0 | 100.00 | 100.00 | 100.00 | 56.96 | 87.91 | 52.17 | 66.50 | 27.79 | 11.53 | 13.24 |

SEQUENCE LISTING

<160> NUMBER OF SEQ ID NOS: 82

<210> SEQ ID NO 1
<211> LENGTH: 1710
<212> TYPE: DNA
<213> ORGANISM: Cochliobolus heterostrophus ATCC 48331

<400> SEQUENCE: 1

| | |
|---|---|
| gccgacacca atgcttggaa gtcccgcagc atctactttg tcctgacgga tcgtattgcc | 60 |
| cgcaacagca gcgacacggg cggctcagcg tgcagcgacc tcggcaacta ctgcggtgga | 120 |
| actttccagg gcctcgagtc taagctcgac tacatcaagg gacttggatt cgatgccatt | 180 |
| tggatcaccc ccgtcgtctc aaacaaggct gctggatacc atggctactg ggccgaggac | 240 |
| ttgtatgccg tcaactcaaa ctacggcact gctgccgact gaagagctt ggttgccgct | 300 |
| gcccatgcca agggcatcta catgatggtc gacgttgtcg caaaccacat gggtcctgga | 360 |
| gcaatcacaa acaaccgccc tgaacctctc aaccaggctt catcatacca ccctccttgc | 420 |
| aacatcgact acaacaacca aaccagtgtc gaggtatgtc aaatagccgg actcccgac | 480 |
| atctacacca ccaagagcga gatccgcacg ctcctcaaca cctgggtcaa ctggctcgta | 540 |
| aacgagtaca gcttcgacgg tgtccgcatc gacaccgtca gcacgtcga aaaggactt | 600 |
| tggcctggct tctctgccgc taccggtgtc tacaacattg gcgaggtgtt tgacggagac | 660 |
| ccagcctacc ttgccccgta cgccaagctt atgcccggcc tcctcaacta cgcagtctac | 720 |
| tacccgatga caacttttta ccagcaaacg ggctcttccc aggcgcttgt agacatgatg | 780 |
| aacactgtca gcaacaccttt ccctgaccca tctgccttgg aaccttcct cgacaaccac | 840 |
| gacaacaagc gctggttgaa cgtcaagaac gaccagactc tgctcaagaa cgctcttgct | 900 |
| tatgtcatcc tcgcacgtgg tatccccatc ttgtactatg gtaccgagca gggatacgct | 960 |
| ggtggtgacg acccagctaa ccgagaggat ctgtggcgca gtggcttcaa caccaatgcc | 1020 |
| aacctctacc aagccatcaa gaaactgacc gccgcccgac aggctgccgg tggtctcgca | 1080 |
| ggaaacgacc acgtccacct gtacgtcgcc gacacggctt acgcctggag ccgtgccaac | 1140 |
| ggcaacctga ttgtcctcac caccaacgct ggcggcaact ccaacaccca gcactgcttc | 1200 |
| aacacgcaaa aggcaaacgg ccgctggacc aacgtctacg caacggcgc caccgtctct | 1260 |
| gccgatagca acggccaaat ctgcgtctcc gtcacaaacg gcgagcccgt tgtcctcctc | 1320 |
| gccggctccg ctaccccccac cactggcact accctctcca cccgcaccgc cactgccacc | 1380 |
| gccacaccaa ccgcatgccc caccgccgtc tccgtctcct tcacccaccg cgtcaccact | 1440 |
| gttcccggtg acaccatcaa aatcactggc aacacggccc agctaggtaa ctggactccc | 1500 |
| gccaacggtc ttgccttgtc cgcagctagc tacacatcca gcaaccctat ctggaccatt | 1560 |
| accgtgcccc tggccgctgg atcctccatc tcgtacaagt ttgtcaagat tgacagtgga | 1620 |
| ggaactgtca cctgggagag tgaccccaac aggtcataca ctgcgccgag ctgccaggcg | 1680 |
| agtgccggtg tgaacagctc atggcaatag | 1710 |

<210> SEQ ID NO 2
<211> LENGTH: 569
<212> TYPE: PRT
<213> ORGANISM: Cochliobolus heterostrophus ATCC 48331
<220> FEATURE:
<221> NAME/KEY: DOMAIN
<222> LOCATION: (13)...(353)
<223> OTHER INFORMATION: Alpha amylase, catalytic domain
<220> FEATURE:

```
<221> NAME/KEY: DOMAIN
<222> LOCATION: (469)...(564)
<223> OTHER INFORMATION: Starch binding domain
<220> FEATURE:
<221> NAME/KEY: SITE
<222> LOCATION: (22)...(25)
<223> OTHER INFORMATION: N-glycosylation site. Prosite id = PS00001
<220> FEATURE:
<221> NAME/KEY: SITE
<222> LOCATION: (148)...(151)
<223> OTHER INFORMATION: N-glycosylation site. Prosite id = PS00001
<220> FEATURE:
<221> NAME/KEY: SITE
<222> LOCATION: (558)...(561)
<223> OTHER INFORMATION: N-glycosylation site. Prosite id = PS00001
<220> FEATURE:
<221> NAME/KEY: SITE
<222> LOCATION: (573)...(576)
<223> OTHER INFORMATION: N-glycosylation site. Prosite id = PS00001

<400> SEQUENCE: 2

Ala Asp Thr Asn Ala Trp Lys Ser Arg Ser Ile Tyr Phe Val Leu Thr
1               5                   10                  15

Asp Arg Ile Ala Arg Asn Ser Ser Asp Thr Gly Gly Ser Ala Cys Ser
            20                  25                  30

Asp Leu Gly Asn Tyr Cys Gly Gly Thr Phe Gln Gly Leu Glu Ser Lys
        35                  40                  45

Leu Asp Tyr Ile Lys Gly Leu Gly Phe Asp Ala Ile Trp Ile Thr Pro
50                  55                  60

Val Val Ser Asn Lys Ala Ala Gly Tyr His Gly Tyr Trp Ala Glu Asp
65                  70                  75                  80

Leu Tyr Ala Val Asn Ser Asn Tyr Gly Thr Ala Ala Asp Leu Lys Ser
                85                  90                  95

Leu Val Ala Ala His Ala Lys Gly Ile Tyr Met Met Val Asp Val
            100                 105                 110

Val Ala Asn His Met Gly Pro Gly Ala Ile Thr Asn Asn Arg Pro Glu
            115                 120                 125

Pro Leu Asn Gln Ala Ser Ser Tyr His Pro Pro Cys Asn Ile Asp Tyr
        130                 135                 140

Asn Asn Gln Thr Ser Val Glu Val Cys Gln Ile Ala Gly Leu Pro Asp
145                 150                 155                 160

Ile Tyr Thr Thr Lys Ser Glu Ile Arg Thr Leu Leu Asn Thr Trp Val
                165                 170                 175

Asn Trp Leu Val Asn Glu Tyr Ser Phe Asp Gly Val Arg Ile Asp Thr
            180                 185                 190

Val Lys His Val Glu Lys Asp Phe Trp Pro Gly Phe Ser Ala Ala Thr
        195                 200                 205

Gly Val Tyr Asn Ile Gly Glu Val Phe Asp Gly Asp Pro Ala Tyr Leu
    210                 215                 220

Ala Pro Tyr Ala Lys Leu Met Pro Gly Leu Leu Asn Tyr Ala Val Tyr
225                 230                 235                 240

Tyr Pro Met Asn Asn Phe Tyr Gln Gln Thr Gly Ser Ser Gln Ala Leu
                245                 250                 255

Val Asp Met Met Asn Thr Val Ser Asn Thr Phe Pro Asp Pro Ser Ala
            260                 265                 270

Leu Gly Thr Phe Leu Asp Asn His Asp Asn Lys Arg Trp Leu Asn Val
        275                 280                 285

Lys Asn Asp Gln Thr Leu Leu Lys Asn Ala Leu Ala Tyr Val Ile Leu
290                 295                 300

Ala Arg Gly Ile Pro Ile Leu Tyr Tyr Gly Thr Glu Gln Gly Tyr Ala
```

|     |     |     |     |     |     |     |     |     |     |     |     |
| --- | --- | --- | --- | --- | --- | --- | --- | --- | --- | --- | --- |
|     | 305 |     |     |     | 310 |     |     |     | 315 |     | 320 |
| Gly | Gly | Asp | Asp | Pro | Ala | Asn | Arg | Glu | Asp | Leu | Trp | Arg | Ser | Gly | Phe |

Gly Gly Asp Asp Pro Ala Asn Arg Glu Asp Leu Trp Arg Ser Gly Phe
305                 310                 315                 320

Asn Thr Asn Ala Asn Leu Tyr Gln Ala Ile Lys Lys Leu Thr Ala Ala
            325                 330                 335

Arg Gln Ala Ala Gly Gly Leu Ala Gly Asn Asp His Val His Leu Tyr
        355                 360                 365

Val Ala Asp Thr Ala Tyr Ala Trp Ser Arg Ala Asn Gly Asn Leu Ile
370                 375                 380

Val Leu Thr Thr Asn Ala Gly Gly Asn Ser Asn Thr Gln His Cys Phe
385                 390                 395                 400

Asn Thr Gln Lys Ala Asn Gly Arg Trp Thr Asn Val Tyr Gly Asn Gly
            405                 410                 415

Ala Thr Val Ser Ala Asp Ser Asn Gly Gln Ile Cys Val Ser Val Thr
            420                 425                 430

Asn Gly Glu Pro Val Val Leu Leu Ala Gly Ser Ala Thr Pro Thr Thr
            435                 440                 445

Gly Thr Thr Leu Ser Thr Arg Thr Ala Thr Ala Thr Ala Thr Pro Thr
450                 455                 460

Ala Cys Pro Thr Ala Val Ser Val Ser Phe Thr His Arg Val Thr Thr
465                 470                 475                 480

Val Pro Gly Asp Thr Ile Lys Ile Thr Gly Asn Thr Ala Gln Leu Gly
            485                 490                 495

Asn Trp Thr Pro Ala Asn Gly Leu Ala Leu Ser Ala Ala Ser Tyr Thr
            500                 505                 510

Ser Ser Asn Pro Ile Trp Thr Ile Thr Val Pro Leu Ala Ala Gly Ser
            515                 520                 525

Ser Ile Ser Tyr Lys Phe Val Lys Ile Asp Ser Gly Gly Thr Val Thr
            530                 535                 540

Trp Glu Ser Asp Pro Asn Arg Ser Tyr Thr Ala Pro Ser Cys Gln Ala
545                 550                 555                 560

Ser Ala Gly Val Asn Ser Ser Trp Gln
            565

<210> SEQ ID NO 3
<211> LENGTH: 1770
<212> TYPE: DNA
<213> ORGANISM: Cochliobolus heterostrophus ATCC 48331

<400> SEQUENCE: 3

```
atgttgttgc tcaacatctt caccacccte ttcttctaca tcacctgcat cgtctccgcc     60
gccgacacca atgcttggaa gtcccgcagc atctactttg tcctgacgga tcgtattgcc    120
cgcaacagca gcgacacggg cggctcagcg tgcagcgacc tcggcaacta ctgcggtgga    180
actttccagg gcctcgagtc taagctcgac tacatcaagg acttggattc gatgccatt    240
tggattaccc ccgtcgtctc aaacaaggct gctggatacc atggctactg ggccgaggac    300
ttgtatgccg tcaactcaaa ctacggcact gctgccgact tgaagagctt ggttgccgct    360
gcccatgcca agggcatcta catgatggtc gacgttgtcg caaaccacat gggtcctgga    420
gcaatcacaa acaaccgccc tgaacctctc aaccaggctt catcatacca ccctccttgc    480
aacatcgact acaacaacca aaccagtgtc gaggtatgtc aaatagccgg actccccgac    540
atctacacca ccaagagcga gatccgcacg ctcctcaaca cctgggtcaa ctggctcgta    600
aacgagtaca gcttcgacgg tgtccgcatc gacaccgtca agcacgtcga aaaggacttt    660
```

```
tggcctggct tctctgccgc taccggtgtc tacaacattg gcgaggtgtt tgacggagac    720
ccagcctacc ttgccccgta cgccaagctt atgcccggcc tcctcaacta cgcagtctac    780
tacccgatga acaactttta ccagcaaacg ggctcttccc aggcgcttgt agacatgatg    840
aacactgtca gcaacacctt ccctgaccca tctgccttgg gaaccttcct cgacaaccac    900
gacaacaagc gctggttgaa cgtcaagaac gaccagactc tgctcaagaa cgctcttgct    960
tatgtcatcc tcgcacgtgg tatccccatc ttgtactatg gtaccgagca gggatacgct   1020
ggtggtgacg acccagctaa ccgagaggat ctgtggcgca gtggcttcaa caccaatgcc   1080
aacctctacc aagccatcaa gaaactgacc gccgcccgac aggctgccgg tggtctcgca   1140
ggaaacgacc acgtccacct gtacgtcgcc gacacggctt acgcctggag ccgtgccaac   1200
ggcaacctga ttgtcctcac caccaacgct ggcggcaact ccaacaccca gcactgcttc   1260
aacacgcaaa aggcaaacgg ccgctggacc aacgtctacg gcaacggcgc caccgtctct   1320
gccgatagca acggccaaat ctgcgtctcc gtcacaaacg gcgagcccgt tgtcctcctc   1380
gccggctccg ctacccccac cactggcact accctctcca cccgcaccgc cactgccacc   1440
gccacaccaa ccgcatgccc caccgccgtc tccgtctcct tcacccaccg cgtcaccact   1500
gttcccggtg acaccatcaa aatcactggc aacacggccc agctaggtaa ctggactccc   1560
gccaacggcc ttgccttgtc cgcagctagc tacacatcca gcaaccctat ctggaccatt   1620
accgtgcccc tggccgctgg atcctccatc tcgtacaagt ttgtcaagat tgacagtgga   1680
ggaactgtca cctgggagag tgaccccaac aggtcataca ctgcgccgag ctgccaggcg   1740
agtgccagtg tgaacagctc atggcaatag                                    1770
```

<210> SEQ ID NO 4
<211> LENGTH: 589
<212> TYPE: PRT
<213> ORGANISM: Cochliobolus heterostrophus ATCC 48331
<220> FEATURE:
<221> NAME/KEY: SIGNAL
<222> LOCATION: (1)...(20)
<220> FEATURE:
<221> NAME/KEY: DOMAIN
<222> LOCATION: (33)...(373)
<223> OTHER INFORMATION: Alpha amylase, catalytic domain
<220> FEATURE:
<221> NAME/KEY: DOMAIN
<222> LOCATION: (489)...(586)
<223> OTHER INFORMATION: Starch binding domain
<220> FEATURE:
<221> NAME/KEY: SITE
<222> LOCATION: (42)...(45)
<223> OTHER INFORMATION: N-glycosylation site. Prosite id = PS00001
<220> FEATURE:
<221> NAME/KEY: SITE
<222> LOCATION: (168)...(171)
<223> OTHER INFORMATION: N-glycosylation site. Prosite id = PS00001
<220> FEATURE:
<221> NAME/KEY: SITE
<222> LOCATION: (578)...(581)
<223> OTHER INFORMATION: N-glycosylation site. Prosite id = PS00001
<220> FEATURE:
<221> NAME/KEY: SITE
<222> LOCATION: (593)...(596)
<223> OTHER INFORMATION: N-glycosylation site. Prosite id = PS00001

<400> SEQUENCE: 4

```
Met Leu Leu Leu Asn Ile Phe Thr Thr Leu Phe Phe Tyr Ile Thr Cys
1               5                   10                  15

Ile Val Ser Ala Ala Asp Thr Asn Ala Trp Lys Ser Arg Ser Ile Tyr
            20                  25                  30

Phe Val Leu Thr Asp Arg Ile Ala Arg Asn Ser Ser Asp Thr Gly Gly
```

-continued

```
             35                  40                  45
Ser Ala Cys Ser Asp Leu Gly Asn Tyr Cys Gly Gly Thr Phe Gln Gly
         50                  55                  60
Leu Glu Ser Lys Leu Asp Tyr Ile Lys Gly Leu Gly Phe Asp Ala Ile
 65                  70                  75                  80
Trp Ile Thr Pro Val Ser Asn Lys Ala Ala Gly Tyr His Gly Tyr
                 85                  90                  95
Trp Ala Glu Asp Leu Tyr Ala Val Asn Ser Asn Tyr Gly Thr Ala Ala
                100                 105                 110
Asp Leu Lys Ser Leu Val Ala Ala His Ala Lys Gly Ile Tyr Met
                115                 120                 125
Met Val Asp Val Val Ala Asn His Met Gly Pro Gly Ala Ile Thr Asn
    130                 135                 140
Asn Arg Pro Glu Pro Leu Asn Gln Ala Ser Ser Tyr His Pro Pro Cys
145                 150                 155                 160
Asn Ile Asp Tyr Asn Asn Gln Thr Ser Val Glu Val Cys Gln Ile Ala
                165                 170                 175
Gly Leu Pro Asp Ile Tyr Thr Thr Lys Ser Glu Ile Arg Thr Leu Leu
                180                 185                 190
Asn Thr Trp Val Asn Trp Leu Val Asn Glu Tyr Ser Phe Asp Gly Val
            195                 200                 205
Arg Ile Asp Thr Val Lys His Val Glu Lys Asp Phe Trp Pro Gly Phe
        210                 215                 220
Ser Ala Thr Gly Val Tyr Asn Ile Gly Glu Val Phe Asp Gly Asp
225                 230                 235                 240
Pro Ala Tyr Leu Ala Pro Tyr Ala Lys Leu Met Pro Gly Leu Leu Asn
                245                 250                 255
Tyr Ala Val Tyr Tyr Pro Met Asn Asn Phe Tyr Gln Gln Thr Gly Ser
                260                 265                 270
Ser Gln Ala Leu Val Asp Met Met Asn Thr Val Ser Asn Thr Phe Pro
            275                 280                 285
Asp Pro Ser Ala Leu Gly Thr Phe Leu Asp Asn His Asp Asn Lys Arg
        290                 295                 300
Trp Leu Asn Val Lys Asn Asp Gln Thr Leu Leu Lys Asn Ala Leu Ala
305                 310                 315                 320
Tyr Val Ile Leu Ala Arg Gly Ile Pro Ile Leu Tyr Tyr Gly Thr Glu
                325                 330                 335
Gln Gly Tyr Ala Gly Gly Asp Asp Pro Ala Asn Arg Glu Asp Leu Trp
                340                 345                 350
Arg Ser Gly Phe Asn Thr Asn Ala Asn Leu Tyr Gln Ala Ile Lys Lys
            355                 360                 365
Leu Thr Ala Ala Arg Gln Ala Ala Gly Gly Leu Ala Gly Asn Asp His
        370                 375                 380
Val His Leu Tyr Val Ala Asp Thr Ala Tyr Ala Trp Ser Arg Ala Asn
385                 390                 395                 400
Gly Asn Leu Ile Val Leu Thr Thr Asn Ala Gly Gly Asn Ser Asn Thr
                405                 410                 415
Gln His Cys Phe Asn Thr Gln Lys Ala Asn Gly Arg Trp Thr Asn Val
                420                 425                 430
Tyr Gly Asn Gly Ala Thr Val Ser Ala Asp Ser Asn Gly Gln Ile Cys
            435                 440                 445
Val Ser Val Thr Asn Gly Glu Pro Val Val Leu Leu Ala Gly Ser Ala
        450                 455                 460
```

```
Thr Pro Thr Thr Gly Thr Thr Leu Ser Thr Arg Ala Thr Ala Thr
465                 470                 475                 480

Ala Thr Pro Thr Ala Cys Pro Thr Ala Val Ser Val Ser Phe Thr His
                485                 490                 495

Arg Val Thr Thr Val Pro Gly Asp Thr Ile Lys Ile Thr Gly Asn Thr
            500                 505                 510

Ala Gln Leu Gly Asn Trp Thr Pro Ala Asn Gly Leu Ala Leu Ser Ala
        515                 520                 525

Ala Ser Tyr Thr Ser Ser Asn Pro Ile Trp Thr Ile Thr Val Pro Leu
    530                 535                 540

Ala Ala Gly Ser Ser Ile Ser Tyr Lys Phe Val Lys Ile Asp Ser Gly
545                 550                 555                 560

Gly Thr Val Thr Trp Glu Ser Asp Pro Asn Arg Ser Tyr Thr Ala Pro
                565                 570                 575

Ser Cys Gln Ala Ser Ala Ser Val Asn Ser Ser Trp Gln
            580                 585
```

<210> SEQ ID NO 5
<211> LENGTH: 2541
<212> TYPE: DNA
<213> ORGANISM: Cochliobolus heterostrophus ATCC 48331

<400> SEQUENCE: 5

```
gtgaagatct acgacgcggc tgaacaggtc tttcagatcc aggaatccgt ctggcctcgc      60
cctgctgatg acgagggcac cgaccctgaa aagtcggctt tgaccttcac ttggaccgat     120
agcccgtttt cttttgccat taaacgtagg gccaccaatg agacgctctt cgatacttcg     180
gcagcttctc ttgttttcga gacgcagtac cttcgcttaa gaaccgctct accacctttg     240
ccaaacctgt acggtcttgg tgaatcaacg gatgctttcc atctcaacac caccaactat     300
acgcgaactc tttggaatcg agatgcctat ggcacgccac caggatccaa cctctacgga     360
gctcacccga tctactttga tcaccgcggt gagaatggta ctcacggtgt tttcttggct     420
agctctgagg gtatggacat caagattgat gatactgacg ccagttcct tgagtacaac     480
actctcggtg gtgttcttga cttctacttc cttgctggac ccggccctaa ggaagttgca     540
actcaatact cagccctttc tggcttgcct gctatgatgc cttactgggg tttcggctca     600
caccaatgca agtatggcta ccgtgatgtt tgggaggttg ccgaggttgt agcaaactac     660
tctgctgctg atatcccact tgagaccatg tggaccgata tcgactacat ggagcttcgc     720
cgcttgttca ccctggatcc cgagcgttac ccgcttgagc ttgttcgcca gcttgtagac     780
tatttgcatg ctcaccaaca gcactacatt ctgatggtca actccgctgt ctggagcggt     840
gactatgatg cctacaacaa cggtgcaaag cttgaagtct ccagaagaa gagcaacggc     900
tccttcgaac agggtgctgt ctggccaggc cctactgtct ttccagattg gttccatccc     960
aacacccaga atactggga tgaggaattc gctcgcttct tcgacccgc tactggtgtt    1020
gatatcgatg actttggaa tgacatgaat gaacccgcca acttctgccc ataccctgc    1080
tcagaccctg aagcctattc tgaggagtcc aagaacccac ccgagccacc ggcggtgcgc    1140
acttctgcag gtcgccaaat ccctggcttc ccagcaggtt ccagccaca gtctaactct    1200
agcactgcaa ggcgttctgt tgtaaaggga ccatctagca tgcgtccttc caagcgccaa    1260
gcgcctaaca gcgctggaga tgctaagcac ctcggtcttc ccggtcgtga tctgatcaac    1320
cccaagtacc agatccacaa cgaagccggt tcaatcagca acaggaccct ggctacggat    1380
atcaagaatt acgatggctc ttatcactac gatacgcaca acttctgggg ctcgatgatg    1440
```

-continued

| | |
|---|---|
| agcattacct ctcacaagtc tatgcaagct cgccgtcccg aaagacggcc attcattatc | 1500 |
| actaggtcat ctttccctgg cctcggttct tatctcggaa agtggcttgg tgacaacgtc | 1560 |
| tccgagtggg cacaataccg cttctcgatt gccggcatct tgaacttcaa caccatcttc | 1620 |
| cagatcccca tggtcggtcc agatatttgc ggtttcgccg aaacacgac cgagactctc | 1680 |
| tgcgcccgct ggaccactct tggtgctttc tacccgttca tgaggaacca cgccggcgac | 1740 |
| acttccatca gccaagaata ctatcgctgg cctctcacca gggccgcagc caagaacgcc | 1800 |
| atcgcagtca ggtacaggct cttggactac ttctacacgg ccttccaccg ccaggccacc | 1860 |
| accggtctac ccagcttgaa ccccctcttc ttccactacc ccaccgacgc caaaaccttc | 1920 |
| ggcattgagc accagttctt ctacggagac agcatcctcg tctcgcccgt cctcgaagaa | 1980 |
| aactccacct cagtctccat ctacctcccc aaagatgtct ctacgacta ctggaccggc | 2040 |
| gagcgcatcc aaggaaacgg cgagaacatt aacctcactg acgtaggatt cgacaccatc | 2100 |
| cccctccacg tcaaaggtgg atccatcctc cctctccgcg ccgaatccgc aaacacaacc | 2160 |
| accgagctcc gcaaacaaaa ctttgtcctc tggatcgcac caaatgctac caaccaagcc | 2220 |
| tctggctcgc tctacctcga tgatggagat ccctcgagc agaagtctac ttcgctcatt | 2280 |
| aacttctcct tcaacaacgg cgccttcagc atgagcggcg atttcggatt cgagactgag | 2340 |
| cttgtcattc agaatatcac catcctgggt acctcgcaga gcgtacaggg ccctgttgcg | 2400 |
| cttaccaagg gctgggaaca taactttggg gctggtgctg gtatgccgca gtttgatagt | 2460 |
| ggtgcagccg agtcgcgtcg agttgttgct gcagtttggg gtttggttgc ggggctgtc | 2520 |
| agtgtttggt tcagcttgta a | 2541 |

<210> SEQ ID NO 6
<211> LENGTH: 846
<212> TYPE: PRT
<213> ORGANISM: Cochliobolus heterostrophus ATCC 48331
<220> FEATURE:
<221> NAME/KEY: DOMAIN
<222> LOCATION: (169)...(710)
<223> OTHER INFORMATION: Glycosyl hydrolases family 31
<220> FEATURE:
<221> NAME/KEY: SITE
<222> LOCATION: (53)...(56)
<223> OTHER INFORMATION: N-glycosylation site. Prosite id = PS00001
<220> FEATURE:
<221> NAME/KEY: SITE
<222> LOCATION: (97)...(100)
<223> OTHER INFORMATION: N-glycosylation site. Prosite id = PS00001
<220> FEATURE:
<221> NAME/KEY: SITE
<222> LOCATION: (134)...(137)
<223> OTHER INFORMATION: N-glycosylation site. Prosite id = PS00001
<220> FEATURE:
<221> NAME/KEY: SITE
<222> LOCATION: (222)...(225)
<223> OTHER INFORMATION: N-glycosylation site. Prosite id = PS00001
<220> FEATURE:
<221> NAME/KEY: SITE
<222> LOCATION: (303)...(306)
<223> OTHER INFORMATION: N-glycosylation site. Prosite id = PS00001
<220> FEATURE:
<221> NAME/KEY: SITE
<222> LOCATION: (349)...(356)
<223> OTHER INFORMATION: Glycosyl hydrolases family 31 active site.
    Prosite id = PS00129
<220> FEATURE:
<221> NAME/KEY: SITE
<222> LOCATION: (405)...(408)
<223> OTHER INFORMATION: N-glycosylation site. Prosite id = PS00001
<220> FEATURE:
<221> NAME/KEY: SITE
<222> LOCATION: (554)...(584)
<223> OTHER INFORMATION: Glycosyl hydrolases family 31 signature 2.

Prosite id = PS00707
<220> FEATURE:
<221> NAME/KEY: SITE
<222> LOCATION: (563)...(566)
<223> OTHER INFORMATION: N-glycosylation site. Prosite id = PS00001
<220> FEATURE:
<221> NAME/KEY: SITE
<222> LOCATION: (671)...(674)
<223> OTHER INFORMATION: N-glycosylation site. Prosite id = PS00001
<220> FEATURE:
<221> NAME/KEY: SITE
<222> LOCATION: (701)...(704)
<223> OTHER INFORMATION: N-glycosylation site. Prosite id = PS00001
<220> FEATURE:
<221> NAME/KEY: SITE
<222> LOCATION: (729)...(732)
<223> OTHER INFORMATION: N-glycosylation site. Prosite id = PS00001
<220> FEATURE:
<221> NAME/KEY: SITE
<222> LOCATION: (746)...(749)
<223> OTHER INFORMATION: N-glycosylation site. Prosite id = PS00001
<220> FEATURE:
<221> NAME/KEY: SITE
<222> LOCATION: (772)...(775)
<223> OTHER INFORMATION: N-glycosylation site. Prosite id = PS00001
<220> FEATURE:
<221> NAME/KEY: SITE
<222> LOCATION: (797)...(800)
<223> OTHER INFORMATION: N-glycosylation site. Prosite id = PS00001

<400> SEQUENCE: 6

Met Lys Ile Tyr Asp Ala Ala Glu Gln Val Phe Gln Ile Gln Glu Ser
1               5                   10                  15

Val Trp Pro Arg Pro Ala Asp Asp Glu Gly Thr Asp Pro Glu Lys Ser
            20                  25                  30

Ala Leu Thr Phe Thr Trp Thr Asp Ser Pro Phe Ser Phe Ala Ile Lys
        35                  40                  45

Arg Arg Ala Thr Asn Glu Thr Leu Phe Asp Thr Ser Ala Ala Ser Leu
    50                  55                  60

Val Phe Glu Thr Gln Tyr Leu Arg Leu Arg Thr Ala Leu Pro Pro Leu
65                  70                  75                  80

Pro Asn Leu Tyr Gly Leu Gly Glu Ser Thr Asp Ala Phe His Leu Asn
                85                  90                  95

Thr Thr Asn Tyr Thr Arg Thr Leu Trp Asn Arg Asp Ala Tyr Gly Thr
            100                 105                 110

Pro Pro Gly Ser Asn Leu Tyr Gly Ala His Pro Ile Tyr Phe Asp His
        115                 120                 125

Arg Gly Glu Asn Gly Thr His Gly Val Phe Leu Ala Ser Ser Glu Gly
    130                 135                 140

Met Asp Ile Lys Ile Asp Asp Thr Asp Gly Gln Phe Leu Glu Tyr Asn
145                 150                 155                 160

Thr Leu Gly Gly Val Leu Asp Phe Tyr Phe Leu Ala Gly Pro Gly Pro
                165                 170                 175

Lys Glu Val Ala Thr Gln Tyr Ser Ala Leu Ser Gly Leu Pro Ala Met
            180                 185                 190

Met Pro Tyr Trp Gly Phe Gly Ser His Gln Cys Lys Tyr Gly Tyr Arg
        195                 200                 205

Asp Val Trp Glu Val Ala Glu Val Val Ala Asn Tyr Ser Ala Ala Asp
    210                 215                 220

Ile Pro Leu Glu Thr Met Trp Thr Asp Ile Asp Tyr Met Glu Leu Arg
225                 230                 235                 240

Arg Leu Phe Thr Leu Asp Pro Glu Arg Tyr Pro Leu Glu Leu Val Arg
                245                 250                 255

-continued

Gln Leu Val Asp Tyr Leu His Ala His Gln His Tyr Ile Leu Met
            260                 265                 270

Val Asn Ser Ala Val Trp Ser Gly Asp Tyr Asp Ala Tyr Asn Asn Gly
            275                 280                 285

Ala Lys Leu Glu Val Phe Gln Lys Lys Ser Asn Gly Ser Phe Glu Gln
290                 295                 300

Gly Ala Val Trp Pro Gly Pro Thr Val Phe Pro Asp Trp Phe His Pro
305                 310                 315                 320

Asn Thr Gln Lys Tyr Trp Asp Glu Glu Phe Ala Arg Phe Phe Asp Pro
                325                 330                 335

Ala Thr Gly Val Asp Ile Asp Gly Leu Trp Asn Asp Met Asn Glu Pro
                340                 345                 350

Ala Asn Phe Cys Pro Tyr Pro Cys Ser Asp Pro Glu Ala Tyr Ser Glu
                355                 360                 365

Glu Ser Lys Asn Pro Pro Glu Pro Pro Ala Val Arg Thr Ser Ala Gly
                370                 375                 380

Arg Gln Ile Pro Gly Phe Pro Ala Gly Phe Gln Pro Gln Ser Asn Ser
385                 390                 395                 400

Ser Thr Ala Arg Arg Ser Val Val Lys Gly Pro Ser Ser Met Arg Pro
                405                 410                 415

Ser Lys Arg Gln Ala Pro Asn Ser Ala Gly Asp Ala Lys His Leu Gly
                420                 425                 430

Leu Pro Gly Arg Asp Leu Ile Asn Pro Lys Tyr Gln Ile His Asn Glu
                435                 440                 445

Ala Gly Ser Ile Ser Asn Arg Thr Leu Ala Thr Asp Ile Lys Asn Tyr
            450                 455                 460

Asp Gly Ser Tyr His Tyr Asp Thr His Asn Phe Trp Gly Ser Met Met
465                 470                 475                 480

Ser Ile Thr Ser His Lys Ser Met Gln Ala Arg Arg Pro Glu Arg Arg
                485                 490                 495

Pro Phe Ile Ile Thr Arg Ser Ser Phe Pro Gly Leu Gly Ser Tyr Leu
                500                 505                 510

Gly Lys Trp Leu Gly Asp Asn Val Ser Glu Trp Ala Gln Tyr Arg Phe
            515                 520                 525

Ser Ile Ala Gly Ile Leu Asn Phe Asn Thr Ile Phe Gln Ile Pro Met
            530                 535                 540

Val Gly Pro Asp Ile Cys Gly Phe Ala Gly Asn Thr Thr Glu Thr Leu
545                 550                 555                 560

Cys Ala Arg Trp Thr Thr Leu Gly Ala Phe Tyr Pro Phe Met Arg Asn
                565                 570                 575

His Ala Gly Asp Thr Ser Ile Ser Gln Glu Tyr Tyr Arg Trp Pro Leu
                580                 585                 590

Thr Arg Ala Ala Ala Lys Asn Ala Ile Ala Val Arg Tyr Arg Leu Leu
                595                 600                 605

Asp Tyr Phe Tyr Thr Ala Phe His Arg Gln Ala Thr Thr Gly Leu Pro
                610                 615                 620

Ser Leu Asn Pro Leu Phe Phe His Tyr Pro Thr Asp Ala Lys Thr Phe
625                 630                 635                 640

Gly Ile Glu His Gln Phe Phe Tyr Gly Asp Ser Ile Leu Val Ser Pro
                645                 650                 655

Val Leu Glu Glu Asn Ser Thr Ser Val Ser Ile Tyr Leu Pro Lys Asp
                660                 665                 670

Val Phe Tyr Asp Tyr Trp Thr Gly Glu Arg Ile Gln Gly Asn Gly Glu
                675                 680                 685

| Asn | Ile | Asn | Leu | Thr | Asp | Val | Gly | Phe | Asp | Thr | Ile | Pro | Leu | His | Val |
| | 690 | | | | | 695 | | | | | 700 | | | | |

| Lys | Gly | Gly | Ser | Ile | Leu | Pro | Leu | Arg | Ala | Glu | Ser | Ala | Asn | Thr | Thr |
| 705 | | | | | 710 | | | | | 715 | | | | | 720 |

| Thr | Glu | Leu | Arg | Lys | Gln | Asn | Phe | Val | Leu | Trp | Ile | Ala | Pro | Asn | Ala |
| | | | | 725 | | | | | 730 | | | | | 735 | |

| Thr | Asn | Gln | Ala | Ser | Gly | Ser | Leu | Tyr | Leu | Asp | Gly | Asp | Ser | Leu |
| | | | 740 | | | | | 745 | | | | | 750 | |

| Glu | Gln | Lys | Ser | Thr | Ser | Leu | Ile | Asn | Phe | Ser | Phe | Asn | Asn | Gly | Ala |
| | | | 755 | | | | | 760 | | | | | 765 | | |

| Phe | Ser | Met | Ser | Gly | Asp | Phe | Gly | Phe | Glu | Thr | Glu | Leu | Val | Ile | Gln |
| 770 | | | | | 775 | | | | | 780 | | | | | |

| Asn | Ile | Thr | Ile | Leu | Gly | Thr | Ser | Gln | Ser | Val | Gln | Gly | Pro | Val | Ala |
| 785 | | | | | 790 | | | | | 795 | | | | | 800 |

| Leu | Thr | Lys | Gly | Trp | Glu | His | Asn | Phe | Gly | Ala | Gly | Ala | Gly | Met | Pro |
| | | | | 805 | | | | | 810 | | | | | 815 | |

| Gln | Phe | Asp | Ser | Gly | Ala | Ala | Glu | Ser | Arg | Arg | Val | Val | Ala | Ala | Val |
| | | | 820 | | | | | 825 | | | | | 830 | | |

| Trp | Gly | Leu | Val | Ala | Gly | Ala | Val | Ser | Val | Trp | Phe | Ser | Leu |
| | | | 835 | | | | | 840 | | | | | 845 |

<210> SEQ ID NO 7
<211> LENGTH: 1572
<212> TYPE: DNA
<213> ORGANISM: Cochliobolus heterostrophus ATCC 48331

<400> SEQUENCE: 7

| atgctccctc | gcgtgttcct | cctcacaggc | ttcgtccacc | atgcctacac | attatcaata | 60 |
| cctcgtcttc | cctccctcgc | cacttttgct | gcttccagcc | gtgtgcagca | acagcaaccg | 120 |
| cttcaagaca | cacttgatgc | ctggataaag | catgaagagc | gtattgcact | cgataaactg | 180 |
| ctcgccaaca | tcgcgcctgg | aggtagcaat | gtccaaggaa | aaggtgtggc | tgagggcacc | 240 |
| gtcatcgcca | gccctagtca | agacggtccg | gactactggt | tccaatgggt | ccgtgacgct | 300 |
| gctatcacca | tggataccct | cgtcaacatc | tatgccgatg | accctcgtc | ctcgcgtgcg | 360 |
| tcttctctat | ccaccatcct | agacgcatac | acctccctcc | aagtgacat | tcagcgcact | 420 |
| tcaaacccgt | ctggcacatt | tgacgacctt | ccggactag | gtgagcccaa | gttccaagtc | 480 |
| gatggcaagc | catttaccgg | ctcgtgggga | cgacctcagc | gcgatgggcc | ggcccttcgc | 540 |
| gcactgacgc | ttatgcatta | tctccgcgag | tacaatgcat | cccatccctc | actatggagc | 600 |
| tctcccaact | cggaagactt | ttttggctcg | ttctacaccg | ctgaaatgcc | ccctcgtagc | 660 |
| atcatcaaag | cagatctcga | gtatgtcagc | catttctgga | accagtcagg | gttcgatctc | 720 |
| tgggaagagg | tcgagggcct | gcacttcttc | accctcatgg | tcagcgcgag | gagtctgagg | 780 |
| gaaggcagtc | acctggcaag | agtctttgga | gacgtcggtg | cggcggattg | gtaccaaaag | 840 |
| caagctggct | acattgagaa | cctgttgggc | aaattctgga | atgcgcaaaa | aggacatctt | 900 |
| gttgagacgc | tttggagcaa | gaggagtggc | ctcgactgcg | gactgcttct | cggctctttg | 960 |
| cacgcccttc | ctaagagcgg | atctgaagat | gatgatgttg | tgtaccctcc | gtggtctgac | 1020 |
| gagattcttg | tttctctgct | tgctttgact | cgagaccagc | gcgaccgttt | ccccatcaac | 1080 |
| agcaatcctt | ctggccagga | tgacgacgat | gacgacgtag | acgagtccac | attccaggga | 1140 |
| acaggccttg | gtcgttatcc | cgaggatgta | tacgacggct | atggaaactc | gaaccgtggt | 1200 |
| ggaaacccat | ggttcctttg | cacctcttct | gccgccgaga | ttctttaccg | caccgcctcg | 1260 |

-continued

```
cacatctctg caactggcaa cttgactctt accgatgttg gccttccctt ttacgagtct    1320
ctcctcggta gctcctccct agatgtcgac gttggcacgt ttggccccac agacgccctt    1380
ttccactccg tcatcgagcg ccttcagagc accggcgacg agtttctgca agtcgtcaag    1440
acgcatgtgg atgccgaggg cagcatgagt gagcagtttg accgtgtaac tgggtacatg    1500
cgtggtgccc agcatttgac ttggagttat ggtgccttt tgcaggctgc tagagcaaga     1560
aagatttctg tg                                                        1572
```

```
<210> SEQ ID NO 8
<211> LENGTH: 524
<212> TYPE: PRT
<213> ORGANISM: Cochliobolus heterostrophus ATCC 48331
<220> FEATURE:
<221> NAME/KEY: DOMAIN
<222> LOCATION: (54)...(518)
<223> OTHER INFORMATION: Glycosyl hydrolases family 15
<220> FEATURE:
<221> NAME/KEY: SITE
<222> LOCATION: (194)...(197)
<223> OTHER INFORMATION: N-glycosylation site. Prosite id = PS00001
<220> FEATURE:
<221> NAME/KEY: SITE
<222> LOCATION: (237)...(240)
<223> OTHER INFORMATION: N-glycosylation site. Prosite id = PS00001
<220> FEATURE:
<221> NAME/KEY: SITE
<222> LOCATION: (239)...(249)
<223> OTHER INFORMATION: Glucoamylase active site region signature.
      Prosite id = PS00820
<220> FEATURE:
<221> NAME/KEY: SITE
<222> LOCATION: (433)...(436)
<223> OTHER INFORMATION: N-glycosylation site. Prosite id = PS00001

<400> SEQUENCE: 8

Met Leu Pro Arg Val Phe Leu Leu Thr Gly Phe Val His His Ala Tyr
1               5                   10                  15

Thr Leu Ser Ile Pro Arg Leu Pro Ser Leu Ala Thr Phe Ala Ala Ser
            20                  25                  30

Ser Arg Val Gln Gln Gln Gln Pro Leu Gln Asp Thr Leu Asp Ala Trp
        35                  40                  45

Ile Lys His Glu Glu Arg Ile Ala Leu Asp Lys Leu Leu Ala Asn Ile
    50                  55                  60

Ala Pro Gly Gly Ser Asn Val Gln Gly Lys Gly Val Ala Glu Gly Thr
65                  70                  75                  80

Val Ile Ala Ser Pro Ser Gln Asp Gly Pro Asp Tyr Trp Phe Gln Trp
                85                  90                  95

Val Arg Asp Ala Ala Ile Thr Met Asp Thr Leu Val Asn Ile Tyr Ala
            100                 105                 110

Asp Asp Pro Ser Ser Ser Arg Ala Ser Ser Leu Ser Thr Ile Leu Asp
        115                 120                 125

Ala Tyr Thr Ser Leu Gln Gly Asp Ile Gln Arg Thr Ser Asn Pro Ser
    130                 135                 140

Gly Thr Phe Asp Asp Leu Ser Gly Leu Gly Glu Pro Lys Phe Gln Val
145                 150                 155                 160

Asp Gly Lys Pro Phe Thr Gly Ser Trp Gly Arg Pro Gln Arg Asp Gly
                165                 170                 175

Pro Ala Leu Arg Ala Leu Thr Leu Met His Tyr Leu Arg Glu Tyr Asn
            180                 185                 190

Ala Ser His Pro Ser Leu Trp Ser Ser Pro Asn Ser Glu Asp Phe Phe
        195                 200                 205
```

Gly Ser Phe Tyr Thr Ala Glu Met Pro Pro Arg Ser Ile Ile Lys Ala
    210                 215                 220

Asp Leu Glu Tyr Val Ser His Phe Trp Asn Gln Ser Gly Phe Asp Leu
225                 230                 235                 240

Trp Glu Glu Val Glu Gly Leu His Phe Phe Thr Leu Met Val Ser Ala
                245                 250                 255

Arg Ser Leu Arg Glu Gly Ser His Leu Ala Arg Val Phe Gly Asp Val
            260                 265                 270

Gly Ala Ala Asp Trp Tyr Gln Lys Gln Ala Gly Tyr Ile Glu Asn Leu
        275                 280                 285

Leu Gly Lys Phe Trp Asn Ala Gln Lys Gly His Leu Val Glu Thr Leu
    290                 295                 300

Trp Ser Lys Arg Ser Gly Leu Asp Cys Gly Leu Leu Gly Ser Leu
305                 310                 315                 320

His Ala Leu Pro Lys Ser Gly Ser Glu Asp Asp Val Val Tyr Pro
                325                 330                 335

Pro Trp Ser Asp Glu Ile Leu Val Ser Leu Leu Ala Leu Thr Arg Asp
            340                 345                 350

Gln Arg Asp Arg Phe Pro Ile Asn Ser Asn Pro Ser Gly Gln Asp Asp
        355                 360                 365

Asp Asp Asp Val Asp Glu Ser Thr Phe Gln Gly Thr Gly Leu Gly
370                 375                 380

Arg Tyr Pro Glu Asp Val Tyr Asp Gly Tyr Gly Asn Ser Asn Arg Gly
385                 390                 395                 400

Gly Asn Pro Trp Phe Leu Cys Thr Ser Ser Ala Ala Glu Ile Leu Tyr
                405                 410                 415

Arg Thr Ala Ser His Ile Ser Ala Thr Gly Asn Leu Thr Leu Thr Asp
            420                 425                 430

Val Gly Leu Pro Phe Tyr Glu Ser Leu Leu Gly Ser Ser Ser Leu Asp
        435                 440                 445

Val Asp Val Gly Thr Phe Gly Pro Thr Asp Ala Leu Phe His Ser Val
450                 455                 460

Ile Glu Arg Leu Gln Ser Thr Gly Asp Glu Phe Leu Gln Val Val Lys
465                 470                 475                 480

Thr His Val Asp Ala Glu Gly Ser Met Ser Glu Gln Phe Asp Arg Val
                485                 490                 495

Thr Gly Tyr Met Arg Gly Ala Gln His Leu Thr Trp Ser Tyr Gly Ala
            500                 505                 510

Phe Leu Gln Ala Ala Arg Ala Arg Lys Ile Ser Val
        515                 520

<210> SEQ ID NO 9
<211> LENGTH: 1467
<212> TYPE: DNA
<213> ORGANISM: Unknown
<220> FEATURE:
<223> OTHER INFORMATION: Obtained from an environmental sample

<400> SEQUENCE: 9
atgttgacat tgaatgtttt gacggcactg ttggcacctg gtgtgctatc atctgccttg    60
cctgctcgcg atctcaatgt gcgtgccgat tcaaagcctc ctgctcttca agccatcctg   120
aataacattg cgccgatgg atctgctgtt tcgggagcat ctgccggcgt tgtggtagca   180
tccccatcta atcggatcc cgattacttt tacacctgga cgcgtgatgc agccttgaca   240
tacaaggtct tgattgatga gctcattgcc ggagacacct cgctggaatc taccatccag   300

```
gactacatct ctgctcaagc aaagctgcag gccgtgtcta acccatctgg tgacttgtcc    360
gatggatcag gtcttgcaga gcccaagtac cacgtggact tgactgcctt cacggaggcc    420
tggggtcgtc ctcagcgcga tggacccgct ctgcgagcga cagctctgat tacctatggt    480
aactatttga tttcgaagga aagacatct gtcgtcaagt cgaacatctg gcccattgtg     540
caaaatgatc tgaactatgt tgcgcaatac tggaaccaaa ccggattcga tctgtgggag    600
gaggtccagg gctcctcatt cttcaccatt gctgcacaac accgcgcatt ggtggaaggc    660
agcgcatttg ccaaggcgct gggagagtcc tgcgagggat gcgattccca ggcacctcag    720
gtcttatgct ccagcaatc tttctggaat ggcaaggctg ttgtttccaa ctttgccaac    780
aatggtcgaa ccggtcttga tgccaattct gtacttactt cgattgtaaa ctttgacccc    840
aaagctccat gcgatgacgt taccttccag ccttgctctg ctcgtgccct gtcgaaccac    900
aagctatacg ttgactcgtt ccgtaagatc tatcccgtga acagcggcaa ggaagctgga    960
actgccgttg ctgttggacg ttatgccgag gacacttaca tgggcggcaa cccatggtac   1020
ttgaccaccc tggccgcggc cgagcagttg tatgatgctc tttaccagtg aagcaactg    1080
ggatcgctgg aaatcaccga ggccagtctt cctttcttca aggatcttgt ttcgtctgcc   1140
gccgctggga agtaccctag ctcctcggaa acttacacgt ccatcactgc cgcagtcaag   1200
aaatatgccg atggatttat ggctgttgtt aaggagcaca cgcctagcga tggatctcta   1260
tccgaacaat tcactcggga caacggcagc ccggcctctg ctaaggactt gacctggtcc   1320
tacgcggcgt tgctgtctgc tactcgacgt gaggctggaa cagtgccccc tagctgggc    1380
gcgtcgactg ccaataaagt gccctcaaag tgtgagggaa gctcggccaa gggaagctac   1440
acgactccat cggtcggcaa gtggtaa                                       1467
```

<210> SEQ ID NO 10
<211> LENGTH: 488
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(22)
<220> FEATURE:
<221> NAME/KEY: DOMAIN
<222> LOCATION: (33)...(449)
<223> OTHER INFORMATION: Glycosyl hydrolases family 15
<220> FEATURE:
<221> NAME/KEY: SITE
<222> LOCATION: (194)...(197)
<223> OTHER INFORMATION: N-glycosylation site. Prosite id = PS00001

<400> SEQUENCE: 10

Met Leu Thr Leu Asn Val Leu Thr Ala Leu Leu Ala Pro Gly Val Leu
1               5                   10                  15

Ser Ser Ala Leu Pro Ala Arg Asp Leu Asn Val Arg Ala Asp Ser Lys
            20                  25                  30

Pro Pro Ala Leu Gln Ala Ile Leu Asn Asn Ile Gly Ala Asp Gly Ser
        35                  40                  45

Ala Val Ser Gly Ala Ser Ala Gly Val Val Ala Ser Pro Ser Lys
    50                  55                  60

Ser Asp Pro Asp Tyr Phe Tyr Thr Trp Thr Arg Asp Ala Ala Leu Thr
65                  70                  75                  80

Tyr Lys Val Leu Ile Asp Glu Leu Ile Ala Gly Asp Thr Ser Leu Glu
                85                  90                  95

```
Ser Thr Ile Gln Asp Tyr Ile Ser Ala Gln Ala Lys Leu Gln Ala Val
            100                 105                 110

Ser Asn Pro Ser Gly Asp Leu Ser Asp Gly Ser Gly Leu Ala Glu Pro
        115                 120                 125

Lys Tyr His Val Asp Leu Thr Ala Phe Thr Glu Ala Trp Gly Arg Pro
    130                 135                 140

Gln Arg Asp Gly Pro Ala Leu Arg Ala Thr Ala Leu Ile Thr Tyr Gly
145                 150                 155                 160

Asn Tyr Leu Ile Ser Lys Glu Lys Thr Ser Val Val Lys Ser Asn Ile
                165                 170                 175

Trp Pro Ile Val Gln Asn Asp Leu Asn Tyr Val Ala Gln Tyr Trp Asn
            180                 185                 190

Gln Thr Gly Phe Asp Leu Trp Glu Glu Val Gln Gly Ser Ser Phe Phe
        195                 200                 205

Thr Ile Ala Ala Gln His Arg Ala Leu Val Glu Gly Ser Ala Phe Ala
    210                 215                 220

Lys Ala Leu Gly Glu Ser Cys Glu Gly Cys Asp Ser Gln Ala Pro Gln
225                 230                 235                 240

Val Leu Cys Phe Gln Gln Ser Phe Trp Asn Gly Lys Ala Val Val Ser
                245                 250                 255

Asn Phe Ala Asn Asn Gly Arg Thr Gly Leu Asp Ala Asn Ser Val Leu
            260                 265                 270

Thr Ser Ile Val Asn Phe Asp Pro Lys Ala Pro Cys Asp Asp Val Thr
        275                 280                 285

Phe Gln Pro Cys Ser Ala Arg Ala Leu Ser Asn His Lys Leu Tyr Val
    290                 295                 300

Asp Ser Phe Arg Lys Ile Tyr Pro Val Asn Ser Gly Lys Glu Ala Gly
305                 310                 315                 320

Thr Ala Val Ala Val Gly Arg Tyr Ala Glu Asp Thr Tyr Met Gly Gly
                325                 330                 335

Asn Pro Trp Tyr Leu Thr Thr Leu Ala Ala Ala Glu Gln Leu Tyr Asp
            340                 345                 350

Ala Leu Tyr Gln Trp Lys Gln Leu Gly Ser Leu Glu Ile Thr Glu Ala
        355                 360                 365

Ser Leu Pro Phe Phe Lys Asp Leu Val Ser Ser Ala Ala Gly Lys
    370                 375                 380

Tyr Pro Ser Ser Ser Glu Thr Tyr Thr Ser Ile Thr Ala Ala Val Lys
385                 390                 395                 400

Lys Tyr Ala Asp Gly Phe Met Ala Val Val Lys Glu His Thr Pro Ser
                405                 410                 415

Asp Gly Ser Leu Ser Glu Gln Phe Thr Arg Asp Asn Gly Ser Pro Ala
            420                 425                 430

Ser Ala Lys Asp Leu Thr Trp Ser Tyr Ala Ala Leu Leu Ser Ala Thr
        435                 440                 445

Arg Arg Glu Ala Gly Thr Val Pro Pro Ser Trp Gly Ala Ser Thr Ala
    450                 455                 460

Asn Lys Val Pro Ser Lys Cys Glu Gly Ser Ser Ala Lys Gly Ser Tyr
465                 470                 475                 480

Thr Thr Pro Ser Val Gly Lys Trp
                485

<210> SEQ ID NO 11
<211> LENGTH: 1746
<212> TYPE: DNA
<213> ORGANISM: Unknown
```

<220> FEATURE:
<223> OTHER INFORMATION: Obtained from an environmental sample

<400> SEQUENCE: 11

```
atgtttaatc aagttctcta tggcttggct gccactgcac tatggcaggg ccaagtcgtc     60
gcttcaccaa gcaaagacaa ctccctcgag aagttcatca ccaagcaagc cgatatttcc    120
atcaaaggtg tcctcgccaa tatcggctct gatggtaaac gtgcacaagg tgcagcgcct    180
ggtgccgtcg tcgcaagccc atcacgagaa gaccctgact attggtacac ttggacgcgt    240
gactcagcct tgacttataa ggtcctcgtc gagcgtctca tccacggcga aaagtctctc    300
cagcggaaga tagacgaata cgtctccgct caagccaaac ttcagaaaac cacaaaccca    360
tccggtagtc cagagtccgg tggtctcggc gagccaaagt tccacgtgaa cctcactgcc    420
ttcaccggat cttggggccg cccacagcgc gatggtcctc ctctgcgtgc tacagccttg    480
accctatacg cagagtggct catctcccac ggagacaagt ccaaggctgt gaacaaagtg    540
tggccagtga ttgagaagga tcttgcgtat actaccaagt tctggaatcg cactgggtat    600
gatctctggg aagaagtcaa tggatcttct ttctttacgc tatcggcttc gcatcgggct    660
ctcattgagg gagcggcttt ggcgaagaag ttgggcaagt cttgccctga ctgtgctgcc    720
aatgcccctc gtgtcctttg cttcatgcag agcttttgga ctggtggtta cattgactcg    780
aacatcaatg tgaaggatgg tcgcaagggc ttggatgcta actccattct gtcatcgatc    840
cacacatttg atcccaactc caaatgcacc gactcgacat tccagccttg ctcctcacga    900
gcgctcgcca accacaaggc ggtggtcgac tctttcaggt ccatctacat tgtcaacaag    960
aacagaggca aggtaaagc cgcagctgtt ggcagataca gtgaggatgt gtactacaac   1020
ggcaaccctt ggtacttgac taccctcgcc gctgctgagc aattgtacgc cgcgctgtac   1080
caatggaaca aggttggggc tgtctcaatt gacgacgttt cttaccttt cttccgggac   1140
cttgtgccta agggatccaa gggcacgtat aagaagaaca gcaagacgta caaggagatc   1200
gtcaaggctg tcaaggccta cgctgacggg tttgtcgctg ttgttcaaac ctacacaccc   1260
aaagatggtt cgctagccga gcagttcgac cgagccactg gtactcccaa atcgcggtc   1320
catctcactt ggtcttacgc ctccttcgtc agcgcgaccg aacgtcgctc cagcatcgtc   1380
tctccctctt ggggcgagag cagcgccaat aaggttcctg cagtatgcga agcagccccg   1440
gcttgtgaca cgacgataac cttcaacgtg aagaatgtgg aagtgtcttc tgaccagaag   1500
gtttacgtcg ttggctccgt gactgaactt ccaactggt cacctgatga gggcatacca   1560
ctcacggagg gtaccaaggg gttgtggagt gccaaggtta agattccttc tgatacaagc   1620
tttgagtata agtacatcaa gaagacaagt ggcggagatg ttacgtggtt gagcgacccg   1680
aacaatcggg ctgttacggg cagtaagtgt ggaagcgcga gtactcttga taatgagtgg   1740
aggtag                                                              1746
```

<210> SEQ ID NO 12
<211> LENGTH: 581
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (38)...(454)
<223> OTHER INFORMATION: Glycosyl hydrolases family 15
<220> FEATURE:

```
<221> NAME/KEY: DOMAIN
<222> LOCATION: (483)...(576)
<223> OTHER INFORMATION: Starch binding domain
<220> FEATURE:
<221> NAME/KEY: SITE
<222> LOCATION: (139)...(142)
<223> OTHER INFORMATION: N-glycosylation site. Prosite id = PS00001
<220> FEATURE:
<221> NAME/KEY: SITE
<222> LOCATION: (199)...(202)
<223> OTHER INFORMATION: N-glycosylation site. Prosite id = PS00001
<220> FEATURE:
<221> NAME/KEY: SITE
<222> LOCATION: (201)...(211)
<223> OTHER INFORMATION: Glucoamylase active site region signature.
      Prosite id = PS00820
<220> FEATURE:
<221> NAME/KEY: SITE
<222> LOCATION: (210)...(213)
<223> OTHER INFORMATION: N-glycosylation site. Prosite id = PS00001

<400> SEQUENCE: 12

Met Phe Asn Gln Val Leu Tyr Gly Leu Ala Ala Thr Ala Leu Trp Gln
1               5                   10                  15

Gly Gln Val Val Ala Ser Pro Ser Lys Asp Asn Ser Leu Glu Lys Phe
            20                  25                  30

Ile Thr Lys Gln Ala Asp Ile Ser Ile Lys Gly Val Leu Ala Asn Ile
        35                  40                  45

Gly Ser Asp Gly Lys Arg Ala Gln Gly Ala Ala Pro Gly Ala Val Val
    50                  55                  60

Ala Ser Pro Ser Arg Glu Asp Pro Asp Tyr Trp Tyr Thr Trp Thr Arg
65                  70                  75                  80

Asp Ser Ala Leu Thr Tyr Lys Val Leu Val Glu Arg Leu Ile His Gly
                85                  90                  95

Glu Lys Ser Leu Gln Arg Lys Ile Asp Glu Tyr Val Ser Ala Gln Ala
            100                 105                 110

Lys Leu Gln Lys Thr Thr Asn Pro Ser Gly Ser Pro Leu Ser Gly Gly
        115                 120                 125

Leu Gly Glu Pro Lys Phe His Val Asn Leu Thr Ala Phe Thr Gly Ser
    130                 135                 140

Trp Gly Arg Pro Gln Arg Asp Gly Pro Pro Leu Arg Ala Thr Ala Leu
145                 150                 155                 160

Thr Leu Tyr Ala Glu Trp Leu Ile Ser His Gly Asp Lys Ser Lys Ala
                165                 170                 175

Val Asn Lys Val Trp Pro Val Ile Glu Lys Asp Leu Ala Tyr Thr Thr
            180                 185                 190

Lys Phe Trp Asn Arg Thr Gly Tyr Asp Leu Trp Glu Glu Val Asn Gly
        195                 200                 205

Ser Ser Phe Phe Thr Leu Ser Ala Ser His Arg Ala Leu Ile Glu Gly
    210                 215                 220

Ala Ala Leu Ala Lys Lys Leu Gly Lys Ser Cys Pro Asp Cys Ala Ala
225                 230                 235                 240

Asn Ala Pro Arg Val Leu Cys Phe Met Gln Ser Phe Trp Thr Gly Gly
                245                 250                 255

Tyr Ile Asp Ser Asn Ile Asn Val Lys Asp Gly Arg Lys Gly Leu Asp
            260                 265                 270

Ala Asn Ser Ile Leu Ser Ser Ile His Thr Phe Asp Pro Asn Ser Lys
        275                 280                 285

Cys Thr Asp Ser Thr Phe Gln Pro Cys Ser Ser Arg Ala Leu Ala Asn
    290                 295                 300
```

-continued

```
His Lys Ala Val Val Asp Ser Phe Arg Ser Ile Tyr Ile Val Asn Lys
305                 310                 315                 320

Asn Arg Gly Lys Gly Lys Ala Ala Ala Val Gly Arg Tyr Ser Glu Asp
            325                 330                 335

Val Tyr Tyr Asn Gly Asn Pro Trp Tyr Leu Thr Thr Leu Ala Ala Ala
        340                 345                 350

Glu Gln Leu Tyr Ala Ala Leu Tyr Gln Trp Asn Lys Val Gly Ala Val
    355                 360                 365

Ser Ile Asp Asp Val Ser Leu Pro Phe Phe Arg Asp Leu Val Pro Lys
370                 375                 380

Gly Ser Lys Gly Thr Tyr Lys Lys Asn Ser Lys Thr Tyr Lys Glu Ile
385                 390                 395                 400

Val Lys Ala Val Lys Ala Tyr Ala Asp Gly Phe Val Ala Val Val Gln
            405                 410                 415

Thr Tyr Thr Pro Lys Asp Gly Ser Leu Ala Glu Gln Phe Asp Arg Ala
        420                 425                 430

Thr Gly Thr Pro Lys Ser Ala Val His Leu Thr Trp Ser Tyr Ala Ser
    435                 440                 445

Phe Val Ser Ala Thr Glu Arg Arg Ser Ser Ile Val Ser Pro Ser Trp
450                 455                 460

Gly Glu Ser Ser Ala Asn Lys Val Pro Ala Val Cys Glu Ala Ala Pro
465                 470                 475                 480

Ala Cys Asp Thr Thr Ile Thr Phe Asn Val Lys Asn Val Glu Val Ser
            485                 490                 495

Ser Asp Gln Lys Val Tyr Val Val Gly Ser Val Thr Glu Leu Ser Asn
        500                 505                 510

Trp Ser Pro Asp Glu Gly Ile Pro Leu Thr Glu Gly Thr Lys Gly Leu
    515                 520                 525

Trp Ser Ala Lys Val Lys Ile Pro Ser Asp Thr Ser Phe Glu Tyr Lys
530                 535                 540

Tyr Ile Lys Lys Thr Ser Gly Gly Asp Val Thr Trp Leu Ser Asp Pro
545                 550                 555                 560

Asn Asn Arg Ala Val Thr Gly Ser Lys Cys Gly Ser Ala Ser Thr Leu
            565                 570                 575

Asp Asn Glu Trp Arg
            580
```

<210> SEQ ID NO 13
<211> LENGTH: 1749
<212> TYPE: DNA
<213> ORGANISM: Fusarium verticillioides GZ3639

<400> SEQUENCE: 13

```
atgtttactc agatcttgta tggcctcacg gccttatctg ccctccaagg tcaggtcact    60
gcatcaccag gcggttccag ccttgatcgc ttcatttcca agaggccga catctccatc    120
aagggcgtgc ttgccaatat tggcgccgat ggcaagcgag cccaaggcgc tgcacctggc    180
gccgttgtag caagtccatc gagaacagat ccagactact ggtacacatg acccgagac    240
tccgccttga catacaaagt ccttgttgag cgcttcattc acggagacaa gtctctccag    300
cgcaagatcg acgaatatgt ctctgcccaa gccaagctcc agggcgtcac caacccatct    360
ggcggccccg agtcaggcgg ccttggggaa cccaagtttc acgtcaacct cacagctttc    420
acaggatcct gggtcgtcc tcaacgagat ggcctcctc tgagagctac tgcattgacg    480
ctgtacgcca actggcttgt ttctcacggc gaccgctcca aggccgtcaa caaggtttgg    540
```

-continued

```
cctgtcattg agaaggatct tgcatacacc gtcaagttct ggaacagaac cggttacgat    600
ctttgggagg aggttaacgg atcttcgttc ttcaccctct ctgcttcaca tcgtgctctg    660
gttgagggag ctgctcttgc taagaagctt ggcaagtctt gctccgactg cgcaaccaac    720 gcccccgtg ttctctgctt catgcaaagc ttctggaccg gcagctacat cgactcgaac     780
atcaatgtca acgatggccg caagggtctt gatgccaact ccattctgtc ttctattcac    840
acctttgatc cttcttcgaa gtgcacagac tctaccttcc agccttgttc ttcaagggct    900
cttgcgaacc acaaggaagt agtggactct ttccgctcca tctatggtgt caacaaaaac   960
agaggtaaag gtaaagctgc tgctgtcggt cgatacagtg aggatgtgta ctacgacggt    1020
aacccttggt acttggctac tcttgctgct gccgagcaac tgtacgctgc tgtctatcaa    1080
tggaacaaga tcggttccat cacagttgat agtgtgtcgc tcccctttttt cagtgacctt    1140 gtaccaaagg tttccaaggg aacctatcgc aagaacagca agacatacaa ggctattatc    1200
aaggctgtca cttcatacgc tgatggcttt gtcgccgttg tgcagaccta tactcccaaa   1260
gatggctccc tcgcagagca gttcgataag tctactggaa ctcccaagtc agctgttcac    1320
ctaacctggt cctacgcctc ctttgtcggt gctgccgagc gtcgtactgg cgtcgttcct    1380
ccagcttggg gcgagagcaa cgccaacaag gtgcctgctg tttgcgaagc agctccagcc    1440
tgcgacacca ccatcacgtt caatgtgaag aacgttgatg tcacgtcgga ccagaaggtt    1500
tacattgttg gcgggatcac tcaactttcc aactgggccc ctgctgacgg cattgcgctt    1560
gaggaatcca cgagccaccaa gggcttgtgg actgtgaagg tcaagattcc atctgatacc    1620
agctttgagt ataagtatat aaagaagacg agtgatggaa ctgttacatg ggagagtgac    1680
cccaataaca gtgcggcgac gggcagcaag tgcggaagca gcagtaccat caacgatgag    1740
tggaggtag                                                            1749
```

```
<210> SEQ ID NO 14
<211> LENGTH: 582
<212> TYPE: PRT
<213> ORGANISM: Fusarium verticillioides GZ3639
<220> FEATURE:
<221> NAME/KEY: SIGNAL
<222> LOCATION: (1)...(21)
<220> FEATURE:
<221> NAME/KEY: DOMAIN
<222> LOCATION: (37)...(453)
<223> OTHER INFORMATION: Glycosyl hydrolases family 15
<220> FEATURE:
<221> NAME/KEY: DOMAIN
<222> LOCATION: (482)...(577)
<223> OTHER INFORMATION: Starch binding domain
<220> FEATURE:
<221> NAME/KEY: SITE
<222> LOCATION: (138)...(141)
<223> OTHER INFORMATION: N-glycosylation site. Prosite id = PS00001
<220> FEATURE:
<221> NAME/KEY: SITE
<222> LOCATION: (200)...(210)
<223> OTHER INFORMATION: Glucoamylase active site region signature.
      Prosite id = PS00820
<220> FEATURE:
<221> NAME/KEY: SITE
<222> LOCATION: (209)...(212)
<223> OTHER INFORMATION: N-glycosylation site. Prosite id = PS00001
<220> FEATURE:
<221> NAME/KEY: SITE
<222> LOCATION: (570)...(573)
<223> OTHER INFORMATION: N-glycosylation site. Prosite id = PS00001

<400> SEQUENCE: 14

Met Phe Thr Gln Ile Leu Tyr Gly Leu Thr Ala Leu Ser Ala Leu Gln
1               5                   10                  15
```

Gly Gln Val Thr Ala Ser Pro Gly Gly Ser Ser Leu Asp Arg Phe Ile
            20                  25                  30

Ser Lys Glu Ala Asp Ile Ser Ile Lys Gly Val Leu Ala Asn Ile Gly
        35                  40                  45

Ala Asp Gly Lys Arg Ala Gln Gly Ala Ala Pro Gly Ala Val Val Ala
50                  55                  60

Ser Pro Ser Arg Thr Asp Pro Asp Tyr Trp Tyr Thr Trp Thr Arg Asp
65                  70                  75                  80

Ser Ala Leu Thr Tyr Lys Val Leu Val Glu Arg Phe Ile His Gly Asp
                85                  90                  95

Lys Ser Leu Gln Arg Lys Ile Asp Glu Tyr Val Ser Ala Gln Ala Lys
            100                 105                 110

Leu Gln Gly Val Thr Asn Pro Ser Gly Gly Pro Glu Ser Gly Gly Leu
            115                 120                 125

Gly Glu Pro Lys Phe His Val Asn Leu Thr Ala Phe Thr Gly Ser Trp
130                 135                 140

Gly Arg Pro Gln Arg Asp Gly Pro Pro Leu Arg Ala Thr Ala Leu Thr
145                 150                 155                 160

Leu Tyr Ala Asn Trp Leu Val Ser His Gly Asp Arg Ser Lys Ala Val
                165                 170                 175

Asn Lys Val Trp Pro Val Ile Glu Lys Asp Leu Ala Tyr Thr Val Lys
            180                 185                 190

Phe Trp Asn Arg Thr Gly Tyr Asp Leu Trp Glu Glu Val Asn Gly Ser
        195                 200                 205

Ser Phe Phe Thr Leu Ser Ala Ser His Arg Ala Leu Val Glu Gly Ala
        210                 215                 220

Ala Leu Ala Lys Lys Leu Gly Lys Ser Cys Ser Asp Cys Ala Thr Asn
225                 230                 235                 240

Ala Pro Arg Val Leu Cys Phe Met Gln Ser Phe Trp Thr Gly Ser Tyr
                245                 250                 255

Ile Asp Ser Asn Ile Asn Val Asn Asp Gly Arg Lys Gly Leu Asp Ala
            260                 265                 270

Asn Ser Ile Leu Ser Ser Ile His Thr Phe Asp Pro Ser Ser Lys Cys
        275                 280                 285

Thr Asp Ser Thr Phe Gln Pro Cys Ser Ser Arg Ala Leu Ala Asn His
        290                 295                 300

Lys Glu Val Val Asp Ser Phe Arg Ser Ile Tyr Gly Val Asn Lys Asn
305                 310                 315                 320

Arg Gly Lys Gly Lys Ala Ala Ala Val Gly Arg Tyr Ser Glu Asp Val
                325                 330                 335

Tyr Tyr Asp Gly Asn Pro Trp Tyr Leu Ala Thr Leu Ala Ala Ala Glu
            340                 345                 350

Gln Leu Tyr Ala Ala Val Tyr Gln Trp Asn Lys Ile Gly Ser Ile Thr
        355                 360                 365

Val Asp Ser Val Ser Leu Pro Phe Phe Ser Asp Leu Val Pro Lys Val
        370                 375                 380

Ser Lys Gly Thr Tyr Arg Lys Asn Ser Lys Thr Tyr Lys Ala Ile Ile
385                 390                 395                 400

Lys Ala Val Thr Ser Tyr Ala Asp Gly Phe Val Ala Val Gln Thr
                405                 410                 415

Tyr Thr Pro Lys Asp Gly Ser Leu Ala Glu Gln Phe Asp Lys Ser Thr
            420                 425                 430

Gly Thr Pro Lys Ser Ala Val His Leu Thr Trp Ser Tyr Ala Ser Phe

```
                435            440             445
Val Gly Ala Ala Glu Arg Arg Thr Gly Val Val Pro Pro Ala Trp Gly
            450                 455                 460

Glu Ser Asn Ala Asn Lys Val Pro Ala Val Cys Glu Ala Ala Pro Ala
465                 470                 475                 480

Cys Asp Thr Thr Ile Thr Phe Asn Val Lys Asn Val Asp Val Thr Ser
                485                 490                 495

Asp Gln Lys Val Tyr Ile Val Gly Gly Ile Thr Gln Leu Ser Asn Trp
                500                 505                 510

Ala Pro Ala Asp Gly Ile Ala Leu Glu Glu Ser Thr Ser Thr Lys Gly
            515                 520                 525

Leu Trp Thr Val Lys Val Lys Ile Pro Ser Asp Thr Ser Phe Glu Tyr
            530                 535                 540

Lys Tyr Ile Lys Lys Thr Ser Asp Gly Thr Val Thr Trp Glu Ser Asp
545                 550                 555                 560

Pro Asn Asn Ser Ala Ala Thr Gly Ser Lys Cys Gly Ser Ser Ser Thr
                565                 570                 575

Ile Asn Asp Glu Trp Arg
            580

<210> SEQ ID NO 15
<211> LENGTH: 1188
<212> TYPE: DNA
<213> ORGANISM: Cochliobolus heterostrophus ATCC 48332

<400> SEQUENCE: 15
atgttgtcca agatcttgct acccgttgtt gcacttgcag ccagtgccaa tgcgcatggc      60
tacctcactt cacccatgag ccgaacaggg ctgaatgcac agtctggggc tgatacgtgc     120
cccgaatgca caattctgga ccggtaaca gcatggcctg atcttgacgc cgcagctgtc      180
ggccgctcgg gtccttgcgg gtacaatgct cgtgtgtcag ttgactacaa ccagcccggg     240
cctcgctggg gttctgagcc cgtcattacc tacaaggctg gggatgtcgt cgatgtacag     300
tggtgtgtag atgccaacgg tgaccatggt ggcatgttca cctaccgcat ctgccaaaac     360
caagctcttg tcgacaagct cttgacccct ggatacctcc ctactgaagc agagaagcaa     420
gcagcagagg attgcttcca agctggagag ttgaagtgca cagatgtccc tggacagaca     480
tgcggattca actctgactg ccagcaaggc caagcctgct ggaggaatga ctggttcaca     540
tgcggtggct tcaacgacaa cctgaaatgc aggagcgtcg acaacgcccc cctaaattca     600
tgctacacca gcatcgcagg cggctacacc gtcagctcaa agatcaaaat cccaaactac     660
accagcaacc acaccctcct ctccttcaaa tggaactctt ccaaaccccc gcaggtctac     720
ctcacctgcg ccgacatcaa aatcaccggc agcagctccg gcacctcccc accccaact      780 tcgagcaaac cccctacgtc ctcctccaag cccacttcca cctccacctc cacctccgca     840
ccctccgcaa cccccaccgc ctgcgccacc cccgtctcca ccgtcgccgt aaccttcaac     900
tccaaaacca ccacctcctt tggccaaacc gtcaaactcg caggttccat ctcccagctc     960
ggcagctgga cactgccaa tgcgcctgcc ctgtccgccg cccagtacac ctcgtccaac    1020
ccgctctgga caaccaccct caacctacct gcaggcacca gcttcgagta caagtacatc    1080
aaagttgaca gtagtggcgc cgtcacgtac gagagtgggg ccaatagaca gtacactgtg    1140
cctaacgggt gcgctaacac tgtcactgta gaagggactt ggaaataa             1188

<210> SEQ ID NO 16
<211> LENGTH: 395
```

```
<212> TYPE: PRT
<213> ORGANISM: Cochliobolus heterostrophus ATCC 48332
<220> FEATURE:
<221> NAME/KEY: SIGNAL
<222> LOCATION: (1)...(20)
<220> FEATURE:
<221> NAME/KEY: DOMAIN
<222> LOCATION: (294)...(390)
<223> OTHER INFORMATION: Starch binding domain
<220> FEATURE:
<221> NAME/KEY: SITE
<222> LOCATION: (222)...(225)
<223> OTHER INFORMATION: N-glycosylation site. Prosite id = PS00001
<220> FEATURE:
<221> NAME/KEY: SITE
<222> LOCATION: (226)...(229)
<223> OTHER INFORMATION: N-glycosylation site. Prosite id = PS00001

<400> SEQUENCE: 16

Met Leu Ser Lys Ile Leu Leu Pro Val Val Ala Leu Ala Ala Ser Ala
1               5                   10                  15

Asn Ala His Gly Tyr Leu Thr Ser Pro Met Ser Arg Thr Gly Leu Asn
            20                  25                  30

Ala Gln Ser Gly Ala Asp Thr Cys Pro Glu Cys Thr Ile Leu Glu Pro
        35                  40                  45

Val Thr Ala Trp Pro Asp Leu Asp Ala Ala Val Gly Arg Ser Gly
    50                  55                  60

Pro Cys Gly Tyr Asn Ala Arg Val Ser Val Asp Tyr Asn Gln Pro Gly
65                  70                  75                  80

Pro Arg Trp Gly Ser Glu Pro Val Ile Thr Tyr Lys Ala Gly Asp Val
                85                  90                  95

Val Asp Val Gln Trp Cys Val Asp Ala Asn Gly Asp His Gly Gly Met
            100                 105                 110

Phe Thr Tyr Arg Ile Cys Gln Asn Gln Ala Leu Val Asp Lys Leu Leu
        115                 120                 125

Thr Pro Gly Tyr Leu Pro Thr Glu Ala Glu Lys Gln Ala Ala Glu Asp
    130                 135                 140

Cys Phe Gln Ala Gly Glu Leu Lys Cys Thr Asp Val Pro Gly Gln Thr
145                 150                 155                 160

Cys Gly Phe Asn Ser Asp Cys Gln Gln Gly Gln Ala Cys Trp Arg Asn
                165                 170                 175

Asp Trp Phe Thr Cys Gly Gly Phe Asn Asp Asn Leu Lys Cys Arg Ser
            180                 185                 190

Val Asp Asn Ala Pro Leu Asn Ser Cys Tyr Thr Ser Ile Ala Gly Gly
        195                 200                 205

Tyr Thr Val Ser Ser Lys Ile Lys Ile Pro Asn Tyr Thr Ser Asn His
    210                 215                 220

Thr Leu Leu Ser Phe Lys Trp Asn Ser Phe Gln Thr Pro Gln Val Tyr
225                 230                 235                 240

Leu Thr Cys Ala Asp Ile Lys Ile Thr Gly Ser Ser Ser Gly Thr Ser
                245                 250                 255

Pro Pro Pro Thr Ser Ser Lys Pro Pro Thr Ser Ser Lys Pro Thr
            260                 265                 270

Ser Thr Ser Thr Ser Thr Ser Ala Pro Ser Ala Thr Pro Thr Ala Cys
        275                 280                 285

Ala Thr Pro Val Ser Thr Val Ala Val Thr Phe Asn Ser Lys Thr Thr
    290                 295                 300

Thr Ser Phe Gly Gln Thr Val Lys Leu Ala Gly Ser Ile Ser Gln Leu
305                 310                 315                 320
```

```
Gly Ser Trp Asn Thr Ala Asn Ala Pro Ala Leu Ser Ala Ala Gln Tyr
            325                 330                 335

Thr Ser Ser Asn Pro Leu Trp Thr Thr Thr Leu Asn Leu Pro Ala Gly
            340                 345                 350

Thr Ser Phe Glu Tyr Lys Tyr Ile Lys Val Asp Ser Ser Gly Ala Val
        355                 360                 365

Thr Tyr Glu Ser Gly Ala Asn Arg Gln Tyr Thr Val Pro Asn Gly Cys
    370                 375                 380

Ala Asn Thr Val Thr Val Glu Gly Thr Trp Lys
385                 390                 395

<210> SEQ ID NO 17
<211> LENGTH: 1938
<212> TYPE: DNA
<213> ORGANISM: Fusarium verticillioides GZ3639

<400> SEQUENCE: 17
atgtactttg tgtcttctgc ctttcttctc ggctcattcg ttcttcagaa cgtcttgggc      60
cgaccaacct tcgatgagag gagtctctta caagagagac agtcttcggt cgactccttt    120
atcaagtctg agagctcaat tgctattgag caactcctct gcaatatcgg ttccgatggc    180
tgcaactcca agaacgtagc cactggtatt gtcattgctt ctccagacac acaggatcct    240
gactactttt acacctggac tcgagatgct gctctagtct tcaagtacgt cgttgatagg    300
ttcatcaacc agtatgatgc tggcttgcag aggaagatcc aggagtacat cgcctcccaa    360
gccaagctcc agggtgtttc caacccttct gggtcgcttt cggatggctc aggtctggga    420
gaggccaagt tcaacgtcga catgagtgcc ttcactggtg gttggggtcg acctcagcga    480
gatggtccag ctctgcgtgc gactgctatg atcacctatg ccaactggct gattgccaac    540
ggctacacct ccacagccaa tgacattgtg tggcctgttg ttcgcaacga ccttaactat    600
gtggctcagt attggaatca aaccggattt gacttgtggg aggaggtcaa gggtagttcg    660
ttcttcacaa ctggttccca gtatcgagct ctcattgaag gcgccgctct ggccaagaag    720
ctcggcaagt cgggagacaa ctactccaac atcgctcctc aggctctctg cttcttgcag    780
acttactgga tctcttctgg caaatacgtc gactctaaca tcaatgtcaa tgacggccgc    840
actggcaagg acgccaacag tatcctgtcg tccatacaca tttcgaccc tgctctgaac    900 tgtgatcccg ccaccttcca gccatgcagt gacaaggccc tcgccaacca aaggcggtt    960 actgactctt ccgctcatg gaacatcaac aagggtatct ctcaaggctc agctgtcgcc   1020
gttggacgat acgtcgaaga tgtctactac aatggcaacc cctggtacct cgctacgctt   1080
gccgcggcag agcagctcta cgatgccatt tatgtctgga agcagcaggg atccatcact   1140
gtgtcggacg tctctctttc gttcttcaag gacctcgtct ctttggtctc taccggaaca   1200
tacgccagtg actctgccac cttcaagagc atcactgacg ccgtctccaa gtatgctgat   1260
gggtatgttg ccatcgttgc aaagtatgtc ggcacagatg gccacctcgc agagcagttt   1320
gacaagaacg acggccatcc tctttctgcc acagacttga cttggtcata tgccgcattc   1380
ctctcagctg ctgatcgtcg agctggtgtt attcctccct cttgggctgg aagcgtggct   1440
gctgtcccca accaatgcgg taccaatact gttgctggat cctactcatc ggctactgca   1500
acttcgttcc cagcatcgca aacacccaag ggtggtgtgc ccactccaac tggcgcccag   1560
acttccactt ccacttccac ttccacttcc agctcgtcca ctggtaccag ttgccctact   1620
gcaacctctg tggctgtcac tttccaagaa gttgtcacca ccaactttgg tgataccatc   1680
aagatcgttg gcaacatcgc tgctctcggt aactgggaca catcaaaggc tgttgccctg   1740
```

```
agcgcctccg actataccgc ctcgaaccct gtgtggaagg ccaccatttc cctaactgca    1800
ggacagtcca tccagtataa gtacatcaat gttaagaagg acggctctct tacctgggag    1860
aaggacccca accgcaccta cgctgttcct aagacatgtg ccacaacggc taccaagtct    1920
gacaagtggc agtcttga                                                  1938
```

<210> SEQ ID NO 18
<211> LENGTH: 645
<212> TYPE: PRT
<213> ORGANISM: Fusarium verticillioides GZ3639
<220> FEATURE:
<221> NAME/KEY: DOMAIN
<222> LOCATION: (46)...(465)
<223> OTHER INFORMATION: Glycosyl hydrolases family 15
<220> FEATURE:
<221> NAME/KEY: DOMAIN
<222> LOCATION: (543)...(639)
<223> OTHER INFORMATION: Starch binding domain
<220> FEATURE:
<221> NAME/KEY: SITE
<222> LOCATION: (209)...(212)
<223> OTHER INFORMATION: N-glycosylation site. Prosite id = PS00001
<220> FEATURE:
<221> NAME/KEY: SITE
<222> LOCATION: (211)...(221)
<223> OTHER INFORMATION: Glucoamylase active site region signature.
    Prosite id = PS00820
<220> FEATURE:
<221> NAME/KEY: SITE
<222> LOCATION: (250)...(253)
<223> OTHER INFORMATION: N-glycosylation site. Prosite id = PS00001
<220> FEATURE:
<221> NAME/KEY: SITE
<222> LOCATION: (633)...(636)
<223> OTHER INFORMATION: N-glycosylation site. Prosite id = PS00001

<400> SEQUENCE: 18

```
Met Tyr Phe Val Ser Ser Ala Phe Leu Leu Gly Ser Phe Val Leu Gln
1               5                   10                  15

Asn Val Leu Gly Arg Pro Thr Phe Asp Glu Arg Ser Leu Leu Gln Glu
            20                  25                  30

Arg Gln Ser Ser Val Asp Ser Phe Ile Lys Ser Glu Ser Ser Ile Ala
        35                  40                  45

Ile Glu Gln Leu Leu Cys Asn Ile Gly Ser Asp Gly Cys Asn Ser Lys
    50                  55                  60

Asn Val Ala Thr Gly Ile Val Ile Ala Ser Pro Asp Thr Gln Asp Pro
65                  70                  75                  80

Asp Tyr Phe Tyr Thr Trp Thr Arg Asp Ala Ala Leu Val Phe Lys Tyr
                85                  90                  95

Val Val Asp Arg Phe Ile Asn Gln Tyr Asp Ala Gly Leu Gln Arg Lys
            100                 105                 110

Ile Gln Glu Tyr Ile Ala Ser Gln Ala Lys Leu Gln Gly Val Ser Asn
        115                 120                 125

Pro Ser Gly Ser Leu Ser Asp Gly Ser Gly Leu Gly Glu Ala Lys Phe
    130                 135                 140

Asn Val Asp Met Ser Ala Phe Thr Gly Gly Trp Gly Arg Pro Gln Arg
145                 150                 155                 160

Asp Gly Pro Ala Leu Arg Ala Thr Ala Met Ile Thr Tyr Ala Asn Trp
                165                 170                 175

Leu Ile Ala Asn Gly Tyr Thr Ser Thr Ala Asn Asp Ile Val Trp Pro
            180                 185                 190

Val Val Arg Asn Asp Leu Asn Tyr Val Ala Gln Tyr Trp Asn Gln Thr
        195                 200                 205
```

```
Gly Phe Asp Leu Trp Glu Glu Val Lys Gly Ser Ser Phe Thr Thr
    210                 215                 220

Gly Ser Gln Tyr Arg Ala Leu Ile Glu Gly Ala Ala Leu Ala Lys Lys
225                 230                 235                 240

Leu Gly Lys Ser Gly Asp Asn Tyr Ser Asn Ile Ala Pro Gln Ala Leu
                245                 250                 255

Cys Phe Leu Gln Thr Tyr Trp Ile Ser Ser Gly Lys Tyr Val Asp Ser
                260                 265                 270

Asn Ile Asn Val Asn Asp Gly Arg Thr Gly Lys Asp Ala Asn Ser Ile
                275                 280                 285

Leu Ser Ser Ile His Asn Phe Asp Pro Ala Leu Asn Cys Asp Pro Ala
    290                 295                 300

Thr Phe Gln Pro Cys Ser Asp Lys Ala Leu Ala Asn His Lys Ala Val
305                 310                 315                 320

Thr Asp Ser Phe Arg Ser Trp Asn Ile Asn Lys Gly Ile Ser Gln Gly
                325                 330                 335

Ser Ala Val Ala Val Gly Arg Tyr Val Glu Asp Val Tyr Tyr Asn Gly
                340                 345                 350

Asn Pro Trp Tyr Leu Ala Thr Leu Ala Ala Ala Glu Gln Leu Tyr Asp
                355                 360                 365

Ala Ile Tyr Val Trp Lys Gln Gln Gly Ser Ile Thr Val Ser Asp Val
    370                 375                 380

Ser Leu Ser Phe Phe Lys Asp Leu Val Ser Leu Val Ser Thr Gly Thr
385                 390                 395                 400

Tyr Ala Ser Asp Ser Ala Thr Phe Lys Ser Ile Thr Asp Ala Val Ser
                405                 410                 415

Lys Tyr Ala Asp Gly Tyr Val Ala Ile Val Ala Lys Tyr Val Gly Thr
                420                 425                 430

Asp Gly His Leu Ala Glu Gln Phe Asp Lys Asn Asp Gly His Pro Leu
    435                 440                 445

Ser Ala Thr Asp Leu Thr Trp Ser Tyr Ala Ala Phe Leu Ser Ala Ala
450                 455                 460

Asp Arg Arg Ala Gly Val Ile Pro Pro Ser Trp Ala Gly Ser Val Ala
465                 470                 475                 480

Ala Val Pro Asn Gln Cys Gly Thr Asn Thr Val Ala Gly Ser Tyr Ser
                485                 490                 495

Ser Ala Thr Ala Thr Ser Phe Pro Ala Ser Gln Thr Pro Lys Gly Gly
                500                 505                 510

Val Pro Thr Pro Thr Gly Ala Gln Thr Ser Thr Ser Thr Ser Thr Ser
    515                 520                 525

Thr Ser Ser Ser Thr Gly Thr Ser Cys Pro Thr Ala Thr Ser Val
530                 535                 540

Ala Val Thr Phe Gln Glu Val Val Thr Asn Phe Gly Asp Thr Ile
545                 550                 555                 560

Lys Ile Val Gly Asn Ile Ala Ala Leu Gly Asn Trp Asp Thr Ser Lys
                565                 570                 575

Ala Val Ala Leu Ser Ala Ser Asp Tyr Thr Ala Ser Asn Pro Val Trp
                580                 585                 590

Lys Ala Thr Ile Ser Leu Thr Ala Gly Gln Ser Ile Gln Tyr Lys Tyr
                595                 600                 605

Ile Asn Val Lys Lys Asp Gly Ser Leu Thr Trp Glu Lys Asp Pro Asn
    610                 615                 620

Arg Thr Tyr Ala Val Pro Lys Thr Cys Ala Thr Thr Ala Thr Lys Ser
```

Asp Lys Trp Gln Ser
            645

<210> SEQ ID NO 19
<211> LENGTH: 1467
<212> TYPE: DNA
<213> ORGANISM: Unknown
<220> FEATURE:
<223> OTHER INFORMATION: Obtained from an environmental sample

<400> SEQUENCE: 19

| | | | | | |
|---|---|---|---|---|---|
| atgttgacat | tgaatgtttt | gacagcactg | ttggctccta | ttgtgctgtc | atctgccttg | 60 |
| cctgctcgcg | atctcaatgc | gcgtgccgat | tcgaagcctg | ctgctcttca | agccatcctg | 120 |
| aacaacattg | gcgccgatgg | atctgctgtt | tcgggagcat | ctgcaggcgt | tgtggtagca | 180 |
| tccccatcca | aatcggatcc | cgattacttt | tacacctgga | ctcgtgatgc | agccttgaca | 240 |
| tacaaggtct | tgattgatga | gttcattgcc | ggagacacct | cgctggaacc | taccatccag | 300 |
| gactacgtct | ctgctcaagc | aaagctgcag | gccgtgtcta | acccatctgg | tgacttgtcc | 360 |
| gatggatcag | gacttgcaga | gcctaagtac | acgtgggact | tgactgcctt | cacggaggcc | 420 |
| tggggtcgtc | ctcagcgcga | cggacccgct | ctgcgagcca | cagcactgat | tacctacggt | 480 |
| aactatttga | tttcgaagga | gagaacatcc | gtcgtcaagt | cgaacatctg | gcccattgtg | 540 |
| caaaatgatc | tcaactatgt | tgcgcaatac | tggaaccaaa | ccggattcga | tctgtgggag | 600 |
| gaggtcgagg | gctcctcgtt | ttttaccatt | gctgcacaac | accgcgcatt | ggtgagggc | 660 |
| agcgcatttg | ccaaggcgct | gggagagtcc | tgcgagggat | gcgattccca | ggcacctcag | 720 |
| gtcctatgct | tccagcagtc | cttctgggat | ggcaaggcta | ttgtttctaa | cttcgccaac | 780 |
| aatggccgaa | ccggtctcga | tgccaattcg | gtgcttacct | cgatcggaaa | cttcgacccc | 840 |
| aaggctccct | gcgatgacgt | gaccttccag | ccttgctctg | ctcgtgccct | gtcgaatcac | 900 |
| aagctatacg | ttgactcgtt | ccgtaagatc | tatcctgtga | acagtggtaa | ggaagctgga | 960 |
| actgccgttg | ctgttggacg | ttattccgaa | gacacttaca | tgggcgggaa | cccatggtat | 1020 |
| ttgaccaccc | tggccgcggc | cgagcagctg | tacgatgctc | tttaccagtg | gaagcaactg | 1080 |
| ggatcgctag | aaatcaccga | gatcagtctt | cctttcttca | aggaccttgt | ttcgtctgcc | 1140 |
| gccgccggaa | agtatcccag | ctcctcggaa | acttacacgt | ccatcactgc | cgcagtcaaa | 1200 |
| aagtatgccg | atggatttgt | ggctgttgtt | aaggagcaca | cgcccagcga | tgggtctctg | 1260 |
| gctgaacaat | acactcggga | caacggcagc | ccggcctctg | ctaaggactt | gacctggtcc | 1320 |
| tacgcggcgc | tcctgtctgc | tacccgccgt | gaggctggaa | cagtgccccc | tacctggggt | 1380 |
| gcgtcgactg | ccaataaggt | accctcaaag | tgtgagggta | gctcggccaa | gggaagctac | 1440 |
| acgacaccat | cagtcggcaa | gtggtaa | | | | 1467 |

<210> SEQ ID NO 20
<211> LENGTH: 488
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(22)
<220> FEATURE:
<221> NAME/KEY: DOMAIN
<222> LOCATION: (33)...(449)
<223> OTHER INFORMATION: Glycosyl hydrolases family 15
<220> FEATURE:

```
<221> NAME/KEY: SITE
<222> LOCATION: (194)...(197)
<223> OTHER INFORMATION: N-glycosylation site. Prosite id = PS00001

<400> SEQUENCE: 20
```

| | | | | | | | | | | | | | | | |
|---|---|---|---|---|---|---|---|---|---|---|---|---|---|---|---|
| Met | Leu | Thr | Leu | Asn | Val | Leu | Thr | Ala | Leu | Leu | Ala | Pro | Ile | Val | Leu |
| 1 | | | | 5 | | | | | 10 | | | | | 15 | |
| Ser | Ser | Ala | Leu | Pro | Ala | Arg | Asp | Leu | Asn | Ala | Arg | Ala | Asp | Ser | Lys |
| | | | | 20 | | | | | 25 | | | | | 30 | |
| Pro | Ala | Ala | Leu | Gln | Ala | Ile | Leu | Asn | Asn | Ile | Gly | Ala | Asp | Gly | Ser |
| | | | 35 | | | | | 40 | | | | | 45 | | |
| Ala | Val | Ser | Gly | Ala | Ser | Ala | Gly | Val | Val | Ala | Ser | Pro | Ser | Lys | |
| | 50 | | | | | 55 | | | | | 60 | | | | |
| Ser | Asp | Pro | Asp | Tyr | Phe | Tyr | Thr | Trp | Thr | Arg | Asp | Ala | Ala | Leu | Thr |
| 65 | | | | | 70 | | | | | 75 | | | | | 80 |
| Tyr | Lys | Val | Leu | Ile | Asp | Glu | Phe | Ile | Ala | Gly | Asp | Thr | Ser | Leu | Glu |
| | | | | 85 | | | | | 90 | | | | | 95 | |
| Pro | Thr | Ile | Gln | Asp | Tyr | Val | Ser | Ala | Gln | Ala | Lys | Leu | Gln | Ala | Val |
| | | | 100 | | | | | 105 | | | | | 110 | | |
| Ser | Asn | Pro | Ser | Gly | Asp | Leu | Ser | Asp | Gly | Ser | Gly | Leu | Ala | Glu | Pro |
| | | 115 | | | | | 120 | | | | | 125 | | | |
| Lys | Tyr | His | Val | Asp | Leu | Thr | Ala | Phe | Thr | Glu | Ala | Trp | Gly | Arg | Pro |
| 130 | | | | | 135 | | | | | 140 | | | | | |
| Gln | Arg | Asp | Gly | Pro | Ala | Leu | Arg | Ala | Thr | Ala | Leu | Ile | Thr | Tyr | Gly |
| 145 | | | | | 150 | | | | | 155 | | | | | 160 |
| Asn | Tyr | Leu | Ile | Ser | Lys | Glu | Arg | Thr | Ser | Val | Val | Lys | Ser | Asn | Ile |
| | | | | 165 | | | | | 170 | | | | | 175 | |
| Trp | Pro | Ile | Val | Gln | Asn | Asp | Leu | Asn | Tyr | Val | Ala | Gln | Tyr | Trp | Asn |
| | | | 180 | | | | | 185 | | | | | 190 | | |
| Gln | Thr | Gly | Phe | Asp | Leu | Trp | Glu | Glu | Val | Glu | Gly | Ser | Ser | Phe | Phe |
| | | | 195 | | | | | 200 | | | | | 205 | | |
| Thr | Ile | Ala | Ala | Gln | His | Arg | Ala | Leu | Val | Glu | Gly | Ser | Ala | Phe | Ala |
| | 210 | | | | | 215 | | | | | 220 | | | | |
| Lys | Ala | Leu | Gly | Glu | Ser | Cys | Glu | Gly | Cys | Asp | Ser | Gln | Ala | Pro | Gln |
| 225 | | | | | 230 | | | | | 235 | | | | | 240 |
| Val | Leu | Cys | Phe | Gln | Gln | Ser | Phe | Trp | Asp | Gly | Lys | Ala | Ile | Val | Ser |
| | | | 245 | | | | | 250 | | | | | 255 | | |
| Asn | Phe | Ala | Asn | Asn | Gly | Arg | Thr | Gly | Leu | Asp | Ala | Asn | Ser | Val | Leu |
| | | | 260 | | | | | 265 | | | | | 270 | | |
| Thr | Ser | Ile | Gly | Asn | Phe | Asp | Pro | Lys | Ala | Pro | Cys | Asp | Asp | Val | Thr |
| | | 275 | | | | | 280 | | | | | 285 | | | |
| Phe | Gln | Pro | Cys | Ser | Ala | Arg | Ala | Leu | Ser | Asn | His | Lys | Leu | Tyr | Val |
| | 290 | | | | | 295 | | | | | 300 | | | | |
| Asp | Ser | Phe | Arg | Lys | Ile | Tyr | Pro | Val | Asn | Ser | Gly | Lys | Glu | Ala | Gly |
| 305 | | | | | 310 | | | | | 315 | | | | | 320 |
| Thr | Ala | Val | Ala | Val | Gly | Arg | Tyr | Ser | Glu | Asp | Thr | Tyr | Met | Gly | Gly |
| | | | 325 | | | | | 330 | | | | | 335 | | |
| Asn | Pro | Trp | Tyr | Leu | Thr | Thr | Leu | Ala | Ala | Glu | Gln | Leu | Tyr | Asp | |
| | | | 340 | | | | | 345 | | | | | 350 | | |
| Ala | Leu | Tyr | Gln | Trp | Lys | Gln | Leu | Gly | Ser | Leu | Glu | Ile | Thr | Glu | Ile |
| | | | 355 | | | | | 360 | | | | | 365 | | |
| Ser | Leu | Pro | Phe | Phe | Lys | Asp | Leu | Val | Ser | Ser | Ala | Ala | Gly | Lys | |
| | 370 | | | | | 375 | | | | | 380 | | | | |
| Tyr | Pro | Ser | Ser | Ser | Glu | Thr | Tyr | Thr | Ser | Ile | Thr | Ala | Ala | Val | Lys |
| 385 | | | | | 390 | | | | | 395 | | | | | 400 |

```
Lys Tyr Ala Asp Gly Phe Val Ala Val Lys Glu His Thr Pro Ser
            405                 410                 415
Asp Gly Ser Leu Ala Glu Gln Tyr Thr Arg Asp Asn Gly Ser Pro Ala
            420                 425                 430
Ser Ala Lys Asp Leu Thr Trp Ser Tyr Ala Ala Leu Leu Ser Ala Thr
            435                 440                 445
Arg Arg Glu Ala Gly Thr Val Pro Pro Thr Trp Gly Ala Ser Thr Ala
    450                 455                 460
Asn Lys Val Pro Ser Lys Cys Glu Gly Ser Ser Ala Lys Gly Ser Tyr
465                 470                 475                 480
Thr Thr Pro Ser Val Gly Lys Trp
            485

<210> SEQ ID NO 21
<211> LENGTH: 1488
<212> TYPE: DNA
<213> ORGANISM: Unknown
<220> FEATURE:
<223> OTHER INFORMATION: Obtained from an environmental sample

<400> SEQUENCE: 21
atggttctag ctcggcttgc ctggcttgcc ggcctggtta gcactgccgt tgctgcgacc      60
ccagcggaat ggcgctcgca gtccatctac ttcatgctca cggatcgttt tgcccggacg     120
gatggttcaa ctactgctgc ctgcgatacc gctgacagaa atactgtgg cggaacctgg      180
cagggaatca ttgacaagct ggactatatc caaggaatgg gctttacagc catttggatc     240
actcctgtga ccgtcaatt gagcggggaa accgcgtacg gagatgccta tcacggatac     300
tggcagcagg atatctattc tctcgattcc aactatggaa ccgcagacga tctcaaggcc     360
ctcgctgcgg cttttgcacga acgcaacatg tatctcatgg tcgatgtcgt agctaaccac     420
atgggctaca atgcccagg tactgacgtg gactacacca aattcaaccc cttcaacgat      480
gcaaagtatt tccactcgta ctgcccaatc accgattaca cgacgacac catgtcgcaa      540
aactgctggc ttggcgataa caaggtctcg ctaccggacc tgaatacaca gagcaaggag     600
gtccaggatc tatggtatga ctgggttggg tctttggtct ccaactactc tatcgacggt     660
ctccgtgtcg acacagtcaa acatgtccag aaagatttct ggcccggcta caacaaagcc     720
gcgggcgtct actgcgtagg cgagatcctt gatggtgacc cagattacac ctgtccatac     780
caggaggtaa tggacggagt gctcaactac ccgatttatt ccccactcct caaggccttc     840
caatcgacct cgggaagcat gaccgatcta tacaacatga tcaacacggt gaaatcgacc     900
tgcaaggact cgacccttct tggaaatttc ttggagaacc acgataaccc ccgttttgcc     960
cacgtcaccg acgacattgc cctcgccaag aacgcagcta cgtttaccat tatggcagac    1020
ggcattccta ttgtctatgc aggacaggag cagcactaca gtggtggcga ggacccggct    1080
aatcgcgaag ctctgtggtt gtcaggatac aacacggaca gtgagctgta caagctcata    1140
gccaaggcca atggtgctag aagccaggcc attgctaagg gtaccaacta tacgatttac    1200
cagaaccaac caatctacaa agatgagagc accatcgcca tgcggaaggg cttcgacggt    1260
ggacagacaa tcactgtcct gacgaatctc ggcgcagggg gtaaagagga ctctgtttcg    1320
attcctgata ccggattcaa ggctggtgca aagttgactg aggtcgtctc ctgcgctagt    1380
gttactgtcg gtgacaatgg ggaggtgtct gtccctatgg cggctggagc gccgaggatt    1440
ttgctcccta ccttttttgct tgagggctcg actctgtgtt catcatag               1488
```

```
<210> SEQ ID NO 22
<211> LENGTH: 495
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(18)
<220> FEATURE:
<221> NAME/KEY: DOMAIN
<222> LOCATION: (31)...(387)
<223> OTHER INFORMATION: Alpha amylase, catalytic domain
<220> FEATURE:
<221> NAME/KEY: SITE
<222> LOCATION: (197)...(200)
<223> OTHER INFORMATION: N-glycosylation site. Prosite id = PS00001
<220> FEATURE:
<221> NAME/KEY: SITE
<222> LOCATION: (218)...(221)
<223> OTHER INFORMATION: N-glycosylation site. Prosite id = PS00001
<220> FEATURE:
<221> NAME/KEY: SITE
<222> LOCATION: (402)...(405)
<223> OTHER INFORMATION: N-glycosylation site. Prosite id = PS00001

<400> SEQUENCE: 22

Met Val Leu Ala Arg Leu Ala Trp Leu Ala Gly Leu Val Ser Thr Ala
1               5                   10                  15

Val Ala Ala Thr Pro Ala Glu Trp Arg Ser Gln Ser Ile Tyr Phe Met
            20                  25                  30

Leu Thr Asp Arg Phe Ala Arg Thr Asp Gly Ser Thr Thr Ala Ala Cys
        35                  40                  45

Asp Thr Ala Asp Arg Lys Tyr Cys Gly Gly Thr Trp Gln Gly Ile Ile
    50                  55                  60

Asp Lys Leu Asp Tyr Ile Gln Gly Met Gly Phe Thr Ala Ile Trp Ile
65                  70                  75                  80

Thr Pro Val Thr Gly Gln Leu Ser Gly Glu Thr Ala Tyr Gly Asp Ala
                85                  90                  95

Tyr His Gly Tyr Trp Gln Gln Asp Ile Tyr Ser Leu Asp Ser Asn Tyr
            100                 105                 110

Gly Thr Ala Asp Asp Leu Lys Ala Leu Ala Ala Ala Leu His Glu Arg
        115                 120                 125

Asn Met Tyr Leu Met Val Asp Val Val Ala Asn His Met Gly Tyr Asn
    130                 135                 140

Gly Pro Gly Thr Asp Val Asp Tyr Thr Lys Phe Asn Pro Phe Asn Asp
145                 150                 155                 160

Ala Lys Tyr Phe His Ser Tyr Cys Pro Ile Thr Asp Tyr Asn Asp Asp
                165                 170                 175

Thr Met Ser Gln Asn Cys Trp Leu Gly Asp Asn Lys Val Ser Leu Pro
            180                 185                 190

Asp Leu Asn Thr Gln Ser Lys Glu Val Gln Asp Leu Trp Tyr Asp Trp
        195                 200                 205

Val Gly Ser Leu Val Ser Asn Tyr Ser Ile Asp Gly Leu Arg Val Asp
    210                 215                 220

Thr Val Lys His Val Gln Lys Asp Phe Trp Pro Gly Tyr Asn Lys Ala
225                 230                 235                 240

Ala Gly Val Tyr Cys Val Gly Glu Ile Leu Asp Gly Asp Pro Asp Tyr
                245                 250                 255

Thr Cys Pro Tyr Gln Glu Val Met Asp Gly Val Leu Asn Tyr Pro Ile
            260                 265                 270

Tyr Tyr Pro Leu Leu Lys Ala Phe Gln Ser Thr Ser Gly Ser Met Thr
```

|  |  |  |  | 275 |  |  |  |  | 280 |  |  |  |  | 285 |
|--|--|--|--|--|--|--|--|--|--|--|--|--|--|--|
Asp Leu Tyr Asn Met Ile Asn Thr Val Lys Ser Thr Cys Lys Asp Ser
    290                       295                       300

Thr Leu Leu Gly Asn Phe Leu Glu Asn His Asp Asn Pro Arg Phe Ala
305                       310                       315                   320

His Val Thr Asp Asp Ile Ala Leu Ala Lys Asn Ala Ala Thr Phe Thr
                  325                       330                   335

Ile Met Ala Asp Gly Ile Pro Ile Val Tyr Ala Gly Gln Glu Gln His
                  340                       345                   350

Tyr Ser Gly Gly Glu Asp Pro Ala Asn Arg Glu Ala Leu Trp Leu Ser
              355                       360                   365

Gly Tyr Asn Thr Asp Ser Glu Leu Tyr Lys Leu Ile Ala Lys Ala Asn
    370                     375                       380

Gly Ala Arg Ser Gln Ala Ile Ala Lys Gly Thr Asn Tyr Thr Ile Tyr
385                      390                       395                   400

Gln Asn Gln Pro Ile Tyr Lys Asp Glu Ser Thr Ile Ala Met Arg Lys
                  405                       410                   415

Gly Phe Asp Gly Gly Gln Thr Ile Thr Val Leu Thr Asn Leu Gly Ala
              420                       425                   430

Gly Gly Lys Glu Asp Ser Val Ser Ile Pro Asp Thr Gly Phe Lys Ala
        435                     440                       445

Gly Ala Lys Leu Thr Glu Val Val Ser Cys Ala Ser Val Thr Val Gly
    450                     455                       460

Asp Asn Gly Glu Val Ser Val Pro Met Ala Ala Gly Ala Pro Arg Ile
465                      470                       475                   480

Leu Leu Pro Thr Phe Leu Leu Glu Gly Ser Thr Leu Cys Ser Ser
                  485                       490                   495

<210> SEQ ID NO 23
<211> LENGTH: 1389
<212> TYPE: DNA
<213> ORGANISM: Unknown
<220> FEATURE:
<223> OTHER INFORMATION: Obtained from an environmental sample

<400> SEQUENCE: 23

| | | |
|---|---|---|
| atgaaactgt cccacaccct gacagctctt ctactccctc tgatatgcac tgtatcagca | 60 |
| gcggatgtga aagcatggaa gtcccgcaat atttactttg ccctgactga tcgcattgcc | 120 |
| cgtggaagcg atgatacagg tggagatgcc tgcggtaacc ttggaaacta ctgcggtgga | 180 |
| actttccaag gcttggagtc taagcttgac tatattaagg ggatgggctt tgatgcaatc | 240 |
| tggatcaccc ctgttatcgc taatgcgcca ggtggatatc atggatactg ggcgcgggat | 300 |
| ctctatagca tcaacgagaa ctatggcacc gctgatgatc tcaaaagcct agttgatgct | 360 |
| gctcataaga aggggatcta tgtcatggca gacgtagttg ccaaccacat gggaggcccc | 420 |
| atcagcgata caagccgga gccattgaac caggagagct cctaccattc cacctgcaca | 480 |
| atcgactact caagccagga tagtgttgaa aactgccgta tcacagcaga cctacctgat | 540 |
| gtgaacacac agagtcccga gatccgtgcc ctcttccaga atgggtcaa atggctcgtc | 600 |
| acggaatacg ggttcgacgg cttgcgcatt gacactgtta agcacgttga aaaggacttc | 660 |
| tggtcggcct tctcctccgc tgccgggggtt tacaccatcg gcgaagtctg ggacggtgac | 720 |
| ccagcttacc ttgccggata tgcacaggac atggacggcc tgctcaacta tgcagtctac | 780 |
| tatcccgtga caactttta ccagcaaaag ggctcttccc aggacatagt tgacatgcat | 840 |
| gataaaatcg acaccgcttt ccctgatccc agcgccctgg gcacattcat agacaatcac | 900 |

-continued

```
gacaatgcgc gatggctgag cgtaaagaat gacaagtcgc ttttgaaaaa cgcactcgcc    960
tacgtgattc tcgcccgggg catccccatt gtctactacg gcacggaaca gggctacgcg   1020
ggcggcaacg accccgcaaa ccgcgaggac ctatggcgca gcaaattcag caccgacgcg   1080
gacttgtaca aggccatatc cctgctctca gcggcgagaa acgcttctgg tggcctcgct   1140
gacaacgacc atgtccatct gtacgtcgcg gagtcggcat atgcgtggag cagggcgggt   1200
ggaaacctca tcgtccttac gtccaatggt ggatctgggt ctgaggctaa tcactgcttc   1260
gactctaaga agcctggtgg gacatggaag aataccttg gagagggac aatcaccgcc    1320 gatgaaggcg gaaaaatttg catctctatc tctaatggtg agcctgcggt gctggttgca   1380
agcacttga                                                          1389
```

<210> SEQ ID NO 24
<211> LENGTH: 462
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(20)
<220> FEATURE:
<221> NAME/KEY: DOMAIN
<222> LOCATION: (33)...(373)
<223> OTHER INFORMATION: Alpha amylase, catalytic domain
<220> FEATURE:
<221> NAME/KEY: SITE
<222> LOCATION: (379)...(382)
<223> OTHER INFORMATION: N-glycosylation site. Prosite id = PS00001

<400> SEQUENCE: 24

```
Met Lys Leu Ser His Thr Leu Thr Ala Leu Leu Pro Leu Ile Cys
1               5                  10                  15

Thr Val Ser Ala Ala Asp Val Lys Ala Trp Lys Ser Arg Asn Ile Tyr
            20                  25                  30

Phe Ala Leu Thr Asp Arg Ile Ala Arg Gly Ser Asp Asp Thr Gly Gly
        35                  40                  45

Asp Ala Cys Gly Asn Leu Gly Asn Tyr Cys Gly Gly Thr Phe Gln Gly
    50                  55                  60

Leu Glu Ser Lys Leu Asp Tyr Ile Lys Gly Met Gly Phe Asp Ala Ile
65                  70                  75                  80

Trp Ile Thr Pro Val Ile Ala Asn Ala Pro Gly Gly Tyr His Gly Tyr
                85                  90                  95

Trp Ala Arg Asp Leu Tyr Ser Ile Asn Glu Asn Tyr Gly Thr Ala Asp
            100                 105                 110

Asp Leu Lys Ser Leu Val Asp Ala Ala His Lys Lys Gly Ile Tyr Val
        115                 120                 125

Met Ala Asp Val Val Ala Asn His Met Gly Gly Pro Ile Ser Asp Asn
    130                 135                 140

Lys Pro Glu Pro Leu Asn Gln Glu Ser Ser Tyr His Ser Thr Cys Thr
145                 150                 155                 160

Ile Asp Tyr Ser Ser Gln Asp Ser Val Glu Asn Cys Arg Ile Thr Ala
                165                 170                 175

Asp Leu Pro Asp Val Asn Thr Gln Ser Pro Glu Ile Arg Ala Leu Phe
            180                 185                 190

Gln Lys Trp Val Lys Trp Leu Val Thr Glu Tyr Gly Phe Asp Gly Leu
        195                 200                 205

Arg Ile Asp Thr Val Lys His Val Glu Lys Asp Phe Trp Ser Ala Phe
```

```
                210                 215                 220
Ser Ser Ala Ala Gly Val Tyr Thr Ile Gly Glu Val Trp Asp Gly Asp
225                 230                 235                 240

Pro Ala Tyr Leu Ala Gly Tyr Ala Gln Asp Met Asp Gly Leu Leu Asn
                245                 250                 255

Tyr Ala Val Tyr Tyr Pro Val Asn Asn Phe Tyr Gln Gln Lys Gly Ser
            260                 265                 270

Ser Gln Asp Ile Val Asp Met His Asp Lys Ile Asp Thr Ala Phe Pro
        275                 280                 285

Asp Pro Ser Ala Leu Gly Thr Phe Ile Asp Asn His Asp Asn Ala Arg
    290                 295                 300

Trp Leu Ser Val Lys Asn Asp Lys Ser Leu Leu Lys Asn Ala Leu Ala
305                 310                 315                 320

Tyr Val Ile Leu Ala Arg Gly Ile Pro Ile Val Tyr Tyr Gly Thr Glu
                325                 330                 335

Gln Gly Tyr Ala Gly Gly Asn Asp Pro Ala Asn Arg Glu Asp Leu Trp
            340                 345                 350

Arg Ser Lys Phe Ser Thr Asp Ala Asp Leu Tyr Lys Ala Ile Ser Leu
        355                 360                 365

Leu Ser Ala Ala Arg Asn Ala Ser Gly Gly Leu Ala Asp Asn Asp His
    370                 375                 380

Val His Leu Tyr Val Ala Glu Ser Ala Tyr Ala Trp Ser Arg Ala Gly
385                 390                 395                 400

Gly Asn Leu Ile Val Leu Thr Ser Asn Gly Gly Ser Gly Ser Glu Ala
                405                 410                 415

Asn His Cys Phe Asp Ser Lys Lys Pro Gly Gly Thr Trp Lys Asn Thr
            420                 425                 430

Phe Gly Glu Gly Thr Ile Thr Ala Asp Glu Gly Gly Lys Ile Cys Ile
        435                 440                 445

Ser Ile Ser Asn Gly Glu Pro Ala Val Leu Val Ala Ser Thr
    450                 455                 460

<210> SEQ ID NO 25
<211> LENGTH: 1923
<212> TYPE: DNA
<213> ORGANISM: Unknown
<220> FEATURE:
<223> OTHER INFORMATION: Obtained from an environmental sample

<400> SEQUENCE: 25
atgactattt ctcgcctctc ctccgtgctt tttgcactgg ctctaggtca aagtgcacta      60
gcagcccctc agctgtctcc tcgtgctaca actagcttgg acgccctggc tgccagtgaa     120
actactgtct ctctcaatgg aatcttggac aacatcggtg ccagcggtgc ctatgctcag     180
agtgccaagg ctggtgttgt tattgccagt cccagcacaa gcagcccgga ttattactac     240
acgtggacca gagactctgc ccttacgtta aaagtcctta tcgatctctt ccgtaatggg     300
aacgtagatc tgcagaccgt cattgaggaa tacatcactg cacaagctta tctacagacc     360
gtctccaacc cctccggaga tctctcaagc ggtgctggtc tcgctgagcc caagttcaac     420
gttgacatga gcgcttacac tggcgcttgg ggacgtccgc aacgcgacgg acctgctctc     480
cgtgctattg ccttgatcga ttttggcaac tggttgattg acaatggata ctctagctat     540
gccgttagca acgtctggcc cattgtacgc aacgatctgt cctacgttgc ccagtactgg     600
agccaaagcg ttatgatct ctgggaggag gtcaacagca tgtccttctt caccattgcc     660
aaccagcacc gtgccctcgt cgagggaagc accttttgccg ccgagttgg tgcatcctgc     720
```

-continued

```
tcgtggtgtg actctcaagc cccccagatc ctctgctaca tgcagaactt ctggaccgga    780
tcttacatca atgccaacac tggcggtggt cgttccggca aggacgccaa cactgttctg    840
gctagtatca gcacttttga tcccgaggct acctgtgacg acgtcacttt ccagccctgc    900
tcctcccgcg ccctggccaa ccacaaagtc tacactgact cgttccgatc tgtctattct    960
ctcgactccg gcattgctga gggcgttgct gtcgcggtag gacgctaccc tgaggattca   1020
tactataacg gcaatccgtg gttttttgacc actctcgctg ctgcggaaca gttgtacgat   1080
gccatatatc aatggaacaa gatcggctcc atcacaatca ccagcacctc tttggctttc   1140
tttaatgacg tctacagctc tgccgctgtt ggcacttacg cctctggcag cactgcctac   1200
acagccattg tcagcgcagt caagacctat gccgacggat atgtcagcat cgtgcaggct   1260
catgccatga ccaacggctc tctctccgag cagtttgaca aggcctccgg tacccagctc   1320
tctgcccgtg atcttacatg gtcgtacgct gccttgctca ctgctaacat gcgccgcaac   1380
ggaattgtgc ctccttcctg gggagctgcc tccgccaact caatcccag ttcttgctct   1440 acgggctctg caactggcac ttacagcact cctaccggaa cctcctggcc cagtacactg   1500
accagcggca ccgcaggtac cactaccact tctgctacta ctaccacctc cacctctgtc   1560
tccaaaacta ccactaccac caccagtact acctcttgca ccaccccgac ctccgtagcc   1620
gtcacctttg acgagattgc aaccacctac tacggcgaga acgtttacat ttctggctcg   1680
atctcgcagc tcggtagctg ggataccagc agtgccattg cgctcagcgc cagccagtac   1740
acttccagca caaacctctg gttcgtgact atcaacctgc ccgctggaac aacctttcag   1800
tacaagtaca ttcgcaagga gtcggatggt tcgattgttt gggagagtga tcctaaccgc   1860
tcgtacactg tgccttccgg ttgtggtgta agcacagcta ctgagagtga tacttggcga   1920
tag                                                                  1923
```

<210> SEQ ID NO 26
<211> LENGTH: 640
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (42)...(457)
<223> OTHER INFORMATION: Glycosyl hydrolases family 15
<220> FEATURE:
<221> NAME/KEY: DOMAIN
<222> LOCATION: (538)...(634)
<223> OTHER INFORMATION: Starch binding domain
<220> FEATURE:
<221> NAME/KEY: SITE
<222> LOCATION: (206)...(216)
<223> OTHER INFORMATION: Glucoamylase active site region signature.
      Prosite id = PS00820
<220> FEATURE:
<221> NAME/KEY: SITE
<222> LOCATION: (431)...(434)
<223> OTHER INFORMATION: N-glycosylation site. Prosite id = PS00001
<220> FEATURE:
<221> NAME/KEY: SITE
<222> LOCATION: (628)...(631)
<223> OTHER INFORMATION: N-glycosylation site. Prosite id = PS00001

<400> SEQUENCE: 26

```
Met Thr Ile Ser Arg Leu Ser Ser Val Leu Phe Ala Leu Ala Leu Gly
1               5                   10                  15
```

```
Gln Ser Ala Leu Ala Ala Pro Gln Leu Ser Pro Arg Ala Thr Thr Ser
            20                  25                  30

Leu Asp Ala Trp Leu Ala Ser Glu Thr Thr Val Ser Leu Asn Gly Ile
            35                  40                  45

Leu Asp Asn Ile Gly Ala Ser Gly Ala Tyr Ala Gln Ser Ala Lys Ala
            50                  55                  60

Gly Val Val Ile Ala Ser Pro Ser Thr Ser Ser Pro Asp Tyr Tyr Tyr
 65                  70                  75                  80

Thr Trp Thr Arg Asp Ser Ala Leu Thr Leu Lys Val Leu Ile Asp Leu
                85                  90                  95

Phe Arg Asn Gly Asn Val Asp Leu Gln Thr Val Ile Glu Glu Tyr Ile
                100                 105                 110

Thr Ala Gln Ala Tyr Leu Gln Thr Val Ser Asn Pro Ser Gly Asp Leu
            115                 120                 125

Ser Ser Gly Ala Gly Leu Ala Glu Pro Lys Phe Asn Val Asp Met Ser
130                 135                 140

Ala Tyr Thr Gly Ala Trp Gly Arg Pro Gln Arg Asp Gly Pro Ala Leu
145                 150                 155                 160

Arg Ala Ile Ala Leu Ile Asp Phe Gly Asn Trp Leu Ile Asp Asn Gly
                165                 170                 175

Tyr Ser Ser Tyr Ala Val Ser Asn Val Trp Pro Ile Val Arg Asn Asp
            180                 185                 190

Leu Ser Tyr Val Ala Gln Tyr Trp Ser Gln Ser Gly Tyr Asp Leu Trp
            195                 200                 205

Glu Glu Val Asn Ser Met Ser Phe Phe Thr Ile Ala Asn Gln His Arg
210                 215                 220

Ala Leu Val Glu Gly Ser Thr Phe Ala Gly Arg Val Gly Ala Ser Cys
225                 230                 235                 240

Ser Trp Cys Asp Ser Gln Ala Pro Gln Ile Leu Cys Tyr Met Gln Asn
                245                 250                 255

Phe Trp Thr Gly Ser Tyr Ile Asn Ala Asn Thr Gly Gly Gly Arg Ser
            260                 265                 270

Gly Lys Asp Ala Asn Thr Val Leu Ala Ser Ile Ser Thr Phe Asp Pro
            275                 280                 285

Glu Ala Thr Cys Asp Asp Val Thr Phe Gln Pro Cys Ser Ser Arg Ala
290                 295                 300

Leu Ala Asn His Lys Val Tyr Thr Asp Ser Phe Arg Ser Val Tyr Ser
305                 310                 315                 320

Leu Asp Ser Gly Ile Ala Glu Gly Val Ala Val Ala Val Gly Arg Tyr
                325                 330                 335

Pro Glu Asp Ser Tyr Tyr Asn Gly Asn Pro Trp Phe Leu Thr Thr Leu
            340                 345                 350

Ala Ala Ala Glu Gln Leu Tyr Asp Ala Ile Tyr Gln Trp Asn Lys Ile
            355                 360                 365

Gly Ser Ile Thr Ile Thr Ser Thr Ser Leu Ala Phe Phe Asn Asp Val
            370                 375                 380

Tyr Ser Ser Ala Ala Val Gly Thr Tyr Ala Ser Gly Ser Thr Ala Tyr
385                 390                 395                 400

Thr Ala Ile Val Ser Ala Val Lys Thr Tyr Ala Asp Gly Tyr Val Ser
                405                 410                 415

Ile Val Gln Ala His Ala Met Thr Asn Gly Ser Leu Ser Glu Gln Phe
            420                 425                 430

Asp Lys Ala Ser Gly Thr Gln Leu Ser Ala Arg Asp Leu Thr Trp Ser
            435                 440                 445
```

Tyr Ala Ala Leu Leu Thr Ala Asn Met Arg Arg Asn Gly Ile Val Pro
    450                 455                 460

Pro Ser Trp Gly Ala Ala Ser Ala Asn Ser Ile Pro Ser Ser Cys Ser
465                 470                 475                 480

Thr Gly Ser Ala Thr Gly Thr Tyr Ser Thr Pro Thr Gly Thr Ser Trp
                485                 490                 495

Pro Ser Thr Leu Thr Ser Gly Thr Ala Gly Thr Thr Thr Ser Ala
                500                 505                 510

Thr Thr Thr Thr Ser Thr Ser Val Ser Lys Thr Thr Thr Thr Thr
                515                 520                 525

Ser Thr Thr Ser Cys Thr Thr Pro Thr Ser Val Ala Val Thr Phe Asp
    530                 535                 540

Glu Ile Ala Thr Thr Tyr Tyr Gly Glu Asn Val Tyr Ile Ser Gly Ser
545                 550                 555                 560

Ile Ser Gln Leu Gly Ser Trp Asp Thr Ser Ser Ala Ile Ala Leu Ser
                565                 570                 575

Ala Ser Gln Tyr Thr Ser Ser Asn Asn Leu Trp Phe Val Thr Ile Asn
                580                 585                 590

Leu Pro Ala Gly Thr Thr Phe Gln Tyr Lys Tyr Ile Arg Lys Glu Ser
                595                 600                 605

Asp Gly Ser Ile Val Trp Glu Ser Asp Pro Asn Arg Ser Tyr Thr Val
                610                 615                 620

Pro Ser Gly Cys Gly Val Ser Thr Ala Thr Glu Ser Asp Thr Trp Arg
625                 630                 635                 640

<210> SEQ ID NO 27
<211> LENGTH: 1911
<212> TYPE: DNA
<213> ORGANISM: Unknown
<220> FEATURE:
<223> OTHER INFORMATION: Obtained from an environmental sample

<400> SEQUENCE: 27
atgtatatcc tgtcttctgc ttttctcctc ggctccctcg ctcttcagag cgttctgggt     60
agaccggcgg ataagatcca agtgagacaa tctggtatcg aggactttat caagtccgag    120
agcccgattg ccatcgagca gcttctgtgc aacattggtt ccgaagggtg ccatgccaag    180
aatgttcccg ctggcatcgt cattgcttct ccagacaccc aagatcccga ctacttttat    240
acctggactc gagatgctgc tcttgttttc aagtatattg tcgacaggtt cattcaccag    300
tacgatgcta ctctccagaa gcgcattcag gagtacattg cctctcaagc caagctccag    360
ggcgtctcca accctctggg atccctctcg gatggctctg gccttggtga agccaagtac    420
tacgtcaacc tgagccccta cactggtggc tgggtcgac ctcaacgtga tggccctgcc    480
cttcgagcca ccgccatgat cacttatgcc aactggctga cgctaacgg ttacacctct    540
acggctaatg acattgtgtg gccgtgatt cgcaacgatc tcaactacgt tgctcagtat    600
tggactcaaa ctggctttga cttgtgggaa gaggtcaggg gtagctcatt cttcacgact    660
gctgctcaat accgagctct cgtcgaaggt gctgcccttg ctaaggctct ggcaagtct    720
ggcgatacct attctaacat tgcgccccaa acactctgct tcttgcagac ctactgggtc    780
tcgaacggta gatacgtcga ctccaacatt aatgtgaacg atggccgcac cggcaaggac    840
gccaacagca tcctcgcatc tatccacaac tttgacccaa gcattggctg tgatgctgca    900
acattccaac cctgcagtga caaggccctc gccaaccaca aggcagtcac cgacaccttc    960
cgctcctaca acctcaacaa gggcatcgca caggagactg ctgtggctat cggaagatac   1020

```
attgaagatg tctactacaa cggcaacccc tggtacctca ccacactcgc cgctgccgag   1080
cagctatatg atgccgtcta cgtctggaag cagaagggat ccatcactgt gactgataca   1140
tctctgtcgt tcttcaagga tcttgtgtcg agtgtttcca ctggcacata tgccagcggc   1200
tcgaccactt tccagcagat tatcgacgcc gtgtcgacct acgccgacgg atacgttgcc   1260
attgttcgca agtacgtggg tccgaacggc gccctggctg agcagttctc caaggacaat   1320
ggcactccca tgtccgctga tgatcttacg tggtcatatg ctgctttcct ctcagccact   1380
gaacgccgag ctggcattgt tcctcctact tggcaaaaga gtgttcctgc agttcccaac   1440
agctgtggat caagcacagt cgttggatca tacacatcgg ccacgcagac ctcgttccct   1500
ccttcgcaaa cccccagga cggcgtgcca actcccacag gaccaactcc caccgacgga   1560
ggacctactt cctctcctac aagctgtgcc atcgccacat ctgtcgacgt caccttaat   1620 gaggttgtca agaccgagta cggcgacacc atcaagattg tcggcagcat cgctgccctg   1680
ggcagctggg acaccacgaa ggccatctcc ctgagcgcct ccgactacac ggcctcgaac   1740
cccctgtgga agacgacaat ctccctcacg gctggtcagt cttttgagta caagtatatc   1800
aacatcaaga aggacggctc gctggtgtgg gagcgtgacc ccaaccgttc ttatactgtt   1860
cccaagactt gtgagaccaa ggctaccaag tcggatagtt ggcaaggata a           1911
```

<210> SEQ ID NO 28  
<211> LENGTH: 636  
<212> TYPE: PRT  
<213> ORGANISM: Unknown  
<220> FEATURE:  
<223> OTHER INFORMATION: Obtained from an environmental sample  
<220> FEATURE:  
<221> NAME/KEY: SIGNAL  
<222> LOCATION: (1)...(20)  
<220> FEATURE:  
<221> NAME/KEY: DOMAIN  
<222> LOCATION: (42)...(461)  
<223> OTHER INFORMATION: Glycosyl hydrolases family 15  
<220> FEATURE:  
<221> NAME/KEY: DOMAIN  
<222> LOCATION: (534)...(630)  
<223> OTHER INFORMATION: Starch binding domain  
<220> FEATURE:  
<221> NAME/KEY: SITE  
<222> LOCATION: (207)...(217)  
<223> OTHER INFORMATION: Glucoamylase active site region signature. Prosite id = PS00820  
<220> FEATURE:  
<221> NAME/KEY: SITE  
<222> LOCATION: (624)...(627)  
<223> OTHER INFORMATION: N-glycosylation site. Prosite id = PS00001

<400> SEQUENCE: 28

```
Met Tyr Ile Leu Ser Ser Ala Phe Leu Leu Gly Ser Leu Ala Leu Gln
1               5                   10                  15

Ser Val Leu Gly Arg Pro Ala Asp Lys Ile Gln Val Arg Gln Ser Gly
            20                  25                  30

Ile Glu Asp Phe Ile Lys Ser Glu Ser Pro Ile Ala Ile Glu Gln Leu
        35                  40                  45

Leu Cys Asn Ile Gly Ser Glu Gly Cys His Ala Lys Asn Val Pro Ala
    50                  55                  60

Gly Ile Val Ile Ala Ser Pro Asp Thr Gln Asp Pro Asp Tyr Phe Tyr
65                  70                  75                  80

Thr Trp Thr Arg Asp Ala Ala Leu Val Phe Lys Tyr Ile Val Asp Arg
                85                  90                  95

Phe Ile His Gln Tyr Asp Ala Thr Leu Gln Lys Arg Ile Gln Glu Tyr
```

```
                      100                 105                 110
Ile Ala Ser Gln Ala Lys Leu Gln Gly Val Ser Asn Pro Ser Gly Ser
            115                 120                 125

Leu Ser Asp Gly Ser Gly Leu Gly Glu Ala Lys Tyr Tyr Val Asn Leu
    130                 135                 140

Ser Pro Tyr Thr Gly Gly Trp Gly Arg Pro Gln Arg Asp Gly Pro Ala
145                 150                 155                 160

Leu Arg Ala Thr Ala Met Ile Thr Tyr Ala Asn Trp Leu Ile Ala Asn
                165                 170                 175

Gly Tyr Thr Ser Thr Ala Asn Asp Ile Val Trp Pro Val Ile Arg Asn
            180                 185                 190

Asp Leu Asn Tyr Val Ala Gln Tyr Trp Thr Gln Thr Gly Phe Asp Leu
        195                 200                 205

Trp Glu Glu Val Arg Gly Ser Ser Phe Phe Thr Thr Ala Ala Gln Tyr
        210                 215                 220

Arg Ala Leu Val Glu Gly Ala Ala Leu Ala Lys Ala Leu Gly Lys Ser
225                 230                 235                 240

Gly Asp Thr Tyr Ser Asn Ile Ala Pro Gln Thr Leu Cys Phe Leu Gln
                245                 250                 255

Thr Tyr Trp Val Ser Asn Gly Arg Tyr Val Asp Ser Asn Ile Asn Val
            260                 265                 270

Asn Asp Gly Arg Thr Gly Lys Asp Ala Asn Ser Ile Leu Ala Ser Ile
        275                 280                 285

His Asn Phe Asp Pro Ser Ile Gly Cys Asp Ala Ala Thr Phe Gln Pro
        290                 295                 300

Cys Ser Asp Lys Ala Leu Ala Asn His Lys Ala Val Thr Asp Thr Phe
305                 310                 315                 320

Arg Ser Tyr Asn Leu Asn Lys Gly Ile Ala Gln Gly Thr Ala Val Ala
                325                 330                 335

Ile Gly Arg Tyr Ile Glu Asp Val Tyr Tyr Asn Gly Asn Pro Trp Tyr
            340                 345                 350

Leu Thr Thr Leu Ala Ala Ala Glu Gln Leu Tyr Asp Ala Val Tyr Val
        355                 360                 365

Trp Lys Gln Lys Gly Ser Ile Thr Val Thr Asp Thr Ser Leu Ser Phe
        370                 375                 380

Phe Lys Asp Leu Val Ser Ser Val Ser Thr Gly Thr Tyr Ala Ser Gly
385                 390                 395                 400

Ser Thr Thr Phe Gln Gln Ile Ile Asp Ala Val Ser Thr Tyr Ala Asp
                405                 410                 415

Gly Tyr Val Ala Ile Val Arg Lys Tyr Val Gly Pro Asn Gly Ala Leu
            420                 425                 430

Ala Glu Gln Phe Ser Lys Asp Asn Gly Thr Pro Met Ser Ala Asp Asp
        435                 440                 445

Leu Thr Trp Ser Tyr Ala Ala Phe Leu Ser Ala Thr Glu Arg Arg Ala
        450                 455                 460

Gly Ile Val Pro Pro Thr Trp Gln Lys Ser Val Pro Ala Val Pro Asn
465                 470                 475                 480

Ser Cys Gly Ser Ser Thr Val Val Gly Ser Tyr Thr Ser Ala Thr Gln
                485                 490                 495

Thr Ser Phe Pro Pro Ser Gln Thr Pro Gln Asp Gly Val Pro Thr Pro
        500                 505                 510

Thr Gly Pro Thr Pro Thr Asp Gly Gly Pro Thr Ser Ser Pro Thr Ser
        515                 520                 525
```

| | | | | | | | | | | | |
|---|---|---|---|---|---|---|---|---|---|---|---|
|Cys|Ala|Ile|Ala|Thr|Ser|Val|Asp|Val|Thr|Phe|Asn|Glu|Val|Val|Lys|
| | | |530| | |535| | | |540| |

Thr Glu Tyr Gly Asp Thr Ile Lys Ile Val Gly Ser Ile Ala Ala Leu
545            550                555                560

Gly Ser Trp Asp Thr Thr Lys Ala Ile Ser Leu Ser Ala Ser Asp Tyr
              565                570                575

Thr Ala Ser Asn Pro Leu Trp Lys Thr Thr Ile Ser Leu Thr Ala Gly
            580                585                590

Gln Ser Phe Glu Tyr Lys Tyr Ile Asn Ile Lys Lys Asp Gly Ser Leu
        595                600                605

Val Trp Glu Arg Asp Pro Asn Arg Ser Tyr Thr Val Pro Lys Thr Cys
    610                615                620

Glu Thr Lys Ala Thr Lys Ser Asp Ser Trp Gln Gly
625                630                635

<210> SEQ ID NO 29
<211> LENGTH: 1767
<212> TYPE: DNA
<213> ORGANISM: Unknown
<220> FEATURE:
<223> OTHER INFORMATION: Obtained from an environmental sample

<400> SEQUENCE: 29

```
atgcttttct cgtcgcttct tcgtgccttg tcagcctcgc ttttggcggg cgctgtccag    60
ggctcaccgg ccaatctcca tgcgcgccaa acctctgtcg accaattcat tcaaacccag   120
gccgaaatat ccatcaaggg ggttctagcg aacatcggtg cagatggatc caaagcccaa   180
ggagcccctg ccgggatcgt cgttgcaagt ccatctcgtt ctaatccaga ctattggtat   240
acctggacca gagacgcagc attgacatac aaggccctca ttgagcgctt tgtcgatggt   300
gatacttctc tccgcacaaa ggtcgacgag tatgtctcag cgcaagcata cctgcaaggc   360
gtgtccaatc catcaggggg gcccgactct ggaggcctag agagcccaa attcaacgta    420
gaccgcaccg ctttcacagg agcatggggg cgaccacagc gtgatgggcc tccgcttcgt   480
gctacagctc tgatcatcta cgcaaactgg ctggttgcaa acgggcagca gagtcaagca   540
ctcaacactg tgtggccggt cattgcaaag gacttggcgt acaccgttcg atactggaac   600
cagacaggct ttgatctgtg ggaagaagta acggatcat cttcttcac gctgtctgcg     660
tcccacagag cgcttgtcga gggcaatgca cttgctcaga actcggaca aacttgcacc    720
ggatgcgcga acgctgcacc ccaggttctc tgctttgtgc aaagcttttg acaggcagc    780
tatattgatt ctaatatcaa tgttaacgat gggcgtacgg gcaaggatgc aaactcaatt   840
ctgtcatcta tccatacgtt tgacccggag gctggatgca ctgatgccac attccaacct   900
tgttcttccc gtgctcttgc aaaccacaag gcagtcactg actctttccg atccgtgtat   960
ggcatcaacc gtggaattgc tcaaggcagt gcagtggccg tgggcaggta ctctgaagat  1020
gtgtattaca acggcaaccc atggtatctt accactctcg ccgctgccga gcaactatac  1080
tctgcgatct atcagtggaa taagaaaggc tccatcaccg tagatgcagt atccctcccc  1140
ttcttccgcg atctagtacc atccatcgcg acaggaacat atgccagcag ctcgtcaacc  1200
tacacatcca tcgtctcagc agtaaagacg tacgcagacg gttacatcag cgtgatccag  1260
aaatacacgc cctcgaacgg cgcgctcgcc gagcaattcg aaaagagcaa tggatcacca  1320
ctgtccgccg cagacctcac ctggtcctac gccgcgttcc tcaccgcaac agagcggcgc  1380
gcaggcgtcg taagtcccac ctggggcgaa cccaccaaca cgttcccccc atcaacctgc  1440
actggcacac ccgcctgcaa cgcgcgcatc acgttcaacg tgcgcgccac caccacgttc  1500
```

```
ggcgacaaca tcttcatcgt ggggcagctg acacagctgg gtaattggga tcctgcgagc   1560
gccgtgccgc tcagtgccag caagtatact agcagcgatc cgttgtggta tgccgatatc   1620
aatctcccgg ccgagacaac gtttgagtac aagtatattc gcaagacgag tgcagggcag   1680
gtggtgtggg agagtgatcc gaatagacgg tatacgacgt ctgcggggtg tggaagtagt   1740
gcgacggtga atgattcttg gaggtag                                       1767

<210> SEQ ID NO 30
<211> LENGTH: 588
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (42)...(458)
<223> OTHER INFORMATION: Glycosyl hydrolases family 15
<220> FEATURE:
<221> NAME/KEY: DOMAIN
<222> LOCATION: (487)...(583)
<223> OTHER INFORMATION: Starch binding domain
<220> FEATURE:
<221> NAME/KEY: SITE
<222> LOCATION: (203)...(206)
<223> OTHER INFORMATION: N-glycosylation site. Prosite id = PS00001
<220> FEATURE:
<221> NAME/KEY: SITE
<222> LOCATION: (205)...(215)
<223> OTHER INFORMATION: Glucoamylase active site region signature.
      Prosite id = PS00820
<220> FEATURE:
<221> NAME/KEY: SITE
<222> LOCATION: (214)...(217)
<223> OTHER INFORMATION: N-glycosylation site. Prosite id = PS00001

<400> SEQUENCE: 30

Met Leu Phe Ser Ser Leu Leu Arg Ala Leu Ser Ala Ser Leu Leu Ala
1               5                   10                  15

Gly Ala Val Gln Gly Ser Pro Ala Asn Leu His Ala Arg Gln Thr Ser
            20                  25                  30

Val Asp Gln Phe Ile Gln Thr Gln Ala Glu Ile Ser Ile Lys Gly Val
        35                  40                  45

Leu Ala Asn Ile Gly Ala Asp Gly Ser Lys Ala Gln Gly Ala Pro Ala
    50                  55                  60

Gly Ile Val Val Ala Ser Pro Ser Arg Ser Asn Pro Asp Tyr Trp Tyr
65                  70                  75                  80

Thr Trp Thr Arg Asp Ala Ala Leu Thr Tyr Lys Ala Leu Ile Glu Arg
                85                  90                  95

Phe Val Asp Gly Asp Thr Ser Leu Arg Thr Lys Val Asp Glu Tyr Val
            100                 105                 110

Ser Ala Gln Ala Tyr Leu Gln Gly Val Ser Asn Pro Ser Gly Gly Pro
        115                 120                 125

Asp Ser Gly Gly Leu Gly Glu Pro Lys Phe Asn Val Asp Arg Thr Ala
    130                 135                 140

Phe Thr Gly Ala Trp Gly Arg Pro Gln Arg Asp Gly Pro Pro Leu Arg
145                 150                 155                 160

Ala Thr Ala Leu Ile Ile Tyr Ala Asn Trp Leu Val Ala Asn Gly Gln
                165                 170                 175

Gln Ser Gln Ala Leu Asn Thr Val Trp Pro Val Ile Ala Lys Asp Leu
            180                 185                 190
```

```
Ala Tyr Thr Val Arg Tyr Trp Asn Gln Thr Gly Phe Asp Leu Trp Glu
        195                 200                 205

Glu Val Asn Gly Ser Ser Phe Phe Thr Leu Ser Ala Ser His Arg Ala
        210                 215                 220

Leu Val Glu Gly Asn Ala Leu Ala Gln Lys Leu Gly Gln Thr Cys Thr
225                 230                 235                 240

Gly Cys Ala Asn Ala Ala Pro Gln Val Leu Cys Phe Val Gln Ser Phe
                245                 250                 255

Trp Thr Gly Ser Tyr Ile Asp Ser Asn Ile Asn Val Asn Asp Gly Arg
                260                 265                 270

Thr Gly Lys Asp Ala Asn Ser Ile Leu Ser Ser Ile His Thr Phe Asp
        275                 280                 285

Pro Glu Ala Gly Cys Thr Asp Ala Thr Phe Pro Cys Ser Ser Arg
        290                 295                 300

Ala Leu Ala Asn His Lys Ala Val Thr Asp Ser Phe Arg Ser Val Tyr
305                 310                 315                 320

Gly Ile Asn Arg Gly Ile Ala Gln Gly Ser Ala Val Ala Val Gly Arg
                325                 330                 335

Tyr Ser Glu Asp Val Tyr Tyr Asn Gly Asn Pro Trp Tyr Leu Thr Thr
                340                 345                 350

Leu Ala Ala Ala Glu Gln Leu Tyr Ser Ala Ile Tyr Gln Trp Asn Lys
355                 360                 365

Lys Gly Ser Ile Thr Val Asp Ala Val Ser Leu Pro Phe Phe Arg Asp
        370                 375                 380

Leu Val Pro Ser Ile Ala Thr Gly Thr Tyr Ala Ser Ser Ser Ser Thr
385                 390                 395                 400

Tyr Thr Ser Ile Val Ser Ala Val Lys Thr Tyr Ala Asp Gly Tyr Ile
                405                 410                 415

Ser Val Ile Gln Lys Tyr Thr Pro Ser Asn Gly Ala Leu Ala Glu Gln
                420                 425                 430

Phe Glu Lys Ser Asn Gly Ser Pro Leu Ser Ala Ala Asp Leu Thr Trp
        435                 440                 445

Ser Tyr Ala Ala Phe Leu Thr Ala Thr Glu Arg Arg Ala Gly Val Val
        450                 455                 460

Ser Pro Thr Trp Gly Glu Pro Thr Asn Asn Val Pro Pro Ser Thr Cys
465                 470                 475                 480

Thr Gly Thr Pro Ala Cys Asn Ala Arg Ile Thr Phe Asn Val Arg Ala
                485                 490                 495

Thr Thr Thr Phe Gly Asp Asn Ile Phe Ile Val Gly Gln Leu Thr Gln
                500                 505                 510

Leu Gly Asn Trp Asp Pro Ala Ser Ala Val Pro Leu Ser Ala Ser Lys
        515                 520                 525

Tyr Thr Ser Ser Asp Pro Leu Trp Tyr Ala Asp Ile Asn Leu Pro Ala
        530                 535                 540

Glu Thr Thr Phe Glu Tyr Lys Tyr Ile Arg Lys Thr Ser Ala Gly Gln
545                 550                 555                 560

Val Val Trp Glu Ser Asp Pro Asn Arg Arg Tyr Thr Thr Ser Ala Gly
                565                 570                 575

Cys Gly Ser Ser Ala Thr Val Asn Asp Ser Trp Arg
                580                 585

<210> SEQ ID NO 31
<211> LENGTH: 1479
<212> TYPE: DNA
```

```
<213> ORGANISM: Unknown
<220> FEATURE:
<223> OTHER INFORMATION: Obtained from an environmental sample

<400> SEQUENCE: 31
atggttctag ctcggcttgc ctggcttgcc ggcctggtta gcactgccat tgctgcgacc      60
ccagcggaat ggcgctcgca gtccatctac ttcatgctca cggatcgttt tgcccggacc     120
gatggttcaa ctactgctgc ctgtgatacc gctgacagaa atactgtgg cggaacctgg      180
cagggtatca ttgacaagct ggactatatc caaggaatgg gctttacggc catttggatc     240
actccggtga ccggtcaatt gagcggggaa accgcgtacg gagatcccta tcacggatac     300
tggcagcagg atatctactc tctcgattcc aactatggaa ccgcagacga tctcaaggcc     360
ctcgctgcgg cttgcacaa acgcgacatg tatctcatgg tcgatgtcgt agcaaaccac     420
atgggctaca atggcgcagg tgctgacgtg gactacacca aattcaaccc cttcaacgat     480
gcaaagtatt tccactccta ctgcccaatc accgattaca acgacgacac catgtcgcaa     540
aactgctggc ttggcgataa caaggtctcg ctaccggatc tgaatacaca gagcaaggag     600
gtgcaggatc tatggtatga ctgggttgga tctttggtct ccaactactc catcgatgga     660
cttcgcgtcg acacagtcaa acatgtccag aaagatttct ggcccggcta acaaaagcc      720
gcgggcgtct actgcgtagg cgaaatcctt gatggtgacc cagattacac ctatccatac     780
caggaggtaa tggacggagt gctcaactac ccgatttact acccactcct caaggccttc     840
cagtcgagct cgggaagcat gaccgatctg tacaacatga tcaacacggt gaaatcgacc     900
tgcaaggact caacccttct tggaaatttc ttggagaacc acgataaccc acgttttgcc     960
catgccaccg atgacattgc cctcgccaag aacgcagcca catttaccat tatggcagat    1020
ggcattccta ttgtctatgc aggacaggag cagcactaca gtggtggcga ggacccggct    1080
aatcgcgagg ctctgtggtt atccggatac aacaccgaca gcgagctgta caagctcatt    1140
gccaaggcca atggtgctag aaaccaggcc attgctaaga gtaccaatta tactatttac    1200
cagaaccacc caatctacaa agacgagagc gccatcgcca tgcggaaggg cttcgtcggt    1260
ggacagacaa tcactgtcct gacgaatctc ggtgcagggg gtaaagagta ttcagtttca    1320
attcctgata ctggattcaa ggctggtgcg aagttgactg aggttgtgtc ctgcactagt    1380
gttactgttg gtgatagtgg ggaggtgtct gttcctatgg cgagtggagc gccgaggatc    1440
ttgctcccca cgtctttgct cgagggctcg gctctgtgc                            1479

<210> SEQ ID NO 32
<211> LENGTH: 493
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(18)
<220> FEATURE:
<221> NAME/KEY: DOMAIN
<222> LOCATION: (31)...(387)
<223> OTHER INFORMATION: Alpha amylase, catalytic domain
<220> FEATURE:
<221> NAME/KEY: SITE
<222> LOCATION: (197)...(200)
<223> OTHER INFORMATION: N-glycosylation site. Prosite id = PS00001
<220> FEATURE:
<221> NAME/KEY: SITE
<222> LOCATION: (218)...(221)
<223> OTHER INFORMATION: N-glycosylation site. Prosite id = PS00001
<220> FEATURE:
<221> NAME/KEY: SITE
```

<222> LOCATION: (402)...(405)
<223> OTHER INFORMATION: N-glycosylation site. Prosite id = PS00001

<400> SEQUENCE: 32

```
Met Val Leu Ala Arg Leu Ala Trp Leu Ala Gly Leu Val Ser Thr Ala
1               5                   10                  15
Ile Ala Ala Thr Pro Ala Glu Trp Arg Ser Gln Ser Ile Tyr Phe Met
                20                  25                  30
Leu Thr Asp Arg Phe Ala Arg Thr Asp Gly Ser Thr Thr Ala Ala Cys
            35                  40                  45
Asp Thr Ala Asp Arg Lys Tyr Cys Gly Gly Thr Trp Gln Gly Ile Ile
        50                  55                  60
Asp Lys Leu Asp Tyr Ile Gln Gly Met Gly Phe Thr Ala Ile Trp Ile
65                  70                  75                  80
Thr Pro Val Thr Gly Gln Leu Ser Gly Glu Thr Ala Tyr Gly Asp Pro
                85                  90                  95
Tyr His Gly Tyr Trp Gln Gln Asp Ile Tyr Ser Leu Asn Ser Asn Tyr
            100                 105                 110
Gly Thr Ala Asp Asp Leu Lys Ala Leu Ala Ala Ala Leu His Lys Arg
        115                 120                 125
Asp Met Tyr Leu Met Val Asp Val Val Ala Asn His Met Gly Tyr Asn
130                 135                 140
Gly Ala Gly Ala Asp Val Asp Tyr Thr Lys Phe Asn Pro Phe Asn Asp
145                 150                 155                 160
Ala Lys Tyr Phe His Ser Tyr Cys Pro Ile Thr Asp Tyr Asn Asp Asp
                165                 170                 175
Thr Met Ser Gln Asn Cys Trp Leu Gly Asp Asn Lys Val Ser Leu Pro
            180                 185                 190
Asp Leu Asn Thr Gln Ser Lys Glu Val Gln Asp Leu Trp Tyr Asp Trp
        195                 200                 205
Val Gly Ser Leu Val Ser Asn Tyr Ser Ile Asp Gly Leu Arg Val Asp
        210                 215                 220
Thr Val Lys His Val Gln Lys Asp Phe Trp Pro Gly Tyr Asn Lys Ala
225                 230                 235                 240
Ala Gly Val Tyr Cys Val Gly Glu Ile Leu Asp Gly Asp Pro Asp Tyr
                245                 250                 255
Thr Tyr Pro Tyr Gln Glu Val Met Asp Gly Val Leu Asn Tyr Pro Ile
            260                 265                 270
Tyr Tyr Pro Leu Leu Lys Ala Phe Gln Ser Ser Ser Gly Ser Met Thr
        275                 280                 285
Asp Leu Tyr Asn Met Ile Asn Thr Val Lys Ser Thr Cys Lys Asp Ser
290                 295                 300
Thr Leu Leu Gly Asn Phe Leu Glu Asn His Asp Asn Pro Arg Phe Ala
305                 310                 315                 320
His Ala Thr Asp Asp Ile Ala Leu Ala Lys Asn Ala Ala Thr Phe Thr
                325                 330                 335
Ile Met Ala Asp Gly Ile Pro Ile Val Tyr Ala Gly Gln Glu Gln His
            340                 345                 350
Tyr Ser Gly Gly Glu Asp Pro Ala Asn Arg Glu Ala Leu Trp Leu Ser
        355                 360                 365
Gly Tyr Asn Thr Asp Ser Glu Leu Tyr Lys Leu Ile Ala Lys Ala Asn
        370                 375                 380
Gly Ala Arg Asn Gln Ala Ile Ala Lys Ser Thr Asn Tyr Thr Ile Tyr
385                 390                 395                 400
```

```
Gln Asn His Pro Ile Tyr Lys Asp Glu Ser Ala Ile Ala Met Arg Lys
                405                 410                 415
Gly Phe Val Gly Gly Gln Thr Ile Thr Val Leu Thr Asn Leu Gly Ala
            420                 425                 430
Gly Gly Lys Glu Tyr Ser Val Ser Ile Pro Asp Thr Gly Phe Lys Ala
        435                 440                 445
Gly Ala Lys Leu Thr Glu Val Val Ser Cys Thr Ser Val Thr Val Gly
    450                 455                 460
Asp Ser Gly Glu Val Ser Val Pro Met Ala Ser Gly Ala Pro Arg Ile
465                 470                 475                 480
Leu Leu Pro Thr Ser Leu Leu Glu Gly Ser Ala Leu Cys
                485                 490
```

<210> SEQ ID NO 33
<211> LENGTH: 1485
<212> TYPE: DNA
<213> ORGANISM: Unknown
<220> FEATURE:
<223> OTHER INFORMATION: Obtained from an environmental sample

<400> SEQUENCE: 33

```
atggtaggct tcaatatctt gactctcgcc ttgctggccc cagctgcact ctcatctgct      60
gtccaccctc accggcgcca gtctggactt gatgccttta ttcagtccga gtcatcggtt     120
tcactccaag gcattctgaa caatatcgga gccaatggct ctgctgtttc aggcgcatcc     180
gccggtgtag ttgttgcgtc accatccaag tcagaccccg attatttta cacttggact     240
cgcgatgcgg ccctgacact cgcggtactg attgaccaat tcatcgcggg agaaagctcc     300
ctagagacgg tcatccagca gtacatctcc gcccaagcaa aactgcagac agtgtccaac     360
ccatcaggag acctgtccga cggttcaggt ctggcagagc ccaaattcca aaccgatctc     420
agcgccttca ctagatcctg gggtcgacct caacgcgatg acctgctct ccgtgcgaca     480
gcgctcatcg tgtacggaaa tcacctcctc tcttccggaa agcagtccgt cgtcaaatcc     540
aacatctggc cgatcgtgca gaacgatctc aactacgtgg cacagtactg gaaccagact     600
ggtttcgatc tgtgggaaga ggtccagggc tcgtcctttt tcaccatcgc agcgcaacac     660
cgtgccctgg tggagggagc tgcattcgcc aaatcgctcg gagaggcctg tgatggctgt     720
gattcacagg ctccgcaggt tctttgcttc ctccaggact tctggaatgg aaatgctgtt     780
gtttctaatc tggcaaatga tggtcgctca gggttggatg ccaattctat cctcagctcg     840
atccagacct tcgatcctag tgccacttgc gatgatagca cttccagcc atgctctggt     900
cgtgcactgc taaaccacaa ggcggtggtt gattctttcc gatccatcta caacattaac     960
agtggtaaag aagctggcaa agccgtggct gttggtcgct atgccgaaga cacctaccag    1020
ggaggcaacc cttggtatct cgctactgct gctgccgccg agcagctgta tgatgctctc    1080
taccagtgga gaaacaggg atcgctggcg attacccaga cgagtcttcc cttcttccag    1140
gatttggact cgactgctcg tgttggcaat tactccagct cttcctcaac ctacacctct    1200
ttgactggcg ctgtcaagac ctatgcggat ggtttcctat cgattgttca gcagtatacg    1260
cccagcaatg gagctctggc cgagcagttc acgcgagaca atggcacccc cgtctctgca    1320
cacgacctga cctggtctta tgcatcattt ttgactgctg ccgaccgtcg caatggaatt    1380
gtccctgcta gctggggtgc atctaaggcc aaccaagtgc cgacgcagtg ccagggcagt    1440
tcagcgacgg ggtcttatac tacgccaact gtggggtcct ggtga                    1485
```

<210> SEQ ID NO 34

```
<211> LENGTH: 494
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (39)...(455)
<223> OTHER INFORMATION: Glycosyl hydrolases family 15
<220> FEATURE:
<221> NAME/KEY: SITE
<222> LOCATION: (52)...(55)
<223> OTHER INFORMATION: N-glycosylation site. Prosite id = PS00001
<220> FEATURE:
<221> NAME/KEY: SITE
<222> LOCATION: (201)...(204)
<223> OTHER INFORMATION: N-glycosylation site. Prosite id = PS00001
<220> FEATURE:
<221> NAME/KEY: SITE
<222> LOCATION: (203)...(213)
<223> OTHER INFORMATION: Glucoamylase active site region signature.
      Prosite id = PS00820

<400> SEQUENCE: 34

Met Val Gly Phe Asn Ile Leu Thr Leu Ala Leu Leu Ala Pro Ala Ala
1               5                   10                  15

Leu Ser Ser Ala Val His Pro His Arg Arg Gln Ser Gly Leu Asp Ala
                20                  25                  30

Phe Ile Gln Ser Glu Ser Ser Val Ser Leu Gln Gly Ile Leu Asn Asn
            35                  40                  45

Ile Gly Ala Asn Gly Ser Ala Val Ser Gly Ala Ser Ala Gly Val Val
        50                  55                  60

Val Ala Ser Pro Ser Lys Ser Asp Pro Asp Tyr Phe Tyr Thr Trp Thr
65                  70                  75                  80

Arg Asp Ala Ala Leu Thr Leu Ala Val Leu Ile Asp Gln Phe Ile Ala
                85                  90                  95

Gly Glu Ser Ser Leu Glu Thr Val Ile Gln Gln Tyr Ile Ser Ala Gln
            100                 105                 110

Ala Lys Leu Gln Thr Val Ser Asn Pro Ser Gly Asp Leu Ser Asp Gly
        115                 120                 125

Ser Gly Leu Ala Glu Pro Lys Phe Gln Thr Asp Leu Ser Ala Phe Thr
130                 135                 140

Arg Ser Trp Gly Arg Pro Gln Arg Asp Gly Pro Ala Leu Arg Ala Thr
145                 150                 155                 160

Ala Leu Ile Val Tyr Gly Asn His Leu Leu Ser Ser Gly Lys Gln Ser
                165                 170                 175

Val Val Lys Ser Asn Ile Trp Pro Ile Val Gln Asn Asp Leu Asn Tyr
            180                 185                 190

Val Ala Gln Tyr Trp Asn Gln Thr Gly Phe Asp Leu Trp Glu Glu Val
        195                 200                 205

Gln Gly Ser Ser Phe Phe Thr Ile Ala Ala Gln His Arg Ala Leu Val
210                 215                 220

Glu Gly Ala Ala Phe Ala Lys Ser Leu Gly Glu Ala Cys Asp Gly Cys
225                 230                 235                 240

Asp Ser Gln Ala Pro Gln Val Leu Cys Phe Leu Gln Asp Phe Trp Asn
                245                 250                 255

Gly Asn Ala Val Val Ser Asn Leu Ala Asn Asp Gly Arg Ser Gly Leu
            260                 265                 270

Asp Ala Asn Ser Ile Leu Ser Ser Ile Gln Thr Phe Asp Pro Ser Ala
        275                 280                 285

Thr Cys Asp Asp Ser Thr Phe Gln Pro Cys Ser Gly Arg Ala Leu Leu
```

```
                290                 295                 300
Asn His Lys Ala Val Val Asp Ser Phe Arg Ser Ile Tyr Asn Ile Asn
305                 310                 315                 320

Ser Gly Lys Glu Ala Gly Lys Ala Val Ala Val Gly Arg Tyr Ala Glu
                325                 330                 335

Asp Thr Tyr Gln Gly Gly Asn Pro Trp Tyr Leu Ala Thr Ala Ala Ala
                340                 345                 350

Ala Glu Gln Leu Tyr Asp Ala Leu Tyr Gln Trp Lys Lys Gln Gly Ser
                355                 360                 365

Leu Ala Ile Thr Gln Thr Ser Leu Pro Phe Phe Gln Asp Leu Asp Ser
                370                 375                 380

Thr Ala Arg Val Gly Asn Tyr Ser Ser Ser Ser Thr Tyr Thr Ser
385                 390                 395                 400

Leu Thr Gly Ala Val Lys Thr Tyr Ala Asp Gly Phe Leu Ser Ile Val
                405                 410                 415

Gln Gln Tyr Thr Pro Ser Asn Gly Ala Leu Ala Glu Gln Phe Thr Arg
                420                 425                 430

Asp Asn Gly Thr Pro Val Ser Ala His Asp Leu Thr Trp Ser Tyr Ala
                435                 440                 445

Ser Phe Leu Thr Ala Ala Asp Arg Arg Asn Gly Ile Val Pro Ala Ser
                450                 455                 460

Trp Gly Ala Ser Lys Ala Asn Gln Val Pro Thr Gln Cys Gln Gly Ser
465                 470                 475                 480

Ser Ala Thr Gly Ser Tyr Thr Thr Pro Thr Val Gly Ser Trp
                485                 490

<210> SEQ ID NO 35
<211> LENGTH: 1914
<212> TYPE: DNA
<213> ORGANISM: Unknown
<220> FEATURE:
<223> OTHER INFORMATION: Obtained from an environmental sample

<400> SEQUENCE: 35
atggctcctc gtttttggac tacgctgtgt gcgctgactc ttggttcagc tgcgctggcc      60
gcgccacagt tggcaccgcg tgcaactggt agcttggaca cttggctggc atccgagaaa     120
gctgttgcaa gggagggtat tctcgataat atcgggtcgg atgggcgta tgctaagagc      180 tcgaagtcgg ggattgtcat tgccagtccg agtacagaca gtcccgatta ttactacact     240
tggactcgtg actcggccct ggtcatgaag accttggtgg acctgttcaa gaatggcgat     300
accgaccttc tcaccgttat cgaggagtac atcagctccc aggcctatat ccagaccgtt     360
tccaacccat ctggaagtct ttcgagtggt ggactcggtg aacccaagtt caatgttgat     420
gaaacatcgt ataccggatc ttggggtcga cctcagcgcg atggtcctgc actccgagct     480
actgcactgg ttgccttcgg acagtggttg attgacaacg atatacatc taccgccacc     540 gatattgtgt ggccaattgt tcgcaatgat ctttcctacg tcgcacaata ctggaacagc     600
tctggatacg acctatggga agaggtcaac ggtgaatcat tcttcaccac cgccgttcaa     660
caccgtgctt tggtcgaggg cagcaagttc gccagccagg tgggatcatc ttgctcctac     720
tgcgactctc aggcaccccca ggttctctgc ttccttcaat catactggac cggctcgtac     780
actctagcca atttcggtag cagccgcaca ggcaaagacg cgaacaccct cctgggcagc     840
attcacacat cgaccccga ggcaggatgc gatgacacga ccttccagcc ttgctcggcc     900
cgcgcgctgg caaatcacaa ggtcgtcact gactcgttcc gctctattta taccgtcaat     960
```

-continued

```
tcaggcaaga gtgcgggaca agcagtggca gttggtcgat accccgagga ttcttactac    1020
aatggtaacc catggtactt gtgcactatg gctgctgccg agcttctcta cgatgctttg    1080
taccaatgga ataaagctgg ctctttgacc atcagcagcg tctcgctgag cttcttcacc    1140
gacctgtaca gctcagctgc aactggtacc tattcatcat ccagttctac gttctcatcg    1200
atagtcagcg cggtgaagac ctacgcggat ggctacatga gcattgccga gcaatatgcc    1260
tatacgaacg gctctatgtc tgaacaattc tccaagtctg atggaactcc agagtctgcc    1320
cgtgacctga cttggtcata tgcagccctg cttaccgcaa acatgcgtcg caactcggtt    1380
gttcccccaa cctggggcga gacatctgca agcagcgtcc cgggaacatg ctccgcgacg    1440
tcggcgacgg gaacctacag cactgcaacc aacacgaact ggcccgtcac attgactggt    1500
ggatcgggct ctactactac tggtggaaca acgaccagca aaaccagcac caccacaact    1560
tccaagacga gcactaccac tacatcatgc acgactccaa ctagtgtggc agttacattt    1620
gatgttatcg cgaccacttc atacggcgag aacatcaagt tggctgggtc aattgctgcc    1680
cttggtagct gggacaccag tagcgctatt gcactaagtg cagataaata tactagctcg    1740
aacaacctat ggtatgtaac tgtgaatctg gctgctggtc aggtcattca gtacaagtat    1800
atccgggttg aaagtgatag tacgattgag tgggagagtg atccgaaccg ctcttatact    1860
gtgccagcag cctgtgccac aactgccgtg acaatcagcg acacttggcg gtaa          1914
```

<210> SEQ ID NO 36
<211> LENGTH: 637
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(20)
<220> FEATURE:
<221> NAME/KEY: DOMAIN
<222> LOCATION: (41)...(455)
<223> OTHER INFORMATION: Glycosyl hydrolases family 15
<220> FEATURE:
<221> NAME/KEY: DOMAIN
<222> LOCATION: (535)...(631)
<223> OTHER INFORMATION: Starch binding domain
<220> FEATURE:
<221> NAME/KEY: SITE
<222> LOCATION: (202)...(205)
<223> OTHER INFORMATION: N-glycosylation site. Prosite id = PS00001
<220> FEATURE:
<221> NAME/KEY: SITE
<222> LOCATION: (204)...(214)
<223> OTHER INFORMATION: Glucoamylase active site region signature.
      Prosite id = PS00820
<220> FEATURE:
<221> NAME/KEY: SITE
<222> LOCATION: (429)...(432)
<223> OTHER INFORMATION: N-glycosylation site. Prosite id = PS00001
<220> FEATURE:
<221> NAME/KEY: SITE
<222> LOCATION: (625)...(628)
<223> OTHER INFORMATION: N-glycosylation site. Prosite id = PS00001

<400> SEQUENCE: 36

Met Ala Pro Arg Phe Trp Thr Thr Leu Cys Ala Leu Thr Leu Gly Ser
1               5                   10                  15

Ala Ala Leu Ala Ala Pro Gln Leu Ala Pro Arg Ala Thr Gly Ser Leu
            20                  25                  30

Asp Thr Trp Leu Ala Ser Glu Lys Ala Val Ala Arg Glu Gly Ile Leu
        35                  40                  45

Asp Asn Ile Gly Ser Asp Gly Ala Tyr Ala Lys Ser Ser Lys Ser Gly

```
                50                  55                  60
Ile Val Ile Ala Ser Pro Ser Thr Asp Ser Pro Asp Tyr Tyr Tyr Thr
65                  70                  75                  80

Trp Thr Arg Asp Ser Ala Leu Val Met Lys Thr Leu Val Asp Leu Phe
                85                  90                  95

Lys Asn Gly Asp Thr Asp Leu Leu Thr Val Ile Glu Glu Tyr Ile Ser
                100                 105                 110

Ser Gln Ala Tyr Ile Gln Thr Val Ser Asn Pro Ser Gly Ser Leu Ser
                115                 120                 125

Ser Gly Gly Leu Gly Glu Pro Lys Phe Asn Val Asp Glu Thr Ser Tyr
130                 135                 140

Thr Gly Ser Trp Gly Arg Pro Gln Arg Asp Gly Pro Ala Leu Arg Ala
145                 150                 155                 160

Thr Ala Leu Val Ala Phe Gly Gln Trp Leu Ile Asp Asn Gly Tyr Thr
                165                 170                 175

Ser Thr Ala Thr Asp Ile Val Trp Pro Ile Val Arg Asn Asp Leu Ser
                180                 185                 190

Tyr Val Ala Gln Tyr Trp Asn Ser Ser Gly Tyr Asp Leu Trp Glu Glu
                195                 200                 205

Val Asn Gly Glu Ser Phe Phe Thr Thr Ala Val Gln His Arg Ala Leu
210                 215                 220

Val Glu Gly Ser Lys Phe Ala Ser Gln Val Gly Ser Ser Cys Ser Tyr
225                 230                 235                 240

Cys Asp Ser Gln Ala Pro Gln Val Leu Cys Phe Leu Gln Ser Tyr Trp
                245                 250                 255

Thr Gly Ser Tyr Thr Leu Ala Asn Phe Gly Ser Ser Arg Thr Gly Lys
                260                 265                 270

Asp Ala Asn Thr Leu Leu Gly Ser Ile His Thr Phe Asp Pro Glu Ala
                275                 280                 285

Gly Cys Asp Asp Thr Thr Phe Gln Pro Cys Ser Ala Arg Ala Leu Ala
                290                 295                 300

Asn His Lys Val Val Thr Asp Ser Phe Arg Ser Ile Tyr Thr Val Asn
305                 310                 315                 320

Ser Gly Lys Ser Ala Gly Gln Ala Val Ala Val Gly Arg Tyr Pro Glu
                325                 330                 335

Asp Ser Tyr Tyr Asn Gly Asn Pro Trp Tyr Leu Cys Thr Met Ala Ala
                340                 345                 350

Ala Glu Leu Leu Tyr Asp Ala Leu Tyr Gln Trp Asn Lys Ala Gly Ser
                355                 360                 365

Leu Thr Ile Ser Ser Val Ser Leu Ser Phe Phe Thr Asp Leu Tyr Ser
370                 375                 380

Ser Ala Ala Thr Gly Thr Tyr Ser Ser Ser Ser Thr Phe Ser Ser
385                 390                 395                 400

Ile Val Ser Ala Val Lys Thr Tyr Ala Asp Gly Tyr Met Ser Ile Ala
                405                 410                 415

Glu Gln Tyr Ala Tyr Thr Asn Gly Ser Met Ser Glu Gln Phe Ser Lys
                420                 425                 430

Ser Asp Gly Thr Pro Glu Ser Ala Arg Asp Leu Thr Trp Ser Tyr Ala
                435                 440                 445

Ala Leu Leu Thr Ala Asn Met Arg Arg Asn Ser Val Val Pro Pro Thr
                450                 455                 460

Trp Gly Glu Thr Ser Ala Ser Ser Val Pro Gly Thr Cys Ser Ala Thr
465                 470                 475                 480
```

```
Ser Ala Thr Gly Thr Tyr Ser Thr Ala Thr Asn Thr Asn Trp Pro Val
            485                 490                 495

Thr Leu Thr Gly Gly Ser Gly Ser Thr Thr Gly Gly Thr Thr Thr
            500                 505                 510

Ser Lys Thr Ser Thr Thr Thr Ser Lys Thr Ser Thr Thr Thr
            515                 520                 525

Ser Cys Thr Thr Pro Thr Ser Val Ala Val Thr Phe Asp Val Ile Ala
            530                 535                 540

Thr Thr Ser Tyr Gly Glu Asn Ile Lys Leu Ala Gly Ser Ile Ala Ala
545                 550                 555                 560

Leu Gly Ser Trp Asp Thr Ser Ser Ala Ile Ala Leu Ser Ala Asp Lys
            565                 570                 575

Tyr Thr Ser Ser Asn Asn Leu Trp Tyr Val Thr Val Asn Leu Ala Ala
            580                 585                 590

Gly Gln Val Ile Gln Tyr Lys Tyr Ile Arg Val Glu Ser Asp Ser Thr
            595                 600                 605

Ile Glu Trp Glu Ser Asp Pro Asn Arg Ser Tyr Thr Val Pro Ala Ala
            610                 615                 620

Cys Ala Thr Thr Ala Val Thr Ile Ser Asp Thr Trp Arg
625                 630                 635
```

<210> SEQ ID NO 37
<211> LENGTH: 1923
<212> TYPE: DNA
<213> ORGANISM: Unknown
<220> FEATURE:
<223> OTHER INFORMATION: Obtained from an environmental sample

<400> SEQUENCE: 37

| | | | | | |
|---|---|---|---|---|---|
| atggctcctc | gattctggat | tgcgctttgg | gcgcttactt | tcggtcaggc | gatcgctgcg | 60 |
| ccgcagatcg | ccttggcacc | tcgcgcgaca | ggtagcttgg | acacctggtt | ggcatcggag | 120 |
| accacggtgg | ccagacaagg | tatcctgaac | aatatcggtt | ccgctggcgc | gtattctgcg | 180 |
| agcgcgaagc | cgggaatcct | gattgctagt | cctagcactt | ccagtcccga | ttattactac | 240 |
| acatggaccc | gtgactctgc | tttggtcttc | aaggccttgg | tggatatgtt | caagaatggt | 300 |
| gacactgccc | ttctcactgt | gatcgaagaa | tatatcagcg | cacaggccta | tccagaca | 360 |
| gtctccaacc | cttctggtgg | tctttccagc | ggaggactcg | gagagcccaa | attcaatgtt | 420 |
| gatgagactg | ccttcaccgg | gtcttggggc | cgccccagc | gtgatggtcc | ggctctccgc | 480 |
| gcaactgcct | tgatctcatt | cggacagtgg | ctccttgaca | acggatactc | cacatacgcg | 540 |
| accaacattg | tttggccggt | tgtacgaaac | gatctctctt | acgttgctca | atactggaac | 600 |
| caaactggat | acgatctctg | gaagagggtt | tccggctcct | ccttcttcac | gattgccgcc | 660 |
| cagcaccgcg | ccttggtgga | aggtagcact | tcgccacca | gggtcggtgc | ttcgtgctca | 720 |
| tactgtgatt | ctcaggcacc | ccaggtgctg | tgcttcctcc | aatccttctg | gactggctca | 780 |
| tacacactgg | ccaactttgg | cggtggccgc | tctggcaaag | acgcgaatac | tcttctcgga | 840 |
| agcattcaca | catttgaccc | cgaggccggc | tgcgatgaca | ccaccttcca | accatgctcg | 900 |
| gctcgagcat | tggccaacca | caaggtggtg | actgactctt | tccgatcggt | ttacacaatc | 960 |
| aactctggga | ttgcggcagg | caaggctgtc | tctgttggcc | gttactcgga | ggattcttac | 1020 |
| tataatggaa | acccttggta | tctgtgtacc | ctggctgcag | cggagcagtt | atatgacgct | 1080 |
| ctttacacgt | ggaatcgggt | tggctctttg | actatcactt | ctgtctcgct | gagtttcttc | 1140 |
| aaagatttgt | acagttctgc | tgctactggt | acctactcat | cgtccagtgc | tacatactct | 1200 |

```
tcgatcgtca gcgcagtcaa gacttacgcc gatggatatg tcagtattgt ggagaactac    1260
gctctgacca atggctctat gtccgagcaa ttttcaaagt ccgatggttc tcaactgtcc    1320
gctcgtgact tgacttggtc atacgcagct cttctcactg ccaatgagcg ccgaaatgcc    1380
gtcgtcccgg cgccatgggg cgagacggcg gccagcagtg tacctgccca atgcagctcc    1440
acttctgcca ctggtacttt cagtacggcc accaacaccg catggccatc gaccctcact    1500
agcggaaccg gaagtggaac caccacgacc ggcactggga cgaccacaaa ggcaaccacc    1560
acaacttcta ccaagactac ctccacgacc acatcatgta ccacaccgac gtcggtggcg    1620
gtgacctttg atgtgattgc caccactgtg tatggagaga atatcaagct tgccggctct    1680
atttctcaac ttggctcgtg ggatacaagc agtgcgattg ctctcagcgc ttcttcttac    1740
acttcaagca accatctttg gtatgtgacg gtcacactgc ccgctggttc taccttcacc    1800
tataagtata ttcgggtcga gagtgatggc tcaatccagt gggagagtga tccaaacttg    1860
tcatacaccg tccctcaagc ttgcggcact tcagctgtca caattagcga tacttggagg    1920
tga                                                                 1923

<210> SEQ ID NO 38
<211> LENGTH: 640
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(19)
<220> FEATURE:
<221> NAME/KEY: DOMAIN
<222> LOCATION: (42)...(456)
<223> OTHER INFORMATION: Glycosyl hydrolases family 15
<220> FEATURE:
<221> NAME/KEY: DOMAIN
<222> LOCATION: (538)...(634)
<223> OTHER INFORMATION: Starch binding domain
<220> FEATURE:
<221> NAME/KEY: SITE
<222> LOCATION: (203)...(206)
<223> OTHER INFORMATION: N-glycosylation site. Prosite id = PS00001
<220> FEATURE:
<221> NAME/KEY: SITE
<222> LOCATION: (205)...(215)
<223> OTHER INFORMATION: Glucoamylase active site region signature.
      Prosite id = PS00820
<220> FEATURE:
<221> NAME/KEY: SITE
<222> LOCATION: (430)...(433)
<223> OTHER INFORMATION: N-glycosylation site. Prosite id = PS00001
<220> FEATURE:
<221> NAME/KEY: SITE
<222> LOCATION: (628)...(631)
<223> OTHER INFORMATION: N-glycosylation site. Prosite id = PS00001

<400> SEQUENCE: 38

Met Ala Pro Arg Phe Trp Ile Ala Leu Trp Ala Leu Thr Phe Gly Gln
 1               5                  10                  15

Ala Ile Ala Ala Pro Gln Ile Ala Leu Ala Pro Arg Ala Thr Gly Ser
            20                  25                  30

Leu Asp Thr Trp Leu Ala Ser Glu Thr Thr Val Ala Arg Gln Gly Ile
        35                  40                  45

Leu Asn Asn Ile Gly Ser Ala Gly Ala Tyr Ser Ala Ser Ala Lys Pro
    50                  55                  60

Gly Ile Leu Ile Ala Ser Pro Ser Thr Ser Ser Pro Asp Tyr Tyr Tyr
65                  70                  75                  80

Thr Trp Thr Arg Asp Ser Ala Leu Val Phe Lys Ala Leu Val Asp Met
```

```
                    85                  90                  95
Phe Lys Asn Gly Asp Thr Ala Leu Leu Thr Val Ile Glu Glu Tyr Ile
                100                 105                 110

Ser Ala Gln Ala Tyr Ile Gln Thr Val Ser Asn Pro Ser Gly Gly Leu
            115                 120                 125

Ser Ser Gly Gly Leu Gly Glu Pro Lys Phe Asn Val Asp Glu Thr Ala
        130                 135                 140

Phe Thr Gly Ser Trp Gly Arg Pro Gln Arg Asp Gly Pro Ala Leu Arg
145                 150                 155                 160

Ala Thr Ala Leu Ile Ser Phe Gly Gln Trp Leu Leu Asp Asn Gly Tyr
                165                 170                 175

Ser Thr Tyr Ala Thr Asn Ile Val Trp Pro Val Val Arg Asn Asp Leu
                180                 185                 190

Ser Tyr Val Ala Gln Tyr Trp Asn Gln Thr Gly Tyr Asp Leu Trp Glu
            195                 200                 205

Glu Val Ser Gly Ser Ser Phe Phe Thr Ile Ala Ala Gln His Arg Ala
        210                 215                 220

Leu Val Glu Gly Ser Thr Phe Ala Thr Arg Val Gly Ala Ser Cys Ser
225                 230                 235                 240

Tyr Cys Asp Ser Gln Ala Pro Gln Val Leu Cys Phe Leu Gln Ser Phe
                245                 250                 255

Trp Thr Gly Ser Tyr Thr Leu Ala Asn Phe Gly Gly Arg Ser Gly
            260                 265                 270

Lys Asp Ala Asn Thr Leu Leu Gly Ser Ile His Thr Phe Asp Pro Glu
        275                 280                 285

Ala Gly Cys Asp Asp Thr Thr Phe Gln Pro Cys Ser Ala Arg Ala Leu
290                 295                 300

Ala Asn His Lys Val Val Thr Asp Ser Phe Arg Ser Val Tyr Thr Ile
305                 310                 315                 320

Asn Ser Gly Ile Ala Ala Gly Lys Ala Val Ser Val Gly Arg Tyr Ser
                325                 330                 335

Glu Asp Ser Tyr Tyr Asn Gly Asn Pro Trp Tyr Leu Cys Thr Leu Ala
            340                 345                 350

Ala Ala Glu Gln Leu Tyr Asp Ala Leu Tyr Thr Trp Asn Arg Val Gly
        355                 360                 365

Ser Leu Thr Ile Thr Ser Val Ser Leu Ser Phe Phe Lys Asp Leu Tyr
    370                 375                 380

Ser Ser Ala Ala Thr Gly Thr Tyr Ser Ser Ser Ala Thr Tyr Ser
385                 390                 395                 400

Ser Ile Val Ser Ala Val Lys Thr Tyr Ala Asp Gly Tyr Val Ser Ile
                405                 410                 415

Val Glu Asn Tyr Ala Leu Thr Asn Gly Ser Met Ser Glu Gln Phe Ser
            420                 425                 430

Lys Ser Asp Gly Ser Gln Leu Ser Ala Arg Asp Leu Thr Trp Ser Tyr
        435                 440                 445

Ala Ala Leu Leu Thr Ala Asn Glu Arg Arg Asn Ala Val Val Pro Ala
450                 455                 460

Pro Trp Gly Glu Thr Ala Ala Ser Ser Val Pro Ala Gln Cys Ser Ser
465                 470                 475                 480

Thr Ser Ala Thr Gly Thr Phe Ser Thr Ala Thr Asn Thr Ala Trp Pro
                485                 490                 495

Ser Thr Leu Thr Ser Gly Thr Gly Ser Gly Thr Thr Thr Thr Gly Thr
            500                 505                 510
```

-continued

```
Gly Thr Thr Thr Lys Ala Thr Thr Thr Ser Thr Lys Thr Thr Ser
        515                 520                 525

Thr Thr Thr Ser Cys Thr Thr Pro Thr Ser Val Ala Val Thr Phe Asp
530                 535                 540

Val Ile Ala Thr Val Tyr Gly Glu Asn Ile Lys Leu Ala Gly Ser
545                 550                 555                 560

Ile Ser Gln Leu Gly Ser Trp Asp Thr Ser Ser Ala Ile Ala Leu Ser
                565                 570                 575

Ala Ser Ser Tyr Thr Ser Ser Asn His Leu Trp Tyr Val Thr Val Thr
                580                 585                 590

Leu Pro Ala Gly Ser Thr Phe Thr Tyr Lys Tyr Ile Arg Val Glu Ser
                595                 600                 605

Asp Gly Ser Ile Gln Trp Glu Ser Asp Pro Asn Leu Ser Tyr Thr Val
        610                 615                 620

Pro Gln Ala Cys Gly Thr Ser Ala Val Thr Ile Ser Asp Thr Trp Arg
625                 630                 635                 640

<210> SEQ ID NO 39
<211> LENGTH: 1896
<212> TYPE: DNA
<213> ORGANISM: Unknown
<220> FEATURE:
<223> OTHER INFORMATION: Obtained from an environmental sample

<400> SEQUENCE: 39
atggctcctc gttttttggac tgcgctttgg gcgcttacgc ttggccatgc cgttgtggcc      60
acgccacaga tattggctcc tcgtgcgact ggcagtttgg atacctggtt ggcgtctgag     120
actgtggtgg caagacaggg tatcttggac aacatcggat cggctggtgc ccatgctgcc     180
aatgcaaagc cgggcgttgt actcgccagc ccgagtacct ccgaccctga ttattattat     240
acttggactc gtgactcggc cctagtgttc aaaaatctgg tcgacatgtt caggagcggc     300
gacagcgctt tgttggaggt tatcgaagaa tacatcagct cgcaggccta tatccagacg     360
gtgtcaaatc catctggagg tcttttccggc ggcggtggat tgggagagcc caagttcaac     420
gccgatgaga cagcttttcac tggctcttgg gacgccctc agcgtgatgg accagccttg     480
cgagccactg ccttgatctc atttggccaa tggcttattg acaatgggta caccacctac     540
gcgaccgaca ttgtctggcc tgtcgtgcgc aatgatctct cctatgtttc ccagtactgg     600
aatcagactg gatttgatct ctgggaagaa gtttctggct catcattctt caccgtcgcg     660
gctcagcacc gcgctttggt ggagggaagc acattcgcaa gtcaggtcgg ttcttcatgt     720
ttgtactgtg actcccaggc tccgcaggtt ctgtgcttcc tacagtcctt ctggactgga     780
tcttacattc tggccaactt tggtggtggc cgctctggga aggacgccaa tacactgctc     840
ggcagcattc acacattcga cccagaggca ggatgcgatg acacgacgtt ccagccttgc     900
tcagcacgag cactcgcaaa ccacaaagtt gtaactgact cgttccgatc gatctactct     960
gtcaactctg gtatcgctgc gggtaaggct gtttctgttg gtcgataccc agaggactca    1020
tactacaatg gtaaccctg gtatctgtgc actttggctg cagctgagca gttgtatgat    1080
gctatctaca catggaaccg tattggttct ttgaccatta cctctgtctc tttgagcttc    1140
ttcaaagacc tatacagctc tgctgcgacc ggcacctact cctcatccag tgatacatac    1200
tcctcgatcg tggccgctgt aaaggaatat gcagatggat atgttagcat cgtggaaaaa    1260
tacgctgcat caagtggttc cttgtccgag caattctcca gtcagatggc tcgcagctg    1320 tcagctcgtg acctgacttg gtcctacgca gccctactta ctgccaatga gcgtcgaaac    1380
```

-continued

```
gccatagtcc ctgcaccatg gggggagaca tctgctagca gtgtccctgg gcagtgtcaa   1440
tatacttcgg ccattggtac ttacagcagc gcaacaaaca ccgcctggcc taccactttg   1500
actagtggat cgggcagtgt aactaccacc aagacgacta ccactacctc gaagccgaca   1560
acaacatcat gcactactcc gaccactgtt gcagtgacgt tcaatgtgat tgctactact   1620
gaatatggcc agaacatcaa actcgctgga tctatctctc aacttggctc atggtcgcca   1680
agcagtgctg tcgcattgag cgcttccaaa tacaccacga gcaaccacct gtggtttgtg   1740
accgtgacac ttccagtagg cactagcttc agctacaagt acatccaggt ggcgagcgat   1800
ggcactatca agtgggaaag tgacccaaac cagtcgtata ccgttcccgc cacgtgtggt   1860
actactgctg tcaccgtcag tgatacatgg aggtag                             1896
```

<210> SEQ ID NO 40
<211> LENGTH: 631
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(20)
<220> FEATURE:
<221> NAME/KEY: DOMAIN
<222> LOCATION: (42)...(457)
<223> OTHER INFORMATION: Glycosyl hydrolases family 15
<220> FEATURE:
<221> NAME/KEY: DOMAIN
<222> LOCATION: (529)...(625)
<223> OTHER INFORMATION: Starch binding domain
<220> FEATURE:
<221> NAME/KEY: SITE
<222> LOCATION: (204)...(207)
<223> OTHER INFORMATION: N-glycosylation site. Prosite id = PS00001
<220> FEATURE:
<221> NAME/KEY: SITE
<222> LOCATION: (206)...(216)
<223> OTHER INFORMATION: Glucoamylase active site region signature.
    Prosite id = PS00820
<220> FEATURE:
<221> NAME/KEY: SITE
<222> LOCATION: (619)...(622)
<223> OTHER INFORMATION: N-glycosylation site. Prosite id = PS00001

<400> SEQUENCE: 40

```
Met Ala Pro Arg Phe Trp Thr Ala Leu Trp Ala Leu Thr Leu Gly His
1               5                   10                  15

Ala Val Val Ala Thr Pro Gln Ile Leu Ala Pro Arg Ala Thr Gly Ser
            20                  25                  30

Leu Asp Thr Trp Leu Ala Ser Glu Thr Val Val Ala Arg Gln Gly Ile
        35                  40                  45

Leu Asp Asn Ile Gly Ser Ala Gly Ala His Ala Ala Asn Ala Lys Pro
    50                  55                  60

Gly Val Val Leu Ala Ser Pro Ser Thr Ser Asp Pro Asp Tyr Tyr Tyr
65                  70                  75                  80

Thr Trp Thr Arg Asp Ser Ala Leu Val Phe Lys Asn Leu Val Asp Met
                85                  90                  95

Phe Arg Ser Gly Asp Ser Ala Leu Leu Glu Val Ile Glu Glu Tyr Ile
            100                 105                 110

Ser Ser Gln Ala Tyr Ile Gln Thr Val Ser Asn Pro Ser Gly Gly Leu
        115                 120                 125

Ser Gly Gly Gly Leu Gly Glu Pro Lys Phe Asn Ala Asp Glu Thr
    130                 135                 140

Ala Phe Thr Gly Ser Trp Gly Arg Pro Gln Arg Asp Gly Pro Ala Leu
```

```
            145                 150                 155                 160
Arg Ala Thr Ala Leu Ile Ser Phe Gly Gln Trp Leu Ile Asp Asn Gly
                165                 170                 175

Tyr Thr Thr Tyr Ala Thr Asp Ile Val Trp Pro Val Arg Asn Asp
            180                 185                 190

Leu Ser Tyr Val Ser Gln Tyr Trp Asn Gln Thr Gly Phe Asp Leu Trp
                195                 200                 205

Glu Glu Val Ser Gly Ser Phe Phe Thr Val Ala Ala Gln His Arg
    210                 215                 220

Ala Leu Val Glu Gly Ser Thr Phe Ala Ser Gln Val Gly Ser Ser Cys
225                 230                 235                 240

Leu Tyr Cys Asp Ser Gln Ala Pro Gln Val Leu Cys Phe Leu Gln Ser
                245                 250                 255

Phe Trp Thr Gly Ser Tyr Ile Leu Ala Asn Phe Gly Gly Arg Ser
            260                 265                 270

Gly Lys Asp Ala Asn Thr Leu Leu Gly Ser Ile His Thr Phe Asp Pro
                275                 280                 285

Glu Ala Gly Cys Asp Asp Thr Thr Phe Gln Pro Cys Ser Ala Arg Ala
    290                 295                 300

Leu Ala Asn His Lys Val Val Thr Asp Ser Phe Arg Ser Ile Tyr Ser
305                 310                 315                 320

Val Asn Ser Gly Ile Ala Ala Gly Lys Ala Val Ser Val Gly Arg Tyr
                325                 330                 335

Pro Glu Asp Ser Tyr Tyr Asn Gly Asn Pro Trp Tyr Leu Cys Thr Leu
                340                 345                 350

Ala Ala Ala Glu Gln Leu Tyr Asp Ala Ile Tyr Thr Trp Asn Arg Ile
                355                 360                 365

Gly Ser Leu Thr Ile Thr Ser Val Ser Leu Ser Phe Phe Lys Asp Leu
            370                 375                 380

Tyr Ser Ser Ala Ala Thr Gly Thr Tyr Ser Ser Ser Asp Thr Tyr
385                 390                 395                 400

Ser Ser Ile Val Ala Ala Val Lys Glu Tyr Ala Asp Gly Tyr Val Ser
                405                 410                 415

Ile Val Glu Lys Tyr Ala Ala Ser Ser Gly Ser Leu Ser Glu Gln Phe
                420                 425                 430

Ser Lys Ser Asp Gly Ser Gln Leu Ser Ala Arg Asp Leu Thr Trp Ser
            435                 440                 445

Tyr Ala Ala Leu Leu Thr Ala Asn Glu Arg Arg Asn Ala Ile Val Pro
            450                 455                 460

Ala Pro Trp Gly Glu Thr Ser Ala Ser Ser Val Pro Gly Gln Cys Gln
465                 470                 475                 480

Tyr Thr Ser Ala Ile Gly Thr Tyr Ser Ser Ala Thr Asn Thr Ala Trp
                485                 490                 495

Pro Thr Thr Leu Thr Ser Gly Gly Ser Val Thr Thr Thr Lys Thr
            500                 505                 510

Thr Thr Thr Thr Ser Lys Pro Thr Thr Thr Ser Cys Thr Thr Pro Thr
            515                 520                 525

Thr Val Ala Val Thr Phe Asn Val Ile Ala Thr Thr Glu Tyr Gly Gln
    530                 535                 540

Asn Ile Lys Leu Ala Gly Ser Ile Ser Gln Leu Gly Ser Trp Ser Pro
545                 550                 555                 560

Ser Ser Ala Val Ala Leu Ser Ala Ser Lys Tyr Thr Ser Asn His
                565                 570                 575
```

Leu Trp Phe Val Thr Val Thr Leu Pro Val Gly Thr Ser Phe Ser Tyr
             580                 585                 590

Lys Tyr Ile Gln Val Ala Ser Asp Gly Thr Ile Lys Trp Glu Ser Asp
         595                 600                 605

Pro Asn Gln Ser Tyr Thr Val Pro Ala Thr Cys Gly Thr Thr Ala Val
     610                 615                 620

Thr Val Ser Asp Thr Trp Arg
625                 630

<210> SEQ ID NO 41
<211> LENGTH: 1563
<212> TYPE: DNA
<213> ORGANISM: Unknown
<220> FEATURE:
<223> OTHER INFORMATION: Obtained from an environmental sample

<400> SEQUENCE: 41
atgctggttc ctgtggtcat tctcacacat tttctccact atgcttgcgc tttctcgata      60
ccccatttgc acttgaaatt tgcgagtgcc agtgacgcac aaataccaca gaagccgctg     120
cgggatacgc tggaagtctg gctcgaagct gaagagcgca tagctctaaa taaattactc     180
gccaacgtag ctccaggcgg tagcaatgtc gagggcaaag gcgtggcacc cggaactgtc     240
attgcgagtc cgagtcagga cgggccagat tattggtatc agtgggttcg agatgccgct     300
atcaccatga atacgctcgt agatttgtat gccgagaacc cttcatccgc cttatcatct     360
cgtctttcga cgaccttaga tgcatacgct tccctacaac gtgatctgca gcatacatca     420
aatccctcgg gctcatttga tgattcgtcc ggccttggtg aaccgaaatt tgaagtcgac     480
ggaacgccat ttacaggctc atggggaagg ccacaacgcg atggaccggc gttaagagcg     540
ctgactctta tgcggtatct tcgagaatac aacgctagcc atccttcgct ttggtcttca     600
aatgaggcta ccgacttcta tagtctttat tacgaagcag atgccacc gcggagcgtg       660
atcaaggcag accttgaata cgtgagccat ttctggaacg aatccagttt tgatctttgg     720
gaagaaacag aaggtcttca cttctttaac ttgatggtca gcgcacgaag tctaagggag     780
ggcagtgagc tagcaagagc atttggagat attggtgcag cagaatggta tatcgaacaa     840
gctggctaca tcgaaaagct tctgagcaaa ttctggaacc gaacaaagg ccatctcgtg       900
gagaccttgt ggagtaagcg ctcaggtcta gattgtggtc ttcttctcgg gtctctacat     960
gctcttcctg ctcagggctt ggaagaagag gcagttttcc cgccctggtc cgacgagatc    1020
ctcgtgagct tgcttgctct gacagaagat caaagagacc gcttcccaat caacagcaac    1080
ccatatgagg atcaagatgg atcccatcca gcgttcgagg gtacaggagt tggacgttat    1140
cccgaagacg tctacgacgg ctatggcacc agtaatcgcg gaggcaaccc atggttccta    1200
tgcacatcaa gcgcagccga aatactgtac cgcagtgctt cttacttcta tacagcctcc    1260
aacctcacca tctccaccgc atctcttccg ttctacacct ccctgcttgc aacttcaagc    1320
ctcgatgtcc aagtcggaac atttggaccc tcagatacgc ttttccactc tgtcatcgag    1380
catctcaagt ccgcaggcga ttcgttcctt gaagttgtga aaacgcatgt agatgatgag    1440
ggacgaatga gcgagcaatt tgacagagtg acgggttata tgcgcggtgc gcgggatttg    1500
acctggagtt acggtgcatt tctacaggcg gtgaaggcgc gaaggagtat tcaggaggtt    1560
tga                                                                 1563

<210> SEQ ID NO 42
<211> LENGTH: 520
<212> TYPE: PRT

-continued

```
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (53)...(512)
<223> OTHER INFORMATION: Glycosyl hydrolases family 15
<220> FEATURE:
<221> NAME/KEY: SITE
<222> LOCATION: (193)...(196)
<223> OTHER INFORMATION: N-glycosylation site. Prosite id = PS00001
<220> FEATURE:
<221> NAME/KEY: SITE
<222> LOCATION: (236)...(239)
<223> OTHER INFORMATION: N-glycosylation site. Prosite id = PS00001
<220> FEATURE:
<221> NAME/KEY: SITE
<222> LOCATION: (427)...(430)
<223> OTHER INFORMATION: N-glycosylation site. Prosite id = PS00001

<400> SEQUENCE: 42
```

Met Leu Val Pro Val Ile Leu Thr His Phe Leu His Tyr Ala Cys
1               5                   10                  15

Ala Phe Ser Ile Pro His Leu His Leu Lys Phe Ala Ser Ala Ser Asp
            20                  25                  30

Ala Gln Ile Pro Gln Lys Pro Leu Arg Asp Thr Leu Glu Val Trp Leu
        35                  40                  45

Glu Ala Glu Glu Arg Ile Ala Leu Asn Lys Leu Leu Ala Asn Val Ala
50                  55                  60

Pro Gly Gly Ser Asn Val Glu Gly Lys Gly Val Ala Pro Gly Thr Val
65                  70                  75                  80

Ile Ala Ser Pro Ser Gln Asp Gly Pro Asp Tyr Trp Tyr Gln Trp Val
                85                  90                  95

Arg Asp Ala Ala Ile Thr Met Asn Thr Leu Val Asp Leu Tyr Ala Glu
            100                 105                 110

Asn Pro Ser Ser Ala Leu Ser Ser Arg Leu Ser Thr Thr Leu Asp Ala
        115                 120                 125

Tyr Ala Ser Leu Gln Arg Asp Leu Gln His Thr Ser Asn Pro Ser Gly
130                 135                 140

Ser Phe Asp Asp Ser Ser Gly Leu Gly Glu Pro Lys Phe Glu Val Asp
145                 150                 155                 160

Gly Thr Pro Phe Thr Gly Ser Trp Gly Arg Pro Gln Arg Asp Gly Pro
                165                 170                 175

Ala Leu Arg Ala Leu Thr Leu Met Arg Tyr Leu Arg Glu Tyr Asn Ala
            180                 185                 190

Ser His Pro Ser Leu Trp Ser Ser Asn Glu Ala Thr Asp Phe Tyr Ser
        195                 200                 205

Leu Tyr Tyr Glu Ala Glu Met Pro Pro Arg Ser Val Ile Lys Ala Asp
210                 215                 220

Leu Glu Tyr Val Ser His Phe Trp Asn Glu Ser Ser Phe Asp Leu Trp
225                 230                 235                 240

Glu Glu Thr Glu Gly Leu His Phe Phe Asn Leu Met Val Ser Ala Arg
                245                 250                 255

Ser Leu Arg Glu Gly Ser Glu Leu Ala Arg Ala Phe Gly Asp Ile Gly
            260                 265                 270

Ala Ala Glu Trp Tyr Ile Glu Gln Ala Gly Tyr Ile Glu Lys Leu Leu
        275                 280                 285

Ser Lys Phe Trp Asn Pro Asn Lys Gly His Leu Val Glu Thr Leu Trp
290                 295                 300

Ser Lys Arg Ser Gly Leu Asp Cys Gly Leu Leu Leu Gly Ser Leu His

```
              305                 310                 315                 320
Ala Leu Pro Ala Gln Gly Leu Glu Glu Ala Val Phe Pro Pro Trp
                325                 330                 335

Ser Asp Glu Ile Leu Val Ser Leu Leu Ala Leu Thr Glu Asp Gln Arg
            340                 345                 350

Asp Arg Phe Pro Ile Asn Ser Asn Pro Tyr Glu Asp Gln Asp Gly Ser
            355                 360                 365

His Pro Ala Phe Glu Gly Thr Gly Val Gly Arg Tyr Pro Glu Asp Val
370                 375                 380

Tyr Asp Gly Tyr Gly Thr Ser Asn Arg Gly Gly Asn Pro Trp Phe Leu
385                 390                 395                 400

Cys Thr Ser Ser Ala Ala Glu Ile Leu Tyr Arg Ser Ala Ser Tyr Phe
                405                 410                 415

Tyr Thr Ala Ser Asn Leu Thr Ile Ser Thr Ala Ser Leu Pro Phe Tyr
                420                 425                 430

Thr Ser Leu Leu Ala Thr Ser Ser Leu Asp Val Gln Val Gly Thr Phe
            435                 440                 445

Gly Pro Ser Asp Thr Leu Phe His Ser Val Ile Glu His Leu Lys Ser
450                 455                 460

Ala Gly Asp Ser Phe Leu Glu Val Val Lys Thr His Val Asp Asp Glu
465                 470                 475                 480

Gly Arg Met Ser Glu Gln Phe Asp Arg Val Thr Gly Tyr Met Arg Gly
                485                 490                 495

Ala Arg Asp Leu Thr Trp Ser Tyr Gly Ala Phe Leu Gln Ala Val Lys
            500                 505                 510

Ala Arg Arg Ser Ile Gln Glu Val
        515                 520

<210> SEQ ID NO 43
<211> LENGTH: 3030
<212> TYPE: DNA
<213> ORGANISM: Cochliobolus heterostrophus ATCC 48332

<400> SEQUENCE: 43
atgacgcaca caagtttcgt ccaggcttct actgtgctgt cctctcttct cgcactcaca      60
gctggccaag cgcccaccac ttcttcaaat ggtggatgga gtactacgct cgctggcacg     120
cccacctact tcaatcccat ctttaccatc cctccatctg cggatgaggg cgttcaacag     180
attcccaaca tctatgaccc acaagccgtg gatgcgcaag acgtttgccc tggttacaca     240
gcatcaaacc ctcagcagag tgatcgtggc ctgaccgcca cgttgaccct ggctggaaag     300
ccatgcaatg tttacggcac cgatatccag gaactagact tgaaagtcga gtaccaggcc     360
aagggaagac tgtcagtcaa cattgtacca agtacactg gtgcaagcaa ccagtcgcat     420
tggattgttc ccgaagatct gattccgcgt cctcaggtcg aggaatcatc cgagcagacc     480
gatctcaagt tcaactgggg aaatgagcca tcttttttggt tcaatgtcga gcgctcctcg     540
actggagaca tcatcttcac aactcaaggc acccatctca tttacgaaaa tcaatttgtt     600
gaatttgtaa acagcctgcc agaggactac aaccttacg gtctgggtga acgaattcac     660
ggtcttcgtc ttaacaacaa cttcactgcg accatctacg ctgctgacgt aggtgatcct     720
atcgaccgca acctgtacgg tagccaccct ttttacctag agaccggta ctttgagaag     780 ggcgaaaact gtagcaccaa gcccttgacg cagtccgaga tcggccagaa gaaggatacc     840
aaaacaaatg gttcgcccta cgagtcgcgt tcccacggcg tttattaccg caacactcat     900
ggtatggacg tggtgctgaa acctgatcac ctaacttgga ggaccctggg aggtgctatt     960
```

-continued

```
gatctgtact tcttcgatgg accttcacag ccggacgtta ctaaagcgta tcaaaaggcg      1020
gctattggcc tgccagcaat gcagcaatac tggacctttg gctttcatca atgccgttgg      1080
ggctaccgca actggaccga gactcgagaa attgttgaga ccatgagagc tttcaacatc      1140
ccaatggaaa ccatctggct cgacattgac tacatggacc agtaccgtga ctttacgctg      1200
gatcccgtgg ctttccctcc ctctgaagtg gccgacttct tcggatggct gcatggaaac      1260
aaccagcatt ttgtacccat cgttgatgca gctatttaca tccccaaccc gcaaaacgca      1320
agcgatgcat atgacacata tacgcgcggc aatgaatctg gtgtgttctt gtccaaccca      1380
gacggcagcc aatatatcgg tgctgtctgg cctgggtaca ccgttttccc tgattggttg      1440
tcgcccaacg gtgtatcttg gtgggtaaag gagatggtcg agtggtacaa agaggtacca      1500
tatagcggtt tctggcttga catgactgaa gtctcttctt tctgcgttgg atcctgtggt      1560
actggcaacg tcaccctgaa cccggctcac ccgcccttct cgcttcccgg tgaggtgaac      1620
aacgtcatct atgattaccc agagagcttc aacatcacaa atggtaccga gcggcgtcc       1680 gcttctgcag cagcttccgc ccaagcatcc aggaaggcaa ctgcgacggc gacggtgacc      1740
gacgaagtga cttctacttc gacaagctac ttccgctcga cccctaccgc tggagagcga      1800
aacatcaact atcctcctta tgtcatcaac cacgtacaag atggcgctga tcttgctgtt      1860
catgctgtca gccccaatgc aactcatgca atggtgtgg aggaatacga tgtccacaac       1920
ctctttggtc accagatcat taacgctact tatcacggtc cctttcggt gttccctgga       1980 aagcggccct ttatcattgg acgctccaca tttgctggca cggcaagtg ggctggtcat       2040 tggggtggcg acaacgcttc taaatgggcc tacatgttct tctcgattcc acaagcactt      2100
tccttttcac tatttggtat tccgatgttt ggtgtcgata cctgcggatt caacggaaac      2160
actgacatgg agctttgctc tcgatggatg cagctttcgg cctttttccc cttttaccgc      2220
aaccacaacg tactctccgc cattccccaa gagccctacc gatgggaggc cgtggcttct      2280
gcttcgagga ccgcaatgca catccgatac tctctgttgc catacatgta cacgctattc      2340
aatgacgctc acaagactgg gtcaactgtg atgcgggcgc tggcatggga attccccaac      2400
gagccccaac tcgctggtgt agatacacaa ttcttgcttg gccaaacat cctagtcacg       2460 cctgtcctcg agcctcaagt tgatactgtc aagggagtgt tccctggtat tgtcgacggc      2520
gagacatggt ttgattggta ttctggcgag cgtgtccaag ccgaggctgg cgtaaacacg      2580
accatctcag cacctttggg ccacatcccg gtatacattc gcggaggttc ggtcctacct      2640
attcaggagc ctggatacac gactaccgag tcccgccgga acccctgggg tctcattgtc      2700
gcactctcca gtgaaggcac tgcatcgggt cacctatacg ttgatgatgg tgagtccatc      2760
gagccagact cgtgcctgaa tgttgcattt gctgctacga gcggaaagtt ggaggttgat      2820
gttcagggcg agttcaagga cacgaacgca cttgccaacg tgacagtttt gggagctcct      2880
gcggtccaaa acgtcaagct gaatggtgag gcgattgatg ctagcaatgt tgattacaac      2940
aagaccagta gcgttttgaa gctgacggga ctcaatgaac tgacaagttc tggagcttgg      3000
cagggtagct ggacgctgac ttgggaataa                                       3030
```

<210> SEQ ID NO 44
<211> LENGTH: 1009
<212> TYPE: PRT
<213> ORGANISM: Cochliobolus heterostrophus ATCC 48332
<220> FEATURE:
<221> NAME/KEY: DOMAIN
<222> LOCATION: (323)...(879)
<223> OTHER INFORMATION: Glycosyl hydrolases family 31

```
<220> FEATURE:
<221> NAME/KEY: SITE
<222> LOCATION: (139)...(142)
<223> OTHER INFORMATION: N-glycosylation site. Prosite id = PS00001
<220> FEATURE:
<221> NAME/KEY: SITE
<222> LOCATION: (230)...(233)
<223> OTHER INFORMATION: N-glycosylation site. Prosite id = PS00001
<220> FEATURE:
<221> NAME/KEY: SITE
<222> LOCATION: (267)...(270)
<223> OTHER INFORMATION: N-glycosylation site. Prosite id = PS00001
<220> FEATURE:
<221> NAME/KEY: SITE
<222> LOCATION: (369)...(372)
<223> OTHER INFORMATION: N-glycosylation site. Prosite id = PS00001
<220> FEATURE:
<221> NAME/KEY: SITE
<222> LOCATION: (445)...(448)
<223> OTHER INFORMATION: N-glycosylation site. Prosite id = PS00001
<220> FEATURE:
<221> NAME/KEY: SITE
<222> LOCATION: (457)...(460)
<223> OTHER INFORMATION: N-glycosylation site. Prosite id = PS00001
<220> FEATURE:
<221> NAME/KEY: SITE
<222> LOCATION: (531)...(534)
<223> OTHER INFORMATION: N-glycosylation site. Prosite id = PS00001
<220> FEATURE:
<221> NAME/KEY: SITE
<222> LOCATION: (559)...(562)
<223> OTHER INFORMATION: N-glycosylation site. Prosite id = PS00001
<220> FEATURE:
<221> NAME/KEY: SITE
<222> LOCATION: (635)...(638)
<223> OTHER INFORMATION: N-glycosylation site. Prosite id = PS00001
<220> FEATURE:
<221> NAME/KEY: SITE
<222> LOCATION: (657)...(660)
<223> OTHER INFORMATION: N-glycosylation site. Prosite id = PS00001
<220> FEATURE:
<221> NAME/KEY: SITE
<222> LOCATION: (695)...(698)
<223> OTHER INFORMATION: N-glycosylation site. Prosite id = PS00001
<220> FEATURE:
<221> NAME/KEY: SITE
<222> LOCATION: (872)...(875)
<223> OTHER INFORMATION: N-glycosylation site. Prosite id = PS00001
<220> FEATURE:
<221> NAME/KEY: SITE
<222> LOCATION: (967)...(970)
<223> OTHER INFORMATION: N-glycosylation site. Prosite id = PS00001
<220> FEATURE:
<221> NAME/KEY: SITE
<222> LOCATION: (995)...(998)
<223> OTHER INFORMATION: N-glycosylation site. Prosite id = PS00001

<400> SEQUENCE: 44

Met Thr His Thr Ser Phe Val Gln Ala Ser Thr Val Leu Ser Ser Leu
1               5                   10                  15

Leu Ala Leu Thr Ala Gly Gln Ala Pro Thr Thr Ser Ser Asn Gly Gly
                20                  25                  30

Trp Ser Thr Thr Leu Ala Gly Thr Pro Thr Tyr Phe Asn Pro Ile Phe
            35                  40                  45

Thr Ile Pro Pro Ser Ala Asp Glu Gly Val Gln Gln Ile Pro Asn Ile
    50                  55                  60

Tyr Asp Pro Gln Ala Val Asp Ala Gln Asp Val Cys Pro Gly Tyr Thr
65                  70                  75                  80

Ala Ser Asn Pro Gln Gln Ser Asp Arg Gly Leu Thr Ala Thr Leu Thr
                85                  90                  95

Leu Ala Gly Lys Pro Cys Asn Val Tyr Gly Thr Asp Ile Gln Glu Leu
            100                 105                 110
```

```
Asp Leu Lys Val Glu Tyr Gln Ala Lys Gly Arg Leu Ser Val Asn Ile
        115                 120                 125

Val Pro Lys Tyr Thr Gly Ala Ser Asn Gln Ser His Trp Ile Val Pro
    130                 135                 140

Glu Asp Leu Ile Pro Arg Pro Gln Val Glu Glu Ser Ser Glu Gln Thr
145                 150                 155                 160

Asp Leu Lys Phe Asn Trp Gly Asn Glu Pro Ser Phe Trp Phe Asn Val
            165                 170                 175

Glu Arg Ser Ser Thr Gly Asp Ile Ile Phe Thr Thr Gln Gly Thr His
            180                 185                 190

Leu Ile Tyr Glu Asn Gln Phe Val Glu Phe Val Asn Ser Leu Pro Glu
        195                 200                 205

Asp Tyr Asn Leu Tyr Gly Leu Gly Glu Arg Ile His Gly Leu Arg Leu
    210                 215                 220

Asn Asn Asn Phe Thr Ala Thr Ile Tyr Ala Ala Asp Val Gly Asp Pro
225                 230                 235                 240

Ile Asp Arg Asn Leu Tyr Gly Ser His Pro Phe Tyr Leu Glu Thr Arg
            245                 250                 255

Tyr Phe Glu Lys Gly Glu Asn Cys Ser Thr Lys Pro Leu Thr Gln Ser
        260                 265                 270

Glu Ile Gly Gln Lys Lys Asp Thr Lys Thr Asn Gly Ser Pro Tyr Glu
        275                 280                 285

Ser Arg Ser His Gly Val Tyr Tyr Arg Asn Thr His Gly Met Asp Val
    290                 295                 300

Val Leu Lys Pro Asp His Leu Thr Trp Arg Thr Leu Gly Gly Ala Ile
305                 310                 315                 320

Asp Leu Tyr Phe Phe Asp Gly Pro Ser Gln Pro Asp Val Thr Lys Ala
            325                 330                 335

Tyr Gln Lys Ala Ala Ile Gly Leu Pro Ala Met Gln Gln Tyr Trp Thr
        340                 345                 350

Phe Gly Phe His Gln Cys Arg Trp Gly Tyr Arg Asn Trp Thr Glu Thr
        355                 360                 365

Arg Glu Ile Val Glu Thr Met Arg Ala Phe Asn Ile Pro Met Glu Thr
    370                 375                 380

Ile Trp Leu Asp Ile Asp Tyr Met Asp Gln Tyr Arg Asp Phe Thr Leu
385                 390                 395                 400

Asp Pro Val Ala Phe Pro Pro Ser Glu Val Ala Asp Phe Phe Gly Trp
            405                 410                 415

Leu His Gly Asn Asn Gln His Phe Pro Ile Val Asp Ala Ala Ile
        420                 425                 430

Tyr Ile Pro Asn Pro Gln Asn Ala Ser Asp Ala Tyr Thr Tyr Thr
        435                 440                 445

Arg Gly Asn Glu Ser Gly Val Phe Leu Ser Asn Pro Asp Gly Ser Gln
    450                 455                 460

Tyr Ile Gly Ala Val Trp Pro Gly Tyr Thr Val Phe Pro Asp Trp Leu
465                 470                 475                 480

Ser Pro Asn Gly Val Ser Trp Trp Val Lys Glu Met Val Glu Trp Tyr
            485                 490                 495

Lys Glu Val Pro Tyr Ser Gly Phe Trp Val Asp Met Thr Glu Val Ser
        500                 505                 510

Ser Phe Cys Val Gly Ser Cys Gly Thr Gly Asn Val Thr Leu Asn Pro
        515                 520                 525

Ala His Pro Pro Phe Ser Leu Pro Gly Glu Val Asn Asn Val Ile Tyr
    530                 535                 540
```

```
Asp Tyr Pro Glu Ser Phe Asn Ile Thr Asn Gly Thr Glu Ala Ala Ser
545                 550                 555                 560

Ala Ser Ala Ala Ala Ser Ala Gln Ala Ser Arg Lys Ala Thr Ala Thr
                565                 570                 575

Ala Thr Val Thr Asp Glu Val Thr Ser Thr Ser Thr Ser Tyr Phe Arg
            580                 585                 590

Ser Thr Pro Thr Ala Gly Glu Arg Asn Ile Asn Tyr Pro Pro Tyr Val
        595                 600                 605

Ile Asn His Val Gln Asp Gly Ala Asp Leu Ala Val His Ala Val Ser
    610                 615                 620

Pro Asn Ala Thr His Ala Asn Gly Val Glu Glu Tyr Asp Val His Asn
625                 630                 635                 640

Leu Phe Gly His Gln Ile Ile Asn Ala Thr Tyr His Gly Leu Leu Ser
                645                 650                 655

Val Phe Pro Gly Lys Arg Pro Phe Ile Ile Gly Arg Ser Thr Phe Ala
            660                 665                 670

Gly Ser Gly Lys Trp Ala Gly His Trp Gly Gly Asp Asn Ala Ser Lys
        675                 680                 685

Trp Ala Tyr Met Phe Phe Ser Ile Pro Gln Ala Leu Ser Phe Ser Leu
    690                 695                 700

Phe Gly Ile Pro Met Phe Gly Val Asp Thr Cys Gly Phe Asn Gly Asn
705                 710                 715                 720

Thr Asp Met Glu Leu Cys Ser Arg Trp Met Gln Leu Ser Ala Phe Phe
                725                 730                 735

Pro Phe Tyr Arg Asn His Asn Val Leu Ser Ala Ile Pro Gln Glu Pro
            740                 745                 750

Tyr Arg Trp Glu Ala Val Ala Ser Ala Ser Arg Thr Ala Met His Ile
        755                 760                 765

Arg Tyr Ser Leu Leu Pro Tyr Met Tyr Thr Leu Phe Asn Asp Ala His
    770                 775                 780

Lys Thr Gly Ser Thr Val Met Arg Ala Leu Ala Trp Glu Phe Pro Asn
785                 790                 795                 800

Glu Pro Gln Leu Ala Gly Val Asp Thr Gln Phe Leu Leu Gly Pro Asn
                805                 810                 815

Ile Leu Val Thr Pro Val Leu Glu Pro Gln Val Asp Thr Val Lys Gly
            820                 825                 830

Val Phe Pro Gly Ile Val Asp Gly Glu Thr Trp Phe Asp Trp Tyr Ser
        835                 840                 845

Gly Glu Arg Val Gln Ala Glu Ala Gly Val Asn Thr Thr Ile Ser Ala
    850                 855                 860

Pro Leu Gly His Ile Pro Val Tyr Ile Arg Gly Gly Ser Val Leu Pro
865                 870                 875                 880

Ile Gln Glu Pro Gly Tyr Thr Thr Thr Glu Ser Arg Arg Asn Pro Trp
                885                 890                 895

Gly Leu Ile Val Ala Leu Ser Ser Glu Gly Thr Ala Ser Gly His Leu
            900                 905                 910

Tyr Val Asp Asp Gly Glu Ser Ile Glu Pro Asp Ser Cys Leu Asn Val
        915                 920                 925

Ala Phe Ala Ala Thr Ser Gly Lys Leu Glu Val Asp Val Gln Gly Glu
    930                 935                 940

Phe Lys Asp Thr Asn Ala Leu Ala Asn Val Thr Val Leu Gly Ala Pro
945                 950                 955                 960

Ala Val Gln Asn Val Lys Leu Asn Gly Glu Ala Ile Asp Ala Ser Asn
```

```
                        965                 970                 975
Val Asp Tyr Asn Lys Thr Ser Ser Val Leu Lys Leu Thr Gly Leu Asn
                980                 985                 990

Glu Leu Thr Ser Ser Gly Ala Trp Gln Gly Ser Trp Thr Leu Thr Trp
            995                 1000                1005

Glu

<210> SEQ ID NO 45
<211> LENGTH: 1380
<212> TYPE: DNA
<213> ORGANISM: Unknown
<220> FEATURE:
<223> OTHER INFORMATION: Obtained from an environmental sample

<400> SEQUENCE: 45
atgaagcttc ttcaactcgc cgccctggtg gcgtccctca gccccttcac caacgctgcc    60
gacgcaaacg cctggaagtc gcgaaacatt tactttgcgc ttacagaccg cgttgcgcgc   120
agcggtagcg ataacggtgg caatgcctgt ggcaatcttg aaattattg tggtggaacg    180 ttcaagggtc ttgaggctaa gcttgattac atcaagggca tgggctttga tgctatctgg   240
attactcctg ttgttgagaa caccgatgga ggataccatg gatactgggc taaagacctg   300
tacgcggtta attccaagta tggtaccaag gatgacttga gaatcttgt caaggctgcc    360 cacggcaaga acatgtacgt catggccgac gtcgtcgcaa accacatggg caagggcatc   420
caaaaccaca gccggagcc cctcaaccag caaagctcct accacagctc ctgcgccatc    480
gactacaaca accaaaacag catcgagcag tgcgaaatcg ccggtctgcc cgatctcaac   540
accggcaagg cagaagtcaa gaaggtcctc aacgactgga tcaagtggct cgtctccgag   600
tacagcttcg acggtatccg catcgacaca gtcaagcacg tcgagaagag cttctggcct   660
gatttccaga aggcagctgg cgttttcgcc atcggtgagg tttgggatgg aagccctgat   720
taccttgctg gttactccaa ggtcatgcct ggtctgctga actatgctat gtactatccc   780
atgaaccgat tctatcagca aagggtgat ccttctgctg tggtggatat gtacaacgag   840
atcagccaga agttcgatga tcctacgcag cttggtacct tcatcgacaa ccacgacaat   900
gcgcgctggt tgagccaaaa gaacgacaag gccctcctca gaacgccct cgcattcacc    960 atcctcgccc gcggtattcc catcgtgtac tacggcaccg aacaaggcta cgcaggaggc  1020
aacgaccccg ccaaccgcga agatctctgg cgcagcaact tcagcaccga ctccgacctg  1080
taccaaacca tttccaagct cggcaaggct cgctccgccg tcgtggtct tgccggcaac   1140 gaccagaaat tcctcaagtc caatgacagc gcactcatct ggagccgcgc agacggcgat  1200
ctgatcgttg ttacgcttaa ccgtggaaag ggatattctg gagagtactg cttcaacact  1260
ggcaagaaca acaagacttg ggatcgtgtt ttgggatctg gaagtgttaa gtctgatggt  1320
agtggtaagc tttgtgttag ctacactaat ggtgagcctg aggttcttgt tgctgcttag  1380

<210> SEQ ID NO 46
<211> LENGTH: 459
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(19)
<220> FEATURE:
<221> NAME/KEY: DOMAIN
<222> LOCATION: (32)...(371)
<223> OTHER INFORMATION: Alpha amylase, catalytic domain
```

```
<220> FEATURE:
<221> NAME/KEY: SITE
<222> LOCATION: (358)...(361)
<223> OTHER INFORMATION: N-glycosylation site. Prosite id = PS00001
<220> FEATURE:
<221> NAME/KEY: SITE
<222> LOCATION: (393)...(396)
<223> OTHER INFORMATION: N-glycosylation site. Prosite id = PS00001
<220> FEATURE:
<221> NAME/KEY: SITE
<222> LOCATION: (430)...(433)
<223> OTHER INFORMATION: N-glycosylation site. Prosite id = PS00001

<400> SEQUENCE: 46
```

| | | | | | | | | | | | | | | |
|---|---|---|---|---|---|---|---|---|---|---|---|---|---|---|
| Met | Lys | Leu | Leu | Gln | Leu | Ala | Ala | Leu | Val | Ala | Ser | Leu | Ser | Pro | Phe |
| 1 | | | | 5 | | | | | 10 | | | | | 15 | |
| Thr | Asn | Ala | Ala | Asp | Ala | Asn | Ala | Trp | Lys | Ser | Arg | Asn | Ile | Tyr | Phe |
| | | | 20 | | | | | 25 | | | | | 30 | | |
| Ala | Leu | Thr | Asp | Arg | Val | Ala | Arg | Ser | Gly | Ser | Asp | Asn | Gly | Gly | Asn |
| | | | 35 | | | | | 40 | | | | | 45 | | |
| Ala | Cys | Gly | Asn | Leu | Gly | Asn | Tyr | Cys | Gly | Gly | Thr | Phe | Lys | Gly | Leu |
| | 50 | | | | | 55 | | | | | 60 | | | | |
| Glu | Ala | Lys | Leu | Asp | Tyr | Ile | Lys | Gly | Met | Gly | Phe | Asp | Ala | Ile | Trp |
| 65 | | | | | 70 | | | | | 75 | | | | | 80 |
| Ile | Thr | Pro | Val | Val | Glu | Asn | Thr | Asp | Gly | Gly | Tyr | His | Gly | Tyr | Trp |
| | | | | 85 | | | | | 90 | | | | | 95 | |
| Ala | Lys | Asp | Leu | Tyr | Ala | Val | Asn | Ser | Lys | Tyr | Gly | Thr | Lys | Asp | Asp |
| | | | 100 | | | | | 105 | | | | | 110 | | |
| Leu | Lys | Asn | Leu | Val | Lys | Ala | Ala | His | Gly | Lys | Asn | Met | Tyr | Val | Met |
| | | | 115 | | | | | 120 | | | | | 125 | | |
| Ala | Asp | Val | Val | Ala | Asn | His | Met | Gly | Lys | Gly | Ile | Gln | Asn | His | Lys |
| | 130 | | | | | 135 | | | | | 140 | | | | |
| Pro | Glu | Pro | Leu | Asn | Gln | Gln | Ser | Ser | Tyr | His | Ser | Ser | Cys | Ala | Ile |
| 145 | | | | | 150 | | | | | 155 | | | | | 160 |
| Asp | Tyr | Asn | Asn | Gln | Asn | Ser | Ile | Glu | Gln | Cys | Glu | Ile | Ala | Gly | Leu |
| | | | | 165 | | | | | 170 | | | | | 175 | |
| Pro | Asp | Leu | Asn | Thr | Gly | Lys | Ala | Glu | Val | Lys | Lys | Val | Leu | Asn | Asp |
| | | | 180 | | | | | 185 | | | | | 190 | | |
| Trp | Ile | Lys | Trp | Leu | Val | Ser | Glu | Tyr | Ser | Phe | Asp | Gly | Ile | Arg | Ile |
| | | | 195 | | | | | 200 | | | | | 205 | | |
| Asp | Thr | Val | Lys | His | Val | Glu | Lys | Ser | Phe | Trp | Pro | Asp | Phe | Gln | Lys |
| | 210 | | | | | 215 | | | | | 220 | | | | |
| Ala | Ala | Gly | Val | Phe | Ala | Ile | Gly | Glu | Val | Trp | Asp | Gly | Ser | Pro | Asp |
| 225 | | | | | 230 | | | | | 235 | | | | | 240 |
| Tyr | Leu | Ala | Gly | Tyr | Ser | Lys | Val | Met | Pro | Gly | Leu | Leu | Asn | Tyr | Ala |
| | | | | 245 | | | | | 250 | | | | | 255 | |
| Met | Tyr | Tyr | Pro | Met | Asn | Arg | Phe | Tyr | Gln | Gln | Lys | Gly | Asp | Pro | Ser |
| | | | 260 | | | | | 265 | | | | | 270 | | |
| Ala | Val | Val | Asp | Met | Tyr | Asn | Glu | Ile | Ser | Gln | Lys | Phe | Asp | Asp | Pro |
| | | | 275 | | | | | 280 | | | | | 285 | | |
| Thr | Gln | Leu | Gly | Thr | Phe | Ile | Asp | Asn | His | Asp | Asn | Ala | Arg | Trp | Leu |
| | | 290 | | | | | 295 | | | | | 300 | | | |
| Ser | Gln | Lys | Asn | Asp | Lys | Ala | Leu | Leu | Lys | Asn | Ala | Leu | Ala | Phe | Thr |
| 305 | | | | | 310 | | | | | 315 | | | | | 320 |
| Ile | Leu | Ala | Arg | Gly | Ile | Pro | Ile | Val | Tyr | Tyr | Gly | Thr | Glu | Gln | Gly |
| | | | | 325 | | | | | 330 | | | | | 335 | |
| Tyr | Ala | Gly | Gly | Asn | Asp | Pro | Ala | Asn | Arg | Glu | Asp | Leu | Trp | Arg | Ser |
| | | | 340 | | | | | 345 | | | | | 350 | | |

Asn Phe Ser Thr Asp Ser Asp Leu Tyr Gln Thr Ile Ser Lys Leu Gly
            355                 360                 365

Lys Ala Arg Ser Ala Val Gly Gly Leu Ala Gly Asn Asp Gln Lys Phe
        370                 375                 380

Leu Lys Ser Asn Asp Ser Ala Leu Ile Trp Ser Arg Ala Asp Gly Asp
385                 390                 395                 400

Leu Ile Val Val Thr Leu Asn Arg Gly Lys Gly Tyr Ser Gly Glu Tyr
                405                 410                 415

Cys Phe Asn Thr Gly Lys Asn Asn Lys Thr Trp Asp Arg Val Leu Gly
            420                 425                 430

Ser Gly Ser Val Lys Ser Asp Gly Ser Gly Lys Leu Cys Val Ser Tyr
        435                 440                 445

Thr Asn Gly Glu Pro Glu Val Leu Val Ala Ala
    450                 455

<210> SEQ ID NO 47
<211> LENGTH: 1905
<212> TYPE: DNA
<213> ORGANISM: Unknown
<220> FEATURE:
<223> OTHER INFORMATION: Obtained from an environmental sample

<400> SEQUENCE: 47

```
atgacacgca ttctcaccct cgcccttcat gggctggctc ttgtccaaag tgttgttggg      60
gctccccaat tggcccccag agcgacaacc agtctggatg catggttggc atcggagacg     120
accgttgcgc tggatgggat ccttgacaac gtgggttcta gtggagccta cgccaaaagt     180
gcgaagtccg gtatcgtgat tgccagtcca agcaccgaca acccagacta ctactacacg     240
tggactcgcg atgctgcgtt gaccgtcaag gccctgatcg atcttttccg caatggcgag     300
acaagccttc agaccgtgat catggagtac attagctctc aggcgtacct ccagaccgta     360
tccaacccct cggggtcctt gtccaccggt ggtctggcag aaccaaaata ttatgtcgat     420
gagactgcct acacgggcag ctggggtcgt ccccagcggg atggtcctgc cctgagagcg     480
acggcgatga tcgactttgg taactggctc attgacaacg atattcaac ctacgcctct      540 aacattgtgt ggccgatcgt ccgcaacgat ctgtcgtacg ttgcccaata ttggaaccaa     600
accggatatg acctctggga agaagtgaac ggatcctcct tcttcaccat gccgtgcag      660 caccgggctc tggtggaagg cagcaccttc gcctccaaag ttggcgcctc atgctcgtgg     720
tgcgactcgc aggcgccgca ggtgctttgc ttcctgcaga gattctggac aggctcgtac     780
atcatggcca ttttggcgg cgggcgatcg ggcaaagatg ccaacaccgt cctgggaagc      840
atccatacct cgacccgaa tgccggttgc gacgacacca cgttccagcc atgctctccg      900
cgagcgctgg cgaaccacaa ggtctacacc gattcgttcc gttctatcta ctctatcaac     960
tcgggaatta gccagggcaa ggctgttgcc gtgggtcgct accccgagga ctcttactac    1020
aatggaaacc cgtggttcct tacgacgttg gctgccgcag agcagttgta cgatgccatt    1080
taccagtggc agaagattgg gtctattacc atcacggacg tctcgctggc cttcttcaag    1140
gatctttaca gctctgcggc cgttgggacg tacgcctctt cgagctcggc cttcacctcc    1200
atcgtgaatg ccgtgaagac gtacgctgat ggatatatga gtattgtgca aacccatgcg    1260
atgacgaatg gctccctttc tgagcagttc ggcaagtccg acggcttctc cctgtccgcc    1320
cgcgatctca cttggtcgta tgcagcccct ctcacagcca acttgagaag aaactcggtc    1380
gttcccccat cctgggtga gacgaccgca actagcgtac cctccgtctg ctccgcgacc    1440
```

-continued

```
tctgccactg gcacctacag taccgccacc aacaccgcgt ggcccagcac tctgaccagc   1500
gggactggcg ctacaacgac cacaagcaag gcgacttcta ctactactac ctcgtcggcc   1560
tcgacgacca cagctggatg tgtcgttccg accgcggtgg cagtcacctt tgatgagatt   1620
gctaccacaa cctatggcga gaatgtctac gtggtgggtt ccatctcgca actgggcagc   1680
tgggacacca gcaaggccgt ggccctgagt gccagcaaat acacctccag caacaatctc   1740
tggtatgcca cggtcaccct tcccgctggg acgaccttcc agtacaagtt catccggggtt   1800 tcgagcagcg ggactgttac atgggagagt gacccgaacc gttcatacac ggttccgtcc   1860
gcttgtggga cgtctactgc ggtggtgaac accacttggc gctag              1905
```

<210> SEQ ID NO 48
<211> LENGTH: 634
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(20)
<220> FEATURE:
<221> NAME/KEY: DOMAIN
<222> LOCATION: (41)...(455)
<223> OTHER INFORMATION: Glycosyl hydrolases family 15
<220> FEATURE:
<221> NAME/KEY: DOMAIN
<222> LOCATION: (532)...(628)
<223> OTHER INFORMATION: Starch binding domain
<220> FEATURE:
<221> NAME/KEY: SITE
<222> LOCATION: (202)...(205)
<223> OTHER INFORMATION: N-glycosylation site. Prosite id = PS00001
<220> FEATURE:
<221> NAME/KEY: SITE
<222> LOCATION: (204)...(214)
<223> OTHER INFORMATION: Glucoamylase active site region signature.
      Prosite id = PS00820
<220> FEATURE:
<221> NAME/KEY: SITE
<222> LOCATION: (213)...(216)
<223> OTHER INFORMATION: N-glycosylation site. Prosite id = PS00001
<220> FEATURE:
<221> NAME/KEY: SITE
<222> LOCATION: (429)...(432)
<223> OTHER INFORMATION: N-glycosylation site. Prosite id = PS00001
<220> FEATURE:
<221> NAME/KEY: SITE
<222> LOCATION: (622)...(625)
<223> OTHER INFORMATION: N-glycosylation site. Prosite id = PS00001
<220> FEATURE:
<221> NAME/KEY: SITE
<222> LOCATION: (639)...(642)
<223> OTHER INFORMATION: N-glycosylation site. Prosite id = PS00001

<400> SEQUENCE: 48

```
Met Thr Arg Ile Leu Thr Leu Ala Leu His Gly Leu Ala Leu Val Gln
1               5                   10                  15

Ser Val Val Gly Ala Pro Gln Leu Ala Pro Arg Ala Thr Thr Ser Leu
            20                  25                  30

Asp Ala Trp Leu Ala Ser Glu Thr Thr Val Ala Leu Asp Gly Ile Leu
        35                  40                  45

Asp Asn Val Gly Ser Ser Gly Ala Tyr Ala Lys Ser Ala Lys Ser Gly
    50                  55                  60

Ile Val Ile Ala Ser Pro Ser Thr Asp Asn Pro Asp Tyr Tyr Tyr Thr
65                  70                  75                  80

Trp Thr Arg Asp Ala Ala Leu Thr Val Lys Ala Leu Ile Asp Leu Phe
                85                  90                  95
```

-continued

```
Arg Asn Gly Glu Thr Ser Leu Gln Thr Val Ile Met Glu Tyr Ile Ser
            100                 105                 110

Ser Gln Ala Tyr Leu Gln Thr Val Ser Asn Pro Ser Gly Ser Leu Ser
            115                 120                 125

Thr Gly Gly Leu Ala Glu Pro Lys Tyr Val Asp Glu Thr Ala Tyr
130                 135                 140

Thr Gly Ser Trp Gly Arg Pro Gln Arg Asp Gly Pro Ala Leu Arg Ala
145                 150                 155                 160

Thr Ala Met Ile Asp Phe Gly Asn Trp Leu Ile Asp Asn Gly Tyr Ser
                165                 170                 175

Thr Tyr Ala Ser Asn Ile Val Trp Pro Ile Val Arg Asn Asp Leu Ser
            180                 185                 190

Tyr Val Ala Gln Tyr Trp Asn Gln Thr Gly Tyr Asp Leu Trp Glu Glu
            195                 200                 205

Val Asn Gly Ser Ser Phe Phe Thr Ile Ala Val Gln His Arg Ala Leu
210                 215                 220

Val Glu Gly Ser Thr Phe Ala Ser Lys Val Gly Ala Ser Cys Ser Trp
225                 230                 235                 240

Cys Asp Ser Gln Ala Pro Gln Val Leu Cys Phe Leu Gln Arg Phe Trp
                245                 250                 255

Thr Gly Ser Tyr Ile Met Ala Asn Phe Gly Gly Arg Ser Gly Lys
            260                 265                 270

Asp Ala Asn Thr Val Leu Gly Ser Ile His Thr Phe Asp Pro Asn Ala
            275                 280                 285

Gly Cys Asp Asp Thr Thr Phe Gln Pro Cys Ser Pro Arg Ala Leu Ala
290                 295                 300

Asn His Lys Val Tyr Thr Asp Ser Phe Arg Ser Ile Tyr Ser Ile Asn
305                 310                 315                 320

Ser Gly Ile Ser Gln Gly Lys Ala Val Ala Val Gly Arg Tyr Pro Glu
                325                 330                 335

Asp Ser Tyr Tyr Asn Gly Asn Pro Trp Phe Leu Thr Thr Leu Ala Ala
            340                 345                 350

Ala Glu Gln Leu Tyr Asp Ala Ile Tyr Gln Trp Gln Lys Ile Gly Ser
            355                 360                 365

Ile Thr Ile Thr Asp Val Ser Leu Ala Phe Phe Lys Asp Leu Tyr Ser
370                 375                 380

Ser Ala Ala Val Gly Thr Tyr Ala Ser Ser Ser Ala Phe Thr Ser
385                 390                 395                 400

Ile Val Asn Ala Val Lys Thr Tyr Ala Asp Gly Tyr Met Ser Ile Val
                405                 410                 415

Gln Thr His Ala Met Thr Asn Gly Ser Leu Ser Glu Gln Phe Gly Lys
            420                 425                 430

Ser Asp Gly Phe Ser Leu Ser Ala Arg Asp Leu Thr Trp Ser Tyr Ala
            435                 440                 445

Ala Leu Leu Thr Ala Asn Leu Arg Arg Asn Ser Val Val Pro Pro Ser
450                 455                 460

Trp Gly Glu Thr Thr Ala Thr Ser Val Pro Ser Val Cys Ser Ala Thr
465                 470                 475                 480

Ser Ala Thr Gly Thr Tyr Ser Thr Ala Thr Asn Thr Ala Trp Pro Ser
                485                 490                 495

Thr Leu Thr Ser Gly Thr Gly Ala Thr Thr Thr Ser Lys Ala Thr
            500                 505                 510

Ser Thr Thr Thr Ser Ser Ala Ser Thr Thr Thr Ala Gly Cys Val
            515                 520                 525
```

```
Val Pro Thr Ala Val Ala Val Thr Phe Asp Glu Ile Ala Thr Thr Thr
    530                 535                 540

Tyr Gly Glu Asn Val Tyr Val Gly Ser Ile Ser Gln Leu Gly Ser
545                 550                 555                 560

Trp Asp Thr Ser Lys Ala Val Ala Leu Ser Ala Ser Lys Tyr Thr Ser
                565                 570                 575

Ser Asn Asn Leu Trp Tyr Ala Thr Val Thr Leu Pro Ala Gly Thr Thr
            580                 585                 590

Phe Gln Tyr Lys Phe Ile Arg Val Ser Ser Ser Gly Thr Val Thr Trp
            595                 600                 605

Glu Ser Asp Pro Asn Arg Ser Tyr Thr Val Pro Ser Ala Cys Gly Thr
    610                 615                 620

Ser Thr Ala Val Val Asn Thr Thr Trp Arg
625                 630

<210> SEQ ID NO 49
<211> LENGTH: 1620
<212> TYPE: DNA
<213> ORGANISM: Aspergillus terreus

<400> SEQUENCE: 49
atgtcctttt tcctgtcctg cctctatctg agcctgtgtg gctcagcact ggcagccaat     60
ctcacgtcat ggaaatccag atccatctac cagacgatga cggacaggtt cgcgcggacc    120
gacggctcga ccaccgccgc gtgcaacacc accgccggtt tatactgcgg agggacgtgg    180
cgcggcacga tcaatcatct cgactacatc caggggatgg gcttcgatgc ggtcatgatc    240
tcccccatca tcgagaatat cgatggccgc gtctcctacg gtgaagccta ccatgggtac    300
tggccgctgg acctggagtc tttgaacaca cgcttcggca cgaaacagga cctcctcgat    360
ttgagtaatg cgctccactc ccgcgggatg tacctgatga tggataccgt gattaataac    420
atggcatata tcacgcgtgg gcaggaccct gcgacggcaa ttgactactc ggtgttcacg    480
ccgttcaaca acgcggatta ttttcatccc tactgcaaga tcacggattg aacaacctc    540 accgacgcta gtctgtgtca gacgggtgat ctggaggtcg cattgcccga cctgttcaca    600
gagcatacgg acgtgcagga tcgtctcata agctgggcca aggaaatgat ccaaacatat    660
tccatcgacg gacttcgcat tgacgccgcc aaacacgtcg atcctgagtt ctctcgcaga    720
ttcgtgaacg aagtcgatgt attcaccacc ggagaggtcc ttcagcgcga agtcgacatc    780
atctgcgact accacaacaa atacatcacc agcatgccca attacccgat ctacttctcc    840
atgctggatg cttttcacaga gggcaacacg tcgtcattga tgagccaagt ggaagcaatg    900
aagggtcctt gtcacgacgt taccgccctt gtgtcttttt ccgagaacca tgaccagccg    960
cggattccca gcatgaacaa agacatcgcg ctcgccaaaa atgttctcac tttcaccatt   1020 cttttgatg gcattcccat ggtctatcaa ggtcaagagc aacacttgga cggatctggg   1080
acaccgaaaa accgtgaagc cctgtggttg tccaagtatg atacccaagc cgaattatac   1140
caactgctcg ccaaactcaa cgcgatccgc aaacatgcca cctccctggg cagcgactac   1200
ctctatgccc aaaccagacc tatctaccgg ggcggaagtg agctcgcatt ctacaaaggc   1260
attgagggcc gacaggtgat tacggttcta tcatcgcaag gcgctcaggg aaatccatac   1320
gatctgtatc tgcccgtgtc atataatccg ggaacagcgg tgatggaggt cctcaactgt   1380
gtgaactcca cggtgggtga cgacggtcag ctcaaggtgc ccatggagaa gggagagccg   1440
cgggtgttct tcccgattga gctgatgggc ggaagcggac tgtgtggata ttccaaggat   1500
```

```
aatgttacgg tttctcagtt gaaaacaggg cacgactcga catcccgggg aagcaagatg    1560
acgggcagtg ctgcacttct tatgatgctg tcgttgggag cgagcctggt gttatggtga    1620
```

<210> SEQ ID NO 50
<211> LENGTH: 539
<212> TYPE: PRT
<213> ORGANISM: Aspergillus terreus
<220> FEATURE:
<221> NAME/KEY: SIGNAL
<222> LOCATION: (1)...(18)
<220> FEATURE:
<221> NAME/KEY: DOMAIN
<222> LOCATION: (31)...(390)
<223> OTHER INFORMATION: Alpha amylase, catalytic domain
<220> FEATURE:
<221> NAME/KEY: SITE
<222> LOCATION: (20)...(23)
<223> OTHER INFORMATION: N-glycosylation site. Prosite id = PS00001
<220> FEATURE:
<221> NAME/KEY: SITE
<222> LOCATION: (49)...(52)
<223> OTHER INFORMATION: N-glycosylation site. Prosite id = PS00001
<220> FEATURE:
<221> NAME/KEY: SITE
<222> LOCATION: (181)...(184)
<223> OTHER INFORMATION: N-glycosylation site. Prosite id = PS00001
<220> FEATURE:
<221> NAME/KEY: SITE
<222> LOCATION: (293)...(296)
<223> OTHER INFORMATION: N-glycosylation site. Prosite id = PS00001
<220> FEATURE:
<221> NAME/KEY: SITE
<222> LOCATION: (469)...(472)
<223> OTHER INFORMATION: N-glycosylation site. Prosite id = PS00001
<220> FEATURE:
<221> NAME/KEY: SITE
<222> LOCATION: (508)...(511)
<223> OTHER INFORMATION: N-glycosylation site. Prosite id = PS00001

<400> SEQUENCE: 50

```
Met Ser Phe Phe Leu Ser Cys Leu Tyr Leu Ser Leu Cys Gly Ser Ala
1               5                   10                  15

Leu Ala Ala Asn Leu Thr Ser Trp Lys Ser Arg Ser Ile Tyr Gln Thr
            20                  25                  30

Met Thr Asp Arg Phe Ala Arg Thr Asp Gly Ser Thr Thr Ala Ala Cys
        35                  40                  45

Asn Thr Thr Ala Gly Leu Tyr Cys Gly Gly Thr Trp Arg Gly Thr Ile
    50                  55                  60

Asn His Leu Asp Tyr Ile Gln Gly Met Gly Phe Asp Ala Val Met Ile
65                  70                  75                  80

Ser Pro Ile Ile Glu Asn Ile Asp Gly Arg Val Ser Tyr Gly Glu Ala
                85                  90                  95

Tyr His Gly Tyr Trp Pro Leu Asp Leu Glu Ser Leu Asn Thr Arg Phe
            100                 105                 110

Gly Thr Lys Gln Asp Leu Leu Asp Leu Ser Asn Ala Leu His Ser Arg
        115                 120                 125

Gly Met Tyr Leu Met Met Asp Thr Val Ile Asn Asn Met Ala Tyr Ile
    130                 135                 140

Thr Arg Gly Gln Asp Pro Ala Thr Ala Ile Asp Tyr Ser Val Phe Thr
145                 150                 155                 160

Pro Phe Asn Asn Ala Asp Tyr Phe His Pro Tyr Cys Lys Ile Thr Asp
                165                 170                 175

Trp Asn Asn Leu Thr Asp Ala Ser Leu Cys Gln Thr Gly Asp Leu Glu
            180                 185                 190

Val Ala Leu Pro Asp Leu Phe Thr Glu His Thr Asp Val Gln Asp Arg
```

```
                195                 200                 205
Leu Ile Ser Trp Ala Lys Glu Met Ile Gln Thr Tyr Ser Ile Asp Gly
210                 215                 220
Leu Arg Ile Asp Ala Ala Lys His Val Asp Pro Glu Phe Leu Ala Arg
225                 230                 235                 240
Phe Val Asn Glu Val Asp Val Phe Thr Thr Gly Val Leu Gln Arg
        245                 250                 255
Glu Val Asp Ile Ile Cys Asp Tyr His Asn Lys Tyr Ile Thr Ser Met
            260                 265                 270
Pro Asn Tyr Pro Ile Tyr Phe Ser Met Leu Asp Ala Phe Thr Glu Gly
        275                 280                 285
Asn Thr Ser Ser Leu Met Ser Gln Val Glu Ala Met Lys Gly Pro Cys
290                 295                 300
His Asp Val Thr Ala Leu Val Ser Phe Ser Glu Asn His Asp Gln Pro
305                 310                 315                 320
Arg Ile Pro Ser Met Asn Lys Asp Ile Ala Leu Ala Lys Asn Val Leu
            325                 330                 335
Thr Phe Thr Ile Leu Phe Asp Gly Ile Pro Met Val Tyr Gln Gly Gln
        340                 345                 350
Glu Gln His Leu Asp Gly Ser Gly Thr Pro Lys Asn Arg Glu Ala Leu
        355                 360                 365
Trp Leu Ser Lys Tyr Asp Thr Gln Ala Glu Leu Tyr Gln Leu Leu Ala
370                 375                 380
Lys Leu Asn Ala Ile Arg Lys His Ala Thr Ser Leu Gly Ser Asp Tyr
385                 390                 395                 400
Leu Tyr Ala Gln Thr Arg Pro Ile Tyr Arg Gly Gly Ser Glu Leu Ala
            405                 410                 415
Phe Tyr Lys Gly Ile Glu Gly Arg Gln Val Ile Thr Val Leu Ser Ser
        420                 425                 430
Gln Gly Ala Gln Gly Asn Pro Tyr Asp Leu Tyr Leu Pro Val Ser Tyr
        435                 440                 445
Asn Pro Gly Thr Ala Val Met Glu Val Leu Asn Cys Val Asn Ser Thr
450                 455                 460
Val Gly Asp Asp Gly Gln Leu Lys Val Pro Met Glu Lys Gly Glu Pro
465                 470                 475                 480
Arg Val Phe Phe Pro Ile Glu Leu Met Gly Ser Gly Leu Cys Gly
            485                 490                 495
Tyr Ser Lys Asp Asn Val Thr Val Ser Gln Leu Lys Thr Gly His Asp
        500                 505                 510
Ser Thr Ser Arg Gly Ser Lys Met Thr Gly Ser Ala Ala Leu Leu Met
        515                 520                 525
Met Leu Ser Leu Gly Ala Ser Leu Val Leu Trp
530                 535

<210> SEQ ID NO 51
<211> LENGTH: 1824
<212> TYPE: DNA
<213> ORGANISM: Aspergillus terreus

<400> SEQUENCE: 51
atgaagtgga ccttctcgct cctcctctta ctgtccgtgt tcggtcaggc tactcatgcc        60
ctgaccccag cagaatggcg cagccagtca atctacttcc tgttgaccga tcgctttggt       120
cgaacagaca attccacaac tgctgcctgt gacaccaccg acagagtata ctgcggtggt       180
agctggcagg gaatcatcaa ccatctcgat tacatccaag ggatgggatt cactgccatc       240
```

```
tggatcaccc cggtcactgg acagttctac gaaaacacgg gcgacggcac ctcctaccat    300
ggatactggc agcaggacat ctacgacctc aactacaact acggaacggc ccaagacctc    360
aagaacctag ccagtgcttt gcacgagcgc ggcatgtatt tgatggttga tgtggttgcc    420
aatcacatgg gctatgacgg agcgggaaac accgtggact acagtgtttt caacccottc    480 tcctcctcca gctactttca cccatactgc ctcatctcca attacgacaa ccagaccaat    540
gttgaagact gctggctggg tgataccacc gtttcgctgc agatctcga cacgacaagc    600 acagccgtgc gggacatctg gtacgactgg gtggcagact tggtcgccaa ctattccatc    660
gacggtctgc gtgtcgacac tgtaaaacac gtcgaaaaag actttggcc cgactacaac    720 agcgcagcag gcgtctactg tgtcggcgag gtcttttcag gcgatcctgc atacacatgc    780
ccgtaccaga actacatgga cggcgtgctc aactatccaa tctactacca gcttctctat    840
gcgtttgagt cgtccagcgg cagcatcagc gatctctata acatgatcag ctccgttgcc    900
tccagctgca aggatcccac actcctgggt aatttcatcg agaaccacga taaccccgc    960 tttgcttcct acacgagcga ctactcgcag gctaagaacg tgatcacctt catcttcctg   1020
agcgacggta ttcccatcgt ctacgccgga caggaacagc actacagcgg aggcagcgac   1080
ccagctaacc gcgaggccac ctggctgtct ggatactcca cgagcgccac gctgtacacc   1140
tggatcgcct ctacaaacca gatccgcagc ctggcgatct ccaaggacgc gggatacgtg   1200
caggccaaga acaaccccct ctactccgat tccaacacca tcgccatgcg caagggcacg   1260
acagccggcg cgcaagtcat caccgtcctc agcaacaagg gcgcctccgg cagctcctac   1320
accctctctt tgagcggcac aggctactcc gccggcgcga ccctggtcga cgtacacc    1380 tgcactacgg tgactgtaga ctcgagcggc aacctgcccg tcccaatgac atccggcttg   1440
ccgcgagtgt ttgtcccgtc gtcctgggtg aatgggagcg cgctttgcaa cacagaatgc   1500
acggccgcca cgtccctccc ggttctcttc gaggaactgg ttacgacgac ctacggggag   1560
aacatttatc tgagcggctc gatcagccag ctgggcagtt ggaatacggc ctcggctgtt   1620
gctctgtcgg cgagtcaata tacctcgtcc aacccgaaat ggtatgtgag tgtgacgttg   1680
cctgtgggca cgtcgttcca gtacaagttt atcaagaagg ggtcggacgg gagtgttgtc   1740
tgggagagtg atccgaaccg gtcgtatacc gttccggctg ggtgcgaggg cgcgacggtg   1800
acagttgctg atacttggag gtga                                          1824
```

<210> SEQ ID NO 52
<211> LENGTH: 607
<212> TYPE: PRT
<213> ORGANISM: Aspergillus terreus
<220> FEATURE:
<221> NAME/KEY: SIGNAL
<222> LOCATION: (1)...(20)
<220> FEATURE:
<221> NAME/KEY: DOMAIN
<222> LOCATION: (33)...(389)
<223> OTHER INFORMATION: Alpha amylase, catalytic domain
<220> FEATURE:
<221> NAME/KEY: DOMAIN
<222> LOCATION: (505)...(602)
<223> OTHER INFORMATION: Starch binding domain
<220> FEATURE:
<221> NAME/KEY: SITE
<222> LOCATION: (44)...(47)
<223> OTHER INFORMATION: N-glycosylation site. Prosite id = PS00001
<220> FEATURE:
<221> NAME/KEY: SITE
<222> LOCATION: (179)...(182)
<223> OTHER INFORMATION: N-glycosylation site. Prosite id = PS00001
<220> FEATURE:

```
<221> NAME/KEY: SITE
<222> LOCATION: (220)...(223)
<223> OTHER INFORMATION: N-glycosylation site. Prosite id = PS00001
<220> FEATURE:
<221> NAME/KEY: SITE
<222> LOCATION: (498)...(501)
<223> OTHER INFORMATION: N-glycosylation site. Prosite id = PS00001
<220> FEATURE:
<221> NAME/KEY: SITE
<222> LOCATION: (595)...(598)
<223> OTHER INFORMATION: N-glycosylation site. Prosite id = PS00001

<400> SEQUENCE: 52

Met Lys Trp Thr Phe Ser Leu Leu Leu Leu Ser Val Phe Gly Gln
1               5                   10                  15

Ala Thr His Ala Leu Thr Pro Ala Glu Trp Arg Ser Gln Ser Ile Tyr
            20                  25                  30

Phe Leu Leu Thr Asp Arg Phe Gly Arg Thr Asp Asn Ser Thr Thr Ala
            35                  40                  45

Ala Cys Asp Thr Thr Asp Arg Val Tyr Cys Gly Gly Ser Trp Gln Gly
50                  55                  60

Ile Ile Asn His Leu Asp Tyr Ile Gln Gly Met Gly Phe Thr Ala Ile
65                  70                  75                  80

Trp Ile Thr Pro Val Thr Gly Gln Phe Tyr Glu Asn Thr Gly Asp Gly
                85                  90                  95

Thr Ser Tyr His Gly Tyr Trp Gln Gln Asp Ile Tyr Asp Leu Asn Tyr
                100                 105                 110

Asn Tyr Gly Thr Ala Gln Asp Leu Lys Asn Leu Ala Ser Ala Leu His
            115                 120                 125

Glu Arg Gly Met Tyr Leu Met Val Asp Val Val Ala Asn His Met Gly
            130                 135                 140

Tyr Asp Gly Ala Gly Asn Thr Val Asp Tyr Ser Val Phe Asn Pro Phe
145                 150                 155                 160

Ser Ser Ser Ser Tyr Phe His Pro Tyr Cys Leu Ile Ser Asn Tyr Asp
                165                 170                 175

Asn Gln Thr Asn Val Glu Asp Cys Trp Leu Gly Asp Thr Thr Val Ser
            180                 185                 190

Leu Pro Asp Leu Asp Thr Thr Ser Thr Ala Val Arg Asp Ile Trp Tyr
            195                 200                 205

Asp Trp Val Ala Asp Leu Val Ala Asn Tyr Ser Ile Asp Gly Leu Arg
210                 215                 220

Val Asp Thr Val Lys His Val Glu Lys Asp Phe Trp Pro Asp Tyr Asn
225                 230                 235                 240

Ser Ala Ala Gly Val Tyr Cys Val Gly Glu Val Phe Ser Gly Asp Pro
                245                 250                 255

Ala Tyr Thr Cys Pro Tyr Gln Asn Tyr Met Asp Gly Val Leu Asn Tyr
            260                 265                 270

Pro Ile Tyr Tyr Gln Leu Leu Tyr Ala Phe Glu Ser Ser Ser Gly Ser
            275                 280                 285

Ile Ser Asp Leu Tyr Asn Met Ile Ser Ser Val Ala Ser Ser Cys Lys
290                 295                 300

Asp Pro Thr Leu Leu Gly Asn Phe Ile Glu Asn His Asp Asn Pro Arg
305                 310                 315                 320

Phe Ala Ser Tyr Thr Ser Asp Tyr Ser Gln Ala Lys Asn Val Ile Thr
            325                 330                 335

Phe Ile Phe Leu Ser Asp Gly Ile Pro Ile Val Tyr Ala Gly Gln Glu
            340                 345                 350
```

-continued

```
Gln His Tyr Ser Gly Gly Ser Asp Pro Ala Asn Arg Glu Ala Thr Trp
        355                 360                 365
Leu Ser Gly Tyr Ser Thr Ser Ala Thr Leu Tyr Thr Trp Ile Ala Ser
370                 375                 380
Thr Asn Gln Ile Arg Ser Leu Ala Ile Ser Lys Asp Ala Gly Tyr Val
385                 390                 395                 400
Gln Ala Lys Asn Asn Pro Phe Tyr Ser Asp Ser Asn Thr Ile Ala Met
                405                 410                 415
Arg Lys Gly Thr Thr Ala Gly Ala Gln Val Ile Thr Val Leu Ser Asn
            420                 425                 430
Lys Gly Ala Ser Gly Ser Ser Tyr Thr Leu Ser Leu Ser Gly Thr Gly
        435                 440                 445
Tyr Ser Ala Gly Ala Thr Leu Val Glu Thr Tyr Thr Cys Thr Thr Val
450                 455                 460
Thr Val Asp Ser Ser Gly Asn Leu Pro Val Pro Met Thr Ser Gly Leu
465                 470                 475                 480
Pro Arg Val Phe Val Pro Ser Ser Trp Val Asn Gly Ser Ala Leu Cys
                485                 490                 495
Asn Thr Glu Cys Thr Ala Ala Thr Ser Leu Pro Val Leu Phe Glu Glu
            500                 505                 510
Leu Val Thr Thr Thr Tyr Gly Glu Asn Ile Tyr Leu Ser Gly Ser Ile
        515                 520                 525
Ser Gln Leu Gly Ser Trp Asn Thr Ala Ser Ala Val Ala Leu Ser Ala
530                 535                 540
Ser Gln Tyr Thr Ser Asn Pro Lys Trp Tyr Val Ser Val Thr Leu
545                 550                 555                 560
Pro Val Gly Thr Ser Phe Gln Tyr Lys Phe Ile Lys Lys Gly Ser Asp
                565                 570                 575
Gly Ser Val Val Trp Glu Ser Asp Pro Asn Arg Ser Tyr Thr Val Pro
            580                 585                 590
Ala Gly Cys Glu Gly Ala Thr Val Thr Val Ala Asp Thr Trp Arg
        595                 600                 605

<210> SEQ ID NO 53
<211> LENGTH: 1389
<212> TYPE: DNA
<213> ORGANISM: Aspergillus terreus

<400> SEQUENCE: 53
atgaagctat cccgcgccct gacagtcttc cttctccacc ttacatccac tgcattggca      60
gcggatgtca atgcgtggaa gtctcgcaat atttactttg ctttgacgga tcgcattgcc     120
cgcagtagcg atgatactgg tggaagtgct tgcggtaacc tgggagacta ctgcggcgga     180
accttccaag gcttgcagtc caagcttgac tacatcaagg ggatgggctt tgatgctatc     240
tggatcactc ctgtggtagc taatgctccg ggtggttatc atggttattg gcacaggat      300 ctctatagta tcaactccaa ctatggcacc gctgatgacc tcaaaagcct ggtcaatgct     360
gctcatgaga agggaatgta tgttatggcg gacgtcgtgg ccaaccacat gggaagtccc     420
atcagcgata acaagcccga gccaatgaac caggagagct cttaccattc agcctgcaca     480
attgactact cagaccagag tagcattgaa gattgccgta tcgcatcaga cctgcccgat     540
gtcaacacag aaagttccga aattcggacc ctcttccagg agtggatcag ctggctggtg     600
aaggaatacc agtttgacgg gctgcgtatc gacacggtca agcatgttga aaaagacttc     660
tggccgggct tctgctctgc cgccggcgtc tacaccatcg gcgaagtctg ggacggcgac     720
```

-continued

```
ccaaactacc ttgctggata cgcaaacagt atggacgctg tgctcaacta cgcaatctac    780
tatcccatga accgattcta ccagcaacag gggtcctcct ccgacatcgt cagcatgcac    840
gatcaaatca gttccctgtt ccccaaccca accgccctcg gcacgttcct ggacaaccac    900
gacaacgccc gttggctgag ccagaagaac gacgcctctc tgctgaaaaa cgccctcgcc    960
tatgtcattc tcgcccgcgg catccccatc gtgtactacg gcacggagca gggctacgcc   1020
ggcggcaatg accccgcaaa ccgcgaggac ctatggcgca gcaacttcga caccgacgcc   1080
gacttgtacc aggccatatc ccggctctcg gcggcgaggg catcatttgg cgggctcgct   1140
gatgacgacc atgtccatct gtatgtcgct gatacggcgt acgcgtggag cagggccggt   1200
ggggacctga ttgtcctcac gtctaatagt ggatctggct ctgagtctaa gtactgcttc   1260
gattcaaaga agcctggtgg atcatggaac aacacctttg aacgggaac atatactgct    1320 gatggtgacg ggcaactctg tgtcaccacc tcaaatggtg aacccgtggt gctggttgca   1380
gatgtgtag                                                          1389
```

<210> SEQ ID NO 54
<211> LENGTH: 462
<212> TYPE: PRT
<213> ORGANISM: Aspergillus terreus
<220> FEATURE:
<221> NAME/KEY: SIGNAL
<222> LOCATION: (1)...(20)
<220> FEATURE:
<221> NAME/KEY: DOMAIN
<222> LOCATION: (33)...(373)
<223> OTHER INFORMATION: Alpha amylase, catalytic domain
<220> FEATURE:
<221> NAME/KEY: SITE
<222> LOCATION: (436)...(439)
<223> OTHER INFORMATION: N-glycosylation site. Prosite id = PS00001

<400> SEQUENCE: 54

```
Met Lys Leu Ser Arg Ala Leu Thr Val Phe Leu Leu His Leu Thr Ser
 1               5                  10                  15

Thr Ala Leu Ala Ala Asp Val Asn Ala Trp Lys Ser Arg Asn Ile Tyr
             20                  25                  30

Phe Ala Leu Thr Asp Arg Ile Ala Arg Ser Ser Asp Asp Thr Gly Gly
         35                  40                  45

Ser Ala Cys Gly Asn Leu Gly Asp Tyr Cys Gly Gly Thr Phe Gln Gly
     50                  55                  60

Leu Gln Ser Lys Leu Asp Tyr Ile Lys Gly Met Gly Phe Asp Ala Ile
 65                  70                  75                  80

Trp Ile Thr Pro Val Val Ala Asn Ala Pro Gly Gly Tyr His Gly Tyr
                 85                  90                  95

Trp Ala Gln Asp Leu Tyr Ser Ile Asn Ser Asn Tyr Gly Thr Ala Asp
            100                 105                 110

Asp Leu Lys Ser Leu Val Asn Ala Ala His Glu Lys Gly Met Tyr Val
        115                 120                 125

Met Ala Asp Val Val Ala Asn His Met Gly Ser Pro Ile Ser Asp Asn
    130                 135                 140

Lys Pro Glu Pro Met Asn Gln Glu Ser Ser Tyr His Ser Ala Cys Thr
145                 150                 155                 160

Ile Asp Tyr Ser Asp Gln Ser Ser Ile Glu Asp Cys Arg Ile Ala Ser
                165                 170                 175

Asp Leu Pro Asp Val Asn Thr Glu Ser Ser Glu Ile Arg Thr Leu Phe
            180                 185                 190

Gln Glu Trp Ile Ser Trp Leu Val Lys Glu Tyr Gln Phe Asp Gly Leu
```

|   |   |   |   | 195 |   |   |   | 200 |   |   |   | 205 |   |   |
|---|---|---|---|---|---|---|---|---|---|---|---|---|---|---|

Arg Ile Asp Thr Val Lys His Val Glu Lys Asp Phe Trp Pro Gly Phe
   210                   215                   220

Cys Ser Ala Ala Gly Val Tyr Thr Ile Gly Glu Val Trp Asp Gly Asp
225                   230                   235                   240

Pro Asn Tyr Leu Ala Gly Tyr Ala Asn Ser Met Asp Ala Val Leu Asn
               245                   250                   255

Tyr Ala Ile Tyr Tyr Pro Met Asn Arg Phe Tyr Gln Gln Gln Gly Ser
           260                   265                   270

Ser Ser Asp Ile Val Ser Met His Asp Gln Ile Ser Ser Leu Phe Pro
       275                   280                   285

Asn Pro Thr Ala Leu Gly Thr Phe Leu Asp Asn His Asp Asn Ala Arg
   290                   295                   300

Trp Leu Ser Gln Lys Asn Asp Ala Ser Leu Leu Lys Asn Ala Leu Ala
305                   310                   315                   320

Tyr Val Ile Leu Ala Arg Gly Ile Pro Ile Val Tyr Tyr Gly Thr Glu
               325                   330                   335

Gln Gly Tyr Ala Gly Gly Asn Asp Pro Ala Asn Arg Glu Asp Leu Trp
           340                   345                   350

Arg Ser Asn Phe Asp Thr Asp Ala Asp Leu Tyr Gln Ala Ile Ser Arg
       355                   360                   365

Leu Ser Ala Ala Arg Ala Ser Phe Gly Gly Leu Ala Asp Asp His
   370                   375                   380

Val His Leu Tyr Val Ala Asp Thr Ala Tyr Ala Trp Ser Arg Ala Gly
385                   390                   395                   400

Gly Asp Leu Ile Val Leu Thr Ser Asn Ser Gly Ser Gly Ser Glu Ser
               405                   410                   415

Lys Tyr Cys Phe Asp Ser Lys Lys Pro Gly Gly Ser Trp Asn Asn Thr
           420                   425                   430

Phe Gly Thr Gly Thr Tyr Thr Ala Asp Gly Asp Gly Gln Leu Cys Val
       435                   440                   445

Thr Thr Ser Asn Gly Glu Pro Val Val Leu Val Ala Asp Val
   450                   455                   460

<210> SEQ ID NO 55
<211> LENGTH: 1269
<212> TYPE: DNA
<213> ORGANISM: Unknown
<220> FEATURE:
<223> OTHER INFORMATION: Obtained from environmental sample

<400> SEQUENCE: 55
atgttgaagc agttcacgaa gcgcctgatc accctgacga gcctgctggc gctcgtcctc      60
gtcgcaccgt tggccagcgc gggcccgctg gatggcaaca gcagcgacgt catgttgcag     120
ggcttccatt ggtactcgta ccagtcgttt ccgtggtggg cgtcatcaa gaacaacgcg     180 gcgagcatca aggccgacgg cttcaccatg gtgtggctgc cgccgcccag cgacgcggcc     240
tccaacgagg gctacctgcc cgccggctc gagctgctgg acagcaagta tggcaccccgg     300 acggacctgg tcaacgccct gtccgcgctg aatgccaatg gtgtgaagcc cattgcggac     360
atcgtcatca accaccgcgt gggcaccacg gcctgggcgg acttcacgct gcctccgtgg     420
ggctcgaacg cggtgtgccg cggcgacgag tggagcgggg ccacgggcaa cgcggatacg     480 ggcgatgget tcaacgccgg gcgcgacatc gatcacacgc agaccttcgt gcaggacggc     540
atcgtcacct ggatgaacaa ctcgctgaag agcgtcgggt tcgcgggttg gcggtatgac     600

-continued

```
tacgtgaagg gctacagcgg ctcctacgtc ggctcgtaca acacccgcac gacgccgtac    660
ttctccgtgg gcgagctgtg gacggacctg gacctgaaca accccaaccc ccaccgccag    720
ctgatcatga attggatcga cgcgacgggt ggccggtccg cggcgttcga cttcacgacc    780
aagggcctgc tgcagcaggc ggtgcagtac aacgagttct ggcggctgaa ggatgcggcg    840
ggcgcgccag cgggtgccat tggttggtgg gcagcgaagt ccgtgacctt catcgacaat    900
cacgacacgg gcccgagcta tccgagcggc ggccagaacc actggccgtt ccctggtgac    960
aagatcctcc aggggtacgc ctacatcctg actcactctg gcatcccctg cgtgtactgg   1020
gtgcactaca aggactgggg ccaggcgaac acggacgcca tcaagaagct gatcagcatc   1080
cgcaagtcca agggcatcac cagcacctcc tcggtgagca tccaggccgc ggacagctcg   1140
aagtacgccg ccatcatcac cggcaacaac ggcaaggtgg ccgtgaagat cggcttcggc   1200
gcctggtctc cgccgggcac ctggacgctg gccacctccg gcaacaacta cgccgtctgg   1260
acgcagtaa                                                          1269
```

<210> SEQ ID NO 56
<211> LENGTH: 422
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(27)
<220> FEATURE:
<221> NAME/KEY: DOMAIN
<222> LOCATION: (36)...(361)
<223> OTHER INFORMATION: Alpha amylase, catalytic domain
<220> FEATURE:
<221> NAME/KEY: DOMAIN
<222> LOCATION: (362)...(422)
<223> OTHER INFORMATION: Alpha-amylase C-terminal beta-sheet domain
<220> FEATURE:
<221> NAME/KEY: SITE
<222> LOCATION: (33)...(36)
<223> OTHER INFORMATION: N-glycosylation site. Prosite id = PS00001
<220> FEATURE:
<221> NAME/KEY: SITE
<222> LOCATION: (188)...(191)
<223> OTHER INFORMATION: N-glycosylation site. Prosite id = PS00001

<400> SEQUENCE: 56

```
Met Leu Lys Gln Phe Thr Lys Arg Leu Ile Thr Leu Thr Ser Leu Leu
1               5                   10                  15

Ala Leu Val Leu Val Ala Pro Leu Ala Ser Ala Gly Pro Leu Asp Gly
            20                  25                  30

Asn Ser Ser Asp Val Met Leu Gln Gly Phe His Trp Tyr Ser Tyr Gln
        35                  40                  45

Ser Phe Pro Trp Trp Gly Val Ile Lys Asn Asn Ala Ala Ser Ile Lys
    50                  55                  60

Ala Asp Gly Phe Thr Met Val Trp Leu Pro Pro Ser Asp Ala Ala
65                  70                  75                  80

Ser Asn Glu Gly Tyr Leu Pro Arg Arg Leu Glu Leu Leu Asp Ser Lys
                85                  90                  95

Tyr Gly Thr Arg Thr Asp Leu Val Asn Ala Leu Ser Ala Leu Asn Ala
            100                 105                 110

Asn Gly Val Lys Pro Ile Ala Asp Ile Val Ile Asn His Arg Val Gly
        115                 120                 125

Thr Thr Gly Trp Ala Asp Phe Thr Leu Pro Pro Trp Gly Ser Asn Ala
    130                 135                 140
```

-continued

```
Val Cys Arg Gly Asp Glu Trp Ser Gly Ala Thr Gly Asn Ala Asp Thr
145                 150                 155                 160

Gly Asp Gly Phe Asn Ala Gly Arg Asp Ile Asp His Thr Gln Thr Phe
                165                 170                 175

Val Gln Asp Gly Ile Val Thr Trp Met Asn Asn Ser Leu Lys Ser Val
            180                 185                 190

Gly Phe Ala Gly Trp Arg Tyr Asp Tyr Val Lys Gly Tyr Ser Gly Ser
        195                 200                 205

Tyr Val Gly Ser Tyr Asn Thr Arg Thr Thr Pro Tyr Phe Ser Val Gly
    210                 215                 220

Glu Leu Trp Thr Asp Leu Asp Leu Asn Asn Pro Asn Pro His Arg Gln
225                 230                 235                 240

Leu Ile Met Asn Trp Ile Asp Ala Thr Gly Gly Arg Ser Ala Ala Phe
                245                 250                 255

Asp Phe Thr Thr Lys Gly Leu Leu Gln Gln Ala Val Gln Tyr Asn Glu
                260                 265                 270

Phe Trp Arg Leu Lys Asp Ala Ala Gly Ala Pro Ala Gly Ala Ile Gly
            275                 280                 285

Trp Trp Ala Ala Lys Ser Val Thr Phe Ile Asp Asn His Asp Thr Gly
290                 295                 300

Pro Ser Tyr Pro Ser Gly Gly Gln Asn His Trp Pro Phe Pro Gly Asp
305                 310                 315                 320

Lys Ile Leu Gln Gly Tyr Ala Tyr Ile Leu Thr His Ser Gly Ile Pro
                325                 330                 335

Cys Val Tyr Trp Val His Tyr Lys Asp Trp Gln Ala Asn Thr Asp
                340                 345                 350

Ala Ile Lys Lys Leu Ile Ser Ile Arg Lys Ser Lys Gly Ile Thr Ser
                355                 360                 365

Thr Ser Ser Val Ser Ile Gln Ala Ala Asp Ser Ser Lys Tyr Ala Ala
                370                 375                 380

Ile Ile Thr Gly Asn Asn Gly Lys Val Ala Val Lys Ile Gly Phe Gly
385                 390                 395                 400

Ala Trp Ser Pro Pro Gly Thr Trp Thr Leu Ala Thr Ser Gly Asn Asn
                405                 410                 415

Tyr Ala Val Trp Thr Gln
                420
```

<210> SEQ ID NO 57
<211> LENGTH: 1581
<212> TYPE: DNA
<213> ORGANISM: Unknown
<220> FEATURE:
<223> OTHER INFORMATION: Obtained from environmental sample

<400> SEQUENCE: 57

```
atgccaaact ggttaaaaga cgctgttttc tacgagattt accctcagtc cttcaaggac     60
accaactgcg acggtatcgg cgacatcaat ggaatcattg agaagctgga ttatgtgaag    120
gagctgggat gcaatgccct ttggatcaat ccttgtttcg attccaccat taaggatgcc    180
ggctacgacg tcagagacta caagaaggta gcacccagat atggcacaaa tgctgacctt    240
tacagattat cggcgaagc ccacaacaga ggcattcacg tactccttga cctggttccg    300
ggccacactt ccgaggaaca tgcgtggttc caggagagca aaaggctga aagaatgaa     360
tacacagacc gctatgtatg gaccaactgc tggatccatg cattgctgg tcatccctat    420
attggcggcg aggctgacag agacggctgc tacatgctga acttctttaa gtgccagcct    480
```

-continued

```
gcccttaact acggattcct taaccgcacc gatgattggc agtctgcacc tgacgcacct      540
gagtgcatcg caacaagaga ggccctcaag gacatcatgc gtttctggct tgaccacggc      600
tgcgatggtt ccgtgttga tatggcagat tctctggtaa agaggatga tgagaacaag       660 tccgctaccg gcgcaatctg gagaaatatt agagaaatgc ttgataagga ctatcctgaa      720
gctgccattg tttcagagtg gagcaatcct cagcaggccc ttaagagcgg cttccacgct      780
gacttctatc ttgatcacca cggaaacggc tataatacccc ttatccgcga caatgagacc     840
ccgggcggcg accacagttt ccttaagaag gatggaaacg gcgatatcat gcgtttcctc      900
ctggattacc tgcccaagta tgacagcacc aagaatgatg ctacataag ctttatcacc       960 tgcaatcacg acactccaag agcccgcaga acactgggct acgatgagct taagattgca     1020
tgggctcttt tcctaacact tcccggagtt ccgttcatct actacggtga tgagattgga     1080
atgagatatc tggacattcc tacgaaggaa ggcggataca caagaaccgg caccagaact     1140
ccaatgcagt gggacaactc caagaaccac ggtttctcag atgcaggtgc tgatgtcctc    1200
tatcttccac aggatccgtc tggcgatgct cctacagtcg aagatcagga aaagatcct     1260 tcttcactcc ttaacgtgac aaaagagctg acagctcttc gccataaata cactgacctg    1320
caggccgatg gctctttga cgtcatctat gcagaaaaag agcagttccc atttatctac     1380
aaacgcggaa atctgctcct tgcgatcaac ccatcagaaa gcaagtccag tgctgccctt    1440
ccggatgagg catatataaa gaaggatgat acaaaagccg gcaagcttac acctgtatac    1500
tcaatcggtg agttcaagca ggaggatcac agcctcacgc ttcagggcca gtccttcgtt    1560
gtcttctcac tcgaatcata a                                               1581
```

<210> SEQ ID NO 58
<211> LENGTH: 526
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (12)...(434)
<223> OTHER INFORMATION: Alpha amylase, catalytic domain
<220> FEATURE:
<221> NAME/KEY: SITE
<222> LOCATION: (170)...(173)
<223> OTHER INFORMATION: N-glycosylation site. Prosite id = PS00001
<220> FEATURE:
<221> NAME/KEY: SITE
<222> LOCATION: (222)...(225)
<223> OTHER INFORMATION: N-glycosylation site. Prosite id = PS00001
<220> FEATURE:
<221> NAME/KEY: SITE
<222> LOCATION: (431)...(434)
<223> OTHER INFORMATION: N-glycosylation site. Prosite id = PS00001

<400> SEQUENCE: 58

```
Met Pro Asn Trp Leu Lys Asp Ala Val Phe Tyr Glu Ile Tyr Pro Gln
1               5                   10                  15

Ser Phe Lys Asp Thr Asn Cys Asp Gly Ile Gly Asp Ile Asn Gly Ile
            20                  25                  30

Ile Glu Lys Leu Asp Tyr Val Lys Glu Leu Gly Cys Asn Ala Leu Trp
        35                  40                  45

Ile Asn Pro Cys Phe Asp Ser Pro Phe Lys Asp Ala Gly Tyr Asp Val
    50                  55                  60

Arg Asp Tyr Lys Lys Val Ala Pro Arg Tyr Gly Thr Asn Ala Asp Leu
65                  70                  75                  80

Tyr Arg Leu Phe Gly Glu Ala His Asn Arg Gly Ile His Val Leu Leu
```

```
                85                  90                  95
Asp Leu Val Pro Gly His Thr Ser Glu Glu His Ala Trp Phe Gln Glu
                100                 105                 110

Ser Lys Lys Ala Glu Lys Asn Glu Tyr Thr Asp Arg Tyr Val Trp Thr
                115                 120                 125

Asn Cys Trp Ile His Gly Ile Ala Gly His Pro Tyr Ile Gly Gly Glu
                130                 135                 140

Ala Asp Arg Asp Gly Cys Tyr Met Leu Asn Phe Phe Lys Cys Gln Pro
145                 150                 155                 160

Ala Leu Asn Tyr Gly Phe Leu Asn Arg Thr Asp Trp Gln Ser Ala
                165                 170                 175

Pro Asp Ala Pro Glu Cys Ile Ala Thr Arg Glu Ala Leu Lys Asp Ile
                180                 185                 190

Met Arg Phe Trp Leu Asp His Gly Cys Asp Gly Phe Arg Val Asp Met
                195                 200                 205

Ala Asp Ser Leu Val Lys Glu Asp Asp Glu Asn Lys Ser Ala Thr Gly
210                 215                 220

Ala Ile Trp Arg Asn Ile Arg Glu Met Leu Asp Lys Asp Tyr Pro Glu
225                 230                 235                 240

Ala Ala Ile Val Ser Glu Trp Ser Asn Pro Gln Gln Ala Leu Lys Ser
                245                 250                 255

Gly Phe His Ala Asp Phe Tyr Leu Asp His His Gly Asn Gly Tyr Asn
                260                 265                 270

Thr Leu Ile Arg Asp Asn Glu Thr Pro Gly Gly Asp His Ser Phe Leu
                275                 280                 285

Lys Lys Asp Gly Asn Gly Asp Ile Met Arg Phe Leu Leu Asp Tyr Leu
                290                 295                 300

Pro Lys Tyr Asp Ser Thr Lys Asn Asp Gly Tyr Ile Ser Phe Ile Thr
305                 310                 315                 320

Cys Asn His Asp Thr Pro Arg Ala Arg Arg Thr Leu Gly Tyr Asp Glu
                325                 330                 335

Leu Lys Ile Ala Trp Ala Leu Phe Leu Thr Leu Pro Gly Val Pro Phe
                340                 345                 350

Ile Tyr Tyr Gly Asp Glu Ile Gly Met Arg Tyr Leu Asp Ile Pro Thr
                355                 360                 365

Lys Glu Gly Gly Tyr Thr Arg Thr Gly Thr Arg Thr Pro Met Gln Trp
                370                 375                 380

Asp Asn Ser Lys Asn His Gly Phe Ser Asp Ala Gly Ala Asp Val Leu
385                 390                 395                 400

Tyr Leu Pro Gln Asp Pro Ser Gly Asp Ala Pro Thr Val Glu Asp Gln
                405                 410                 415

Glu Lys Asp Pro Ser Ser Leu Leu Asn Val Thr Lys Glu Leu Thr Ala
                420                 425                 430

Leu Arg His Lys Tyr Thr Asp Leu Gln Ala Asp Gly Ser Phe Asp Val
                435                 440                 445

Ile Tyr Ala Glu Lys Glu Gln Phe Pro Phe Ile Tyr Lys Arg Gly Asn
                450                 455                 460

Leu Leu Leu Ala Ile Asn Pro Ser Glu Ser Lys Ser Ser Ala Ala Leu
465                 470                 475                 480

Pro Asp Glu Ala Tyr Ile Lys Lys Asp Thr Lys Ala Gly Lys Leu
                485                 490                 495

Thr Pro Val Tyr Ser Ile Gly Glu Phe Lys Gln Glu Asp His Ser Leu
                500                 505                 510
```

Thr Leu Gln Gly Gln Ser Phe Val Val Phe Ser Leu Glu Ser
    515                   520                   525

<210> SEQ ID NO 59
<211> LENGTH: 1572
<212> TYPE: DNA
<213> ORGANISM: Unknown
<220> FEATURE:
<223> OTHER INFORMATION: Obtained from environmental sample

<400> SEQUENCE: 59

```
atgcccggat ggttgaagga tgcagtattt tacgaaatct accccccagtc ctttgccgat    60 tcaaacggcg acgggatcgg tgatctgcag gggatcatcg gaaagcttga ctatgtgaag   120
gagcttggat gcaacgcgct ctggatcaat ccctgttacg attcgccctt aaggatgcc    180 ggctacgacg tccgcgacta caaaaaggtg gccgaaaggt acggcacaaa cgacgatctg   240
aaggagctct tttcaaaggc acatgagaag ggcatccacg tccttctgga cctggtcccc   300
ggccacacct ccgaggaaca cgcctggttt aaggagagtt caaaagccga aagaacgag    360 tttccggcc gctatatctg gaccggacac tggctcgagg cgtaccagg tcatccctgg     420 atcgcgggag aatgcgaaag accggcctgc tatatgctca acttcttcaa atgccagccg   480
gccctgaatt acggttttt acatcccgaa aagccctggc agtcctccac ggattcccct    540
gaggcgagag cgacacatga agccatgaag atgtcatgc gcttctggct ggacgccggc   600
tgcgacggct ccgcgtgga catggcagac agccttgtaa aggatgatga cgagaagaaa   660
tcctgtacct gcgcgctgtg gcgcgaggtg aggcagatgc tcgatgacga ttatccggag   720
gccgccatca tctccgagtg gtccaatccc gaattggcca ttaattccgc acattttcac   780
atggacttct gtctcgacca cgcgagcaac ggttatcata cacttctcag ggattactgg   840
ggtgacgacg gcgacaacag cttttttcaaa gccggcggtc acggcgatgt gatgcgtttc   900
cttgatgact atctgcccag atatgaggcg acaaaggata cggctttat aagccttata   960 tcctgcaatc acgacaccag aaggcctgct tattctctct cagagcgcga gatcaaggtg  1020
gcctatgcct ttatctatac gatgcccggc gtcccctttg tctactacgg ggacgagata  1080
gcgatgagat atctggatct tcccaccaaa gaaggcggat atgacaggac cggcagcagg  1140
acgccgatgc agtgggatgg cggcgccaac ttcggtttct cctccgctcc gcggacaaa   1200 ctctacctgc cgcaggatcc ctcaaaggat gctcccacgg cagagaaggc catggccgat  1260
cccgcctctg tatatcacgt gataaaaagcc cttctgacca taagacatga gcacaaagca  1320 tgcaggcgg acggcggatt ggaagtacta tacgccgaaa aagaaaagct tccctttgtt   1380
tacgcaagaa gaagcggcga cgacggcgtg ctggtggcgc tcaatccgtc attaaatgag  1440
gtctcagccc gggtgaacgc cgcagtggat gacgagctcc tctccctcgg tgagacctcc  1500
gtatcctgtg aaggcagcga gagcaccata accatggggc ctcagtcatt catcatattt  1560
aagctggcct ga                                                        1572
```

<210> SEQ ID NO 60
<211> LENGTH: 523
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (12)...(435)
<223> OTHER INFORMATION: Alpha amylase, catalytic domain

<400> SEQUENCE: 60

```
Met Pro Gly Trp Leu Lys Asp Ala Val Phe Tyr Glu Ile Tyr Pro Gln
1               5                   10                  15

Ser Phe Ala Asp Ser Asn Gly Asp Gly Ile Gly Asp Leu Gln Gly Ile
            20                  25                  30

Ile Gly Lys Leu Asp Tyr Val Lys Glu Leu Gly Cys Asn Ala Leu Trp
            35                  40                  45

Ile Asn Pro Cys Tyr Asp Ser Pro Phe Lys Asp Ala Gly Tyr Asp Val
50                  55                  60

Arg Asp Tyr Lys Lys Val Ala Glu Arg Tyr Gly Thr Asn Asp Asp Leu
65                  70                  75                  80

Lys Glu Leu Phe Ser Lys Ala His Glu Lys Gly Ile His Val Leu Leu
                85                  90                  95

Asp Leu Val Pro Gly His Thr Ser Glu Glu His Ala Trp Phe Lys Glu
                100                 105                 110

Ser Ser Lys Ala Glu Lys Asn Glu Phe Ser Gly Arg Tyr Ile Trp Thr
            115                 120                 125

Gly His Trp Leu Glu Gly Val Pro Gly His Pro Trp Ile Ala Gly Glu
            130                 135                 140

Cys Glu Arg Pro Ala Cys Tyr Met Leu Asn Phe Phe Lys Cys Gln Pro
145                 150                 155                 160

Ala Leu Asn Tyr Gly Phe Leu His Pro Glu Lys Pro Trp Gln Ser Ser
                165                 170                 175

Thr Asp Ser Pro Glu Ala Arg Ala Thr His Glu Ala Met Lys Asp Val
                180                 185                 190

Met Arg Phe Trp Leu Asp Ala Gly Cys Asp Gly Phe Arg Val Asp Met
            195                 200                 205

Ala Asp Ser Leu Val Lys Asp Asp Glu Lys Lys Ser Cys Thr Cys
210                 215                 220

Ala Leu Trp Arg Glu Val Arg Gln Met Leu Asp Asp Asp Tyr Pro Glu
225                 230                 235                 240

Ala Ala Ile Ile Ser Glu Trp Ser Asn Pro Glu Leu Ala Ile Asn Ser
                245                 250                 255

Ala His Phe His Met Asp Phe Cys Leu Asp His Ala Ser Asn Gly Tyr
            260                 265                 270

His Thr Leu Leu Arg Asp Tyr Trp Gly Asp Asp Gly Asp Asn Ser Phe
            275                 280                 285

Phe Lys Ala Gly Gly His Gly Asp Val Met Arg Phe Leu Asp Asp Tyr
            290                 295                 300

Leu Pro Arg Tyr Glu Ala Thr Lys Asp Asn Gly Phe Ile Ser Leu Ile
305                 310                 315                 320

Ser Cys Asn His Asp Thr Arg Arg Pro Ala Tyr Ser Leu Ser Glu Arg
                325                 330                 335

Glu Ile Lys Val Ala Tyr Ala Phe Ile Tyr Thr Met Pro Gly Val Pro
                340                 345                 350

Phe Val Tyr Tyr Gly Asp Glu Ile Ala Met Arg Tyr Leu Asp Leu Pro
            355                 360                 365

Thr Lys Glu Gly Gly Tyr Asp Arg Thr Gly Ser Arg Thr Pro Met Gln
            370                 375                 380

Trp Asp Gly Gly Ala Asn Phe Gly Phe Ser Ser Ala Pro Ala Asp Lys
385                 390                 395                 400

Leu Tyr Leu Pro Gln Asp Pro Ser Lys Asp Ala Pro Thr Ala Glu Lys
                405                 410                 415

Ala Met Ala Asp Pro Ala Ser Val Tyr His Val Ile Lys Ala Leu Leu
```

```
                420             425             430
Thr Ile Arg His Glu His Lys Ala Leu Gln Ala Asp Gly Gly Leu Glu
            435             440             445
Val Leu Tyr Ala Glu Lys Glu Lys Leu Pro Phe Val Tyr Ala Arg Arg
        450             455             460
Ser Gly Asp Asp Gly Val Leu Val Ala Leu Asn Pro Ser Leu Asn Glu
465             470             475             480
Val Ser Ala Arg Val Asn Ala Ala Val Asp Asp Glu Leu Leu Ser Leu
                485             490             495
Gly Glu Thr Ser Val Ser Cys Glu Gly Ser Glu Ser Thr Ile Thr Met
            500             505             510
Gly Pro Gln Ser Phe Ile Ile Phe Lys Leu Ala
            515             520

<210> SEQ ID NO 61
<211> LENGTH: 2061
<212> TYPE: DNA
<213> ORGANISM: Unknown
<220> FEATURE:
<223> OTHER INFORMATION: Obtained from environmental sample

<400> SEQUENCE: 61
atggtagcag ctttgggct ctacggagct gccttgctca ccccaatggc ggcacaggcc      60
gaaacgggca gagaagtcat gctgcagggc tttaactgga attccacctc gcaagcgggt    120
gggcactata atgagctggc aaatcgtgct ggtgaaatcg ctggggctgg tatcgacatt    180
gtttggttcc cacctccatc cagagccgca gaccgggttg ataccctgcc aacgagtgg    240 tataatatga actccaatta tggaaatcgg acgactctac aggcggctat cgggaatctt    300
cgcaacaacg tgtcaaaac cgtcgcggat attgtcgtta ccaccgtgt gggcacaacg    360 aattgggcgg acttcacgaa tccttctttc ggtgataaca accgtgccat cacacgcgat    420
gatgaatggc atcagtcgtc gggtaactgg ataccggtg aggcgtatag tgccgcccgt    480
gacttggacc acacctacgg ccccgtgcaa aatgagatta aaaactggct gaattggttg    540
aagagtgaca tcggctttga tggttggcgc tatgatatgt caagggatt cagcgggtac    600 tatgtgggcg agtacaacac agcaactagc ccctacattt ccgttggtga gttcttcgac    660
tatgatcgcc agaaggtggt cggctggatc aacgccacca atgctcgctc tcgcgccttc    720
gattttccaa cacgcaacct cctctatgtg gctgtcaccc aaaacaacta cggagttctt    780
cgtgatggtg aaggtaaggc caatggactc atcggttggt ggccacaacg ggctatcaca    840
ttcattgaga accatgatac ggaagaagcc cgcaacggtg agtacacccc cgccttcccc    900
caatgggcta ccatgcaggg ttatgcctac attttgacgc accccggcat tccatgcgtt    960
ttctggaatg attggcgttg ggacttccgt tcggaaatca atcaactgat cgccatccgc   1020
agggcccaag catcaacga tggcagcagc ctcagcatcc aggttgccga tggcagccgc   1080
tacggggcga tcatcaatgg aaacacggcg gtcaagattg gtcctggaaa ctggagccca   1140
agtggtagtt ggacgctggc tgccgccgga ccaattacg ccgtctggac aaacggtggc   1200
ggaacaccaa cgccaacacc cacaccaacc ccaactcagg gccccacaac ggttacttgg   1260
aatccatcca ctccgacagc cggacaaaat gtgacgatca cttatccttc cggccgctcc   1320
cttgccagtt cctccaacgt caacctctac tggggtgtca atggatggac caatgtccaa   1380
accaaagcga tgaccaagaa cagttccaat gactggacaa ccacgatcac acttccctcc   1440
aacacaacac gtttgaactt tgtgttcaat aacggctcca gttgggacaa caacagcagt   1500
```

```
caggattgga atgtcaacgt gaccgctgta acgcccacac caacaccgac accgactccc   1560
acacctacgg caactccgac accgacaccc accccgacgc ccactgccac acccacccca   1620
actccgactc cttcgatcat ttggtatcgc atcgaagccc gtcacagtgg taaagttcta   1680
gacgttgcca gtcatcaac ttcaaacggt ggcaatgtgc atcagtggtc ttatgctggt    1740
ggacagaacc aacaatggcg tgttgtcgac gctgggaacg ggtttgttta catcctaaac   1800
cggaacagtg gaaaagcact tgaagtgggc aacttctcca ccagtaacgg cgggaacgtc   1860
cagcaatggg attatgccgg tggttccagt caacagtgga agctcattga gacgaccaac   1920
ggatatgtgc aaatccagaa tcggaacagc ggcaaagcca ttgatgtttc cgctgcttcg   1980
actaccaatg gtgccaacat ccatcagtgg acctacggcg gcggcaacaa tcagcagtgg   2040
aagctgatcc caatcaatta a                                             2061
```

<210> SEQ ID NO 62
<211> LENGTH: 686
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)
<220> FEATURE:
<221> NAME/KEY: DOMAIN
<222> LOCATION: (25)...(340)
<223> OTHER INFORMATION: Alpha amylase, catalytic domain
<220> FEATURE:
<221> NAME/KEY: DOMAIN
<222> LOCATION: (341)...(398)
<223> OTHER INFORMATION: Alpha-amylase C-terminal beta-sheet domain
<220> FEATURE:
<221> NAME/KEY: DOMAIN
<222> LOCATION: (547)...(680)
<223> OTHER INFORMATION: Ricin-type beta-trefoil lectin domain
<220> FEATURE:
<221> NAME/KEY: SITE
<222> LOCATION: (34)...(37)
<223> OTHER INFORMATION: N-glycosylation site. Prosite id = PS00001
<220> FEATURE:
<221> NAME/KEY: SITE
<222> LOCATION: (90)...(93)
<223> OTHER INFORMATION: N-glycosylation site. Prosite id = PS00001
<220> FEATURE:
<221> NAME/KEY: SITE
<222> LOCATION: (234)...(237)
<223> OTHER INFORMATION: N-glycosylation site. Prosite id = PS00001
<220> FEATURE:
<221> NAME/KEY: SITE
<222> LOCATION: (436)...(439)
<223> OTHER INFORMATION: N-glycosylation site. Prosite id = PS00001
<220> FEATURE:
<221> NAME/KEY: SITE
<222> LOCATION: (474)...(477)
<223> OTHER INFORMATION: N-glycosylation site. Prosite id = PS00001
<220> FEATURE:
<221> NAME/KEY: SITE
<222> LOCATION: (488)...(491)
<223> OTHER INFORMATION: N-glycosylation site. Prosite id = PS00001
<220> FEATURE:
<221> NAME/KEY: SITE
<222> LOCATION: (498)...(501)
<223> OTHER INFORMATION: N-glycosylation site. Prosite id = PS00001
<220> FEATURE:
<221> NAME/KEY: SITE
<222> LOCATION: (504)...(507)
<223> OTHER INFORMATION: N-glycosylation site. Prosite id = PS00001
<220> FEATURE:
<221> NAME/KEY: SITE
<222> LOCATION: (513)...(516)
<223> OTHER INFORMATION: N-glycosylation site. Prosite id = PS00001
<220> FEATURE:
<221> NAME/KEY: SITE

```
<222> LOCATION: (620)...(623)
<223> OTHER INFORMATION: N-glycosylation site. Prosite id = PS00001

<400> SEQUENCE: 62

Met Val Ala Gly Phe Gly Leu Tyr Gly Ala Leu Leu Thr Pro Met
1               5                   10                  15

Ala Ala Gln Ala Glu Thr Gly Arg Glu Val Met Leu Gln Gly Phe Asn
                20                  25                  30

Trp Asn Ser Thr Ser Gln Ala Gly Gly His Tyr Asn Glu Leu Ala Asn
            35                  40                  45

Arg Ala Gly Glu Ile Ala Gly Ala Gly Ile Asp Ile Val Trp Phe Pro
        50                  55                  60

Pro Pro Ser Arg Ala Ala Asp Arg Val Gly Tyr Leu Pro Asn Glu Trp
65                  70                  75                  80

Tyr Asn Met Asn Ser Asn Tyr Gly Asn Arg Thr Thr Leu Gln Ala Ala
                    85                  90                  95

Ile Gly Asn Leu Arg Asn Gly Val Lys Thr Val Ala Asp Ile Val
                100                 105                 110

Val Asn His Arg Val Gly Thr Thr Asn Trp Ala Asp Phe Thr Asn Pro
            115                 120                 125

Ser Phe Gly Asp Asn Asn Arg Ala Ile Thr Arg Asp Asp Glu Trp His
    130                 135                 140

Gln Ser Ser Gly Asn Trp Asp Thr Gly Glu Ala Tyr Ser Ala Ala Arg
145                 150                 155                 160

Asp Leu Asp His Thr Tyr Gly Pro Val Gln Asn Glu Ile Lys Asn Trp
                165                 170                 175

Leu Asn Trp Leu Lys Ser Asp Ile Gly Phe Asp Gly Trp Arg Tyr Asp
            180                 185                 190

Met Val Lys Gly Phe Ser Gly Tyr Tyr Val Gly Glu Tyr Asn Thr Ala
        195                 200                 205

Thr Ser Pro Tyr Ile Ser Val Gly Glu Phe Phe Asp Tyr Asp Arg Gln
210                 215                 220

Lys Val Val Gly Trp Ile Asn Ala Thr Asn Ala Arg Ser Arg Ala Phe
225                 230                 235                 240

Asp Phe Pro Thr Arg Asn Leu Leu Tyr Val Ala Val Thr Gln Asn Asn
                245                 250                 255

Tyr Gly Val Leu Arg Asp Gly Glu Gly Lys Ala Asn Gly Leu Ile Gly
                260                 265                 270

Trp Trp Pro Gln Arg Ala Ile Thr Phe Ile Glu Asn His Asp Thr Glu
            275                 280                 285

Glu Ala Arg Asn Gly Glu Tyr Thr Pro Ala Phe Pro Gln Trp Ala Thr
        290                 295                 300

Met Gln Gly Tyr Ala Tyr Ile Leu Thr His Pro Gly Ile Pro Cys Val
305                 310                 315                 320

Phe Trp Asn Asp Trp Arg Trp Asp Phe Arg Ser Glu Ile Asn Gln Leu
                325                 330                 335

Ile Ala Ile Arg Arg Ala Gln Gly Ile Asn Asp Gly Ser Ser Leu Ser
                340                 345                 350

Ile Gln Val Ala Asp Gly Ser Arg Tyr Gly Ala Ile Ile Asn Gly Asn
            355                 360                 365

Thr Ala Val Lys Ile Gly Pro Gly Asn Trp Ser Pro Ser Gly Ser Trp
        370                 375                 380

Thr Leu Ala Ala Ala Gly Thr Asn Tyr Ala Val Trp Thr Asn Gly Gly
385                 390                 395                 400
```

```
Gly Thr Pro Thr Pro Thr Pro Thr Pro Thr Gln Gly Pro Thr
            405                 410                 415
Thr Val Thr Trp Asn Pro Ser Thr Pro Thr Ala Gly Gln Asn Val Thr
                420                 425                 430
Ile Thr Tyr Pro Ser Gly Arg Ser Leu Ala Ser Ser Ser Asn Val Asn
            435                 440                 445
Leu Tyr Trp Gly Val Asn Gly Trp Thr Asn Val Gln Thr Lys Ala Met
    450                 455                 460
Thr Lys Asn Ser Ser Asn Asp Trp Thr Thr Ile Thr Leu Pro Ser
465                 470                 475                 480
Asn Thr Thr Arg Leu Asn Phe Val Phe Asn Asn Gly Ser Ser Trp Asp
                485                 490                 495
Asn Asn Ser Ser Gln Asp Trp Asn Val Asn Val Thr Ala Val Thr Pro
            500                 505                 510
Thr Pro Thr Pro Thr Pro Thr Pro Thr Ala Thr Pro Thr Pro
            515                 520                 525
Thr Pro Thr Pro Thr Pro Thr Ala Thr Pro Thr Pro Thr Pro
        530                 535                 540
Ser Ile Ile Trp Tyr Arg Ile Glu Ala Arg His Ser Gly Lys Val Leu
545                 550                 555                 560
Asp Val Ala Ser Ala Ser Thr Ser Asn Gly Gly Asn Val His Gln Trp
                565                 570                 575
Ser Tyr Ala Gly Gly Gln Asn Gln Gln Trp Arg Val Val Asp Ala Gly
            580                 585                 590
Asn Gly Phe Val Tyr Ile Leu Asn Arg Asn Ser Gly Lys Ala Leu Glu
        595                 600                 605
Val Gly Asn Phe Ser Thr Ser Asn Gly Gly Asn Val Gln Gln Trp Asp
610                 615                 620
Tyr Ala Gly Gly Ser Ser Gln Gln Trp Lys Leu Ile Glu Thr Thr Asn
625                 630                 635                 640
Gly Tyr Val Gln Ile Gln Asn Arg Asn Ser Gly Lys Ala Ile Asp Val
                645                 650                 655
Ser Ala Ala Ser Thr Thr Asn Gly Ala Asn Ile His Gln Trp Thr Tyr
            660                 665                 670
Gly Gly Gly Asn Asn Gln Gln Trp Lys Leu Ile Pro Ile Asn
        675                 680                 685

<210> SEQ ID NO 63
<211> LENGTH: 1611
<212> TYPE: DNA
<213> ORGANISM: Unknown
<220> FEATURE:
<223> OTHER INFORMATION: Obtained from environmental sample

<400> SEQUENCE: 63
atgacagagt ggtggcgtgg tgcagtgacc tatcaagtct atccaaggtc gtttcaggac      60
agcaacggcg acggcatcgg cgacctgccc ggcatcaccg cccggcttga gtatctggcc     120
gatcttggcg tggacgcggt ctggctgtca ccgttcttca aaagcccgat gaaggacatg     180
ggctatgacg tcagcgacta ttgcgatgtc gatccggtct tcggcaccct cgccgatttt     240
gacgccctgc tggcccgcgc gcatgagctg gggctcaagg tgatcatcga ccaggtcctt     300
agccacagtt ccgacctgca ccctgccttt gtgaccagtc gcagcgaccg cgtgaacccg     360
aaggcggact ggtatgtctg ggccgatccc aagcccgacg gcagcccgcc caacaactgg     420
ctgtcggtgt tcggtggctc ggcatgggcc tgggacgcgc gcagaaaaca gtattacctg     480
```

-continued

| | |
|---|---|
| cacaatttcc tgaccagcca gccggacctg aactaccaca acccgaaggt gcaggactgg | 540 |
| gcgctggaca catgcgtttc tggctggacc cggggcgtgg acgggttccg ctttgacacc | 600 |
| gtcaactact tcttccacga tcccttgttg cgcagcaacc ctgccgatca ccgcaacaag | 660 |
| cctgaggctg acggcaatcc ctacggcatg cagtaccacc tgcatgacaa gaaccagccc | 720 |
| gagaacctga tctggatgga gcggatacgg gtgcttctgg accaatacgg tgccgcaagc | 780 |
| gtcggcgaga tgggcgaaag tcaccacgcc atccggatga tgggcgacta caccgctccg | 840 |
| gggcggctgc atcaatgcta cagctttgaa ttcatggggt atgaatacac cgcaaacctg | 900 |
| ttccgggacc ggatagaaag cttttttcaag ggtgccccta aaggctggcc gatgtgggcg | 960 |
| ttttcaaacc acgatgtcgt ccgccatgtc agtcgctggg caaaacatgg cctcaccccc | 1020 |
| gaggcggttg ccaagcagac aggtgcgttg cttctgtcgc ttgagggctc gatctgcctg | 1080 |
| tgggagggcg aggagctggg ccagaccgat accgaactgg ccttggatga gttgaccgat | 1140 |
| ccgcagggca tcgtcttttg ccccgaaccg atcggccgcg acaatactcg gacgccaatg | 1200 |
| gtttgggacg catcgccgca tggcgggttt tcgaccgtca caccctggct gccggtgaaa | 1260 |
| ccggaacagg ccgcgcgtca tgtggccggg caaaccggtg atgccgcctc ggtgctggaa | 1320 |
| agctaccggg cgatgctggc cttccggcgc gctgaaccgg cccttaggac cgggcggacg | 1380 |
| cggtttctgg atctggccga accggttctg ggctttgtgc gcggcgaagg ggagggtgcg | 1440 |
| atcctgtgcc tgttcaatct gtcgcctgtt gcgcggggggg ttgcggtcga aggcgtgggc | 1500 |
| ccgccgatcg gcccgggcca gcaggctatc ctttcgggcg gacggctagg ccttggcccg | 1560 |
| aacggcgccg ccttcctgcg ggtgaccgga acagtccgcg ttctggacta a | 1611 |

<210> SEQ ID NO 64
<211> LENGTH: 536
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (12)...(449)
<223> OTHER INFORMATION: Alpha amylase, catalytic domain

<400> SEQUENCE: 64

Met Thr Glu Trp Trp Arg Gly Ala Val Thr Tyr Gln Val Tyr Pro Arg
1               5                   10                  15

Ser Phe Gln Asp Ser Asn Gly Asp Gly Ile Gly Asp Leu Pro Gly Ile
            20                  25                  30

Thr Ala Arg Leu Glu Tyr Leu Ala Asp Leu Gly Val Asp Ala Val Trp
        35                  40                  45

Leu Ser Pro Phe Phe Lys Ser Pro Met Lys Asp Met Gly Tyr Asp Val
    50                  55                  60

Ser Asp Tyr Cys Asp Val Asp Pro Val Phe Gly Thr Leu Ala Asp Phe
65                  70                  75                  80

Asp Ala Leu Leu Ala Arg Ala His Glu Leu Gly Leu Lys Val Ile Ile
                85                  90                  95

Asp Gln Val Leu Ser His Ser Ser Asp Leu His Pro Ala Phe Val Thr
            100                 105                 110

Ser Arg Ser Asp Arg Val Asn Pro Lys Ala Asp Trp Tyr Val Trp Ala
        115                 120                 125

Asp Pro Lys Pro Asp Gly Ser Pro Pro Asn Asn Trp Leu Ser Val Phe
    130                 135                 140

Gly Gly Ser Ala Trp Ala Trp Asp Ala Arg Arg Lys Gln Tyr Tyr Leu

```
            145                 150                 155                 160
His Asn Phe Leu Thr Ser Gln Pro Asp Leu Asn Tyr His Asn Pro Lys
                165                 170                 175

Val Gln Asp Trp Ala Leu Asp Asn Met Arg Phe Trp Leu Asp Arg Gly
            180                 185                 190

Val Asp Gly Phe Arg Phe Asp Thr Val Asn Tyr Phe Phe His Asp Pro
        195                 200                 205

Leu Leu Arg Ser Asn Pro Ala Asp His Arg Asn Lys Pro Glu Ala Asp
    210                 215                 220

Gly Asn Pro Tyr Gly Met Gln Tyr His Leu His Asp Lys Asn Gln Pro
225                 230                 235                 240

Glu Asn Leu Ile Trp Met Glu Arg Ile Arg Val Leu Leu Asp Gln Tyr
                245                 250                 255

Gly Ala Ala Ser Val Gly Glu Met Gly Glu Ser His His Ala Ile Arg
            260                 265                 270

Met Met Gly Asp Tyr Thr Ala Pro Gly Arg Leu His Gln Cys Tyr Ser
        275                 280                 285

Phe Glu Phe Met Gly Tyr Glu Tyr Thr Ala Asn Leu Phe Arg Asp Arg
    290                 295                 300

Ile Glu Ser Phe Phe Lys Gly Ala Pro Lys Gly Trp Pro Met Trp Ala
305                 310                 315                 320

Phe Ser Asn His Asp Val Val Arg His Val Ser Arg Trp Ala Lys His
                325                 330                 335

Gly Leu Thr Pro Glu Ala Val Ala Lys Gln Thr Gly Ala Leu Leu Leu
            340                 345                 350

Ser Leu Glu Gly Ser Ile Cys Leu Trp Glu Gly Glu Leu Gly Gln
        355                 360                 365

Thr Asp Thr Glu Leu Ala Leu Asp Glu Leu Thr Asp Pro Gln Gly Ile
    370                 375                 380

Val Phe Trp Pro Glu Pro Ile Gly Arg Asp Asn Thr Arg Thr Pro Met
385                 390                 395                 400

Val Trp Asp Ala Ser Pro His Gly Gly Phe Ser Thr Val Thr Pro Trp
                405                 410                 415

Leu Pro Val Lys Pro Glu Gln Ala Ala Arg His Val Ala Gly Gln Thr
            420                 425                 430

Gly Asp Ala Ala Ser Val Leu Glu Ser Tyr Arg Ala Met Leu Ala Phe
        435                 440                 445

Arg Arg Ala Glu Pro Ala Leu Arg Thr Gly Arg Thr Arg Phe Leu Asp
    450                 455                 460

Leu Ala Glu Pro Val Leu Gly Phe Val Arg Gly Glu Gly Gly Ala
465                 470                 475                 480

Ile Leu Cys Leu Phe Asn Leu Ser Pro Val Ala Arg Gly Val Ala Val
                485                 490                 495

Glu Gly Val Gly Pro Pro Ile Gly Pro Gly Gln Ala Ile Leu Ser
            500                 505                 510

Gly Gly Arg Leu Gly Leu Gly Pro Asn Gly Ala Ala Phe Leu Arg Val
        515                 520                 525

Thr Gly Thr Val Arg Val Leu Asp
    530                 535

<210> SEQ ID NO 65
<211> LENGTH: 1386
<212> TYPE: DNA
<213> ORGANISM: Unknown
<220> FEATURE:
```

-continued

<223> OTHER INFORMATION: Obtained from environmental sample

<400> SEQUENCE: 65

```
atgaagttga agtaccttgc cttagttttg ttggctgtgg cttcgatagg cctactctcg      60
actccagtgg gtgctgccaa gtactccgaa ctcgaagagg gcggtgttat aatgcaggcc     120
ttctactggg atgttcccgg aggggaatc tggtgggaca ccataagaca gaaaatcccg      180
gagtggtacg acgctggaat ctcggcgata tggattcctc cagctagcaa agggatgggc     240
ggtggttatt ccatgggcta cgatccctac gatttctttg acctcggcga gtactatcag     300
aagggaacag ttgagacgcg cttcggctca aaggaggaac tggtgaacat gataaacacc     360
gcacactcct atggcataaa ggtgatagcg gacatagtca taaaccaccg cgccggtgga     420
gaccttgagt ggaacccctt tgtaaacaac tatacttgga cagacttctc caaggtcgcc     480
tccggtaaat acacggccaa ctaccttgac ttccacccaa acgaggtcaa gtgctgcgat     540
gagggtacat ttggtgactt tccggacatc gcccacgaga gagctggga tcagtactgg      600
ctctgggcaa gcaatgagag ctacgccgca tatctccgga gcatagggat cgatgcatgg     660
cgtttcgact acgtcaaagg ttacggagcg tgggttgtta atgactggct cagctggtgg     720
ggaggctggg ccgttggaga gtactgggac acgaacgttg atgcactcct taactgggca     780
tacgacagcg gtgccaaggt cttttgacttc ccgctctact acaagatgga cgaagccttt     840
gacaacacca acatccccgc tttggtttac gccctccaga acggaggaac agtcgtttcc     900
cgcgatccct tcaaggcagt aactttcgtt gccaaccacg atacagatat aatctggaac     960
aagtatccgg cttatgcgtt catccttacc tatgagggac agcctgttat attttaccgc    1020
gactacgagg agtggctcaa caaggataag cttaacaacc ttatctggat acacgagcac    1080
cttgccggag gaagtaccaa gatcctctac tacgataacg atgagctaat attcatgagg    1140
gagggctacg ggagcaagcc gggcctcata acctacataa acctcggaaa cgactgggcc    1200
gagcgctggg tgaacgtcgg ctcaaagttt gccggctaca caatccatga atacacaggc    1260
aatctcggtg gctgggttga caggtgggtt cagtacgatg gatgggttaa actgacggca    1320
cctcctcatg atccagccaa cggatattac ggctactcag tctggagcta cgcaggcgtc    1380
ggatga                                                              1386
```

<210> SEQ ID NO 66
<211> LENGTH: 461
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(25)
<220> FEATURE:
<221> NAME/KEY: DOMAIN
<222> LOCATION: (35)...(368)
<223> OTHER INFORMATION: Alpha amylase, catalytic domain
<220> FEATURE:
<221> NAME/KEY: SITE
<222> LOCATION: (152)...(155)
<223> OTHER INFORMATION: N-glycosylation site. Prosite id = PS00001
<220> FEATURE:
<221> NAME/KEY: SITE
<222> LOCATION: (208)...(211)
<223> OTHER INFORMATION: N-glycosylation site. Prosite id = PS00001

<400> SEQUENCE: 66

```
Met Lys Leu Lys Tyr Leu Ala Leu Val Leu Leu Ala Val Ala Ser Ile
1               5                   10                  15
```

-continued

```
Gly Leu Leu Ser Thr Pro Val Gly Ala Ala Lys Tyr Ser Glu Leu Glu
            20                  25                  30
Glu Gly Gly Val Ile Met Gln Ala Phe Tyr Trp Asp Val Pro Gly Gly
        35                  40                  45
Gly Ile Trp Trp Asp Thr Ile Arg Gln Lys Ile Pro Glu Trp Tyr Asp
 50                  55                  60
Ala Gly Ile Ser Ala Ile Trp Ile Pro Pro Ala Ser Lys Gly Met Gly
 65                  70                  75                  80
Gly Gly Tyr Ser Met Gly Tyr Asp Pro Tyr Asp Phe Phe Asp Leu Gly
                85                  90                  95
Glu Tyr Tyr Gln Lys Gly Thr Val Glu Thr Arg Phe Gly Ser Lys Glu
            100                 105                 110
Glu Leu Val Asn Met Ile Asn Thr Ala His Ser Tyr Gly Ile Lys Val
        115                 120                 125
Ile Ala Asp Ile Val Ile Asn His Arg Ala Gly Gly Asp Leu Glu Trp
130                 135                 140
Asn Pro Phe Val Asn Asn Tyr Thr Trp Thr Asp Phe Ser Lys Val Ala
145                 150                 155                 160
Ser Gly Lys Tyr Thr Ala Asn Tyr Leu Asp Phe His Pro Asn Glu Val
                165                 170                 175
Lys Cys Cys Asp Glu Gly Thr Phe Gly Asp Phe Pro Asp Ile Ala His
            180                 185                 190
Glu Lys Ser Trp Asp Gln Tyr Trp Leu Trp Ala Ser Asn Glu Ser Tyr
        195                 200                 205
Ala Ala Tyr Leu Arg Ser Ile Gly Ile Asp Ala Trp Arg Phe Asp Tyr
210                 215                 220
Val Lys Gly Tyr Gly Ala Trp Val Val Asn Asp Trp Leu Ser Trp Trp
225                 230                 235                 240
Gly Gly Trp Ala Val Gly Glu Tyr Trp Asp Thr Asn Val Asp Ala Leu
                245                 250                 255
Leu Asn Trp Ala Tyr Asp Ser Gly Ala Lys Val Phe Asp Phe Pro Leu
            260                 265                 270
Tyr Tyr Lys Met Asp Glu Ala Phe Asp Asn Thr Asn Ile Pro Ala Leu
        275                 280                 285
Val Tyr Ala Leu Gln Asn Gly Gly Thr Val Val Ser Arg Asp Pro Phe
290                 295                 300
Lys Ala Val Thr Phe Val Ala Asn His Asp Thr Asp Ile Ile Trp Asn
305                 310                 315                 320
Lys Tyr Pro Ala Tyr Ala Phe Ile Leu Thr Tyr Glu Gly Gln Pro Val
                325                 330                 335
Ile Phe Tyr Arg Asp Tyr Glu Glu Trp Leu Asn Lys Asp Lys Leu Asn
            340                 345                 350
Asn Leu Ile Trp Ile His Glu His Leu Ala Gly Gly Ser Thr Lys Ile
        355                 360                 365
Leu Tyr Tyr Asp Asn Asp Glu Leu Ile Phe Met Arg Glu Gly Tyr Gly
370                 375                 380
Ser Lys Pro Gly Leu Ile Thr Tyr Ile Asn Leu Gly Asn Asp Trp Ala
385                 390                 395                 400
Glu Arg Trp Val Asn Val Gly Ser Lys Phe Ala Gly Tyr Thr Ile His
                405                 410                 415
Glu Tyr Thr Gly Asn Leu Gly Gly Trp Val Asp Arg Trp Val Gln Tyr
            420                 425                 430
Asp Gly Trp Val Lys Leu Thr Ala Pro His Asp Pro Ala Asn Gly
        435                 440                 445
```

```
Tyr Tyr Gly Tyr Ser Val Trp Ser Tyr Ala Gly Val Gly
    450             455             460
```

<210> SEQ ID NO 67
<211> LENGTH: 2022
<212> TYPE: DNA
<213> ORGANISM: Unknown
<220> FEATURE:
<223> OTHER INFORMATION: Obtained from environmental sample

<400> SEQUENCE: 67

| | | | | | |
|---|---|---|---|---|---|
| ttgaaaaaaa | acaccattag | cgccctggtc | gcaggtatgg | tattaggctt | tgcatccaac | 60 |
| gcaatggcgg | ttcctagaac | cgcttttgta | cacctctttg | aatggaaatg | gaagatgtt | 120 |
| gcacaggagt | gtgaaacatt | tctcggacct | aaaggctttg | ccgcagtgca | agtctctccg | 180 |
| ccaactaaat | ctcacaacac | ggatgcatgg | tggggccgtt | atcaacccgt | tagttatgct | 240 |
| tttgaaggac | gcagcggtaa | tcgcagccaa | tttaaaaata | tggtgcaacg | ttgtaaagct | 300 |
| gtaggcgtcg | atatatacgt | agatgcagtg | attaaccaca | tggcagccta | cgacagaaat | 360 |
| ttccctgatg | tacccctatag | cagtaatgac | tttaactcct | gtacaggaga | tattgactat | 420 |
| aataaccgtt | ggcaaacaca | gcattgtgat | ttagtcggtc | ttaatgatct | aaaaacagga | 480 |
| tctgactacg | tccgccaaaa | aatagcggat | tatatgaacg | acgcaatcag | tatgggtgta | 540 |
| gctggtttcc | gtattgatgc | agccaaacat | ataccagcag | gtgatatagc | tgccattaaa | 600 |
| ggtaaattaa | atggtaatcc | atacatcttc | aagaggtaa | ttggtgcatc | cggcgaacct | 660 |
| gttcgaccga | ctgaatacac | ctttatcggt | ggtgtcacgg | aatttcaatt | tgctcgaaaa | 720 |
| ttgggtccag | ccttccgcaa | tagtaatatt | gcttggttaa | aagacattgg | cagtcaaatg | 780 |
| gaattatcca | gtgctgatgc | cgtaacattt | gtaacgaatc | atgatgaaga | gcgtcataac | 840 |
| ccgaatggtc | ctatttggca | cggcgttcaa | ggtaatggtt | atgcattagc | aaatatttc | 900 |
| accttagctt | acccttacgg | ctatccaaaa | atcatgtcag | gatacttctt | ccacggtgac | 960 |
| tttaacgcag | ctccaccaag | cagtggtata | cacacaggaa | atgcgtgtgg | ttttgatggc | 1020 |
| ggagactggg | tatgcgaaca | caaatggcgc | ggtattgcta | catggttgc | cttccgcaac | 1080 |
| tatacagcaa | gcgaatggcg | tatcagtaat | tggtggcaaa | acagtaacga | ccaaattgct | 1140 |
| tttggtcgcg | gtggtttagg | ttttgttgtt | attaataaac | gtgctaatgg | tagcattaat | 1200 |
| caaagttttg | atacgggaat | gcctgatggc | caatactgta | acataataga | agctaacttt | 1260 |
| gatgaaagca | ccggccaatg | tagtgcagct | acagattcca | acggtcaagc | cgttattacc | 1320 |
| gtcagtggtg | ggcaagctaa | ctttaatgta | gcaggcgatc | atgctgctgc | aattcatgtt | 1380 |
| ggcgcaaaaa | ttggtgatca | atgtagtggt | gatgattgcc | catgtacagg | atccgattgt | 1440 |
| aataatgatc | ctaaacctga | ttttgcagta | ccagcaacat | caatttgtac | atcagaaaat | 1500 |
| ttacctacgc | tatattactg | gggagcacag | cctacagata | gcttagcgaa | tgcagcttgg | 1560 |
| ccaggtgtcg | caatgcaaac | aaatggcgac | tttaagtgtc | atgatttagg | tgtcgaacta | 1620 |
| accaaaatta | acgccatctt | tagtgacaat | ggtgcaaata | aaacagctga | tctaactgtt | 1680 |
| actggtgcag | gttgttataa | agacgggact | tggagcacct | acaaaattg | tggcttttgaa | 1740 |
| attaccggtg | cacaaaccaa | tccagtcggt | ggcgacgaag | tctggtactt | ccgaggtact | 1800 |
| gctaatgact | ggggtaaagc | acaattagat | tatgacgcaa | ctagcggttt | gtattacaca | 1860 |
| atacaaagct | ttaatggtga | agaagcacct | gcgcgtttta | aaattgataa | tggtagttgg | 1920 |
| actgaagctt | atccaacagc | tgattaccaa | gttacagata | acaattcata | ccgcattaac | 1980 | tttaatagcg atagcaaagc gattacagta aacgcacaat aa                    2022

```
<210> SEQ ID NO 68
<211> LENGTH: 673
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(23)
<220> FEATURE:
<221> NAME/KEY: DOMAIN
<222> LOCATION: (27)...(359)
<223> OTHER INFORMATION: Alpha amylase, catalytic domain
<220> FEATURE:
<221> NAME/KEY: DOMAIN
<222> LOCATION: (372)...(463)
<223> OTHER INFORMATION: Alpha amylase, C-terminal all-beta domain
<220> FEATURE:
<221> NAME/KEY: SITE
<222> LOCATION: (88)...(91)
<223> OTHER INFORMATION: N-glycosylation site. Prosite id = PS00001
<220> FEATURE:
<221> NAME/KEY: SITE
<222> LOCATION: (365)...(368)
<223> OTHER INFORMATION: N-glycosylation site. Prosite id = PS00001
<220> FEATURE:
<221> NAME/KEY: SITE
<222> LOCATION: (402)...(405)
<223> OTHER INFORMATION: N-glycosylation site. Prosite id = PS00001
<220> FEATURE:
<221> NAME/KEY: SITE
<222> LOCATION: (406)...(409)
<223> OTHER INFORMATION: N-glycosylation site. Prosite id = PS00001
<220> FEATURE:
<221> NAME/KEY: SITE
<222> LOCATION: (561)...(564)
<223> OTHER INFORMATION: N-glycosylation site. Prosite id = PS00001
<220> FEATURE:
<221> NAME/KEY: SITE
<222> LOCATION: (646)...(649)
<223> OTHER INFORMATION: N-glycosylation site. Prosite id = PS00001
<220> FEATURE:
<221> NAME/KEY: SITE
<222> LOCATION: (664)...(667)
<223> OTHER INFORMATION: N-glycosylation site. Prosite id = PS00001

<400> SEQUENCE: 68

Met Lys Lys Asn Thr Ile Ser Ala Leu Val Ala Gly Met Val Leu Gly
1               5                   10                  15

Phe Ala Ser Asn Ala Met Ala Val Pro Arg Thr Ala Phe Val His Leu
                20                  25                  30

Phe Glu Trp Lys Trp Glu Asp Val Ala Gln Glu Cys Glu Thr Phe Leu
            35                  40                  45

Gly Pro Lys Gly Phe Ala Ala Val Gln Val Ser Pro Pro Thr Lys Ser
        50                  55                  60

His Asn Thr Asp Ala Trp Trp Gly Arg Tyr Gln Pro Val Ser Tyr Ala
65                  70                  75                  80

Phe Glu Gly Arg Ser Gly Asn Arg Ser Gln Phe Lys Asn Met Val Gln
                85                  90                  95

Arg Cys Lys Ala Val Gly Val Asp Ile Tyr Val Asp Ala Val Ile Asn
            100                 105                 110

His Met Ala Ala Tyr Asp Arg Asn Phe Pro Asp Val Pro Tyr Ser Ser
        115                 120                 125

Asn Asp Phe Asn Ser Cys Thr Gly Asp Ile Asp Tyr Asn Asn Arg Trp
    130                 135                 140

Gln Thr Gln His Cys Asp Leu Val Gly Leu Asn Asp Leu Lys Thr Gly
145                 150                 155                 160
```

Ser Asp Tyr Val Arg Gln Lys Ile Ala Asp Tyr Met Asn Asp Ala Ile
            165                 170                 175

Ser Met Gly Val Ala Gly Phe Arg Ile Asp Ala Ala Lys His Ile Pro
            180                 185                 190

Ala Gly Asp Ile Ala Ala Ile Lys Gly Lys Leu Asn Gly Asn Pro Tyr
            195                 200                 205

Ile Phe Gln Glu Val Ile Gly Ala Ser Gly Glu Pro Val Arg Pro Thr
210                 215                 220

Glu Tyr Thr Phe Ile Gly Gly Val Thr Glu Phe Gln Phe Ala Arg Lys
225                 230                 235                 240

Leu Gly Pro Ala Phe Arg Asn Ser Asn Ile Ala Trp Leu Lys Asp Ile
            245                 250                 255

Gly Ser Gln Met Glu Leu Ser Ser Ala Asp Ala Val Thr Phe Val Thr
            260                 265                 270

Asn His Asp Glu Glu Arg His Asn Pro Asn Gly Pro Ile Trp His Gly
            275                 280                 285

Val Gln Gly Asn Gly Tyr Ala Leu Ala Asn Ile Phe Thr Leu Ala Tyr
            290                 295                 300

Pro Tyr Gly Tyr Pro Lys Ile Met Ser Gly Tyr Phe His Gly
305                 310                 315                 320

Phe Asn Ala Ala Pro Pro Ser Ser Gly Ile His Thr Gly Asn Ala Cys
            325                 330                 335

Gly Phe Asp Gly Gly Asp Trp Val Cys Glu His Lys Trp Arg Gly Ile
            340                 345                 350

Ala Asn Met Val Ala Phe Arg Asn Tyr Thr Ala Ser Glu Trp Arg Ile
            355                 360                 365

Ser Asn Trp Trp Gln Asn Ser Asn Asp Gln Ile Ala Phe Gly Arg Gly
            370                 375                 380

Gly Leu Gly Phe Val Val Ile Asn Lys Arg Ala Asn Gly Ser Ile Asn
385                 390                 395                 400

Gln Ser Phe Asp Thr Gly Met Pro Asp Gly Gln Tyr Cys Asn Ile Ile
            405                 410                 415

Glu Ala Asn Phe Asp Glu Ser Thr Gly Gln Cys Ser Ala Ala Thr Asp
            420                 425                 430

Ser Asn Gly Gln Ala Val Ile Thr Val Ser Gly Gly Gln Ala Asn Phe
            435                 440                 445

Asn Val Ala Gly Asp His Ala Ala Ile His Val Gly Ala Lys Ile
            450                 455                 460

Gly Asp Gln Cys Ser Gly Asp Cys Pro Cys Thr Gly Ser Asp Cys
465                 470                 475                 480

Asn Asn Asp Pro Lys Pro Asp Phe Ala Val Pro Ala Thr Ser Ile Cys
            485                 490                 495

Thr Ser Glu Asn Leu Pro Thr Leu Tyr Tyr Trp Gly Ala Gln Pro Thr
            500                 505                 510

Asp Ser Leu Ala Asn Ala Ala Trp Pro Gly Val Ala Met Gln Thr Asn
            515                 520                 525

Gly Asp Phe Lys Cys His Asp Leu Gly Val Glu Leu Thr Lys Ile Asn
            530                 535                 540

Ala Ile Phe Ser Asp Asn Gly Ala Asn Lys Thr Ala Asp Leu Thr Val
545                 550                 555                 560

Thr Gly Ala Gly Cys Tyr Lys Asp Gly Thr Trp Ser Thr Leu Gln Asn
            565                 570                 575

Cys Gly Phe Glu Ile Thr Gly Ala Gln Thr Asn Pro Val Gly Gly Asp

```
                580              585               590
Glu Val Trp Tyr Phe Arg Gly Thr Ala Asn Asp Trp Gly Lys Ala Gln
            595                 600                 605

Leu Asp Tyr Asp Ala Thr Ser Gly Leu Tyr Tyr Thr Ile Gln Ser Phe
        610                 615                 620

Asn Gly Glu Glu Ala Pro Ala Arg Phe Lys Ile Asp Asn Gly Ser Trp
625                 630                 635                 640

Thr Glu Ala Tyr Pro Thr Ala Asp Tyr Gln Val Thr Asp Asn Asn Ser
                645                 650                 655

Tyr Arg Ile Asn Phe Asn Ser Asp Ser Lys Ala Ile Thr Val Asn Ala
            660                 665                 670

Gln

<210> SEQ ID NO 69
<211> LENGTH: 1455
<212> TYPE: DNA
<213> ORGANISM: Unknown
<220> FEATURE:
<223> OTHER INFORMATION: Obtained from environmental sample

<400> SEQUENCE: 69
atgaaccgtc caggcacggg cgcctcgggg cgcccacaat ctcgctccgc cacgtcgtgg      60
caatcccgca acggcggctg gctgctcgcc tcgctgctgg ccgtgtgttt cgcaacggcg     120
cccgtgcgcg ccgatgtcat cctgcatgca ttcaactggc cgtatgcgac ggtcgaagcc     180
cgcgccaacg agctgcgaga cctgggctat cgcgccgtac tggtcgcacc gccggtgaag     240
tccgaaggca atgcgtggtg ggcgcgctac cagccgcagg actaccgggt catcgagcat     300
ccgctcggca tcgcgagtc gttcgtgcgc atgtccagtg ctctgcgcgc ccgcggcatt     360
cgcgtctacg ccgacatcgt gctgaatcac atggccaatg aagccccgca gcgaccggat     420
ctgaactacc ccgtcaacg ggtcctggat cagtatgcag gcaataccgc gtacttcgcg     480
cagcaacgac tctacggcga tctccgctac aacttcatgt cggcctggga ctttggcccc     540
gcccactgca tcggcaacta ccacgacgtc tggcaggtgc agaactggcg gctgtgcagc     600
ggcgctggcg atgccggcct gcccgacctg ctggccagcg attacatcgt cggacagcag     660
cgcacctatc tccaggcact gaagaacctc ggcgtctccg ggttgcgcat cgacgcggcc     720
aagcacatgc cgctcagcca catcaaccgc gtactgactg ccgacctcaa ggccggcatg     780
catgtgttcg gcgaagtcat cacccacggt ggcgtcggtg atcccgaata cgatctgttt     840 ctccggcccct atctggatgg caccgatcac ggtgcctacg acttcccgct cttcgaggcg     900
atccgccgcg cattcggctt cggtggcagc atgagcaccc tggtcgatcc tggggccgtc     960
ggactggccc tgcccaatgc ccggtcgatc accttcaccg tcacccacga catcccgaac    1020
aatggtgtgt ccggcatct gctgctggat gccggcgacg aaaccctggc gtacgcctac    1080
atcctgggtc gtgacggcgg cagtccactg ctgtactccg atcacaacga gagcggcgac    1140
aaccgctggg ttcatgccta tcggcgcaac gacctcgcgg ccatgatccg ctttcacaat    1200
gccaatcatg gcaatgacat gcaggtgctc gcacacggga actgccatct gctctttcgc    1260
cgcggcaatc gcggcatcgt ggcgatcaac aagtgcgggc atacggtcaa cgccacggtg    1320
aacatgaaca cagtgtgct gtggtggcat accccgtatc gcgatgtcct tgatgccggc    1380
agcgtggtgc agattggcag cgccagccac acgttcagcc ttccgccgcg gcgcgctcgg    1440
atgtggctgc gctga                                                    1455
```

```
<210> SEQ ID NO 70
<211> LENGTH: 484
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(44)
<220> FEATURE:
<221> NAME/KEY: DOMAIN
<222> LOCATION: (45)...(399)
<223> OTHER INFORMATION: Alpha amylase, catalytic domain
<220> FEATURE:
<221> NAME/KEY: SITE
<222> LOCATION: (381)...(384)
<223> OTHER INFORMATION: N-glycosylation site. Prosite id = PS00001
<220> FEATURE:
<221> NAME/KEY: SITE
<222> LOCATION: (443)...(446)
<223> OTHER INFORMATION: N-glycosylation site. Prosite id = PS00001
<220> FEATURE:
<221> NAME/KEY: SITE
<222> LOCATION: (449)...(452)
<223> OTHER INFORMATION: N-glycosylation site. Prosite id = PS00001

<400> SEQUENCE: 70

Met Asn Arg Pro Gly Thr Gly Ala Ser Gly Arg Pro Gln Ser Arg Ser
1               5                   10                  15

Ala Thr Ser Trp Gln Ser Arg Asn Gly Gly Trp Leu Leu Ala Ser Leu
            20                  25                  30

Leu Ala Val Cys Phe Ala Thr Ala Pro Val Arg Ala Asp Val Ile Leu
        35                  40                  45

His Ala Phe Asn Trp Pro Tyr Ala Thr Val Glu Ala Arg Ala Asn Glu
    50                  55                  60

Leu Arg Asp Leu Gly Tyr Arg Ala Val Leu Val Ala Pro Pro Val Lys
65                  70                  75                  80

Ser Glu Gly Asn Ala Trp Trp Ala Arg Tyr Gln Pro Gln Asp Tyr Arg
                85                  90                  95

Val Ile Glu His Pro Leu Gly Asn Arg Glu Ser Phe Val Arg Met Ser
            100                 105                 110

Ser Ala Leu Arg Ala Arg Gly Ile Arg Val Tyr Ala Asp Ile Val Leu
        115                 120                 125

Asn His Met Ala Asn Glu Ala Pro Gln Arg Pro Asp Leu Asn Tyr Pro
    130                 135                 140

Gly Gln Arg Val Leu Asp Gln Tyr Ala Gly Asn Thr Ala Tyr Phe Ala
145                 150                 155                 160

Gln Gln Arg Leu Tyr Gly Asp Leu Arg Tyr Asn Phe Met Ser Ala Trp
                165                 170                 175

Asp Phe Gly Pro Ala His Cys Ile Gly Asn Tyr His Asp Val Trp Gln
            180                 185                 190

Val Gln Asn Trp Arg Leu Cys Ser Gly Ala Gly Asp Ala Gly Leu Pro
        195                 200                 205

Asp Leu Leu Ala Ser Asp Tyr Ile Val Gly Gln Gln Arg Thr Tyr Leu
    210                 215                 220

Gln Ala Leu Lys Asn Leu Gly Val Ser Gly Leu Arg Ile Asp Ala Ala
225                 230                 235                 240

Lys His Met Pro Leu Ser His Ile Asn Arg Val Leu Thr Ala Asp Leu
                245                 250                 255

Lys Ala Gly Met His Val Phe Gly Glu Val Ile Thr His Gly Gly Val
            260                 265                 270

Gly Asp Pro Glu Tyr Asp Leu Phe Leu Arg Pro Tyr Leu Asp Gly Thr
```

```
                275                 280                 285
Asp His Gly Ala Tyr Asp Phe Pro Leu Phe Glu Ala Ile Arg Arg Ala
        290                 295                 300
Phe Gly Phe Gly Gly Ser Met Ser Thr Leu Val Asp Pro Gly Ala Val
305                 310                 315                 320
Gly Leu Ala Leu Pro Asn Ala Arg Ser Ile Thr Phe Thr Val Thr His
                325                 330                 335
Asp Ile Pro Asn Asn Gly Val Phe Arg His Leu Leu Asp Ala Gly
        340                 345                 350
Asp Glu Thr Leu Ala Tyr Ala Tyr Ile Leu Gly Arg Asp Gly Gly Ser
            355                 360                 365
Pro Leu Leu Tyr Ser Asp His Asn Glu Ser Gly Asp Asn Arg Trp Val
        370                 375                 380
His Ala Tyr Arg Arg Asn Asp Leu Ala Ala Met Ile Arg Phe His Asn
385                 390                 395                 400
Ala Asn His Gly Asn Asp Met Gln Val Leu Ala His Gly Asn Cys His
                405                 410                 415
Leu Leu Phe Arg Arg Gly Asn Arg Gly Ile Val Ala Ile Asn Lys Cys
            420                 425                 430
Gly His Thr Val Asn Ala Thr Val Asn Met Asn Asn Ser Val Leu Trp
            435                 440                 445
Trp His Thr Pro Tyr Arg Asp Val Leu Asp Ala Gly Ser Val Val Gln
        450                 455                 460
Ile Gly Ser Ala Ser His Thr Phe Ser Leu Pro Pro Arg Arg Ala Arg
465                 470                 475                 480
Met Trp Leu Arg

<210> SEQ ID NO 71
<211> LENGTH: 1719
<212> TYPE: DNA
<213> ORGANISM: Unknown
<220> FEATURE:
<223> OTHER INFORMATION: Obtained from environmental sample

<400> SEQUENCE: 71
gtgcccgaac tgaaatggtg gcagacagct atattttatc aaatctaccc gcgctctttc      60
gccgacggca acggcgatgg catcggcgat ttcaaaggca tcatcggcaa actcgattat     120
ctacaaaatc ttggcataga tgcgctctgg ctctcgcctc acttcccctc ccccaactgg     180
gattgcggct acgatatcag cgattaccgc aacgttgcgc ggaatacgg cacgctggac      240
gatttcaaaa ccttcctgag cgaatcgcac aaacgcggta tccgcgtcat tctcgacctc     300
gtgctgaatc acacctccga tgaacatccg tggttcatcg aatcgaaatc cagccgcgat     360
aatcccaaat ccgattggta tgtgtgggtc gatacgccgc caacaattg gcagtcctgc     420
ttcgatggcg atgcctggac atacgtccct gaacgcggcc aatattatta tcactacttc     480
atgaaacagc agcccgatct caactggcat aatccgcagg tcaaacaggc catgtgggag     540
gcggtgcgct tctggctcga tctcggcgtg acggcttcc gcctgacgc catcggcacg       600
atctacgaag acccaaatct cacgccgcat aatgtcccga tgaatttggc tgagctgcgt     660
cacttcacag atgtcgccaa aacgccggaa gagatcaagc tcaaagaaaa atactggcac     720
gacatgttca agcatcaatg gggtcagccc ggcgttcatg acctgatgaa agaactgcgc     780
gccatcctcg atgaatatga tggcgaccgc atgctggtcg cgaagatga caacatcgat     840
tacatgggca acggagacga cgaattgcag ctggtcttca acttcccgtt gatgcgcgcc     900
```

```
gatcgtctca cccccgacca tattcggcgc aaccaaaaag agcgtttgac tcgtctgaat    960
gctttacccg ttaaaggctg ggcttgcaac acgctcggca accatgatag ttcacgcgtc   1020
tacaccaaat tcggtgaccg gatccacggc gcggaccatg cacgtctcaa cctggcgctt   1080
ttgctcaccc tgcacggcac gccgttctta tacaacggcg aagagatcgg catgaccgac   1140
cacatcatta ccgatcccac caaactgcgc gacaccatgg caacctggta ttacaacagc   1200
cttgtcaacg aaatgaaggt cgagccagcg gaggccgccc ttcgcgccgg acagatgacg   1260
cgcgacaaaa accgtacccc catgcaatgg gacaataagc ccaatgccgg ttttttgccca   1320
gataaagccg aaccctggtt gccagtcaac cccaattacc gcgcaggcat taacgtccgc   1380
gagcaaacat cgaacccgaa ctcgctgctc aattactata aacgtctcat ccacttgcgg   1440
cgggaaacgc ctgccttgat cgctggagat tacgttccgc ttcaccagac atccaaagat   1500
catctggcct tcctgcgcaa aacagattca caaacgatcc tggtcgtttt gaattactcc   1560
cccaataaat tggaattgga tttctcgcgc accgtcgaaa tgaaaggccg cccgctgatc   1620
gcaattttct ccagcgcaga tgaccgcccg caggcggcac aaagcccaaa gaaagtatcg   1680
gtcggcgctt acggagttct gctggcagaa gtaaaatag                          1719
```

<210> SEQ ID NO 72
<211> LENGTH: 572
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (14)...(405)
<223> OTHER INFORMATION: Alpha amylase, catalytic domain
<220> FEATURE:
<221> NAME/KEY: SITE
<222> LOCATION: (104)...(107)
<223> OTHER INFORMATION: N-glycosylation site. Prosite id = PS00001
<220> FEATURE:
<221> NAME/KEY: SITE
<222> LOCATION: (525)...(528)
<223> OTHER INFORMATION: N-glycosylation site. Prosite id = PS00001

<400> SEQUENCE: 72

```
Met Pro Glu Leu Lys Trp Trp Gln Thr Ala Ile Phe Tyr Gln Ile Tyr
 1               5                  10                  15

Pro Arg Ser Phe Ala Asp Gly Asn Gly Asp Ile Gly Asp Phe Lys
                20                  25                  30

Gly Ile Ile Gly Lys Leu Asp Tyr Leu Gln Asn Leu Gly Ile Asp Ala
            35                  40                  45

Leu Trp Leu Ser Pro His Phe Pro Ser Pro Asn Trp Asp Cys Gly Tyr
 50                  55                  60

Asp Ile Ser Asp Tyr Arg Asn Val Ala Pro Glu Tyr Gly Thr Leu Asp
 65                  70                  75                  80

Asp Phe Lys Thr Phe Leu Ser Glu Ser His Lys Arg Gly Ile Arg Val
                 85                  90                  95

Ile Leu Asp Leu Val Leu Asn His Thr Ser Asp Glu His Pro Trp Phe
            100                 105                 110

Ile Glu Ser Lys Ser Ser Arg Asp Asn Pro Lys Ser Asp Trp Tyr Val
        115                 120                 125

Trp Val Asp Thr Pro Pro Asn Asn Trp Gln Ser Cys Phe Asp Gly Asp
    130                 135                 140

Ala Trp Thr Tyr Val Pro Glu Arg Gly Gln Tyr Tyr His Tyr Phe
145                 150                 155                 160
```

-continued

```
Met Lys Gln Gln Pro Asp Leu Asn Trp His Asn Pro Gln Val Lys Gln
                165                 170                 175

Ala Met Trp Glu Ala Val Arg Phe Trp Leu Asp Leu Gly Val Asp Gly
            180                 185                 190

Phe Arg Leu Asp Ala Ile Gly Thr Ile Tyr Glu Asp Pro Asn Leu Thr
        195                 200                 205

Pro His Asn Val Pro Met Asn Leu Ala Glu Leu Arg His Phe Thr Asp
    210                 215                 220

Val Ala Lys Thr Pro Glu Glu Ile Lys Leu Lys Glu Lys Tyr Trp His
225                 230                 235                 240

Asp Met Phe Lys His Gln Trp Gly Gln Pro Gly Val His Asp Leu Met
                245                 250                 255

Lys Glu Leu Arg Ala Ile Leu Asp Glu Tyr Asp Gly Asp Arg Met Leu
            260                 265                 270

Val Gly Glu Asp Asp Asn Ile Asp Tyr Met Gly Asn Gly Asp Asp Glu
        275                 280                 285

Leu Gln Leu Val Phe Asn Phe Pro Leu Met Arg Ala Asp Arg Leu Thr
    290                 295                 300

Pro Asp His Ile Arg Arg Asn Gln Lys Glu Arg Leu Thr Arg Leu Asn
305                 310                 315                 320

Ala Leu Pro Val Lys Gly Trp Ala Cys Asn Thr Leu Gly Asn His Asp
                325                 330                 335

Ser Ser Arg Val Tyr Thr Lys Phe Gly Asp Arg Ile His Gly Ala Asp
            340                 345                 350

His Ala Arg Leu Asn Leu Ala Leu Leu Thr Leu His Gly Thr Pro
        355                 360                 365

Phe Leu Tyr Asn Gly Glu Glu Ile Gly Met Thr Asp His Ile Ile Thr
    370                 375                 380

Asp Pro Thr Lys Leu Arg Asp Thr Met Ala Thr Trp Tyr Tyr Asn Ser
385                 390                 395                 400

Leu Val Asn Glu Met Lys Val Glu Pro Ala Glu Ala Leu Arg Ala
                405                 410                 415

Gly Gln Met Thr Arg Asp Lys Asn Arg Thr Pro Met Gln Trp Asp Asn
            420                 425                 430

Lys Pro Asn Ala Gly Phe Cys Pro Asp Lys Ala Glu Pro Trp Leu Pro
        435                 440                 445

Val Asn Pro Asn Tyr Arg Ala Gly Ile Asn Val Arg Glu Gln Thr Ser
    450                 455                 460

Asn Pro Asn Ser Leu Leu Asn Tyr Tyr Lys Arg Leu Ile His Leu Arg
465                 470                 475                 480

Arg Glu Thr Pro Ala Leu Ile Ala Gly Asp Tyr Val Pro Leu His Gln
                485                 490                 495

Thr Ser Lys Asp His Leu Ala Phe Leu Arg Lys Thr Asp Ser Gln Thr
            500                 505                 510

Ile Leu Val Val Leu Asn Tyr Ser Pro Asn Lys Leu Glu Leu Asp Phe
        515                 520                 525

Ser Arg Thr Val Glu Met Lys Gly Arg Pro Leu Ile Ala Ile Phe Ser
    530                 535                 540

Ser Ala Asp Asp Arg Pro Gln Ala Ala Gln Ser Pro Lys Lys Val Ser
545                 550                 555                 560

Val Gly Ala Tyr Gly Val Leu Leu Ala Glu Val Lys
                565                 570

<210> SEQ ID NO 73
```

<211> LENGTH: 1836
<212> TYPE: DNA
<213> ORGANISM: Thermomyces lanuginosus ATCC 200065

<400> SEQUENCE: 73

```
ttgtgcgcgg cccttggact cgccgccttg atcgtccaag gcggagaagc cagacctgaa        60
acaaccgtcc cacatgcaac gggctcgctc gacgacttcc tcgccgcaca gagtccgatt       120
gctttccaag gcatcctgaa caatatcggg cctagcggag cgtactcgga aggtgtcaat       180
ccgggtgtgg tcattgcgag tccaagtaaa caagatcccg actactttta cacctgggtg       240
cgcgacgctg ctctcactgt ccaatatctg gtggaggagc tggttgcagg aaatgccagt       300
cttcagttcc tcattcagga ctacatcagc tcccaggcac gactgcagac ggtggaaaat       360
ccatccggct ccctctcgtc gggtggtcta ggagagccca gtttcatgt cgacgagacc        420
gcctttacgg actcctgggg ccgaccacag cgggacggcc cgcctctccg cgccattgcc       480
atgatttcgt ttgccaatta cctgattgac aacggtcatc aatcgactgt ggaggacatc       540
atctggccga ttgttcgcaa tgacttgtcc tatgtctcgc agcattggaa cgaaacaact       600
tttgacatct gggaggaagt ccatagctca tcgttttca ccacggctgt ccagtaccgt        660
gctctggtcc aaggcagtgc cttggctagc aagctcggcc atacctgcga caactgcggg       720
tcccaagcac cgcagatcct ttgcttcctg cagtcgtatt ggaccgggtc gcacatctta       780
gccaacaccg gtggcggccg ctcgggaaag gacgtcagca cgatcctcgg cgtcattggc       840
tcgtttgatc cgaacgccga ctgtgatgac gttaccttcc agcccctgct cggcccgggct      900
cttgcaaatc acaagcaggt cgttgacagc ttccgcagta tctatgccat caacgctggc       960
atcccgtcag ggtcggctgt tgcggttgga cgttatcccg aggatgtcta tcagggtgga      1020
caccctggt acctaacaac ggctgcgcg gcggagcagc tttacgacgc catttaccag        1080
tggaaccatg tagggcacat cgacatcaat gctgtcaatc tggacttctt caagagcatt      1140
tatccgtcag ccgccgaggg cacatacaca tcagactctt caacatttca agacattata      1200
tctgctgtac ggacctatgc ggacgggttt ctcagcgtaa ttgagaaata cactccgccg      1260
gataacttgc ttgccgagca gttccaccgg gagacgggca ttccactatc ggcagcttct      1320
ctgacatggt cctacgccgc gctcaacacg gccgcgcagc ggcgagcgtc aatcgtgccc      1380
tcaccgtgga actctaacag cacagatctc ccggacaaat gctcggcaac ctcggcaaca      1440
gggccgtatg ccacgcccac aaacacggca tggccaacca ctacgcagcc accggagcgg      1500
ccggcatgca caccgccgtc ggaagtaaca ctcaccttca acgcgctcgt cgacaccgcg      1560
tttggccaga atatttatct cgtgggctcc attccggagc tcggatcgtg ggatccggcc      1620
aacgccctct tgatgagcgc aaagagctgg actagcggaa atccggtctg gacgctatcc      1680
atttcccttc cagcaggaac ctcttttgag tacaagttca ttcgaaagga tgatggttcc      1740
tcggatgttg tctgggaaag tgacccgaat cgttcgtaca acgtgccgaa ggattgcggt      1800
gccaacacgg ccaccgtgaa ttcttggtgg cgatga                                1836
```

<210> SEQ ID NO 74
<211> LENGTH: 611
<212> TYPE: PRT
<213> ORGANISM: Thermomyces lanuginosus ATCC 200065
<220> FEATURE:
<221> NAME/KEY: DOMAIN
<222> LOCATION: (39)...(453)
<223> OTHER INFORMATION: Glycosyl hydrolases family 15
<220> FEATURE:
<221> NAME/KEY: DOMAIN
<222> LOCATION: (508)...(605)

```
<223> OTHER INFORMATION: Starch binding domain
<220> FEATURE:
<221> NAME/KEY: SITE
<222> LOCATION: (99)...(102)
<223> OTHER INFORMATION: N-glycosylation site. Prosite id = PS00001
<220> FEATURE:
<221> NAME/KEY: SITE
<222> LOCATION: (200)...(203)
<223> OTHER INFORMATION: N-glycosylation site. Prosite id = PS00001
<220> FEATURE:
<221> NAME/KEY: SITE
<222> LOCATION: (473)...(476)
<223> OTHER INFORMATION: N-glycosylation site. Prosite id = PS00001
<220> FEATURE:
<221> NAME/KEY: SITE
<222> LOCATION: (599)...(602)
<223> OTHER INFORMATION: N-glycosylation site. Prosite id = PS00001

<400> SEQUENCE: 74
```

| | | | | | | | | | | | | | | | |
|---|---|---|---|---|---|---|---|---|---|---|---|---|---|---|---|
| Met | Cys | Ala | Ala | Leu | Gly | Leu | Ala | Ala | Leu | Ile | Val | Gln | Gly | Gly | Glu |
| 1 | | | | 5 | | | | | 10 | | | | | 15 | |
| Ala | Arg | Pro | Glu | Thr | Thr | Val | Pro | His | Ala | Thr | Gly | Ser | Leu | Asp | Asp |
| | | | 20 | | | | | 25 | | | | | 30 | | |
| Phe | Leu | Ala | Ala | Gln | Ser | Pro | Ile | Ala | Phe | Gln | Gly | Ile | Leu | Asn | Asn |
| | | | 35 | | | | | 40 | | | | | 45 | | |
| Ile | Gly | Pro | Ser | Gly | Ala | Tyr | Ser | Glu | Gly | Val | Asn | Pro | Gly | Val | Val |
| 50 | | | | | 55 | | | | | 60 | | | | | |
| Ile | Ala | Ser | Pro | Ser | Lys | Gln | Asp | Pro | Asp | Tyr | Phe | Tyr | Thr | Trp | Val |
| 65 | | | | | 70 | | | | | 75 | | | | | 80 |
| Arg | Asp | Ala | Ala | Leu | Thr | Val | Gln | Tyr | Leu | Val | Glu | Glu | Leu | Val | Ala |
| | | | | 85 | | | | | 90 | | | | | 95 | |
| Gly | Asn | Ala | Ser | Leu | Gln | Phe | Leu | Ile | Gln | Asp | Tyr | Ile | Ser | Ser | Gln |
| | | | 100 | | | | | 105 | | | | | 110 | | |
| Ala | Arg | Leu | Gln | Thr | Val | Glu | Asn | Pro | Ser | Gly | Ser | Leu | Ser | Ser | Gly |
| | | | 115 | | | | | 120 | | | | | 125 | | |
| Gly | Leu | Gly | Glu | Pro | Lys | Phe | His | Val | Asp | Glu | Thr | Ala | Phe | Thr | Asp |
| | 130 | | | | | 135 | | | | | 140 | | | | |
| Ser | Trp | Gly | Arg | Pro | Gln | Arg | Asp | Gly | Pro | Pro | Leu | Arg | Ala | Ile | Ala |
| 145 | | | | | 150 | | | | | 155 | | | | | 160 |
| Met | Ile | Ser | Phe | Ala | Asn | Tyr | Leu | Ile | Asp | Asn | Gly | His | Gln | Ser | Thr |
| | | | | 165 | | | | | 170 | | | | | 175 | |
| Val | Glu | Asp | Ile | Ile | Trp | Pro | Ile | Val | Arg | Asn | Asp | Leu | Ser | Tyr | Val |
| | | | 180 | | | | | 185 | | | | | 190 | | |
| Ser | Gln | His | Trp | Asn | Glu | Thr | Thr | Phe | Asp | Ile | Trp | Glu | Glu | Val | His |
| | | | 195 | | | | | 200 | | | | | 205 | | |
| Ser | Ser | Ser | Phe | Phe | Thr | Thr | Ala | Val | Gln | Tyr | Arg | Ala | Leu | Val | Gln |
| | 210 | | | | | 215 | | | | | 220 | | | | |
| Gly | Ser | Ala | Leu | Ala | Ser | Lys | Leu | Gly | His | Thr | Cys | Asp | Asn | Cys | Gly |
| 225 | | | | | 230 | | | | | 235 | | | | | 240 |
| Ser | Gln | Ala | Pro | Gln | Ile | Leu | Cys | Phe | Leu | Gln | Ser | Tyr | Trp | Thr | Gly |
| | | | | 245 | | | | | 250 | | | | | 255 | |
| Ser | His | Ile | Leu | Ala | Asn | Thr | Gly | Gly | Gly | Arg | Ser | Gly | Lys | Asp | Val |
| | | | 260 | | | | | 265 | | | | | 270 | | |
| Ser | Thr | Ile | Leu | Gly | Val | Ile | Gly | Ser | Phe | Asp | Pro | Asn | Ala | Asp | Cys |
| | | | 275 | | | | | 280 | | | | | 285 | | |
| Asp | Asp | Val | Thr | Phe | Gln | Pro | Cys | Ser | Ala | Arg | Ala | Leu | Ala | Asn | His |
| | 290 | | | | | 295 | | | | | 300 | | | | |
| Lys | Gln | Val | Val | Asp | Ser | Phe | Arg | Ser | Ile | Tyr | Ala | Ile | Asn | Ala | Gly |
| 305 | | | | | 310 | | | | | 315 | | | | | 320 |

```
Ile Pro Ser Gly Ser Ala Val Ala Val Gly Arg Tyr Pro Glu Asp Val
                325                 330                 335

Tyr Gln Gly Gly His Pro Trp Tyr Leu Thr Thr Ala Ala Ala Ala Glu
            340                 345                 350

Gln Leu Tyr Asp Ala Ile Tyr Gln Trp Asn His Val Gly His Ile Asp
                355                 360                 365

Ile Asn Ala Val Asn Leu Asp Phe Phe Lys Ser Ile Tyr Pro Ser Ala
    370                 375                 380

Ala Glu Gly Thr Tyr Thr Ser Asp Ser Ser Thr Phe Gln Asp Ile Ile
385                 390                 395                 400

Ser Ala Val Arg Thr Tyr Ala Asp Gly Phe Leu Ser Val Ile Glu Lys
                405                 410                 415

Tyr Thr Pro Pro Asp Asn Leu Leu Ala Glu Gln Phe His Arg Glu Thr
                420                 425                 430

Gly Ile Pro Leu Ser Ala Ala Ser Leu Thr Trp Ser Tyr Ala Ala Leu
                435                 440                 445

Asn Thr Ala Ala Gln Arg Arg Ala Ser Ile Val Pro Ser Pro Trp Asn
    450                 455                 460

Ser Asn Ser Thr Asp Leu Pro Asp Lys Cys Ser Ala Thr Ser Ala Thr
465                 470                 475                 480

Gly Pro Tyr Ala Thr Pro Thr Asn Thr Ala Trp Pro Thr Thr Thr Gln
                485                 490                 495

Pro Pro Glu Arg Pro Ala Cys Thr Pro Pro Ser Glu Val Thr Leu Thr
                500                 505                 510

Phe Asn Ala Leu Val Asp Thr Ala Phe Gly Gln Asn Ile Tyr Leu Val
                515                 520                 525

Gly Ser Ile Pro Glu Leu Gly Ser Trp Asp Pro Ala Asn Ala Leu Leu
                530                 535                 540

Met Ser Ala Lys Ser Trp Thr Ser Gly Asn Pro Val Trp Thr Leu Ser
545                 550                 555                 560

Ile Ser Leu Pro Ala Gly Thr Ser Phe Glu Tyr Lys Phe Ile Arg Lys
                565                 570                 575

Asp Asp Gly Ser Ser Asp Val Val Trp Glu Ser Asp Pro Asn Arg Ser
                580                 585                 590

Tyr Asn Val Pro Lys Asp Cys Gly Ala Asn Thr Ala Thr Val Asn Ser
                595                 600                 605

Trp Trp Arg
    610

<210> SEQ ID NO 75
<211> LENGTH: 1344
<212> TYPE: DNA
<213> ORGANISM: Unknown
<220> FEATURE:
<223> OTHER INFORMATION: Obtained from an environmental sample

<400> SEQUENCE: 75
atgaaccggg ttaagagact ttcgattttg gtcgttcttt tccttaccgc cttcattccg     60 actgttttg ccggcgagca gcctctcgcc atctttcacg ccctttaacga cccccttcact    120 cttgttgaat cctatgtctg cgaactcgcc gggcagggat actcacatgt ccagatatct    180
ccagcgcaga agtcgaaccc tgctcgagcc tggtatgccc ggtatcaacc cgtagatttt    240
actgtcatcg aagggatggg cactgagagc gatctgagga agctcacgga taaggcccac    300
gcgtgtggaa taaggtgat cgccgatgtg gtcttcaacc acatgtcgag catggacgag     360 tacaagggc ttgacaagtt tccgggactt gctcctgctg atttccaccg gcagtgcggc     420
```

```
atcgattatt caaaacgaga ttcggtgcgg aactgttggc tcggaggcga cttgcccgat    480
ctggaccagt cccggccgag ggtacaggat gttcagagag cccacataag gaagctcctt    540
tccctcggca tagacggctt ccgcttcgat gcggctaaac acatcgaccc cattgttgtg    600
aaagactaca tcgatctcat cgacagggag agcaacggca ggacctggaa ctacctcgag    660
gtcatcgagg atgacggcac tcaggccacg gactacaact ggatagcggc agtgaccgat    720
ttcgtcctct acaaggagtc gttgaggaag gccttcagtc tcggcgggga cctgcgatcg    780
ctcaagatgc ctgtggctgt caatgattcg cggagtatcg tcttcgggag aaatcacgac    840
accgtgccgg agaataacca gaactgcatc gtcggctgct acgacagccg ggaggactcc    900
tatcttgcca cggcatacgt cctggcccgc gaatcgggag tcccgctggt cctcaactgg    960
gacaactacg acgcgcccta catcagcacc ggcgtgaagt tccgccagat catgacgcag   1020
cgaggacgat cggccatgaa cgtgaaggag aatgtgctgg gcgtcatcga cagtcctgtc   1080
gtcatgatga tggagcgcgg gagtgaaggc ttttcgtcc tcaacaagag cgccgaccgg   1140
ttcgatatcc cagttctgga tctgacactg accaatctcg agggatgtta tcgggagctg   1200
agaagaaaat tcaccgtcgc catcgagaga agtacggta agaaatttgt cacccggtgg   1260
ggacgatggg accggggggg cctcgaaatc tacggccgcg acgctctcta cttcatacgg   1320
gaaccctggg agcagtgcag gtaa                                          1344
```

<210> SEQ ID NO 76
<211> LENGTH: 447
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(24)

<400> SEQUENCE: 76

Met Asn Arg Val Lys Arg Leu Ser Ile Leu Val Val Leu Phe Leu Thr
1               5                   10                  15

Ala Phe Ile Pro Thr Val Phe Ala Gly Glu Gln Pro Leu Ala Ile Phe
            20                  25                  30

His Ala Phe Asn Asp Pro Phe Thr Leu Val Glu Ser Tyr Val Cys Glu
        35                  40                  45

Leu Ala Gly Gln Gly Tyr Ser His Val Gln Ile Ser Pro Ala Gln Lys
    50                  55                  60

Ser Asn Pro Ala Arg Ala Trp Tyr Ala Arg Tyr Gln Pro Val Asp Phe
65                  70                  75                  80

Thr Val Ile Glu Gly Met Gly Thr Glu Ser Asp Leu Arg Lys Leu Thr
                85                  90                  95

Asp Lys Ala His Ala Cys Gly Ile Lys Val Ile Ala Asp Val Val Phe
            100                 105                 110

Asn His Met Ser Ser Met Asp Glu Tyr Lys Gly Leu Asp Lys Phe Pro
        115                 120                 125

Gly Leu Ala Pro Ala Asp Phe His Arg Gln Cys Gly Ile Asp Tyr Ser
    130                 135                 140

Lys Arg Asp Ser Val Arg Asn Cys Trp Leu Gly Gly Asp Leu Pro Asp
145                 150                 155                 160

Leu Asp Gln Ser Arg Pro Arg Val Gln Asp Val Gln Arg Ala His Ile
                165                 170                 175

Arg Lys Leu Leu Ser Leu Gly Ile Asp Gly Phe Arg Phe Asp Ala Ala

```
                180             185              190
Lys His Ile Asp Pro Ile Val Val Lys Asp Tyr Ile Asp Leu Ile Asp
            195                 200                 205

Arg Glu Ser Asn Gly Arg Thr Trp Asn Tyr Leu Glu Val Ile Glu Asp
            210                 215                 220

Asp Gly Thr Gln Ala Thr Asp Tyr Asn Trp Ile Ala Ala Val Thr Asp
225                 230                 235                 240

Phe Val Leu Tyr Lys Glu Ser Leu Arg Lys Ala Phe Ser Leu Gly Gly
                245                 250                 255

Asp Leu Arg Ser Leu Lys Met Pro Val Ala Val Asn Asp Ser Arg Ser
            260                 265                 270

Ile Val Phe Gly Arg Asn His Asp Thr Val Pro Glu Asn Asn Gln Asn
            275                 280                 285

Cys Ile Val Gly Cys Tyr Asp Ser Arg Glu Asp Ser Tyr Leu Ala Thr
            290                 295                 300

Ala Tyr Val Leu Ala Arg Glu Ser Gly Val Pro Leu Val Leu Asn Trp
305                 310                 315                 320

Asp Asn Tyr Asp Ala Pro Tyr Ile Ser Thr Gly Val Lys Phe Arg Gln
                325                 330                 335

Ile Met Thr Gln Arg Gly Arg Ser Ala Met Asn Val Lys Glu Asn Val
            340                 345                 350

Leu Gly Val Ile Asp Ser Pro Val Met Met Met Glu Arg Gly Ser
            355                 360                 365

Glu Gly Phe Phe Val Leu Asn Lys Ser Ala Asp Arg Phe Asp Ile Pro
370                 375                 380

Val Leu Asp Leu Thr Leu Thr Asn Leu Glu Gly Cys Tyr Arg Glu Leu
385                 390                 395                 400

Arg Arg Lys Phe Thr Val Ala Ile Glu Arg Lys Tyr Gly Lys Lys Phe
                405                 410                 415

Val Thr Arg Trp Gly Arg Trp Asp Arg Gly Leu Glu Ile Tyr Gly
            420                 425                 430

Arg Asp Ala Leu Tyr Phe Ile Arg Glu Pro Trp Glu Gln Cys Arg
            435                 440                 445
```

<210> SEQ ID NO 77
<211> LENGTH: 1311
<212> TYPE: DNA
<213> ORGANISM: Artificial Sequence
<220> FEATURE:
<223> OTHER INFORMATION: Synthetically generated polynucleotide

<400> SEQUENCE: 77

```
atggccaagt acctggagct cgaagagggc ggggtcataa tgcaggcgtt ctactgggac    60
gtgccttcag gaggaatatg gtgggacaca atacggcaga agataccgga gtggtacgat   120
gccggaatct ccgcaatatg gattcctccc gcgagcaagg gtatgagcgg cggctattcg   180
atgggctacg acccctacga ttattttgac ctcggtgagt actaccagaa gggaacggtg   240
gaaacgaggt tcggctcaaa gcaggagctc ataaacatga taaacacggc ccatgcctac   300
ggcataaagg tcatagcgga catcgtcata aaccaccgcg caggcggaga cctcgagtgg   360
aacccgttcg ttggggacta cacctggacg gacttctcaa aggtggcctc gggcaaaatat   420
actgccaact acctcgactt ccacccgaac gagctccatg cgggcgattc cggaacattt   480
ggaggctatc ccgacatatg ccacgacaag agctgggacc agtactggct ctgggccagc   540
caggagagct acgcggcata tctcaggagc atcggcatcg atgcctggcg ctttgactac   600
```

-continued

```
gtgaagggct acggagcgtg ggtcgtcaag gactggctca actggtgggg cggctgggcc      660
gttggcgagt actgggacac caacgttgat gcactcctca actgggccta ctcgagcggc      720
gccaaggtct tcgacttccc gctctactac aagatggacg cggcctttga caacaagaac      780
attcccgcac tcgtcgaggc cctcaagaac ggggcacag tcgtcagccg cgacccgttt      840
aaggccgtaa ccttcgttgc aaaccacgac accgatataa tctggaacaa gtatccagcc      900
tacgcgttca tcctcaccta cgagggccag ccgacaatat tctaccgcga ctacgaggag      960
tggctcaaca aggataagct caagaacctc atctggatac atgacaacct cgccggagga     1020
agcacgagca tagtttacta cgacagcgac gagatgatct tcgtgaggaa cggctatgga     1080
agcaagcctg gccttataac ttacatcaac ctcggctcga gcaaggttgg aaggtgggtt     1140
tatgtgccga agttcgcggg cgcgtgcatc cacgagtata ctggtaacct cggaggctgg     1200
gtagacaagt acgtctactc aagcggctgg gtctatctcg aagctccagc ttacgaccct     1260
gccaacgggc agtatggcta ctccgtgtgg agctactgcg gtgttgggtg a              1311
```

<210> SEQ ID NO 78
<211> LENGTH: 436
<212> TYPE: PRT
<213> ORGANISM: Artificial Sequence
<220> FEATURE:
<223> OTHER INFORMATION: Synthetically generated polypeptide

<400> SEQUENCE: 78

```
Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
```

```
                        245                 250                 255
Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
            355                 360                 365

Ile Asn Leu Gly Ser Ser Lys Val Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 79
<211> LENGTH: 1764
<212> TYPE: DNA
<213> ORGANISM: Artificial sequence
<220> FEATURE:
<223> OTHER INFORMATION: Synthetically generated polynucleotide

<400> SEQUENCE: 79
cttactccag ctgagtggag gtctcagagc atctacttcc tcctcactga tcgcttcggc      60
aggaccgata actctactac cgctgcttgc gataccactg atagggttta ctgcggcggc     120
tcttggcagg gcatcatcaa ccacctggat tacatccagg gcatgggctt cactgctatc     180
tggatcactc cagtgactgg ccagttctac gagaacactg gcgatggcac ttcataccac     240
ggctactggc agcaggatat ctacgacctg aactacaact acggcactgc tcaggatctt     300
aagaacctgg cttctgctct tcacgagagg ggcatgtacc tgatggtgga tgtggtggct     360
aaccacatgg gctacgatgg cgctggcaac actgtggatt actccgtgtt caacccattc     420
agcagcagct cttacttcca cccgtactgc ctgatcagca actacgacaa ccagaccaac     480
gttgaggatt gctggcttgg cgatacaacc gtgtctctgc agacctgga  taccacttct     540 actgctgtga gggatatctg gtatgattgg gtggccgatc ttgtggctaa ctactctatc     600
gatggcctga gggtggacac tgttaagcac gtggagaagg atttctggcc agactacaac     660
tctgctgctg gcgtttactg tgttggggag gttttctctg gcgatccagc ttacacttgc     720
ccgtaccaga actacatgga tggcgtgctg aactacccaa tctactacca gctcctgtac     780
gctttcgagt caagctctgg ctctatcagc gacctgtaca catgatcag cagcgtggct     840 tcttcttgca aggacccaac ccttcttggc aactttatcg agaaccacga caacccacgc     900
ttcgctagct acaccagcga ttactctcag gccaagaacg tgatcacctt catcttcctc     960
```

-continued

| | |
|---|---|
| tcagacggca tcccaatcgt ttacgctggc caggagcagc attactctgg cggctctgat | 1020 |
| ccagctaacc gcgaggctac ttggctttct ggctactcta cctctgctac cctgtacact | 1080 |
| tggatcgcta gcactaacca gatccgctca ctggctatct ctaaggatgc tggctacgtc | 1140 |
| caggctaaga acaacccatt ctactccgac tctaacacca tcgctatgag gaagggcact | 1200 |
| actgctggcg ctcaggtgat cactgtgctg tctaacaagg gcgcttctgg ctcttcttac | 1260 |
| acccttctc tgtctggcac tggctactct gctggcgcta ctcttgtgga gacctacacc | 1320 |
| tgcaccactg tgaccgttga ttcttctggc aacctgccag tgccaatgac ttctggcctt | 1380 |
| ccaagggtgt tcgttccaag ctcttgggtt aacggctctg ctctgtgcaa cactgagtgc | 1440 |
| actgctgcta cttctctgcc agtgctgttc gaggagctgg tgactactac ttacggcgag | 1500 |
| aacatctacc ttagcggctc tatctctcag cttggctctt ggaacactgc ttctgctgtg | 1560 |
| gctcttcctg ctagccagta caccagctct aacccaaagt ggtacgtgtc tgtgactctt | 1620 |
| ccagtgggca ctagcttcca gtacaagttt atcaagaagg ctctgacgg ctctgttgtt | 1680 |
| tgggagagcg acccaaacag gtcttacact gttccagctg gctgcgaggg cgctactgtt | 1740 |
| actgttgccg atacctggcg ctga | 1764 |

```
<210> SEQ ID NO 80
<211> LENGTH: 1710
<212> TYPE: DNA
<213> ORGANISM: Artificial sequence
<220> FEATURE:
<223> OTHER INFORMATION: Synthetically generated polynucleotide

<400> SEQUENCE: 80
```

| | |
|---|---|
| gccgatacaa acgcttggaa gagccgctct atctacttcg tgctgaccga taggatcgct | 60 |
| aggaactctt ctgatactgg cggctctgct tgctctgatc ttggcaacta ctgcggcggc | 120 |
| actttccagg gccttgagag caagctggat tacatcaagg ccttggctt cgatgctatc | 180 |
| tggatcactc cagtggtgtc taacaaggct gctggctacc acggctactg gctgaggat | 240 |
| ctgtacgctg tgaactctaa ctacggcact gctgctgatc tgaagtctct ggtggctgct | 300 |
| gctcacgcta agggcatcta catgatggtg gacgtggtgg ctaaccacat gggcccaggc | 360 |
| gctatcacta caacaggcc agagccactt aaccaggctt caagctacca tccaccgtgc | 420 |
| aacatcgact acaacaacca gacttctgtg gaggtttgcc agatcgctgg ccttccagat | 480 |
| atctacacca ccaagagcga gatcaggact ctgctgaaca cttgggtgaa ctggcttgtg | 540 |
| aacgagtact ctttcgatgg cgtcaggatc gataccgtta agcacgtgga gaaggatttc | 600 |
| tggccaggct ctctgctgc tactggcgtt acaacatcg gcgaggtgtt cgatggcgat | 660 |
| ccagcttacc ttgctccata cgccaagctg atgccaggcc ttcttaacta cgccgtgtac | 720 |
| tacccgatga caacttcta ccagcagact ggctcttctc aggctctggt ggacatgatg | 780 |
| aacaccgtgt ccaacacttt cccagatccc tctgctcttg gcaccttcct ggacaaccac | 840 |
| gataacaagc ggtggctgaa cgtgaagaac gatcagaccc tgctgaagaa cgctctggct | 900 |
| tacgttatcc ttgctagggg catcccaatc ctttactacg gcacagagca gggctacgct | 960 |
| ggcggcgatg atccagctaa ccgcgaggat ctttggcgct ctggcttcaa cactaacgcc | 1020 |
| aacctgtacc aggctatcaa gaagctgact gctgctaggc aggctgctgg cggccttgct | 1080 |
| ggcaacgatc acgtccacct gtacgtggct gatactgctt acgcttggtc tagggctaac | 1140 |
| ggcaacctga tcgtgcttac tactaacgct ggcggcaact ctaacactca gcactgcttc | 1200 |
| aacacccaga aggctaacgg ccgctggact aacgtttacg gcaacggcgc tactgtttct | 1260 |

| | |
|---|---:|
| gctgatagca acggccaaat ctgcgtgtct gttactaacg gcgagccagt ggttcttctt | 1320 |
| gctggctctg ctactccaac tactggcacc accctgtcta ctaggactgc taccgctact | 1380 |
| gctacaccaa ctgcttgccc aaccgctgtg tctgtgtctt tcacccacag ggtgacaact | 1440 |
| gttccaggcg acacgatcaa gatcactggc aacactgccc agcttggcaa ctggactcca | 1500 |
| gctaacggcc ttgctctttc tgctgctagc tacaccagct ctaacccaat ctggaccatc | 1560 |
| actgtgccac ttgctgctgg ctctagcatc agctacaagt tcgtgaagat cgattctggc | 1620 |
| ggcactgtta cttgggagag cgacccaaac aggtcttaca ctgctccatc ttgccaggct | 1680 |
| tcagctagcg ttaacagcag ctggcagtaa | 1710 |

<210> SEQ ID NO 81
<211> LENGTH: 1851
<212> TYPE: DNA
<213> ORGANISM: Artificial sequence
<220> FEATURE:
<223> OTHER INFORMATION: Synthetically generated polynucleotide

<400> SEQUENCE: 81

| | |
|---|---:|
| gaggctgctc cacagcttgc tccaagggct actacctctc tggatgcttg gcttgcttct | 60 |
| gagaccactg ttgctctgga tgggattctt gataatgttg gctcttctgg cgcttacgct | 120 |
| aagtctgcta agtcaggcat cgtgatcgct tctccatcta ccgacaaccc ggactactac | 180 |
| tacacttgga ccagggatgc tgctcttact gtgaaggccc tgatcgatct tttcaggaac | 240 |
| ggcgagacct ctcttcagac tgtgatcatg gagtacatca gctctcaggc ttacctccag | 300 |
| actgtgtcta acccatctgg ctcactttct actggcggcc ttgccgagcc aaagtactac | 360 |
| gtggatgaga ctgcttacac tggctcttgg ggcaggccac agagggatgg cccagctctt | 420 |
| agggctactg ccatgatcga tttcggcaac tggcttatcg ataacggcta ctctacctac | 480 |
| gctagcaaca ttgtgtggcc aattgtgagg aacgatctgt cttacgtggc tcagtactgg | 540 |
| aaccagactg gctacgatct ttgggaggag gttaacggct ctagcttctt cactatcgcc | 600 |
| gttcagcaca gggctcttgt tgagggctct accttcgctt ctaaggttgg ggcttcttgc | 660 |
| tcttggtgcg attctcaggc tccacaggtt ctgtgcttcc ttcagaggtt ctggactggc | 720 |
| tcttacatca tggctaactt cggcggcggc cgctctggca aggacgctaa cactgtgctg | 780 |
| ggctctatcc acactttcga tccaaacgct ggctgcgacg atacaacttt ccagccatgc | 840 |
| tctccaaggg ctctggctaa ccacaaggtg tacaccgata gcttccgctc tatctactct | 900 |
| atcaacagcg gcatctctca gggcaaggct gttgctgttg ccgctaccc agaggattct | 960 |
| tactacaacg gcaacccgtg gttccttact actcttgctg ctgccgagca gctttacgat | 1020 |
| gctatctacc agtggcagaa gatcggctct atcaccatca ctgacgtgtc tctggccttc | 1080 |
| ttcaaggacc tgtactcttc tgctgctgtt ggcacctacg cttctagctc ttctgccttc | 1140 |
| acctctatcg tgaacgccgt taagacttac gctgacggct acatgtctat cgttcagacc | 1200 |
| cacgctatga ctaacggctc tctgtctgag cagttcggca agtctgatgg cttctctctg | 1260 |
| tctgctaggat atctgacttg gtcttacgct gctctgctga ctgctaacct taggcgcaac | 1320 |
| tctgttgttc caccatcttg gggcgagact actgctactt ctgtgccatc tgtgtgctct | 1380 |
| gctacttcag ctaccggcac ctactctacc gctactaaca ctgcttggcc atctactctg | 1440 |
| acatctggca ctggcgctac cactactacc tctaaggcta cctctaccac cactaccagc | 1500 |
| tctgcttcta ctactactgc tggctgcgtt gttccaactg ctgtggctgt gaccttcgac | 1560 |
| gagatcgcta ctactactta cggcgagaac gtgtacgttg tgggctctat ctctcagctt | 1620 |

```
ggcagctggg atacttctaa ggctgtggcc ctgtctgctt ctaagtacac cagcagcaac   1680
aacctttggt acgctaccgt tactcttcca gctggcacca ctttccagta caagtttatc   1740
agggtgtcat cttcaggcac tgtgacctgg gagtctgatc caaacaggtc ttacaccgtg   1800
ccatctgctt gcggcacttc tactgctgtg gtgaacacca cttggcgcta a            1851

<210> SEQ ID NO 82
<211> LENGTH: 1860
<212> TYPE: DNA
<213> ORGANISM: Artificial sequence
<220> FEATURE:
<223> OTHER INFORMATION: Synthetically generated polynucleotide

<400> SEQUENCE: 82
gccccacagc tttctccaag ggctaccacc tctcttgatg cttggctggc ttctgagacc     60
actgttagcc tgaacgggat tcttgataat atcggcgctt caggcgctta cgctcagtct    120
gctaaggctg gcgttgttat cgctagccca agcacctcta gcccagacta ctactacacc    180
tggaccaggg attctgctct gacccttaag gtgctgatcg accttttcag gaacggcaac    240
gttgatcttc agaccgtgat cgaggagtac atcactgctc aggcttacct tcagactgtg    300
agcaacccat ctggcgatct ttcttcaggc gctggccttg ccgagccaaa gttcaacgtg    360
gacatgtctg cttacactgg cgcttggggc aggccacaga gggatggccc agctcttagg    420
gctatcgccc ttatcgattt cggcaactgg cttatcgata acggctactc tagctacgct    480
gtgtctaatg tgtggccaat tgtgaggaac gatctgtctt acgtggctca gtactggtct    540
cagtctggct acgatctttg ggaggaggtg aacagcatgt ctttcttcac catcgctaac    600
cagcacaggg ctcttgttga gggctctact ttcgctggca gagttggcgc ttcttgctct    660
tggtgcgatt ctcaggctcc acagatcctt tgctacatgc agaatttctg gaccggctct    720
tacatcaacg ctaacactgg cggcggccgc tctggcaagg atgctaacac cgtgctggct    780
agcatctcta ctttcgaccc agaggctact tgcgatgatg tgaccttcca gccatgctct    840
tctagggctc tggctaacca caaggtgtac accgattctt ccgctctgt gtactctctt    900 gactctggga tcgctgaggg cgttgctgtt gctgttggcc gctacccaga ggattcttac    960
tacaacggca acccgtggtt ccttactact cttgctgctg ccgagcagct ttacgacgct   1020
atctaccagt ggaacaagat cggctctatc accatcacct ctacctcact ggcttttctt   1080
aacgacgtgt actcttctgc tgctgttggc acttacgctt caggctctac cgcttacact   1140
gctatcgtgt ccgctgttaa gacttacgct gacggctacg tgtctatcgt tcaggctcac   1200
gctatgacta acggctctct gtctgagcag ttcgataagg cttctggcac tcagctttct   1260
gctagggatc tgacctggtc ttacgctgct ctgctgactg ctaacatgag gcgcaacggc   1320
atcgttccac catcttgggg cgctgcttca gctaactcta tcccaagctc ttgctctact   1380
ggctctgcta ctggcactta ctctacccca actggcactt cttggccatc tactctgact   1440
tcaggcactg ctggcaccac tactacctct gctaccacca ccacctctac tagcgtgtct   1500
aagaccacca ccactaccac ttctactacc agctgcacca ctccaacttc agtggctgtg   1560
accttcgatg agatcgctac cacttactac ggcgagaacg tgtacatcag cggctctatc   1620
tctcagcttg gcagctggga tacttcttct gccatcgccc tttctgcttc tcagtacacc   1680
agcagcaaca acctgtggtt cgtgaccatc aaccttccag ctggcactac tttccagtac   1740
aagtatatca ggaaggagtc tgacggctct atcgttgggg agagcgaccc aaacaggtct   1800
tacactgtgc catctggctg cggcgtttct actgctaccg agagcgatac ttggcgctaa   1860
```

AMYLASES AND GLUCOAMYLASES, NUCLEIC ACIDS ENCODING THEM AND METHODS FOR MAKING AND USING THEM

CROSS-REFERENCE TO RELATED APPLICATIONS

This application is the national phase of PCT application PCT/US2007/088631 having an international filing date of Dec. 21, 2007, which claims benefit of Provisional Application Ser. No. 60/877,068 filed Dec. 21, 2006 and Provisional Application Ser. No. 60/892,823 filed Mar. 2, 2007. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 564462015300Seqlist.txt | Jun. 19, 2009 | 309,747 bytes |

This application is being filed electronically via the USPTO EFS-WEB server, as authorized and set forth in MPEP §1730 II.B.2.(a)(A), and the electronic filing includes an electronically submitted sequence (SEQ ID) listing; the entire content of this sequence listing is herein incorporated by reference for all purposes. The sequence listing is identified on the electronically filed .txt file as follows:

| File Name | Date of Creation | Size (bytes) |
|---|---|---|
| 564462015340Seqlist.txt | Dec. 20, 2007 | 309,764 |

TECHNICAL FIELD

This invention relates to molecular and cellular biology and biochemistry. In one aspect, the invention is directed to polypeptides having an amylase and/or glucoamylase activity, polynucleotides encoding the polypeptides, and methods for making and using these polynucleotides and polypeptides. In one aspect, the polypeptides of the invention can be used as the endo-acting amylases (for example, alpha amylases) or as the exo-acting glucoamylases, e.g., to catalyze the hydrolysis of polysaccharides comprising glucose monomers, such as starch (a polymer of glucose monomers joined by 1,4-alpha or 1,6-alpha linkages), into sugars. In one aspect, the invention is directed to polypeptides having thermostable amylase and/or glucoamylase activity, including alpha amylases activity or a 1,4-alpha-D-glucan glucohydrolase activity. In one aspect, the polypeptides of the invention can be used as amylases (for example, alpha amylases) or glucoamylases to catalyze the hydrolysis of polysaccharides such as starch into sugars, such as glucose. The invention is also directed to nucleic acid constructs, vectors, and host cells comprising the nucleic acid sequences of the invention as well as recombinant methods for producing the polypeptides of the invention. The invention is also directed to the use of amylases and/or glucoamylases of the invention in polysaccharide (e.g., starch) conversion processes, including production of high fructose corn syrup (HFCS), ethanol, dextrose, and dextrose syrups.

BACKGROUND

Starch is a complex carbohydrate often found in the human diet. The structure of starch is glucose polymers linked by α-1,4 and α-1,6 glucosidic bonds. Commercially, glucoamylases are used to further hydrolyze cornstarch, which has already been partially hydrolyzed with an alpha-amylase. The most widely utilized glucoamylase is produced from the fungus *Aspergillus niger*; one of the problems with the commercial use of this enzyme is its relatively low thermostability.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by amylase. A starch granule is composed of: 69-74% amylopectin, 26-31% amylose, 11-14% water, 0.2-0.4% protein, 0.5-0.9% lipid, 0.05-0.1% ash, 0.02-0.03% phosphorus, 0.1% pentosan. Approximately 70% of a granule is amorphous and 30% is crystalline.

Staling of baked products (such as bread) has been recognized as a problem which becomes more serious as more time lies between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. The increase in crumb firmness, which is considered as the most important aspect of staling, is recognized by the consumer a long time before the bread product has otherwise become unsuitable for consumption.

There is a need in the industry for new amylases, e.g., acid amylases, useful for various uses including commercial cornstarch liquefaction processes or improved manufacturing having new or improved performance characteristics over the industry standard enzymes, e.g., from *Bacillus licheniformis*. There is also an industry drive to identify amylases and glucoamylases capable of efficiently hydrolyzing granular starch (e.g. raw granular starch) at low temperatures without the need for a high temperature starch gelatinization step; the enzymes of the invention, e.g. amylases, glucoamylases and glucosidases, can be utilized to fulfill this need.

There is also a need for new amylases having utility in automatic dish wash (ADW) products and laundry detergent. In ADW products, the amylase will function at pH 10-11 and at 45-60° C. in the presence of calcium chelators and oxidative conditions. For laundry, activity at pH 9-10 and 40° C. in the appropriate detergent matrix will be required. Amylases are also useful in textile desizing, brewing processes, starch modification in the paper and pulp industry and other processes described in the art.

SUMMARY

The invention provides isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention, e.g., an exemplary nucleic acid of the invention, over a region of at least about 10, 15, 20, 25, 30, 35, 40, 45, 50, 55, 60, 65, 70, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. In one aspect, the nucleic acid encodes at least one polypeptide having an amylase and/or glucoamylase activity, and the sequence identities are determined by analysis with a sequence comparison algorithm or by a visual inspection. In another aspect, the invention provides nucleic acids for use as probes, inhibitory molecules (e.g., antisense, iRNAs, such as siRNA, microRNA or miRNAs), transcriptional or translational regulation, and the like.

Exemplary nucleic acids of the invention include isolated, synthetic or recombinant nucleic acids comprising a nucleic acid sequence as set forth in SEQ ID NO:1, SEQ ID NO:3, SEQ ID NO:5, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:80, SEQ ID NO:81 and/or SEQ ID NO:82, and/or subsequences thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of a gene or transcript (message).

Exemplary nucleic acids of the invention also include isolated, synthetic or recombinant nucleic acids encoding a polypeptide of the invention, e.g., an exemplary polypeptide having a sequence as set forth in SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76 and/or SEQ ID NO:78, and subsequences thereof and variants thereof, and polypeptides having at least about 50%, 51%, etc., or more, to 100%, as described herein, sequence identity to an exemplary polypeptide of the invention.

In one aspect, the polypeptide of the invention has an endo-acting amylase activity (e.g., as an alpha amylase) or an exo-acting glucoamylase activity (alternative amylase activities described further, below). In one aspect the polypeptide of the invention acts as an immunogen or epitope. In one embodiment, the polypeptides of the invention can catalyze the hydrolysis of polysaccharides and/or oligosaccharides comprising glucose monomers, such as starch (a polymer of glucose monomers joined by 1,4-alpha or 1,6-alpha linkages).

Amylases and/or glucoamylases of the invention can be used commercially in the initial stages (liquefaction) of polysaccharide, oligosaccharide or starch processing; in wet corn milling; in alcohol production; as cleaning agents in detergent matrices; in the textile industry for starch desizing; in baking applications; in the beverage industry; in oilfields in drilling processes; in inking of recycled paper and in animal feed. Amylases and/or glucoamylases of the invention can be used in textile desizing, brewing processes, polysaccharide, oligosaccharide or starch modification in the paper and pulp industry and other processes. For example, the invention provides methods for liquefaction saccharification as illustrated in FIG. 5 using polypeptides of the invention.

Amylases and/or glucoamylases of the invention can be used to catalyze the hydrolysis of polysaccharides, e.g., starches, into sugars; or to hydrolyze internal α-1,4-glucosidic linkages in starch to produce smaller molecular weight malto-dextrins. Because the breakdown of polysaccharides and/or oligosaccharides, e.g., starches, is important in the digestive system and in commercial preparation processes, amylases and/or glucoamylases of the invention are used in foods and feeds and processes for preparing them, and in or as digestive aids. Amylases and/or glucoamylases of the invention can be used in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper; and in animal feed.

Enzymes of the invention can have an exo-acting glucoamylase activity and can be used to further hydrolyze cornstarch which has already been partially hydrolyzed with an alpha-amylase (which also can be a polypeptide of the invention) to produce glucose; and in aspect of this process of the invention the glucose is converted to a mixture of glucose and fructose by a glucose isomerase enzyme. In another aspect of this process of the invention, this mixture is enriched with fructose to produce a high fructose corn syrup. In alternative aspects, polypeptides of the invention are used in any of step of polysaccharide, oligosaccharide or starch to fructose processing, e.g., including the four steps: liquefaction of granular starch, saccharification of the liquefied polysaccharide, oligosaccharide or starch into dextrose, purification, and isomerization to fructose. One aspect of the invention using at least one polypeptide of the invention comprises a polysaccharide, oligosaccharide or starch liquefaction process for converting a concentrated suspension of polysaccharide, oligosaccharide or starch polymer granules into a solution of soluble shorter chain length dextrins of low viscosity.

The invention also provides an enzymatic liquefaction process using at least one polypeptide of the invention comprising adjusting the pH of a granular polysaccharide, oligosaccharide or starch slurry to the pH optimum of an enzyme of the invention (e.g., a glucoamylase or an amylase of the invention) to be utilized, e.g., between 6.0 and 6.5, or between about 5.5 and 7.0; calcium hydroxide, sodium hydroxide or sodium carbonate can be added for this purpose (the addition of calcium hydroxide has the advantage of also providing calcium ions which are known to stabilize the alpha-amylase against inactivation). In one aspect, upon addition of the amylase (e.g., an alpha-amylase) of the invention, the suspension is pumped through a steam jet to instantaneously raise the temperature to between 80° C. to 115° C., and the starch is immediately gelatinized and, due to the presence of alpha-amylase, depolymerized through random hydrolysis of a (1-4) glycosidic bonds by the alpha-amylase to a fluid mass which is easily pumped.

In alternative aspects to this polysaccharide and/or oligosaccharide (e.g., starch) liquefaction process, an amylase (e.g., an alpha-amylase) and/or a glucoamylase of the invention is added to the polysaccharide (e.g., starch) suspension, the suspension is held at a temperature of 80-100° C. to partially hydrolyze the granules, e.g., starch granules, and the partially hydrolyzed polysaccharide/starch suspension is pumped through a jet at temperatures in excess of about 105° C. to thoroughly gelatinize any remaining granular structure. After cooling the gelatinized polysaccharide/starch, a second addition of a glucoamylase and/or an amylase of the invention (e.g., an alpha-amylase) can be made to further hydrolyze the polysaccharide/starch.

In one aspect, the invention also provides amylase-encoding and glucoamylase-encoding nucleic acids with a common novelty in that they are derived from mixed cultures, e.g., from environmental sources. The invention provides amylase-encoding and glucoamylase-encoding nucleic acids isolated from mixed cultures comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 10, 15, 20, 25, 30, 35, 40, 45, 50, 55, 60, 65, 70, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues, wherein the nucleic acid encodes at least one polypeptide having an amylase and/or glucoamylase activity, and the sequence identities are determined by analysis with a sequence comparison algorithm or by a visual inspection.

In one aspect, the invention provides amylase-encoding and glucoamylase-encoding nucleic acids isolated from mixed cultures, e.g., from environmental sources, comprising a nucleic acid of the invention, e.g., an exemplary nucleic acid of the invention, e.g., a sequence as set forth in SEQ ID NO:1, SEQ ID NO:3, SEQ ID NO:5, SEQ ID NO:9, SEQ ID NO:11, etc., and subsequences thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of a gene or transcript; or, a nucleic acid encoding a polypeptide of the invention.

In one aspect, the invention also provides amylase-encoding and glucoamylase-encoding nucleic acids with a common novelty in that they are derived from environmental sources (see Table 1 below, 2nd column for examples of sequences isolated from "unknown" or environmental sources), e.g., mixed environmental sources. In one aspect, the invention provides amylase-encoding and glucoamylase-encoding nucleic acids isolated from environmental sources, e.g., mixed environmental sources, comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 25, 30, 40, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues, wherein the nucleic acid encodes at least one polypeptide having an amylase and/or glucoamylase activity, and the sequence identities are determined by analysis with a sequence comparison algorithm or by a visual inspection.

In one aspect, the invention provides amylase-encoding and glucoamylase-encoding nucleic acids isolated from environmental sources, e.g., mixed environmental sources, comprising a nucleic acid of the invention, e.g., an exemplary nucleic acid sequence of the invention as set forth in SEQ ID NO:1, SEQ ID NO:3, SEQ ID NO:5, SEQ ID NO:9, SEQ ID NO:11, etc., SEQ ID NO:583, SEQ ID NO:585, and subsequences thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of a gene or transcript; or, a nucleic acid encoding a polypeptide of the invention.

In one aspect, the invention also provides glucoamylases and amylases, and amylase-encoding and glucoamylase-encoding nucleic acids, with a common novelty in that they are derived from archael sources, including the archael-derived amylases and/or glucoamylases of the invention.

In one aspect, the sequence comparison algorithm is a BLAST version 2.2.2 algorithm where a filtering setting is set to blastall -p blastp -d "nr pataa"-F F, and all other options are set to default.

Another aspect of the invention is an isolated, synthetic or recombinant nucleic acid including at least 10 consecutive bases of a nucleic acid sequence of the invention, sequences substantially identical thereto, and the sequences complementary thereto.

In one aspect, the amylase activity comprises α-amylase or β-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. The glucoamylase and/or amylase activity can comprise an α-amylase activity, a β-amylase activity, a 1,4-α-D-glucan glucohydrolase activity, an exoamylase activity, a glucan α-maltotetrahydrolase activity, a maltase activity, an isomaltase activity, a glucan 1,4, α-glucosidase activity, an α-glucosidase activity, a sucrase activity or an agarase activity (e.g., a β-agarase activity).

The amylase activity can comprise hydrolyzing glucosidic bonds. In one aspect, the glucosidic bonds comprise an α-1,4-glucosidic bond. In another aspect, the glucosidic bonds comprise an α-1,6-glucosidic bond. In one aspect, the amylase activity comprises hydrolyzing glucosidic bonds in polysaccharides, e.g., starches, e.g., liquefied starch. The amylase activity can further comprise hydrolyzing glucosidic bonds into maltodextrins. In one aspect, the amylase activity comprises cleaving a maltose or a D-glucose unit from non-reducing end of the starch.

In one aspect, the isolated, synthetic or recombinant nucleic acid encodes a polypeptide having an amylase and/or glucoamylase activity which is thermostable. The polypeptide can retain an amylase activity under conditions comprising a temperature range of anywhere between about 0° C. to about 37° C., or, between about 37° C. to about 95° C. or more, e.g., 98° C., 100° C. or more; between about 55° C. to about 85° C., between about 70° C. to about 95° C., or, between about 90° C. to about 95° C. For example, the exemplary polypeptide having a sequence as set forth in SEQ ID NO:437 is thermostable, retaining 50% activity after 25 minutes at 100° C. in the absence of added calcium.

In another aspect, the isolated, synthetic or recombinant nucleic acid encodes a polypeptide having an amylase and/or glucoamylase activity which is thermotolerant. The polypeptide can retain an amylase and/or glucoamylase activity after exposure to a temperature in the range from greater than 37° C. to about 95° C. or anywhere in the range from greater than 55° C. to about 85° C. In one aspect, the polypeptide retains an amylase and/or glucoamylase activity after exposure to a temperature in the range from greater than 90° C. to about 95° C. at pH 4.5.

The invention provides isolated, synthetic or recombinant nucleic acids comprising a sequence that hybridizes under stringent conditions to a nucleic acid of the invention, e.g., an exemplary nucleic acid of the invention, a nucleic acid comprising a sequence as set forth in SEQ ID NO:1, SEQ ID NO:3, SEQ ID NO:5, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:80, SEQ ID NO:81 and/or SEQ ID NO:82, and/or fragments or subsequences thereof. In one aspect, the nucleic acid encodes a polypeptide having an amylase and/or glucoamylase activity. The nucleic acid can be at least about 25, 30, 40, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length or the full length of the gene or transcript. In one aspect, the stringent conditions include a wash step comprising a wash in 0.2×SSC at a temperature of about 65° C. for about 15 minutes. In one aspect, stringent conditions comprise hybridization under conditions comprising a buffer having 0.15M NaCl for 15 minutes at 72° C.

The invention provides a nucleic acid probe for identifying a nucleic acid encoding a polypeptide having an amylase and/or glucoamylase activity, wherein the probe comprises at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence comprising a sequence of the invention, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence of the invention, or fragments or subsequences thereof.

The invention provides a nucleic acid probe for identifying a nucleic acid encoding a polypeptide having an amylase and/or glucoamylase activity, wherein the probe comprises a nucleic acid comprising a sequence at least about 10, 15, 20, 25, 30, 35, 40, 45, 50, 55, 60, 65, 70, 75, 80, 90, 100, 125, 150, 175, 200, 250, 300, 350, 400, 450, 500, 550, 600, 650, 700, 750, 800, 850, 900, 950, 1000 or more residues having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention, wherein the sequence identities are determined by analysis with a sequence comparison algorithm or by visual inspection.

The probe can comprise an oligonucleotide comprising at least about 10 to 50, about 20 to 60, about 30 to 70, about 40 to 80, or about 60 to 100 consecutive bases of a nucleic acid sequence of the invention, or a subsequence thereof.

The invention provides an amplification primer sequence pair for amplifying a nucleic acid encoding a polypeptide having an amylase and/or glucoamylase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence.

The invention provides methods of amplifying a nucleic acid encoding a polypeptide having an amylase and/or glucoamylase activity comprising amplification of a template nucleic acid with an amplification primer sequence pair capable of amplifying a nucleic acid sequence of the invention, or fragments or subsequences thereof.

The invention provides expression cassettes (including, e.g., vectors and cloning vehicles) comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector. In alternative embodiments, the plant promoter is a corn seed embryo-specific: globulin promoter (see, e.g., Belanger (1991) Molecular basis for allelic polymorphism of the maize Globulin-1 gene. Genetics 129:863-872); or a corn seed endosperm-specific: γ-zein promoter (see, e.g., Lopes (1995) Identification of two opaque2 modifier loci in Quality Protein Maize. Mol. Gen. Genet. 247: 603-613); or a rice seed endosperm-specific: GTL1 promoter (see, e.g., Takaiwa (1991) Analysis of the 5' flanking region responsible for the endosperm-specific expression of a rice glutelin chimeric gene in transgenic tobacco. Plant Mol. Biol. 16:49-58).

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cells (or "host cells") comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be from any plant, for example plants used for forage and/or feed for any animal, including ruminants, or as a source of feedstock to produce energy or fuel. Plants of particular interest may include crop plants and feedstock plants, for example, maize, alfalfa, sunflower, Brassica, soybean, cotton, safflower, peanut, sorghum, wheat, oat, rye, millet, barley, rice, conifers, grasses, e.g., switch grass and Miscanthus, legume crops, e.g., pea, bean and soybean, starchy tuber/roots, e.g., potato, sweet potato, cassava, taro, canna, sugar beet, sugar cane and the like.

The invention provides transgenic non-human animals comprising a nucleic acid of the invention or an expression cassette (e.g., a vector) of the invention. In one aspect, the animal is a mouse. The invention provides cells or cell lines isolated from these transgenic non-human animals.

The invention provides transgenic plants comprising a nucleic acid of the invention or an expression cassette (e.g., a vector) of the invention. The transgenic plant can be any plant, but in one embodiment the plant would be used for forage and/or feed for any animal or as a feedstock to produce energy or fuel, such as, maize, alfalfa, sunflower, Brassica, soybean, cotton, safflower, peanut, sorghum, wheat, oat, rye, millet, barley, rice, conifers, grasses, e.g., switch grass and Miscanthus, legume crops, e.g., pea, bean and soybean, starchy tuber/roots, e.g., potato, sweet potato, cassava, taro, canna, sugar beet, sugar cane and the like.

The invention provides transgenic seeds comprising a nucleic acid of the invention or an expression cassette (e.g., a vector) of the invention. The transgenic seed can from any plant, but in one embodiment the plant would be used for forage and/or feed for any animal or as a feedstock to produce energy or fuel, such as, maize, alfalfa, sunflower, Brassica, soybean, cotton, safflower, peanut, sorghum, wheat, oat, rye, millet, barley, rice, conifers, grasses, e.g., switch grass and Miscanthus, legume crops, e.g., pea, bean and soybean, starchy tuber/roots, e.g., potato, sweet potato, cassava, taro, canna, sugar beet, sugar cane and the like.

Any plant, plant part, plant tissue, plant seed or plant cell may be used for introduction of a nucleotide of the invention, either stably (e.g., as a transgenic plant, or cell or cell line derived therefrom) or transiently; thus the invention provides plants, plant parts, plant tissues, plant seeds and plant cells comprising a nucleic acid and/or polypeptide of the invention, wherein the plant can be (but is not limited to) corn (*Zea mays*), *Brassica* sp. (e.g., *B. napus, B. rapa, B. juncea*), including those *Brassica* species useful as sources of seed oil, such as canola, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta* sp., e.g., *Beta vulgaris*), sugarcane (*Saccharum* spp.), Andropogoneae (grasses), Chenopodiaceae (flowering plants), oats, barley, vegetables, ornamentals, and conifers; and vegetables, e.g., tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*); and ornamentals, including azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), canna (*Cannaceae* spp.) and chrysanthemum; and conifers that may be used, including, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*); and leguminous plants, including, but are not limited to, beans and peas, where in alternative aspects beans may include guar, locust bean, fenugreek, soybean, garden beans, cowpea, mungbean, lima bean, fava bean, lentils, chickpea, etc., and legumes can include, but are not limited to, *Arachis*, e.g., peanuts, *Vicia*, e.g., crown vetch, hairy vetch, adzuki bean, mung bean, and chickpea, Lupinus, e.g., lupine, *trifolium, Phaseolus*, e.g., common bean and lima bean, *Pisum*, e.g., field bean, Melilotus, e.g., clover, *Medicago*, e.g., alfalfa, *Lotus*, e.g., trefoil, lens, e.g., lentil, and false indigo; also including forage and turf grasses, such as alfalfa, switchgrass (*Panicum virgatum*), Miscanthus, orchard grass, tall fescue, perennial ryegrass, creeping bent grass, and redtop.

In alternative aspects, plants, plant parts, plant tissues, plant seeds and plant cells comprising a nucleic acid and/or polypeptide of the invention also include crop plants and plants used to produce energy or fuel (e.g., ethanol or other biofuels, e.g., bioethanols, biopropanols, biobutanols, or biodiesel), for example, corn, alfalfa, sunflower, Brassica, soybean, cotton, safflower, peanut, sorghum, wheat, oat, rye, millet, barley, rice, conifers, grasses, e.g., switch grass and Miscanthus, legume crops, e.g., pea, bean and soybean, starchy tuber/roots, e.g., potato, sweet potato, cassava, taro, canna, sugar cane and/or sugar beet and the like.

The invention provides an antisense oligonucleotide comprising a nucleic acid sequence complementary to or capable of hybridizing under stringent conditions to a nucleic acid of the invention. The invention provides methods of inhibiting the translation of an amylase message in a cell comprising administering to the cell or expressing in the cell an antisense oligonucleotide comprising a nucleic acid sequence complementary to or capable of hybridizing under stringent conditions to a nucleic acid of the invention.

The invention provides an isolated, synthetic or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 10, 15, 20, 25, 30, 35, 40, 45, 50, 55, 60, 65, 70, 75, 80, 90, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more residues, or over the full length of the polypeptide, and the sequence identities are determined by analysis with a sequence comparison algorithm or by a visual inspection. Exemplary polypeptide or peptide sequences of the invention include SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76 and/or SEQ ID NO:78, and/or subsequences thereof and variants thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of an enzyme. Exemplary polypeptide or peptide sequences of the invention include sequence encoded by a nucleic acid of the invention. Exemplary polypeptide or peptide sequences of the invention include polypeptides or peptides specifically bound by an antibody of the invention. In one aspect, a polypeptide of the invention has at least one amylase activity, e.g., an alpha amylase activity.

In alternative embodiments, the polypeptides of the invention lack a signal sequence (leader sequence) and/or a carbohydrate binding module. In alternative embodiments, the polypeptides of the invention further comprise one or more heterologous sequences, which can comprise a heterologous signal sequence (leader sequence), a heterologous catalytic domain (CD) (i.e., active site), or a heterologous carbohydrate binding module, or epitope, purification tag or label. In one aspect, the heterologous signal sequence, heterologous carbohydrate binding module or heterologous catalytic domain (CD) is derived from another amylase enzyme (an amylase other than an enzyme of this invention), or is derived from a non-amylase enzyme.

In alternative embodiments, the polypeptides of the invention have an amylase activity or can be used to generate antibodies which bind specifically to an exemplary polypeptide of the invention (e.g., SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76 and/or SEQ ID NO:78).

In alternative embodiments, the polypeptides of the invention can be synthetic or in a peptidomimetic form.

Another aspect of the invention is an isolated, synthetic or recombinant polypeptide or peptide including at least 10, 15, 20, 25, 30, 35, 40, 45, 50, 75, 100, 125, 150, 175, 200, 225, 250, 300, 350, 400, 450 or 500 or more consecutive amino acid residues of a polypeptide or peptide sequence of the invention, sequences substantially identical thereto, and the sequences complementary thereto.

In one aspect, the amylase activity of a polypeptide or peptide of the invention comprises an α-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. The amylase activity can comprise a glucoamylase activity, a 1,4-α-D-glucan glucohydrolase activity, an α-amylase activity, an exoamylase activity, or a β-amylase activity. The amylase activity can comprise hydrolyzing glucosidic bonds. In one aspect, the glucosidic bonds comprise an α-1,4-glucosidic bond. In another aspect, the glucosidic bonds comprise an α-1,6-glucosidic bond. In one aspect, the amylase activity comprises hydrolyzing glucosidic bonds in starch, e.g., liquefied starch. The amylase activity can further comprise hydrolyzing glucosidic bonds into maltodextrins. In one aspect, the amylase activity comprises cleaving a maltose or a D-glucose unit from non-reducing end of the starch.

In one aspect, the amylase activity of the invention comprises a glucoamylase activity, which can comprise catalysis of the hydrolysis of glucosidic bonds. The glucoamylase activity of the invention can comprise catalyzing the stepwise hydrolytic release of D-glucose from the non-reducing ends of starch or other related dextrins. The glucoamylase activity can comprise a 1,4-α-D-glucan glucohydralase activity. The glucoamylase activity can comprise catalysis of the hydrolysis of malto-dextrins resulting in the generation of free glucose. The glucoamylase activity can comprise an exoamylase activity. The glucoamylase activity can comprise an α-amylase or a β-amylase activity. The hydrolyzed glucosidic bonds can comprise α-1,4-glucosidic bonds or α-1,6-glucosidic bonds. The glucoamylase activity can comprise hydrolyzing glucosidic bonds in a starch. The glucoamylase activity can further comprise hydrolyzing glucosidic bonds in the starch to produce maltodextrines. The glucoamylase activity can comprise cleaving a maltose or a D-glucose unit from non-reducing end of the starch.

In one aspect, the amylase and/or glucoamylase activity can be thermostable. The polypeptide can retain an amylase and/or glucoamylase activity under conditions comprising a temperature range of between about 37° C. to about 95° C., between about 55° C. to about 85° C., between about 70° C. to about 95° C., or between about 90° C. to about 95° C. In another aspect, the amylase and/or glucoamylase activity can be thermotolerant. The polypeptide can retain an amylase and/or glucoamylase activity after exposure to a temperature in the range from greater than 37° C. to about 95° C., or in the range from greater than 55° C. to about 85° C. In one aspect, the polypeptide can retain an amylase and/or glucoamylase activity after exposure to a temperature in the range from greater than 90° C. to about 95° C. at pH 4.5.

In one aspect, the amylase activity and/or glucoamylase activity is thermostable, e.g., wherein the polypeptide retains an amylase activity and/or glucoamylase activity under conditions comprising a temperature range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermostable polypeptides according to the invention retains activity, e.g., an amylase activity and/or glucoamylase activity, at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one aspect, the amylase activity and/or glucoamylase activity is thermotolerant, e.g., wherein the polypeptide retains an amylase activity and/or glucoamylase activity after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermotolerant polypeptides according to the invention can retain activity, e.g. an amylase activity and/or glucoamylase activity, after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides according to the invention retains activity, e.g. amylase activity and/or glucoamylase activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one aspect, the amylase activity and/or glucoamylase activity of polypeptides encoded by nucleic acids of the invention retain activity under acidic conditions comprising about pH 6.5, pH 6, pH 5.5, pH 5, pH 4.5, pH 4.0, pH 3.5, pH 3.0 or less (more acidic) pH, or, retain an amylase activity and/or glucoamylase activity after exposure to acidic conditions comprising about pH 6.5, pH 6, pH 5.5, pH 5, pH 4.5, pH 4.0, pH 3.5, pH 3.0 or less (more acidic) pH; or, retain activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic) or, retain an amylase activity and/or glucoamylase activity after exposure to basic conditions comprising about pH 7, pH 7.5 pH 8.0, pH 8.5, pH 9, pH 9.5, pH 10, pH 10.5, pH 11, pH 11.5, pH 12, pH 12.5 or more (more basic). In one aspect, amylase activity and/or glucoamylase activity of polypeptides encoded by nucleic acids of the invention retain activity at a temperature of at least about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more, and a basic pH of at least about pH 7.5 pH 8.0, pH 8.5, pH 9, pH 9.5, pH 10, pH 10.5, pH 11, pH 11.5, pH 12, pH 12.5 or more (more basic).

In one aspect, the isolated, synthetic or recombinant polypeptide can comprise the polypeptide of the invention that lacks a signal sequence. In one aspect, the isolated, synthetic or recombinant polypeptide can comprise the polypeptide of the invention comprising a heterologous signal sequence, such as a heterologous amylase or non-amylase signal sequence.

In one aspect, the invention provides a signal sequence comprising a peptide as set forth in Table 1. In one aspect, the invention provides a signal sequence consisting of a peptide as set forth in Table 1. In one aspect, the invention provides chimeric proteins comprising a first domain comprising a signal sequence of the invention and at least a second domain. The protein can be a fusion protein. The second domain can comprise an enzyme. The enzyme can be any glucoamylase and/or amylase (e.g., a glucoamylase or an amylase of the invention, or, another amylase or glucoamylase).

In one aspect, the enzymatic activity (e.g., glucoamylase and/or an amylase activity) of an enzyme of this invention comprises a specific activity at about 37° C. in the range from about 1 to about 1200 units per milligram of protein, or, about 100 to about 1000 units per milligram of protein. In another aspect, the enzymatic activity (e.g., glucoamylase and/or an amylase activity) of an enzyme of this invention comprises a specific activity from about 100 to about 1000 units per milligram of protein, or, from about 500 to about 750 units per milligram of protein. Alternatively, the enzymatic activity (e.g., glucoamylase and/or an amylase activity) of an enzyme of this invention comprises a specific activity at 37° C. in the range from about 1 to about 750 units per milligram of protein, or, from about 500 to about 1200 units per milligram of protein. In one aspect, the enzymatic activity (e.g., glucoamylase and/or an amylase activity) of an enzyme of this invention comprises a specific activity at 37° C. in the range from about 1 to about 500 units per milligram of protein, or, from about 750 to about 1000 units per milligram of protein. In another aspect, the enzymatic activity (e.g., glucoamylase and/or an amylase activity) of an enzyme of this invention comprises a specific activity at 37° C. in the range from about 1 to about 250 units per milligram of protein. Alternatively, the enzymatic activity (e.g., glucoamylase and/or an amylase activity) of an enzyme of this invention comprises a specific activity at 37° C. in the range from about 1 to about 100 units per milligram of protein. In another aspect, the thermotolerance comprises retention of at least half of the specific activity of the enzymatic activity (e.g., glucoamylase and/or an amylase activity) of an enzyme of this invention at 37° C. after being heated to an elevated temperature, such as a temperature from about 0° C. to about 20° C., about 20° C. to about 37° C., about 37° C. to about 50° C., about 50° C. to about 70° C., about 70° C. to about 75° C., about 75° C. to about 80° C., about 80° C. to about 85° C., about 85° C. to about 90° C., about 90° C. to about 95° C., about 95° C. to about 100° C., about 100° C. to about 110° C., or higher. Alternatively, the thermotolerance can comprise retention of specific activity at 37° C. in the range from about 1 to about 1200 units per milligram of protein, or, from about 500 to about 1000 units per milligram of protein, after being heated to an elevated temperature. In another aspect, the thermotolerance can comprise retention of specific activity at 37° C. in the range from about 1 to about 500 units per milligram of protein after being heated to an elevated temperature, as described above.

The invention provides isolated, synthetic or recombinant polypeptides of the invention, wherein the polypeptide comprises at least one glycosylation site. In one aspect, glycosylation can be an N-linked glycosylation. In one aspect, the polypeptide can be glycosylated after being expressed in a *P. pastoris* or a *S. pombe*. The invention also provides methods for adding glycosylation to a polypeptide, either post-translationally or chemically, to change the property of the polypeptides, e.g., its thermal stability, solubility, tendency to aggregate, and the like.

In one aspect, the polypeptide can retain the enzymatic activity (e.g., glucoamylase and/or an amylase activity) of an enzyme of this invention under conditions comprising about pH 6.5, pH 6, pH 5.5, pH 5, pH 4.5, pH 4.0, pH 3.5, pH 3.0 or less (more acidic) pH. In another aspect, the polypeptide can retain the enzymatic activity (e.g., glucoamylase and/or an amylase activity) of an enzyme of this invention under conditions comprising about pH 7, pH 7.5 pH 8.0, pH 8.5, pH 9, pH 9.5, pH 10, pH 10.5, pH 11.0, pH 11.5, pH 12, pH 12.5 or more (more basic) pH. In one aspect, the polypeptide can retain the enzymatic activity (e.g., glucoamylase and/or an amylase activity) of an enzyme of this invention after exposure to conditions comprising about pH 6.5, pH 6, pH 5.5, pH 5, pH 4.5, pH 4.0, pH 3.5, pH 3.0 or less (more acidic) pH. In another aspect, the polypeptide can retain the enzymatic activity (e.g., glucoamylase and/or an amylase activity) of an enzyme of this invention after exposure to conditions comprising about pH 7, pH 7.5 pH 8.0, pH 8.5, pH 9, pH 9.5, pH 10, pH 10.5, pH 11.0, pH 11.5, pH 12, pH 12.5 or more (more basic) pH.

The invention provides protein preparations comprising a polypeptide of the invention, wherein the protein preparation comprises a liquid, a solid or a gel.

The invention provides heterodimers comprising a polypeptide of the invention and a second domain. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides having an amylase and/or glucoamylase activity, wherein the polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized nucleic acid of the invention. The invention provides arrays comprising an antibody of the invention.

The invention provides isolated, synthetic or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention, e.g., an antibody that specifically binds to a polypeptide of the invention or to a polypeptide encoded by a nucleic acid of the invention.

The invention provides food supplements for an animal comprising a polypeptide of the invention, e.g., a polypeptide encoded by the nucleic acid of the invention. In one aspect, the polypeptide in the food supplement can be glycosylated. The invention provides edible enzyme delivery matrices comprising a polypeptide of the invention, e.g., a polypeptide encoded by the nucleic acid of the invention. In one aspect, the delivery matrix comprises a pellet. In one aspect, the polypeptide can be glycosylated. In one aspect, the amylase activity is thermotolerant. In another aspect, the amylase activity is thermostable.

The invention provides method of isolating or identifying a polypeptide having an amylase and/or glucoamylase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having an amylase and/or glucoamylase activity.

The invention provides methods of making an anti-amylase antibody comprising administering to a non-human animal a nucleic acid of the invention or a polypeptide of the invention or subsequences thereof in an amount sufficient to generate a humoral immune response, thereby making an anti-glycoamylase and/or anti-amylase antibody. The invention provides methods of making an anti-glycoamylase and/or anti-amylase immune comprising administering to a non-human animal a nucleic acid of the invention or a polypeptide of the invention or subsequences thereof in an amount sufficient to generate an immune response.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having an amylase and/or glucoamylase activity comprising the following steps: (a) providing a polypeptide of the invention; or a polypeptide encoded by a nucleic acid of the invention; (b) providing an amylase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having an amylase and/or glucoamylase activity. In one aspect, the substrate can be a polysaccharide, oligosaccharide or starch, e.g., a liquefied starch.

The invention provides methods for identifying an amylase or glucoamylase substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as an amylase or a glucoamylase substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of an amylase or a glucoamylase activity comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the amylase or glucoamylase, wherein a change in the amylase or glucoamylase activity measured in the presence of the test compound compared to the activity in the absence of the test compound provides a determination that the test compound modulates the amylase or glucoamylase activity. In one aspect, the amylase or a glucoamylase activity can be measured by providing an amylase or glucoamylase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of amylase or glucoamylase activity. An increase in the amount of the substrate or a decrease in the amount of the reaction product with the test compound as compared to the amount of substrate or reaction product without the test compound identifies the test compound as an inhibitor of amylase or glucoamylase activity.

The invention provides computer systems comprising a processor and a data storage device wherein said data storage device has stored thereon a polypeptide sequence or a nucleic acid sequence of the invention (e.g., a polypeptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having an amylase and/or glucoamylase activity from an environmental sample comprising the steps of: (a) providing an amplification primer sequence pair for amplifying a nucleic acid encoding a polypeptide having an amylase and/or glucoamylase activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide having an amylase and/or glucoamylase activity from an environmental sample. One or each member of the amplification primer sequence pair can comprise an oligonucleotide comprising at least about 10 to 50 consecutive bases of a sequence of the invention.

The invention provides methods for isolating or recovering a nucleic acid encoding a polypeptide having an amylase and/or glucoamylase activity from an environmental sample comprising the steps of: (a) providing a polynucleotide probe comprising a nucleic acid of the invention or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide having an amylase and/or glucoamylase activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having an amylase and/or glucoamylase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant amylase or glucoamylase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until an amylase or glucoamylase having an altered or different activity or an altered or different stability from that of a polypeptide encoded by the template nucleic acid is produced. In one aspect, the variant amylase or glucoamylase polypeptide is thermotolerant, and retains some activity after being exposed to an elevated temperature. In another aspect, the variant amylase or glucoamylase polypeptide has increased glycosylation as compared to the amylase or glucoamylase encoded by a template nucleic acid. Alternatively, the variant amylase or glucoamylase polypeptide has an amylase or glucoamylase activity under a high temperature, wherein the amylase or glucoamylase encoded by the template nucleic acid is not active under the high temperature. In one aspect, the method can be iteratively repeated until an amylase or glucoamylase coding sequence having an altered codon usage from that of the template nucleic acid is produced. In another aspect, the method can be iteratively repeated until an amylase or glucoamylase gene having higher or lower level of message expression or stability from that of the template nucleic acid is produced.

The invention provides methods for modifying codons in a nucleic acid encoding a polypeptide having an amylase and/or glucoamylase activity to increase its expression in a host cell, the method comprising the following steps: (a) providing a nucleic acid of the invention encoding a polypeptide having an amylase and/or glucoamylase activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having an amylase and/or glucoamylase activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding an amylase or glucoamylase.

The invention provides methods for modifying codons in a nucleic acid encoding a polypeptide having an amylase and/or glucoamylase activity to increase its expression in a host cell, the method comprising the following steps: (a) providing a nucleic acid of the invention encoding an amylase or glucoamylase polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having an amylase and/or glucoamylase activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified amylase or glucoamylase active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes an amylase or glucoamylase active site or an amylase or glucoamylase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified amylase or glucoamylase active sites or substrate binding sites. In one aspect, the method comprises mutagenizing the first nucleic acid of step (a) by a method comprising an optimized directed evolution system, gene site-saturation mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises an amylase or glucoamylase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing an amylase or glucoamylase enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the amylase or glucoamylase enzyme, thereby modifying a small molecule by an amylase or glucoamylase enzymatic reaction. In one aspect, the method can comprise a plurality of small molecule substrates for the enzyme of step (a), thereby generating a library of modified small molecules produced by at least one enzymatic reaction catalyzed by the amylase or glucoamylase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule which exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of an amylase or glucoamylase enzyme comprising the steps of: (a) providing an amylase or glucoamylase enzyme, wherein the enzyme comprises a polypeptide of the invention, or a polypeptide encoded by a nucleic acid of the invention, or a subsequence thereof; and (b) deleting a plurality of amino acid residues from the sequence of step (a) and testing the remaining subsequence for an amylase or glucoamylase activity, thereby determining a functional fragment of an amylase or glucoamylase enzyme. In one aspect, the amylase or glucoamylase activity is measured by providing an amylase or glucoamylase substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods for hydrolyzing polysaccharide, oligosaccharide or starch, comprising the following steps: (a) providing a polypeptide having an amylase and/or glucoamylase activity, wherein the polypeptide comprises a polypeptide of the invention; (b) providing a composition comprising a polysaccharide, oligosaccharide or starch; and (c) contacting the polypeptide of step (a) with the composition of step (b) under conditions wherein the polypeptide hydrolyzes the polysaccharide, oligosaccharide or starch. In one aspect, the composition comprising polysaccharide, oligosaccharide or starch, that comprises an α-1,4-glucosidic bond or an α-1,6-glucosidic bond. In one aspect, the amylase activity is an α-amylase or a beta-amylase activity. In one aspect, the α-amylase activity hydrolyzes internal bonds in a starch or other polysaccharide.

The invention provides methods for liquefying or removing a polysaccharide, oligosaccharide or starch, from a composition comprising the following steps: (a) providing a polypeptide having an amylase and/or glucoamylase activity, wherein the polypeptide comprises a polypeptide of the invention; (b) providing a composition comprising a polysaccharide, oligosaccharide or starch; and (c) contacting the polypeptide of step (a) with the composition of step (b) under conditions wherein the polypeptide removes or liquefies the polysaccharide, oligosaccharide or starch.

The invention provides methods of increasing thermotolerance or thermostability of an amylase polypeptide, the method comprising glycosylating an amylase or glucoamylase polypeptide, wherein the polypeptide comprises at least thirty contiguous amino acids of a polypeptide of the invention; or a polypeptide encoded by a nucleic acid sequence of the invention, thereby increasing the thermotolerance or thermostability of the amylase or glucoamylase polypeptide. In one aspect, the amylase or glucoamylase specific activity can be thermostable or thermotolerant at a temperature in the range from greater than about 37° C. to about 95° C.

The invention provides methods for overexpressing a recombinant amylase or glucoamylase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides detergent compositions comprising a polypeptide of the invention or a polypeptide encoded by a nucleic acid of the invention, wherein the polypeptide comprises an amylase or glucoamylase activity. In one aspect, the amylase or glucoamylase can be a nonsurface-active amylase or glucoamylase. In another aspect, the amylase or glucoamylase can be a surface-active amylase or glucoamylase.

The invention provides methods for washing an object comprising the following steps: (a) providing a composition comprising a polypeptide having an amylase and/or glucoamylase activity, wherein the polypeptide comprises: a polypeptide of the invention or a polypeptide encoded by a nucleic acid of the invention; (b) providing an object; and (c) contacting the polypeptide of step (a) and the object of step (b) under conditions wherein the composition can wash the object.

The invention provides methods for hydrolyzing a polysaccharide, oligosaccharide or starch, e.g., in a feed or a food prior to consumption by an animal, comprising the following steps: (a) obtaining a composition, e.g., a feed material, comprising a polysaccharide, oligosaccharide or starch, wherein the polypeptide comprises: a polypeptide of the invention or a polypeptide encoded by a nucleic acid of the invention; and (b) adding the polypeptide of step (a) to the composition, e.g., the feed or food material, in an amount sufficient for a sufficient time period to cause hydrolysis of the polysaccharide, oligosaccharide or starch, thereby hydrolyzing the polysaccharide, oligosaccharide or starch. In one aspect, the food or feed comprises rice, corn, barley, wheat, legumes, or potato.

For example, in one embodiment, the invention provide compositions comprising a combination of an amylase and a glucoamylase (where one or both of these enzymes is an enzyme of this invention) for the hydrolysis of a polysaccharide, oligosaccharide or starch, e.g., a rice, corn, barley, wheat, legumes, or potato starch. In one aspect, enzyme loading for a combination of an amylase and a glucoamylase comprises a 1:10 amylase:glucoamylase ratio; wherein in one embodiment a total enzyme load is between 0.015%-0.0255% enzyme necessary to completely hydrolyze 33% of a flour, e.g., a corn flour. Alternative exemplary ranges for loading are around 0.01% (w/w) for hydrolysis of 23% purified corn starch and between 0.015%-0.2% (w/w) for hydrolysis of corn starch in 33% corn flour.

The invention provides methods for textile desizing comprising the following steps: (a) providing a polypeptide having an amylase and/or glucoamylase activity, wherein the polypeptide comprises a polypeptide of the invention or a polypeptide encoded by a nucleic acid of the invention; (b) providing a fabric; and (c) contacting the polypeptide of step (a) and the fabric of step (b) under conditions wherein the amylase or glucoamylase can desize the fabric.

The invention provides methods for deinking of paper or fibers comprising the following steps: (a) providing a polypeptide having an amylase and/or glucoamylase activity, wherein the polypeptide comprises a polypeptide of the invention; (b) providing a composition comprising paper or fiber; and (c) contacting the polypeptide of step (a) and the composition of step (b) under conditions wherein the polypeptide can deink the paper or fiber.

The invention provides methods for treatment of lignocellulosic fibers comprising the following steps: (a) providing a polypeptide having an amylase and/or glucoamylase activity, wherein the polypeptide comprises a polypeptide of the invention; (b) providing a lignocellulosic fiber; and (c) contacting the polypeptide of step (a) and the fiber of step (b) under conditions wherein the polypeptide can treat the fiber thereby improving the fiber properties.

The invention provides methods for producing a high-maltose or a high-glucose syrup comprising the following steps: (a) providing a polypeptide having an amylase and/or glucoamylase activity, wherein the polypeptide comprises an enzyme of the invention; (b) providing a composition comprising a polysaccharide, oligosaccharide or starch; and (c) contacting the polypeptide of step (a) and the fabric of step (b) under conditions wherein the polypeptide of step (a) can liquefy the composition of step (b) thereby producing a soluble polysaccharide, oligosaccharide or starch, hydrolysate and saccharify the soluble polysaccharide, oligosaccharide or starch, hydrolysate thereby producing the syrup. In one aspect, the starch can be from rice, corn, barley, wheat, legumes, potato, or sweet potato.

The invention provides methods for improving the flow of the polysaccharide-comprising, e.g., a starch-containing, production fluids comprising the following steps: (a) providing a polypeptide having an amylase and/or glucoamylase activity, wherein the polypeptide comprises a polypeptide of the invention; (b) providing production fluid; and (c) contacting the polypeptide of step (a) and the production fluid of step (b) under conditions wherein the amylase or glucoamylase can hydrolyze the polysaccharide, oligosaccharide or starch, in the production fluid thereby improving its flow by decreasing its density. In one aspect, the production fluid can be from a subterranean formation.

The invention provides anti-staling compositions comprising a polypeptide of the invention or a polypeptide encoded by a nucleic acid of the invention. The invention provides methods for preventing staling of the baked products comprising the following steps: (a) providing a polypeptide having an amylase and/or glucoamylase activity, wherein the polypeptide comprises a polypeptide of the invention; (b) providing a composition containing a polysaccharide, oligosaccharide or starch, used for baking; (c) combining the polypeptide of step (a) with the composition of the step (b) under conditions wherein the polypeptide can hydrolyze the polysaccharide, oligosaccharide or starch, in the composition used for baking thereby preventing staling of the baked product. In one aspect, the baked product can be bread.

The invention provides methods for using amylase or glucoamylase in brewing or alcohol production comprising the following steps: (a) providing a polypeptide having an amylase and/or glucoamylase activity, wherein the polypeptide comprises a polypeptide of the invention; (b) providing a composition containing a polysaccharide, oligosaccharide or starch, and used for brewing or in alcohol production; (c) combining the polypeptide of step (a) with the composition of the step (b) under conditions wherein the polypeptide can hydrolyze the polysaccharide, oligosaccharide or starch, in the composition used for brewing or in alcohol production. In one aspect, the composition containing a polysaccharide, oligosaccharide or starch, can be beer.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell.

The invention also provides a process for preparing a dough or a baked product prepared from the dough which comprises adding an amylase or glucoamylase of the invention to the dough in an amount which is effective to retard the staling of the bread. The invention also provides a dough comprising said amylase or glucoamylase and a premix comprising flour together with said amylase or glucoamylase. Finally, the invention provides an enzymatic baking additive, which contains said amylase or glucoamylase. The use of the amylase or glucoamylase in accordance with the present invention provides an improved anti-staling effect as measured by, e.g. less crumb firming, retained crumb elasticity, improved slice-ability (e.g. fewer crumbs, non-gummy crumb), improved palatability or flavor.

The enzyme-comprising compositions of the invention (e.g., comprising polypeptides, nucleic acids and/or antibodies of this invention) can be formulated in a variety of forms, e.g., as liquids, gels, pills, tablets, sprays, powders, food, feed pellets or encapsulated forms, including nanoencapsulated forms. Any of these embodiments can be designed or further formulated as delayed release or "controlled release" compositions.

The invention provides delayed release ("controlled release") compositions comprising an desired ingredient coated by a latex polymer (or equivalent) coating. In one aspect, the desired ingredient comprises an enzyme, e.g., an enzyme of the invention. In one aspect, a coated composition comprises a drug or pharmaceutical. In one aspect, the desired ingredient comprises a small molecule, a drug, a polysaccharide, a lipid, a nucleic acid, a vitamin, an antibiotics or an insecticide. In one aspect, the desired ingredient comprises a pellet or a matrix, e.g., a pellet or a matrix comprising an edible material (e.g., as an animal food or feed or supplement or medicament). The invention also provides methods for the "controlled release" or "delayed release" of a composition, wherein the composition is coated by a latex polymer (or equivalent) coating.

In one aspect, the latex polymer coating comprises a latex paint, or equivalent. The latex polymer coating can comprise a (meth)acrylate, a vinyl acetate, a styrene, an ethylene, a vinyl chloride, a butadiene, a vinylidene chloride, a vinyl versatate, a vinyl propionate, a t-butyl acrylate, an acrylonitrile, a neoprene, a maleate, a fumarate, equivalents thereof, combinations thereof and/or derivatives thereof.

The invention provides methods for the delayed release or controlled release of a composition comprising: (i) (a) providing a composition, and, providing a latex polymer coating; and (b) coating the composition with the latex polymer coating; (ii) the method of (i), wherein the composition comprises a drug or pharmaceutical; or (iii) the method of (i) or (ii), wherein the composition comprises or consists of a polypeptide encoded by the nucleic acid of claim 1.

The invention provides oil well drilling fluids comprising the polypeptides of the invention. The invention provides methods for changing the viscosity of a composition comprising: (i) (a) providing a composition and a polypeptide of the invention, and, providing a composition; and (b) treating the composition with t a polypeptide of the invention; or (ii) the method of (i), wherein the composition comprises a soil or a drilling mud.

The invention provides methods for aiding in the carrying away of drilling mud comprising: (a) providing a composition and a polypeptide of the invention, and a drilling mud; and (b) treating the drilling mud with a composition comprising a polypeptide of the invention.

The invention provides bio-bleaching solutions comprising a polypeptide of the invention. The invention provides methods for bio-bleaching a composition comprising: (i) (a) providing a composition and a polypeptide of the invention; and (b) treating the composition with a polypeptide of the invention; or (ii) the method of (i), wherein the composition is a paper or a pulp product.

The invention provides methods for making a fuel comprising: (i) (a) providing a polypeptide of the invention; (b) providing a composition comprising a polysaccharide, oligosaccharide or starch; and (c) contacting the polypeptide of (a) with the composition of (b) under conditions wherein the polypeptide hydrolyzes the polysaccharide, oligosaccharide or starch; or (ii) the method of (i) wherein the polypeptide is a thermostable enzyme; (iii) the method of (i) wherein the fuel is ethanol-based.

The invention provides disinfectants comprising a polypeptide of the invention.

The invention provides biodefense or bio-detoxifying agents comprising a polypeptide of the invention.

The invention provides dairy products comprising a polypeptide of the invention.

The invention provides methods for processing a biomass material comprising lignocellulose comprising (i) (a) providing a composition comprising a polypeptide of the invention, and, providing a biomass material; and (b) contacting the composition comprising a polypeptide of the invention, with the biomass material; (ii) the method of (i), wherein the biomass material comprises or is derived from an agricultural crop, or is a byproduct of a food or a feed production, or is a lignocellulosic waste product, or is a plant residue or a waste paper or waste paper product; (iii) the method of (i) or (ii), wherein the polypeptide has activity comprising an amylase, a glucoamylase, glucosidase, e.g. alpha-glucosidase or beta-glucosidase activity; (iv) the method of any of (ii), wherein the plant residue comprise stems, leaves, hulls, husks, cobs, wood, wood chips, wood pulp and sawdust, or, the paper waste comprises discarded or used photocopy paper, computer printer paper, notebook paper, notepad paper, typewriter paper, newspapers, magazines, cardboard and paper-based packaging materials; or (v) the method of (i) to (iv), wherein the processing of the biomass material generates a bioethanol, biopropanol, biobutanol, or a biodiesel; (vi) the method of (i) to (v), wherein the biomass material comprises a lignocellulose.

The invention provides biomass materials comprising a polypeptide of the invention.

The invention provides methods for making bioethanol, biopropanol, biobutanol, or a biodiesel comprising: (i) (a) providing a polypeptide of the invention, and, providing a composition comprising a polysaccharide or oligosaccharide; and (b) contacting the composition comprising a polysaccharide or oligosaccharide with a polypeptide of the invention; (ii) the method of (i), wherein the composition comprising a polysaccharide or oligosaccharide comprises a plant, plant product or plant derivative; (iii) the method of (ii), wherein the plant or plant product comprises cane sugar plants or plant products, beets or sugarbeets, wheat, corn, soybeans, potato, rice or barley; (iv) the method of any of (i) to (iii), wherein the polypeptide has activity comprising an amylase, a glucoamylase, glucosidase, e.g. alpha-glucosidase or beta-glucosidase activity; or (v) the method of any of (i) to (iv), wherein the polysaccharide or oligosaccharide comprises a fermentable sugar.

The invention provides methods for making a fuel comprising (i) (a) providing a polypeptide of the invention, and, providing a composition comprising a fermentable sugar; and (b) contacting the composition comprising a fermentable sugar with a polypeptide of the invention; (ii) the method of (i), wherein the composition comprising a fermentable sugar comprises a plant, plant product or plant derivative; (iii) the method of (ii), wherein the plant or plant product comprises cane sugar plants or plant products, beets or sugarbeets, wheat, corn, soybeans, potato, rice or barley; (iv) the method of any of (i) to (iii), wherein the polypeptide has activity comprising an amylase, a glucoamylase, glucosidase, e.g. alpha-glucosidase or beta-glucosidase activity; or (v) the method of any of (i) to (iv), wherein the fuel comprises a bioethanol or a gasoline-ethanol mix, or comprises a bioethanol, biopropanol, biobutanol, or a biodiesel.

The invention provides fuels comprising (a) a polypeptide of the invention; (b) the fuel of (a), wherein the polypeptide has activity comprising amylase, glucoamylase, glucosidase, e.g. alpha-glucosidase or beta-glucosidase activity; (c) the fuel of (a) or (b), wherein the fuel is derived from a plant material, or the fuel is derived from a potato, soybean (rapeseed), barley, rye, corn, oats, wheat, beet or sugar cane; or (d)

the fuel of any of (a) to (c), wherein the fuel comprises a bioethanol or a gasoline-ethanol mix, or comprises a bioethanol, biopropanol, biobutanol, or a biodiesel.

The invention provides methods for producing a sugar (e.g., a monosaccharide), the method comprising: (i) (a) providing at least one polypeptide having an amylase or a glucoamylase activity; (b) providing a composition comprising a polysaccharide or an oligosaccharide; and (c) contacting the composition of step (b) with the polypeptide of step (a), thereby generating sugars; (ii) the method of (i), wherein the composition comprising a polysaccharide or an oligosaccharide comprises a starch; (iii) the method of any of (i) or (ii), wherein the polysaccharide, oligosaccharide and/or sugar comprises or is a fermentable sugar; (iv) the method of any of (i), (ii), or (iii), further comprising fermenting the sugar to produce an alcohol; or (v) the method of (iv), wherein the alcohol is an ethanol, propanol or butanol.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 22 illustrates the characterization of the peptides generated in this pepsin digest of SEQ ID NO:52; and FIG. 23A illustrates the small peptide isolation scheme used for the peptides generated by the proteolysis of SEQ ID NO:52 by pepsin; FIG. 23D illustrates the sequence of the peptides identified by the LC MS/MS analysis; FIG. 23E and FIG. 23F illustrate the "Asn-Xaa-Ser/Thr" sequins (motifs) in the sequence output (highlighted in blue); asparagines predicted to be N-glycosylated are highlighted in red, as discussed in detail in Example 22, below.

FIG. 24 illustrates Table 1, which summarizes data comparing initial rates of granular corn starch and soluble starch (dextrin) hydrolysis by exemplary enzymes of the invention and a benchmark enzyme A. niger glucoamylase, as discussed in detail in Example 23, below.

FIG. 26 illustrates tables summarizing the efficiency of exemplary enzyme purification protocols on selected enzymes of this invention, and corresponding activity data on, inter alia, raw starch and soluble starch comparing purified and unpurified enzyme, as discussed in detail in Example 18, below.

FIG. 28A shows data demonstrating the effect of temperature on the activity of e.g., an exemplary glucoamylase of the invention with granular starch as a substrate, as discussed in detail in Example 29, below.

FIG. 28B shows data demonstrating the effect of temperature on the activity of e.g., an exemplary glucoamylase of the invention with soluble starch (dextrin) as a substrate, as discussed in detail in Example 29, below.

FIG. 29A shows data demonstrating the effect of pH on the activity of e.g., an exemplary glucoamylase of the invention with granular starch as a substrate, as discussed in detail in Example 29, below.

FIG. 29B shows data demonstrating the effect of pH on the activity of e.g., an exemplary glucoamylase of the invention with soluble starch (dextrin) as a substrate, as discussed in detail in Example 29, below.

FIG. 30 shows data demonstrating the effect of temperature on starch hydrolysis by the characterized α-amylases, as discussed in detail in Example 29, below.

FIG. 31A shows data demonstrating the effect pH on the activities of exemplary α-Amylases and/or glucoamylases of the invention with Granular Starch as substrate, as discussed in detail in Example 29, below.

FIG. 31B shows data demonstrating the effect pH on the activities of exemplary α-Amylases and/or glucoamylases of the invention with Soluble Starch as substrate, as discussed in detail in Example 29, below.

Like reference symbols in the various drawings indicate like elements.

DETAILED DESCRIPTION

Figure 1:
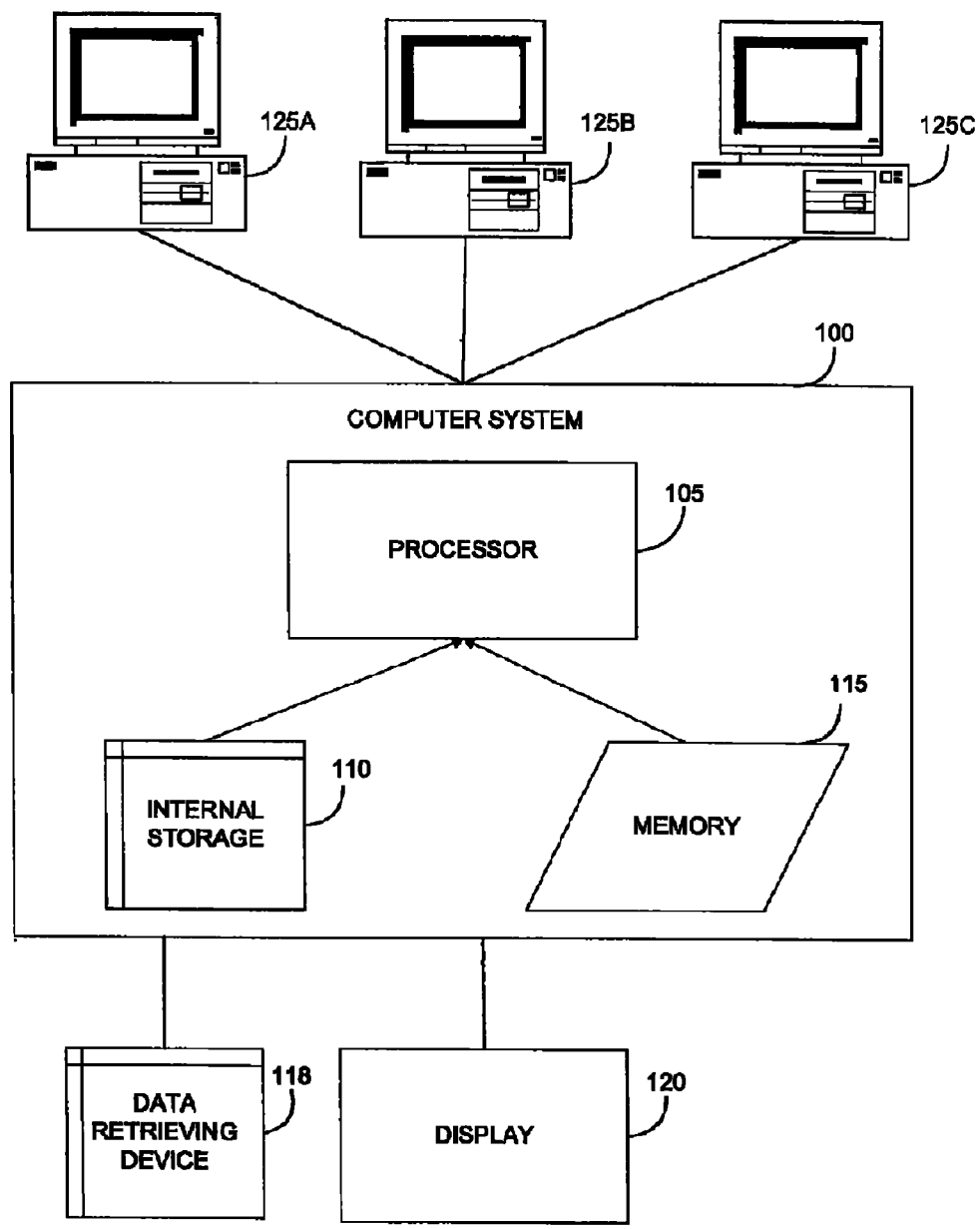
FIG. 1 is a block diagram of a computer system.

The invention provides amylase enzymes, e.g., an alpha amylases, polynucleotides encoding the enzymes, methods of making and using these polynucleotides and polypeptides. The invention is directed to novel polypeptides having an amylase and/or glucoamylase activity, e.g., an alpha amylase activity, nucleic acids encoding them and antibodies that bind to them. The polypeptides of the invention can be used in a variety of diagnostic, therapeutic, and industrial contexts. The polypeptides of the invention can be used as, e.g., an additive for a detergent, for processing foods and for chemical synthesis utilizing a reverse reaction. Additionally, the polypeptides of the invention can be used in fabric treatment, alcohol production, and as additives to food or animal feed.

In one aspect, the amylases and/or glucoamylases of the invention are active at a high and/or at a low temperature, or, over a wide range of temperature. For example, they can be active in the temperatures ranging between 20° C. to 90° C., between 30° C. to 80° C., or between 40° C. to 70° C. The invention also provides amylases that have activity at alkaline pHs or at acidic pHs, e.g., low water acidity. In alternative aspects, the Amylases and/or glucoamylases of the invention can have activity in acidic pHs as low as pH 5.5, pH 5.0, pH 4.5, pH 4.0, and pH 3.5. In alternative aspects, the Amylases and/or glucoamylases of the invention can have activity in alkaline pHs as high as pH 8, pH 9.5, pH 10, pH 10.5, and pH 11. In one aspect, the Amylases and/or glucoamylases of the invention are active in the temperature range of between about 40° C. to about 70° C. under conditions of low water activity (low water content). For example, the invention provides amylases, including glucoamylases, with the ability to hydrolyze a polysaccharide, oligosaccharide or starch, e.g., a granular starch (including raw granular starch), at low temperatures, e.g., in the range of about 30° C. to 40° C.; at low pH, e.g., in the range of about pH 3.5 to pH 6.0; and, at low temperatures and low pH, e.g., in the range of about 30° C. to 40° C. and at low pH in the range of about pH 3.5 to pH 6.0.

The invention also provides methods for further modifying the exemplary Amylases and/or glucoamylases of the invention to generate proteins with desirable properties. For example, amylases generated by the methods of the invention can have altered enzymatic activity, thermal stability, pH/activity profile, pH/stability profile (such as increased stability at low, e.g. pH<6 or pH<5, or high, e.g. pH>9, pH values), stability towards oxidation, Ca$^{2+}$ dependency, specific activity and the like. The invention provides for altering any property of interest. For instance, the alteration may result in a variant which, as compared to a parent enzyme, has altered enzymatic activity, or, pH or temperature activity profiles.

Generating and Manipulating Nucleic Acids

In one aspect, the invention provides isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 10, 15, 20, 25, 30, 35, 40, 45, 50, 55, 60, 65, 70, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. In one aspect, the nucleic acid encodes at least one polypeptide having an amylase and/or glucoamylase activity, e.g., an alpha amylase activity.

"Synthetic" nucleic acids (including oligonucleotides), polypeptides or proteins of the invention include those prepared by any chemical synthesis, e.g., as described, below.

The phrases "nucleic acid" or "nucleic acid sequence" includes oligonucleotides, nucleotides, polynucleotides, or to a fragment of any of these, to DNA or RNA (e.g., mRNA, rRNA, tRNA) of genomic, recombinant or synthetic origin which may be single-stranded or double-stranded and may represent a sense or antisense strand, to peptide nucleic acid (PNA), or to any DNA-like or RNA-like material, natural or synthetic in origin, including, e.g., iRNA such as miRNA or siRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

The invention provides "recombinant" and synthetic nucleic acids, which can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein.

"Oligonucleotide" includes either a single stranded polydeoxynucleotide or two complementary polydeoxynucleotide strands, which may be chemically synthesized (i.e., as synthetic nucleic acids). In alternative embodiments, synthetic nucleic acids and oligonucleotides of the invention have no 5' phosphate and thus will not ligate to another oligonucleotide without adding a phosphate with an ATP in the presence of a kinase. In alternative embodiments, a synthetic oligonucleotide can ligate to a fragment that has not been dephosphorylated.

The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

The invention provides isolated and recombinant nucleic acids, including expression cassettes such as expression vectors encoding the polypeptides of the invention. The invention provides probes comprising or consisting of nucleic acids of the invention. The invention also includes methods for discovering new amylase sequences using the nucleic acids of the invention. The invention also includes methods for inhibiting the expression of amylase genes, transcripts and polypeptides using the nucleic acids of the invention. Also provided are methods for modifying the nucleic acids of the invention by, e.g., synthetic ligation reassembly, optimized directed evolution system and/or gene site saturation mutagenesis (GSSM).

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

The invention provides methods for optimizing amylase enzymes and enzyme-encoding nucleic acid sequences, e.g., making "variant sequences", comprising use of sequences of the invention using, e.g., "saturation mutagenesis" or "GSSM" (includes a method that uses degenerate oligonucleotide primers to introduce point mutations into a polynucleotide, as described in detail, below); "optimized directed evolution system" or "optimized directed evolution" (includes a method for reassembling fragments of related nucleic acid sequences, e.g., related genes, and explained in detail, below) and/or "synthetic ligation reassembly" or "SLR" (includes a method of ligating oligonucleotide fragments in a non-stochastic fashion, and explained in detail, below). "Variant" includes polynucleotides or polypeptides of the invention modified at one or more base pairs, codons, introns, exons, or amino acid residues (respectively) yet still retain the biological activity of an amylase and/or glucoamylase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant amylase having activity at a pH or temperature, for example, that is different from an exemplary enzyme of this invention, or a wild-type amylase, are provided herein.

Nucleic acids of the invention can be completely or partially synthetic, and in alternative aspects, they can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACS), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. Promoters that are used to practice this invention include all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters used to practice this invention can be those that drive expression continuously under most environmental conditions and states of development or cell differentiation. Promoters used to practice this invention can be "inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

In one embodiment, a promoter sequence can be "operably linked to" a coding sequence of the invention, e.g., when RNA polymerase which initiates transcription at the promoter will transcribe the coding sequence into mRNA.

Promoters used to practice this invention include "tissue-specific" promoters, which are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

The expression control sequence(s) used to practice this invention can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I. Promoters suitable for expressing a polypeptide in bacteria include the *E. coli* lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express an amylase and/or glucoamylase of the invention in a tissue-specific manner. The invention also provides plants or seeds that express an amylase and/or a glucoamylase of the invention in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation.

Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, e.g., ACT11 from *Arabidopsis* (Huang (1996) *Plant Mol. Biol.* 33:125-139); Cat3 from *Arabidopsis* (GenBank No. U43147, Zhong (1996) *Mol. Gen. Genet.* 251:196-203); the gene encoding stearoyl-acyl carrier protein desaturase from *Brassica napus* (Genbank No. X74782, Solocombe (1994) *Plant Physiol.* 104:1167-1176); GPc1 from maize (GenBank No. X15596; Martinez (1989) *J. Mol. Biol.* 208: 551-565); the Gpc2 from maize (GenBank No. U45855, Manjunath (1997) *Plant Mol. Biol.* 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro baciliform virus (RTBV), which replicates only in phloem cells in infected rice plants, with its promoter which drives strong phloem-specific reporter gene expression; the cassaya vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of amylase-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the *Arabidopsis* LEAFY gene promoter. See also Cardon (1997) Plant J 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fb12A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant. Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically—(e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato, sugar cane, sugar beet, or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the amylase-producing nucleic acids of the invention will allow the grower to select plants with the optimal starch/sugar ratio. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

If proper polypeptide expression is desired, a polyadenylation region at the 3'-end of the coding region should be included. The polyadenylation region can be derived from the natural gene, from a variety of other plant genes, or from genes in the Agrobacterial T-DNA.

The invention provides "expression cassettes" comprising any sequence of the invention "operably linked" to a transcriptional regulator; e.g., wherein "operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et. al. (*Science* 261: 754-756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources, such as *Bacillus*. These problems may apply to the nucleotide sequence of this invention and the modification of these genes can be undertaken using techniques now well known in the art. The following problems may be encountered:

Codon Usage

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

GC/AT Content

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

Sequences Adjacent to the Initiating Methionine

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210) have suggested one sequence as a consensus translation initiator for the expression of the *E. coli* uidA gene in plants. Further, Joshi, *N.A.R.* 15: 6643-6653 (1987), has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | |
|---|---|---|---|---|---|---|---|---|---|
| −10 | −9 | −8 | −7 | −6 | −5 | −4 | −3 | −2 | −1 |
| C3 | 8 | 4 | 6 | 2 | 5 | 6 | 0 | 10 | 7 |
| T3 | 0 | 3 | 4 | 3 | 2 | 1 | 1 | 1 | 0 |
| A2 | 3 | 1 | 4 | 3 | 2 | 3 | 7 | 2 | 3 |
| G6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

Removal of Illegitimate Splice Sites

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy). In most cases it is preferable to assay the expression of gene constructions using transient assay protocols (which are well known in the art) prior to their transfer to transgenic plants.

Plant Promoters

The compositions of the invention may contain nucleic acid sequences for transformation and expression in a plant of interest. The nucleic acid sequences may be present in DNA constructs or expression cassettes. In alternative embodiments, "expression cassette" as used herein means a nucleic acid molecule capable of directing expression of a particular nucleotide sequence in an appropriate host cell, comprising a promoter operatively linked to the nucleotide sequence of interest, which is operatively linked to termination signals. It also typically comprises sequences required for proper translation of the nucleotide sequence. The coding region usually codes for a protein of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. In alternative embodiments, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In alternative embodiments, the promoter can also be specific to a particular tissue or organ or stage of development.

The present invention encompasses the transformation of plants with expression cassettes capable of expressing polynucleotides. In alternative embodiments, the expression cassette will include in the 5'-3' direction of transcription, a transcriptional and translational initiation region (i.e., a promoter) and a polynucleotide of interest. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et. al. (2003) *Plant J.* 34:383-92 and Chen et. al. (2003) *Plant J.* 36:731-40 for examples of sequences allowing for inducible expression.

In alternative embodiments, the regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. In alternative embodiments, operably linked means that the nucleotide sequences being linked are contiguous.

Any promoter capable of driving expression in the plant of interest may be used in the practice of the invention. The promoter may be native or analogous or foreign or heterologous to the plant host. In alternative embodiments, the terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

In alternative embodiments, a "homologous" nucleic acid (e.g. DNA) sequence is a nucleic acid (e.g. DNA or RNA) sequence naturally associated with a host cell into which it is introduced.

The choice of promoters to be included can depend upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

In alternative embodiments, suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et. al., Plant Cell, 1:855-866 (1989); Bustos, et. al., Plant Cell, 1:839-854 (1989); Green, et. al., EMBO J. 7, 4035-4044 (1988); Meier, et. al., Plant Cell, 3, 309-316 (1991); and Zhang, et. al., Plant Physiology 110: 1069-1079 (1996).

In alternative embodiments, tissue preferred regulated genes and/or promoters which have been reported in plants can be used. Reported tissue preferred genes that can be used in alternative embodiments include the genes encoding the seed storage proteins (such as napin, cruciferin, beta-conglycinin, and phaseolin, prolamines, glutelins, globulins, and zeins) zeins or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et. al., (1991) Seed Science Research, 1:209). Examples of tissue-specific promoters that can be used to practice this invention, which have been described, include the lectin (Vodkin, Prog. Clin. Biol. Res., 138; 87 (1983); Lindstrom et. al., (1990) Der. Genet., 11:160), corn alcohol dehydrogenase 1 (Dennis et. al., Nucleic Acids Res., 12:3983 (1984)), corn light harvesting complex (see, e.g., Simpson, (1986) Science, 233:34; Bansal (1992) Proc. Natl. Acad. Sci. USA 89:3654), corn heat shock protein (see, e.g., Odell et. al., (1985) Nature, 313:810; pea small subunit RuBP carboxylase (see, e.g., Poulsen et. al., (1986) Mol. Gen. Genet., 205:193-200; Cashmore et. al., (1983) Gen. Eng. of Plants, Plenum Press, New York, 29-38); Ti plasmid mannopine synthase (see, e.g., Langridge et. al., (1989) Proc. Natl. Acad. Sci. USA, 86:3219-3223), Ti plasmid nopaline synthase (Langridge et. al., (1989) Proc. Natl. Acad. Sci. USA, 86:3219-3223), petunia chalcone isomerase (see, e.g., vanTunen (1988) EMBO J. 7:1257); bean glycine rich protein 1 (see, e.g., Keller (1989) Genes Dev. 3:1639); truncated CaMV 35S (see, e.g., Odell (1985) Nature 313:810); potato patatin (see, e.g., Wenzler (1989) Plant Mol. Biol. 13:347; root cell (see, e.g., Yamamoto (1990) Nucleic Acids Res. 18:7449); maize zein (see, e.g., Reina (1990) Nucleic Acids Res. 18:6425; Lopes et. al. (1995) Mol. Gen. Genet. 247: 603-613; Kriz (1987) Mol. Gen. Genet. 207:90; Wandelt (1989) Nucleic Acids Res., 17:2354; Langridge (1983) Cell, 34:1015; Reina (1990) Nucleic Acids Res., 18:7449), ADP-gpp promoter (see, e.g., U.S. Pat. No. 7,102,057); globulin-1 (see, e.g., Belanger (1991) Genetics 129:863); α-globulin (Sunilkumar, et. al. (2002), Transgenic Res. 11:347-359); α-tubulin; cab (see, e.g., Sullivan (1989) Mol. Gen. Genet., 215:431); PEPCase (see e.g., Hudspeth & Grula, (1989) Plant Molec. Biol., 12:579-589); R gene complex-associated promoters (Chandler et. al., (1989) Plant Cell, 1:1175); pea vicilin promoter (Czako et. al., (1992) Mol. Gen. Genet., 235:33; U.S. Pat. No. 5,625,136); GTL1 promoter (Takaiwa et. al. (1991) Plant Mol. Biol. 16 (1), 49-58); chalcone synthase promoters (Franken et. al., (1991) EMBO J., 10:2605); and/or a GY1 promoter (Sims & Goldburg (1989) Nuc. Acid Res. 17(11) 4368) and the like.

In alternative embodiments, a class of fruit-preferred promoters expressed at or during antithesis through fruit development, at least until the beginning of ripening, is used, e.g., as discussed in U.S. Pat. No. 4,943,674. The promoter for polygalacturonase gene is active in fruit ripening. A polygalacturonase gene also can be used, e.g., as described in U.S. Pat. Nos. 4,535,060, 4,769,061, 4,801,590, and 5,107,065.

Other examples of tissue-preferred promoters that can be used include those that direct expression in leaf cells following damage to the leaf (for example, from chewing insects), in tubers (for example, patatin gene promoter), and in fiber cells (an example of a developmentally-regulated fiber cell protein is E6 (John & Crow (1992) PNAS 89:5769-5773). The E6 gene is most active in fiber, although low levels of transcripts are found in leaf, ovule and flower.

In alternative embodiments, promoters active in photosynthetic tissue can be used in order to drive transcription in green tissues such as leaves and stems; these promoters are suitable when they drive expression only or predominantly in such tissues. In alternative embodiments, the promoter may confer expression constitutively throughout the plant, or differentially with respect to the green tissues, or differentially with respect to the developmental stage of the green tissue in which expression occurs, or in response to external stimuli.

Examples of promoters that can be used to practice this invention include the ribulose-1,5-bisphosphate carboxylase (RbcS) promoters such as the RbcS promoter from eastern larch (*Larix laricina*), the pine cab6 promoter (Yamamoto et. al. (1994) Plant Cell Physiol. 35:773-778), the Cab-1 gene promoter from wheat (Fej es et. al. (1990) Plant Mol. Biol. 15:921-932), the CAB-1 promoter from spinach (Lubberstedt et. al. (1994) Plant Physiol. 104:997-1006), the cab1R promoter from rice (Luan et. al. (1992) Plant Cell 4:971-981), the pyruvate orthophosphate dikinase (PPDK) promoter from corn (Matsuoka et. al. (1993) Proc. Natl. Acad. Sci. USA 90:9586-9590), the tobacco Lhcb1*2 promoter (Cerdan et. al. (1997) Plant Mol. Biol. 33:245-255), the *Arabidopsis thaliana* SUC2 sucrose-H+ symporter promoter (Truernit et. al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346.

The tissue specificity of some "tissue preferred" promoters may not be absolute; in alternative embodiments reporter genes such as Gus or green fluorescent protein, cyan fluorescent protein, yellow fluorescent protein or red fluorescent protein are used. In alternative embodiments tissue preferred expression can be achieved with "leaky" expression by a combination of different tissue-preferred promoters. Other tissue preferred promoters can be used, and they can be isolated by one skilled in the art (see U.S. Pat. No. 5,589,379).

In one aspect, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant. Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotic. For example, gene expression systems that are activated in the presence of a chemical ligand, including ethanol, such as can be found in WO 96/27673; WO 93/01294; WO 94/03619; WO 02/061102, all of which are hereby incorporated by reference. The maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); estrogen, such as, the ecdysone receptor (WO 01/52620) or, a salicylic acid-responsive element (Stange (1997) Plant J. 11:1315-1324). Using chemically—(e.g., hormone- or pesticide-) induced promoters, i.e., promoter responsive to a chemical which can be applied to the transgenic plant in the field, expression of a polypeptide of the invention can be induced at a particular stage of development of the plant.

Examples of some constitutive promoters which can be used to practice this invention, and which have been described, include rice actin 1 (Wang et. al. (1992) Mol. Cell. Biol., 12:3399; U.S. Pat. No. 5,641,876); other actin isoforms (McElroy et. al. (1990) Plant Cell 2: 163-171 and McElroy et. al. (1991) Mol. Gen. Genet. 231: 150-160); CaMV 35S (Odell et. al. (1985) Nature, 313:810); CaMV 19S (Lawton et. al. (1987) Plant Mol. Biol. 9:315-324; U.S. Pat. No. 5,639,949); nos (Ebert et. al. (1987) PNAS USA 84:5745-5749); Adh (Walker et. al. (1987) PNAS USA 84:6624-6628), sucrose synthase (Yang & Russell (1990) PNAS USA 87:4144-4148); and the ubiquitin promoters (e.g. sunflower—Binet et. al. (1991) Plant Science 79: 87-94; maize—Christensen et. al. (1989) Plant Molec. Biol. 12: 619-632; and *Arabidopsis*—Callis et. al., J. Biol. Chem. (1990) 265:12486-12493; and Norris et. al., Plant Mol. Biol. (1993) 21:895-906.

A variety of transcriptional terminators can be used in expression cassettes to practice this invention. These transcriptional terminators are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Numerous sequences have been found to enhance gene expression from within the transcriptional unit and these sequences can be used in conjunction with the genes of this invention to increase their expression in transgenic plants. For example, various intron sequences have been shown to enhance expression, particularly in monocotyledonous cells. For example, the introns of the maize Adh1 gene have been found to significantly enhance the expression of the wild-type gene under its cognate promoter when introduced into maize cells.

In alternative embodiments, non-translated leader sequences derived from viruses can be used to enhance expression, and these are particularly effective in dicotyledonous cells. In alternative embodiments, leader sequences from Tobacco Mosaic Virus (TMV, the "W-sequence"), Maize Chlorotic Mottle Virus (MCMV), and Alfalfa Mosaic Virus (AMV) are used, and these have been shown to be effective in enhancing expression (e.g. Gallie et. al. Nucl. Acids Res. 15: 8693-8711 (1987); Skuzeski et. al. Plant Molec. Biol. 15: 65-79 (1990)).

Targeting of the Gene Product Within the Cell

In alternative embodiments, various mechanisms for targeting gene products are used; and these are known to exist in plants, and the sequences controlling the functioning of these mechanisms have been characterized in some detail.

Sequences have been characterized which cause the targeting of gene products to other cell compartments.

Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference). In alternative embodiments, various signal sequence are used, e.g., the signal sequence may be an N-terminal signal sequence from waxy, an N-terminal signal sequence from γ-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). In alternative embodiments, amino terminal sequences are used in conjunction with carboxy terminal sequences; these are responsible for vacuolar targeting of gene products (Shinshi et. al. (1990) Plant Molec. Biol. 14: 357-368).

The signal sequence selected can include the known cleavage site, and the fusion constructed should take into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Expression Vectors and Cloning Vehicles

The invention provides expression vectors and cloning vehicles comprising nucleic acids of the invention, e.g., sequences encoding the amylases and/or glucoamylases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBLUESCRIPT™ (pBluescript) plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed with the present invention. "Plasmids" can be commercially available, publicly available on an unrestricted basis, or can be constructed from available plasmids in accord with published procedures. Equivalent plasmids to those described herein are known in the art and will be apparent to the ordinarily skilled artisan.

The invention provides "expression cassettes" comprising any sequence of the invention "operably linked" to a transcriptional regulator; the term "expression cassette" as used herein can refer to a nucleotide sequence which is capable of affecting expression of a structural gene (e.g., a protein coding sequence, such as an amylase and/or a glucoamylase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors used to practice this invention include, but are not limited to replicons (e.g., RNA replicons, bacteriophages) to which fragments of DNA may be attached and become replicated. Vectors used to practice this invention include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal mini-chromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant. Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Host Cells and Transformed Cells

The invention also provides a transformed, transfected, infected or transduced cell comprising a nucleic acid sequence of the invention, e.g., a sequence encoding an amylase and/or a glucoamylase, and/or a glucanase of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia, Bacillus, Streptomyces, Salmonella, Pseudomonas* and *Staphylococcus*, including, e.g., *Escherichia coli, Lactococcus lactis, Bacillus subtilis, Bacillus cereus, Salmonella typhimurium, Pseudomonas fluorescens*. Exemplary yeast cells include any species of *Pichia, Saccharomyces, Schizosaccharomyces,* or *Schwanniomyces*, including *Pichia pastoris, Saccharomyces cerevisiae,* or *Schizosaccharomyces pombe*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann Rev. Genet. 22:421-477; U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Amplification of Nucleic Acids

In practicing the invention, nucleic acids of the invention and nucleic acids encoding the polypeptides of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 25, 30, 40, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

The phrase "substantially identical" in the context of two nucleic acids or polypeptides, can refer to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention over a region of at least about 10, 20, 30, 40, 50, 100, 150, 200, 250, 300, 350, 400, 450, 500, 550, 600, 650, 700, 750, 800, 850, 900, 950, 1000 or more residues, or a region ranging from between about 50 residues to the full length of the nucleic acid or polypeptide. Nucleic acid sequences of the invention can be substantially identical over the entire length of a polypeptide coding region.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or sequence identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence, e.g., a sequence of the invention, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of the invention, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned.

Methods of alignment of sequence for comparison are well known in the art. In alternative aspects, optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms also can be used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs)

by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

Figure 3:
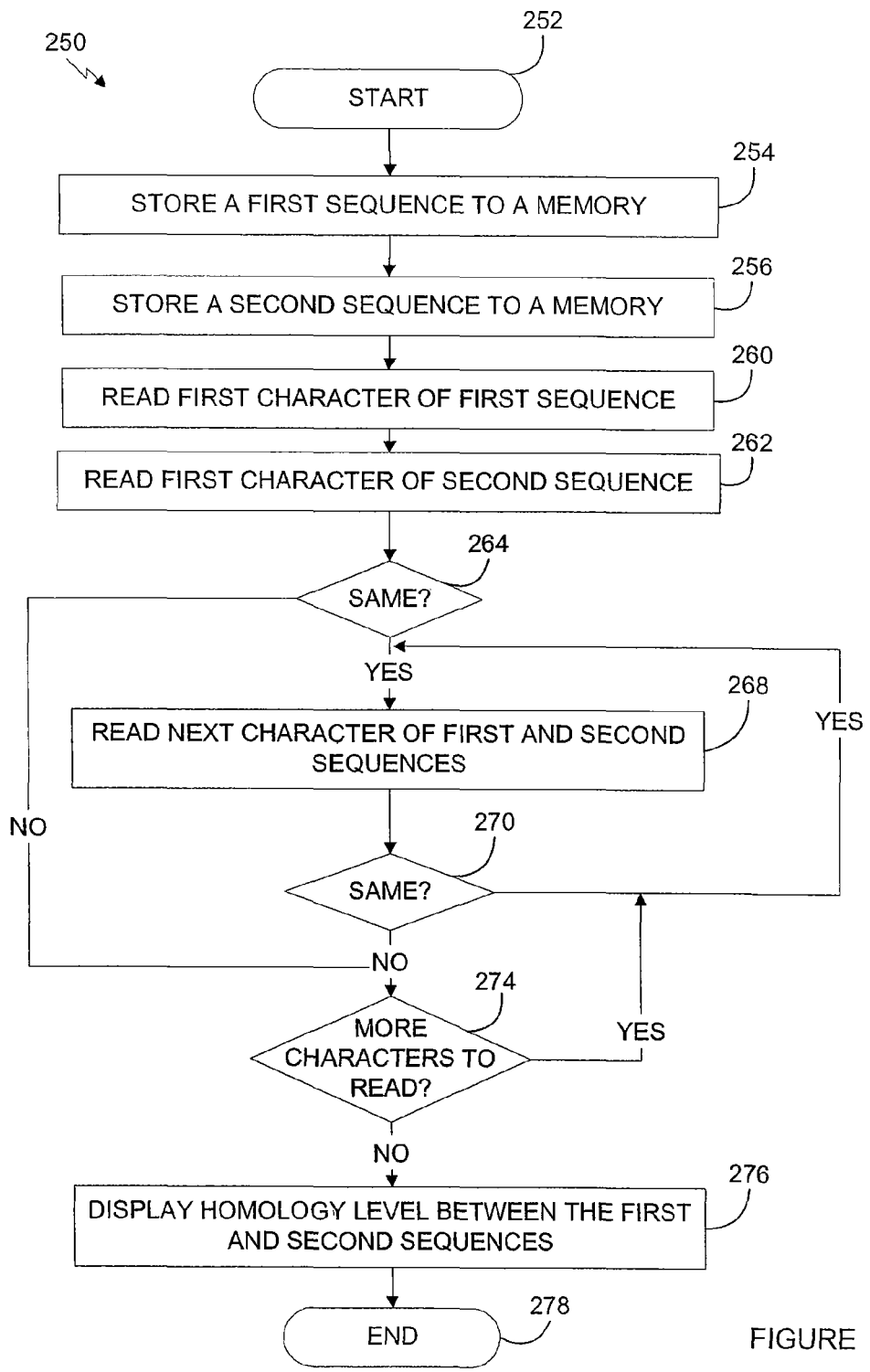
FIG. 3 is a flow diagram illustrating one aspect of a process in a computer for determining whether two sequences are homologous.

The default values used in this exemplary aspect of the invention, and to determine the values in FIG. 3, as discussed above, include:
"Filter for low complexity: ON
Word Size: 3
Matrix: Blosum62
Gap Costs: Existence:11
Extension:1"

Other default settings can be: filter for low complexity OFF, word size of 3 for protein, BLOSUM62 matrix, gap existence penalty of −1 and a gap extension penalty of −1. An exemplary NCBI BLAST 2.2.2 program setting has the "-W" option default to 0. This means that, if not set, the word size defaults to 3 for proteins and 11 for nucleotides.

Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

The invention also provides computers and processors comprising computer program products comprising sequences of the invention; and as used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a-c in a network or wide area network to provide centralized access to the computer system 100. Software for accessing and processing the nucleotide or amino acid sequences of the invention can reside in main memory 115 during execution. In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of the invention stored on a computer readable medium to reference sequences stored on a computer readable medium to identify homologies or structural motifs.

Figure 2:
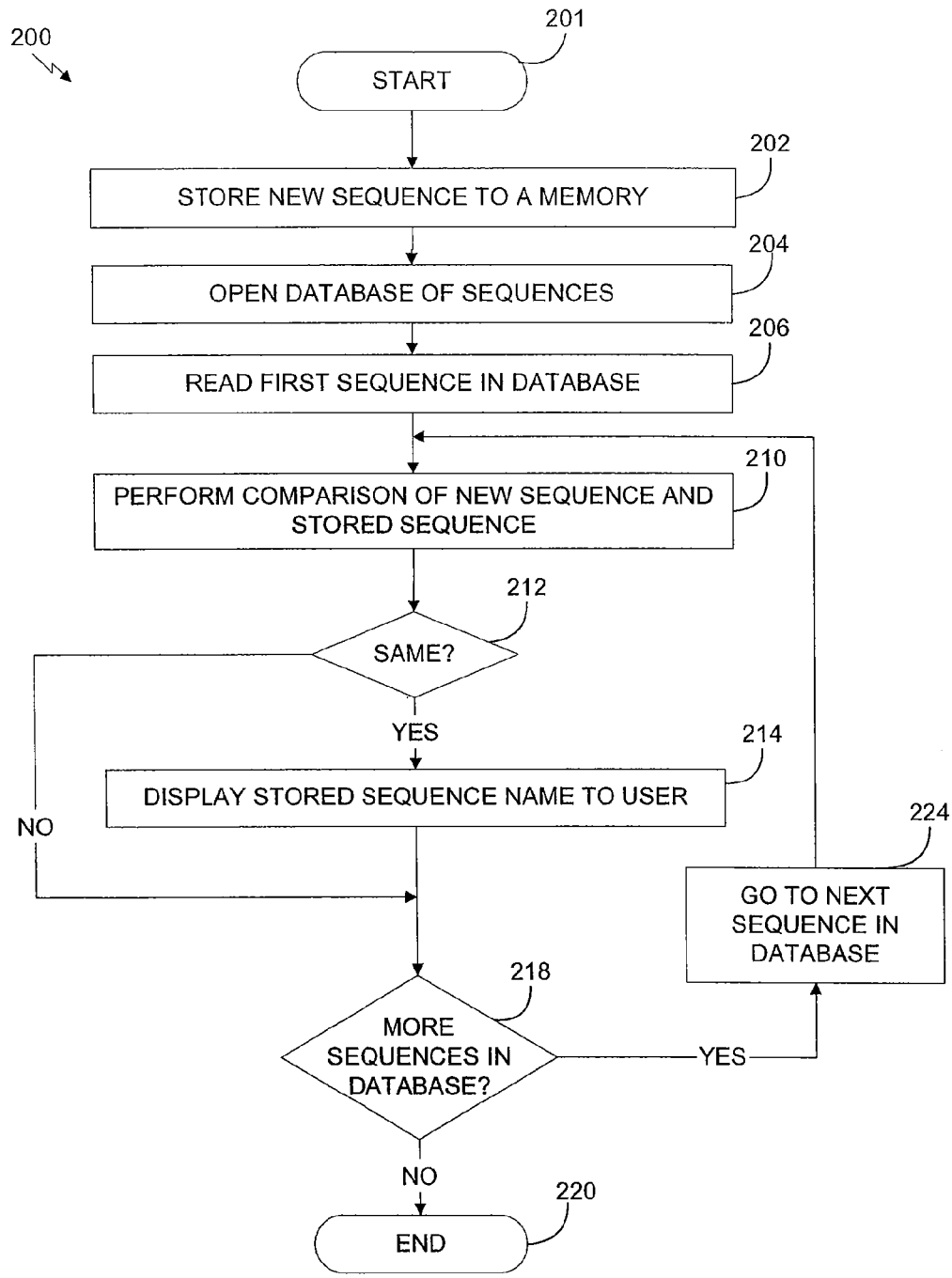
FIG. 2 is a flow diagram illustrating one aspect of a process for comparing a new nucleotide or protein sequence with a database of sequences in order to determine the homology levels between the new sequence and the sequences in the database.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 3. The method can be performed by reading a sequence of the invention and the reference sequences through the use of the computer program and identifying differences with the computer program.

Figure 4:
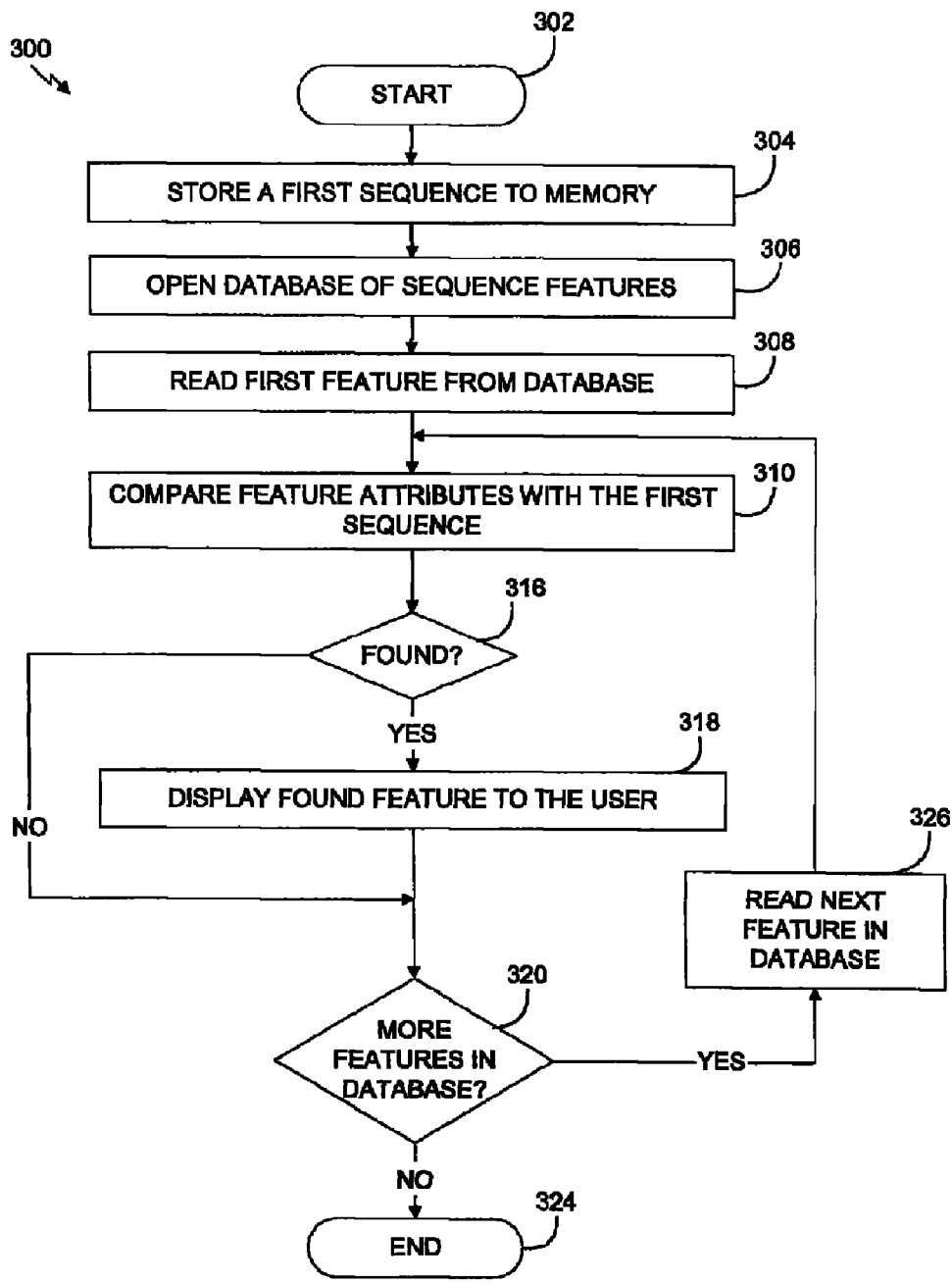
FIG. 4 is a flow diagram illustrating one aspect of an identifier process 300 for detecting the presence of a feature in a sequence.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention can be stored and manipulated in a variety of data processor programs in a variety of formats. For example, a sequence can be stored as text in a word processing file, such as Microsoft-WORD or WORDPERFECT or as an ASCII file in a variety of database programs familiar to those of skill in the art, such as DB2™, SYBASE™, or ORACLE™. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MACPATTERN™ (EMBL), DiscoveryBase (Molecular Applications Group), GENEMINE™ (Molecular Applications Group), LOOK™ (Molecular Applications Group), MACLOOK™ (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB™ (Brutlag et al. Comp. App. Biosci. 6:237-245, 1990), Catalyst (Molecular Simulations Inc.), CATALYST™/SHAPE™ (Molecular Simulations Inc.), CERIUS2.DB ACCESS™ (Molecular Simulations Inc.), HYPOGEN™ (Molecular Simulations Inc.), INSIGHT II™, (Molecular Simulations Inc.), DISCOVER™ (Molecular Simulations Inc.), CHARMM™ (CHARMm™) (Molecular Simulations Inc.), Felix (Molecular Simulations Inc.), DELPHI™, (Molecular Simulations Inc.), QUANTEMM™, (Molecular Simulations Inc.), HOMOLOGY™ (Molecular Simulations Inc.), MODELER™ (Molecular Simulations Inc.), ISIS™ (Molecular Simulations Inc.), QUANTA™/ Protein Design (Molecular Simulations Inc.), WEBLAB™ (Molecular Simulations Inc.), WEBLAB DIVERSITY EXPLORER™ (Molecular Simulations Inc.), GENE EXPLORER™ (Molecular Simulations Inc.), SEQFOLD™ (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated, synthetic or recombinant nucleic acids that hybridize under stringent conditions to an exemplary sequence of the invention, or a nucleic acid that encodes a polypeptide of the invention. The stringent conditions can be highly stringent conditions, medium stringent conditions, low stringent conditions, including the high and reduced stringency conditions described herein. In one aspect, it is the stringency of the wash conditions that set forth the conditions which determine whether a nucleic acid is within the scope of the invention, as discussed below.

"Hybridization" protocols used to practice this invention include processes by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

In alternative embodiments, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C.

Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 ug/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate nucleic acids of the invention.

Oligonucleotides Probes and Methods for Using them

The invention also provides nucleic acid probes that can be used, e.g., for identifying nucleic acids encoding a polypeptide with an amylase activity or fragments thereof or for identifying amylase genes. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency can vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization can be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO4, pH 7.0, 5.0 mM Na$_2$EDTA, 0.5% SDS, 10×Denhardt's, and 0.5 mg/ml polyriboadenylic acid. Approximately 2×10$^7$ cpm (specific activity 4–9×10$^8$ cpm/ug) of $^{32}$P end-labeled oligonucleotide probe can then added to the solution. After 12-16 hours of incubation, the membrane is washed for 30 minutes at room temperature (RT) in 1×SET (150 mM NaCl, 20 mM Tris hydrochloride, pH 7.8, 1 mM Na$_2$EDTA) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6 (log [Na+])+0.41 (fraction G+C)−(0.63% formamide)-(600/N) where N is the length of the probe. Prehybridization may be carried out in 6×SSC, 5×Denhardt's reagent, 0.5% SDS, 100 μg/ml denatured fragmented salmon sperm DNA or 6×SSC, 5×Denhardt's reagent, 0.5% SDS, 100 μg/ml denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na$^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization protocols used to practice this invention may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity ("homology") to an exemplary nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention can be used to isolate nucleic acids which encode polypeptides having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, sequence identity (homology) to a polypeptide of the invention comprising at least 5, 10, 15, 20, 25, 30, 35, 40, 50, 75, 100, or 150 consecutive amino acids, as determined using a sequence alignment algorithm (e.g., such as the FASTA version 3.0t78 algorithm with the default parameters, or a BLAST 2.2.2 program with exemplary settings as set forth herein).

Inhibiting Expression of Amylase

The invention provides nucleic acids complementary to (e.g., antisense sequences to) the nucleic acid sequences of the invention, e.g., nucleic acids comprising antisense, siRNA, miRNA, ribozymes. Antisense sequences are capable of inhibiting the transport, splicing or transcription of amylase-encoding and glucoamylase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind amylase gene or message, in either case preventing or inhibiting the production or function of amylase. The association can be through sequence specific hybridization. Another useful class of inhibitors includes oligonucleotides which cause inactivation or cleavage of amylase message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity.

The inventions methods and compositions for inhibition of expression of amylase, glucoamylase, glucosidase and other polysaccharide hydrolyzing enzymes can have a variety of industrial applications. For example, inhibition of glucosidase expression can slow or prevent spoilage. Spoilage can occur when polysaccharides, lipids or polypeptides, e.g., structural polysaccharides, are enzymatically degraded. This can lead to the deterioration, or rot, of fruits and vegetables. In one aspect, use of compositions of the invention that inhibit the expression and/or activity of glucosidases, e.g., antibodies, antisense oligonucleotides, ribozymes and RNAi, are used to slow or prevent spoilage. Thus, in one aspect, the invention provides methods and compositions comprising application onto a plant or plant product (e.g., a fruit, seed, root, leaf, etc.) antibodies, antisense oligonucleotides, ribozymes and RNAi of the invention, e.g., to slow or prevent spoilage, or for another purpose. These compositions also can be expressed by the plant (e.g., a transgenic plant) or another organism (e.g., a bacterium or other microorganism transformed with a glucosidase gene of the invention).

Antisense Oligonucleotides

The invention provides antisense oligonucleotides capable of binding amylase message which can inhibit proteolytic activity by targeting mRNA. Strategies for designing antisense oligonucleotides are well described in the scientific and patent literature, and the skilled artisan can design such amylase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense amylase sequences of the invention (see, e.g., Gold (1995) J. of Biol. Chem. 270:13581-13584).

Inhibitory Ribozymes

The invention provides ribozymes capable of binding amylase message. These ribozymes can inhibit amylase activity by, e.g., targeting mRNA. Strategies for designing ribozymes and selecting the amylase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising an amylase enzyme sequence of the invention (which includes both sense and antisense strands). The RNAi molecule can comprise a double-stranded RNA (dsRNA) molecule, e.g., siRNA and/or miRNA. The RNAi molecule comprises a double-stranded RNA (dsRNA) molecule. The RNAi can inhibit expression of an amylase gene. In one aspect, the RNAi, e.g., siRNA and/or miRNA, is about 10, 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding an amylase. These methods can be repeated or used in various combinations to generate amylases having an altered or different activity or an altered or different stability from that of an amylase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photo-activated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255: 373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the α-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of Escherichia coli: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application serial No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE°OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., gene site saturation mutagenesis (GSSM), synthetic ligation reassembly (SLR), or a combination thereof are used to modify the nucleic acids of the invention to generate amylases with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM

The invention also provides methods for making enzyme using Gene Site Saturation mutagenesis, or, GSSM, as described herein, and also in U.S. Pat. Nos. 6,171,820 and 6,579,258.

In one aspect, codon primers containing a degenerate N,N,G/T sequence are used to introduce point mutations into a polynucleotide, e.g., an amylase or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., amylases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased proteolytic activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process(es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate polypeptides, e.g., amylases or antibodies of the invention, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773,900; 6,740,506; 6,713,282; 6,635,449; 6,605,449; 6,537,776.

In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template.

Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate polypeptides, e.g., amylases or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Alternatively protocols for practicing these methods of the invention can be found in U.S. Pat. Nos. 6,773,900; 6,740,506; 6,713,282; 6,635,449; 6,605,449; 6,537,776; 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Pat. Nos. 6,773,900; 6,740,506; 6,713,282; 6,635,449; 6,605,449; 6,537,776; 6,361,974.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB™ (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new amylase phenotype is identified, re-isolated, again modified, re-tested for activity. This process can be iteratively repeated until a desired phenotype is engineered. For example, an entire biochemical anabolic or catabolic pathway can be engineered into a cell, including, e.g., starch hydrolysis activity.

Similarly, if it is determined that a particular oligonucleotide has no affect at all on the desired trait (e.g., a new amylase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In vivo Shuffling

In vivo shuffling of molecules can be used in methods of the invention that provide variants of polypeptides of the invention, e.g., antibodies, amylases, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide (e.g., an amylase and/or a glucoamylase of the invention) and a second polynucleotide (e.g., an enzyme, such as an amylase and/or a glucoamylase of the invention or any other amylase, or, a tag or an epitope). The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides additional methods for making sequence variants of the nucleic acid (e.g., amylase) sequences of the invention. The invention also provides additional methods for isolating amylases using the nucleic acids and polypeptides of the invention. In one aspect, the invention provides for variants of an amylase coding sequence (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM MnCl$_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM MgCl$_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250 (see also discussion, above).

The invention also provides variants of polypeptides of the invention (e.g., amylases) comprising sequences in which one or more of the amino acid residues (e.g., of an exemplary polypeptide of the invention) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, e.g., the exemplary polypeptides of the invention, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group. A conservative amino acid substitution can also comprise substituting one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an amylase, resulting in modification of the structure of the polypeptide, without significantly altering its biological activity. For example, amino- or carboxyl-terminal amino acids that are not required for amylase activity can be removed.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., amylase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying amylase-encoding and glucoamylase-encoding nucleic acids to modify codon usage, and codon optimized amylase-encoding and glucoamylase-encoding nucleic acids, including the exemplary SEQ ID NO:79, SEQ ID NO:80, SEQ ID NO: 81 and SEQ ID NO: 82; these exemplary amylase-encoding and glucoamylase-encoding nucleic acids of the invention were generated as discussed in detail in Example 28, below, from SEQ ID NO:51, SEQ ID NO:3, SEQ ID NO: 47 and SEQ ID NO:25, respectively:

| Enzyme | Wild-type SEQ ID NO: | Codon-optimized SEQ ID NO: |
|---|---|---|
| Amylase | 51 | 79 |
| Amylase | 3 | 80 |
| Glucoamylase | 47 | 81 |
| Glucoamylase | 25 | 82 |

In one aspect, the invention provides methods for modifying codons in a nucleic acid encoding an amylase to increase or decrease its expression in a host cell. The invention also provides nucleic acids encoding an amylase modified to increase its expression in a host cell, amylase so modified, and methods of making the modified amylases. The method comprises identifying a "non-preferred" or a "less preferred" codon in amylase-encoding and glucoamylase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as any species from the genus *Escherichia* or *Pseudomonas*, e.g., *Escherichia coli* and *Pseudomonas fluorescens*); or gram positive bacteria, such as any species from the genus *Bacillus, Streptomyces, Lactococcus, Lactobacillus*, e.g., *Bacillus cereus, Lactobacillus gasseri, Lactococcus lactis, Lactococcus cremoris, Bacillus subtilis*. Exemplary host cells also include eukaryotic organisms, e.g., various yeast, such as *Schizosaccharomyces* sp., *Aspergillus* sp., *Hansenula* sp., *Kluyveromyces* sp., *Pichia* sp. and *Saccharomyces* sp., including, e.g., *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an amylase isolated from a bacterial cell are modified such that the nucleic acid is optimally expressed in a bacterial cell different from the bacteria from which the amylase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-human Animals

The invention provides transgenic non-human animals comprising a nucleic acid, a polypeptide (e.g., an amylase), an expression cassette or vector or a transfected or transformed cell of the invention. The invention also provides methods of making and using these transgenic non-human animals.

The transgenic non-human animals can be, e.g., goats, rabbits, sheep, pigs, cows, rats and mice, comprising the nucleic acids of the invention. These animals can be used, e.g., as in vivo models to study amylase activity, or, as models to screen for agents that change the amylase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111, 166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Patent No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing an amylase and/or a glucoamylase of the invention, or, a fusion protein comprising an amylase and/or a glucoamylase of the invention.

Transgenic Plants and Seeds

The invention provides transgenic plants and seeds comprising a nucleic acid, a polypeptide (e.g., a glucanase, mannanase, or xylanase), an expression cassette or vector or a transfected or transformed cell of the invention. The invention also provides plant products, e.g., oils, seeds, leaves, extracts and the like, comprising a nucleic acid and/or a polypeptide (e.g., a glucanase, mannanase, or xylanase) of the invention. The transgenic plant can be dicotyledonous (a dicot) or monocotyledonous (a monocot). The invention provides transgenic plants with a modified taste, solids content and/or texture, wherein that modification is generated by expressing at least one enzyme of the invention either constitutively or selectively in the transgenic plant (or seed, or fruit, etc.), as described, e.g., in U.S. Pat. Application No. 20060195940.

The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

In alternative embodiments, "stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations. Introduction into the genome of a desired plant can be such that the enzyme is regulated by endogenous transcriptional or translational control elements. Transformation techniques for both monocotyledons and dicotyledons are well known in the art.

The nucleic acids of the invention can be used to confer desired traits on essentially any plant. Nucleic acids of the invention can be used to manipulate metabolic pathways of a plant in order to optimize or alter host's expression of glucanase, mannanase, or xylanase. They can change amylase, glucoamylase, glucanase, mannanase, or xylanase activity in a plant. Alternatively, an amylase, glucoamylase, glucanase, mannanase, or xylanase of the invention can be used in production of a transgenic plant to produce a compound not naturally produced by that plant. This can lower production costs or create a novel product. In one embodiment, the enzyme of the invention may be expressed in such a way that the enzyme will not come in contact with it's substrate until desired. For example, an enzyme of the invention may be targeted and retained in the endoplasmic reticulum of a plant cell. Retention of the enzyme, in the endoplasmic reticulum of the cell, will prevent the enzyme from coming in contact with its substrate. The enzyme and substrate may then be brought into contact through any means able to disrupt the subcellular architecture, such as, grinding, milling, heating, and the like. See, WO 98/11235, WO 2003/18766, and WO 2005/096704, all of which are hereby incorporated by reference.

Selectable marker genes can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. Selection markers used routinely in transformation include the nptII gene, which confers resistance to kanamycin and related antibiotics (Messing & Vierra. Gene 19: 259-268 (1982); Bevan et. al., Nature 304:184-187 (1983)), the bar gene, which confers resistance to the herbicide phosphinothricin (White et. al., Nucl. Acids Res 18: 1062 (1990), Spencer et. al. Theor. Appl. Genet. 79: 625-631 (1990)), the hph gene, which confers resistance to the antibiotic hygromycin (Blochinger & Diggelmann, Mol Cell Biol 4: 2929-2931), the dhfr gene, which confers resistance to methatrexate (Bourouis et. al., EMBO J. 2(7): 1099-1104 (1983)), the EPSPS gene, which confers resistance to glyphosate (U.S. Pat. Nos. 4,940,935 and 5,188,642), Alternatively, transgenic plant material can be identified through a positive selection system, such as, the system utilizing the mannose-6-phosphate isomerase gene, which provides the ability to metabolize mannose (U.S. Pat. Nos. 5,767, 378 and 5,994,629).

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. One or more of the sequences of the invention may be combined with sequences that confer resistance to insect, disease, drought, increase yield, improve nutritional quality of the grain, improve ethanol yield and the like.

For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) Science 233:496-498; Fraley (1983) Proc. Natl. Acad. Sci. USA 80:4803 (1983); Gene Transfer to Plants, Potrykus, ed. (Springerlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci. USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a glucanase, mannanase, or xylanase) of the invention. The desired effects can be passed to future plant generations by standard propagation means.

Any plant may be used for introduction of the nucleotide of interest, including, but not limited to, corn or maize (*Zea mays*), *Brassica* sp. (e.g., *B. napus, B. rapa, B. juncea*), particularly those *Brassica* species useful as sources of seed oil, such as canola, alfalfa (*Medicago sativa*), rice (*Oryza sativa*), rye (*Secale cereale*), sorghum (*Sorghum bicolor, Sorghum* vulgare), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (Beta vulgaris), sugarcane (*Saccharum* spp.), oats, barley, vegetables, ornamentals, and conifers.

Vegetables may include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals may include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), canna (*Cannaceae* spp.) and chrysanthemum. Conifers that may be employed, including, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Leguminous plants may include, but are not limited to, beans and peas. Beans may include guar, locust bean, fenugreek, soybean, garden beans, cowpea, mungbean, lima bean, fava bean, lentils, chickpea, etc. Legumes may include, but are not limited to, *Arachis*, e.g., peanuts, *Vicia*, e.g., crown vetch, hairy vetch, adzuki bean, mung bean, and chickpea, Lupinus, e.g., lupine, *trifolium, Phaseolus*, e.g., common bean and lima bean, *Pisum*, e.g., field bean, Melilotus, e.g., clover, *Medicago*, e.g., alfalfa, *Lotus*, e.g., trefoil, lens, e.g., lentil, and false indigo. Forage and turf grasses may include alfalfa, switchgrass (*Panicum virgatum*), *Miscanthus*, orchard grass, tall fescue, perennial ryegrass, creeping bent grass, and redtop.

Plants of particular interest may include crop plants and plants used to produce energy or fuel, for example, maize, alfalfa, sunflower, *Brassica*, soybean, cotton, safflower, peanut, sorghum, wheat, oat, rye, millet, barley, rice, conifers, grasses, e.g., switch grass and *Miscanthus*, legume crops, e.g., pea, bean and soybean, starchy tuber/roots, e.g., potato, sweet potato, cassaya, taro, *canna*, sugar beet, sugar cane and the like.

In alternative embodiments, the nucleic acids of the invention are expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides transgenic plants to be used for producing large amounts of the polypeptides (e.g., a glucanase, mannanase, or xylanase or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

In one aspect, the invention provides isolated, synthetic or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76 and/or SEQ ID NO:78, and subsequences thereof and variants thereof. The sequence identity (homology) can be over the full length of the polypeptide, or, the identity can be over a region of at least about 10, 15, 20, 25, 30, 35, 40, 45, 50, 55, 60, 65, 70, 75, 80, 90, 100, 125, 150, 175, 200, 250, 300, 350, 400, 450, 500, 550, 600, 650, 700 or more residues.

In one embodiment, the polypeptides of the invention can catalyze the hydrolysis of polysaccharides comprising glucose monomers, such as starch (a polymer of glucose monomers joined by 1,4-alpha or 1,6-alpha linkages). In one aspect, the polypeptide has an amylase activity, e.g., an alpha amylase activity, endoamylase activity, or a glucoamylase activity; and the term "amylase" as used herein also includes enzyme activity which catalyzes the hydrolysis of a polysaccharide, oligosaccharide or starch. Amylases and/or glucoamylases of the invention include polypeptides having an α-amylase activity, a β-amylase activity, a glucoamylase activity, a 1,4-α-D-glucan glucohydrolase activity, an exoamylase activity, a glucan α-maltotetrahydrolase activity, a maltase activity, an isomaltase activity, a glucan 1,4, α-glucosidase activity, an α-glucosidase activity, a sucrase activity or an agarase activity (e.g., a (3-agarase activity). For example, an amylase activity of the invention includes α-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. An amylase activity of the invention includes polypeptides having glucoamylase activity, such as the ability to hydrolase glucose polymers linked by α-1,4- and α-1,6-glucosidic bonds. In one aspect, the polypeptides of the invention have glucoamylase activity, hydrolyzing internal α-1,4-glucosidic linkages to yield smaller molecular weight malto-dextrins. An amylase activity of the invention also includes glucan 1,4-α-glucosidase activity, or, 1,4-α-D-glucan glucohydrolase, commonly called glucoamylase but also called amyloglucosidase and γ-amylase that, in one aspect, releases 3-D-glucose from 1,4-α-, 1,6-α- and 1,3-α-linked glucans. An amylase activity of the invention also includes exo-amylase activity.

In one embodiment, the polypeptides of the invention can be used to generate an antibody that specifically binds to (is specific for) a polypeptide of the invention, e.g., an exemplary enzyme of the invention (e.g., SEQ ID NO:2, SEQ ID NO:4, etc.).

In one aspect, the glucoamylase activity of a polypeptide of the invention comprises catalysis of the hydrolysis of glucosidic bonds. The glucoamylase activity can comprise catalyzing the step-wise hydrolytic release of D-glucose from the non-reducing ends of starch or other related dextrins. The glucoamylase activity can comprise a 1,4-α-D-glucan glucohydralase activity. The glucoamylase activity can comprise catalysis of the hydrolysis of malto-dextrins resulting in the generation of free glucose. The glucoamylase activity can comprise an exoamylase activity. The glucoamylase activity can comprise an α-amylase or a β-amylase activity. The hydrolyzed glucosidic bonds can comprise α-1,4-glucosidic bonds or α-1,6-glucosidic bonds. The glucoamylase activity can comprise hydrolyzing glucosidic bonds in a polysaccharide, oligosaccharide or starch. The glucoamylase activity can further comprise hydrolyzing glucosidic bonds in the starch to produce maltodextrines. The glucoamylase activity can comprise cleaving a maltose or a D-glucose unit from non-reducing end of the polysaccharide, oligosaccharide or starch.

In one aspect, the invention provides alpha-amylases (α-amylases) that are endo-acting enzymes that can hydrolyze starch, a polymer of glucose monomers joined by 1,4-alpha or 1,6-alpha linkages, to short maltodextrins. In one aspect, the invention provides glucoamylases that are exo-acting hydrolases that can release beta-D-glucose from the non-reducing ends of starch and related saccharides. Amylases and glucoamylases of this invention can be used commercially to liquefy and saccharify starch during ethanol production using processes such as the dry milling process. In one aspect of a process of the invention, the dry milling process ground whole corn (the mash) is subjected to an elevated temperature (to promote gelatinization of starch) and hydrolyzed by one or more thermostable amylases, including at least one enzyme of the invention, resulting in polysaccharide, e.g., starch, liquefaction. In one aspect, the hydrolyzed polysaccharide, e.g., starch, is further digested by a glucoamylase of the invention, which can be added after the mash temperature cools down; and in one aspect, the glucose released from the polysaccharide, e.g., starch, is fermented to ethanol by yeast added at the conclusion of the polysaccharide, e.g., starch, hydrolysis process, or during saccharification of the polysaccharide, e.g., starch.

In one aspect, glucosidases (e.g., glucoamylases, alpha glucosidases) of the invention hydrolyze internal polysaccharide bonds, e.g., α-1,4- and 1,6-glucosidic bonds in a polysaccharide, oligosaccharide or starch, to produce smaller molecular weight maltodextrines. In one aspect, this hydrolysis is largely at random. Thus, the invention provides methods for producing smaller molecular weight maltodextrines. Glucosidases of the invention can be used in laboratory and industrial settings to hydrolyze a polysaccharide, oligosaccharide or starch, or any maltodextrine-comprising compound for a variety of purposes. These glucosidases can be used alone to provide specific hydrolysis or can be combined with other glucosidases to provide a "cocktail" with a broad spectrum of activity. Exemplary uses include the removal or partial or complete hydrolysis of a polysaccharide, oligosaccharide or starch, or any maltodextrine-comprising compound from biological, food, animal feed, pharmaceutical or industrial samples.

For example, the glucosidases (e.g., glucoamylases) of the invention can be formulated in laundry detergents to aid in the removal of polysaccharide-comprising, e.g., starch-containing, stains. Glucosidases of the invention can be used as cleaning agents in detergent matrices (see industrial applications below). The glucosidases of the invention can be used in the initial stages (liquefaction) of polysaccharide, e.g., starch, processing, in wet corn milling, in alcohol production, in the textile industry for starch desizing, in baking applications, in the beverage industry, in oilfields in drilling processes; in inking of recycled paper; and in animal feed.

Glucosidases of the invention (e.g., glucoamylases) can have a glucosidase activity under various conditions, e.g., extremes in pH and/or temperature, oxidizing agents, and the like. The invention provides methods leading to alternative glucosidase preparations with different catalytic efficiencies and stabilities, e.g., towards temperature, oxidizing agents and changing wash conditions. In one aspect, glucosidase variants can be produced using techniques of site-directed mutagenesis and/or random mutagenesis. In one aspect, directed evolution can be used to produce a great variety of glucosidase variants with alternative specificities and stability.

The proteins of the invention are also useful as research reagents to identify amylase and/or glucoamylase modulators, e.g., activators or inhibitors of amylase and/or glucoamylase activity. Briefly, test samples (compounds, broths, extracts, and the like) are added to amylase and/or glucoamylase assays to determine their ability to inhibit substrate cleavage Inhibitors identified in this way can be used in industry and research to reduce or prevent undesired proteolysis. As with amylase and/or glucoamylase, inhibitors can be combined to increase the spectrum of activity.

An amylase and/or glucoamylase activity of the invention also includes hydrolyzing a polysaccharide, oligosaccharide or starch, at high temperatures, low temperatures, alkaline pHs and at acidic pHs. For example, in one aspect, the invention provides polypeptides, and nucleic acids encoding them, having an amylase and/or glucoamylase activity which is thermostable. The polypeptide can retain an amylase and/or glucoamylase activity under conditions comprising a temperature range of between about 37° C. to about 95° C.; between about 55° C. to about 85° C., between about 70° C. to about 95° C., or, between about 90° C. to about 95° C. In another aspect, a polypeptide of the invention can have a amylase and/or glucoamylase activity which is thermotolerant. The polypeptide can retain an amylase and/or glucoamylase activity after exposure to a temperature in the range from greater than 37° C. to about 95° C. or anywhere in the range from greater than 55° C. to about 85° C. In one aspect, the polypeptide retains an amylase activity after exposure to a temperature in the range from greater than 90° C. to about 95° C. at pH 4.5.

The invention provides "amino acids" or "amino acid sequences of the invention", including an oligopeptide, peptide, polypeptide, or protein sequence, or to a fragment, portion, or subunit of any of these, and to naturally occurring, recombinant or synthetic molecules. The terms "polypeptide" and "protein" include amino acids joined to each other by peptide bonds or modified peptide bonds, i.e., peptide isosteres, or non-peptide bonds (synthetic bonds, synthetic polypeptides) and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

The invention also provides "amylase variants" and "glucoamylase variants" which can comprise an amino acid sequence which is derived from the amino acid sequence of a "precursor amylase", e.g., in one aspect, an exemplary sequence of the invention (e.g., SEQ ID NO:2, SEQ ID NO:4, etc., or any polypeptide of this invention). The precursor glycoamylase or amylase also can include naturally-occurring glucoamylases or amylases and recombinant amylases. The amino acid sequence of the glucoamylase or amylase variant can be "derived" from the precursor glucoamylase or amylase amino acid sequence by the substitution, deletion or insertion of one or more amino acids of the precursor amino acid sequence. Such modification can be of the "precursor DNA sequence" which encodes the amino acid sequence of the precursor amylase rather than manipulation of the precursor amylase enzyme per se. Suitable methods for such manipulation of the precursor DNA sequence include methods disclosed herein, as well as methods known to those skilled in the art.

Activities of exemplary sequences of the invention are listed in the table ("Table 1") immediately below. To aid in reading the table, for example, in the first row, SEQ ID NO:1, 2, represent the exemplary polypeptide of the invention having a sequence as set forth in SEQ ID NO:2, encoded by, e.g., SEQ ID NO:1; and this exemplary sequence was initially isolated from *Cochliobolus heterostrophus*, ATCC 48331; no signal sequence is predicted (but under certain cell in vivo conditions, the sequence may have a signal sequence); the polypeptide has "glycosidase" activity, which can be more specifically designated "amylase" enzyme activity; and the corresponding "EC" number for amylase enzymes (an EC number is the number assigned to a type of enzyme according to a scheme of standardized enzyme nomenclature developed by the Enzyme Commission of the Nomenclature Committee of the International Union of Biochemistry and Molecular Biology, or IUBMB); "CMB20" designating "carbohydrate binding domain"; and the last column indicates a "genetic source", or the source of the exemplary sequence as determined by homology analysis of the 18/16S RNA of the cell from which it was initially isolated. In the second row, SEQ ID NO:11, 12, represent the exemplary polypeptide of the invention having a sequence as set forth in SEQ ID NO:12, encoded by, e.g., SEQ ID NO:11; and this exemplary sequence was initially isolated from an unknown source; the "SS site" designates the amino terminal resides that are the signal sequence, and for SEQ ID NO:12 it is the amino terminal 21 amino acid residues that make up the signal sequence (or, MFNQVLYGLAATALWQGQVVA, i.e., residues 1 to 21 of SEQ ID NO:12); and the polypeptide has "glycosidase" activity, which can be more specifically designated as a "glycoamylase" enzyme activity; this enzyme having an EC number of 3.2.1.3; with "carbohydrate binding domain"; and a genetic match of the 18/16S RNA of the cell from which it was initially isolated is *Fusarium equiseti*.

TABLE 1

| SEQ ID NO: | Source | SS site | Signal Sequence | General Activity | An Exemplary Specific Activity | EC Number | CBM20 | Source (as determined by 18/16S RNA) |
|---|---|---|---|---|---|---|---|---|
| 1, 2 | *Cochliobolus heterostrophus* ATCC 48331 | | | Glycosidase | amylase | 3.2.1.1 | CBM20 | *Cochliobolus heterostrophus* |
| 11, 12 | Unknown | AA 1-21 | MFNQVLYGLAATALWQGQVVA | Glycosidase | glucoamylase | 3.2.1.3 | CBM20 | *Fusarium equiseti* 100% |
| 13, 14 | *Fusarium verticillioides* GZ3639 | AA 1-21 | MFTQILYGLTALSALQGQVTA | Glycosidase | glucoamylase | 3.2.1.3 | CBM20 | *Fusarium verticillioides* GZ3639 |
| 15, 16 | *Cochliobolus heterostrophus* ATCC 48332 | AA 1-20 | MLSKILLPVVALAASANAHG | Glycosidase | glucoamylase | | CBM20 | *Cochliobolus heterostrophus* |
| 17, 18 | *Fusarium verticillioides* GZ3639 | | | Glycosidase | glucoamylase | 3.2.1.3 | CBM20 | *Fusarium verticillioides* GZ3639 |
| 19, 20 | Unknown | AA 1-22 | MLTLNVLTALLAPIVLSSALPA | Glycosidase | glucoamylase | 3.2.1.3 | no | *Penicillium chrysogenum* 100% |

TABLE 1-continued

| SEQ ID NO: | Source | SS site | Signal Sequence | General Activity | An Exemplary Specific Activity | EC Number | CBM20 | Source (as determined by 18/16S RNA) |
|---|---|---|---|---|---|---|---|---|
| 21, 22 | Unknown | AA 1-18 | MVLARLAWLAGLVSTAVA | Glycosidase | amylase | 3.2.1.1 | no | Penicillium expansum 99% |
| 23, 24 | Unknown | AA 1-20 | MKLSHTLTALLLPLICTVSA | Glycosidase | amylase | 3.2.1.1 | no | Penicillium chrysogenum 100% |
| 25, 26 | Unknown | AA 1-21 | MTISRLSSVLFALALGQSALA | Glycosidase | glucoamylase | 3.2.1.3 | CBM20 | Penicillium verruculosum 100% |
| 27, 28 | Unknown | AA 1-20 | MYILSSAFLLGSLALQSVLG | Glycosidase | glucoamylase | 3.2.1.3 | CBM20 | Fusarium merismoides 99% |
| 29, 30 | Unknown | AA 1-21 | MLFSSLLRALSASLLAGAVQG | Glycosidase | glucoamylase | 3.2.1.3 | CBM20 | Phoma herbarum 99 |
| 3, 4 | Cochliobolus heterostrophus ATCC 48331 | AA 1-20 | MLLLNIFTTLFFYITCIVSA | Glycosidase | amylase | 3.2.1.1 | CBM20 | Cochliobolus heterostrophus |
| 31, 32 | Unknown | AA 1-18 | MVLARLAWLAGLVSTAIA | Glycosidase | amylase | 3.2.1.1 | no | Penicillium chrysogenum 100% |
| 33, 34 | Unknown | AA 1-18 | MVGFNILTLALLAPAALS | Glycosidase | glucoamylase | 3.2.1.3 | no | Penicillium herquei 99% |
| 35, 36 | Unknown | AA 1-20 | MAPRFWTTLCALTLGSAALA | Glycosidase | glucoamylase | 3.2.1.3 | CBM20 | Fusarium oxysporum 100% |
| 37, 38 | Unknown | AA 1-19 | MAPRFWIALWALTFGQAIA | Glycosidase | glucoamylase | 3.2.1.3 | CBM20 | Cordyceps ophioglossoides 99% |
| 39, 40 | Unknown | AA 1-20 | MAPRFWTALWALTLGHAVVA | Glycosidase | glucoamylase | 3.2.1.3 | CBM20 | Penicillium chrysogenum 100% |
| 41, 42 | Unknown | | | Glycosidase | glucoamylase | 3.2.1.3 | no | Cucurbitaria berberidis 98% |
| 43, 44 | Cochliobolus heterostrophus ATCC 48332 | AA 1-23 | MTHTSFVQASTVLSSLLALTA GQ | Glycosidase | α-glucosidase | | | Cochliobolus heterostrophus |
| 45, 46 | Unknown | AA 1-19 | MKLLQLAALVASLSPFTNA | Glycosidase | amylase | 3.2.1.1 | no | Fusarium equiseti 100% |
| 47, 48 | Unknown | AA 1-20 | MTRILTLALHGLALVQSVVG | Glycosidase | glucoamylase | 3.2.1.3 | CBM20 | Aspergillus versicolor 99 |
| 49, 50 | Aspergillus terreus | AA 1-18 | MSFFLSCLYLSLCGSALA | Glycosidase | amylase | 3.2.1.1 | no | Aspergillus terreus |
| 5, 6 | Cochliobolus heterostrophus ATCC 48331 | | | Glycosidase | α-glucosidase | | | Cochliobolus heterostrophus |
| 51, 52 | Aspergillus terreus | AA 1-20 | MKWTFSLLLLLSVFGQATHA | Glycosidase | amylase | 3.2.1.1 | CBM20 | Aspergillus terreus |
| 53, 54 | Aspergillus terreus | AA 1-20 | MKLSRALTVFLLHLTSTALA | Glycosidase | amylase | 3.2.1.1 | no | Aspergillus terreus |
| 55, 56 | Unknown | AA 1-27 | MLKQFTKRLITLTSLLALVL VAPLASA | Glycosidase | | 3.2.1.1 | | |
| 57, 58 | Unknown | | | Glycosidase | | 3.2.1.10 | | |
| 59, 60 | Unknown | | | Glycosidase | | 3.2.1.10 | | |

TABLE 1-continued

| SEQ ID NO: | Source | SS site | Signal Sequence | General Activity | An Exemplary Specific Activity | EC Number | CBM20 | Source (as determined by 18/16S RNA) |
|---|---|---|---|---|---|---|---|---|
| 61, 62 | Unknown | AA 1-20 | MVAGFGLYGAALLTPMAAQA | Glycosidase | | 3.2.1.1 | | |
| 63, 64 | Unknown | | | Glycosidase | | 3.2.1.20 | | |
| 65, 66 | Unknown | AA 1-25 | MKLKYLALVLLAVASIGLLS TPVGA | Glycosidase | | 3.2.1.1 | | |
| 67, 68 | Unknown | AA 1-23 | MKKNTISALVAGMVLGFASNA MA | Glycosidase | | 3.2.1.1 | | |
| 69, 70 | Unknown | AA 1-44 | MNRPGTGASGRPQSRSATSW QSRNGGWLLASLLAVCFATA PVRA | Glycosidase | | 3.2.1.1 | | |
| 7, 8 | Cochliobolus heterostrophus ATCC 48331 | | | Glycosidase | glucoamylase | 3.2.1.3 | no | Cochliobolus heterostrophus |
| 71, 72 | Unknown | | | Glycosidase | | 3.2.1.20 | | |
| 73, 74 | Thermomyces lanuginosus ATCC 200065 | | | Glycosidase | | 3.2.1.3 | | |
| 75, 76 | Unknown | AA 1-24 | | Glycosidase | amylase | 3.2.1.1 | | |
| 9, 10 | Unknown | AA 1-22 | MLTLNVLTALLAPGVLSSAL PA | Glycosidase | glucoamylase | 3.2.1.3 | no | Penicillium expansum 99% |

Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, such as an amylase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary amylase and/or glucoamylase of the invention. Peptides of the invention can be useful as, e.g., labeling probes, antigens, toleragens, motifs, amylase active sites.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked Glycosylation can be added to any polypeptide of the invention to generate an enzyme that is more thermotolerant or thermostable than the "parent" enzyme (to which the glycosylation was added). The glycosylation can be added by either chemical or by cellular biosynthetic mechanisms.

The invention provides amylases having a broad range of specific activity over a broad range of temperatures, e.g., at about 37° C. in the range from about 10 to 10,000, or, 100 to about 1000 units per milligram of protein. Amylases and/or glucoamylases of the invention can also have activity at temperatures as high as 120° C. In alternative aspects, the amylase used in these methods is active at these temperatures, e.g., active at temperatures in a range of between about 80° C. to about 115° C., between about 100° C. to about 110° C., and from about 105° C. to about 108° C. However, amylases and/or glucoamylases of the invention can also have activity at low temperatures, e.g., as low as 4° C. to 5° C.

The Tm of an enzyme of the invention can be shifted (for example, can be shifted between about 10° C. to 90° C.) by heat activation. For example, the Tm of SEQ ID NO:336/337 can be shifted about 17° C. to 87° C. by heat activation: for example, 80° C. preincubation for 5 minutes.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has an amylase activity.

Polypeptide mimetic compositions of the invention can contain any combination of non-natural structural components (e.g., they can be completely or partially synthetic, or "mimetic"). In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC) Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'-N=C=N-R') such as, e.g., 1-cyclohexyl-3(2-morpholinyl-(4-ethyl) carbodiimide or 1-ethyl-3(4-azonia-4,4-dimetholpentyl) carbodiimide Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention provides novel glucoamylases and amylases (e.g., alpha amylases), including the exemplary enzymes of the invention, nucleic acids encoding them, antibodies that bind them, and methods for making and using them. In one aspect, the polypeptides of the invention have an amylase and/or glucoamylase activity, as described herein, including, e.g., the ability to hydrolyze polysaccharides, oligosaccharides and/or starches, into sugars. In one aspect, the polypeptides of the invention have a glucoamylase or an amylase (e.g., alpha amylase) activity. In alternative aspects, the amylases and/or glucoamylases of the invention have activities that have been modified from those of the exemplary amylases and/or glucoamylases described herein.

The invention includes amylases and/or glucoamylases of the invention with and without signal sequences (including signal sequences of the invention, see e.g., Table 1, or other signal sequences) and the signal sequences themselves (e.g., Table 1). The invention also include polypeptides (e.g., fusion proteins) comprising a signal sequence of the invention, see, e.g., Table 1. The polypeptide comprising a signal sequence of the invention can be an amylase and/or a glucoamylase of the invention or another amylase or another enzyme or other polypeptide.

The invention includes immobilized amylases, glucoamylases, anti-glucoamylase, anti-amylase antibodies and fragments thereof. The invention provides methods for inhibiting amylase and/or glucoamylase activity, e.g., using dominant negative mutants or anti-amylase or anti-glucoamylase antibodies of the invention. The invention includes heterocomplexes, e.g., fusion proteins, heterodimers, etc., comprising the amylases and/or glucoamylases of the invention.

In one aspect, amylases (e.g., alpha amylases) and/or glucoamylases of the invention hydrolyze internal polysaccharide or oligosaccharide bonds, e.g., α-1,4- and 1,6-glucosidic bonds in starch to produce smaller molecular weight maltodextrines. In one aspect, this hydrolysis is largely at random. Thus, the invention provides methods for producing smaller molecular weight maltodextrines.

Amylases and/or glucoamylases of the invention can be used in laboratory and industrial settings to hydrolyze polysaccharide, oligosaccharide or starch or any maltodextrine-comprising compound for a variety of purposes. These amylases and/or glucoamylases can be used alone to provide specific hydrolysis or can be combined with other amylases to provide a "cocktail" with a broad spectrum of activity. Exemplary uses include the removal or partial or complete hydrolysis of polysaccharide, oligosaccharide or starch or any maltodextrine-comprising compound from biological, food, animal feed, pharmaceutical or industrial samples.

For example, the amylases of the present invention can be formulated in laundry detergents to aid in the removal of polysaccharide-comprising, e.g., starch-containing, stains. In one aspect, the invention provides detergents comprising amylases and/or glucoamylases of the invention, including amylases and/or glucoamylases active under alkaline conditions, and methods of making and using them. These detergent compositions include laundry and dishwashing (e.g., autodishwashing) solutions and application. Amylases and/or glucoamylases of the invention can be used as cleaning agents in any detergent matrices (see industrial applications below). The amylases and/or glucoamylases of the present invention can be used in the initial stages (liquefaction) of polysaccharide, e.g., starch, processing, in wet corn milling, in alcohol production, in the textile industry for polysaccharide, e.g., starch, desizing, in baking applications, in the beverage industry, in oilfields in drilling processes; in inking of recycled paper; and in animal feed.

Amylases and/or glucoamylases of the invention can have an amylase activity under various conditions, e.g., extremes in pH and/or temperature, oxidizing agents, and the like. The invention provides methods leading to alternative amylase preparations with different catalytic efficiencies and stabilities, e.g., towards temperature, oxidizing agents and changing wash conditions. In one aspect, amylase variants can be produced using techniques of site-directed mutagenesis and/or random mutagenesis. In one aspect, directed evolution can be used to produce a great variety of amylase variants with alternative specificities and stability.

The invention also provides methods of discovering new amylases and/or glucoamylases using the nucleic acids, polypeptides and antibodies of the invention. In one aspect, lambda phage libraries are screened for expression-based discovery of amylases. In one aspect, the invention uses lambda phage libraries in screening to allow detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

The present invention includes amylase and/or glucoamylase enzymes which are non-naturally occurring carbonyl hydrolase variants (e.g., amylase and/or glucoamylase variants) having a different proteolytic activity, stability, substrate specificity, pH profile and/or performance characteristic as compared to the precursor carbonyl hydrolase from which the amino acid sequence of the variant is derived. Specifically, such amylase variants have an amino acid sequence not found in nature, which is derived by substitution of a plurality of amino acid residues of a precursor amylase and/or glucoamylase with different amino acids. The precursor amylase and/or glucoamylase may be a naturally-occurring amylase or a recombinant amylase. The useful amylase and/or glucoamylase variants encompass the substitution of any of the naturally occurring L-amino acids at the designated amino acid residue positions.

Amylase and Glucoamylase Signal Sequences

The invention provides signal sequences consisting of or comprising a peptide having a sequence comprising residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30 or 1 to 31, 1 to 32, 1 to 33, 1 to 34, 1 to 35, 1 to 36, 1 to 37, 1 to 38, or 1 to 39, or longer, of a polypeptide of the invention. For example, the invention provides amylase (e.g., alpha amylase) or glucoamylase signal sequences and nucleic acids encoding these signal sequences, e.g., exemplary peptides of the invention having sequences as set forth in the Table above.

The amylase and/or glucoamylase signal sequences of the invention can be isolated peptides, or, sequences joined to another amylase and/or glucoamylase or a non-amylase or non-glucoamylase polypeptide, e.g., as a fusion protein. In one aspect, the invention provides polypeptides comprising amylase and/or glucoamylase signal sequences of the invention. In one aspect, polypeptides comprising amylase and/or glucoamylase signal sequences of the invention comprise sequences heterologous to an amylase and/or a glucoamylase of the invention (e.g., a fusion protein comprising an amylase signal sequence of the invention and sequences from another amylase or a non-amylase protein). In one aspect, the invention provides amylases and/or glucoamylases of the invention with heterologous signal sequences, e.g., sequences with a yeast signal sequence. For example, an amylase and/or a glucoamylase of the invention comprising a heterologous signal sequence in a vectors, e.g., a pPIC series vector (Invitrogen, Carlsbad, Calif.).

In one aspect, the signal sequences of the invention are identified following identification of novel amylase and/or glucoamylase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from between about 13 to 36, or anywhere from between about 10 to 40, amino acid residues. Various methods of recognition of signal sequences are known to those of skill in the art. For example, in one aspect, novel amylase signal peptides are identified by a method referred to as SIGNALP™. SignalP™ uses a combined neural network which recognizes both signal peptides and their cleavage sites; see, e.g., Nielsen (1997) "Identification of prokaryotic and eukaryotic signal peptides and prediction of their cleavage sites", Protein Engineering, vol. 10, no. 1, p. 1-6.

It should be understood that in some aspects amylases and/or glucoamylases of the invention may not have signal sequences. In one aspect, the invention provides the amylases and/or glucoamylases of the invention lacking all or part of a signal sequence, e.g. the signal sequences of the invention (see Table 1). In one aspect, the invention provides a nucleic acid sequence encoding a signal sequence from one amylase operably linked to a nucleic acid sequence of a different amylase or, optionally, a signal sequence from a non-amylase protein may be desired. Table 1 shows exemplary signal sequences of the invention.

Amylase and Glycoamylase Prepro and Signal Sequences and Catalytic Domains

In addition to signal sequences (e.g., signal peptides (SPs)), as discussed above, the invention provides prepro domains and catalytic domains (CDs). The SPs, prepro domains and/or CDs of the invention can be isolated, synthetic or recombinant peptides or can be part of a fusion protein, e.g., as a heterologous domain in a chimeric protein. The invention provides nucleic acids encoding these catalytic domains (CDs) (e.g., "active sites"), prepro domains and signal sequences (SPs, e.g., a peptide having a sequence comprising/consisting of amino terminal residues of a polypeptide of the invention).

The amylase and/or glucoamylase signal sequences (SPs), catalytic domains (CDs) and/or prepro sequences of the invention can be isolated peptides, or, sequences joined to another amylase or a non-amylase or a non-glucoamylase polypeptide, e.g., as a fusion (chimeric) protein. In one aspect, polypeptides comprising amylase signal sequences SPs and/or prepro of the invention comprise sequences heterologous to amylases and/or glucoamylases of the invention (e.g., a fusion protein comprising an SP and/or prepro of the invention and sequences from another amylase and/or glucoamylase, or a non-amylase or a non-glucoamylase protein). In one aspect, the invention provides amylases and/or glucoamylases of the invention with heterologous CDs, SPs and/or prepro sequences, e.g., sequences with a yeast signal sequence. An amylase and/or a glucoamylase of the invention can comprise a heterologous CD, SP and/or prepro in a vector, e.g., a pPIC series vector (Invitrogen, Carlsbad, Calif.).

In one aspect, SPs, CDs, and/or prepro sequences of the invention are identified following identification of novel amylase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from 13 to 45 or more amino acid residues. Various methods of recognition of signal sequences are known to those of skill in the art. For example, in one aspect, novel hydrolase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

In some aspects, an amylase and/or a glucoamylase of the invention may not have SPs and/or prepro sequences, and/or catalytic domains (CDs). In one aspect, the invention provides amylases and/or glucoamylases lacking all or part of an SP, a CD and/or a prepro domain. In one aspect, the invention provides a nucleic acid sequence encoding a signal sequence (SP), a CD and/or prepro from one amylase and/or glucoamylase operably linked to a nucleic acid sequence of a different amylase and/or glucoamylase, or, optionally, a signal sequence (SPs), a CD and/or prepro domain from a non-amylase or non-glucoamylase protein may be desired.

The invention also provides isolated, synthetic or recombinant polypeptides comprising signal sequences (SPs), prepro domain and/or catalytic domains (CDs) of the invention and heterologous sequences. The heterologous sequences are sequences not naturally associated (e.g., to an amylase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated, synthetic or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., amylase and/or a glucoamylase sequence). Similarly in one aspect, the invention provides isolated, synthetic or recombinant nucleic acids encoding these polypeptides. Thus, in one aspect, the isolated, synthetic or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

The polypeptides of the invention include amylases and/or a glucoamylases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include amylases and/or a glucoamylases inactive for other reasons, e.g., before "activation" by a post-translational processing event, e.g., an endo- or exo-peptidase or proteinase action, a phosphorylation event, an amidation, a glycosylation or a sulfation, a dimerization event, and the like. Methods for identifying "prepro" domain sequences, CDs, and signal sequences are well known in the art, see, e.g., Van de Ven (1993) Crit. Rev. Oncog. 4(2):115-136. For example, to identify a prepro sequence, the protein is purified from the extracellular space and the N-terminal protein sequence is determined and compared to the unprocessed form.

The polypeptides of the invention include all active forms, including active subsequences, e.g., catalytic domains (CDs) or active sites, of an enzyme of the invention. In one aspect, the invention provides catalytic domains or active sites as set forth below. In one aspect, the invention provides a peptide or polypeptide comprising or consisting of an active site domain as predicted through use of a database such as Pfam (which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent.

Hybrid Amylases and Glucoamylases, and Peptide Libraries

In one aspect, the invention provides hybrid amylases and/or a glucoamylases and fusion proteins, including peptide libraries, comprising sequences of the invention. The peptide libraries of the invention can be used to isolate peptide modulators (e.g., activators or inhibitors) of targets, such as amylase and/or a glucoamylase substrates, receptors, enzymes. The peptide libraries of the invention can be used to identify formal binding partners of targets, such as ligands, e.g., cytokines, hormones and the like.

In one aspect, the fusion proteins of the invention (e.g., the peptide moiety) are conformationally stabilized (relative to linear peptides) to allow a higher binding affinity for targets. The invention provides fusions of amylases and/or glucoamylases of the invention and other peptides, including known and random peptides. They can be fused in such a manner that the structure of the amylases and/or a glucoamylases is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g., an allelic or interspecies variation of an amylase and/or a glucoamylase sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed amylase and/or a glucoamylase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using assays of proteolytic activities. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides amylases and/or a glucoamylases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. amylase and/or a glucoamylase activity) although variants can be selected to modify the characteristics of the amylases and/or a glucoamylases as needed.

In one aspect, amylases and/or glucoamylases of the invention comprise epitopes or purification tags, signal sequences or other fusion sequences, etc. In one aspect, the Amylases and/or glucoamylases of the invention can be fused to a random peptide to form a fusion polypeptide. By "fused" or "operably linked" herein is meant that the random peptide and the amylase and/or a glucoamylase are linked together, in such a manner as to minimize the disruption to the stability of the amylase and/or a glucoamylase structure, e.g., it retains amylase and/or a glucoamylase activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

Screening Methodologies and "On-Line" Monitoring Devices

In practicing the methods of the invention, a variety of apparatus and methodologies can be used to in conjunction with the polypeptides and nucleic acids of the invention, e.g., to screen polypeptides for amylase and/or a glucoamylase activity, to screen compounds as potential modulators, e.g., activators or inhibitors, of an amylase and/or a glucoamylase activity, for antibodies that bind to a polypeptide of the invention, for nucleic acids that hybridize to a nucleic acid of the invention, to screen for cells expressing a polypeptide of the invention and the like.

Capillary Arrays

Capillary arrays, such as the GIGAMATRIXT™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube. The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides of the invention can be immobilized to or applied to an array, e.g., an "array" or "microarray" or "biochip" or "chip", which in one embodiment comprises a plurality of target elements, each target element comprising a defined amount of one or more polypeptides (including antibodies) or nucleic acids immobilized onto a defined area of a substrate surface, where at least one of the "target elements" is a polypeptide (e.g., an enzyme or antibody) of the invention, or a nucleic acid of the invention.

Arrays of the invention can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of an amylase and/or a glucoamylase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-based Screening Methods

The invention provides isolated, synthetic or recombinant antibodies that specifically bind to an amylase and/or a glucoamylase of the invention. These antibodies can be used to isolate, identify or quantify the amylases and/or glucoamylases of the invention or related polypeptides. These antibodies can be used to isolate other polypeptides within the scope the invention or other related amylases and/or a glucoamylase. The antibodies can be designed to bind to an active site of an amylase and/or a glucoamylase. Thus, the invention provides methods of inhibiting amylases and/or a glucoamylases using the antibodies of the invention.

The invention provides antibodies that comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polypeptides or peptides can be used to generate antibodies which bind specifically to the polypeptides, e.g., the amylases and/or a glucoamylases of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides (e.g., amylases and/or a glucoamylase) from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, transgenic seeds or plants or plant parts, polypeptides (e.g., amylases and/or a glucoamylase) and/or antibodies of the invention. The kits also can contain instructional material teaching the methodologies and industrial uses of the invention, as described herein.

Measuring Metabolic Parameters

The methods of the invention provide whole cell evolution, or whole cell engineering, of a cell to develop a new cell strain having a new phenotype, e.g., a new or modified amylase and/or a glucoamylase activity, by modifying the genetic composition of the cell. The genetic composition can be modified by addition to the cell of a nucleic acid of the invention. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the amylases and/or glucoamylases of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:
- identity of all pathway substrates, products and intermediary metabolites
- identity of all the chemical reactions interconverting the pathway metabolites, the stoichiometry of the pathway reactions,
- identity of all the enzymes catalyzing the reactions, the enzyme reaction kinetics,
- the regulatory interactions between pathway components, e.g. allosteric interactions, enzyme-enzyme interactions etc,
- intracellular compartmentalization of enzymes or any other supramolecular organization of the enzymes, and,
- the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., an amylase and/or a glucoamylase message) or generating new (e.g., amylase and/or a glucoamylase) transcripts in a cell. This increased or decreased expression can be traced by testing for the presence of an amylase and/or a glucoamylase of the invention or by amylase and/or a glucoamylase activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., an amylase and/or a glucoamylase) or generating new polypeptides in a cell. This increased or decreased expression can be traced by determining the amount of amylase and/or a glucoamylase present or by amylase and/or a glucoamylase activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Industrial Applications

The invention provides many industrial uses and medical applications for the amylases, glucoamylase, and glucosidases and other polypeptides (e.g., antibodies) of the invention. For example, the invention provides enzymes and methods for liquefying polysaccharide, e.g., starch. Many amylases and/or a glucoamylases and glucosidases used in processes for converting liquefied polysaccharide, e.g., starch, to glucose are unable to hydrolyze alpha (1,6) linkages, and this deficiency leaves approximately 5% of the sugar as pannose and isomaltose. However, in one aspect, enzymes of the invention can convert polysaccharide, e.g., starch, to glucose to maximize glucose production, including converting liquefied polysaccharide, e.g., starch, to glucose. In one aspect, the invention provides enzymes and methods for hydrolyzing 1,4-alpha and/or 1,6-alpha linkages (e.g., hydrolyzing starches) and hydrolyzing pannose and isomaltase. The glucosidases of the invention can be used in a variety of industrial processes, including biomass conversion to fuels (e.g., biofuels, such as bioethanol, biopropanol, biobutanol, or a biodiesel and the like), e.g., including their use in the initial stages (liquefaction) of polysaccharide, e.g., starch, processing, in wet corn milling, in alcohol production, in the textile industry for polysaccharide, e.g., starch, desizing, in baking applications, in the beverage industry, in oilfields in drilling processes; in inking of recycled paper; and in animal feed. Thus, the invention also provides a fuel, e.g., a biofuel (such as a bioethanol, biopropanol, biobutanol, or a biodiesel), comprising a polypeptide of the invention.

Detergent Compositions

The invention provides detergent compositions comprising one or more polypeptides of the invention, for example, amylases and/or glucoamylases of the invention, such as alpha amylases, etc., and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Amylases and/or glucoamylases of the invention can facilitate the removal of polysaccharide-comprising, e.g., starchy, stains by means of catalytic hydrolysis of a polysaccharide and/or oligosaccharide, e.g., starch. Amylases and/or glucoamylases of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of amylase and/or glucoamylase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Amylases and/or glucoamylases of the present invention can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, as well as builders and stabilizers. The addition of amylases and/or glucoamylases of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. In one aspect, a polypeptide of the invention (e.g., an alkaline-active amylase and/or glucoamylase) is used in a detergent, i.e., as a detergent additive. The detergent composition of the invention may, for example, be formulated as a hand or machine laundry detergent composition comprising a polypeptide of the invention. Detergent compositions of the invention include laundry and dishwashing (e.g., autodishwashing) solutions and application. A laundry additive suitable for pre-treatment of stained fabrics can comprise a polypeptide of the invention. A fabric softener composition can comprise a polypeptide of the invention. Alternatively, a polypeptide of the invention can be formulated as a detergent composition for use in general household hard surface cleaning operations. In alternative aspects, detergent additives and detergent compositions of the invention may comprise one or more other enzymes such as a protease, a lipase, a cutinase, another amylase and/or glucoamylase, a carbohydrase, a cellulase, a pectinase, a mannanase, an arabinase, a galactanase, a xylanase, an oxidase, e.g., a lactase, and/or a peroxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, amylase and/or glucoamylase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

Treating Fabrics

The invention provides methods of treating fabrics using one or more polypeptides of the invention. The polypeptides of the invention can be used in any fabric-treating method, which are well known in the art, see, e.g., U.S. Pat. No. 6,077,316. For example, in one aspect, the feel and appearance of a fabric is improved by a method comprising contacting the fabric with an amylase and/or a glucoamylase of the invention in a solution. In one aspect, the fabric is treated with the solution under pressure.

In one aspect, the enzymes of the invention are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes of the invention can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. The invention provides a method of desizing comprising enzymatic hydrolysis of the size by the action of an enzyme of the invention.

The enzymes of the invention can be used to desize fabrics, including cotton-containing fabrics, as detergent additives, e.g., in aqueous compositions. The invention provides methods for producing a stonewashed look on indigo-dyed denim fabric and garments. For the manufacture of clothes, the fabric can be cut and sewn into clothes or garments, which is afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of finishing denim garments (e.g., a "bio-stoning process"), enzymatic desizing and providing softness to fabrics using the amylases and/or glucoamylases of the invention. The invention provides methods for quickly softening denim garments in a desizing and/or finishing process.

Foods and Food Processing: Liquification of Polysaccharides, e.g., Starch

Figure 12:
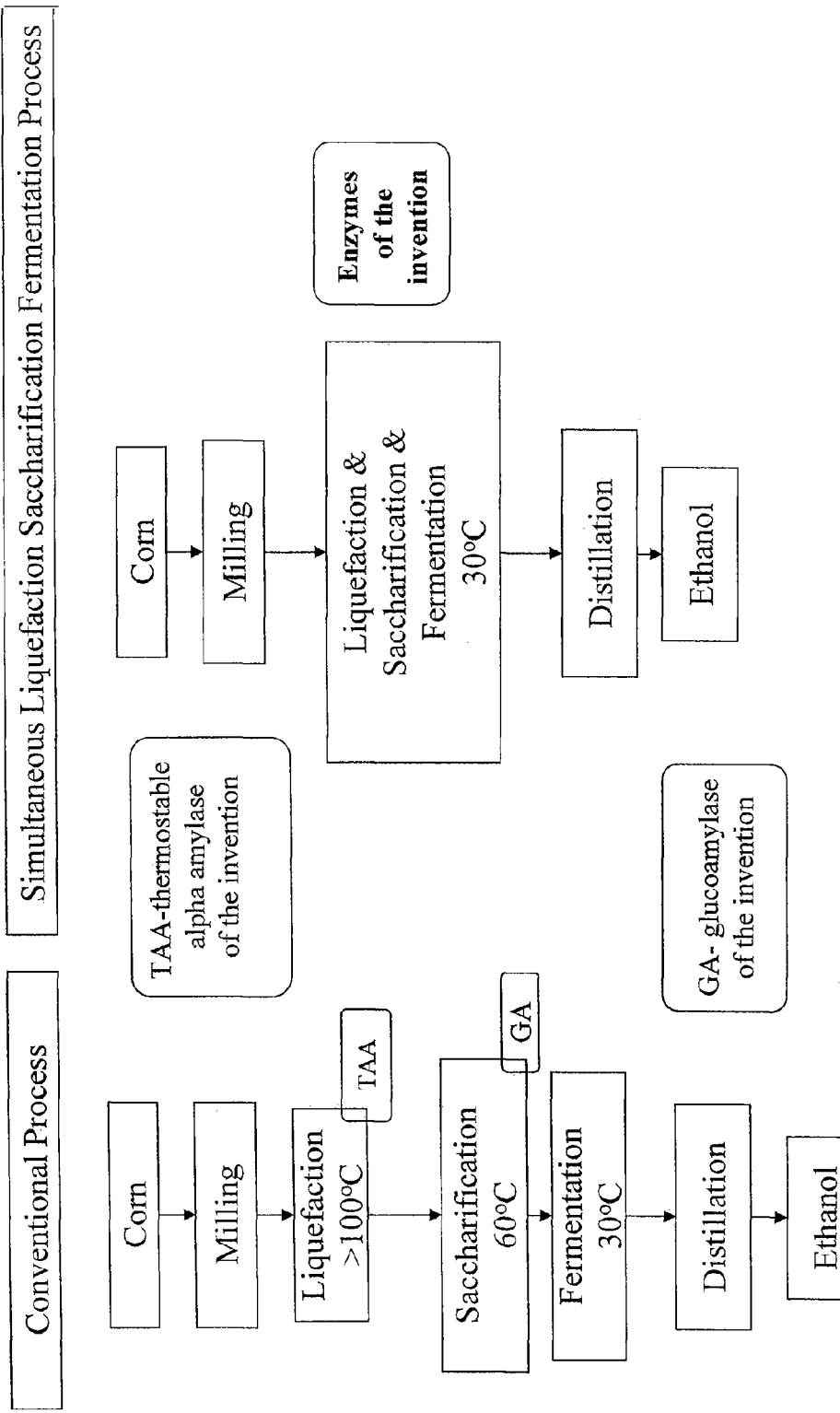
FIG. 12 illustrates how enzymes of the invention can be used in ethanol production from corn by dry milling, including their use in both "conventional processes" and "simultaneous liquefaction saccharification and fermentation processes", as discussed in detail, below.

The enzymes of the invention have numerous applications in food processing industry. The amylases and/or glucoamylases of the invention are used in starch to fructose processing. In alternative aspect, processes of the invention comprise polysaccharide, e.g., starch, to fructose processing comprising four steps: liquefaction of granular starch, saccharification of the liquefied polysaccharide, e.g., starch, into dextrose, purification, and isomerization to fructose; and one, several or all of these steps can comprise use of one or more enzymes of the invention. Enzymes of the invention can be used in ethanol production from a biomass, e.g., a corn or a grass, by wet or by dry milling; for example, FIG. 12 illustrates how enzymes of the invention can be used in ethanol production from corn by dry milling, including their use in both "conventional processes" and "simultaneous liquefaction saccharification and fermentation processes"

The invention provides methods of polysaccharide, e.g., starch, liquefaction using the enzymes of the invention. Concentrated suspensions of starch polymer granules are converted into a solution of soluble shorter chain length dextrins of low viscosity. This step is useful for convenient handling with standard equipment and for efficient conversion to glucose or $10^3$ other sugars. In one aspect, the granular starch is liquefied by gelatinizing the granules by raising the temperature of the granular starch to over about 72° C. The heating process instantaneously disrupts the insoluble starch granules to produce a water soluble starch solution. The solubilized starch solution can then be liquefied by an amylase and/or a glucoamylase of the invention. Thus, the invention provides enzymatic starch liquefaction processes using an amylase and/or a glucoamylase of the invention.

Figure 7:
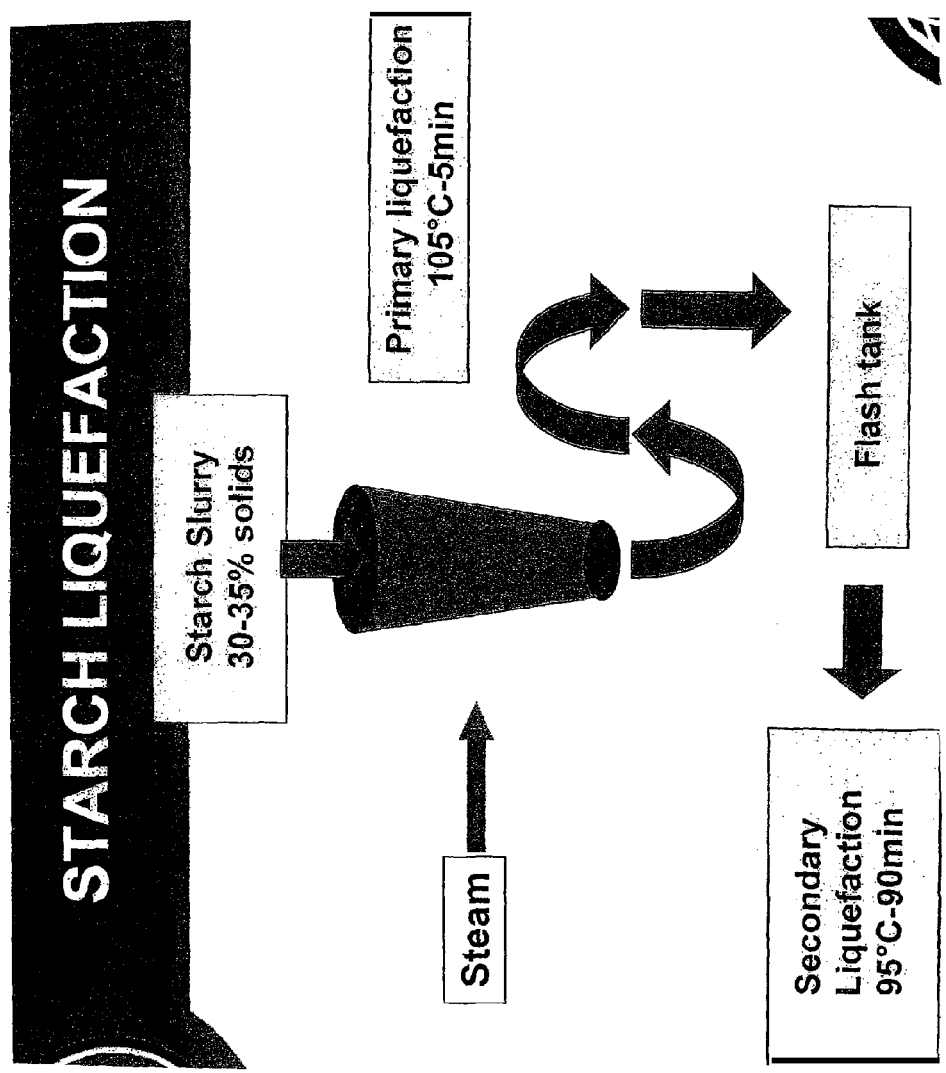
FIG. 7, FIG. 8 and FIG. 9 illustrate alternative exemplary polysaccharide, e.g., starch, processing methods (e.g., industrial processes), as discussed in detail, below.
Figure 8:
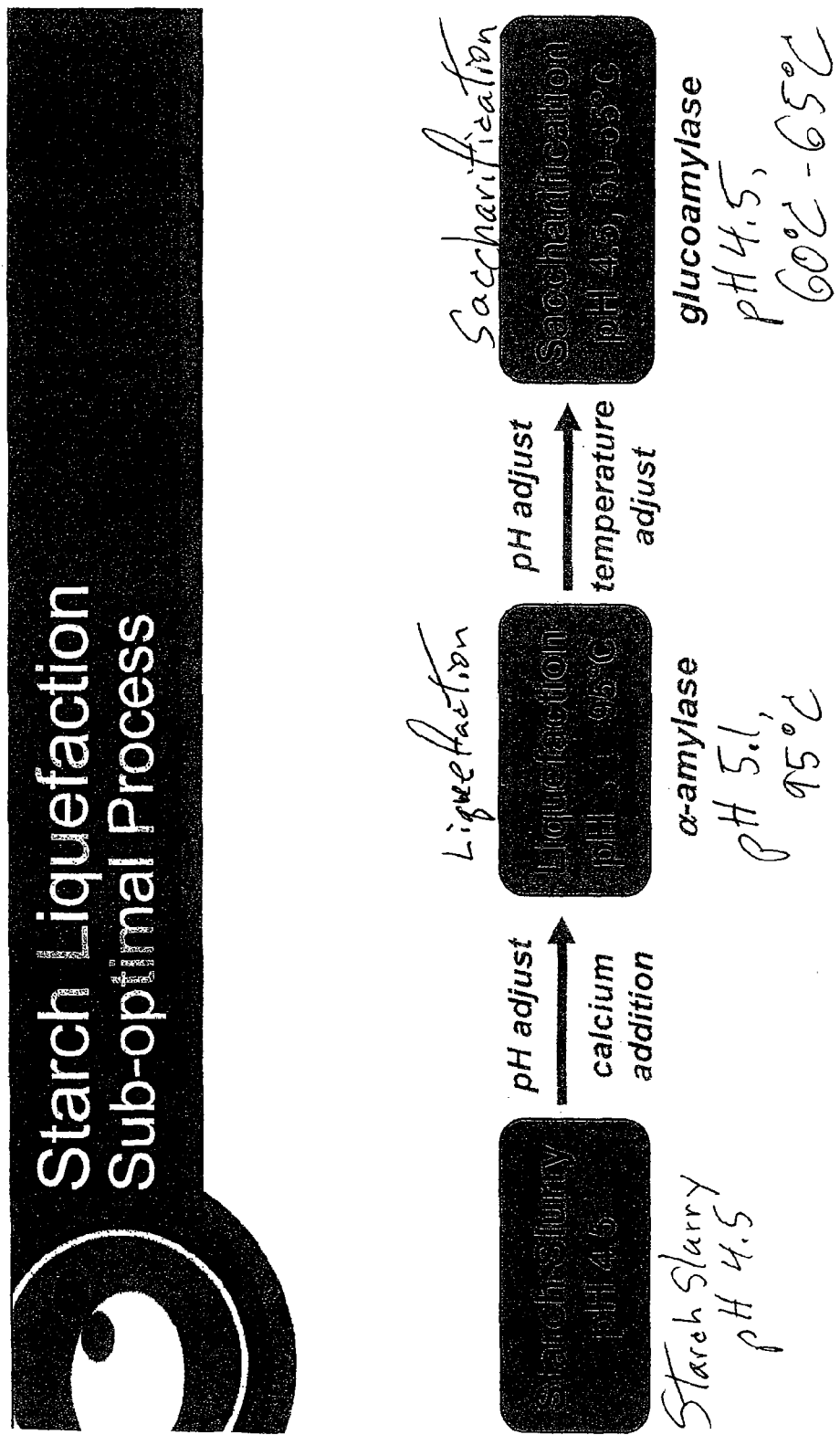
Figure 9:
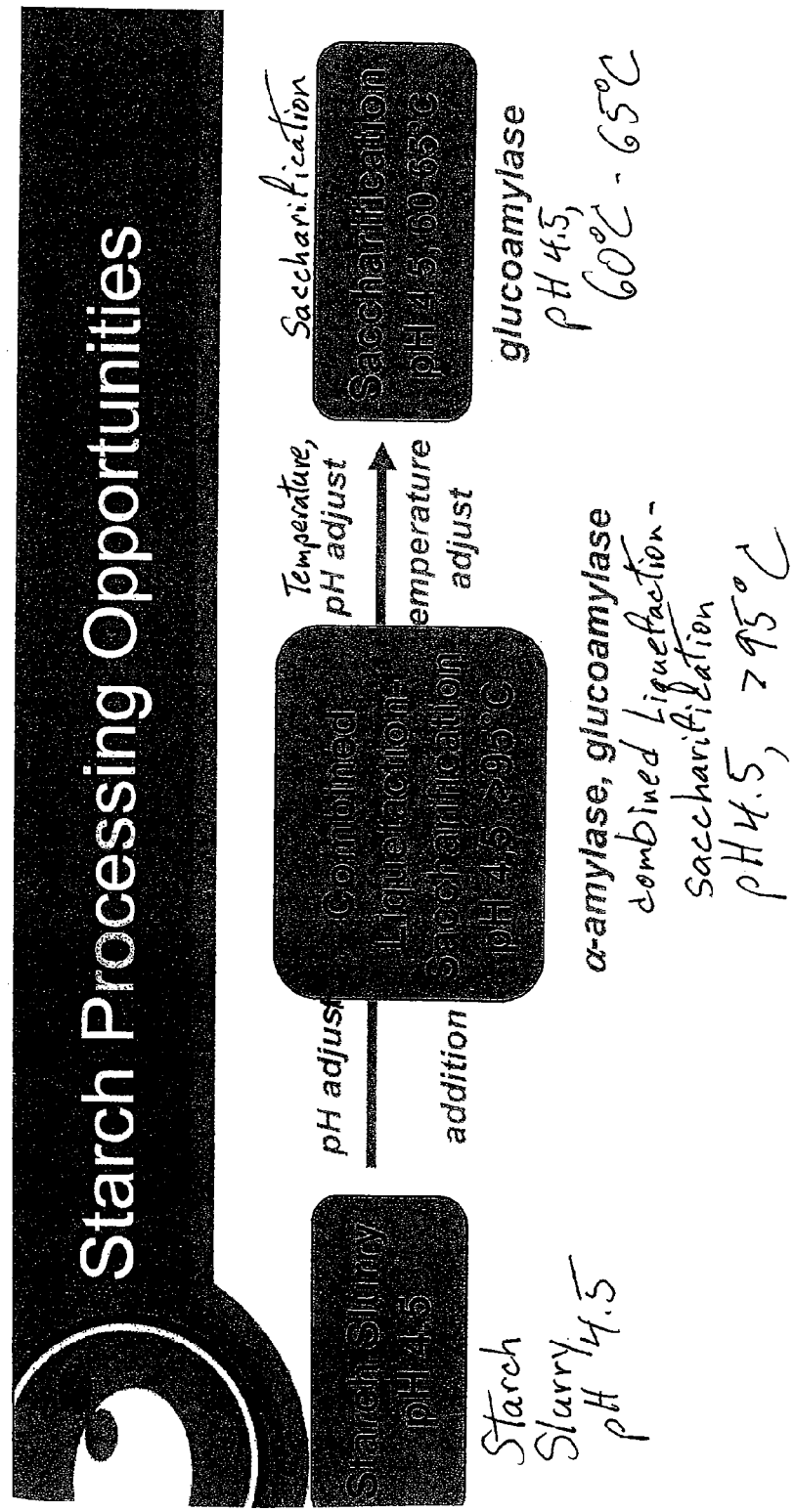

FIG. 7, FIG. 8 and FIG. 9 illustrate alternative exemplary starch processes, including starch liquefaction processes, of the invention using at least one enzyme of the invention. For example, FIG. 7 illustrates an exemplary starch liquefaction process of the invention comprising treating a starch slurry (e.g., having about 30% to 35% solids) with steam for primary liquefaction (e.g., at about 105° C. for about 5 minutes), input into a flash tank, followed by secondary liquefaction (e.g., at about 90° C. to 95° C. for about 90 minutes), each or one of these steps involving use of an enzyme of the invention. FIG. 8 illustrates another exemplary starch liquefaction process of the invention comprising treating a starch slurry at about between pH 4 to pH 5, e.g., pH 4.5, adjusting the pH, calcium addition, liquefaction at about pH 5 to pH 6, e.g., pH 5.4, at about 95° C. using an amylase (e.g., alpha amylase) and/or glucoamylase of the invention, followed by another pH and temperature adjustment for saccharification at about between pH 4 to pH 5, e.g., pH 4.5, at a temperature of between about 60° C. to 65° C. using an amylase (e.g., alpha amylase) and/or glucoamylase of the invention. FIG. 9 illustrates another exemplary starch process of the invention comprising treating a starch slurry at about between pH 4 to pH 5, e.g., pH 4.5, (optional adjusting pH, calcium addition), combined liquefaction-saccharification using an alpha amylase and/or a glucoamylase of the invention at about between pH 4 to pH 5, e.g., pH 4.5, at a temperature of greater than about 90° C., or, greater than about 95° C., followed by another pH and temperature adjustment for saccharification at about between pH 4 to pH 5, e.g., pH 4.5, at a temperature of between about 60° C. to 65° C. using a glucoamylase of the invention. In one aspect, the combined liquefaction-saccharification of the invention is a "one-pot" process. In one aspect, the entire process is a "one-pot" process. Any one of these processes, and any one of these steps, can also comprise, or can further comprise, another enzyme of the invention (e.g., a glucosidase such as an α-1,6-glucosidase, a maltase, etc.), or another enzyme such as a pullulanase or an isomerase.

An exemplary enzymatic liquefaction process involves adjusting the pH of a granular starch slurry to between 6.0 and 6.5 and the addition of calcium hydroxide, sodium hydroxide or sodium carbonate. In one aspect, calcium hydroxide is added. This provides calcium ions to stabilize the glucoamylase of the invention against inactivation. In one aspect, upon addition of amylase, the suspension is pumped through a steam jet to instantaneously raise the temperature to between 80°-115° C. In one aspect, the starch is immediately gelatinized and, due to the presence of amylase, depolymerized through random hydrolysis of α-1,4-glycosidic bonds by amylase to a fluid mass. The fluid mass can be easily pumped.

The invention provides various enzymatic polysaccharide, oligosaccharide and/or starch liquefaction processes using an amylase and/or a glucoamylase of the invention. In one aspect of the liquefaction process of the invention, an amylase is added to the polysaccharide, oligosaccharide and/or starch suspension and the suspension is held at a temperature of between about 80°-100° C. to partially hydrolyze the polysaccharide, oligosaccharide and/or starch granules. In one aspect, the partially hydrolyzed polysaccharide, oligosaccharide and/or starch suspension is pumped through a jet at temperatures in excess of about 105° C. to thoroughly gelatinize any remaining granular structure. In one aspect, after cooling the gelatinized starch, a second addition of amylase and/or glucoamylase is made to further hydrolyze the polysaccharide, oligosaccharide and/or starch.

The invention provides enzymes and processes for hydrolyzing liquid (liquefied) and granular polysaccharide, oligosaccharide and/or starch. Such starch can be derived from any source, e.g., corn, wheat, milo, sorghum, rye or bulgher. The invention applies to any grain starch source which is useful in liquefaction, e.g., any other grain or vegetable source known to produce starch suitable for liquefaction. The methods of the invention comprise liquefying starch from any natural material, such as rice, germinated rice, corn, barley, milo, wheat, legumes and sweet potato. The liquefying process can substantially hydrolyze the starch to produce a syrup. The temperature range of the liquefaction can be any liquefaction temperature which is known to be effective in liquefying starch. For example, the temperature of the polysaccharide, oligosaccharide and/or starch can be between about 80° C. to about 115° C., between about 100° C. to about 110° C., and from about 105° C. to about 108° C. In alternative aspects, the amylase and/or glucoamylase used in these methods is active at these temperatures, e.g., active at temperatures in a range of between about 80° C. to about 115° C., between about 100° C. to about 110° C., and from about 105° C. to about 108° C.

Figure 5:
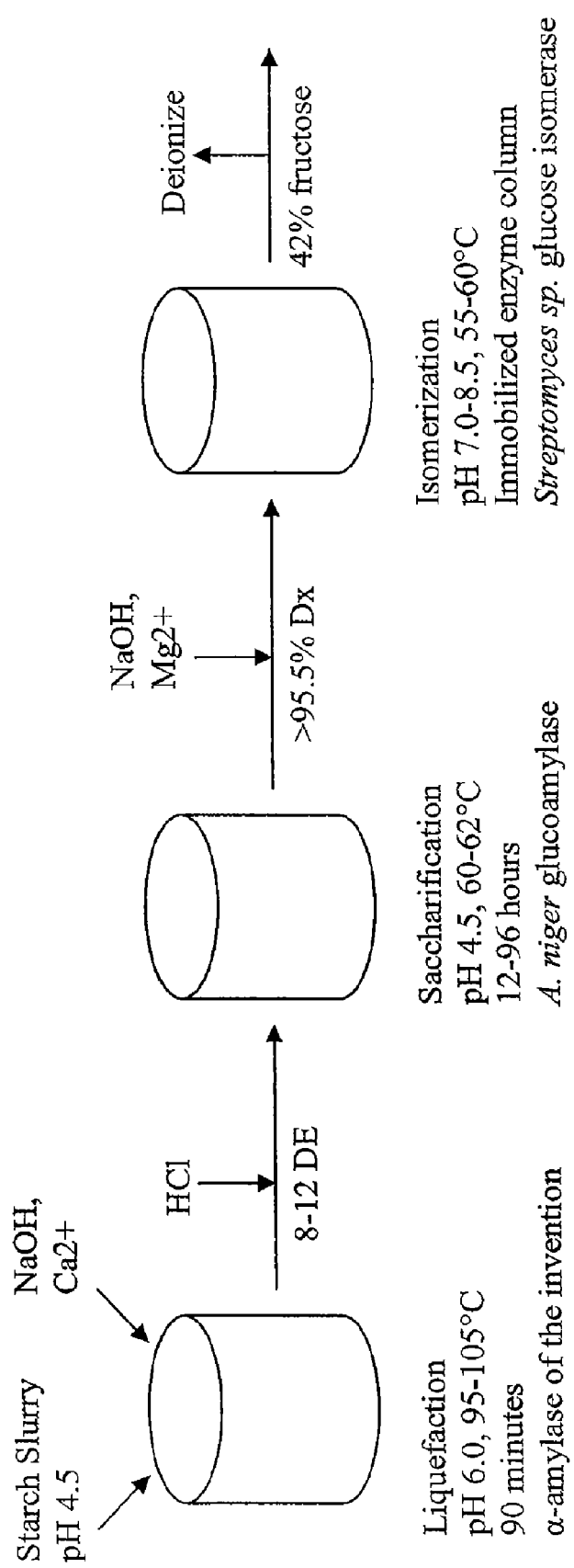
FIG. 5 illustrates an exemplary method of the invention for liquefaction saccharification, as discussed in detail, below.

The invention provides methods for liquefaction saccharification as illustrated in FIG. 5. In one aspect, amylases (such as alpha amylases) and/or glucoamylases of the invention are used in the illustrated liquefaction step (some current industrial methods use *B. licheniformis* α-amylase). In one aspect, the process takes place at about pH 6.0 at a temperature anywhere in the range of between about 95° C. to 105° C., for a length of time anywhere between about 0.5 and 5 hours, e.g., 60, 90 or 120 minutes. In one aspect, in a corn steep process, prior to liquefaction cellulases, proteases and/or protein thioreductases are added.

In one aspect of a liquefaction process of the invention, an amylase and/or a glucoamylase of the invention that has activity at about pH 4.5 (or, anywhere between about pH 5 and pH 5), that may or may not be $Ca^{2+}$ dependent is added Eliminating the addition of salts in the front end of the process eliminates the need to remove them at the back end of the process. In one aspect of a liquefaction process of the invention, an amylase that is more active is used. This can allow one to decrease the amount of enzyme needed. In one aspect, liquefaction and saccharification are done in the same pot, as a "one-pot process," for example, under conditions comprising about 90° C. to 95° C. (or, anywhere between about 80° C. to 105° C.), as about a 3 hour process (or, as a process lasting between about 1 and 5 hours). In this aspect, the enzyme load can be cut in half again.

In one aspect of a saccharification process of the invention, an amylase and/or glucoamylase of the invention is used. In one aspect, amylases and/or glucoamylases of the invention are used in a saccharification step (in addition to or in place of an *A. niger* glucoamylase). In one aspect, the process takes place at about pH 4.5, in a temperature range of between about 60° C. to 62° C. (or, anywhere in the range of between about 50° C. to 72° C., or, between about 40° C. to 80° C.) as a process lasting between about 12 and 96 or more hours. In one aspect of a saccharification process of the invention, a glucoamylase of the invention is used to give a higher level of dextrose in the syrup. In one aspect, other enzymes are added, e.g., pullulanases to increase the amount of glucose.

In one aspect, one, some or all of the enzymes used in processes of the invention (including the enzymes of the invention) are immobilized, e.g., immobilized on any surface, e.g., a flat surface or an enzyme column, e.g., immobilized on an array, a bead, fiber, pore, capillary and the like. In one aspect, by being immobilized, they can be reused.

In one aspect, the invention provides "enzyme cocktails" using at least one enzyme of the invention. In one aspect, "enzyme cocktails" are used in the processes of the invention, e.g., including the liquefaction saccharification methods as illustrated in FIG. 5. For example, in one aspect, cell wall degrading enzymes (CWDE) are used, e.g., for textile, pulp and paper, and laundry processes of the invention, including, e.g., combinations of cellulases, hemicellulases, xylanase, galactomannanases, gluco-mannanases, arabinofuranosidases, and others. In one aspect, "enzyme cocktails" used in the processes of the invention for bio-bleaching (e.g., pulp and paper, laundry processes), include combinations of laccases, peroxidases, oxidases and the like. In one aspect, cell wall degrading enzymes are combined with bio-bleaching enzymes and enzymes of the invention to degrade plant cell walls to release color agents.

One exemplary enzyme cocktail of the invention comprising at least one amylase and/or glucoamylase of the invention can hydrolyze approximately great than 95% of the starch in milled corn into fermentable sugars in no more than 60 hours at about 30 to 40° C. and at about pH 3.5 to pH 5.5 in the presence of yeast. In one aspect, the total quantity of enzyme protein required is not greater than 50 grams/ton of corn (0.005% w/w).

Enzymes of the invention can be used to treat dairy products; and the invention provides dairy products comprising a polypeptide of the invention, wherein optionally the dairy product comprises a milk, an ice cream, a cheese or a yoghurt.

Enzymes of the invention can be used in simultaneous liquefaction saccharification and fermentation (SLSF) processes; and advantages to using enzymes of this invention can include:

Lower energy costs due to elimination of high temperature step;
Improved yield due to more rapid fermentation;
Reduced risk of bacterial contamination;
yeast produces ethanol earlier than in conventional process;
Reduced storage and handling of bulk yeast.

Properties of enzymes of the invention used in these processes of the invention can include: raw polysaccharide, oligosaccharide and/or starch hydrolyzing activity; temperature and pH activity profiles compatible with process conditions; high activity on non-gelatinized polysaccharide, oligosaccharide and/or starch; and/or active on 'resistant' fraction of raw starch.

In alternative aspects, enzymes of the invention have amylase and/or glucoamylase activity and can hydrolyze (partially or completely) polysaccharide, oligosaccharide and/or starch granules having complex multi-level structures, including amorphous and crystalline regions and/or branched and linear chains, e.g., can hydrolyze (partially or completely) raw starch, including: RS I—physically inaccessible starch; RS II—resistant starch granules as in raw potato and banana; RS III—retrograded as in cooked potato.

Processes to Produce High MW Dextrose Syrups

The invention provides processes to produce high MW dextrose syrups using enzymes of the invention, including methods for producing oligosaccharides having a MW tightly groups at about 20,000 MW. In one aspect, amylases and/or glucoamylases of the invention can be used to liquefy a polysaccharide-comprising, oligosaccharide-comprising and/or starch starch-comprising composition, e.g., a corn starch, to produce an oligosaccharide pattern that is tightly grouped at about 20,000 MW (Bacillus amylases will produce syrups containing much higher MW fragments, and high MW oligosaccharides are not fully converted to glucose by glucoamylases, e.g., Aspergillus glucoamylases, during saccharification).

In one aspect, using the amylases and/or glucoamylases of the invention to catalyze the hydrolysis of a starch-comprising composition, e.g., a corn starch, the approximately 20,000 MW fragments are produced. These approximately 20,000 MW fragments can be rapidly and fully converted to glucose. Thus, in one aspect, saccharified syrups resulting from Bacillus amylase liquefaction contain less dextrose than saccharified syrups from liquefaction using amylases and/or glucoamylases of the invention.

Processes to Produce Homogenous Maltodextrins

The invention provides processes to produce homogenous maltodextrins using enzymes of the invention. The homogenous maltodextrins produced by the methods of the invention can be used in a wide variety of food, drug and coating applications. In one aspect, amylases and/or glucoamylases of the invention can be used to generate an extremely uniform maltodextrin composition (conventional manufacturing processes using either acid or enzymatic hydrolysis of starch result in a broad, typically bimodal MW distribution of oligosaccharides). The homogenous maltodextrins produced by the methods of the invention have a homogenous MW distribution and can be used in a variety of maltodextrin-comprising products, resulting in lower viscosity, clear (no haze) solutions, better coating properties, better film-forming properties, and the like.

In one aspect, amylases and/or glucoamylases of the invention are used to liquefy corn starch to produce a uniform maltodextrin-comprising composition. In one aspect, the liquefication is conducted at a pH of between about pH 4.5 to about pH 6.5, e.g., pH 5.0 or 5.5, at temperatures up to about 105° C. The uniform maltodextrin composition can be produced at DE's ranging from about 5 to as high as about 20. The syrups produced by these amylases and/or glucoamylases of the invention can be filtered, treated with charcoal and/or spray-dried to yield the maltodextrin-comprising product.

In one aspect, one or more other enzymes are used in conjunction with a composition comprising enzymes of the invention for use in starch to fructose processing, liquefaction of granular starch, and processes to produce homogenous maltodextrins or high MW dextrose syrups, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Enzymatic Dry Milling Processes

The invention provides enzymatic dry milling processes using an amylase and/or a glucoamylase of the invention; exemplary processes are illustrated in FIG. 12. In dry milling, whole grain is ground and combined with water. The germ is optionally removed by flotation separation or equivalent techniques. The resulting mixture, which contains polysaccharide, e.g., starch, fiber, protein and other components of the grain, is liquefied using amylase. In one aspect, enzymatic liquefaction is done at lower temperatures than the polysaccharide, e.g., starch, liquification processes discussed above. In one aspect, after gelatinization the polysaccharide, e.g., starch, solution is held at an elevated temperature in the presence of amylase until a DE of 10-20 is achieved. In one aspect, this is a period of about 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

Enzymes of the invention can be used in biomass wet or dry milling processes. For example, in one aspect of an exemplary dry milling process whole grain is ground and combined with water and treated with an enzyme of the invention. The germ can be removed by flotation separation or equivalent techniques. In one aspect, the resulting mixture, which contains polysaccharide, e.g., starch, fiber, protein and other components of the grain, is liquefied using a glucoamylase and/or an amylase of the invention (e.g., an alpha-amylase). In one aspect, this enzymatic liquefaction is at a relatively lower temperature when using the dry milling process; however, low temperature liquefaction is believed to be less efficient than high temperature liquefaction in converting polysaccharide, e.g., starch, to soluble dextrins. Thus, in one aspect, the invention provides a further step wherein after gelatinization the polysaccharide, e.g., starch, solution is held at an elevated temperature in the presence of a glucoamylase and/or an amylase of the invention (e.g., an alpha-amylase), which in one aspect is until a DE of about 10 to 20 is achieved, usually a period of about 1 to 3 hours (dextrose equivalent (DE) is the industry standard for measuring the concentration of total reducing sugars, calculated as D-glucose on a dry weight basis; unhydrolyzed granular starch has a DE of virtually zero, whereas the DE of D-glucose is defined as 100).

In alternative aspects, use of amylases and/or glucoamylases of the invention in dry mill ethanol processes can provide operational advantages, for example: rapid reduction in viscosity of slurried corn flour, making an increase in dissolved solids and throughput possible without additional capital investment; superior thermal stability to best competitor, which eliminates split dosing; some amylases and/or glucoamylases of the invention are thermostable enzymes—and this eliminates the need to dose before jet cooking and after; lower viscosities are obtained at higher process temperatures, and provides improved microbial control in slurry tank (process is run at higher temperature, so unwanted microbes are killed); lower liquefaction pH, which eliminates need for pH adjustment, decreases scale formation (calcium oxalate precipitate forms on hardware, etc.; if liquefaction done at low pH, there is a higher potential for scale formation) and reduces byproduct formation.

In summary, in alternative aspects amylases and/or glucoamylases of the invention can be thermostable enzymes that can meet key industry needs, for example, under certain conditions, rapidly reduces viscosity of high dry solids corn flour slurry, can be thermostable (optimum temperature 95° C.), can be calcium independent, can be active under low pH optimum, and can tolerate up to 30% recycled backset. In one aspect, the recommended dose is in the range of between about 0.4 to 0.6 kg/MT starch.

Enzymatic Wet Milling Processes

Figure 6:
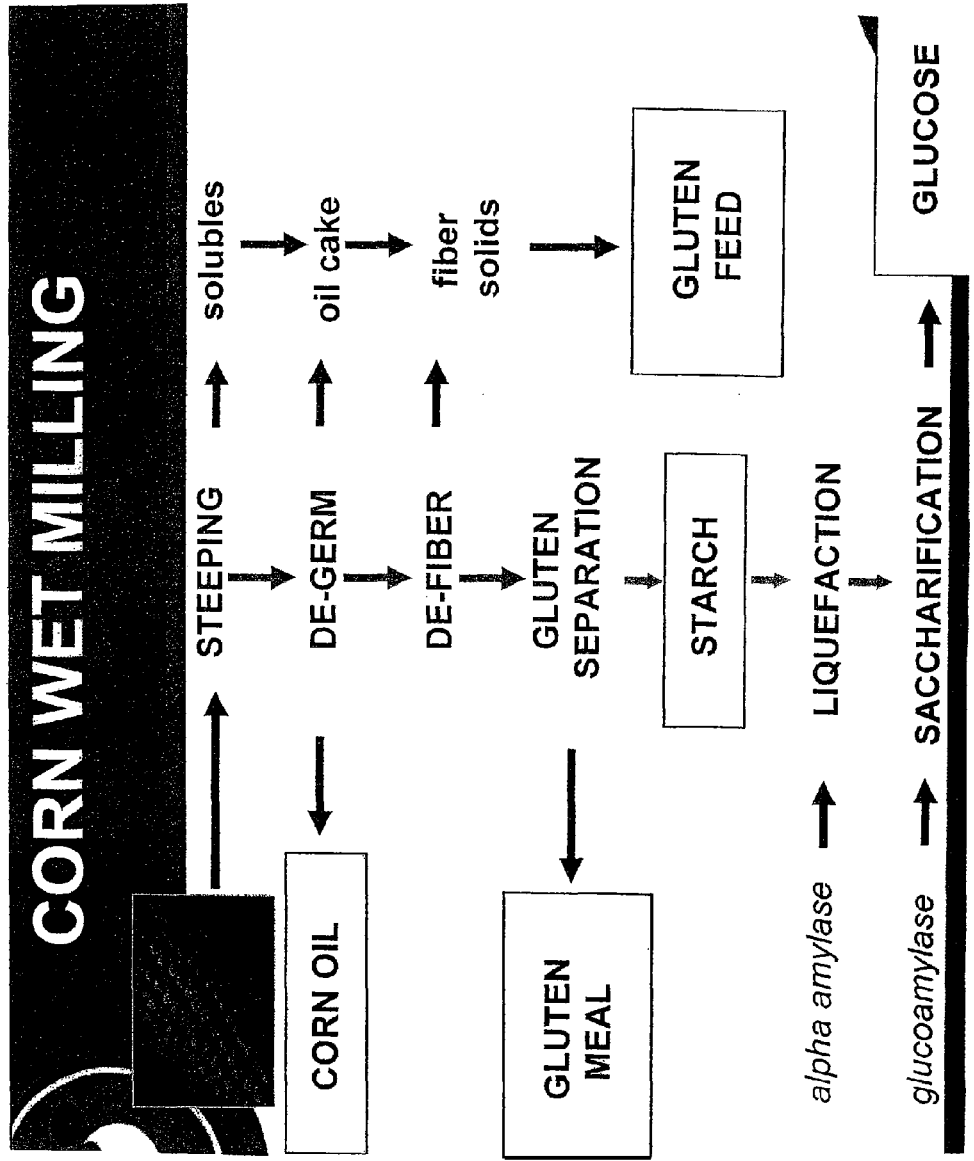
FIG. 6 illustrates an exemplary corn wet milling process of the invention using at least one enzyme of the invention, as discussed in detail, below.

The invention provides wet milling processes, e.g., corn wet milling, using an enzyme, e.g., a glucoamylase and/or an amylase, of the invention. Corn wet milling is a process which produces corn oil, gluten meal, gluten feed and polysaccharide, e.g., starch. Thus, the invention provides methods of making corn oil, gluten meal, gluten feed and polysaccharide, e.g., starch, using an enzyme of the invention. In one aspect, an alkaline-amylase and/or alkaline-glucoamylase of the invention is used in the liquefaction of polysaccharide, e.g., starch. In one aspect, an amylase and/or glucoamylase of the invention is used in saccharification to produce glucose. An exemplary corn wet milling process of the invention (using at least one enzyme of the invention) is illustrated in FIG. 6. FIG. 6 illustrates an exemplary corn oil process of the invention comprising steeping, de-germing, de-fibering and gluten separation, followed by liquefaction using an enzyme of the invention (e.g., an alpha amylase), and saccharification using an enzyme of the invention (e.g., glucoamylase).

In one aspect, corn (a kernel that consists of a outer seed coat (fiber), polysaccharide, e.g., starch, a combination of starch and glucose and the inner germ), is subjected to a four step process, which results in the production of starch. In one aspect, the corn is steeped, de-germed, de-fibered, and the gluten is separated. In a steeping process the solubles are taken out. The product remaining after removal of the solubles is de-germed, resulting in production of corn oil and production of an oil cake, which is added to the solubles from the steeping step. The remaining product is de-fibered and the fiber solids are added to the oil cake/solubles mixture. This mixture of fiber solids, oil cake and solubles forms a gluten feed. After de-fibering, the remaining product is subjected to gluten separation. This separation results in a gluten meal and starch. The starch is then subjected to liquefaction and saccharification using polypeptides of the invention to produce glucose.

FIG. 6 illustrates an exemplary corn wet milling process of the invention (using at least one enzyme of the invention). FIG. 7, FIG. 8 and FIG. 9 illustrate alternative exemplary starch processing methods (e.g., industrial processes), including starch liquefaction processes, of the invention (using at least one enzyme of the invention).

Enzymes of the invention can be used in biomass wet dry milling processes; e.g., a corn wet milling, to produces a vegetable (e.g., a corn) oil, a gluten meal, a gluten feed and/or a starch. In one aspect, an alkaline-amylase of the invention is used in the liquefaction of starch and a glucoamylases (which also can be an enzyme of the invention) is used in saccharification, producing glucose. In one aspect, the biomass (e.g., a corn kernel, which consists of an outer seed coat (fiber), starch, a combination of starch and glucose and the inner germ) is subjected to a four step process to produce starch. The biomass (e.g., a corn) is steeped, de-germed, de-fibered, and finally the gluten is separated. In the steeping process, the solubles are taken out. The product remaining after removal of the solubles is de-germed, resulting in production of a vegetable oil (e.g., a corn oil) and production of an oil cake, which is added to the solubles from the steeping step. The remaining product is de-fibered and the fiber solids are added to the oil cake/solubles mixture. This mixture of fiber solids, oil cake and solubles forms a gluten feed. After de-fibering, the remaining product is subjected to gluten separation. This separation results in a gluten meal and starch. In one aspect, the starch then subjected to liquefaction and saccharification (e.g., using enzymes of the invention) to produce glucose.

The invention also provides a high yield process for producing high quality corn fiber gum by treatment of corn fiber with an enzyme of the invention followed by hydrogen peroxide treatment to obtain an extract of milled corn fiber. See, e.g., U.S. Pat. No. 6,147,206.

In one aspect, one or more other enzymes are used in conjunction with a composition comprising enzymes of the invention for use with these dry or wet milling processes, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Anti-staling Processes

The invention provides anti-staling processes (e.g., of baked products such as bread) using an amylase and/or a glucoamylase of the invention. The invention provides methods to slow the increase of the firmness of the crumb (of the baked product) and a decrease of the elasticity of the crumb using an amylase and/or a glucoamylase of the invention. Staling of baked products (such as bread) is more serious as time passes between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. Amylases and/or glucoamylases of the invention are used to retard staling of the bread as described e.g., in U.S. Pat. Nos. 6,197,352; 2,615,810; 3,026,205; Silberstein (1964) Baker's Digest 38:66-72.

In one aspect, an enzyme of the invention is used to retard the staling of baked products while not hydrolyzing starch into the branched dextrins. Branched dextrins are formed by cleaving off the branched chains of the dextrins generated by α-amylase hydrolysis which cannot be degraded further by the α-amylase. This can produce a gummy crumb in the resulting bread. Accordingly, the invention provides a process for retarding the staling of baked products (e.g., leavened baked products) comprising adding an enzyme of the invention comprising exoamylase activity to a flour or a dough used for producing a baked product. Exoamylases and/or glucoamylases of the invention can have glucoamylase, β-amylase (which releases maltose in the beta-configuration) and/or maltogenic amylase activity.

The invention also provides a process for preparing a dough or a baked product prepared from the dough which comprises adding an amylase and/or a glucoamylase of the invention to the dough in an amount which is effective to retard the staling of the bread. The invention also provides a dough comprising said amylase and a premix comprising flour together with said amylase. Finally, the invention provides an enzymatic baking additive, which contains said amylase.

Animal Feeds and Additives

The invention provides feeds, foods, food additives, feed additives, nutritional supplements and/or dietary supplements comprising a polypeptide of this invention for humans and animals; and the invention provides methods for treating humans and animals using feeds, foods, food additives, feed additives, nutritional supplements and/or dietary supplements comprising a polypeptide of this invention; and/or using a glucoamylase and/or amylase enzyme of the invention. The invention provides human and/or animal feeds, foods, food additives, feed additives, nutritional supplements and/or dietary supplements comprising amylases and/or glucoamylases of the invention. In one aspect, treating human and/or animal feeds, foods, additives, food additives, feed additives, nutritional supplements and/or dietary supplements using amylase and/or glucoamylases enzymes of the invention can help in the availability of polysaccharide, e.g., starch, in the human and/or animal feed, food, additive, food additive, feed additive, nutritional supplement and/or dietary supplement. This can result in release of readily digestible and easily absorbed sugars.

Use of a glucoamylase and/or an amylase of the invention can increase the digestive capacity of animals and birds. Use of an amylase and/or a glucoamylase of the invention can ensure availability of an adequate nutrient supply for better growth and performance. In one aspect, the enzymes of the invention can be added as feed additives, or in feeds, foods, additives, food additives, feed additives, nutritional supplements and/or dietary supplements, for animals. In another aspect, the feeds, foods, additives, food additives, feed additives, nutritional supplements and/or dietary supplements, e.g., animal feed, can be treated with an amylase and/or a glucoamylase of the invention prior to animal consumption. In another aspect, an amylase and/or a glucoamylase of the invention may be supplied by expressing the enzymes directly in transgenic feed crops (as, e.g., transgenic plants, seeds and the like), such as corn. As discussed above, the invention provides transgenic plants, plant parts and plant cells comprising a nucleic acid sequence encoding a polypeptide of the invention. In one aspect, the nucleic acid is expressed such that an amylase and/or a glucoamylase of the invention is produced in recoverable quantities. The amylase and/or glucoamylase of the invention can be recovered from any plant or plant part. Alternatively, the plant or plant part containing the recombinant polypeptide can be used as such for improving the quality of a food or feed, feed additive, nutritional supplement and/or dietary supplement, and the like, e.g., improving nutritional value, palatability, and rheological properties, or to destroy an antinutritive factor.

Paper or Pulp Treatment

The enzymes of the invention can be in paper or pulp treatment or paper deinking. For example, in one aspect, the invention provides a paper treatment process using amylases and/or glucoamylases of the invention. In one aspect, the enzymes of the invention can be used to modify polysaccharide, e.g., starch, in the paper thereby converting it into a liquefied form. In another aspect, paper components of recycled photocopied paper during chemical and enzymatic deinking processes. In one aspect, amylases and/or glucoamylases of the invention can be used in combination with cellulases. The paper can be treated by the following three processes: 1) disintegration in the presence of an enzyme of the invention, 2) disintegration with a deinking chemical and an enzyme of the invention, and/or 3) disintegration after soaking with an enzyme of the invention. The recycled paper treated with amylase can have a higher brightness due to removal of toner particles as compared to the paper treated with just cellulase. While the invention is not limited by any particular mechanism, the effect of an amylase and/or a glucoamylase of the invention may be due to its behavior as surface-active agents in pulp suspension.

The invention provides methods of treating paper and paper pulp using one or more polypeptides of the invention. The polypeptides of the invention can be used in any paper- or pulp-treating method, which are well known in the art, see, e.g., U.S. Pat. Nos. 6,241,849; 6,066,233; 5,582,681. For example, in one aspect, the invention provides a method for deinking and decolorizing a printed paper containing a dye, comprising pulping a printed paper to obtain a pulp slurry, and dislodging an ink from the pulp slurry in the presence of an enzyme of the invention (other enzymes can also be added). In another aspect, the invention provides a method for enhancing the freeness of pulp, e.g., pulp made from secondary fiber, by adding an enzymatic mixture comprising an enzyme of the invention (can also include other enzymes, e.g., pectinase enzymes) to the pulp and treating under conditions to cause a reaction to produce an enzymatically treated pulp. The freeness of the enzymatically treated pulp is increased from the initial freeness of the secondary fiber pulp without a loss in brightness.

In one aspect, one or more other enzymes are used in conjunction with a composition comprising enzymes of the invention for use with these pulp and/or paper treatment methods, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Repulping: Treatment of Lignocellulosic Materials

The invention also provides a method for the treatment of lignocellulosic fibers, wherein the fibers are treated with a polypeptide of the invention, in an amount which is efficient for improving the fiber properties. The amylases and/or glucoamylases of the invention may also be used in the production of lignocellulosic materials such as pulp, paper and cardboard, from polysaccharide, e.g., starch, reinforced waste paper and cardboard, especially where repulping occurs at pH above 7 and where amylases can facilitate the disintegration of the waste material through degradation of the reinforcing polysaccharide, e.g., starch. The amylases and/or glucoamylases of the invention can be useful in a process for producing a papermaking pulp from starch-coated printed paper. The process may be performed as described in, e.g., WO 95/14807.

An exemplary process comprises disintegrating the paper to produce a pulp, treating with a polysaccharide-degrading, e.g., starch-degrading, enzyme before, during or after the disintegrating, and separating ink particles from the pulp after disintegrating and enzyme treatment. See also U.S. Pat. No. 6,309,871 and other US patents cited herein. Thus, the invention includes a method for enzymatic deinking of recycled paper pulp, wherein the polypeptide is applied in an amount which is efficient for effective de-inking of the fiber surface.

Waste Treatment

The enzymes of the invention can be used in a variety of other industrial applications, e.g., in waste treatment. For example, in one aspect, the invention provides a solid waste digestion process using enzymes of the invention. The methods can comprise reducing the mass and volume of substantially untreated solid waste. Solid waste can be treated with an enzymatic digestive process in the presence of an enzymatic solution (including an enzyme of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

In one aspect, one or more other enzymes are used in conjunction with a composition comprising enzymes of the invention for use with these waste treatment methods, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Oral Care Products

The invention provides oral care product comprising an amylase and/or a glucoamylase of the invention. Exemplary oral care products include toothpastes, dental creams, gels or tooth powders, odontics, mouth washes, pre- or post brushing rinse formulations, chewing gums, lozenges, or candy. See, e.g., U.S. Pat. No. 6,264,925.

In one aspect, one or more other enzymes are used in conjunction with an oral care composition comprising enzymes of the invention, and for use with these methods, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Brewing and Fermenting

The invention provides methods of brewing (e.g., fermenting) beer comprising a glucoamylase and/or an amylase of the invention. In one exemplary process, starch-containing raw materials are disintegrated and processed to form a malt. A glucoamylase and/or an amylase of the invention can be used at any point in a fermentation process. For example, amylases and/or glucoamylases of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15-25° C. for 3 to 6 days when enzyme synthesis is stimulated under the control of gibberellins. During this time amylase levels rise significantly. In one aspect, amylases and/or glucoamylases of the invention are added at this (or any other) stage of the process. The action of the amylase results in an increase in fermentable reducing sugars. This can be expressed as the diastatic power, DP, which can rise from around 80 to 190 in 5 days at 12° C.

Amylases and/or glucoamylases of the invention can be used in any beer producing process, as described, e.g., in U.S. Pat. Nos. 5,762,991; 5,536,650; 5,405,624; 5,021,246; 4,788,066.

In one aspect, one or more other enzymes are used in conjunction with a feed, feed or drink comprising enzymes of the invention, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Use in Drilling Well and Mining Operations

The invention also includes methods using enzymes of the invention in well and drilling operations, e.g., gas, oil or other drilling or mining operations. For example, in one aspect, enzymes of the invention are used to increase the flow of production fluids from a subterranean formation, e.g., a well or a mine. In one aspect, the enzymes of the invention are used to remove viscous polysaccharide-containing and/or starch-containing fluids that can be damaging, e.g., fluids formed during production operations. These polysaccharide-containing and/or starch-containing fluids can be found within a subterranean formation which surrounds a completed well bore. In one aspect, an amylase and/or a glucoamylase of the invention is used in an oil well drilling fluid to aid in the carrying away of drilling mud.

The invention provides methods for changing the viscosity of a composition comprising: providing a composition and the polypeptide of the invention, and a composition; and treating the composition with the polypeptide of the invention; and in one aspect, of the method, the composition comprises a soil or a drilling mud.

In one aspect, the use of these methods of the invention allows production fluids (comprising enzymes of the invention) to flow from the well bore or a mine. The methods can comprise reducing the flow of production fluids from the formation below expected flow rates and formulating an enzyme treatment by blending together an aqueous fluid and a polypeptide of the invention. The methods can comprise pumping the enzyme treatment to a desired location within the well bore or other drilled shaft and allowing the enzyme treatment to degrade the viscous, starch-containing, damaging fluid. The methods can comprise removing the fluid from the subterranean formation to the well or shaft surface. In one aspect, the enzyme treatment is effective to attack the alpha glucosidic linkages in the starch-containing fluid. In one aspect, amylases and/or glucoamylases of the invention are used in mine drilling, well drilling (e.g., gas or oil well drilling), and the like to carry away drilling mud, e.g., while drilling the hole (well bore or shaft).

The enzymes of the invention can be used in any well, shaft or mine drilling operation, many of which are well known in the art. For example, the invention provides methods of introducing an enzyme of the invention, which in one aspect can also comprise an oil or gas field production chemical, into a rock formation comprising oil and/or gas, which comprises passing a microemulsion comprising the enzyme (and, in one aspect, the chemical) down a production well and then into the formation. In one aspect, a production well is subjected to a "shut-in" treatment whereby an aqueous composition comprising an enzyme of the invention is injected into the production well under pressure and "squeezed" into the formation and held there. See, e.g., U.S. Pat. No. 6,581,687.

In one aspect, the amylases and/or glucoamylases of the invention used in gas, oil or other drilling or mining operations are active at high or low pH and/or high or low temperatures, e.g., amylases and/or glucoamylases of the invention used in these processes are active under conditions comprising about pH 6.5, pH 6, pH 5.5, pH 5, pH 4.5 or pH 4, or lower, or, under conditions comprising about pH 7, pH 7.5 pH 8.0, pH 8.5, pH 9, pH 9.5, pH 10, pH 10.5 or pH 11 or higher. In one aspect, the amylases and/or glucoamylases of the invention used in these processes are active under conditions comprising a temperature range of anywhere between about 0° C. to about 37° C., or, between about 37° C. to about 95° C. or more, or, between about 80° C. to about 120° C., e.g., 85° C., 90° C., 95° C., 98° C., 100° C., 105° C., 110° C., 115° C., 120° C. or more.

In one aspect, one or more other enzymes are used in conjunction with a composition comprising enzymes of the invention for use with these methods, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

In one aspect, enzymes or enzyme cocktails of the invention that are used in these gas, oil or other drilling or mining operations, or including any oil and gas well washing and/or fracturing processes, are active at high or low pH and/or high or low temperatures, e.g., polymer-degrading or polysaccharide-degrading ("polymer breaker") enzymes of this invention, which include using "cocktails" of these and other enzymes such as amylase, glucoamylase, xanthanase, glycosidase and/or cellulase enzymes, or a lignin degrading enzyme, alpha amylase, beta amylase, glucoamylase, dextrinase, cellulase, cellobiohydrolase, avicelase, carboxymethylcellulase, beta-glucanase, glucosidase, xylanase, mannanase, arabinofuranosidase, laccase, lignin peroxidase, pectinase, pectate lyase, xanthanase, xanthan lyase, xanthan depolymerase, pullulanase, lichenase, pachymanase, lipase, protease, proteinase, phytase, peptidase and catalase, which include using "cocktails" of these and other enzymes, are used in these processes are active under conditions comprising about pH 6.5, pH 6, pH 5.5, pH 5, pH 4.5, pH 4.0, pH 3.5, pH 3.0 or less (more acidic), or, under conditions comprising about pH 7, pH 7.5 pH 8.0, pH 8.5, pH 9, pH 9.5, pH 10, pH 10.5, pH 11.0, pH 11.5, pH 12, pH 12.5 or more (more basic). In one aspect, enzymes or enzyme cocktails of the invention used in these processes are active under conditions comprising a temperature range of anywhere between about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 120° C. or more.

In one embodiment, the "pH trigger mechanism" comprises use of a thermophilic enzymes, for example a "pyrolase" such as the polypeptide SEQ ID NO:4 and/or SEQ ID NO:6 (encoded, e.g., by SEQ ID NO:3 and SEQ ID NO:5, respectively). In one aspect, the invention provides a system comprising one or more enzymes entrained in a mud or its ingredients in a dry form, e.g., a guar gum powder, sand or a buffer salt. In one aspect, the enzyme remains dormant or "less active" because of low temperature of the mud, or remains dormant or "less active" because the amount of enzyme loading is adjusted such that no or less "premature" (unwanted) degradation (of substrate) occurs until the mud is heated to higher temperatures conducive to the activation of the enzyme(s). This embodiment can be referenced as "an entrained enzyme system with a temperature trigger mechanism".

In one aspect, the composition and methods of the invention are used to degrade polymers in a "mud", which in alternative embodiments comprises a water-containing medium in which enzyme, polysaccharide and other components are mixed. In one aspect, the composition and methods of the invention are used as a solution or a dry powder, which can be mixed with an ingredient or component of the "mud". In one aspect, the enzyme is incorporated/entrained into the ingredients of the mud prior to the actual mud preparation. For example, an exemplary formulation or mixture used to practice this invention comprises a starch, xanthan or cellulose powder mixed with one or more enzyme(s), or a mixture of buffer salts and enzyme(s), wherein each of such enzyme-containing ingredients can then be used to prepare the mud.

Use of Free and Immobilized Enzymes in Hydraulic Fracturing and Drilling Operations:

The invention provides compositions and methods comprising the inclusion of polymer-breaking (polymer-degrading), e.g., polysaccharide-degrading, enzymes in a free form or in an immobilized form, e.g., in an immobilized form as on a coating, e.g., of a particle, e.g., of a sand grain or a ceramic material such as a sintered bauxite.

In one aspect, the compositions and methods comprising the inclusion of polymer-breaking (polymer-degrading), e.g., polysaccharide-degrading, enzymes in or on a resin or similar material that coats particles, e.g., sand grains or a ceramic material such as a sintered bauxite; these particles (e.g., sand grains) can be used as the proppant or with a proppant (e.g., a resin-coated sand or high-strength ceramic materials) in a hydraulic fracturing fluid. In one aspect, a proppant used to practice this invention is a sized particles mixed with a fracturing fluid to hold fractures open after a hydraulic fracturing treatment. In addition to naturally occurring sand grains, man-made or specially engineered proppants, such as resin-coated sand or high-strength ceramic materials like sintered bauxite, can also be used. Proppant materials can be sorted for size and sphericity to provide an efficient conduit for production of fluid from the reservoir to the wellbore. After the settling of the sand in the well fissures and fractures, the resin-bound enzymes can diffuse out and work on the concentrated and unbroken polymer that is often deposited on the formation surface at the completion of fracturing operations. Thus, this aspect of the invention can effectively remove a polysaccharide, a xanthan or a guar, e.g., a guar filter cake, from fractured oil and gas wells, and/or can enhance the permeability of the fractured zone.

In one embodiment, during the hydraulic fracturing operations, large volumes of water, sand, auxiliary chemicals (including enzymes and the mixtures of enzymes of this invention) and a polysaccharide-based polymer (e.g., a guar and/or its derivatives) are mixed and injected under pressure into the oil and/or gas wells to 'fracture' the surrounding formation and enhance the flow of gas or oil into the wellbore. Enzymes and enzyme mixtures as described herein can be used to hydrolyze these polysaccharide polymers and reduce the viscosity of the fluid (used in the hydraulic fracturing operations) for better penetration into the formation and more effective flow back at the end of the operation.

In one embodiment, the compositions and methods of this invention are used in enzymatic hydrolysis of base polymers (e.g., polysaccharide-based polymers, such as guar, xanthan and/or their derivatives); practicing this invention can solve the problem where enzymatic hydrolysis of these base polymers may be incomplete to leave some "unbroken" polymer in the fluid used in the hydraulic fracturing operations. As the fluid water content is lost to the formation the fluid becomes more concentrated and the unbroken polymers form a thick filter cake; this filter cake plugs the formation pores and reduces the flow of oil or gas into the wellbore—in one embodiment, the compositions and methods of this invention are used to break up these filter cake plugs.

Fracturing fluids contain large amounts of sand, commonly referred to as the proppant. As the fluid is pumped into the well, the proppant settles into the fissures and fractures and prevents them from closing. This helps enhance the porosity and permeability of the formation for better gas/oil flow. The sand grains are often coated with different industrial resins to increase their mechanical strength and prevent them from crushing under formation pressure. Thus, in one embodiment, the invention provides compositions and methods using free or immobilized polymer-degrading ("polymer-breaking") enzymes around, in or on the coating material of the sand. In one aspect, this is done by entrapment of the enzyme in the resin or by immobilization on the coating surface. Thus, in this aspect, enzyme(s) used to practice this invention can remain in contact with the filter cake thereby providing continual hydrolysis of the concentrated polymer, removing the cake from the fractures, and enhancing the permeability of the fractured formation.

In on aspect, the invention provides methods using these described enzyme in drilling operations, e.g., a typical drilling operation, where a well is created by drilling a hole 5 to 30 inches (13-76 cm) diameter into the earth with an oil rig, which rotates a drill bit. After the hole is drilled, a steel pipe (casing) slightly smaller than the hole is placed in the hole, and secured with cement. The casing provides structural integrity to the newly drilled wellbore in addition to isolating potentially dangerous high pressure zones from each other and from the surface.

With these zones safely isolated and the formation protected by the casing, the well can be drilled deeper (into potentially more-unstable and violent formations) with a smaller bit, and also cased with a smaller size casing. A wells can have 2 to 5 sets of subsequently smaller hole sizes drilled inside one another, each cemented with casing.

To drill the well, the drill bit, aided by rotary torque and the compressive weight of drill collars above it, breaks up the earth. Drilling fluid, or "mud", comprising the inclusion of polymer-breaking (polymer-degrading), e.g., polysaccharide-degrading, enzymes and enzyme mixtures of this invention, in a free form or in an immobilized form, is pumped down the inside of the drill pipe. The fluid exits at the drill bit and aids to break up the rock, keeping pressure on top of the bit, as well as cleaning, cooling and lubricating the bit.

The generated rock "cuttings" are swept up by the drilling fluid as it circulates back to surface outside the drill pipe. Fluid comprising polymer-breaking (polymer-degrading), e.g., polysaccharide-degrading, enzymes and enzyme mixtures of this invention, in a free form or in an immobilized form, can be added at this stage, too.

The fluids then go over "shakers" which shakes out the cuttings over screens allowing the good fluid to return back into the pits. Fluid comprising polymer-breaking (polymer-degrading), e.g., polysaccharide-degrading, enzymes and enzyme mixtures of this invention, in a free form or in an immobilized form, can be added at this stage, too.

These processes of the invention can be facilitated by addition of polymer-breaking (polymer-degrading), e.g., polysaccharide-degrading, enzymes and enzyme mixtures of this invention, in a free form or in an immobilized form. The drilling rig can contain all necessary equipment to circulate the drilling fluid, hoist and turn the pipe, control downhole pressures, remove cuttings from the drilling fluid, and generate onsite power for these operations.

The enzymes, enzyme mixtures, and methods of the invention can be practiced with any drilling mud or drilling fluid (some prefer to reserve the term "drilling fluid" for more sophisticated and well-defined "muds"), or any fluid used in operations to drill boreholes into the earth. The enzymes, enzyme mixtures, and methods of the invention can be practiced while drilling oil and/or natural gas wells and on exploration drilling rigs, including use with simpler holes.

The enzymes, enzyme mixtures, and methods of the invention can be used in, mixed with and/or practiced together with any well or drilling operation, e.g., where any mud is used, including use of any of the three main classification schemes of mud, where "mud" is used broadly and is separated into 3 categories based on the main component that makes up the mud: (1) "Water Based Mud" (WBM), which can be subdivided into dispersed and non-dispersed muds; (2) "Non Aqueous" or more commonly "Oil Based Mud" (OBM), including synthetic oils (SBM); and/or (3) Gaseous or Pneumatic mud.

The enzymes, enzyme mixtures, and methods of the invention can be used in, mixed with and/or practiced together with any well or drilling operation, e.g., can also be used in or with:
production wells when they are drilled primarily for producing oil or gas, once the producing structure and characteristics are established,
appraisal wells when they are used to assess characteristics (such as flowrate) of a proven hydrocarbon accumulation,
exploration wells when they are drilled purely for exploratory (information gathering) purposes in a new area,
wildcat wells when a well is drilled, based on a large element of hope, in a frontier area where very little is known about the subsurface.

The enzymes, enzyme mixtures, and methods of the invention can be used in, mixed with and/or practiced together with any well or drilling operation, e.g., can also be used in conjunction with methods, equipment and/or drilling operations as described, e.g., in U.S. Patent Application Publication No. 20070089910, Hewson, et al., describing, e.g., methods of forming a supported subterranean well bore, and uses, e.g., a positive displacement mud motor.

The enzymes, enzyme mixtures, and methods of the invention can be used in, mixed with and/or practiced together with methods, equipment and/or drilling operations as described, e.g., in U.S. Patent Application Publication No. 20070084638, Bohnsack; C., et al., describing, e.g., a system for facilitating flow of settled solids with drilling fluid from a container, the system including pressure nozzle apparatus with at least one nozzle from which is flowable fluid under pressure, powered rotation apparatus for selectively rotating the pressure nozzle apparatus so that the at least one nozzle is movable within the container as fluid is pumped through the at least one nozzle into the container; and, in one aspect, translation apparatus for moving the pressure nozzle apparatus with respect to the container as fluid under pressure is pumped to the at least one rotating nozzle. Mud tanks and mud pits are also described, and the enzymes, enzyme mixtures, and methods of the invention can be used in or with any of these fluids, and/or in any mud tanks and mud pits used in these types of operations.

The enzymes, enzyme mixtures, and methods of the invention can be used in, mixed with and/or practiced together with methods, equipment and/or drilling operations as described, e.g., in U.S. Patent Application Publication No. 20070081157, Csutak; S., et al., describing, e.g., apparatus for estimating a property of a fluid downhole comprising an ultraviolet (UV) light source for inducing light into the fluid at a wavelength that produces Raman scattered light at wavelengths that are shorter than wavelengths of substantial fluorescence reflected from the fluid in response to the induced light; a detector that detects a spectrum of the Raman scattered light and provides signals in response to the detected spectrum; and a processor that processes the signals to provide an estimate of the a property of the fluid. The enzymes, enzyme mixtures, and methods of the invention can be used in or with any of these fluids, and/or in operations to estimate filtrate contamination in a formation fluid. For example, these methods include detecting Raman scatters at a plurality of wavelengths of at least one component present in an oil-based mud that is not naturally present in the formation, and enzymes, enzyme mixtures, and methods of the invention can be used to aid in the accuracy of this detection.

The enzymes, enzyme mixtures, and methods of the invention can be used in, mixed with and/or practiced together with methods, equipment and/or drilling operations as described, e.g., in U.S. Patent Application Publication No. 20070075706, Chen, S., et al., describing, e.g., methods of evaluating an earth formation comprising making measurements with a downhole tool in a borehole in the earth formation; measuring a Quality factor of an antenna of the downhole tool at depths where the measurements are made; and using the measured Q and a resistivity of a mud in the borehole and a formation resistivity, and/or a borehole size indicator (BSI), for estimating the other of the formation resistivity and BSI, including measuring the resistivity of the mud in the borehole. The enzymes, enzyme mixtures, and methods of the invention can be used in or with any of these fluids, and/or in operations to evaluate an earth formation.

The enzymes, enzyme mixtures, and methods of the invention can be used in, mixed with and/or practiced together with methods, equipment and/or drilling operations as described, e.g., in U.S. Patent Application Publication No. 20070068675, Barry, M., et al, describing, e.g., methods for drilling and completing a gravel packed well, comprising drilling a wellbore with a drilling fluid, conditioning the drilling fluid, running the gravel packing assembly tools to depth in the wellbore with the conditioned drilling-fluid, and gravel packing a wellbore interval with a completion-fluid. The completion fluid may be the same as the drilling-fluid. This method may be combined with alternate-path sand screen technology to ensure proper distribution of the gravel pack. The proper fluids for drilling, gravel packing and sand screens installation are essential for well completion success. Careful planning, well preparation and completion execution are required to increase completion productivity and longevity. Usually, a minimum of three fluids have been used to drill and complete gravel packed wells. The first fluid is a solids-laden drilling-fluid used to drill the completion interval. The second fluid is a solids-free completion-fluid used to displace the solids-laden drilling-fluid and to run sand-exclusion equipment and gravel packing tools in a generally solids-free environment. The third fluid is a carrier fluid for the gravel during gravel packing of the completion interval. The enzymes, enzyme mixtures, and methods of the invention can be used in or with any of these fluids (including solids-laden drilling-fluids, solids-free completion-fluids and/or carrier fluids), and/or in operations for drilling and completing a gravel packed well.

The enzymes, enzyme mixtures, and methods of the invention can be used in, mixed with and/or practiced together with methods, equipment and/or drilling operations as described, e.g., in U.S. Patent Application Publication No. 20070066491, Bicerano; J., et al., use of particles in the construction, drilling, completion and/or fracture stimulation of oil and natural gas wells; for example, as a proppant partial monolayer, a proppant pack, an integral component of a gravel pack completion, a ball bearing, a solid lubricant, a drilling mud constituent, and/or a cement additive, including use of thermoset polymer particles for use in applications requiring lightweight particles possessing high stiffness, strength, temperature resistance, and/or resistance to aggressive environments. The enzymes, enzyme mixtures, and methods of the invention can be used in or with any of these gravel packs, ball bearings, solid lubricants, drilling mud constituents, cement additives and/or the described thermoset polymer particles. The enzymes, enzyme mixtures, and methods of the invention can be used in or with nanofillers and/or nanocomposites, including heterogeneous nanocomposite morphologies.

The enzymes, enzyme mixtures, and methods of the invention can be used in, mixed with and/or practiced together with methods, equipment and/or drilling operations as described, e.g., in U.S. Patent Application Publication No. 20070039735, Robertson; B., et al., describing, e.g., methods of sealing a permeable zone within a subterranean formation, comprising: preparing a plugging composition comprising oil, clay, magnesium chloride, and magnesium oxide powder; and contacting the plugging composition with water in the subterranean formation such that the plugging composition forms a sealing mass, thereby substantially sealing a permeable zone within the subterranean formation.

The enzymes, enzyme mixtures, and methods of the invention can be used in, mixed with and/or practiced together with variable density drilling muds comprising compressible particulate materials, e.g., as described in U.S. Patent Application Publication No. 20070027036, Polizzotti; R., et al. The enzymes, enzyme mixtures, and methods of the invention can be used in or with, e.g., drilling muds comprising a compressible particulate material in the drilling mud, wherein density of the drilling mud changes due to a volume change of the compressible particulate material in response to pressure or temperature changes and wherein the compressible particulate material is configured to maintain the density of the drilling mud between a pore pressure gradient and a fracture gradient based on the volume change of the compressible particulate material in response to pressure changes at certain depths.

The enzymes, enzyme mixtures, and methods of the invention can be used to modify the viscosity of the drilling mud alone or in conjunction with the described (see Polizzotti; R., et al.) compressible materials, e.g., to place the fluid viscosity within pumpability requirements, and/or to adjust the pore pressure gradient and the fracture gradient. The enzymes, enzyme mixtures, and methods of the invention can be used to effect a volume change in the drilling mud, e.g., where the drilling mud rheology is configured to achieve a desired composite drilling mud rheology.

In one aspect, the enzymes, enzyme mixtures, and methods of the invention are used to alter the properties of the drilling mud to provide a desired composite a mud gel point, e.g., a mud gel point that can suspend rock cuttings in an annulus of a wellbore during drilling operations; and/or to alter the viscosity of the drilling mud in conjunction with, or alone (without), compressible hollow objects (see Polizzotti; R., et al.) to alter pumpability requirements.

In one aspect, the enzymes, enzyme mixtures, and methods of the invention are used to alter the properties well fluids comprising drilling muds, well cleanup fluids, workover fluids, spacer fluids, gravel pack fluids, acidizing fluids and/or fracturing fluids. In one aspect, the enzymes, enzyme mixtures, and methods of the invention are used to facilitate drilling, completing and/or stimulating a subterranean formation using a variable density fluid, and to modify the variable density fluid.

In one aspect, the enzymes, enzyme mixtures, and methods of the invention are used in methods of drilling, completing and/or stimulating subterranean formations using a variable density fluid, e.g., by modifying and/or "adjusting" the density of the fluid; for example, a method (see Polizzotti; R., et al.) comprising the steps of: introducing a fluid having a density that varies as a function of pressure into the subterranean formation, where the fluid comprises a base fluid and a portion of elastic particles; and drilling, completing and/or stimulating a subterranean formation using the variable density fluid (which can comprise the enzymes, enzyme mixtures of the invention, or have been modified by the methods of the invention).

In one aspect, the enzymes, enzyme mixtures, and methods of the invention are used with the methods and compositions as described in U.S. Pat. No. 4,099,583, describing, e.g., a dual gradient drilling system, where a lighter fluid is injected into the mud return annulus (typically in the riser) or other pathway to reduce the mud density from the injection point upwards, and the enzymes, enzyme mixtures, and methods of the invention can modify and/or "adjust" the density of this fluid.

In one aspect, the enzymes, enzyme mixtures, and methods of the invention are used with the methods and compositions as described in U.S. Pat. Nos. 6,530,437 and 6,588,501, describing a multi-gradient drilling method and an apparatus for reduction of hydrostatic pressure in sub sea risers; and U.S. Pat. Nos. 6,422,326, 6,156,708, 5,910,467 and 5,881,826, describing the addition of various fluid aphrons to drilling mud formulations.

In one aspect, the enzymes, enzyme mixtures, and methods of the invention are used with the methods and compositions as described in U.S. Pat. No. 6,497,289, describing use of solid expandable liners, e.g., as tubular systems that are run into a well and expanded.

In alternative embodiments, the enzymes, enzyme mixtures, and methods of the invention are used to tailor drilling mud density with depth so that the effective mud weight remains between the pore pressure and the fracture gradient at all depths. The required variation in mud density can be achieved by changing the properties of fluids with the enzymes, enzyme mixtures, and methods of the invention to modify/change volume and density, to effect a change in response to pressure. The enzymes, enzyme mixtures, and methods of the invention can be used with any particulate components, e.g., various shapes, such as spheres, cubes, pyramids, oblate or prolate spheroids, cylinders, pillows and/or other shapes or structures. The enzymes, enzyme mixtures, and methods of the invention can be used with any particulate components, e.g., compressible hollow objects which are filled with pressurized gas, or compressible solid materials or objects as described in Polizzotti; R., et al., supra.

In alternative aspects, the enzymes, enzyme mixtures, and methods of the invention can be used in or with any well or drilling operation, e.g., including directional drilling, sometimes known as slant drilling, to drill non-vertical wells; including used in any of directional drillings three main groups; Oilfield Directional Drilling, Utility Installation Directional Drilling (commonly known as H.D.D./Horizontal Directional Drilling/Directional boring); and/or in-seam directional drilling (Coal-Bed methane).

In one aspect, the enzymes, enzyme mixtures, and methods of the invention can be used in conjunction with well logging, a technique used in the oil and gas industry for recording rock and fluid properties to find hydrocarbon zones in the geological formations within the Earth's crust. Logging can be performed to measure the effect of practicing the methods of this invention, e.g., pumping fluids comprising the enzymes or enzyme mixtures of this invention into a well. A logging procedure may consist of lowering a 'logging tool' on the end of a wireline into an oil well (or hole) to measure the rock and fluid properties of the formation. An interpretation of these measurements is then made to locate and quantify potential depth zones containing oil and gas (hydrocarbons). Logging tools developed over the years measure the electrical, acoustic, radioactive, electromagnetic, and other properties of the rocks and their contained fluids. Logging is usually performed as the logging tools are pulled out of the hole. This data is recorded to a printed record called a Well Log' and is normally transmitted digitally to office locations. Well logging is performed at various intervals during the drilling of the well and when the total depth is drilled, which could range in depths from 300 m to 8000 m (1000 ft to 25,000 ft) or more.

In addition to the methods, enzymes or enzymes mixtures described herein, the methods, the enzyme muds or other drilling fluids used to practice this invention can comprise (use of) a water-based drilling mud that can comprise a bentonite clay (gel), and in some aspects, also comprising additives such as barium sulfate (barite), calcium carbonate (chalk) or hematite. Various thickeners also can be used to influence the viscosity of the fluid, e.g., lignosulfonates, xanthan gum, guar gum, glycol, carboxymethylcellulose, polyanionic cellulose (PAC), or starch. The enzymes or enzymes mixtures described herein, used to practice this invention can be used to modify the properties of (e.g., the viscosity of) the fluids, e.g., to modify the properties of lignosulfonates, xanthan gum, guar gum, glycol, carboxymethylcellulose, polyanionic cellulose (PAC), or starch.

The methods, enzymes or enzymes mixtures described herein, used to practice this invention can be used to modify the properties of deflocculants, which are used to reduce viscosity of clay-based muds; anionic polyelectrolytes, e.g., acrylates, polyphosphates, lignosulfonates (Lig) or tannic acid derivates such as Quebracho (red mud was the name for a Quebracho-based mixture, named after the color of the red tannic acid salts; it was commonly used in 1940s to 1950s, then became obsolete when lignosulfates became available).

The methods, enzymes or enzymes mixtures described herein, used to practice this invention can be used in (e.g., added to) water injectors for injecting water into a formation, either to maintain reservoir pressure or simply to dispose of water produced with a hydrocarbon (e.g., because even after treatment, it would be too oily and too saline to be considered clean for dumping, e.g., dumping overboard or into a fresh water source in the case of onshore wells). Thus, the methods and compositions (e.g., mixtures of enzymes, immobilized enzymes) of this invention are used with water injection as an element of reservoir management and produced water disposal.

The methods, enzymes or enzymes mixtures described herein, used to practice this invention can be used in (e.g., added to) aquifer producers, e.g., as in intentionally producing reservoir water for re-injection (e.g., in a well bore) to manage pressure; this is in effect moving reservoir water from where it is not as useful, to where it is more useful. These wells will generally only be used if produced water from the oil or gas producer is insufficient for reservoir management purposes. Thus, in one aspect, the methods and compositions (e.g., mixtures of enzymes, immobilized enzymes) of this invention are used with aquifer produced water and/or sea water.

Delayed Release Compositions

The invention provides delayed release or "controlled release" compositions comprising a desired composition coated by a latex polymer, e.g., a latex paint, or equivalent. The delayed release/controlled release compositions of the invention can comprise any desired composition, including enzymes or any active ingredient, including small molecules, drugs, polysaccharides, lipids, nucleic acids, vitamins, antibiotics, insecticides, and the like. In one aspect, the coating will not readily dissolve at a relatively low temperature but will decompose to release the desired composition (e.g., enzyme) at a relatively higher temperature.

The invention provides methods for the delayed release/controlled release of compositions wherein the composition is coated by a latex polymer, e.g., a latex paint, or equivalent.

The delayed release/controlled release compositions and methods of the invention can be used for a variety of medical and industrial applications, for example, in one aspect, delayed release/controlled release enzyme compositions of the invention comprise enzymes involved in guar fracturing fluids in enhanced oil recovery operations.

The oilfield guar degrading application of the invention is facilitated by a coating that will not readily dissolve at low temperature but will decompose to release the enzyme at higher temperatures.

In another aspect, the delayed release/controlled release enzyme compositions of the invention comprise animal feeds or nutritional supplements comprising, e.g., enzymes, vitamins, antibiotics and/or other food, drug or nutritional supplements. These active compounds in the animal feeds or nutritional supplements are protected from pelleting conditions or gastric digestion by the coating on a delayed release/controlled release composition of the invention.

In one aspect, the release is a temperature activated release, e.g., the desired composition (e.g., enzyme) is released at an elevated temperature, e.g., between about 37° C. to about 95° C. or more, e.g., 85° C., 90° C., 95° C., 98° C., 100° C. or more. The rate of release can be controlled by the thickness or amount of "barrier" or latex polymer, applied to the desired composition, e.g., a pellet or matrix comprising the desired composition. Thus, the invention provides pellets or matrices having a range of thicknesses of latex polymer or equivalent and methods of using them.

The invention provides delayed release/controlled release enzyme compositions, e.g., in one aspect, comprising an enzyme of the invention. In one aspect, the invention provides an enzyme (e.g., an enzyme of the invention), or a pelleted composition comprising an enzyme (e.g., an enzyme of the invention), coated with a latex polymer, e.g., a latex paint, or equivalent. In one aspect, the invention provides methods of making delayed release enzyme compositions comprising coating an enzyme (e.g., an enzyme of the invention), or a pelleted composition comprising an enzyme (e.g., an enzyme of the invention), with a latex polymer, e.g., a latex paint, or equivalent. In one aspect, the invention provides methods of making delayed release/controlled release compositions comprising coating a desired compound with a latex polymer, e.g., a latex paint, or equivalent.

Latex polymers that are used in the delayed release/controlled release compositions (e.g., delayed release/controlled release enzyme compositions) and methods of the invention include, but are not limited to, various types such as the following: acrylics; alkyds; celluloses; coumarone-indenes; epoxys; esters; hydrocarbons; maleics; melamines; natural resins; oleo resins; phenolics; polyamides; polyesters; rosins; silicones; styrenes; terpenes; ureas; urethanes; vinyls; and the like. Latex polymers that are used in the delayed release compositions and methods of the invention also include, but are not limited to, one or more homo- or copolymers containing one or more of the following monomers: (meth)acrylates; vinyl acetate; styrene; ethylene; vinyl chloride; butadiene; vinylidene chloride; vinyl versatate; vinyl propionate; t-butyl acrylate; acrylonitrile; neoprene; maleates; fumarates; and the like, including plasticized or other derivatives thereof.

The amount of latex polymer used in the latex composition of the invention is not critical, but may be any amount following well established procedures using latex polymers. In alternative aspects, the amount of dry latex polymer is at least about 1, or, from about 2 to about 50, or, from about 3 to about 40 weight percent of the total latex composition. The latex composition of the invention may optionally contain other components such as those generally used in latex compositions. These additional components include, but are not limited to, one or more of the following: solvents such as aliphatic or aromatic hydrocarbons, alcohols, esters, ketones, glycols, glycol ethers, nitroparaffins or the like; pigments; fillers, dryers; flatting agents; plasticizers; stabilizers; dispersants; surfactants; viscosifiers including polymeric associative thickeners, polysaccharide-based thickeners and so on; suspension agents; flow control agents; defoamers; antiskinning agents; preservatives; extenders; filming aids; crosslinkers; surface improvers; corrosion inhibitors; and other ingredients useful in latex compositions. In one aspect, latex compositions of the invention having improved rheology and stability are provided by combining the latex polymer and a polysaccharide with water following established procedures. See, e.g., U.S. Pat. Nos. 6,372,901; 5,610,225.

In one aspect, in making a pelleted or matrix-comprising composition of the invention comprising an active composition, e.g., an enzyme (e.g., an enzyme of the invention), coated with a latex polymer, e.g., a latex paint, or equivalent, the active composition (e.g., enzyme) is embedded in the body of the pellet (in one aspect, a majority, or all, of the active composition (e.g., enzyme) is embedded in the pellet. Thus, harsh chemicals, e.g., the latex coating, which may be an inactivator of the desired, active ingredient, can be used to coat the surface of the pellet or matrix. The composition of the coating can be broken down by agents such as heat, acid, base, pressure, enzymes, other chemicals and the like, to have a controlled release of the desired enzymatic activity triggered by the exposure to the coating-degrading agent.

In one aspect, an active composition, e.g., an enzyme (e.g., an enzyme of the invention, or another enzyme, e.g., a mannanase), is dispersed in a corn term meal and/or a corn starch matrix (e.g., as a pellet). This mixture (e.g., pellet) disintegrates within ten minutes in room temperature (e.g., about 22° C.) water to release all (100%) of the active composition, e.g., releases all of the enzymatic activity. At higher temperatures, the rate of release increases. This is not an acceptable rate of disintegration for many uses.

However, as a delayed release/controlled release composition of the invention, i.e., when this mixture is coated with a latex polymer, e.g., a latex paint, or equivalent, the disintegration of the mixture (e.g., pellet, matrix) is delayed. The rate and extent of release can be controlled by the thickness of the coating (barrier) applied to the pellet or matrix. For example, a coated particle will release only 30% of the activity after six hours in 22° C. water. At 60° C., 50% of the enzyme is released in 90 minutes. At 80° C., 80% of the enzyme is released during one hour.

In one aspect, one or more other enzymes are added to a delayed release/controlled release composition of the invention, e.g., including other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Biomass Conversion and Production of Clean Bio Fuels

The invention provides enzymes and methods for the conversion of biomass to fuels (e.g., bioethanol, biopropanol, biobutanol, or biodiesel) and chemicals. Thus, the compositions and methods of the invention provide effective and sustainable alternatives to use of petroleum-based products. The invention provides organisms expressing enzymes of the invention for participation in chemical cycles involving natural biomass conversion. In one aspect, enzymes and methods for the conversion are used in enzyme ensembles for the efficient depolymerization of biomass polymers to metabolizable carbon moieties. As discussed above, the invention provides methods for discovering and implementing the most effective of enzymes to enable these important new "biomass conversion" and alternative energy industrial processes.

In one aspect, the polypeptides of the invention are used in processes for converting lignocellulosic and/or starch biomass to ethanol. The invention also provides processes for making ethanol ("bioethanol"), propanol ("biopropanol"), butanol ("biobutanol"), or diesel fuel ("biodiesel"), from compositions comprising starch and/or lignocellulosic biomass. The lignocellulose and/or starch biomass material can be obtained from agricultural crops, as a byproduct of food or feed production, or as lignocellulosic waste products, such as plant residues and waste paper. Examples of suitable plant residues for treatment with polypeptides of the invention include stems, leaves, hulls, husks, cobs and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials.

In one aspect, the enzymes and methods of the invention can be used in conjunction with more "traditional" means of making ethanol from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506; 6,423,145.

Another exemplary method that incorporates use of enzymes of the invention comprises catalyzing the hydrolysis of polysaccharides comprising glucose monomers, such as starch (a polymer of glucose monomers joined by 1,4-alpha or 1,6-alpha linkages), into sugars; this can be used in conjunction with enzyme for hydrolyzing lignocellulosic material containing hemicellulose, cellulose and lignin. In one aspect, the biomass is subjected to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose, which can be hydrolyzed with enzymes of this invention. See, e.g., U.S. Pat. No. 5,536,325. Enzymes of the invention can be added at any stage of this exemplary process.

Another exemplary method incorporating enzymes of the invention comprises processing a lignocellulose-containing biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention comprises prehydrolyzing lignocellulosic material in a prehydrolysis reactor; adding an acidic liquid to the solid lignocellulosic material to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

Methods of the invention for the enzymatic degradation of lignocellulose, e.g., for production of ethanol from lignocellulosic material, can also comprise use of ultrasonic treatment of the biomass material; see, e.g., U.S. Pat. No. 6,333,181.

Another exemplary process for making a biofuel comprising, e.g., a bioethanol, biopropanol, biobutanol, or a biodiesel, using enzymes of the invention comprises pretreating a starting material comprising a lignocellulosic feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., an amylase or a glucoamylase, of this invention. U.S. Pat. No. 6,090,595.

Exemplary conditions for enzyme hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

In one aspect of these biofuel (such as a bioethanol, biopropanol, biobutanol, or a biodiesel) generating processes of the invention using at least one enzyme of the invention, one or more other enzymes are added, e.g., other amylases, beta-galactosidases, catalases, laccases, cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1, 3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Thus, the invention provides methods for processing a biomass material comprising lignocellulose comprising contacting a composition comprising a polypeptide of the invention, wherein optionally the biomass material comprises or is derived from an agricultural crop, or is a byproduct of a food or a feed production, or is a lignocellulosic waste product, or is a plant residue or a waste paper or waste paper product, and optionally the polypeptide has activity comprising amylase, glucoamylase, glucosidase, e.g. alpha-glucosidase or beta-glucosidase activity, and optionally the plant residue comprise stems, leaves, hulls, husks, cobs, wood, wood chips, wood pulp and sawdust, and optionally the paper waste comprises discarded or used photocopy paper, computer printer paper, notebook paper, notepad paper, typewriter paper, newspapers, magazines, cardboard and paper-based packaging materials, and optionally the processing of the biomass material generates a bioethanol. The invention provides biomass material comprising a polypeptide of the invention.

The invention provides methods for making biofuel (such as a bioethanol, biopropanol, biobutanol, or a biodiesel) comprising contacting a composition comprising a fermentable sugar with a polypeptide of the invention, wherein optionally the composition comprising a fermentable sugar comprises a plant, plant product or plant derivative, and optionally the plant or plant product comprises cane sugar plants or plant products, beets or sugarbeets, wheat, corn, soybeans, potato, rice or barley, and optionally the polypeptide has activity comprising amylase, glucoamylase, glucosidase, e.g. alpha-glucosidase or beta-glucosidase activity.

The invention provides methods for making a fuel (such as a bioethanol, biopropanol, biobutanol, or a biodiesel) comprising contacting a composition comprising a fermentable sugar with a polypeptide of the invention, wherein optionally the composition comprising a fermentable sugar comprises a plant, plant product or plant derivative, and optionally the plant or plant product comprises cane sugar plants or plant products, beets or sugarbeets, wheat, corn, soybeans, potato, rice or barley, and optionally the polypeptide has activity comprising amylase, glucoamylase, glucosidase, e.g. alpha-glucosidase or beta-glucosidase activity, and optionally the fuel comprises a bioethanol or a gasoline-ethanol mix. The invention provides fuels comprising a polypeptide of the invention, wherein optionally the polypeptide has activity comprising amylase, glucoamylase, glucosidase, e.g. alpha-glucosidase or beta-glucosidase activity, wherein optionally the fuel is derived from a plant material, which optionally comprises potatoes, soybean (rapeseed), barley, rye, corn, oats, wheat, beets or sugar cane, and optionally the fuel comprises a bioethanol, biopropanol, biobutanol, biodiesel and/or a gasoline-ethanol mix.

In another aspect, plant material comprising the enzymes described herein can be used in an industrial process to produce fuel or energy. Enzymes expressed in plants can be added to, mixed into or sprayed onto feedstock material. Alternatively, the enzymes could be directly expressed in the feedstock material. In one embodiment, plant material expressing enzymes could be ground, milled, heated or the like, in order to disrupt the physical integrity of the plant cells or organs that contain the enzyme, thereby releasing the enzyme to come in contact with the substrate. Exemplary sources of plant material include, but are not limited to, maize, alfalfa, sunflower, Brassica, soybean, cotton, safflower, peanut, sorghum, wheat, oat, rye, millet, barley, rice, conifers, grasses, e.g., switch grass and Miscanthus, legume crops, e.g., pea, bean and soybean, starchy tuber/roots, e.g., potato, sweet potato, cassaya, taro, canna and sugar beet and the like.

The invention provides polypeptide, including amylases and/or glucoamylases of the invention and antibodies, and methods for the conversion of a biomass or any lignocellulosic material (e.g., any composition comprising cellulose, hemicellulose and lignin), to a fuel (e.g., bioethanol, biopropanol, biobutanol, biopropanol, biomethanol, biodiesel), in addition to feeds, foods and chemicals. For example, in one aspect, an enzyme of the invention has β-glucosidase activity to liberate D-glucose from cellobiose dimers. In one aspect, the enzymes have exo- or endo-beta-glucanase activity.

Thus, the compositions and methods of the invention provide effective and sustainable alternatives or adjuncts to use of petroleum-based products, e.g., as a mixture of a biofuel such as biomethanol, bioethanol, biopropanol, biobutanol, and the like, to diesel fuel, gasoline, kerosene and the like. The invention provides organisms expressing enzymes of the invention for participation in chemical cycles involving natural biomass conversion. In one aspect, enzymes and methods for the conversion are used in enzyme ensembles for the efficient depolymerization of polysaccharides, cellulosic and/or hemicellulosic polymers to metabolizeable (e.g., fermentable) carbon moieties. The invention provides methods for discovering and implementing the most effective of enzymes to enable these important new "biomass conversion" and alternative energy industrial processes.

The compositions and methods of the invention can be used to provide effective and sustainable alternatives or adjuncts to use of petroleum-based products, e.g., as a mixture of bioethanol, biopropanol, biobutanol, biopropanol, biomethanol and/or biodiesel and gasoline. The invention provides organisms expressing enzymes of the invention for participation in chemical cycles involving natural biomass conversion. The invention provides methods for discovering and implementing the most effective of enzymes to enable these important new "biomass conversion" and alternative energy industrial processes.

The invention provides methods, enzymes and mixtures of enzymes or "cocktails" of the invention, for processing a material, e.g. a biomass material, comprising a cellooligsaccharide, an arabinoxylan oligomer, a lignin, a lignocellulose, a xylan, a glucan, a cellulose and/or a fermentable sugar comprising contacting the composition with a polypeptide of the invention, or a polypeptide encoded by a nucleic acid of the invention, wherein optionally the material is derived from an agricultural crop (e.g., wheat, barley, potatoes, switchgrass, poplar wood), is a byproduct of a food or a feed production, is a lignocellulosic waste product, or is a plant residue or a waste paper or waste paper product, and optionally the plant residue comprise stems, leaves, hulls, husks, corn or corn cobs, corn stover, corn fiber, hay, straw (e.g. rice straw or wheat straw), sugarcane bagasse, sugar beet pulp, citrus pulp, and citrus peels, wood, wood thinnings, wood chips, wood pulp, pulp waste, wood waste, wood shavings and sawdust, construction and/or demolition wastes and debris (e.g. wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g. the paper fraction of municipal solid waste, municipal wood waste, and municipal green waste, along with other materials containing sugar, starch, and/or cellulose can be used. Optionally the processing of the material, e.g. the biomass material, generates a bioalcohol, e.g., a bioethanol, biomethanol, biobutanol or biopropanol.

Alternatively, the polypeptide of the invention may be expressed in the biomass plant material or feedstock itself.

The methods of the invention also include taking the converted lignocellulosic material (processed by enzymes of the invention) and making it into a fuel (e.g. a bioalcohol, e.g., a bioethanol, biomethanol, biobutanol or biopropanol, or biodiesel) by fermentation and/or by chemical synthesis. In one aspect, the produced sugars are fermented and/or the non-fermentable products are gasified.

The methods of the invention also include converting algae, virgin vegetable oils, waste vegetable oils, animal fats and greases (e.g. tallow, lard, and yellow grease), or sewage, using enzymes of the invention, and making it into a fuel (e.g. a bioalcohol, e.g., a bioethanol, biomethanol, biobutanol or biopropanol, or biodiesel) by fermentation and/or by chemical synthesis or conversion.

The enzymes of the invention (including, for example, organisms, such as microorganisms, e.g., fungi, yeast or bacteria, making and in some aspects secreting recombinant enzymes of the invention) can be used in or included/integrated at any stage of any biomass conversion process, e.g., at any one step, several steps, or included in all of the steps, or all of the following methods of biomass conversion processes, or all of these biofuel alternatives:

Direct combustion: the burning of material by direct heat and is the simplest biomass technology; can be very economical if a biomass source is nearby.

Pyrolysis: is the thermal degradation of biomass by heat in the absence of oxygen. In one aspect, biomass is heated to a temperature between about 800 and 1400 degrees Fahrenheit, but no oxygen is introduced to support combustion resulting in the creation of gas, fuel oil and charcoal.

Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic digestion: converts organic matter to a mixture of methane, the major component of natural gas, and carbon dioxide. In one aspect, biomass such as waterwaste (sewage), manure, or food processing waste, is mixed with water and fed into a digester tank without air.

Fermentation

Alcohol Fermentation: fuel alcohol is produced by converting cellulosic mass and/or starch to sugar, fermenting the sugar to alcohol, then separating the alcohol water mixture by distillation. Feedstocks such as dedicated crops (e.g., wheat, barley, potatoes, switchgrass, poplar wood), agricultural residues and wastes (e.g. rice straw, corn stover, wheat straw, sugarcane bagasse, rice hulls, corn fiber, sugar beet pulp, citrus pulp, and citrus peels), forestry wastes (e.g. hardwood and softwood thinnings, hardwood and softwood residues from timber operations, wood shavings, and sawdust), urban wastes (e.g. paper fraction of municipal solid waste, municipal wood waste, municipal green waste), wood wastes (e.g. saw mill waste, pulp mill waste, construction waste, demolition waste, wood shavings, and sawdust), and waste paper or other materials containing sugar, starch, and/or cellulose can be converted to sugars and then to alcohol by fermentation with yeast. Alternatively, materials containing sugars can be converted directly to alcohol by fermentation.

Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.

Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.

Hydrolysis: includes hydrolysis of a compound, e.g., a biomass, such as a lignocellulosic material, catalyzed using an enzyme of the instant invention.

Congeneration: is the simultaneous production of more than one form of energy using a single fuel and facility. In one aspect, biomass cogeneration has more potential growth than biomass generation alone because cogeneration produces both heat and electricity.

In one aspect, the polypeptides of the invention have enzymatic activity (including, e.g., an amylase or a glucoamylase activity) for generating a fuel (e.g. a bioalcohol, e.g., a bioethanol, biomethanol, biobutanol or biopropanol, or biodiesel) from an organic material, e.g., a biomass, such as compositions derived from plants and animals, including any agricultural crop or other renewable feedstock, an agricultural residue or an animal waste, the organic components of municipal and industrial wastes, or construction or demolition wastes or debris, or microorganisms such as algae or yeast.

In one aspect, polypeptides of the invention are used in processes for converting lignocellulosic biomass to a fuel (e.g. a bioalcohol, e.g., a bioethanol, biomethanol, biobutanol or biopropanol, or biodiesel), or otherwise are used in processes for hydrolyzing or digesting biomaterials such that they can be used as a fuel (e.g. a bioalcohol, e.g., a bioethanol, biomethanol, biobutanol or biopropanol, or biodiesel), or for making it easier for the biomass to be processed into a fuel.

In an alternative aspect, polypeptides of the invention, including the mixture of enzymes or "cocktails" of the invention, are used in processes for a transesterification process reacting an alcohol (like ethanol, propanol, butanol, propanol, methanol) with a triglyceride oil contained in a vegetable oil, animal fat or recycled greases, forming fatty acid alkyl esters (biodiesel) and glycerin. In one aspect, biodiesel is made from soybean oil or recycled cooking oils. Animal's fats, other vegetable oils, and other recycled oils can also be used to produce biodiesel, depending on their costs and availability. In another aspect, blends of all kinds of fats and oils are used to produce a biodiesel fuel of the invention.

Enzymes of the invention, including the mixture of enzymes or "cocktails" of the invention, can also be used in glycerin refining. The glycerin by-product contains unreacted catalyst and soaps that are neutralized with an acid. Water and alcohol are removed to produce 50% to 80% crude glycerin. The remaining contaminants include unreacted fats and oils, which can be processes using the polypeptides of the invention. In a large biodiesel plants of the invention, the glycerin can be further purified, e.g., to 99% or higher purity, for the pharmaceutical and cosmetic industries.

Fuels (including bioalcohols such as bioethanols, biomethanols, biobutanols or biopropanols, or biodiesels) made using the polypeptides of the invention, including the mixture of enzymes or "cocktails" of the invention, can be used with fuel oxygenates to improve combustion characteristics. Adding oxygen results in more complete combustion, which reduces carbon monoxide emissions. This is another environmental benefit of replacing petroleum fuels with biofuels (e.g., a fuel of the invention). A biofuel made using the compositions and/or methods of this invention can be blended with gasoline to form an E10 blend (about 5% to 10% ethanol and about 90% to 95% gasoline), but it can be used in higher concentrations such as E85 or in its pure form. A biofuel made using the compositions and/or methods of this invention can be blended with petroleum diesel to form a B20 blend (20% biodiesel and 80% petroleum diesel), although other blend levels can be used up to B100 (pure biodiesel).

The invention also provides processes for making biofuels (including bioalcohols such as bioethanols, biomethanols, biobutanols or biopropanols, or biodiesels) from compositions comprising lignocellulosic biomass. The lignocellulose biomass material can be obtained from agricultural crops, as a byproduct of food or feed production, or as lignocellulosic waste products, such as plant residues, waste paper or construction and/or demolition wastes or debris. Examples of suitable plant sources or plant residues for treatment with polypeptides of the invention include kelp, algae, grains, seeds, stems, leaves, hulls, husks, corn cobs, corn stover, straw, grasses (e.g., Indian grass, such as *Sorghastrum nutans*; or, switch grass, e.g., *Panicum* species, such as *Panicum virgatum*), and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials. Examples of construction and demolition wastes and debris include wood, wood scraps, wood shavings and sawdust.

In one embodiment, the enzymes, including the mixture of enzymes or "cocktails" of the invention, and methods of the invention can be used in conjunction with more "traditional" means of making ethanol, methanol, propanol, butanol, propanol and/or diesel from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506 and 6,423,145.

Another exemplary method that incorporated use of enzymes of the invention, including the mixture of enzymes or "cocktails" of the invention, comprises hydrolyzing lignocellulosic material containing hemicellulose, cellulose and lignin, or any other polysaccharide that can be hydrolyzed by an enzyme of this invention, by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention (including the invention's mixtures, or "cocktails" of enzymes) can be added at any stage of this exemplary process.

Another exemplary method that incorporated use of enzymes of the invention, including the mixture of enzymes or "cocktails" of the invention, comprises processing a lignocellulose-containing biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention, including the mixture of enzymes or "cocktails" of the invention, comprises prehydrolyzing lignocellulosic material in a prehydrolysis reactor; adding an acidic liquid to the solid lignocellulosic material to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

In one aspect, methods of the invention for the enzymatic degradation of lignocellulose, e.g., for production of biofuels (including bioalcohols such as bioethanols, biomethanols, biobutanols or biopropanols, or biodiesels) from lignocellulosic material, can also comprise use of ultrasonic treatment of the biomass material; see, e.g., U.S. Pat. No. 6,333,181.

In another aspect, methods of the invention for producing biofuels (including bioalcohols such as bioethanols, biomethanols, biobutanols or biopropanols, or biodiesels) from a cellulosic substrate comprise providing a reaction mixture in the form of a slurry comprising cellulosic substrate, an enzyme of this invention and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260). In one aspect, experiment or theoretical calculations can determine an optimum feeding frequency. In one aspect, additional quantities of the cellulosic substrate and the enzyme are provided into the reaction vessel at an interval(s) according to the optimized feeding frequency.

One exemplary process for making biofuels (including bioalcohols such as bioethanols, biomethanols, biobutanols or biopropanols, or biodiesels) of the invention is described in U.S. Pat. App. Pub. Nos. 20050069998; 20020164730; and in one aspect comprises stages of grinding the lignocellulosic biomass (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press, introducing the solid fraction in a fermentation deposit and adding one or more enzymes of the invention, e.g., an amylase, glucoamylase, and/or glucosidase enzyme (e.g., dissolved in citrate buffer pH 4.8).

Another exemplary process for making biofuels (including bioalcohols such as bioethanols, biomethanols, biobutanols or biopropanols, or biodiesels) of the invention comprising bioethanols, biomethanols, biobutanols or biopropanols using enzymes of the invention comprises pretreating a starting material comprising a lignocellulosic feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for using enzymes of the invention in the hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

Amylases and/or glucoamylases of the invention can be used in the conversion of biomass to fuels, and in the production of ethanol, e.g., as described in PCT Application Nos. WO0043496 and WO8100857. Amylases and/or glucoamylases of the invention can be used to produce fermentable sugars and glucan-containing biomass that can be converted into fuel ethanol.

Pharmaceutical Compositions, Disinfectants and Dietary Supplements

The invention also provides pharmaceutical compositions, disinfectants and dietary supplements (e.g., dietary aids) comprising enzymes of the invention (e.g., enzymes having amylase, glucoamylase or glucosidase activity). In one aspect, the pharmaceutical compositions and dietary supplements (e.g., dietary aids) are formulated for oral ingestion, e.g., to improve the digestibility of foods and feeds having a high starch, cellulose or lignocellulosic component.

Periodontal treatment compounds can comprise an enzyme of the invention, e.g., as described in U.S. Pat. No. 6,776,979. Compositions and methods for the treatment or prophylaxis of acidic gut syndrome can comprise an enzyme of the invention, e.g., as described in U.S. Pat. No. 6,468,964.

In another aspect, wound dressings, implants and the like comprise antimicrobial (e.g., antibiotic-acting) enzymes, including an enzyme of the invention. Enzymes of the invention can also be used in alginate dressings, antimicrobial barrier dressings, burn dressings, compression bandages, diagnostic tools, gel dressings, hydro-selective dressings, hydrocellular (foam) dressings, hydrocolloid dressings, I.V dressings, incise drapes, low adherent dressings, odor absorbing dressings, paste bandages, post operative dressings, scar management, skin care, transparent film dressings and/or wound closure. Enzymes of the invention can be used in wound cleansing, wound bed preparation, to treat pressure ulcers, leg ulcers, burns, diabetic foot ulcers, scars, IV fixation, surgical wounds and minor wounds. Enzymes of the invention can be used to in sterile enzymatic debriding compositions, e.g., ointments. In various aspects, the cellulase is formulated as a tablet, gel, pill, implant, liquid, spray, powder, food, feed pellet or as an encapsulated formulation.

Biodefense Applications

In other aspects, enzymes of the invention, e.g., amylases, glucoamylases or glucosidases, can be used in biodefense, e.g., destruction of spores or bacteria. Use of enzymes of the invention in biodefense applications offer a significant benefit, in that they can be very rapidly developed against any currently unknown or biological warfare agents of the future. In addition, enzymes of the invention can be used for decontamination of affected environments. In aspect, the invention provides a biodefense or bio-detoxifying agent comprising a polypeptide of the invention having amylase, glucoamylase or glucosidase activity.

The invention will be further described with reference to the following examples; however, it is to be understood that the invention is not limited to such examples.

EXAMPLES

Example 1

Identification and Characterization of Thermostable α-Amylases

The following example describes exemplary methods for determining if a polypeptide is within the scope of the invention. Screening programs can be carried out under neutral and low pH conditions. DNA sequence and bioinformatic analyses can classify amylases.

Biochemical Studies

Biochemical analysis of amylase genomic clones can be used to determine if any have a pH optima of less than pH 6. Lysates of these genomic clones can be tested for thermal tolerance by incubation at 70° C., 80° C., 90° C. or 100° C. for 10 minutes and measurement of residual activity at pH 4.5. Those clones retaining >50% activity after heat treatment at 80° C. are chosen for further analysis. These clones can be incubated at 90° C. for 10 minutes at pH 6.0 and 4.5 and tested for residual activity at pH 4.5. Thermal activity of the clones with residual activity after heat treatment at 90° C. at pH 4.5 can be measured at room temperature, 70° C. and 90° C. at pH 4.5.

In one aspect, starch-degrading enzymes are screened for activity on raw starch and 'resistant' starch for any form of hydrolase activity, including amylase, pullulanase, cyclodextrin glycosyltransferase, glucoamylases other any other glucosidase activity. In one aspect, the identified active enzymes are characterized, e.g., by specific activity and specificity for branched sugars and/or longer oligosaccharides.

In one aspect, fungal isolates are investigated for novel enzymes using, e.g., probes and/or discovery processes of the invention, for example, screening gDNA and/or cDNA libraries made from animals, microorganisms or insects, e.g., the gut contents of insects that attack and consume stored grains, including screening environmental libraries for under-represented enzymes. Combinations of enzymes can be evaluated.

In one aspect, stability tests are performed: e.g., purified enzymes in their own storage buffer, as compared to activity of fresh enzyme, if tested; e.g., aliquots of 20 ul stored at lower temperatures, e.g., at between about 4° C. to −20° C. to −80° C.; and in one aspect, activity is retested in granular and soluble starch monthly Amylases can be evaluated under a variety of conditions. In the following protocols N° 2 yellow dent corn can be used as a starch source.

Exemplary Liquefaction Assay

A starch slurry comprising 35% dry solids ("DS") is subjected to primary liquefaction for five minutes under various temperatures in the range of 95° C. to 119° C. (e.g., at about 110° C.), with an enzyme concentration of between 0.2 to 0.8 gram/kilogram (g/kg) starch DS, with added calcium in the range of between zero and 30 parts per million (ppm), at pH 4.0 to pH 5.6. Secondary liquefaction comprised conditions of 120 minutes at 95° C.

Exemplary Saccharification Assay

Saccharification is initially tested using 35% dry solids ("DS") (starch slurry) and glucoamylase AMG 300L (Novozymes A/S, Denmark) at 0.225 AGU/gram DS (AGU=amyloglucosidase, or glucoamylase, units), pH 4.3, at 60° C. for 44 hours.

In one aspect, exemplary amylases and/or glucoamylases of the invention are used in a dosage range of between 0.5 to 0.7 kg/MT DS starch.

The invention provides methods for making nutritive sweeteners using enzymes of the invention, e.g., processes comprising the above described liquefaction and saccharification protocols using any amylase and/or glucoamylase of the invention. In one aspect, the dosage range for an enzyme of the invention in these processes is between about 0.5 to 0.7 gram per kg starch DS, a jet temperature (e.g., using a jet cooker) of about 110° C., pH 4.5, no added calcium.

Dry Mill Ethanol Production

The invention provides methods for Dry Mill Ethanol Production using enzymes of the invention. In evaluating enzymes of the invention for use in Dry Mill Ethanol Production, particularly, liquefaction of dry mill corn flour, a bench scale reactor can be used with corn flour sourced from commercial dry mill TERMAMYL™ SC (Novozymes A/S, Denmark) amylase can be used as a competitive benchmark. In alternative aspects, optimum conditions are 85° C., pH 5.7. Five independent variables can be studied: temperature (in a range of between 80° C. to 100° C.), enzyme dose of between 0.2 to 1.0 g/kg starch, pH 4.4 to 6.0, calcium in a range between 0 ppm to 200 ppm, and a recycled backset between about 0% to 40%.

At 95° C., in some embodiments, amylases and/or glucoamylases of the invention can reduce viscosity of dry mill corn flour more rapidly than TERMAMYL™ SC (Novozymes A/S, Denmark) amylase at its optimum conditions, including at 85° C. The rate of viscosity reduction by amylases can be influenced most by enzyme dose and temperature. Alternative optimal ranges can be in the range of 0.4 to 0.6 g/kg starch, with an optimum temperature at 95° C.

In some embodiments, amylases and/or glucoamylases of the invention can be effective at a lower pH and a higher temperature than TERMAMYL™ SC (Novozymes A/S, Denmark) amylase at a pH in the range between pH 4.4 and pH 5.6. Calcium addition can have a minimal effect on rate of viscosity reduction at 95° C.

The activities of the purified enzymes were compared in different storage buffers, as listed below, after 1 week of incubation at 37° C. The buffer with the lowest loss of activity compared to the activity of the same enzyme kept at +4° C. was selected as the storage buffer of choice. Exemplary assay conditions to test for amylase activity, e.g., to determine if a polypeptide of the invention retains activity under particular conditions, include (MPB: Methylparaben):

- 20% Glucose, 0.1% MPB in PBS, pH 7.2@37° C.
- 20% Glucose, 0.1% MPB in Acetate Buffer, pH 5@37° C.
- 20% Sucrose, 0.1% MPB in PBS, pH 7.2@37° C.
- 20% Sucrose, 0.1% MPB in Acetate Buffer, pH 5@37° C.
- 0.1% MPB in PBS, pH 7.2@37° C.
- 0.1% MPB in Acetate Buffer, pH 5@37° C.
- PBS, pH 7.2@37° C.
- Acetate Buffer, pH 5@37° C.
- 20% Glucose, 0.1% MPB in PBS, pH 7.2@4° C.
- 20% Glucose, 0.1% MPB in Acetate Buffer, pH 5@4° C.
- 20% Sucrose, 0.1% MPB in PBS, pH 7.2@4° C.
- 20% Sucrose, 0.1% MPB in Acetate Buffer, pH 5@4° C.
- 20% Maltose in PBS (50 mM sodium phosphate pH7.5; 100 mM NaCl)
- 0.1% MPB in PBS, pH 7.2@4° C.
- 0.1% MPB in Acetate Buffer, pH 5@4° C.
- PBS, pH 7.2@4° C.
- Acetate Buffer, pH 5@4° C.

Figure 13:
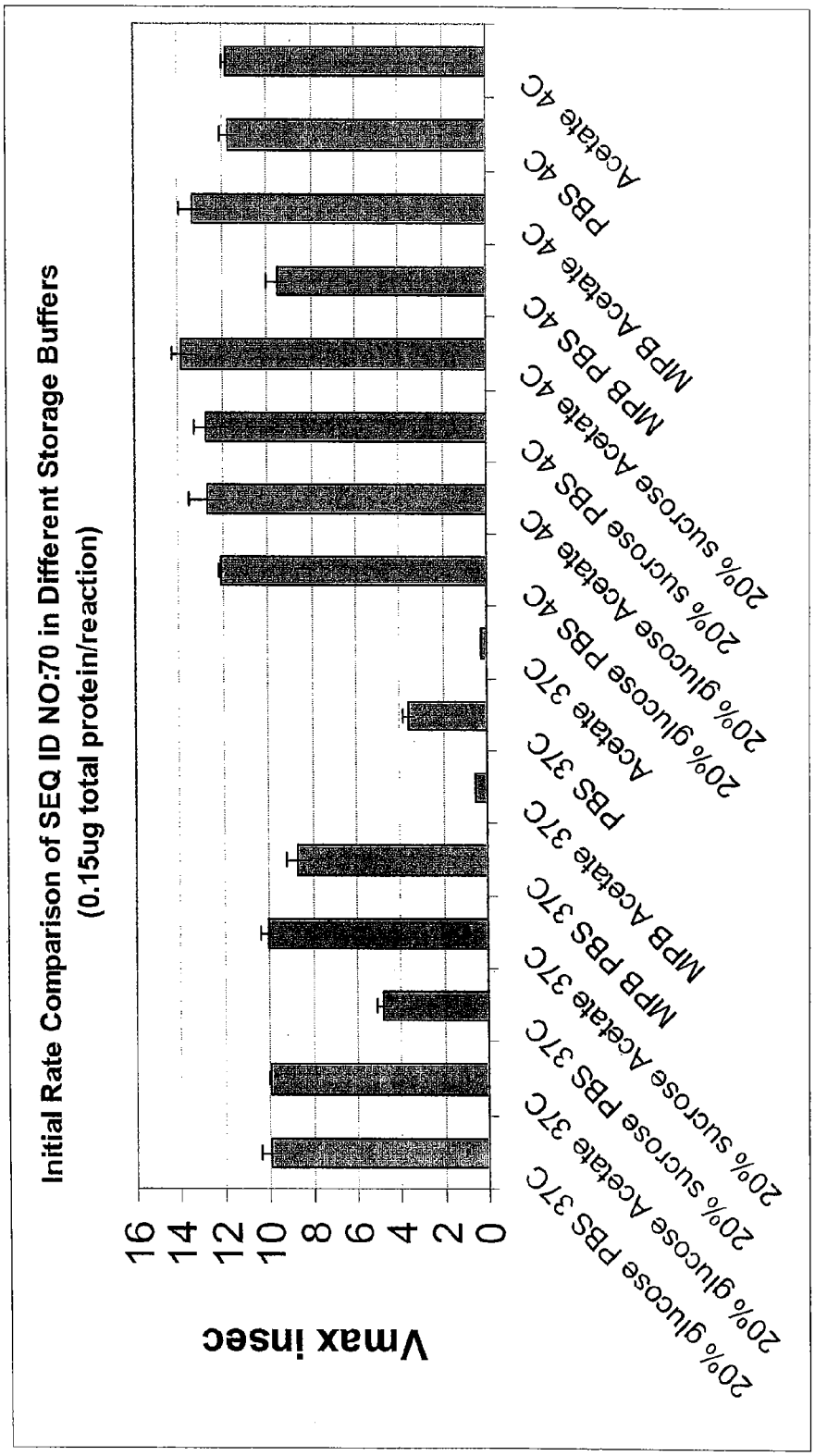
FIG. 13, FIG. 14, FIG. 15, FIG. 16, FIG. 17, FIG. 18, FIG. 19 and FIG. 20, illustrate rate comparisons of exemplary enzymes of the invention in different storage buffers, as discussed in detail in Example 1, below.
Figure 14:
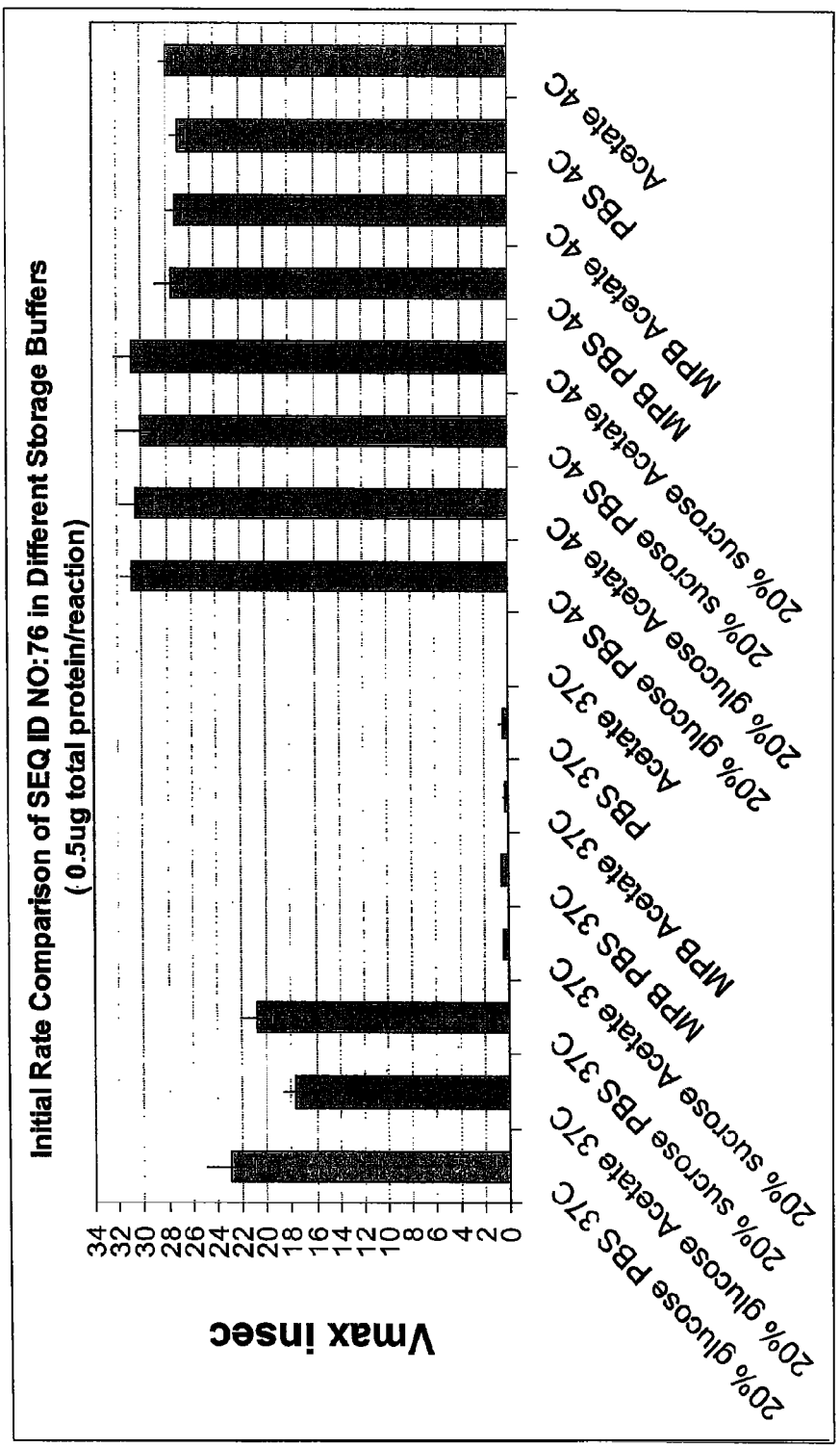
Figure 15:
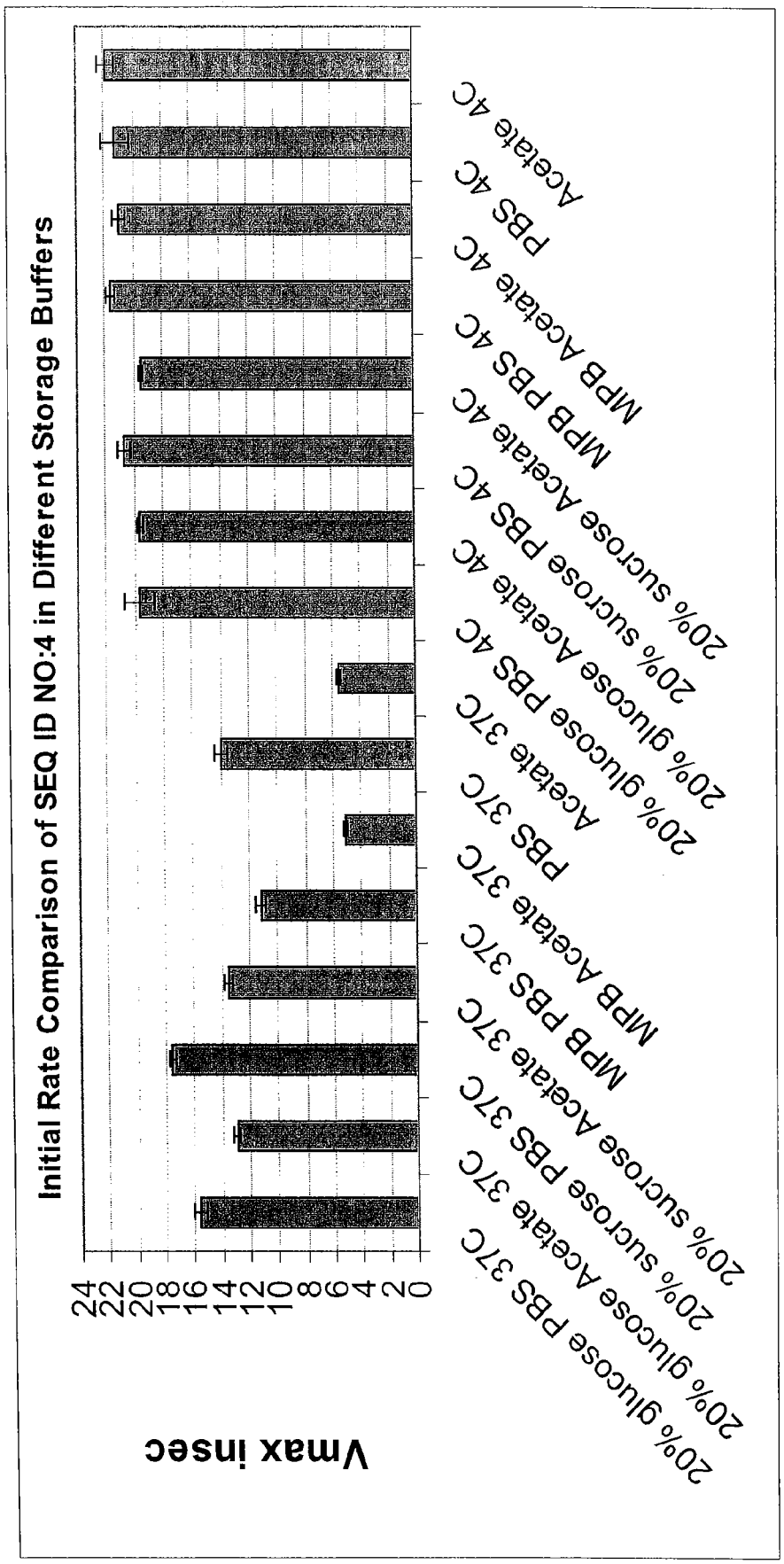
Figure 16:
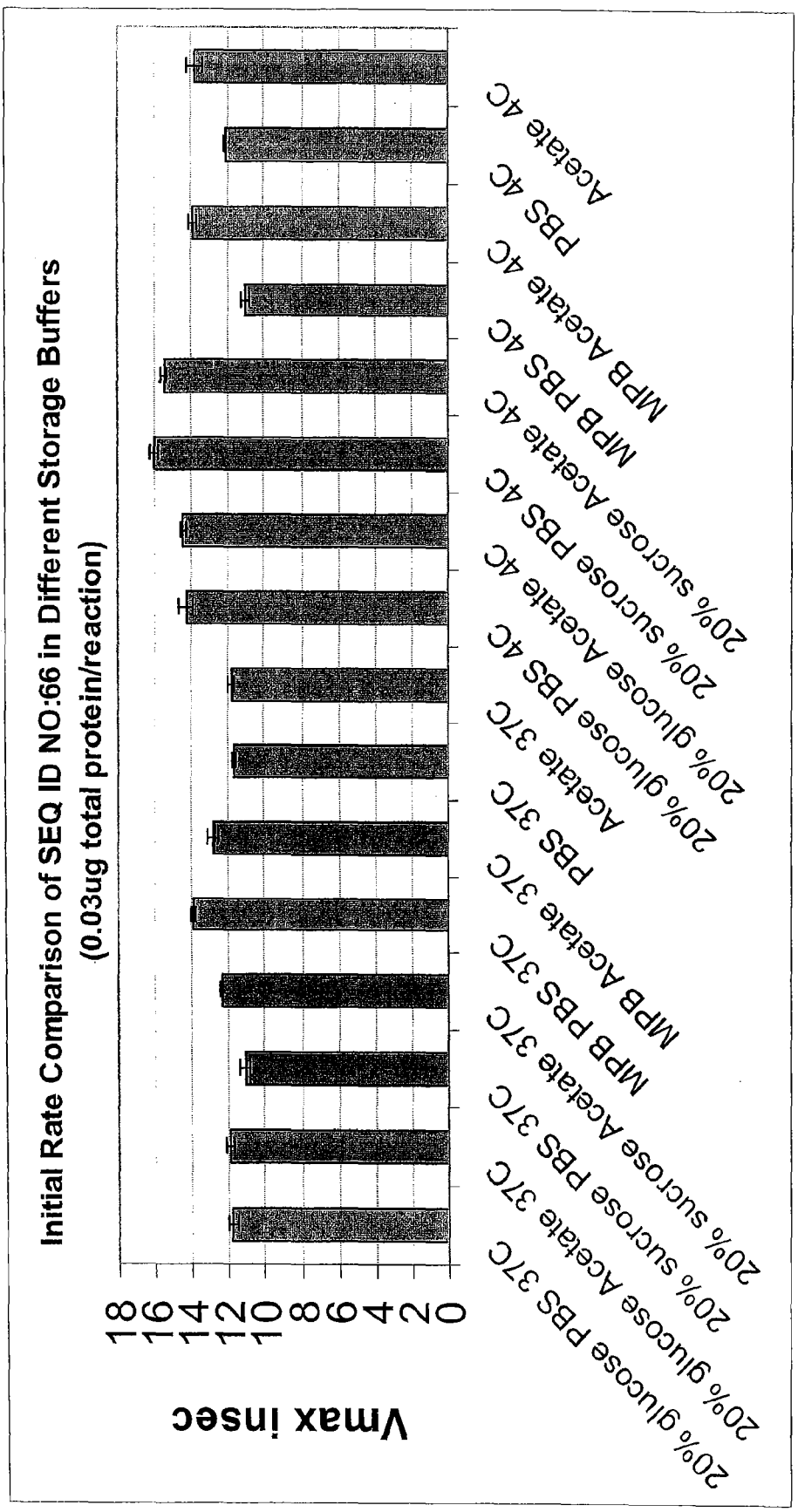
Figure 17:
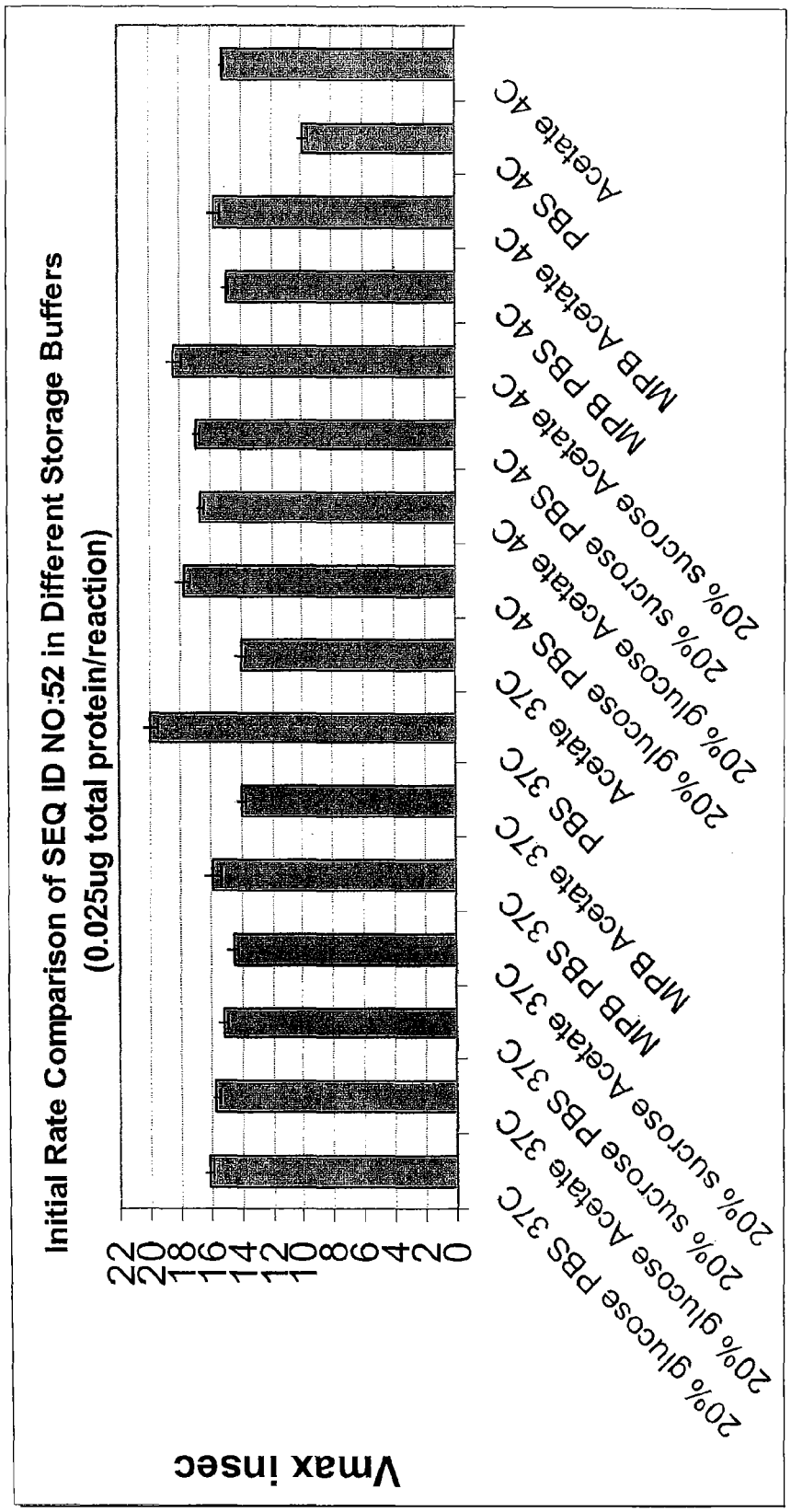
Figure 18:
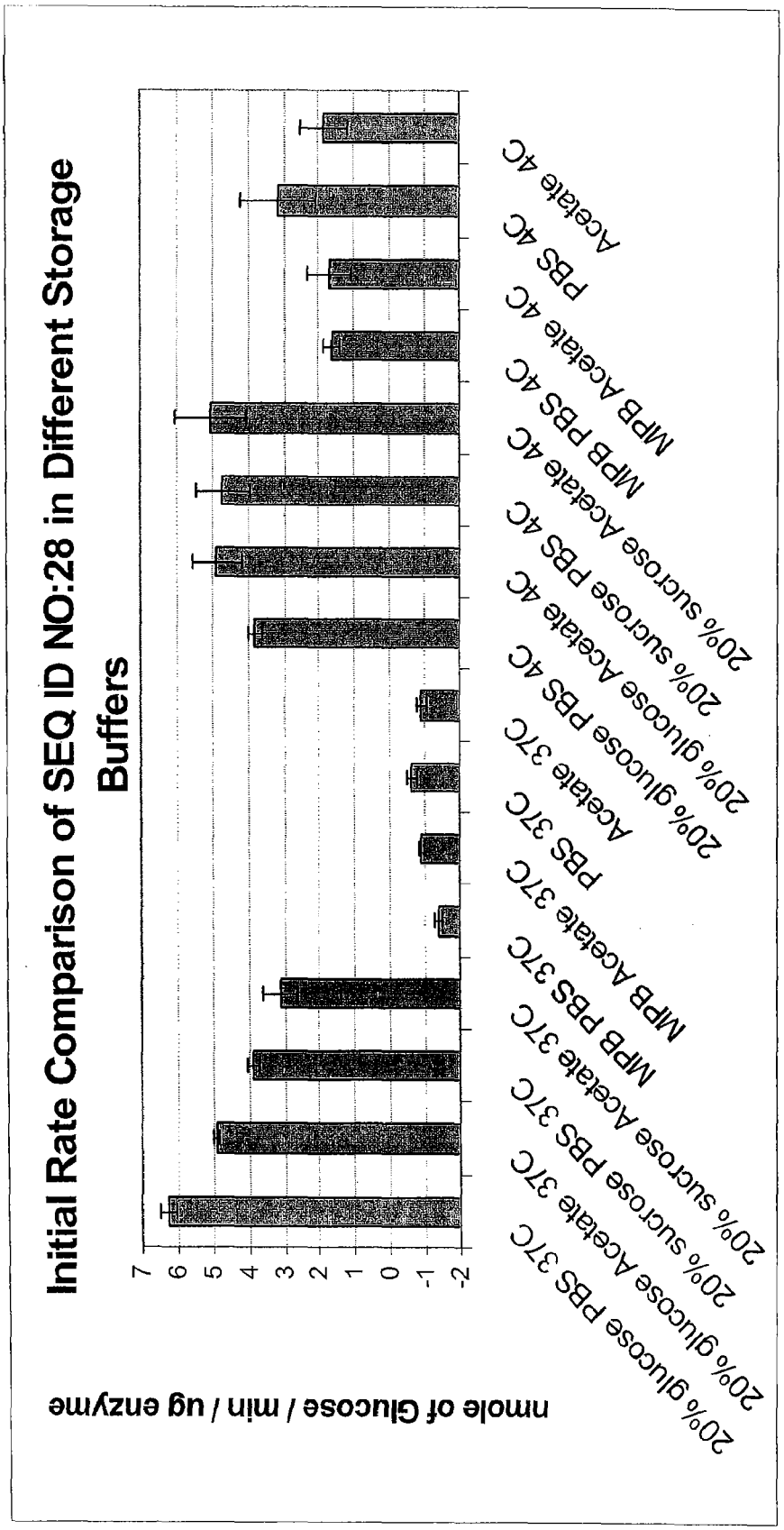
Figure 19:
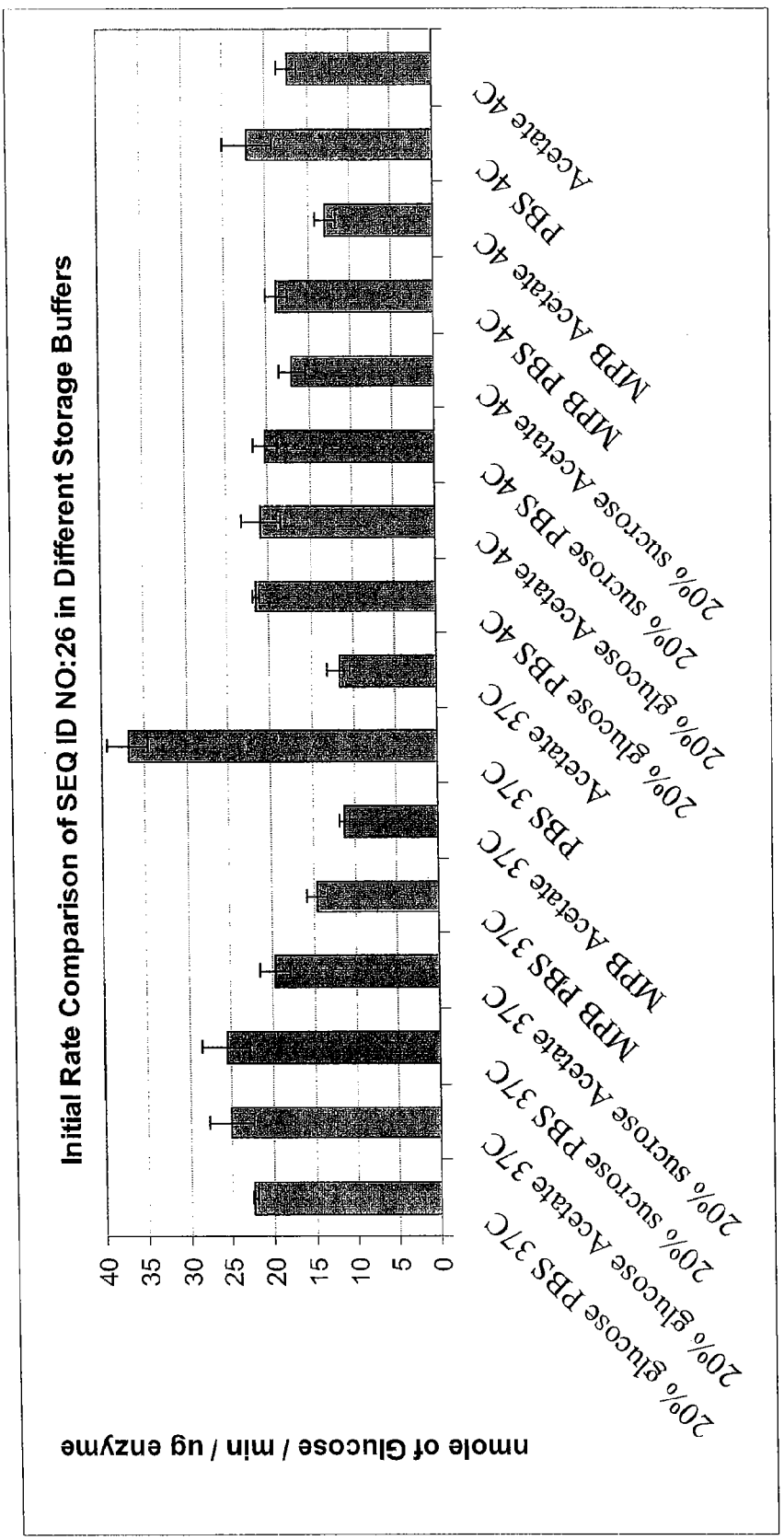
Figure 20:
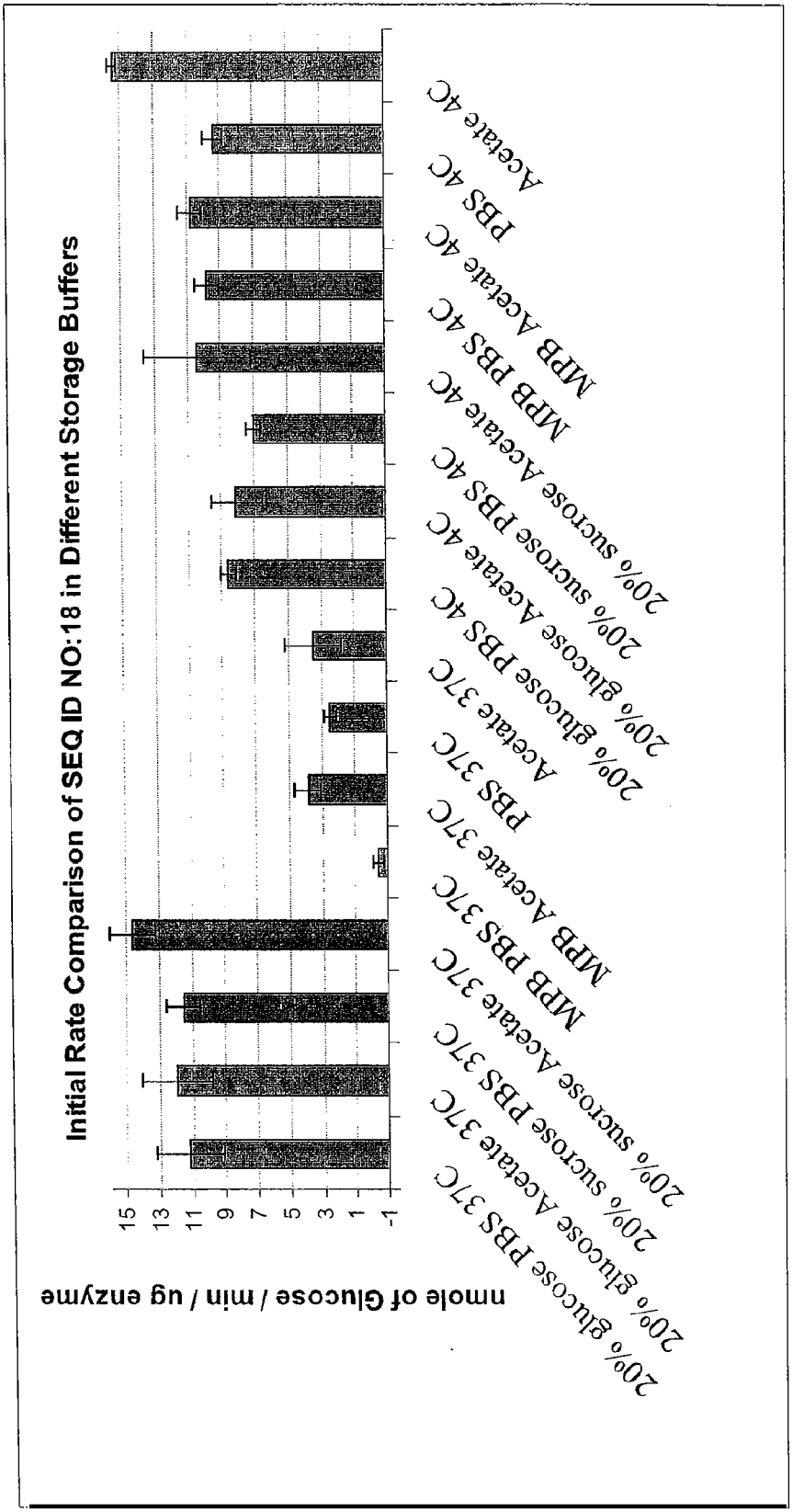

Exemplary enzymes of the invention that have been tested under these exemplary assay conditions include: SEQ ID NO:26; SEQ ID NO:18; SEQ ID NO:4; SEQ ID NO:28; SEQ ID NO:48; SEQ ID NO:76; SEQ ID NO:52; SEQ ID NO:70; SEQ ID NO:66. For SEQ ID NO:26 and SEQ ID NO:4, 20% sucrose in 1×PBS, pH 7 with 0.1% methyl paraben (SMP*) was chosen, and for SEQ ID NO:18, 20% sucrose in 50 mM sodium acetate with 150 mM sodium chloride and 0.1% methyl paraben (SMA**) was chosen. FIG. 13 illustrates an initial rate comparison (using Vmax) of the exemplary enzyme SEQ ID NO:70 in different storage buffers (as indicated in the figure); 0.15 ug total protein per reaction; FIG. 14 illustrates an initial rate comparison (using Vmax) of the exemplary enzyme SEQ ID NO:76 in different storage buffers (as indicated in the figure); 0.5 ug total protein per reaction; FIG. 15 illustrates an initial rate comparison (using Vmax) of the exemplary enzyme SEQ ID NO:4 in different storage buffers (as indicated in the figure); FIG. 16 illustrates an initial rate comparison (using Vmax) of the exemplary enzyme SEQ ID NO:66 in different storage buffers (as indicated in the figure); 0.03 ug total protein per reaction; FIG. 17 illustrates an initial rate comparison (using Vmax) of the exemplary enzyme SEQ ID NO:52 in different storage buffers (as indicated in the figure); 0.025 ug total protein per reaction; FIG. 18 illustrates an initial rate comparison (using nmole of glucose per mM per ug of enzyme) of the exemplary enzyme SEQ ID NO:28 in different storage buffers (as indicated in the figure); FIG. 19 illustrates an initial rate comparison (using nmole of glucose per min per ug of enzyme) of the exemplary enzyme SEQ ID NO:26 in different storage buffers (as indicated in the figure); FIG. 20 illustrates an initial rate comparison (using nmole of glucose per min per ug of enzyme) of the exemplary enzyme SEQ ID NO:18 in different storage buffers (as indicated in the figure).

Bradford and BCA assays as well as SDS PAGE and Absorbance at A280 were used to determine the concentration of the purified proteins. The standardized amylase solution (Sigma A6211) was used as a reference in these assays, and BSA. Concentration by BCA and A280 was similar, but not by Bradford using BSA as a standard.

In these assays, protein (enzyme) was purified by precipitation; hydrophobic interaction; size exclusion; ion exchange; affinity; and in one exemplary protocol, protein (enzyme) was purified by precipitation, hydrophobic interaction, ion exchange and as a last step, affinity (chromatography).

The exemplary SEQ ID NO:18, SEQ ID NO:4 and SEQ ID NO:26 were purified by either ammonium sulfate (SEQ ID NO:26) or ethanol precipitation (SEQ ID NO:18 and SEQ ID NO:4). Lyophilized supernatants from cultures expressing the enzymes of interest were resuspended in water at a concentration of about 1 g/5 ml. SEQ ID NO:18 and SEQ ID NO:4 were precipitated by addition of cold ethanol (2 volumes of protein solution). SEQ ID NO:26 was precipitated in 80% ammonium sulfate solution. After precipitation the protein suspensions were dialyzed once against water and subsequently against storage buffer.

Stability of purified exemplary enzymes of this invention was tested in either PBS at pH 7 or PBS pH 7.5 (in this case, the parameters were 50 mM sodium phosphate; 100 mM NaCl) or in 50 mM sodium acetate pH 5.2 with 150 mM NaCl added. Glucose (20%) or sucrose (20%) was added to the buffers as well as an antimicrobial, 0.1% methyl paraben (Sigma). The enzymes were incubated in their respective buffers at 37° C. for 1 week and the enzyme activity was tested and compared to the activity of the same enzyme stored at +4° C.

The concentration of each purified enzyme was estimated using 4 different methods: Bradford assay with amylase Sigma A-6211 as standard, BCA assay with Sigma A-6211 as standard, absorbance at 280 nm in 8M urea, and densitometric measurement of stained protein after SDS PAGE, using Sigma A-6211 amylase as the reference. The numbers obtained with these different methods for each of the purified proteins are presented in Table 3.1. For final quantification, the concentration obtained by measuring absorbance at 280 nm in 8M urea was used.

A summary of the large scale purification for these assays is:

| Summary of Recover Amount based on Absorbance Value | | | |
|---|---|---|---|
| | mg/ml | Volume (ml) | Total mg |
| SEQ ID NO: 18 | 53.94 | 111 | 5987.34 |
| SEQ ID NO: 26 | 39.23 | 86.8 | 3405.164 |
| SEQ ID NO: 4 | 70.01 | 55.4 | 3878.554 |

| Summary of Purity | | | | |
|---|---|---|---|---|
| | Before Purification | | After Purification | |
| | A260/A280 | Expression Ratio | A260/A280 | Expression Ratio |
| SEQ ID NO: 18 | 0.52 | 91% | 0.59 | 92% |
| SEQ ID NO: 26 | 0.56 | 85% | 0.65 | 86% |
| SEQ ID NO: 4 | 0.67 | 91% | 0.73 | 85% |

| Summary of Activity | | | | |
|---|---|---|---|---|
| | Raw Starch | | Soluble | |
| | Purified | Unpurified | Purified | Unpurified |
| SEQ ID NO: 18 | 10.7228 ± 0.7925 | 6.4828 ± 0.5681 | 40.6725 ± 1.7016 | 24.7354 ± 3.821 |
| SEQ ID NO: 26 | 5.7837 ± 0.2271 | 4.0691 ± 0.2864 | 17.4833 ± 0.7831 | 14.1849 ± 0.3761 |
| SEQ ID NO: 4 | 6.47 ± 0.34 | 4.074 ± 0.35 | 127.37 ± 1.78 | 116.52 ± 1.27 |

Estimation of Enzyme Concentration by Different Methods

| | Bradford | BCA (A6211) | Absorbance (Urea) |
|---|---|---|---|
| SEQ ID NO: 18 | 71.10 | 57.64 | 53.94 |
| SEQ ID NO: 26 | 43.98 | 57.64 | 39.29 |
| SEQ ID NO: 4 | 69.20 | 57.64 | 70.01 |

Example 2

Thermostable Amylases Active at Alkaline pH

The following example describes an exemplary method for determining if a polypeptide is within the scope of the invention, e.g., is a thermostable amylase.

Commercial automatic dish wash (ADW) formulations can be used to determine if a polypeptide is within the scope of the invention, e.g., is a thermostable amylase. Studies can include the identification of high pH amylases; and enzymes having the ability to degrade starch. DNA sequence and bioinformatics analyses can classify many of these genes as amylases, or having other enzyme specificities, e.g., neopullulanases, amylopullulanases and amylomaltases.
Biochemical Studies One exemplary method for determining if a polypeptide is within the scope of the invention, e.g., is a thermostable amylase, is to test for activity where the enzyme can hydrolyze starch at alkaline pH, e.g., up to pH 10, and about 50° C.

Soluble protein is purified to homogeneity and specific activity (units/mg, where 1 unit=μmol reducing sugars/min) is measured at pH 8 and pH 10 (40° C. and 50° C.) using 2% starch in buffer. Specific activity can be determined by removing samples at various time points during a 30 minute reaction and analyzing for reducing sugars. The initial rate can be determined by fitting the progress curves to a linear equation.
Stability Studies Stability in the presence of the ADW formulation can be measured by biochemical analysis. The benchmark for these studies can be a commercial enzyme in the formulation matrix. The measured activity after the incubation can be expressed as a percentage of the original activity.
Wash Tests Wash tests using starch coated slides can be carried out to gauge the performance of each a purified enzyme of the invention as compared to a commercial amylase. Spaghetti starch coated slides can be prepared according to protocol: two pre-weighed starch coated slides are placed back to back in a 50 mL conical tube and 25 mL of ADW solution, +/−enzyme are added per tube. The tubes are incubated for 20 minutes at 50° C. with gentle rotation on a vertical carousel. Following the incubation period, the slides are immediately rinsed in water and oven dried overnight. All trials are run in duplicate and the commercial enzyme was run as a positive control. The results can be expressed as net starch removed, e.g. % of starch removed in ADW with enzyme, minus the % of starch removed in ADW alone.

Example 3

Gene Optimization

The following example describes an exemplary method for determining if a polypeptide is within the scope of the invention, e.g., assessing enzyme performance in the presence of ADW performance.

The properties of enzymes may be improved by various evolution strategies, including Gene Site Saturation Mutagenesis™ (GSSM™) and GeneReassembly™ technologies (Diversa Corporation, San Diego, Calif.). Such techniques will be applied to the amylase nucleic acids of the invention in order to generate pools of variants that can be screened for improved performance. In one aspect, parental molecules for evolution include any nucleic acid of the invention, e.g., sequences encoding SEQ ID NO:2; SEQ ID NO:4; SEQ ID NO:6, etc.

A high throughput screen (HTS) can be used to assess enzyme performance in the presence of ADW performance. HTS can be automated and has showed consistent results for the parental amylases.

Example 4

Characterization of α-Amylases having Activity at Alkaline pH

The following example describes exemplary methods for determining if a polypeptide is within the scope of the invention, for example, has alpha-amylase activity at alkaline pH.

Amylases and/or glucoamylases of the invention having activity at alkaline pH can be characterized using kinetics on 2% starch at pH 8 and 10 (40° C. and 50° C.). 1 unit of activity can be defined as release of 1 mmol reducing sugars per minute.

Example 5

Amylase Activity Assay

BCA Reducing Ends Assay

The following example describes an exemplary method for determining if a polypeptide is within the scope of the invention, for example, by a BCA reducing ends assay. Amylase activity of clones of interest can be determined using the following methodology.

1. Prepare 2 substrate solutions, as follows:
   a) 2% soluble starch (potato or granular corn starch) pH 8 solution by dissolving 2 gm potato starch in 100 ml 100 mM sodium phosphate pH 8).
   b) 2% soluble starch (potato) pH 10 solution by dissolving 2 gm potato starch in 100 ml 100 mM sodium carbonate.
   Heat both solutions in a boiling water bath, while mixing, for 30-40 minutes until starch dissolves.
2. Prepare Solution A from 64 mg/ml sodium carbonate monohydrate, 24 mg/ml sodium bicarbonate and 1.95 mg/ml BCA (4,4'-dicarboxy-2,2'-biquinoline disodium salt (Sigma Chemical cat #D-8284). Added above to dH2O.
3. Prepare solution B by combining 1.24 mg/ml cupric sulfate pentahydrate and 1.26 mg/ml L-serine. Add mixture to dH2O.
4. Prepare a working reagent of a 1:1 ration of solutions A and B.
5. Prepare a Maltose standard solution of 10 mM Maltose in dH2O, where the 10 mM maltose is combined in 2% soluble starch at desired pH to a final concentration of 0, 100, 200, 300, 400, 600 nM. The standard curve will be generated for each set of time-points. Since the curve is determined by adding 10 ul of the standards to the working reagent it works out to 0, 1, 2, 3, 4, 6 nmole maltose.
6. Aliquot 1 ml of substrate solution into microcentrifuge tubes, equilibrate to desired temperature (5 min) in heat block or heated water bath. Add 50 ul of enzyme solution to the inside of the tube lid.
7. While solution is equilibrating mix 5 ml of both solution A & B. Aliquot 100 ul to 96 well PCR plate. Set plate on ice.
8. After 5 minute temperature equilibration, close lid on tubes, invert and vortex 3 times. Immediately aliquot 10 ul into plate as t=0 (zero time point). Leave enzyme mixture in heat block and aliquot 10 ul at each desired time point (e.g. 0, 5, 10, 15, 20, 30 minutes).
9. Ensure that 12 wells are left empty (only working reagent aliquotted) for the addition of 10 ul of standards, for the standard curve.
10. When all time points are collected and standards are added, cover plate and heated to 80° C. for 35 min. Cool plate on ice for 10 min Add 100 ul H2O to all wells. Mix and aliquot 100 ul into flat bottomed 96-well plate and read absorbance at 560 nm.
11. Zero each sample's time points against its own t=0 (subtract the average t=0 A560 value from other average A560 values). Convert the $A560_{(experimental)}$ to umole (Divide $A560_{(experimental)}$ by the slope of the standard curve (A560/umole). Generate a slope of the time points and the umole (in umole/min), multiply by 100 (as the umole value only accounts for the 10 ul used in the assay, not the amount made in the 1 ml rxn). To get the specific activity divide the slope (in umole/min) by the mg of protein. All points should be done at a minimum in duplicate with three being best. Divide protein concentration (mg/ml) by any dilution to get mg used in assay.

Divide the above slope by mg used in assay to get specific activity

Specific Activity=24.93 umole/min/mg

See for example, Dominic W. S. Wong, Sarah B. Batt, and George H. Robertson (2000) J. Agric. Food Chem. 48:4540-4543; Jeffrey D. Fox and John F. Robyt, (1991) Anal. Biochem. 195, 93-96.

Example 6

Screening for α-Amylase Activity

The following example describes an exemplary method for determining if a polypeptide is within the scope of the invention. Amylase activity of clones can be assessed by a number of methods known in the art. The following is an exemplary methodology. The number of plaques screened, per plate, can be approximately 10,000 pfu's. For each DNA library: at least 50,000 plaques per isolated library and 200,000 plaques per non-isolated library should be screened depending upon the pfu titer for the λ Zap Express amplified lysate.

Titer Determination of Lambda Library

1) μL of Lambda Zap Express amplified library stock added to 600 μL $E. coli$ MRF' cells ($OD_{600}$=1.0). To dilute MRF' stock, 10 mM $MgSO_4$ is used.
2) Incubate at 37° C. for 15 minutes.
3) Transfer suspension to 5-6 mL of NZY top agar at 50° C. and gently mix.
4) Immediately pour agar solution onto large (150 mm) NZY media plate.
5) Allow top agar to solidify completely (approximately 30 minutes), then invert plate.
6) Incubate the plate at 39° C. for 8-12 hours.
7) Number of plaques is approximated. Phage titer determined to give 10,000 pfu/plate. Dilute an aliquot of Library phage with SM buffer if needed.

Substrate Screening

1) Lambda Zap Express (50,000 pfu) from amplified library added to 600 μL of $E. coli$ MRF' cells (OD600=1.0). For non-environment libraries, prepare 4 tubes (50,000 pfu per tube).
2) Incubate at 37° C. for 15 minutes.
3) While phage/cell suspensions are incubating, 1.0 mL of red starch substrate (1.2% w/v) is added to 6.0 mL NZY top agar at 50° C. and mixed thoroughly. Keep solution at 50° C. until needed.
4) Transfer 1/5 (10,000 pfu) of the cell suspension to substrate/top agar solution and gently mixed.
5) Solution is immediately poured onto large (150 mm) NZY media plate.
6) Allow top agar to solidify completely (approximately 30 minutes), then invert plate.
7) Repeat procedures 4-6 4 times for the rest of the cell suspension (1/5 of the suspension each time).
8) Incubate plates at 39° C. for 8-12 hours.
9) Plate observed for clearing zones (halos) around plaques.
10) Plaques with halos are cored out of agar and transferred to a sterile micro tube. A large bore 200 μL pipette tip works well to remove (core) the agar plug containing the desired plaque.
11) Phages are re-suspended in 500 μL SM buffer. 20 μL Chloroform is added to inhibit any further cell growth.
12) Pure phage suspension is incubated at room temperature for 4 hours or overnight before next step.

Isolation of Pure Clones 1) 10 μL of re-suspended phage suspension is added to 500 μL of $E. coli$ MRF' cells (OD600=1.0).
2) Incubate at 37° C. for 15 minutes.
3) While phage/cell suspension is incubating, 1 mL of red starch substrate (1.2% w/v) is added to 6.0 mL NZY top agar at 50° C. and mixed thoroughly. Keep solution at 50° C. until needed.
4) Cell suspension is transferred to substrate/top agar solution and gently mixed.

5) Solution is immediately poured onto large (150 mm) NZY media plate.
6) Allow top agar to solidify completely (approximately 30 minutes), then invert plate.
7) Plate incubated at 39° C. for 8-12 hours.
8) Plate observed for a clearing zone (halo) around a single plaque (pure clone). If a single plaque cannot be isolated, adjust titer and re-plate phage suspension.
9) Single plaque with halo is cored out of agar and transferred to a sterile micro tube. A large bore 200 µL pipette tip works well to remove (core) the agar plug containing the desired plaque. To amplify the titer, core 5 single active plaques into a micro tube.
10) Phages are re-suspended in 500 µL SM buffer. 20 µL Chloroform is added to inhibit any further cell growth.
11) Pure phage suspension is incubated at room temperature for 4 hours or overnight before next step. The pure phage suspension is stored at −80° C. by adding DMSO into the phage suspension (7% v/v).

Excision of Pure Clone
1) 100 µL of pure phage suspension is added to 200 µL $E.\ coli$ MRF' cells (OD600=1.0). To this, 1.0 µL of EXASSIST helper phage (>1×106 pfu/mL; Stratagene) is added. Use 2059 Falcon tube for excision.
2) Suspension is incubated at 37° C. for 15 minutes.
3) 3.0 mL of 2×YT media is added to cell suspension.
4) Incubate at 30° C. for at least 6 hours or overnight while shaking.
5) Tube transferred to 70° C. for 20 minutes. The phagemid suspension can be stored at 4° C. for 1 to 2 months.
6) 100 µL of phagemid suspension transferred to a micro tube containing 200 µL of $E.\ coli$ Exp 505 cells (OD600=1.0).
7) Suspension incubated at 37° C. for 15 minutes.
8) 300 µL of SOB is added to the suspension.
9) Suspension is incubated at 37° C. for 30 to 45 minutes.
10) 100 µL of suspension is transferred to a small (90 mm) LB media plate containing Kanamycin (LB media with Kanamycin 50 µg/mL) for Zap Express DNA libraries or Ampicillin (LB media with Kanamycin 100 µg/mL) for Zap II DNA libraries.
11) The rest of suspension is transferred to another small LB media plate.
12) Use sterile glass beads to evenly distribute suspension on the plate.
13) Plates are incubated at 30° C. for 12 to 24 hours.
14) Plate observed for colonies.
15) Inoculate single colony into LB liquid media containing suitable antibiotic and incubate at 30° C. for 12 to 24 hours.
16) Glycerol stock can be prepared by adding 80% glycerol into liquid culture (15% v/v) and stored at −80° C.

Activity Verification
1) 50 µL of liquid culture is transferred to a micro tube. Add 500 µL of 8% pH7 Amylopectin Azure into the same tube. Prepare 2 tubes for each clone.
2) Activity is tested at 50° C. for 3 hours and overnight. Use pH 7 buffer as control.
3) Cool the test specimen at ice-water bath for 5 minutes.
4) Add 750 µL of Ethanol and mixed thoroughly.
5) Centrifuge at 13000 rpm (16000 g's) for 5 minutes.
6) Measure OD of the supernatant at 595 nm.

RFLP Analysis
1) 1.0 mL of liquid culture is transferred to a sterile micro tube.
2) Centrifuge at 13200 rpm (16000 g's) for 1 minute.
3) Discard the supernatant. Add another 1.0 mL of liquid culture into the same sterile micro tube.
4) Centrifuge at 13200 rpm (16000 g's) for 1 minute.
5) Discard the supernatant.
6) Follow QIAPREP™ spin mini kit protocol for plasmid isolation.
7) Check DNA concentration using BioPhotometer.
8) Use Sac I and Kpn I for first double digestion. Incubate at 37° C. for 1 hour.
9) Use Pst I and Xho I for second double digestion. Incubate at 37° C. for 1 hour.
10) Add Loading dye into the digested sample.
11) Run the digested sample on a 1.0% agarose gel for 1-1.5 hours at 120 volts.
12) View gel with gel imager. All clones with a different digest pattern can be sequence analyzed.

Example 7

Assay for Amylases

The following example describes an exemplary method for determining if a polypeptide is within the scope of the invention.

Preparation of Host Cultures
1. Start an overnight culture of XL1-BLUE™ MRF host cells. Use a single colony from a streak plate to inoculate 10 mL LB supplemented with 20 ug/mL tetracycline. Grow overnight culture shaking at 37° C. for at least 16 hours.
2. Using aseptic technique, inoculate a fresh 100 mL of $LB_{Tet}$ day culture with XL1-BLUE™ MRF host from the overnight $LB_{Tet}$ culture.
3. Grow in a 37° C. shaker until the OD reaches 0.75-1.0.
4. Pellet host cells at 1000×g for 10 minutes and gently resuspend in 10 mM $MgSO_4$ at ODS.
5. Dilute a small amount of host cells to OD1 for use in titering and pintooling.
6. Host preparations can be used for up to 1 week when stored on ice or at 4° C.
   To shorten growth time for the day culture, use ½X the usual Tet concentration in LB (½X=10 ug/mL), or omit the antibiotic altogether.
   Do not use NZY when selecting with Tetracycline. The high $Mg^{++}$ concentration in NZY medium renders Tet inactive.

Titering Lambda Libraries
7. Place three sterile microfuge tubes in a rack.
8. Aliquot 995 uL prepared host cells in one tube and 45 uL prepared OD1 host cells into each of the two remaining tubes.
9. Add 5 uL of lambda library to the tube containing 995 uL host cells and mix by vortexing. This results in a dilution factor of 200.
10. Prepare 1/2,000 and 1/20,000 dilutions by consecutively adding 5 uL of previous dilution to the remaining two tubes containing 45 uL prepared host cells. Mix by vortexing after each dilution was made.
11. Allow phage to adsorb to host by incubating at 37° C. for 15 minutes.
12. Meanwhile, pipet 100 uL of prepared OD1 host cells to each of three Falcon 2059 tubes.
13. Add 5 uL of each dilution to a separate 2059 tube containing host cells.
14. Plate each by adding 3 mL top agar to each tube and quickly pour over 90 mm NZY plates. Ensure a smooth, even distribution before the top agar hardens.
15. Invert plates and incubate at 37° C. overnight.
16. Count plaques and calculate titer of the library stock (in plaque forming units (pfu) per uL).

Lambda Microtiter Screening For Amylases
Preparation
1. Prepare a sufficient amount of XL1-Blue MRF host culture, as described above, for the amount of screening planned. A culture of 100 mL is usually sufficient for screening 2-3 libraries.
2. Autoclave several bottles compatible with the QFill2 dispenser. These are the wide-mouth Corning bottles, 250 mL containing a sealing ring around the lip.
3. Make sure there are sufficient amounts of plates, top agar, BODIPY starch, red starch solution, etc. available for the screen.
4. Schedule the Day 2 robot run with a representative from Automation.

Day 1
1. Label the 1536-well plates (black) with library screen and plate number. Tough-Tags™ tube stickers, cut in half width-wise, are ideal for labeling 1536 well plates.
2. Calculate volumes of library, host cells and NZY medium necessary for the screen. This is easily done with an Excel spreadsheet.
3. Combine the calculated volumes of lambda library and OD5 host cells in a sterile 250 mL wide-mouth Corning bottle (containing a sealing ring).
4. Allow adsorption to occur at 37° C. for 15 minutes.
5. Add the calculated volume of NZY medium and mix well. This is referred to as the cell-phage-medium suspension.
6. Perform a concomitant titer by combining 50 uL of the cell-phage-medium suspension with 250 uL of OD1 host cells in a Falcon 2059 tube, then plating with 9 mL of top agar onto a 150 mm NZY plate. Incubate concomitant titer plate at 37° C. overnight.
7. Load the dispenser with the remainder of the suspension and array each labeled 1536-well plate at 4 uL per well. If the dispenser leaves air bubbles in some wells, they can be removed by centrifuging the plates at 200×g for 1 minute.
8. Add 0.5 uL of positive control phage to well position AD46 of at least two of the assay plates. Use a strong amylase-positive lambda clone for this purpose.
9. Incubate assay plates at 37° C. overnight in a humidified (95%) incubator.

Day 2
1. Count the pfu on the concomitant titer plate and determine the average seed density per well (in pfu per well).
2. Pintool at least 2 plates of each library screen (preferably the 2 containing positive controls) as follows:
   a) Prepare 2 host lawn plates to act as a surface on which to pintool: combine 250 uL of OD1 host cells with 2 mL 2% red starch and plate with 9 mL top agar onto 150 mm NZY plates. Hold each plate as level as possible as the top agar solidifies in order to produce an even hue of red across the plate.
   b) Using a twice flame-sterilized 1536 position pintool, replicate at least 2 of the screening plates onto the host lawn plates.
   c) Place the pintooled recipient plates in a laminar flow hood with the lids off for about 15-30 minutes (to vent off excess moisture).
   d) Replace the lids and incubate inverted at 37° C. overnight.
3. Prepare the 2×BODIPY starch substrate buffer as follows:
   a) Calculate the total volume of 2× substrate buffer solution needed for all screening plates at 4 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
4. Take plates and substrate buffer to the automation room and program the robot with the following parameters:
   a) dispense 4 uL substrate buffer per well
   b) $1^{st}$ read at 1 hour post-substrate, $2^{nd}$ read at 9 hours, and third read at 17 hours; with 37° C. incubation between reads
   c) excitation filter: 485 nm; emission filter: 535 nm
   d) set the Spectrafluor gain at 70, or the optimal gain for the batch of 2× substrate buffer prepared.
   e) ensure that the incubator used will protect assay plates from light.

Day 3
1. Check pintooled plates for clearings in the bacterial lawn at all positions corresponding to wells on the associated assay plate. Also check for clearings in the red starch in any of the pin positions. If plates containing positive controls were used for pintooling, you should be able to see a large clearing zone in the red background. Be wary of contaminants that also form clearing zones in red starch (see comment "Contaminants That Form Clearing Zones in Red Starch" at end of Example 7).
2. Identify putative hits from the data file produced by the robot computer. The KANAL program produced by Engineering simplifies data analysis. As a rule of thumb, a putative hit is characterized as a well having signal intensity rising at least 1.5 fold over background.
3. For each putative, remove 2 uL from the well and add to a tube containing 500 uL SM buffer and 50 uL $CHCl_3$. Vortex to mix and store at 4° C. This solution will be referred to hereafter as the 4e-3 stock. The original screening plates should be stored at 4° C., protected from light, at least until breakouts are complete.

This is an exemplary method of breaking out putative hits. It is a liquid phase assay that relies on confirmation of activity on BODIPY starch. Alternatively, putative hits can be plated directly onto solid phase plates containing red starch such that 2,000-3,000 pfu per hit are examined for clearing zones. However, inability to observe clearing zones on red starch is not necessarily an indication that a putative hit was a false positive. It would then need to be assayed using the format in which it was originally identified (i.e., liquid phase using BODIPY starch as substrate). In addition, very weak positives are more easily identified using the method detailed below.

Day 1
1. In a sterile 50 mL conical tube, combine 0.5 mL OD5 host cells with 45.5 mL NZY. This will be referred to as the host-medium suspension.
2. For each putative hit to be analyzed, aliquot 1 mL of host-medium suspension into each of 3 three sterile microfuge tubes.
3. Set the 12-channel pipetman in multidispense mode with an aliquot size of 20 uL and an aliquot number of 2×. Mount the pipetman with a clean set of sterile tips.
4. Pour about 1 mL of host-medium suspension into a new sterile solution basin and load the multichannel pipetman.
5. Dispense 20 uL per well into the last row (row P) of a black 384-well plate (12 channels×2=24 wells). This row will be used later for the controls.
6. Expel the remaining liquid in the tips by touching the tips against the surface of the basin and pressing the RESET button on the pipetman. Lay the pipetman down in a way to prevent contamination of the tips. There is no need to change the tips at this point.
7. Pour the remainder of the fluid in the basin into a waste container (like a beaker) taking care to avoid splash-back contamination.
8. For the first putative to be analyzed, take 111 uL of the 4e-3 stock (see Day 2 in *Lambda Microtiter Screening for Amylases*) and add it to the first in a set of three tubes containing 1 mL host-medium suspension (step 2). Vortex to mix. This is Dilution A.
9. Take 111 uL of Dilution A and add to the next tube in the set. Vortex to mix. This is Dilution B.
10. Take 111 uL of Dilution B and add to the last tube in the set. Vortex to mix. This is Dilution C. You should now have three dilutions of phage, where concentrations of each differ by a factor of 10.
11. Pour the contents of Dilution C (the most dilute of the 3 samples) into the solution basin and load the multichannel pipetman.
12. Dispense 20 uL per well into the first row of the 384-well plate (12 channels×2=24 wells).
13. Expel the remaining liquid in the tips by touching the tips against the surface of the basin and pressing the RESET button on the pipetman. Lay the pipetman down in a way to prevent contamination of the tips. There is no need to change the tips at this point.
14. Empty the basin as described above.
15. Pour the contents of Dilution B into the same basin and load the multichannel pipetman.
16. Dispense 20 uL per well into the second row of the 384-well plate.
17. Perform steps 13-16 similarly to dispense Dilution A into the third row of the plate.
18. After all three dilutions have been arrayed into the first 3 rows of the plate, discard all tips and the solution basin into the biohazardous waste container.
19. Mount the pipetman with a clean set of sterile tips and open a new sterile solution basin.
20. Repeat steps 8-19 for each remaining putative hit, using remaining rows on the plate up to row O. Five putative hits can be analyzed on one 384-well plate, with the last row (row P) saved for the controls.
21. Add 0.5 uL of each control to a separate well. Use at least 2-3 separate controls, preferably covering a range of activity.
22. Incubate assay plates at 37° C. overnight in a humidified (95%) incubator.

Day 2
1. Pintool all breakout plates onto a host lawn with red starch using the same method described for Day 2 in *Lambda Microtiter Screening for Amylases*, except that a 384 position pintool is used.
2. Prepare the 2×BODIPY starch substrate buffer as follows:
   a) Calculate the total volume of 2× substrate buffer solution needed for all breakout plates at 20 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
3. Dispense 20 uL per well into all breakout plates.
4. Wrap all plates in aluminum foil and incubate at room temperature for 2-6 hours.
5. Read each plate in the Spectrafluor with the following settings:
   a) fluorescence read (excitation filter: 485 nm; emission filter: 535 nm)
   b) plate definition: 384 well black
   c) read from the top
   d) optimal gain
   e) number of flashes: 3
6. On the resulting Excel spreadsheet, chart each putative's 3 rows in a separate graph and check for activity. Ensure that the positives controls produced signals over background.
7. For each putative that appears to have a real signal among the wells, harvest a sample from a positive well as follows:
   a) Select a positive well from a row representing the highest initial dilution.
   b) Transfer 2 uL from that well into a tube containing 500 uL SM and 50 uL $CHCl_3$. This is referred to as the breakout stock.
   c) Store at 4° C.
8. Using methods previously described, plate about 10 uL of each breakout stock onto 150 mm NZY plates using red starch. The objective is to obtain several (at least 20) well-separated plaques from which to core isolates.

Day 3
1. Check pintooled plates for an acceptable incidence of clearings in the bacterial lawn corresponding to wells on the associated assay plate. Also check for clearings in the red starch in the positive controls and in any tested putatives. Be wary of contaminants that also form clearing zones in red starch (see below).

2. From the solid phase plates containing dilutions of breakout stocks, core several isolated plaques, each into 500 uL SM with 50 uL CHCl$_3$. This is referred to as the isolate stock.
3. The isolate stocks can then be individually tested on BODIPY starch using methods described above. This step can be skipped if the plaque that was cored in step 2 produced a clearing zone in the red starch background. The isolate stocks were then be individually tested on BODIPY starch using methods described above. However, this step may be skipped if the plaque that was cored in step 2 produced a clearing zone in the red starch background.

Excisions
Day 1
1. In a Falcon 2059 tube, mix 200 uL OD1 XL1-Blue MRF host, 100 uL lambda isolate stock and 1 uL EXASSIST™ phage stock.
2. Incubate in 37° C. shaker for 15 minutes.
3. Add 3 mL NZY medium.
4. Incubate in 30° C. shaker overnight.

Day 2
1. Heat to excision tube to 70° C. for 20 minutes.
2. Centrifuge 1000×g for 10 minutes.
3. In a Falcon 2059 tube, combine 50 uL supernatant with 200 uL EXP505™ OD1 host.
4. Incubate in 37° C. shaker for 15 minutes.
5. Add 300 uL SOB medium.
6. Incubate in 37 C shaker for 30-45 minutes.
7. Plate 50 uL on large LB$_{kan50}$ plate using sterile glass beads. If the plates are "dry", extra SOB medium can be added to help disburse the cells.
8. Incubate plate at 30° C. for at least 24 hours.
9. Culture an isolate for sequencing and/or RFLP.

Growth at 30° C. reduces plasmid copy number and is used to mitigate the apparent toxicity of some amylase clones.

Contaminants That Form Clearing Zones in Red Starch

When using red starch on solid medium to assay phage for amylase activity, it is common to see contaminating colony forming units (cfu) that form clearing zones in the red starch. For pintooled plates, it is important to distinguish amylase-positive phage clones from these contaminants whenever they align with a particular well position. The source of the contaminating microbes is presumably the 2% red starch stock solution, which cannot be sterilized by autoclaving or by filtering after preparation. It is thought that they are opportunistic organisms that survive by metabolizing the red starch. In order to reduce these contaminants, sterile techniques can be used when making 2% red starch solutions and store the stocks either at 4° C. or on ice.

Example 8

Characterization of Alpha Amylase pH Optimum and Specific Activity Determination The following example describes an exemplary method for determining if a polypeptide is within the scope of the invention, e.g., by alpha amylase activity pH optimum and specific activity determination.

Enzymes of this invention can be used, for example, for both starch liquefaction for corn wet milling and desizing for textiles; e.g., in some embodiments enzymes of the invention have a pH optimum of 4.5 to 5.0; at this lower pH, it is possible to use little or no calcium which lowers overall operating costs and less byproduct formation. In addition, at this low pH, there is decreased chemical usage and ion exchange load. The industry standard *B. licheniformis* amylase is suboptimal in both thermostability and pH optimum. In some embodiments enzymes of the invention have a higher application specific activity compared to *B. licheniformis* amylase and therefore much less enzyme is required to hydrolyze a ton of starch (e.g., in some embodiments, as much as 20-fold less enzyme can be used).

The pH optimum for the hydrolysis of starch can be determined by reacting 50 uL of enzyme, 0.35 U/ml, with a 100 ml of 1% soluble starch solution (0.0175 U/g of starch) for 30 minutes at 95 degrees C. The reducing ends generated in the liquefied starch solution can be measured by the neocupronine assay, described herein. The percent hydrolysis of cornstarch can be determined by measuring the number of sugar reducing ends produced with the neocupronine assay. Seventy grams of buffer solution (pH4-7) was weighed and 100 ppm of calcium can be added. Thirty grams of cornstarch can be mixed into the buffer solution to form a starch slurry. The enzyme can be added and the vessels sealed and incubated at 95 degrees C. for 30 minutes with an initial heating rate of six degrees C. per minute. A 1 ml sample can be extracted from the reaction beakers and analyzed by the neocupronine assay. In some embodiments enzymes of the invention have an optimum between pH 4.5 and 5, while the commercial *B. licheniformis* amylase performs optimally at about pH 6.0.

Example 9

Amylase Activity Assays

The following example describes, inter alia, exemplary methods for determining if a polypeptide is within the scope of the invention, e.g., by the assays described below.

Assay Using RBB-starch 75 ul of RBB-starch substrate (1% RBB-insoluble corn starch in 50 mM NaAc buffer, pH=4.5) is added into each well of a new 96-well plate (V-bottom). Five micro-liters of enzyme lysate is transferred into each well with substrate using BIOMEK™ or ZYMARK™. The plates are sealed with aluminum sealing tape and shaken briefly on the shaker. The plates are incubated at 90° C. for 30 minutes, followed by cooling at room temperature for about 5 to 10 minutes. One hundred micro-liters of 100% ethanol is added to each well, the plates sealed and shaken briefly on the shaker. The plates are then centrifuged 4000 rpm for 20 minutes using bench-top centrifuge. 100 ul of the supernatant is transferred into a new 96-well plate (flat bottom) by BIOMEK™ and read OD$_{595}$. Controls should be used.

Assay Using FITC-starch

Add 50 ul of substrate (0.01% FITC-starch in 100 mM NaAc buffer, pH=4.5) into each well of a new 384-well plate. Transfer 5 ul of enzyme lysate into each well with substrate and incubate the plate at room temperature overnight. The polarization change of the substrate, excitation 485 nm, emission 535 nm, is read for each well. Controls should be used. 96 well plates can be used for all assays.

Confirmation of New Active Clones

Each positive clone from screening is grown and induced using a standard protocol. Each clone is examined for growth (i.e., cell density over time), activity at per cell level (RBB-starch assay and liquefaction assay), expression (protein gel)

Example 10

Exemplary Protocol for Liquefying Starch and Measuring Results

The following example described and exemplary protocol for liquefying starch using amylases and/or glucoamylases of the invention. One exemplary assay uses liquefied starch at pH 4.5 or 6.5 using the reaction conditions show below:

Reaction Conditions: 100 mM $PO_4$ pH 6.5, 1% (w/w) liquefied starch DE 12 at 55° C. Both TLC and HPLC assays are done to verify activity. pH profiles for the amylases to be tested are run using phosphate buffer pHed from 3.0-6.5, at 55° C. From the amount of observable hydrolysis, it can be visually demonstrated that some clones are more (or less) active at certain pH values than at other values at the above indicated reaction conditions.

An exemplary protocol for the saccharification of liquefied starch at pH 6.5:

Adjust the pH of the liquefied starch to the pH at which the saccharification(s) is performed. Liquefy starch in 100 mM sodium acetate buffer, pH 4.5 with 100 mM sodium phosphate salts added so that before saccharification, the pH is adjusted to pH 6.5.

Weigh 5 gram samples of liquefied starch into tared bottles. Use 0.04% (w/w) OPTIDEXL-400™ or approximately 400 mL of 1-10 diluted stock OPTIDEXL-400™ per 100 grams of liquefied starch.

Calculate the milligrams of OPTIDEXL-400™ contained in the 400 mL of 1-10 diluted stock OPTIDEXL-400™. Next, calculate the volume of lysates needed to give the same concentration of enzyme as the OPTIDEX L-400™.

Add enzymes to liquefied starch samples and incubate at desired temperature) (50C.°. After 18 hours determine DE and prepare a sample for HPLC analysis.

An exemplary DE Determination:

Exemplary Neocuproine Assay:

A 100 ml sample is added to 2.0 ml of neocuproine solution A (40 g/L sodium carbonate, 16 g/L glycine, 0.45 g/L copper sulfate). To this is added 2.0 ml of neocuproine solution B (1.2 g/L neocuproine hydrochloride-Sigma N-1626). The tubes are mixed and heated in a boiling water bath for 12 minutes; cooled, diluted to 10 ml volume with DI water and the OD read at 450 nm on the spectrophotometer. The glucose equivalent in the sample is extrapolated from the response of a 0.2 mg/ml glucose standard run simultaneously.

Exemplary HPLC Analysis:

Saccharification carbohydrate profiles are measured by HPLC (Bio-Rad Aminex HPX-87A column in silver form, 80° C.) using refractive index detection. Mobile phase is filtered Millipore water used at a flow rate of 0.7 ml/min. Saccharification samples are diluted 1-10 with acidified DI water (5 drops of 6 M HCl into 200 mL DI water) then filtered through a 0.45 mm syringe filter. Injection volume is 20 uL.

Exemplary TLC:

Reaction products were w/d at hourly timepoints and spotted and dried on a TLC plate. The Plate was then developed in 10:90 water:isopropanol and visualized with either a vanillin stain or CAM stain and then heated to show reducible sugars. The liquefied starch was partially hydrolyzed to glucose in cases where activity was observed.

Example 11

Starch Liquefaction Using Amylases and/or Glucoamylases of the Invention

This example describes an exemplary method of the invention for liquefying starch using amylases and/or glucoamylases of the invention.

Amylase concentrate can be prepared from fermentation broths by heat treatment, cell washing, alkaline extraction using microfiltration and ultrafiltration (48% overall yield). The UF concentrate can be neutralized with acetic acid and formulated with 30% glycerol at pH 4.5. The activity level of the slurry formulation can be representative of a commercial product (120 $U^1$/g-0.5 kg/ton starch).

Standard Amylase Activity Assay

A 1 mL cuvette containing 950 µL of 50 mM MOPS pH 7.0 containing 5 mM PNP-α-D—hexa-(1→4)-glucopyranoside is placed in the Peltier temperature controller of the Beckman DU-7400 spectrophotometer preheated to 80° C. The spectrophotometer is blanked at 405 nm and 50 µL of the enzyme solution is added to the cuvette, mixed well and the increase in the $OD_{405nm}$ is monitored over a one-minute interval. The $\Delta OD_{405nm/min}$ rate is converted to a standard unit of µmole/minute from the $OD_{405nm}$ response of 50 µL of 1 µmole/mL PNP in 950 mL 50 mM MOPS at pH 7.0-80° C. One standard unit of thermostable alpha amylase (DTAA) is equal to the amount of enzyme that will catalyze the release of 1 µmole/mL/minute of pNP under the defined conditions of the assay.

Standard Glucoamylase Activity Assay

A 1 mL cuvette containing 950 µL of 50 mM MOPS pH 7.0 containing 5 mM pNP-α-D-glucopyranoside is placed in a Peltier temperature controller of a DU-7400™ spectrophotometer (Beckman) preheated to 60° C. The spectrophotometer is blanked at 405 nm and 50 µL of the enzyme solution is added to the cuvette, mixed well and the increase in the $OD_{405nm}$ is monitored over a one-minute interval. The $\Delta OD_{405nm}$/min rate is converted to a standard unit of µmole/minute from the $OD_{405nm}$ response of 50 µL of 1 mmole/mL pNP in 950 mL 50 mM MOPS at pH 7.0-60° C. One standard unit of glucoamylase (DGA) is equal to the amount of enzyme that will catalyze the release of 1 mmole/mL/minute of pNP under the defined conditions of the assay.

Dextrose Equivalent Determination

The neocuproine assay method can be used to measure the DE. Selected samples can be measured by a procedure described herein, and/or by a GPC analyst using the GPC Fehlings procedure.

Neocuproine Assay

A 100 µl sample is added to 2.0 ml of neocuproine solution A (40 g/L sodium carbonate, 16 g/L glycine, 0.45 g/L copper sulfate). To this is added 2.0 ml of neocuproine solution B (1.2 g/L neocuproine hydrochloride-Sigma N-1626). The tubes are mixed and heated in a boiling water bath for 12 minutes; cooled, diluted to 10 ml volume with DI water and the OD read at 450 nm on the spectrophotometer. The glucose equivalent in the sample is extrapolated from the response of a 0.2 mg/ml glucose standard run simultaneously.

The starch sample is diluted ~1 to 16 with DI water with the exact dilution recorded. Ten milliliters of the diluted sample is added to 20 mls of DI water. Ten milliliters of Fehlings solution A and B are added to the diluted starch. The sample is boiled for 3 minutes and cooled on ice. Ten milliliters of 30% KI and 10 ml of 6N $H_2SO_4$ is added. The solution is titrated against 0.1N sodium thiosulfate. The titrant volume is recorded and used to calculate the DE.

Residual Starch Determination

Post-saccharification samples can be checked for residual starch using the Staley iodine procedure. Twenty grams of sample is weighed into a large weigh dish. 45 μL of Iodine solution is added to the weigh dish and the starch solution is mixed well. Dark blue indicates the presence of starch, a light blue-green indicates slight starch, light green indicates a trace of starch and yellow-red, absence of starch. Iodine solution is prepared by dissolving 21.25 grams of iodine and 40.0 grams of potassium iodide in one liter of water.

Oligosaccharide Profile

Liquefaction and saccharification carbohydrate profiles can be measured by HPLC (e.g., an AMINEX HPX-87C™ column (Bio-Rad) in calcium form −80° C.) using refractive index detection.

Gel Permeation Chromatography

The molecular weight distribution can be determined by chromatography, e.g., on a PL AQUAGEL-OH column™ with mass detection by refractive index (Waters Model 2410). A Model T60™ (Viscotek) detector can be used for continuous viscosity and light scattering measurements.

Capillary Electrophoresis

A Beckman Coulter P/ACE MDQ™ Glycoprotein System for separation of APTS derivatized oligosaccharides on a fused silica capillary can be used; in one aspect, detection by laser-induced fluorescence is used.

Primary Liquefaction

Line starch directly from the GPC process is pumped into a 60 liter feed tank where pH, DS (dry solids) and calcium level can be adjusted before liquefaction. The amylase is added to the slurry. The 32% DS slurry is pumped at 0.7 liter/minute by a positive displacement pump to the jet—a pressurized mixing chamber where the starch slurry is instantaneously heated to greater than 100° C. by steam injection. The gelatinized partially liquefied starch is pumped through a network of piping (still under pressure) to give the desired dwell time (5 minutes) at temperature. The pressure is released into a flash tank and samples can be taken. Samples were taken in duplicate.

Secondary Liquefaction

The liquefied starch is collected in one liter glass bottles and held in a water bath at 95 C for 90 minutes.

Saccharification

Liquefied starch is cooled to 60° C., the pH adjusted to 4.5 and the samples treated with glucoamylase. Saccharification progress can be monitored over time, e.g., by HPLC.

The liquefied syrups produced with each amylase are adjusted to approximately pH 2.5 with 6N HCl immediately after the 90 minute secondary liquefaction to inactivate any residual amylase. The syrups are then adjusted to pH 4.5, placed in a 60° C. water bath and saccharified with three levels of glucoamylase. The extent of saccharification is monitored by HPLC at 18-88 hour time points.

The liquefied syrups are saccharified with the standard dosage −0.04% of a double-strength glucoamylase—and two lower dosages (50% and 25%) to monitor any differences in the saccharification progress.

Saccharification progress data can be analyzed by % dextrose development vs time, e.g., with 0.04% glucoamylases; or, % dextrose development vs time, e.g., with 0.02% glucoamylases.

Post-Saccharification Sugar Profile

Molecular Weight Distribution

The molecular weight distribution of syrups liquefied to DE's of 12 and 18 by amylases and/or glucoamylases of the invention, and in some aspects, using controls, e.g., commercial enzymes, e.g., *Bacillus licheniformis* or commercial *Bacillus stearothermophilus*, can be measured by gel permeation chromatography using detection by refractive index, light scattering and viscosity. Both the *B. licheniformis* and *B. stearothermophilus* amylases generate a bimodal distribution—the primary peak centered at 2000, a secondary peak at 32,000 with a shoulder extending past the 160,000 range. The lower molecular weight peak represents approximately 60% of the total mass of the sample. In some embodiments, amylases and/or glucoamylases of the invention can exhibit a single peak at 2000 with very little above 30,000.

HPLC

The DE 12 and 18 syrups produced by amylases and/or glucoamylases of the invention (and the control commercial enzymes, e.g., amylases from *Bacillus licheniformis* and/or commercial *Bacillus stearothermophilus* amylases) can be analyzed by HPLC. Both techniques produce fingerprints characteristic of each class of amylase; the oligosaccharide patterns are different for *B. licheniformis* amylase vs *B. stearothermophilus* amylase, and amylases and/or glucoamylases of the invention are also expected to produce fingerprints characteristic of their enzyme classes. The liquefied syrups of the invention (e.g., syrups made by methods of the invention and/or made by enzymes of the invention) exhibit evidence of greater branching in the oligosaccharides. HPLC only resolve the oligosaccharides in the <DP15 range—larger fragments are not visible in these techniques. *Bacillus* amylases are known to liquefy starch in a manner such that the amylopectin fraction is hydrolyzed less extensively than the amylose fraction. These >DP30 amylopectin fragments are contained in the high molecular weight fraction centered at 32,000 and consequently, little evidence of branching is seen in the HPLC analyses of the *Bacillus* liquefied syrups. In one aspect, <DP15 oligosaccharides in liquefied syrups made using amylases and/or glucoamylases of the invention contain fragments from both amylose and amylopectin.

Example 12

Starch Liquefaction at Acidic Conditions Using Amylases and/or Glucoamylases of the Invention The invention provides methods for liquefying starch using amylases and/or glucoamylases of the invention, including amylases active under acidic conditions, e.g., between about pH 4.0 and 5.0, e.g., pH 4.5. In one embodiment, the conversion of starch to glucose can be catalyzed by the sequence action of two enzymes: an endoamylase of the invention, e.g., an amylase, such as an alpha-amylases, and an exoamylase, e.g., a glucoamylase of the invention, to liquefy the starch (e.g., the hydrolysis of high molecular weight glucose polymers to oligosaccharides consisting of 2 to 20 glycose units, typically a dextrose equivalent of 10 to 12, by an amylase of the invention), followed by saccharification with an exoamylase, e.g., a glucoamylase (which can be a glucoamylase of the invention).

In one aspect, processing is in a corn wet milling plant producing a starch slurry having a pH or about 4.0 to 4.5. In one aspect, the pH is raised, e.g., to 5.8 to 6.0 before liquefaction to accommodate an alpha amylase with a low pH activity and stability (which can be an alpha amylase of the invention). In one aspect, amylases and/or glucoamylases of the invention can liquefy starch at pH 4.5 to dextrose equivalents ranging from 12 to 18; in one aspect, using alpha Amylases and/or glucoamylases of the invention at levels of about 3 to 6 grams per ton of starch. In this aspect, use of alpha Amylases and/or glucoamylases of the invention enable starch liquefaction to be conducted at pH 4.5.

In one aspect, starch liquefaction is conducted at pH 4.5 for 5 minutes at 105° C. to 90 minutes at 95° C. using amylases and/or glucoamylases of the invention. The quantity of enzyme can be adjusted in order to adjust a target DE of 12 to 15 after liquefaction. In one aspect, the liquefied starch is then saccharified with a glucoamylase, e.g., an *Aspergillis* glucoamylase, for about 48 hours at about pH 4.5 and 60° C. If the saccharified syrup does not contain at least 95% glucose, the target liquefaction DE is raised and the saccharification repeated until the liquefaction eventually does produce a saccharified syrup containing more than 95% glucose. The amylase protein required to produce a suitable liquefied feedstock for saccharification can be determined, e.g., by PAGE or HPLC.

Example 13

Starch Liquefaction Using Amylases and/or Glucoamylases of the Invention

This example describes an exemplary method for liquefying starch using amylases and/or glucoamylases of the invention; and described use of commercial *Bacillus licheniformis* and *Bacillus stearothermophilus* amylases as controls. These assays can compare the saccharification progress and final dextrose levels from syrups generated by enzymes of the invention and commercial amylases.

Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100. One exemplary process of the invention uses an enzyme dosage of about 60 to 70 Units/kilo starch at pH 4.5 to reach a 19 DE.

Oligosaccharide patterns generated by amylases and/or glucoamylases of the invention and commercial amylases can be analyzed by molecular weight (MW) distribution using, e.g., gel permeation chromatography with detection by light scattering and viscosity. In one aspect, amylases and/or glucoamylases of the invention can generate an 18DE and a uniform oligosaccharide MW distribution, with nothing greater than 20,000. This is consistent with the lower viscosity for syrups of the invention (e.g., syrups made by methods of the invention, or, made using enzymes of the invention). The DP (degrees of polymerization) profiles as measured by HPLC also can be used to analyze differences in action pattern.

Amylase concentrate are prepared from fermentation broths by heat treatment, cell washing, alkaline extraction using microfiltration and ultrafiltration (UF). The UF concentrate is neutralized with acetic acid and formulated with 30% glycerol at pH 4.5. The activity level of the slurry formulation can be analyzed, e.g., 120 U1/g-0.5 kg/ton starch is representative of a commercial product.

Example 14

Alkaline Amylases for Laundry and Autodishwash Applications

In one aspect, the invention provides detergents comprising amylases and/or glucoamylases of the invention, including amylases and/or glucoamylases active under alkaline conditions, and methods of making and using them.

The invention provides alkali-stable amylase and/or glucoamylase enzymes, which can be compared to commercial benchmark enzyme(s) with respect to features important in laundry and automatic dishwashing (ADW) applications:

An ADW wash test on starch-coated slides.

Amylase and/or glucoamylase enzyme activity testing in the presence of a laundry/ADW formulation using a soluble substrate.

In the presence of chelators, amylase and/or glucoamylase enzyme activity testing.

Amylase and/or glucoamylase enzyme activity testing and alkaline pH optima ranges determined (e.g., from pH 10 to 11).

Amylase and/or glucoamylase enzyme activity testing for thermophilic properties, e.g., performance at about 65° to 70° C.

Amylase and/or glucoamylase activity can be measured either by a reducing sugar assay or by monitoring the fluorescence at 520 nm (485 nm excitation) when BODIPY-starch was used. Initial rates can be calculated and converted to a percentage of the maximum rate.

Application Testing

Experiments can be designed to assess the activity and stability of alkaline amylases and/or glucoamylases of the invention in laundry/ADW formulations and with the components individually. Amylase and/or glucoamylase activity can be assessed under conditions comprising the chelator EDTA and/or hydrogen peroxide; commercial benchmark enzymes can be controls.

For example, purified proteins are incubated at 50° C. in the presence or absence of 5 mM EDTA for a desired time(s), after which residual amylase activity is measured using soluble substrate. Activity in the presence of EDTA is expressed as the % of activity in the absence of chelator. Alternatively, enzyme activity in the presence of peroxide hydroxide can be assessed. Purified proteins are incubated at 50° C. in the presence or absence of 1M $H_2O_2$ for a desired time, after which amylase activity is measured using soluble starch. Activity in the presence of peroxide hydroxide is presented as the % of activity in the absence of $H_2O_2$. Enzyme activity can be tested in an ADW solution (distilled water, hardening solution, bleach, chelators, surfactants) with soluble substrate (BODIPY-starch). Purified proteins can be reacted with soluble starch at 40° C. in the presence of laundry/ADW formulation. Initial rates are calculated over 5 minutes and expressed as fluorescent units (FU)/s per ng of protein.

Wash tests with starch-coated slides can be performed as follows: purified proteins are incubated with slides at 50° C. for 30 min in the presence of ADW solution (distilled water, water hardening solution, bleach, chelators, surfactants). Starch removal is measured comparing weight loss after the enzyme treatment to the initial weight of the slide.

Characterization of Exemplary Amylases

The gene encoding the amylase can be modified to comprise a Starch/Carbohydrate Binding Domain. The proteins can be expressed with and without a C-terminal histidine tag, and in non-glycosylating and a glycosylating host. Enzymes can be expressed in Host/His tag combinations, and pH and temperature optimas determined. Enzymes expressed in a glycosylating host with a His tag can be used for test experiments. The presence of the His tag should not affect specific activity, however, glycosylation may result in a slightly lower specific activity than that without glycosylation.

Example 15

Identification and Characterization of a Thermostable Amylase

The following example describes exemplary protocols for the identification and characterization of thermostable amylases.

In one study, 350 fungal isolates were screened on solid medium containing granular starch as the sole source of carbon. Strains that completely hydrolyzed starch or displayed significant growth were submitted for cDNA isolation and proteomics analysis of their secreted proteins. A combination of Sequence Based Discovery and Proteomic Analysis was employed for recovering DNA sequences encoding amylases, glucoamylases and glucosidases that were shown by proteomics to be secreted during growth on granular starch.

The recovered full-length cDNA sequences were subcloned for expression in *Pichia pastoris* and the expressed proteins were further characterized with the BCA assay (which was used to determine the increase in concentration of reducing ends during hydrolysis of starch by the amylases) and the Glucose Oxidase (GO) assay (which was used for detecting glucose released from starch by the glucoamylases), exemplary protocols for both of these assays are described herein.

TABLE 1

| SEQ ID NOs: | Enzyme activity class | CBM20 | Source (as determined by 18S RNA) |
|---|---|---|---|
| SEQ ID NO: 50 (encoded by, e.g., SEQ ID NO: 49) | amylase | no | *Aspergillus terreus* |
| SEQ ID NO: 52 (encoded by, e.g., SEQ ID NO: 51) | amylase | CBM20 | *Aspergillus terreus* |
| SEQ ID NO: 54 (encoded by, e.g., SEQ ID NO: 53) | amylase | no | *Aspergillus terreus* |
| SEQ ID NO: 4 (encoded by, e.g., SEQ ID NO: 3) | amylase | CBM20 | *Cochliobolus heterostrophus* |
| SEQ ID NO: 2 (encoded by, e.g., SEQ ID NO: 1) | amylase | CBM20 | *Cochliobolus heterostrophus* |
| SEQ ID NO: 32 (encoded by, e.g., SEQ ID NO: 31) | amylase | no | *Penicillium chrysogenum* 100% |
| SEQ ID NO: 46 (encoded by, e.g., SEQ ID NO: 45) | amylase | no | *Fusarium equiseti* 100% |
| SEQ ID NO: 22 (encoded by, e.g., SEQ ID NO: 21) | amylase | no | *Penicillium expansum* 99% |
| SEQ ID NO: 24 (encoded by, e.g., SEQ ID NO: 23) | amylase | no | *Penicillium chrysogenum* 100% |
| SEQ ID NO: 8 (encoded by, e.g., SEQ ID NO: 7) | glucoamylase | no | *Cochliobolus heterostrophus* |
| SEQ ID NO: 16 (encoded by, e.g., SEQ ID NO: 15) | glucoamylase | CBM20 | *Cochliobolus heterostrophus* |
| SEQ ID NO: 14 (encoded by, e.g., SEQ ID NO: 13) | glucoamylase | CBM20 | *Fusarium verticillioides* GZ3639 |
| SEQ ID NO: 18 (encoded by, e.g., SEQ ID NO: 17) | glucoamylase | CBM20 | *Fusarium verticillioides* GZ3639 |
| SEQ ID NO: 10 (encoded by, e.g., SEQ ID NO: 9) | glucoamylase | no | *Penicillium expansum* 99% |
| SEQ ID NO: 12 (encoded by, e.g., SEQ ID NO: 11) | glucoamylase | CBM20 | *Fusarium equiseti* 100% |
| SEQ ID NO: 26 (encoded by, e.g., SEQ ID NO: 25) | glucoamylase | CBM20 | *Penicillium verruculosum* 100% |
| SEQ ID NO: 20 (encoded by, e.g., SEQ ID NO: 19) | glucoamylase | no | *Penicillium chrysogenum* 100% |
| SEQ ID NO: 28 (encoded by, e.g., SEQ ID NO: 27) | glucoamylase | CBM20 | *Fusarium merismoides* 99% |
| SEQ ID NO: 30 (encoded by, e.g., SEQ ID NO: 29) | glucoamylase | CBM20 | *Phoma herbarum* 99 |
| SEQ ID NO: 34 (encoded by, e.g., SEQ ID NO: 33) | glucoamylase | no | *Penicillium herquei* 99% |
| SEQ ID NO: 36 (encoded by, e.g., SEQ ID NO: 35) | glucoamylase | CBM20 | *Fusarium oxysporum* 100% |
| SEQ ID NO: 38 (encoded by, e.g., SEQ ID NO: 37) | glucoamylase | CBM20 | *Cordyceps ophioglossoides* 99% |
| SEQ ID NO: 40 (encoded by, e.g., SEQ ID NO: 39) | glucoamylase | CBM20 | *Penicillium chrysogenum* 100% |
| SEQ ID NO: 42 (encoded by, e.g., SEQ ID NO: 41) | glucoamylase | no | *Cucurbitaria berberidis* 98% |
| SEQ ID NO: 48 (encoded by, e.g., SEQ ID NO: 47) | glucoamylase | CBM20 | *Aspergillus versicolor* 99 |
| SEQ ID NO: 44 (encoded by, e.g., SEQ ID NO: 43) | α-glucosidase | | *Cochliobolus heterostrophus* |
| SEQ ID NO: 6 (encoded by, e.g., SEQ ID NO: 5) | α-glucosidase | | *Cochliobolus heterostrophus* |

Fungal isolates were screened on modified solid media according to Marlida (2000) World J. Microbiol. Biotechnol. 16:573-578. The medium contained Czapek Dox salts and 1% MIMAIZE$^{260}$™ (HiMaize$^{260}$, National Starch & Chemical, Bridgewater, N.J.) resistant starch as the sole source of carbon. The MIMAIZE$^{260}$™ starch was added to the cool agar without sterilization in order to preserve the granular structure of the starch. Additionally the same fungal strains were screened on a medium with 0.5% red starch (Megazyme, Ireland) in order to identify strains that secreted amylolytic enzymes.

After 5 days of growth, isolates that grew well on resistant starch and secreted starch—degrading enzymes, visualized by a clearing zone on the red starch medium, were chosen as "primary hits". In the second step, primary hits were grown in liquid medium with Czapek Dox salts and 1% resistant starch (MIMAIZE$^{260}$™) as the sole source of carbon for approximately 2 weeks. Strains that completely cleared the starch solution or displayed significant growth in this medium were submitted for cDNA isolation and proteomics analysis of culture supernatants. The combination of Sequence Based Discovery and proteomics was employed for recovering sequences encoding amylases and glucoamylases.

Sequence Based Discovery was performed using two approaches. In one, universal degenerate primers for PCR recovery of amylase and glucoamylase genes were designed based on alignment of known fungal protein sequences. In the other approach, universal degenerate primers were combined in PCR with primers based on the peptide sequences obtained from the proteomics analysis of culture supernatants from fungal isolates grown on granular starch. In both cases the primers were used for PCR with template DNA comprising cDNA made from the same starch-digesting fungal strains. By this means, partial gene sequences were recovered. Peptide data were also used to facilitate recovery of full-length versions of the partial sequences using 5' and 3' RACE PCR.

For known fungal species with pre-sequenced genomes, proteomics analysis was used to determine the sequences of peptides derived from putative amylases using the following approach: 1) Following SDS-PAGE analysis of samples derived from fungal extracts grown on resistant starch as the sole source of carbon, individual bands were subjected to protease digestion; 2) Mass spectroscopy analysis of recovered peptides was carried out on an LCQ instrument; 3) Peptide sequences were determined by SEQUEST™ (Sage-N Research, Inc. and Thermo Scientific) database searches.

For unknown fungal species, the peptide sequences where determined by a method similar to the one described above with the exception that the accurate masses of peptides and their constituent amino acids were determined using a QTOF instrument. The sequences of the recovered peptides were used as a template to produce degenerate oligonucleotide primers for PCR amplification of the genes from cDNA made from the relevant fungal species grown on MIMAIZE[260]™ granular starch.

The recovered full-length cDNA sequences encoding amylases and glucoamylases were subcloned for expression in *Pichia pastoris* and the expressed proteins were further characterized using the BCA assay for measuring the increase in concentration of reducing ends during starch hydrolysis by amylases, and the GO assay for the detection of glucose released during starch hydrolysis by glucoamylases.

For determining the activity of both amylases and glucoamylases, starch hydrolysis reactions were performed as follows: Assays were performed in triplicate in an Eppendorf tabletop incubator with constant shaking (800 rpm), at 37° C. and pH 5.0 in 50 mM sodium acetate buffer containing 1% raw granular starch. Reactions were started by adding the enzyme to the reaction mix. At different time points aliquots of the reactions were withdrawn and quenched either by addition of 1M Tris pH 7.5 (glucoamylases) or BCA reagent (amylases).

BCA assay for measuring the increase in concentration of reducing ends. The activity of alpha-amylases was measured by the appearance of reducing groups formed during the hydrolysis of starch. The BCA—Bicincochinic Acid (Copper-BCA) assay of Reducing Sugars was performed according to Wong (2000) Microassay for rapid screening of alpha-amylase activity, J. Agric. Food Chem. 48:4540-4543; and, Fox (1991) Miniaturization of three carbohydrate analyses using a micro sample plate reader, Anal. Biochem. 195:93-96, was used.

A 10 μl aliquot of amylase starch hydrolysis reaction was quenched into 100 μl of BCA reagent (consisting of 64 mg/mL sodium carbonate monohydrate, 24 mg/mL sodium bicarbonate, 1.95 mg/mL BCA, 1.24 mg/mL cupric sulfate pentahydrate, 1.26 mg/mL L-serine). Color development occurred during incubation of the quenched reaction at 80° C. for 35 minutes, and was followed by absorbance determination at 560 nm. Initial rates were calculated over a 50 mM reaction time. A standard curve using maltose was constructed to correlate $A_{560nm}$ with the concentration of generated reducing sugars (nmoles). Specific activity was expressed as nmoles/min/μg enzyme.

Glucose oxidase/peroxidase (GO) assay for the quantification of glucose released during starch hydrolysis: The activity of glucoamylases was measured by the modified GO (coupled glucose oxidase) assay according to Bergmeyer, In Determination with Glucose Oxidase and Peroxidase; Bergmeyer, H. U., Ed.; *Methods of Enzymatic Analysis,* 2nd Ed.; 1974; pp 1205-1212).

GO reactions were started by adding 10 μl of the quenched starch hydrolysis reaction to 90 μl of PBS containing glucose oxidase (0.1 U/ml), peroxidase (0.25 U/ml) and 0.05 mM Amplex Red, in black Nunc 96 well plates. Plates were kept at room temperature in the dark for 30 mM prior to reading on a fluorescence plate reader with Ex/Em 545/590 nm. A standard curve constructed with glucose was used to assess the amount of glucose produced in the hydrolysis reactions. Initial rates of starch hydrolysis (nmols of glucose released from 1% granular starch/min/μg glucoamylase) were determined by plotting the amount of glucose released over time, and calculating the slope of the best linear fit through the data points.

Figure 10:
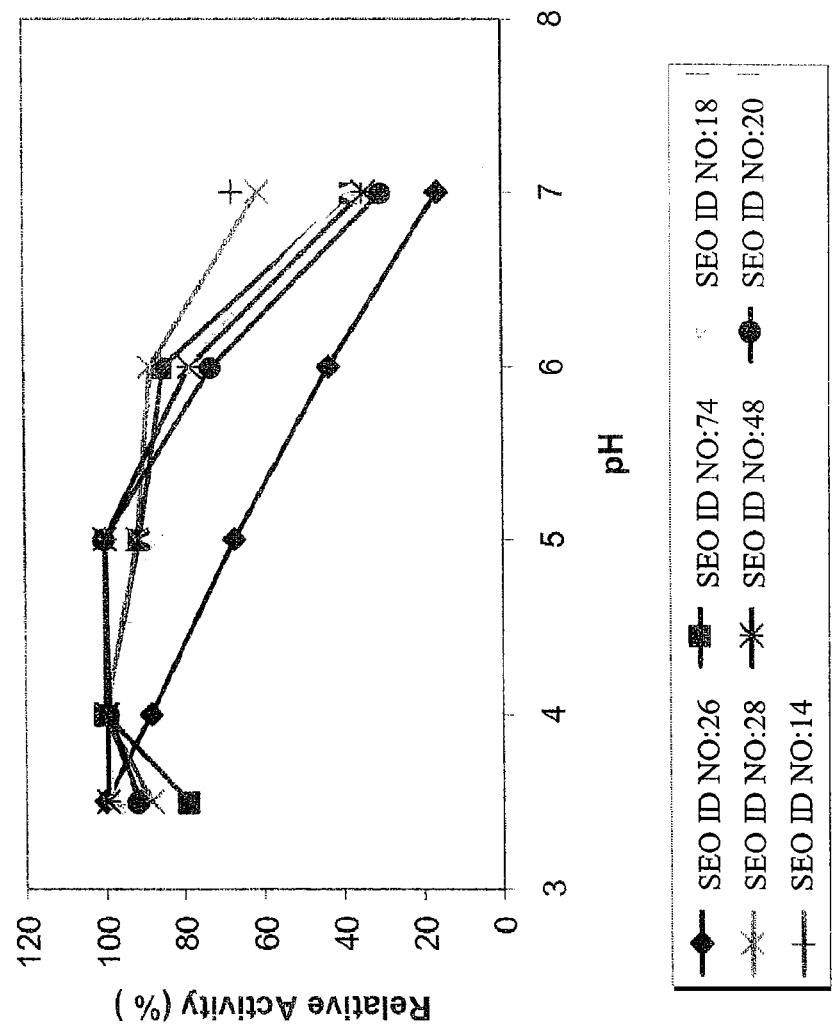
FIG. 10 and FIG. 11 illustrate the influence of pH in the range of between about pH 3.5 to 6.0 on the hydrolysis of starch by seven (7) glucoamylases and two (2) amylases of this invention, as discussed in detail, below.
Figure 11:
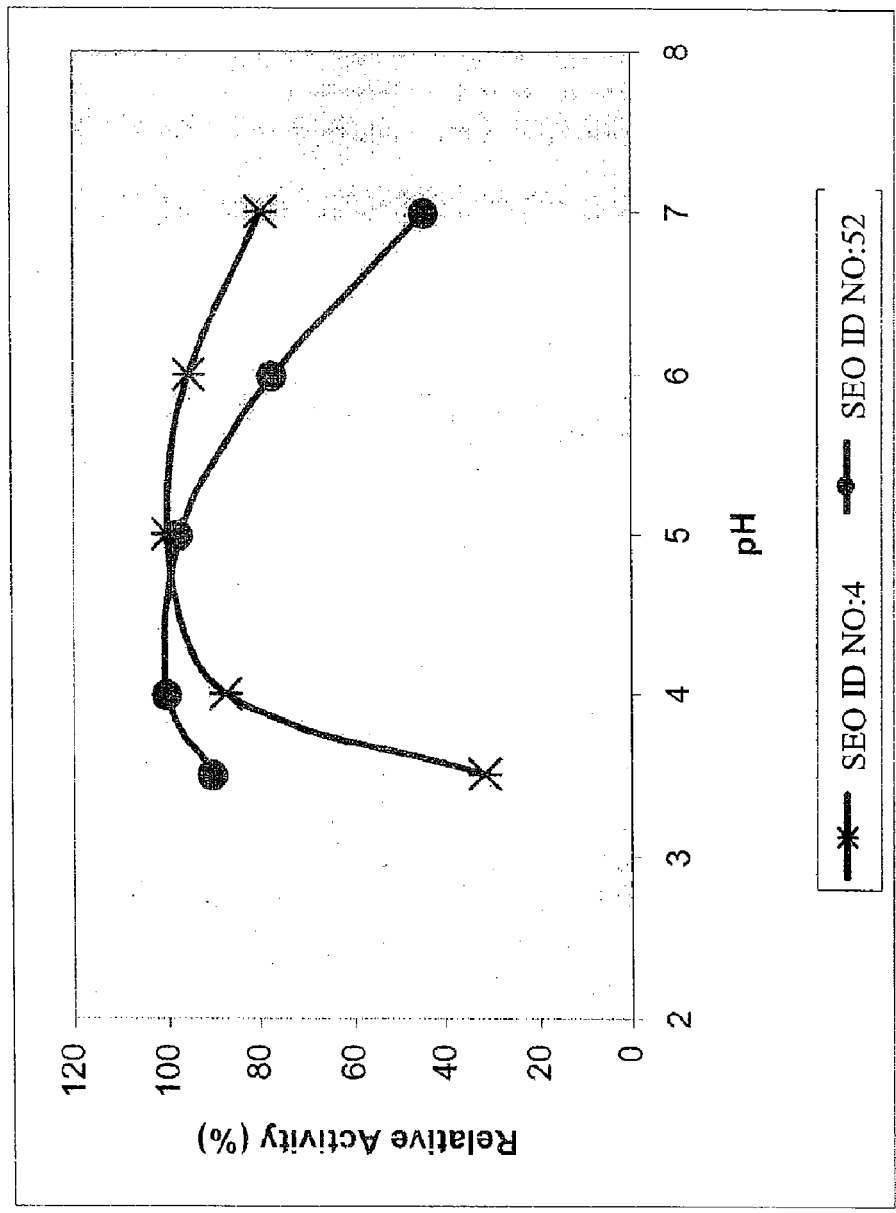

The influence of pH in the range of between about pH 3.5 to 6.0 on the hydrolysis of starch by seven (7) exemplary glucoamylases and two exemplary amylases of this invention is illustrated in FIG. 10 and FIG. 11. FIG. 10 illustrates data showing the influence of pH on granular starch hydrolysis by seven (7) exemplary glucoamylases of this invention at 37° C.; initial rates were calculated over 15 min and converted to the percentage of the maximum observed rate. FIG. 11 illustrates data showing the influence of pH on granular starch hydrolysis by SEQ ID NO:4 (encoded by, e.g., SEQ ID NO:3) and SEQ ID NO:52 (encoded by, e.g., SEQ ID NO:51) amylases at 37° C.; initial rates were calculated over 50 min and converted to the percentage of the maximum observed rate.

Other assays can also be used to characterize an enzyme of the invention, and some exemplary protocols are described, below:

Exemplary Nucleic Acid Extraction Protocol: Microorganisms, e.g., filamentous fungus, are grown in liquid culture. Biomass is collected and high molecular weight genomic DNA is isolated using DNEASY™ (DNeasy) Plant Maxi Kit (Qiagen, Valencia, Calif.) using standard protocols. Total RNA can be isolated using RNEASY™ (RNeasy) Plant Mini Kit (Qiagen) using standard protocols.

Exemplary Library Construction Protocol: genomic DNA can be partially digested with restriction enzymes and fragments between 1-10 kb can be purified for construction of a genome library. The fragments can be ligated into the vector Lambda Zap Express™ (Stratagene, San Diego, Calif.) and packaged into infectable phage as per manufacturer's instructions.

Exemplary Library Screening Protocol: Lambda libraries can be used to infect XL1 Blue MRF™ cells (Stratagene) in top agar. Approximately 50,000 pfu of phage can be added to 600 ul of cells OD600=1. The mixture is incubated at 37° C. for 15 minutes in a water bath and then added to 6 ml melted 0.7% top agar and plated onto NZY agar plates. The plate is then incubated overnight at 39° C. A nylon circle (F. Hoffmann-La Roche Ltd., Basel Switzerland) can be laid on top of the resulting plaque lawn and lifted back up with some of the phage adhering to the nylon. The nylon can be submerged in 1.5M NaCl, 0.5M NaOH for 2 minutes, 1.5M NaCl, 0.5M Tris pH 7.6 for 5 minutes and 2×SSC, 0.2M Tris pH7.6 for 30 seconds. The nylon filter is then UV crosslinked, e.g., in a Stratagene crosslinker PCR fragments from amylase, e.g., glucoamylases, genes can be used probes, e.g., using an Expand High Fidelity PCR Kit™ (Roche) using 30 cycles of 95° C. for 20 seconds, 55° C. for 30 seconds, and 72° C. for 1 minute in a thermal cycler. The isolated PCR fragment can be prepared as a radioactive probe using the Prime It Kit™ (Stratagene) following manufacturer's instructions.

The library filter lifts are washed in a prehybridization solution (e.g., DIG EASY HYB™, Roche) for two hours at 42° C. in a hybridization oven (Robbins). The probe can be added to 15 ml fresh DIG EASY HYB™ and used to replace the prehybridization solution. The filter is washed with probe overnight, e.g., at 45° C. The probe can be removed and the filter washed once with 2×SSC, 0.1% SDS for 15 minutes, and twice with 0.1×SSC, 0.1% SDS for 15 minutes each. The nylon filter can be exposed to x-ray film overnight at −80 C. Following developing, hybridization spots on the x-ray film can be used to identify clones from the original plate. An agar plug can be taken from the plate where the spots lined up and suspended in SM buffer to release the phage into solution. Several isolated plaques corresponding to genomic fragments containing all or part of an amylase gene can be thus isolated.

100 ul of isolated phage stock can be added to 200u1 XL-1 BLUE MRF™ cells (Stratagene) and 1 ul EXASSIST™ helper phage (Stratagene). The mixture can be incubated at 37 C for 15 minutes, and 3 ml of 2×YT media can be added. This can be incubated at 37° C. with shaking for 2.5 hours. The mix can be heated for 20 minutes at 70° C. and cooled on ice. 100 ul of the mix can be removed and added to 200 ul SOLR cells (Stratagene) and incubated at 37° C. for 15 minutes. 50 ul can be plated on LB kanamycin (50 ug/ml) plates and incubated overnight at 37° C. Resulting colonies may contain cloned genomic fragments in the plasmid pBK-CMV.

Exemplary Sequencing Protocol: DNA sequencing on candidate clones can be performed with the BIGDYE TERMINATOR™ cycle sequencing VERSION 2.0 Kit™ (Applied Biosystems, Foster City, Calif.) and a 3700 DNA Analyzer™ (Applied Biosystems) using manufacturer's protocols. Potential introns can be identified by comparing this sequence with consensus sequences for introns in known amylases.

Exemplary cDNA Synthesis Protocol: PCT primers are used in a cDNA synthesis reaction using a THERMO-SCRIPT™ rtPCR Kit™ (Invitrogen) using manufacturer's protocols.

Exemplary Expression Cloning Protocol: PCT primers are used to generate a PCR fragment using the cDNA clone as a template using 30 cycles of 95° C. for 20 seconds, 55° C. for 30 seconds, 72° C. for 2 minutes, using EXPAND HIGH FIDELITY PCR Kit™ (Roche) and manufacturer's protocols. The PCR fragments are digested with the restriction enzymes and ligated into the corresponding restriction sites of a plasmid, e.g., pPIC Z™ alpha (Invitrogen). The construct can be transformed into a yeast, e.g., *Pichia pastoris* Strain X-33™ (Invitrogen) where the construct integrates stably into the *Pichia* chromosome. Selection can be based on resistance to zeocin. The construct can be designed such that the *Pichia* clone can be induced with methanol to secrete the mature amylase into the media. A 1-liter culture of the expression clone can be inoculated with an overnight yeast starter culture in BMGY and grown overnight at 30° C. in a shake flask. The yeast cells are collected by centrifugation the following day and resuspended in 1 liter of BMMY. The cells are cultured at 30° C. in a shake flask for 3 days with methanol added to 0.5% final every 24 hours. The media containing the expressed glucoamylase enzyme are then collected and tested in a glucoamylase activity assay and SDS PAGE electrophoresed using standard protocols to determine the protein size.

Primers also can designed for overexpression in *Escherichia coli*. PCR primers are used to generate a PCR product as before, from the cDNA template. The PCR fragment can be digested with the restriction enzymes and ligated into corresponding restriction sites of the plasmid, e.g., a pSE420 (Invitrogen). The construct can be transformed into *Escherichia coli*, e.g., Strain XL-1 Blue MR (Stratagene). Selection for the plasmid can be based on ampicillin resistance. The amylase gene can be under the control of a lac-z promoter and can be induced with IPTG (isopropyl-thio-galactopyranoside). The construct can be designed such that the mature glucoamylase gene will be expressed within the *Escherichia* cell and will contain an extra methionine residue at the N-terminus.

Exemplary "Standard" assay: Enzyme aliquots can be added to a solution of 5 mM buffer, 3 mM malto-oligosaccharides (Sigma, M-3639) in a waterbath. 100 ul aliquots can be removed at time points to 200 ul glucose oxidase reagent (Sigma, GAGO-20) and incubated 37° C., 30 min. The reaction can be stopped with addition of 12 N sulfuric acid and the absorbance at 540 nm determined. The full-length version of the enzyme can be tested for pH, temperature and substrate utilization.

Exemplary "Activity" Assay: Enzyme activity can be measured by the release of free glucose from an oligo-dextrin substrate. The liberated glucose can be oxidized in a coupled reaction resulting in a colored product. An enzyme aliquot can be added to solution of 5 mM buffer, 3 mM malto-oligosaccharides (Sigma, M-3639) in a water bath. 100 ul aliquots can be removed at time points to 200u1 glucose oxidase reagent (Sigma, GAGO-20) and incubated 37° C., 30 min. The reaction is stopped with addition of 12 N sulfuric acid and the absorbance at 540 nm determined. Time points are then plotted to determine the relative rate for the reaction. pH Profile: Acetate buffer (pH 4.0, 4.5, 5.0, and 5.4) as well as phosphate buffer (pH 6.2, 7.0, 8.1) can be used in an activity assay to determine the relative rate for the glucoamylase at each pH.

Temperature Profile: The relative rate of the enzyme at various temperatures (e.g., 50° C., 60° C., 70° C., 80° C., and 85° C.) can be determined in acetate buffer pH 5.3.

Temperature Stability Data: Enzyme can be added to 5 mM acetate buffer at a desired indicated temperature. Enzyme aliquots can be removed to ice at 4 minute intervals. The aliquots are then tested for activity on substrate for 20 minutes at 70° C.

Substrate Utilization: The dextrins maltose, maltotriose, panose, maltotetraose, and maltoheptaose can be substituted for the malto-oligosaccharides in the activity assay to test for substrate utilization of an amylase, e.g., a glucoamylase. Rate of glucose release for various substrates can be tested in 5 mM acetate buffer, 70° C.

Example 16

Amylase Activity Assay

BCA Reducing Ends Assay

The following example describes an exemplary method for determining if a polypeptide is within the scope of the invention, for example, by a BCA reducing ends assay. Amylase (including, e.g., glucoamylase) activity can be determined using the following methodology.

1. Prepare 2 substrate solutions, as follows:
  a) 2% soluble starch (potato or granular corn starch) pH 8 solution by dissolving 2 gm potato starch in 100 ml 100 mM sodium phosphate pH 8).
  b) 2% soluble starch (potato) pH 10 solution by dissolving 2 gm potato starch in 100 ml 100 mM sodium carbonate.

Heat both solutions in a boiling water bath, while mixing, for 30-40 minutes until starch dissolves.

2. Prepare Solution A from 64 mg/ml sodium carbonate monohydrate, 24 mg/ml sodium bicarbonate and 1.95 mg/ml BCA (4,4'-dicarboxy-2,2'-biquinoline disodium salt (Sigma Chemical cat #D-8284). Added above to $dH_2O$.

3. Prepare solution B by combining 1.24 mg/ml cupric sulfate pentahydrate and 1.26 mg/ml L-serine. Add mixture to $dH_2O$.

4. Prepare a working reagent of a 1:1 ration of solutions A and B.

5. Prepare a Maltose standard solution of 10 mM Maltose in $dH_2O$, where the mM maltose is combined in 2% soluble starch at desired pH to a final concentration of 0, 100, 200, 300, 400, 600 μM. The standard curve will be generated for each set of time-points. Since the curve is determined by adding 10 ul of the standards to the working reagent it works out to 0, 1, 2, 3, 4, 6 nmole maltose.

6. Aliquot 1 ml of substrate solution into microcentrifuge tubes, equilibrate to desired temperature (5 min) in heat block or heated water bath. Add 50 ul of enzyme solution to the inside of the tube lid.

7. While solution is equilibrating mix 5 ml of both solution A & B. Aliquot 100 ul to 96 well PCR plate. Set plate on ice.

8. After 5 minute temperature equilibration, close lid on tubes, invert and vortex 3 times. Immediately aliquot 10 ul into plate as t=0 (zero time point). Leave enzyme mixture in heat block and aliquot 10 ul at each desired time point (e.g. 0, 5, 10, 15, 20, 30 minutes).

9. Ensure that 12 wells are left empty (only working reagent aliquotted) for the addition of 10 ul of standards, for the standard curve.

10. When all time points are collected and standards are added, cover plate and heated to 80° C. for 35 min Cool plate on ice for 10 min Add 100 ul H$_2$O to all wells. Mix and aliquot 100 ul into flat bottomed 96-well plate and read absorbance at 560 nm.

11. Zero each sample's time points against its own t=0 (subtract the average t=0 A560 value from other average A560 values). Convert the A560$_{(experimental)}$ to umole (Divide A560$_{(experimental)}$ by the slope of the standard curve (A560/umole). Generate a slope of the time points and the umole (in umole/min), multiply by 100 (as the umole value only accounts for the 10 ul used in the assay, not the amount made in the 1 ml rxn). To get the specific activity divide the slope (in umole/min) by the mg of protein. All points should be done at a minimum in duplicate with three being best. Divide protein concentration (mg/ml) by any dilution to get mg used in assay. Divide the above slope by mg used in assay to get specific activity. See for example, Wong (2000) J. Agric. Food Chem. 48:4540-4543; Fox (1991) Anal. Biochem. 195, 93-96.

Example 17

Screening for Amylase activity

The following example describes an exemplary method for determining if a polypeptide is within the scope of the invention. Amylase (e.g., glucoamylase) activity of clones can be assessed by a number of methods known in the art. The following is an example of methodology that can be used.

The number of plaques screened, per plate, can be approximately 10,000 pfu's. For each DNA library: about 50,000 plaques per isolated library and 200,000 plaques per non-isolated library can be screened depending upon the pfu titer for the λ, Zap Express amplified lysate.

Titer Determination of Lambda Library
1) μL of Lambda Zap Express amplified library stock added to 600 μL E. coli MRF' cells (OD$_{600}$=1.0). To dilute MRF' stock, 10 mM MgS0$_4$ is used.
2) Incubate at 37° C. for 15 minutes.
3) Transfer suspension to 5-6 mL of NZY top agar at 50° C. and gently mix. Immediately pour agar solution onto large (150 mm) NZY media plate.
4) Allow top agar to solidify completely (approximately 30 minutes), then invert plate.
5) Incubate the plate at 39° C. for 8-12 hours.
6) Number of plaques is approximated. Phage titer determined to give 10,000 pfu/plate.
7) Dilute an aliquot of Library phage with SM buffer if needed.

Substrate Screening

Lambda Zap Express (50,000 pfu) from amplified library added to 600 μL of E. coli MRF' cells (OD600=1.0). For non-environment libraries, prepare 4 tubes (50,000 pfu per tube).

Incubate at 37° C. for 15 minutes.

While phage/cell suspension are incubating, 1.0 mL of red starch substrate (1.2% w/v) is added to 6.0 mL NZY top agar at 50° C. and mixed thoroughly. Keep solution at 50° C. until needed.

Transfer 1/5 (10,000 pfu) of the cell suspension to substrate/top agar solution and gently mixed.

Solution is immediately poured onto large (150 mm) NZY media plate.

Allow top agar to solidify completely (approximately 30 minutes), then invert plate.

Repeat procedures 4-6 four times for the rest of the cell suspension (1/5 of the suspension each time).

Incubate plates at 39° C. for 8-12 hours.

Plate observed for clearing zones (halos) around plaques.

Plaques with halos are cored out of agar and transferred to a sterile micro tube. A large bore 200 μL pipette tip works well to remove (core) the agar plug containing the desired plaque.

Phages are re-suspended in 500 μL SM buffer. 20 μL chloroform is added to inhibit any further cell growth.

Pure phage suspension is incubated at room temperature for 4 hours or overnight before next step.

Isolation of Pure Clones

10 μL of re-suspended phage suspension is added to 500 μL of E. coli MRF' cells (OD600=1.0).

Incubate at 37° C. for 15 minutes.

While phage/cell suspension is incubating, 1 mL of red starch substrate (1.2% w/v) is added to 6.0 mL NZY top agar at 50° C. and mixed thoroughly. Keep solution at 50° C. until needed.

Cell suspension is transferred to substrate/top agar solution and gently mixed.

Solution is immediately poured onto large (150 mm) NZY media plate.

Allow top agar to solidify completely (approximately 30 minutes), then invert plate.

Plate incubated at 39° C. for 8-12 hours.

Plate observed for a clearing zone (halo) around a single plaque (pure clone). If a single plaque cannot be isolated, adjust titer and re-plate phage suspension.

Single plaque with halo is cored out of agar and transferred to a sterile micro tube. A large bore 200 μL pipette tip works well to remove (core) the agar plug containing the desired plaque. To amplify the titer, core 5 single active plaques into a micro tube.

Phages are re-suspended in 500 μL SM buffer. 20 μL Chloroform is added to inhibit any further cell growth.

Pure phage suspension is incubated at room temperature for 4 hours or overnight before next step. The pure phage suspension is stored at −80° C. by adding DMSO into the phage suspension (7% v/v).

Excision of Pure Clone

100 μL of pure phage suspension is added to 200 μL E. coli MRF' cells (OD600=1.0). To this, 1.0 μL of EXASSIST™ helper phage (>1×106 pfu/mL; Stratagene) is added. Use 2059 Falcon tube for excision.

Suspension is incubated at 37° C. for 15 minutes.

3.0 mL of 2×YT media is added to cell suspension.

Incubate at 30° C. for at least 6 hours or overnight while shaking.

Tube transferred to 70° C. for 20 minutes. The phagemid suspension can be stored at 4° C. for 1 to 2 months.

100 μL of phagemid suspension transferred to a micro tube containing 200 μL of E. coli Exp 505 cells (OD600=1.0).

Suspension incubated at 37° C. for 15 minutes.

300 μL of SOB is added to the suspension.

Suspension is incubated at 37° C. for 30 to 45 minutes.

100 µL of suspension is transferred to a small (90 mm) LB media plate containing Kanamycin (LB media with Kanamycin 50 µg/mL) for Zap Express DNA libraries or Ampicillin (LB media with Kanamycin 100 µg/mL) for Zap II DNA libraries.

The rest of suspension is transferred to another small LB media plate.

Use sterile glass beads to evenly distribute suspension on the plate.

Plates are incubated at 30° C. for 12 to 24 hours.

Plate observed for colonies.

Inoculate single colony into LB liquid media containing suitable antibiotic and incubate at 30° C. for 12 to 24 hours.

Glycerol stock can be prepared by adding 80% glycerol into liquid culture (15% v/v) and stored at −80° C.

Activity Verification

50 µL of liquid culture is transferred to a micro tube. Add 500 µL of 8% pH 7 Amylopectin Azure into the same tube. Prepare 2 tubes for each clone.

Activity is tested at 50° C. for 3 hours and overnight. Use pH 7 buffer as control.

Cool the test specimen at ice-water bath for 5 minutes.

Add 750 µL of Ethanol and mixed thoroughly.

Centrifuge at 13000 rpm (16000 g's) for 5 minutes.

Measure OD of the supernatant at 595 nm.

RFLP Analysis 1.0 mL of liquid culture is transferred to a sterile micro tube.

Centrifuge at 13200 rpm (16000 g's) for 1 minute.

Discard the supernatant. Add another 1.0 mL of liquid culture into the same sterile micro tube.

Centrifuge at 13200 rpm (16000 g's) for 1 minute.

Discard the supernatant.

Follow QIAPREP™ spin mini kit protocol for plasmid isolation.

Check DNA concentration using BioPhotometer.

Use Sac I and Kpn I for first double digestion. Incubate at 37° C. for 1 hour.

Use Pst I and Xho I for second double digestion. Incubate at 37° C. for 1 hour.

Add Loading dye into the digested sample.

Run the digested sample on a 1.0% agarose gel for 1-1.5 hours at 120 volts.

View gel with gel imager. All clones with a different digest pattern will be sent for sequence analysis.

Example 18

Exemplary Protocols for Purifying Enzymes

The following example describes exemplary protocols for purifying enzymes of this invention.

SEQ ID NO:52: 6 g of lyophilized supernatant of *P. pastoris* culture (see discussion in Example 25, below) expressing SEQ ID NO:52 was suspended in 24 mL of H$_2$O and precipitated with cold ethanol. Precipitated pellet was resuspended in approximately 40 mL of H$_2$O and dialyzed O/N against water. After dialysis a concentrated acetate buffer pH 6.0 was added to the sample to get a final concentration of 50 mM. The protein bound to the column (Q SEPHAROSE™; Amersham Pharmacia resin poured in a XK 50™ column) in 50 mM Na acetate pH6.0 and was eluted during a gradient between 0 and 400 mM NaCl in Na acetate pH6.0. Contaminating proteins were removed from the column with 1M NaCl in Na acetate pH6.0. Elution of amylase from the Q SEPHAROSE™ was tracked with SDS PAGE and activity assays using BODIPY-starch as a substrate. Multiple purifications were run to obtain enough protein to meet the requirement of approximately 1 g. The purified fractions from these runs were pooled together and concentrated by stir cell concentrator.

SEQ ID NO:48: 24 g of lyophilized supernatant of *P. pastoris* culture expressing SEQ ID NO:48 was suspended in 20 mL of 50 mM carbonate buffer pH 10.0; 100 mM NaCl and precipitated with cold ethanol. Precipitated pellet was resuspended in approximately 20 mL of 50 mM acetate buffer pH 5.2; 500 mM NaCl, and dialyzed O/N against 50 mM malic buffer pH 3.5; 500 mM NaCl. The protein bound to the 100 mL agarose—amylose (NEB) column in 50 mM malic buffer pH3.5; 500 mM NaCl and was eluted with 0.5% corn dextrin in 50 mM carbonate buffer pH 10.0; 50 mM NaCl. Contaminating proteins were removed from the column with 50 mM sodium phosphate buffer pH 7.5; 100 mM NaCl. Elution of glucoamylase from the agarose-amylose was tracked with SDS PAGE.

Other enzymes of the invention, including the exemplary enzymes, can be purified using these protocols or variations thereof, or analogous protocols.

FIG. 26 illustrates tables summarizing the efficiency of these purification protocols for the exemplary SEQ ID NO:4, SEQ ID NO:18, SEQ ID NO:26, and corresponding activity data on, inter alia, raw starch and soluble starch comparing purified and unpurified enzyme.

Purified enzyme preparations of the exemplary SEQ ID NO:52 and SEQ ID NO:26 were analyzed for activity (the ability to hydrolyze) in raw starch fermentations; this data on the purity (determined by densitometric analysis), concentration, quantity and storage buffer is summarized:

|  | SEQ ID NO: 52 | SEQ ID NO: 48 |
| --- | --- | --- |
| Class | Alpha-amylase | Glucoamylase |
| Storage Buffer | GMP* | GMA** |
| Concentration | 25 mg/ml | 25 mg/ml |
| Volume Sent | 40 ml | 20 |
| Total Amount | 1.0 g | 0.5 g |
| Purity | >90% | >95% |

*GMP - 20% glucose; 0.1% methyl paraben, PBS pH 7.0
**GMA - 20% glucose; 0.1% methyl paraben; 50 mM sodium acetate pH 5.2; 100 mM NaCl.

Example 19

Exemplary Protocol for Liquefying Starch and Measuring Results

The following example describes exemplary protocols for liquefying starch using, e.g., enzymes of this invention. Reaction Conditions: 100 mM PO$_4$ pH 6.5, 1% (w/w) liquefied starch DE 12 at 55° C. Both TLC and HPLC assays can be done to verify activity.

An exemplary protocol for the saccharification of liquefied starch at pH 6.5:

Adjust the pH of the liquefied starch to the pH at which the saccharification(s) will be performed. Liquefy starch in 100 mM sodium acetate buffer, pH 4.5 with 100 mM sodium phosphate salts added so that before saccharification, the pH could be adjusted to pH 6.5.

Weigh 5 gram samples of liquefied starch into tared bottles.

Use 0.04% (w/w) OPTIDEXL-400™ or approximately 400 mL of 1-10 diluted stock OPTIDEXL-400™ per 100 grams of liquefied starch.

Calculate the milligrams of OPTIDEX L-400™ contained in the 400 mL of 1-10 diluted stock OPTIDEXL-400™. Next, calculate the volume of lysates needed to give the same concentration of enzyme as the OPTIDEX L-400™.

Add enzymes to liquefied starch samples and incubate at desired temperature)(50 C.°. After 18 hours determine DE and prepare a sample for HPLC analysis.

An Exemplary DE Determination:

Exemplary Neocuproine Assay:

A 100 ml sample can be added to 2.0 ml of neocuproine solution A (40 g/L sodium carbonate, 16 g/L glycine, 0.45 g/L copper sulfate). To this can be added 2.0 ml of neocuproine solution B (1.2 g/L neocuproine hydrochloride-Sigma N-1626). The tubes can be mixed and heated in a boiling water bath for 12 minutes; cooled, diluted to 10 ml volume with DI water and the OD read at 450 nm on the spectrophotometer. The glucose equivalent in the sample can be extrapolated from the response of a 0.2 mg/ml glucose standard run simultaneously.

Exemplary HPLC Analysis:

Saccharification carbohydrate profiles are measured by HPLC (Bio-Rad Aminex HPX-87A column in silver form, 80° C.) using refractive index detection. Mobile phase is filtered Millipore water used at a flow rate of 0.7 ml/min Saccharification samples are diluted 1-10 with acidified DI water (5 drops of 6 M HCl into 200 mL DI water) then filtered through a 0.45 mm syringe filter. Injection volume is 20 uL.

Exemplary TLC:

Reaction products can be w/d at hourly timepoints and spotted and dried on a TLC plate. The plate can be then developed in 10:90 water:isopropanol and visualized with either a vanillin stain or CAM stain and then heated to show reducible sugars. The liquefied starch can be partially hydrolyzed to glucose in cases where activity was observed.

Example 20

Starch Liquefaction Using Glucoamylases

This example describes an exemplary method of the invention for liquefying starch using amylases and/or glucoamylases of the invention. Glucoamylase concentrate can be prepared from fermentation broths by heat treatment, cell washing, alkaline extraction using microfiltration and ultrafiltration (48% overall yield). The UF concentrate can be neutralized with acetic acid and formulated with 30% glycerol at pH 4.5. The activity level of a commercial product can be about 120 U$^1$/g-0.5 kg/ton starch.

Exemplary Glucoamylase Activity Assay

A 1 mL cuvette containing 950 µL of 50 mM MOPS pH 7.0 containing 5 mM PNP-α-D—hexa-(1→4)-glucopyranoside is placed in the Peltier temperature controller of the Beckman DU-7400 spectrophotometer preheated to 80° C. The spectrophotometer is blanked at 405 nm and 50 µL of the enzyme solution is added to the cuvette, mixed well and the increase in the $OD_{405nm}$ is monitored over a one-minute interval. The $\Delta OD_{405nm/min}$ rate is converted to a standard unit of µmole/minute from the $OD_{405nm}$ response of 50 µL of 1 µmole/mL PNP in 950 mL 50 mM MOPS at pH 7.0-80° C. One standard unit of thermostable alpha glucoamylase (DTAA) is equal to the amount of enzyme that will catalyze the release of 1 µmole/mL/minute of pNP under the defined conditions of the assay.

Standard Glucoamylase Activity Assay

A 1 mL cuvette containing 950 µL of 50 mM MOPS pH 7.0 containing 5 mM pNP-α-D-glucopyranoside is placed in the Peltier temperature controller of the Beckman DU-7400 spectrophotometer preheated to 60° C. The spectrophotometer is blanked at 405 nm and 50 µL of the enzyme solution is added to the cuvette, mixed well and the increase in the $OD_{405nm}$ is monitored over a one-minute interval. The $\Delta OD_{405nm/min}$ rate is converted to a standard unit of µmole/minute from the $OD_{405nm}$ response of 50 µL of 1 µmole/mL pNP in 950 mL 50 mM MOPS at pH 7.0-60° C. One standard Diversa unit of glucoamylase (DGA) is equal to the amount of enzyme that will catalyze the release of 1 µmole/mL/minute of pNP under the defined conditions of the assay.

Dextrose Equivalent Determination

The neocuproine method is used to measure the DE. Selected samples were measured by both the procedure described above, and by a GPC analyst using the GPC Fehlings procedure.

Neocuproine Assay

A 100 µl sample is added to 2.0 ml of neocuproine solution A (40 g/L sodium carbonate, 16 g/L glycine, 0.45 g/L copper sulfate). To this is added 2.0 ml of neocuproine solution B (1.2 g/L neocuproine hydrochloride-Sigma N-1626). The tubes were mixed and heated in a boiling water bath for 12 minutes; cooled, diluted to 10 ml volume with DI water and the OD read at 450 nm on the spectrophotometer. The glucose equivalent in the sample is extrapolated from the response of a 0.2 mg/ml glucose standard run simultaneously.

The starch sample is diluted ~1 to 16 with DI water with the exact dilution recorded. Ten milliliters of the diluted sample is added to 20 mls of DI water. Ten milliliters of Fehlings solution A and B were added to the diluted starch. The sample is boiled for 3 minutes and cooled on ice. Ten milliliters of 30% KI and 10 ml of 6N $H_2SO_4$ is added. The solution is titrated against 0.1N sodium thiosulfate. The titrant volume is recorded and used to calculate the DE.

Residual Starch Determination

Post-saccharification samples were checked for residual starch using the Staley iodine procedure.

Twenty grams of sample is weighed into a large weigh dish. 45 µL of Iodine solution is added to the weigh dish and the starch solution is mixed well. Dark blue indicates the presence of starch, a light blue-green indicates slight starch, light green indicates a trace of starch and yellow-red, absence of starch. Iodine solution is prepared by dissolving 21.25 grams of iodine and 40.0 grams of potassium iodide in one liter of water.

Oligosaccharide Profile

Liquefaction and saccharification carbohydrate profiles were measured by HPLC (Bio-Rad AMINEX HPX-87C™ column in calcium form −80° C.) using refractive index detection.

Gel Permeation Chromatography

The molecular weight distribution is determined by chromatography on a PL AQUAGEL-OH™ column with mass detection by refractive index (Waters Model 2410). A Viscotek Model T60™ detector is used for continuous viscosity and light scattering measurements.

Capillary Electrophoresis

Beckman Coulter P/ACE MDQ™ Glycoprotein System—separation of APTS derivatized oligosaccharides on a fused silica capillary—detection by laser-induced fluorescence.

Primary Liquefaction

Line starch directly from the GPC process is pumped into a 60 liter feed tank where pH, DS (dry solids) and calcium level can be adjusted before liquefaction. The glucoamylase is added to the slurry. The 32% DS slurry is pumped at 0.7 liter/minute by a positive displacement pump to the jet—a pressurized mixing chamber where the starch slurry is instantaneously heated to greater than 100° C. by steam injection. The gelatinized partially liquefied starch is pumped through a network of piping (still under pressure) to give the desired dwell time (5 minutes) at temperature. The pressure is released into a flash tank and samples can be taken. Samples were taken in duplicate.

Secondary Liquefaction

The liquefied starch is collected in one liter glass bottles and held in a water bath at 95° C. for 90 minutes.

Saccharification

Liquefied starch is cooled to 60° C., the pH adjusted to 4.5 and the samples treated with glucoamylase. Saccharification progress is monitored over time by HPLC.

Saccharification

The liquefied syrups produced with each glucoamylase were adjusted to approximately pH 2.5 with 6N HCl immediately after the 90 minute secondary liquefaction to inactivate any residual glucoamylase. The syrups were then adjusted to pH 4.5, placed in a 60° C. water bath and saccharified with three levels of glucoamylase. The extent of saccharification is monitored by HPLC at 18 to 88 hour time points.

The liquefied syrups were saccharified with the standard dosage −0.04% of a double-strength glucoamylase—and two lower dosages (50% and 25%) to monitor any differences in the saccharification progress.

Saccharification Progress—% dextrose development vs time −0.04% glucoamylase.

Example 21

Exemplary Starch Liquefaction Process

This example describes an exemplary starch liquefaction process of the invention comprising use of enzymes of the invention. The conversion of starch to glucose can be catalyzed by the sequence action of two enzymes: amylases (e.g., alpha-amylases), including enzymes of the invention, to liquefy the starch (e.g., the hydrolysis of high molecular weight glucose polymers to oligosaccharides consisting of 2 to 20 glycose units, typically a dextrose equivalent of 10 to 12, by a glucoamylase of the invention), followed by saccharification with a glucoamylase (which can be a glucoamylase of the invention). In one aspect, processing is in a corn wet milling plant producing a starch slurry having a pH or about 4.0 to 4.5. In one aspect, the pH is raised, e.g., to 5.8 to 6.0 before liquefaction to accommodate a glucoamylase with a low pH activity and stability. In one aspect, amylases and/or glucoamylases of the invention can liquefy starch at pH 4.5 to dextrose equivalents ranging from 12 to 18; in one aspect, using glucoamylases of the invention at levels of about 3 to 6 grams per ton of starch. In this aspect, use of glucoamylases of the invention enables starch liquefaction to be conducted at pH 4.5.

In one aspect, starch liquefaction is conducted at pH 4.5 for 5 minutes at 105° C. to 90 minutes at 95° C. using glucoamylases of the invention. The quantity of enzyme is adjusted in order to adjust a target DE of 12 to 15 after liquefaction. In one aspect, the liquefied starch is then saccharified with a glucoamylase, e.g., an *Aspergillis* glucoamylase, for about 48 hours at about pH 4.5 and 60° C. If the saccharified syrup did not contain at least 95% glucose, the target liquefaction DE is raised and the saccharification repeated until the liquefaction eventually did produce a saccharified syrup containing more than 95% glucose. The glucoamylase protein required to produce a suitable liquefied feedstock for saccharification is determined by PAGE.

Example 22

Identification of Peptides Resulting from Protease Proteolysis in Simulated Gastric Fluid (SGF) Test This example describes the identification of small peptides resulting from pepsin proteolysis of the exemplary enzyme of the invention SEQ ID NO:52 (encoded, e.g., by SEQ ID NO:51). This example also describes the evaluation of activity of exemplary enzymes of the invention in in vitro "Simulated Gastric Fluid" (SGF) tests. The SGF tests showed that all the enzymes were quickly digested by the gastric protease pepsin. In one case a small pepsin-resistant fragment was observed after 60 minutes of treatment.

Figure 21:
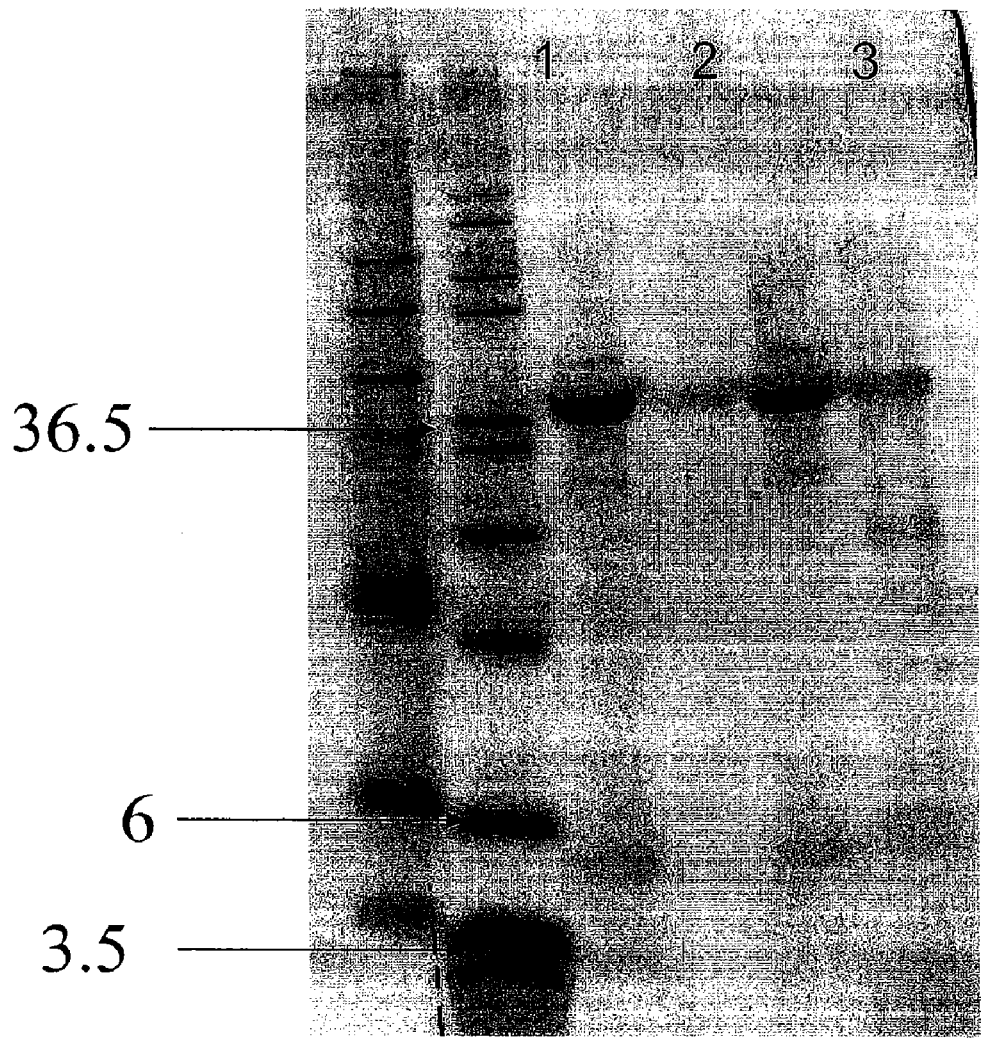
FIG. 21 illustrates an SDS PAGE showing the results of proteolysis of exemplary enzyme SEQ ID NO:52 by pepsin.

FIG. 21 illustrates an SDS PAGE showing the results of proteolysis (in vitro digestibility, the SGF test) of SEQ ID NO:52 by pepsin at pH 1.3; pepsin cuts at the C-terminus of Lys (K) and Phe (F) residues (the upper arrow indicates a 36.5 K band, the middle arrow a 5 K band (see discussion, below), and the lower arrow a 3 K band). SEEBLUE PLUS2™ prestained Standard from Invitrogen, and MARKER12™ from Invitrogen was used. All the samples were run on 16% Tricine gels. A common band present in all tests is pepsin.

FIG. 22 illustrates the characterization of the peptides generated in this digest of SEQ ID NO:52, as identified using LC MS/MS (Liquid Chromatography/Mass Spectrometry/Mass Spectrometry) analysis; an N-linked glycosylation site is identified.

Figure 23B:
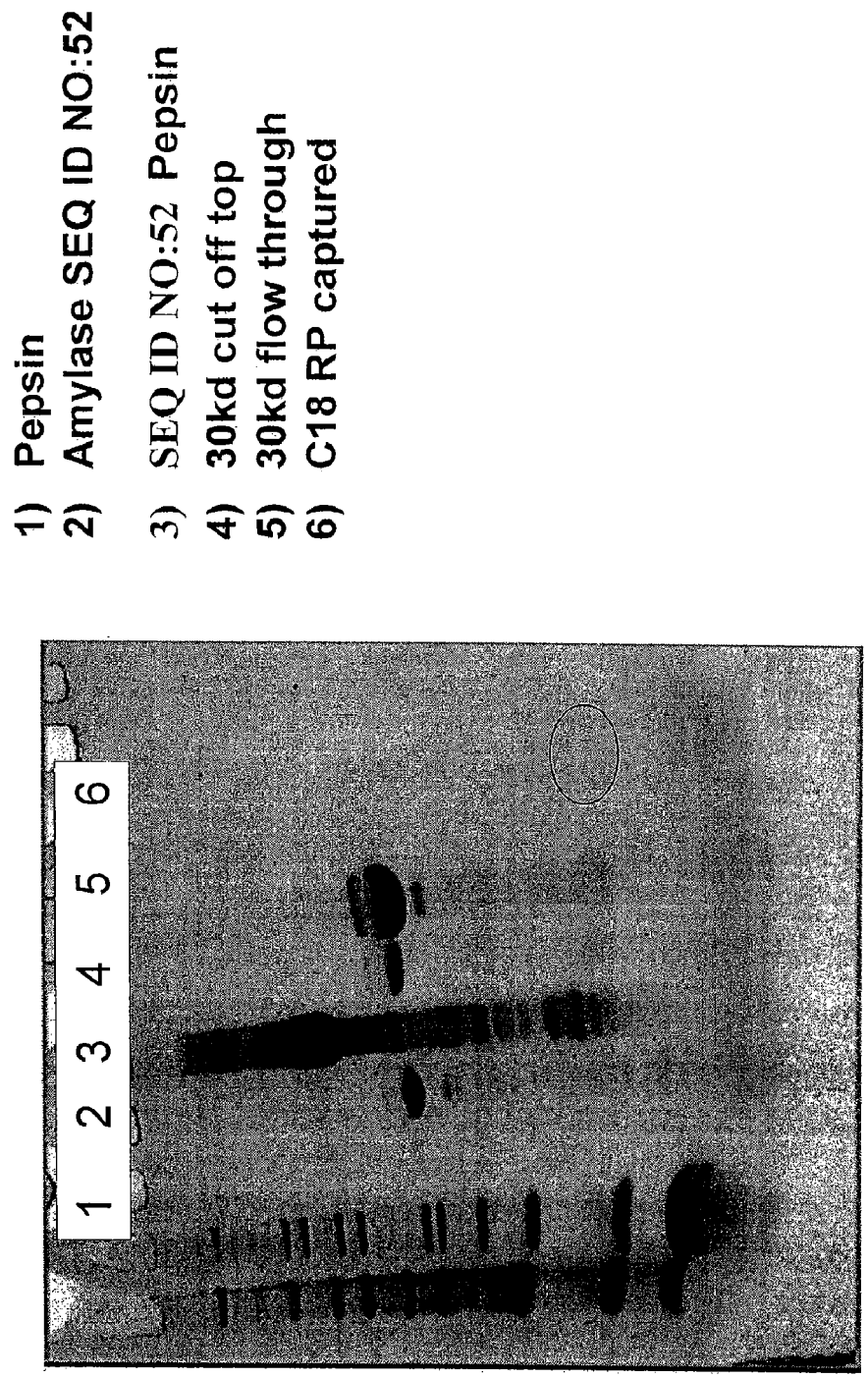
FIG. 23B illustrates an SDS PAGE of the results of the small peptide isolation scheme.

FIG. 23A illustrates the small peptide isolation scheme used (for the peptides generated by the proteolysis of SEQ ID NO:52 by pepsin). FIG. 23B is discussed, below, and illustrates an SDS PAGE of the results of the small peptide isolation scheme, where lane 1 is pepsin only, lane 2 is undigested amylase SEQ ID NO:52, lane 3 is the amylase SEQ ID NO:52 digested by pepsin, lane 4 is the 30 kd cut-off top as illustrated in FIG. 23A, lane 5 is the 30 kd flow-through as illustrated in FIG. 23A, lane 6 is the sample captured by C18 RP (C18 reverse phase column chromatography) as illustrated in FIG. 23A.

Figure 23C:
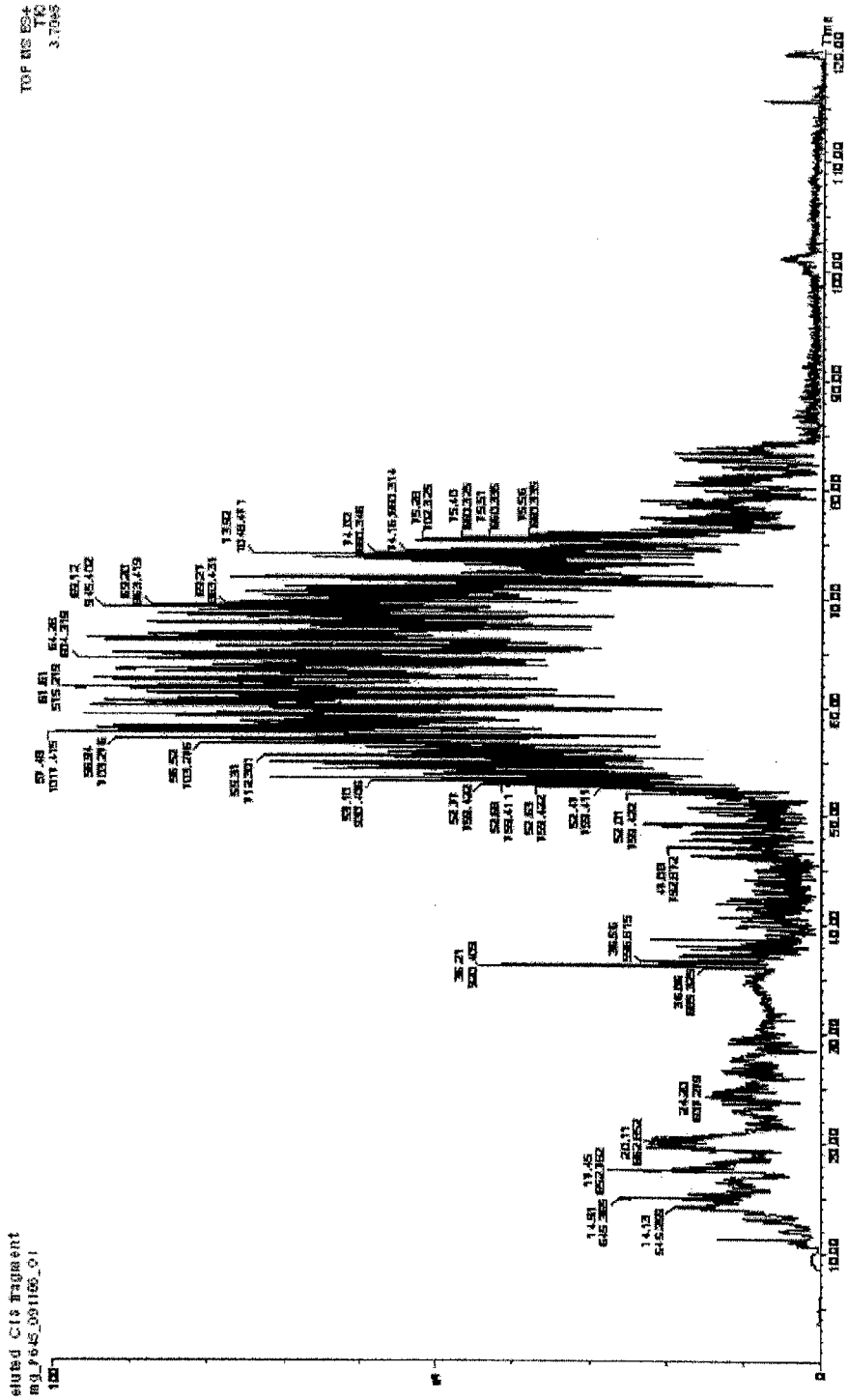
FIG. 23C illustrates the LC/MS profile of the C18 RP eluted fraction.

FIG. 23C illustrates the LC/MS profile of the C18 RP eluted fraction, and is discussed, below.

FIG. 23D illustrates the sequence of the peptides identified by the LC MS/MS analysis; FIG. 23E and FIG. 23F illustrate the "Asn-Xaa-Ser/Thr" sequins (motifs) in the sequence output (highlighted in blue); asparagines predicted to be N-glycosylated are highlighted in red.

In Vitro Digestibility Assays: No full-length versions of any of the enzymes tested were detected by SDS-PAGE after SGF treatment, indicating that pepsin had digested each of the full-length proteins; after 60 minutes of SGF treatment, small proteolytic fragments, about 6 kDa in size, were observed in digests of α-amylase SEQ ID NO:52 (see discussion in Example 22).

Activity Test after Pepsin Treatment: To determine if there is any residual activity remaining after pepsin treatment, the SGF test was modified and activity tests were performed with dextrin as substrate for glucoamylases and BODIPY-starch as substrate for α-amylases. No residual activity was observed for any of the enzymes tested, after SGF treatment for 60 minutes. The loss of activity was caused either by pepsin digestion of the test proteins (e.g. SEQ ID NO:4, SEQ ID NO:76 and SEQ ID NO:2), by the inactivation of the enzyme under the low pH reaction conditions, or both.

To identify the pepsin resistant peptide band, migrating at 5 kDa range on a SDS-PAGE, small peptides where enriched by filtering the sample over a 30 kDa filter membrane. The flow through was further purified using a C18 solid phase extraction column. The recovered peptides where then analyzed by Edmond degradation N-terminal sequencing, LC-MS, and LC tandem mass spectroscopy to determine the peptide sequence. The samples analyzed by LC tandem mass spectroscopy were first treated with trypsin protease.

Peptide purification: To determine the sequence of the 5 kDa peptide band, the peptide was enriched by first passing the pepsin treated SEQ ID NO:52 reaction over a 30 KDa filter membrane. The flow-through was then purified using a C18 solid phase extraction column. The recovered peptides formed a band at the 5kDa range on an SDS-PAGE. FIG. 23B illustrates an SDS-PAGE analysis of the pepsin resistant alpha-amylase SEQ ID NO:52 peptide. This gel was Coomassie stained. Lane 1 is the pepsin protease. Lane 2 is the amylase SEQ ID NO:52. Lane 3 is the amylase SEQ ID NO:52 treated with pepsin protease. Lane 4 is same as sample 3 which did not flow through a 30 kDa filter membrane. Lane 5 is the flow through of sample in lane 3 after passed through a 30 kDa filter membrane. Lane 6 is sample 5 after recovery from a C18 solid phase extraction column.

To determine the peptide masses in the recovered sample the peptides where analyzed by LC-MS analysis over a C18 reverse phase column. The m/z profile of this sample showed that there are multiple masses of various m/z values that are present in this sample, as illustrated in FIG. 23C, an LC-MS analysis of the amylase SEQ ID NO:52 small peptides. The solid phase was a C18 RP material. A gradient of 5%-80% ACN (15-90 minutes) was used as the mobile phase in the experiment.

Edmond degradation N-terminal sequencing: To determine the sequence of the SEQ ID NO:52 small peptides, the purified peptides where sent for N-terminal sequencing using Edmond degradation method. The results for this analysis were inconclusive, since, a number of different amino acids were released at each cleavage step. This result was consistent with the LC/MS analysis that showed that there are more than one prominent species of peptides present in this sample.

LC tandem mass spectroscopy analysis: To determine the sequence of peptides present in the amylase SEQ ID NO:52 purified peptide fraction, these where treated with trypsin protease and analyzed by LC MS/MS. This analysis resulted in the identification of the following seven peptides; these peptide sequences were identified by SEQUEST™ searches from the LC MS/MS analysis of the amylase SEQ ID NO:52 small tryptic peptides:

| Peptide | Peptide sequence | Residue location within SEQ ID NO: 52 |
|---|---|---|
| 1 | AGQEQHYSGGSDPANR | 349-364 |
| 2 | VFSGDPAYTCPYQN | 251-264 |
| 3 | SGDPAYTCPYQN | 253-264 |
| 4 | SLLLLLSVFGQATHA | 6-20 |
| 5 | YENTGDGTSYHG | 90-101 |
| 6 | VYCGGSWQGIINHLD | 56-70 |
| 7 | GYSAGATLVETYTCT | 448-462 |

It also determined that there were a number of peptide peaks in the LC-MS spectrum that their MS/MS profile did not match neither SEQ ID NO:52 nor other peptides in the database. One possible reason for this could be the complex N-linked glycosylation modification of the parent protein that takes place in the host organism, *Pichia pastoris*. To test this hypothesis, the extracted peptides were first treated with PNGase F to remove their N-linked glycosyl groups. The resulting peptides where then trypsin treated and where subjected to LC MS/MS analysis to determine their peptide composition. This analysis determined that there where at least 6 different peptide species present in the sample (see table summary above). The resolution of these peptides, post deglycosylation treatment, suggests that these peptides where part of other peptides that where glycosylated in the sample.

In conclusion, N-terminal sequencing and LC-MS analysis showed that the 5 KDa peptide band resulting from the pepsin protease digestion of amylase SEQ ID NO:52 is composed of many different peptide species. This is most likely due to incomplete digestion of the amylase SEQ ID NO:52 by the pepsin protease partly due to glycosylation state of these peptides. Thus, there is no one prominent peptide species in the MS spectra—multiple peptides are present; multiple different peptides species were sequenced in the sample; N-terminal chemical sequencing also provided evidence for the presence of multiple peptides; there is one peptide species that only appears after PNGase F deglycosylation of the sample, suggesting a glycosylation-related event is responsible for the appearance of this peptide.

This exemplary series of protocols can be used on any polypeptide of the invention, e.g., an exemplary sequence of the invention, to determine sequence, motifs, including glycosylation motifs, active sites and the like.

Example 23

Low Temperature-active Amylases

This example describes making and characterizing exemplary enzymes of the invention SEQ ID NO:56, SEQ ID NO:52; SEQ ID NO:62; SEQ ID NO:70, that are active at low temperatures, including having the ability to hydrolyze starch at low temperatures. This example also describes the development of an enzyme cocktail of the invention that can hydrolyze >95% of the starch in milled corn into fermentable sugars in no more than 60 hours at about 30 to 40° C. and about pH 3.5 to pH 5.5 in the presence of yeast. In one aspect, the total quantity of enzyme protein required is not greater than 50 grams/ton of corn, e.g., in alternative embodiments 0.05% w/w, or 0.005% w/w, or anywhere in the range of between 0.05% w/w to 0.005% w/w.

The initial reaction rates for starch hydrolysis were determined; and the influence of pH at varying ranges, e.g., in the range of about pH 3.5-7.0, and temperatures at varying ranges, e.g., in the range of about 30-40° C., on activity of enzymes of the invention were studied; the bond-type specificity of exemplary amylases and/or glucoamylases of the invention was also determined.

Methods:

1. Determination of Protein Concentration

Lyophilized supernatants of *P. pastoris* cultures expressing glucoamylases and α-amylases were suspended in water at a concentration of ~10 mg of powder/ml. After protein content determination by the Bradford protocol, 5 μg of protein sample and standardized BSA solution were run on a 4-20% Tris-Glycine gradient gel. The gel was scanned on a BioRad GS800™ gel scanner following Coomassie blue staining.

The Bio-Rad QUANTITY ONE™ software was used for the quantification of the BSA and glucoamylase (or α-amylases) bands, and the actual enzyme concentration was then calculated. Protein concentration was adjusted accordingly and confirmed by additional SDS PAGE.

2. Determination of Initial Reaction Rates.

Unless mentioned otherwise, assays were performed in triplicate at 37° C. and pH 5.0 in buffer (50 mM $NaCH_3CO_2$, 10 mM $CaCl_2$; 10 mM $NaN_3$ and 0.01% Triton X-100) containing 1% raw starch, or 0.5% dextrin or 1% "soluble corn starch". Assays were performed at 0.5 ml scale for glucoamylase and 0.25 ml scale for alpha-amylase α-amylase) in an Eppendorf tabletop incubator with constant shaking (800 rpm).

For glucoamylases, reactions were started by adding the enzyme (final concentration 0.25 µg/ml) to the reaction mix. At 0, 2.5, 5, 7.5, 10, 15, 20 and 30 mM, 50 µl aliquots of the reactions were withdrawn and quenched by addition to 100 µl of 1M Tris buffer, pH 7.5. For alpha-amylases (α-amylases), reactions were started by adding the enzyme (final concentration 0.4 µg total protein/ml for SEQ ID NO:56, 13434 and SEQ ID NO:52; 2 µg/ml for SEQ ID NO:62; 4 µg/ml for SEQ ID NO:70) to the reaction mix, and 10 µl aliquots of reactions were withdrawn and quenched in BCA reagent at 2, 5, 10, 15, 20, 25, 30, and 40 min. For determination of temperature profiles, assays were performed at 30, 34, 37 and 40° C.

The effect of pH on glucoamylase and amylase activities was evaluated at pH 3.5, 4, 5, 6 and 7, using the broad pH range Britton—Robinson buffer (50 mM $CH_3COOH$; $H_3PO_4$; $H_3BO_3$). Parallel reactions at pH 4, 5 and 6 were also performed in the presence of 50 mM acetate buffer to ensure that the buffer used did not influence the results. For the determination of pH profile of two calcium-dependent alpha-amylases (α-amylases) SEQ ID NO:56 and SEQ ID NO:62, malic acid/acetate/MES buffers were used instead of Britton-Robinson.

Preparation of "soluble corn starch" for reaction with alpha-amylases. Dextrin (Sigma D2006) could not be used as a substrate in the BCA alpha-amylase reactions due to the high reducing ends background. Therefore a heated corn starch (Syngenta material) was employed as a substrate. 2% corn starch was dissolved in deionized water and heated with mixing in a boiling water bath for 30-40 minutes, until the starch had dissolved and the solution appeared milky, but translucent. The solution of heated starch was used for 2 days, after which time some signs of retrogradation were observed (appearance of starch clumps), and the solution was discarded.

3. Glucose Oxidase/Peroxidase (go) Assay for the Quantification of Glucose Released During Starch Hydrolysis A coupled glucose oxidase/peroxidase (GO) assay was used to determine the amount of glucose released by glucoamylase during starch hydrolysis. GO reactions were started by adding 10 µl of the quenched starch hydrolysis reaction to 90 µl of PBS containing glucose oxidase (0.1 U/ml), peroxidase (0.25 U/ml) and 0.05 mM Amplex Red, in black Nunc 96-well plates. Plates were kept at room temperature in the dark for 30 mM prior to reading on a fluorescent plate reader with Ex/Em 545/590 nm. A standard curve with glucose concentrations of 0 to 100 µM was used to assess the amount of glucose produced in the hydrolysis reactions. Initial rates of starch hydrolysis (nmols of glucose released from 1% granular starch/min/µg glucoamylase) were determined by plotting the amount of glucose released over time, and calculating the slope of the best linear fit through the data points.

4. BCA Assay for Determining the Increase in Concentration of Reducing Ends During Starch Hydrolysis.

A 10 µl aliquot of amylase starch hydrolysis reaction was quenched into 100 µl of BCA reagent (consisting of 64 mg/mL sodium carbonate monohydrate, 24 mg/mL sodium bicarbonate, 1.95 mg/mL BCA, 1.24 mg/mL cupric sulfate pentahydrate, 1.26 mg/mL L-serine). Color development occurred during incubation of the quenched reaction at 80° C. for 35 minutes and was followed by absorbance determination at 560 nm Initial rates were calculated over a 40 min reaction time. A standard curve using maltose (0-54 µM) was constructed to correlate $A_{560nm}$ with the concentration of generated reducing sugars (nmoles). Specific activity was expressed as nmoles/min/µg enzyme.

5. Bond-type Specificity of Glucoamylases with Maltose and Isomaltose as Substrates.

Reactions were started by adding the enzyme (final concentration 5 µg/ml for maltose, and 30 µg/ml for isomaltose) to the reaction mix. At 2, 5, 10, 15, 20, 25, 30 and 40 mM, 5 µl aliquots of the reactions were withdrawn and quenched by addition to 10 µl of 1M Tris buffer, pH 7.5. Nine substrate concentrations were used in the studies, ranging from 0 to 12 mM for maltose and 2.5 to 120 mM for isomaltose. The reactions were performed in triplicate at 37° C. and pH 5.0 in buffer (50 mM $NaCH_3CO_2$, 10 mM $CaCl_2$), at 50 ul scale in an Eppendorf tabletop incubator with constant shaking (800 rpm). Glucose production was measured at the end of the reaction using the glucose oxidase/peroxidase (GO) assay.
Results
1. Characterization of Glucoamylases:

1.1 Initial reaction rates: Initial rates for granular and soluble starch hydrolysis are presented in Table 2, illustrated in FIG. 24. As can be seen from Table 2, amylases and/or glucoamylases of the invention displayed up to 3× better activity (SEQ ID NO:48) against granular starch, with similar or slightly better activity on soluble starch when compared to the benchmark *A. niger* enzyme. SEQ ID NO:20 did not appear to display any activity against granular starch under the conditions tested (probably due to the lack of a Starch Binding Domain). Table 2 (FIG. 24) summarizes data comparing initial rates of granular corn starch and soluble starch (dextrin) hydrolysis by exemplary enzymes of the invention (including those with glucoamylases activity) and a benchmark enzyme *A. niger* glucoamylase at 37° C., pH 5.0; initial rates are expressed as nmols of glucose/min/µg of glucoamylase protein released from 1% granular starch or from 0.5% dextrin. Each number is the average value from 6-10 data points.

1.2 Temperature profile: The effect of temperature on the activity of exemplary enzymes of the invention, including glucoamylases, on granular starch as a substrate was determined; a "benchmark" enzyme, the commercially available *A. niger* glucoamylase, was used. Glucose release was measured 30, 32, 34, 36, 38 and 40° C. at pH 5.0. Activities of glucoamylases increased with temperature; they were most active at 40° C. but retained approximately 50% of peak activity at 30° C.

Figure 25:
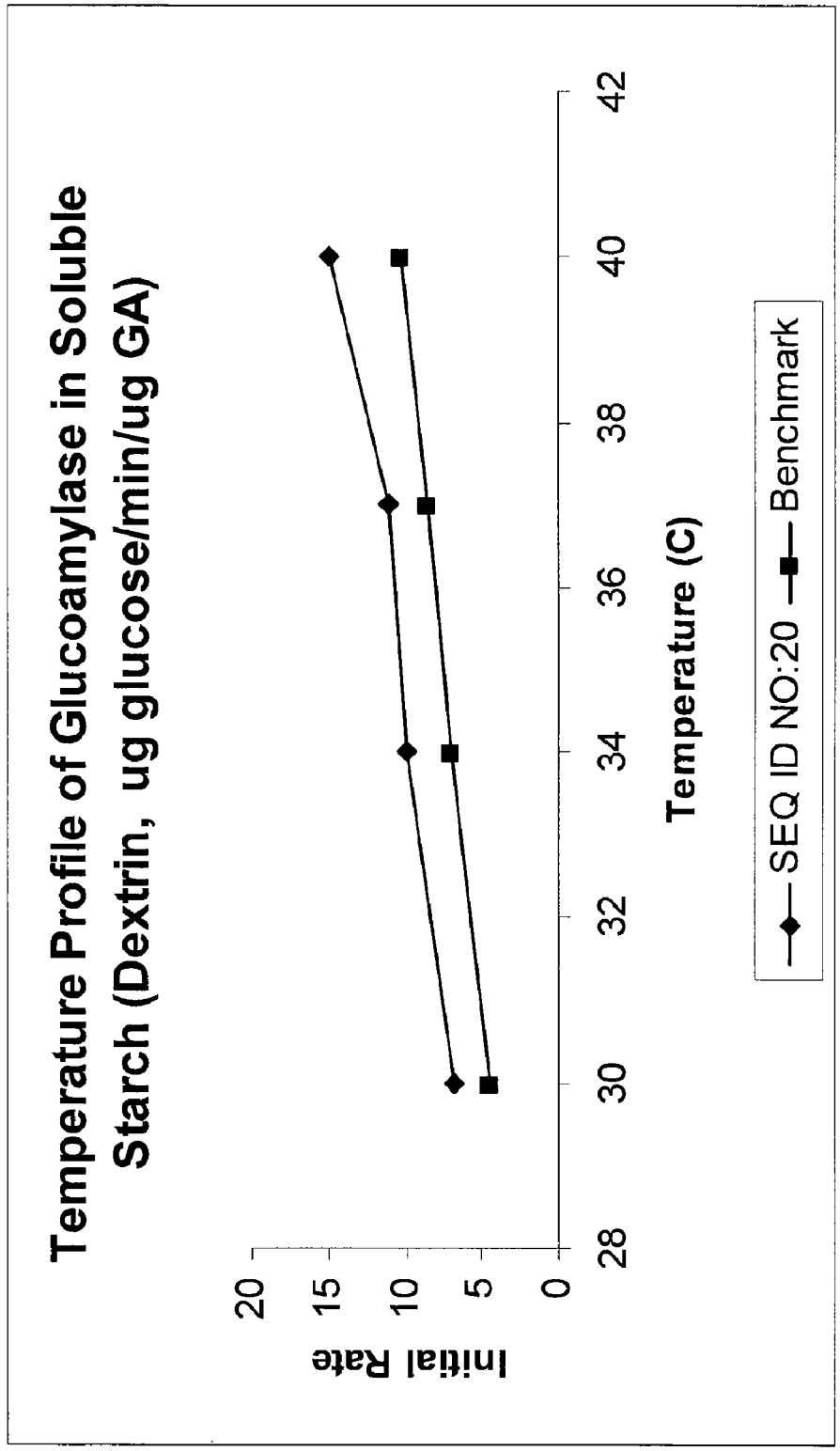
FIG. 25 illustrates the effect of temperature on the activity of the exemplary glucoamylase SEQ ID NO:20 and the A. niger "benchmark" enzyme with soluble starch (dextrin) as a substrate, as discussed in detail in Example 23, below.

FIG. 25 illustrates the effect of temperature on the activity of the exemplary glucoamylase SEQ ID NO:20 and the *A. niger* "benchmark" with soluble starch (dextrin) as a substrate. Glucose release was measured at the indicated temperature at pH 5.0.

1.3 pH profile: The influence of pH on starch hydrolysis was tested with both granular and soluble starch, respectively. All glucoamylases hydrolyzed both substrates best at lower pH, with the exemplary SEQ ID NO:26 being the most acidic in character. For both substrates, glucose release was measured at the indicated pH at 37° C. Initial rates were calculated over 20 min and converted to a percentage of the maximum rate.

1.4 Bond-type cleavage specificity: The kinetic parameters for the hydrolysis of maltose (α-1,4-linkage) and isomaltose (α-1,6-linkage) were determined for 7 selected glucoamylases and the "benchmark" *A. niger* glucoamylase. The experiments were conducted with lyophilized *P. pastoris* lysates and the proteins were not purified; therefore only data independent of protein concentration are reported herein. Table 3, below, summarizes values of $K_M$ for maltose and isomaltose and the ratio of $k_{cat}/K_M$ for maltose compared to $k_{cat}/K_M$ for isomaltose. These parameters determined for *A. niger* glucoamylase are in good agreement with published data; e.g., $K_M$ for maltose is reported to be 1.2-2.1 mM; $K_M$ for isomaltose is reported to be 19.8-42.0 and $k_{cat}/K_M$ for maltose over $k_{cat}/K_M$ for isomaltose is reported to be between 300-600, according to Frandesen (1995) Biochemistry. 34:10162-10169; Sierks and Svensson (1996) Biochemistry 35:1865-1871; Fagerstrom and Kalkkinen (1995) Biotechnol. Appl. Biochem. 21:223-231.

Table 3, summarizes the kinetic parameters for hydrolysis of maltose and isomaltose by seven exemplary glucoamylases of this invention and a "benchmark" *A. niger* glucoamylases; each number is the average value from 5 different experiments:

TABLE 3

|  | Maltose $K_M$ (mM) | Isomaltose $K_M$ (mM) | $k_{cat}/K_M$ (maltose)/ $k_{cat}/K_M$ (isomaltose) |
| --- | --- | --- | --- |
| SEQ ID NO: 28 | 0.61 ± 0.06 | 11.94 ± 4.99 | 750 |
| SEQ ID NO: 74 | 1.87 ± 0.17 | 11.55 ± 2.92 | 481 |
| SEQ ID NO: 20 | 2.62 ± 0.19 | 53.97 ± 23.17 | 897 |
| SEQ ID NO: 14 | 2.67 ± 0.15 | 41.5 ± 5.05 | 116 |
| SEQ ID NO: 26 | 0.98 ± 0.33 | 12.18 ± 0.64 | 456 |
| SEQ ID NO: 48 | 2.26 ± 0.12 | 21.69 ± 3 | 565 |
| SEQ ID NO: 18 | 1.01 ± 0.09 | 11.74 ± 7.74 | 415 |
| *A. niger* glucoamylase | 0.93 ± 0.1 | 18.72 ± 3.95 | 249 |

As can be seen from Table 3, the exemplary glucoamylase SEQ ID NO:20 was most strongly selective for maltose and had nearly 900-fold higher specificity towards α-1,4-linkages relative to α-1,6-bonds. The least selective glucoamylase was SEQ ID NO:14 with ~100-fold higher specificity towards α-1,4-bonds relative to α-1,6-bonds.

Example 24

Characterization of Alpha-Amylases and/or Glucoamylases of the Invention

This example describes the characterization of alpha-Amylases and/or glucoamylases of the invention.

Initial reaction rates: The initial rates of hydrolysis of granular and soluble starch by eight (8) exemplary α-amylases were compared with a "benchmark" α-amylase from *A. oryzae*, and the results are summarized in Table 4, below. Due to the relatively high background seen in BCA assays with *A. oryzae* α-amylase from Sigma (A6211), a second preparation of the same amylase from Megazyme (E-ANAAM™) was also evaluated. Results obtained with both preparations were very similar. As can be seen from Table 34, all amylases tested displayed significantly higher activity against soluble starch when compared with granular starch. However, this difference was less marked for the exemplary Amylases and/or glucoamylases of the invention than for the "benchmark" *A. oryzae* enzyme.

Table 4 shows data comparing initial rates of hydrolysis of granular corn starch and soluble corn starch by eight (8) exemplary α-Amylases and/or glucoamylases of the invention and the "benchmark" α-amylase from *A. oryzae* at 37° C. and pH 5 (note: *Initial rates are expressed as nmole of reducing ends released from 1% starch/min/μg of α-amylase protein for SEQ ID NO:56, SEQ ID NO:62, SEQ ID NO:2, and SEQ ID NO:52; **Initial rates for SEQ ID NO:70, SEQ ID NO:66 and SEQ ID NO:76 are expressed as nmoles of reducing ends released from 1% starch/min/μg of total protein; each number is an average value from 5 data points:

TABLE 4

| Enzyme | Initial rate* ± SD Granular starch | Initial rate* ± SD Soluble starch |
| --- | --- | --- |
| SEQ ID NO: 56 | 15.7 ± 1.67 | 1607.9 ± 518.22 |
| SEQ ID NO: 70** | 2.1 ± 0.24 | 28.4 ± 3.81 |
| SEQ ID NO: 62 | 3.5 ± 0.37 | 139.6 ± 55.96 |
| SEQ ID NO: 66** | 0.8 ± 0.09 | 81.3 ± 31.11 |
| SEQ ID NO: 2 | 7 ± 0.75 | 381.2 ± 74.15 |
| SEQ ID NO: 52 | 10.3 ± 1.75 | 248.2 ± 28.46 |
| SEQ ID NO: 76** | 2.6 ± 0.41 | 160.3 ± 42.62 |
| *A. oryzae* amylase (MegazymeE-ANAAM) | 0.4 ± 0.07 | 498.7 ± 64.78 |

Temperature profile: The effect of temperature on starch hydrolysis by the characterized α-amylases was determined Activity was measured at pH 5.0 during 40 min incubation at the indicated temperature, and initial rates were calculated and plotted against time. Activities of amylases were affected by temperature to a different degree. Five of the exemplary Amylases and/or glucoamylases of the invention SEQ ID NO:56, SEQ ID NO:70, SEQ ID NO:76 and SEQ ID NO:66, were most active at 40° C. and retained approximately 30% of activity at 30° C. Activities of SEQ ID NO:2, SEQ ID NO:52 and SEQ ID NO:62 were only marginally affected by changes in temperature over the range investigated.

pH profile: The influence of pH on exemplary Amylases and/or glucoamylases of the invention on starch hydrolysis was tested with both granular and soluble starch substrates, and the results were determined. The increase in reducing ends was measured at the indicated pH at 37° C. Initial rates were calculated over 40 min and converted to a percentage of the maximum rate. The exemplary SEQ ID NO:52 (originally of fungal origin) had the lowest pH optimum (approximately pH 4). Another exemplary enzyme SEQ ID NO:2 (also originally of fungal origin) also displayed preference for acidic pH, with an apparent optimum at approximately pH 4.5-5. The exemplary amylase SEQ ID NO:66 (originally of Archaeal origin) had an apparent optimum of approximately pH 5.0, retaining approximately 70% of peak activity at pH 4.0. The remaining exemplary enzymes of the invention had apparent optima between pH 5.0 and 6.0, and were almost inactive at pH 4.0 and 3.5.

Example 25

Expression of Amylases and/or Glucoamylases of the Invention in Host Cells

This example describes the evaluation of expression of exemplary enzymes of the invention in different hosts cells; in particular, the expression of three (3) exemplary amylases in different expression hosts: *Pichia pastoris*, *Hansenula polymorpha*, and *Cochliobolus heterostrophus* were studied.

*H. polymorpha*: Two expression vectors (Artes Biotechnology GmbH, Erkrath, Germany) were used: pFPMT-Mfa™ with a formate dehydrogenase promoter and pTPS1-Mfa™ with a trehalose-6-phosphate synthase promoter. In both vectors the secretion signal used was the pre-prosequence of the mating-factor MFa1 from *Saccharomyces cerevisiae*.

Plasmids with subcloned amylase genes were introduced into *H. polymorpha* competent cells by electroporation. 96 colonies from each transformation were selected and grown for approximately 30 (3 passages) to 80 (8 passages) generations by various sub-culturing steps, under selective conditions in liquid medium (YNB-Glucose). These steps allow for increasing the copy number and facilitate the integration of the plasmid into the chromosome. After these 3 or 8 passaging steps, transformants were cultivated under non-selective conditions (YPD medium) to test for plasmid stabilization (loss of any non-integrated plasmid). Screening for positive clones was performed on Red Starch—agar plates. Clones with larger than the control (same gene expressed in *P. pastoris*) clearing zone were selected as primary hits. Amylase expression by the selected clones was confirmed by assaying culture supernatants on BODIPY-starch substrate, and SDS PAGE was used for visualization of the protein produced. 1 L cultures were prepared for further testing.

*Cochliobolus heterostrophus*. cDNA and gDNA of amylase from *C. heterostrophus* were subcloned into pCh-ubi (ubiquitin promoter) and pCh-GPD (GPD promoter) and targeted to the PKS18 locus of the C5 strain of *C. heterostrophus* by PEG-mediated protoplast transformation, using linearized construct DNA. One of the constructs, a genomic version under an ubi (ubiquitin) promoter, was also introduced into the JMD3 strain from which the amylase—encoding gene had been deleted. Similarly, as in the case of *P. pastoris*, screening of the transformants was performed on red starch plates and confirmed by BODIPY-starch assays and SDS PAGE with culture supernatants. No difference was observed in expression between the cDNA and the genomic versions. Similarly no significant difference was observed with the two different promoters.

Results: Strains of: *H. polymorpha* and *C. heterostrophus* expressing, for comparison, 3 exemplary amylase-encoding and glucoamylase-encoding genes were constructed, in addition to 3 original *P. pastoris* strains. All strains used for comparisons and preliminary fermentation yields obtained with these strains are presented in Table 5, summary estimated expression yields (g/L) of exemplary Amylases and/or glucoamylases of the invention produced in *Pichia*:

TABLE 5

| Origin of the amylase gene | *Pichia pastoris* |
|---|---|
| fungal | SEQ ID NO: 2 0.01* |
| bacterial | SEQ ID NO: 70 0.07* |
| archaeal | SEQ ID NO: 66 0.13* |

*fermentation yield

Following the expression evaluation, protein purity, specific activity and performance in granular starch hydrolysis assays were compared. These comparisons led to the following conclusions:

No significant biochemical differences were observed between enzymes expressed in the different hosts.

Expression in *Hansenula* did not appear to result in an improvement over the expression observed in *P. pastoris*. Furthermore, the expressed proteins appeared to be highly glycosylated.

Example 26

Raw Starch Fermentation Using Amylases of this Invention

This example describes exemplary methods for raw starch fermentation using amylases of this invention.

Fifteen (15) exemplary enzymes consisting of eight (8) alpha-amylases and seven (7) glucoamylases were initially identified. The "lead" exemplary enzymes were determined based on activity at temperatures from 30° to 40° C., pH range from 3.5-7.0, and hydrolysis of 1% raw starch. Unpurified microbial enzyme was first analyzed for amount of proteins and expression ratios; and then evaluated in raw starch fermentations. The total enzyme loading and ratios of alpha-amylases to glucoamylases were then determined.

Note: for the raw starch fermentation work, all enzymes were obtained by expression in *Pichia pastoris*, except for SEQ ID NO:78 (encoded, e.g., by SEQ ID NO:77), which was expressed in *Pseudomonas fluorescens* (e.g., as described in JBC, 2002, 277(29):26501-26507).

TABLE 1.1

Enzyme Expression and Relative Purity of "lead" exemplary alpha-amylases and glucoamylases

| Enzyme*** | protein/powder (g/g)* | Expression ratio** |
|---|---|---|
| SEQ ID NO: 56 | 0.12 ± 0.42 | 0.6 |
| SEQ ID NO: 52 | 0.09 ± 0.003 | 0.6 |
| SEQ ID NO: 66 | 0.05 ± 0.005 | 0.1 (0.5****) |
| SEQ ID NO: 66 | 0.05 | 0.1 (0.5****) |
| SEQ ID NO: 66 | 0.059 ± 0.002 | 0.5**** |
| SEQ ID NO: 66 | 0.085 | 0.5**** |
| SEQ ID NO: 2 | 0.03 ± 0.005 | 0.3 |
| SEQ ID NO: 2 | 0.03 ± 0.002 | 0.3 |
| SEQ ID NO: 70 | 0.09 ± 0.003 | 0.05 (0.25****) |
| SEQ ID NO: 70 | 0.126 ± 0.002 | 0.25**** |
| SEQ ID NO: 70 | 0.131 | 0.25**** |
| SEQ ID NO: 62 | 0.2 ± 0.03 | 0.75 |
| SEQ ID NO: 78 | 10 (mgs/ml) | 0.25 |
| SEQ ID NO: 76 | 0.1 ± 0.01 | 0.2 |
| SEQ ID NO: 26 | 0.2 ± 0.026 | 0.8 |
| SEQ ID NO: 28 | 0.15 ± 0.076 | 0.45 |
| SEQ ID NO: 28 | 0.36 ± 0.042 | 0.45 |
| SEQ ID NO: 18 | 0.24 ± 0.096 | 0.8 |
| SEQ ID NO: 74 | 0.21 ± 0.016 | 0.8 |
| SEQ ID NO: 48 | 0.28 ± 0.098 | 0.5 |
| SEQ ID NO: 20 | 0.28 ± 0.066 | 0.7 |
| SEQ ID NO: 14 | 0.21 ± 0.155 | 0.2 |
| Control (empty vector) | 0.0063 | |

*protein content was determined using Bradford's protocol.
**expressed as percentage of total protein in clarified lysate; determined by SDS PAGE using 5 µg protein loadings, and the Bio-Rad Quantity One software.
***where an enzyme appears several times in this list, different lots were used.
****value after de-glycosylation.

Experimental Methods

Raw Starch Fermentation

All fermentations were done using Yellow Dent II corn, milled on the Ultra Centrifugal Mill by Glen Mills at 12,000 rpm through a 0.5 mm screen. The corn flour was analyzed on a Mettler HB-43™ moisture balance to determine moisture content and then 10 g dry weight of corn flour was measured into a 50 ml flask with stir bar. Water was then added followed by the addition of tetracycline (0.5 mg), H2SO4 (175 µl of 0.9 M solution), unpurified/purified enzyme stocks, and yeast to bring the total slurry to 33% total solids. The flasks were placed on a stir plate in 30° C. for 72 hours. Samples were taken at 50 or 72 hours of fermentation for analyses. Sigma *Aspergillus niger* glucoamylase (A-7095) was used as the benchmark added at 2.065 Units (approximately 0.707 mg total protein, or 0.07% total protein loading)/g dw of flour and the test enzyme total loading (%) is based on the total weight of expressed enzyme (g)/dry weight of corn flour in fermentation (g).

To analyze ethanol content and sugar profiles, 1.5 ml of fermentation slurry was taken from each flask at 50 or 72 hours, placed in a 1.8 ml microfuge tube, and spun down at 13000 rpm for 5 minutes. The supernatant was poured into a 0.45 µm spin-x column, spun down at 7000 rpm for 5 minutes, and 200 µA of the spin through was aliquoted into an HPLC vial and analyzed by HPLC. A Waters HPLC equipped with a refractive index detector was used. The column used was the Bio-Rad AMINEX HPX-87H™ (Cat. #: 125-0140). The mobile phase used was 0.005 M $H_2SO_4$ at 0.6 mL/minute.

Preparation of Standards

The standards used for the analysis described herein contain glucose, maltose, maltotriose, maltodextrin, fructose, glycerol, lactic acid, acetic acid, succinic acid, ethanol and methanol. One composite standard is prepared and subsequently diluted to produce the varying concentrations needed to establish standard curves for each compound. All reagents used for standard preparation should be stored in a dessicator cabinet, refrigerated or stored per manufacturers' recommendations. The most accurate means of measuring the components should be employed. Into a clean dry 100 mL volumetric flask add all dry reagents.

Add ~35 mL water and swirl to dissolve solids.

Place a 50 mL Falcon tube on the balance add 25 mL water and then tare.

To the water add glycerol, ethanol, methanol, lactic and acetic acids.

Gently vortex to mix and add contents to volumetric flask with sugar solution. Rinse 50 mL Falcon tube 3 times with ~5 mL water each time and add rinse to volumetric flask.

Bring entire volume of flask to 100 mL. This solution represents the mixed 20% ethanol standard. The solution is sterilized using a Millipore STERIFLIP™ 0.22 or 0.45 µm filter.

Dilutions of this standard are used to create the mixed 5, 10, and 15% ethanol standards.

A mixed 5% standard consists of 1 part mixed 20% standard and 3 parts water.

A mixed 10% standard is a simple 1:1 dilution of the mixed 20% standard.

A mixture of 3 parts mixed 20% standard and 1 part water will create the mixed 15% standard.

A certified 10.3% v/v ethanol standard (Sigma Cat.# E2385) should be run each time a new standard is prepared or monthly to verify the accuracy of the Mixed standard set.

Results

Several alpha-amylases and glucoamylases were tested in combinations in raw starch fermentations at different total enzyme loadings of 0.001, 0.01, and 0.1% (w/w). The alpha-amylases tested were SEQ ID NO:56, SEQ ID NO:70, SEQ ID NO:52, SEQ ID NO:2, SEQ ID NO:62, and SEQ ID NO:66, SEQ ID NO:76. The glucoamylases tested were SEQ ID NO:48, SEQ ID NO:26, SEQ ID NO:18, SEQ ID NO:74, SEQ ID NO:28, SEQ ID NO:14, and SEQ ID NO:20. All combinations were given an ID to be used in the experimental process. Total enzyme loading was calculated based on the expression ratio information provided herein. The alpha-amylase to glucoamylase ratio was determined based on previous data. Ethanol yield was measured after 50 or 72 hours of fermentation by HPLC analysis. Results indicated that all enzyme combinations produced various levels of ethanol and some combinations outperformed the Sigma GA benchmark (Table 1.2).

TABLE 1.2

Ethanol yield in raw starch fermentations of "lead" exemplary alpha-Amylases and Glucoamylases after 50 hours of fermentation[a].

| | Alpha-amylase (AA) | glucoamylase (GA) | AA:GA ratio | Ethanol Yield (% v/v) | | |
|---|---|---|---|---|---|---|
| | | | | 0.001% total enzyme loading | 0.01% total enzyme loading | 0.1% total enzyme loading |
| Combo 1 | SEQ ID NO: 56 | SEQ ID NO: 26 | 2:1 | 6.12 | 11.60 | 15.56 |
| Combo 2 | SEQ ID NO: 56 | SEQ ID NO: 18 | 1:2 | 6.97 | 12.53 | 15.69 |
| Combo 3 | SEQ ID NO: 56 | SEQ ID NO: 28 | 1:2 | 5.96 | 11.06 | 16.42 |
| Combo 4 | SEQ ID NO: 56 | SEQ ID NO: 74 | 1:2 | 6.83 | 11.49 | 14.29 |
| Combo 5 | SEQ ID NO: 56 | SEQ ID NO: 20 | 1:2 | 4.28 | 5.61 | 7.55 |
| Combo 6 | SEQ ID NO: 56 | SEQ ID NO: 48 | 1:2 | 6.40 | 12.58 | 15.86 |
| Combo 7 | SEQ ID NO: 66 | SEQ ID NO: 26 | 1:2 | 7.39 | 15.38 | N/A |
| Combo 8 | SEQ ID NO: 66 | SEQ ID NO: 18 | 1:2 | 5.84 | 12.81 | N/A |
| Combo 9 | SEQ ID NO: 66 | SEQ ID NO: 28 | 1:2 | 6.12 | 12.62 | N/A |
| Combo 10 | SEQ ID NO: 66 | SEQ ID NO: 74 | 1:2 | 7.02 | 12.29 | N/A |
| Combo 11 | SEQ ID NO: 66 | SEQ ID NO: 20 | 1:2 | 4.48 | 5.72 | N/A |
| Combo 12 | SEQ ID NO: 66 | SEQ ID NO: 48 | 1:2 | 6.54 | 14.16 | N/A |
| Combo 13 | SEQ ID NO: 70 | SEQ ID NO: 26 | 1:2 | 9.08 | 15.04 | 16.76 |
| Combo 14 | SEQ ID NO: 70 | SEQ ID NO: 18 | 1:2 | 7.86 | 13.00 | 14.71 |
| Combo 15 | SEQ ID NO: 70 | SEQ ID NO: 74 | 1:2 | 8.18 | 13.27 | 16.40 |
| Combo 16 | SEQ ID NO: 70 | SEQ ID NO: 48 | 1:2 | 8.36 | 13.80 | 15.90 |
| Combo 17 | SEQ ID NO: 52 | SEQ ID NO: 26 | 1:2 | 7.92 | 12.67 | 15.15 |
| Combo 18 | SEQ ID NO: 52 | SEQ ID NO: 18 | 2:1 | 10.66 | 16.10 | 14.92 |
| Combo 19 | SEQ ID NO: 52 | SEQ ID NO: 48 | 1:2 | 10.88 | 15.97 | 14.87 |
| Combo 20 | SEQ ID NO: 62 | SEQ ID NO: 26 | 1:2 | 7.30 | 12.67 | 15.68 |
| Combo 21 | SEQ ID NO: 62 | SEQ ID NO: 48 | 1:2 | 7.24 | 11.13 | 14.84 |

TABLE 1.2-continued

Ethanol yield in raw starch fermentations of "lead" exemplary alpha-Amylases and Glucoamylases after 50 hours of fermentation[a].

| | Alpha-amylase (AA) | glucoamylase (GA) | AA:GA ratio | Ethanol Yield (% v/v) | | |
|---|---|---|---|---|---|---|
| | | | | 0.001% total enzyme loading | 0.01% total enzyme loading | 0.1% total enzyme loading |
| Combo 22 | SEQ ID NO: 2 | SEQ ID NO: 26 | 2:1 | 9.20 | 14.56 | 15.36 |
| Combo 23 | SEQ ID NO: 2 | SEQ ID NO: 48 | 1:2 | 9.81 | 15.42 | 15.61 |
| Combo 24 | SEQ ID NO: 56 | SEQ ID NO: 14 | 1:2 | 5.46 | 7.86 | 13.67 |
| Combo 25 | SEQ ID NO: 70 | SEQ ID NO: 14 | 2:1 | 6.99 | 10.85 | 15.72 |
| Combo 26 | SEQ ID NO: 78 | SEQ ID NO: 48 | 1:2 | N/A | N/A | 16.13[a] |
| Combo 27 | SEQ ID NO: 78 | SEQ ID NO: 26 | 1:2 | N/A | N/A | 16.88[a] |
| Combo 28 | SEQ ID NO: 76 | SEQ ID NO: 48 | 1:2 | N/A | N/A | 17.15[a] |
| Sigma GA control | | | | N/A | N/A | 16.82[b] |

[a]Ethanol yield after 72 hours of fermentation.
[b]Total enzyme loading was estimated to be approximately 0.07%.

Example 27

Expression of Enzymes in Plants; Raw Starch Fermentation

This example describes plant expression of nine exemplary enzymes of this invention (enzymes not having codon optimization), and raw starch fermentation using plant material.

Five (5) alpha-amylases, SEQ ID NO:52, SEQ ID NO:4, SEQ ID NO:70, SEQ ID NO:66, and SEQ ID NO:76 and 4 glucoamylases, SEQ ID NO:48, SEQ ID NO:18, SEQ ID NO:26, and SEQ ID NO:28 were chosen for plant expression based on high ethanol yield of the microbial enzymes in raw starch fermentation. This maize expression was carried out with the gene sequences without codon optimization. The objectives of this study were to evaluate the potential expression levels of these enzymes and to evaluate whether expression of these enzymes would have detrimental effect on maize agronomics through out its developmental stages.

Experimental Methods
Vector Construction

Table 2.1 summarized the abbreviations used for the DNA elements in the maps shown below.

TABLE 2.1

Abbreviations used in the construct maps

| Name | Function | Description |
|---|---|---|
| cAMY(SEQ ID NO: 66)-02 | CDS | Alpha amylase, SEQ ID NO: 66, minus the native leader, attached to a Gamma Zein signal sequence targeting to the apoplast |
| cAmy(SEQ ID NO: 18)-02 | CDS | Glucoamylase, SEQ ID NO: 18, minus the native leader, attached to a Gamma Zein signal sequence targeting to the apoplast |
| cAmy(SEQ ID NO: 52)-02 | CDS | Alpha amylase, SEQ ID NO: 52, minus the native leader, attached to a Gamma Zein signal sequence targeting to the apoplast |
| cAmy(SEQ ID NO: 28)-02 | CDS | Glucoamylase, SEQ ID NO: 28, minus the native leader, attached to a Gamma Zein signal sequence targeting to the apoplast |
| cAmy(SEQ ID NO: 26)-02 | CDS | Glucoamylase, SEQ ID NO: 26, minus the native leader, attached to a Gamma Zein signal sequence targeting to the apoplast |
| cAmy(SEQ ID NO: 48)-02 | CDS | Glucoamylase, SEQ ID NO: 48, minus the native leader, attached to a Gamma Zein signal sequence targeting to the apoplast |
| cAmy(SEQ ID NO: 76)-02 | CDS | Alpha-amylase, SEQ ID NO: 76, minus the native leader, attached to the gamma zein signal sequence, targeting to the apoplast |
| cAmy(SEQ ID NO: 70)-02 | CDS | Alpha-amylase, SEQ ID NO: 70, minus the native leader, attached to a Gamma Zein signal sequence targeting to the apoplast |

The exemplary vector designated "15745", below, is a binary vector containing an alpha amylase, the exemplary SEQ ID NO:70 minus its native leader. The native leader was replaced with the Gamma Zein signal sequence for targeting to the apoplast. The Gamma Zein-SEQ ID NO:70 fusion is expressed using the Gamma Zein promoter. The binary vector also contains a Ubi-PMI-Nos cassette for mannose selection.

A fragment of cAmy(SEQ ID NO:70)-01, containing amino acids 86-525 (plus stop codon), was PCR amplified from plasmid 15649. The PCR amplification introduced an AfeI site at the 5' end and a BglII site at the 3' end of the fragment. The addition of the AfeI site added an alanine amino acid in front of the cAmy(SEQ ID NO:70) fragment (SY1709: 92-93). This PCR amplicon was cloned into pCR2.1-TOPO and sequenced to verify the presence of the new restriction enzyme sites (SY1709:111-112, 122-124). Once verified, cAmy(SEQ ID NO:70) was digested out of the TOPO backbone via AfeI/BglII. Similarly, construct 15460ZeinAmyVN was digested with AfeI/BglII. This backbone and cAmy(SEQ ID NO:70) were ligated together. When ligated, cAmy(SEQ ID NO:70) stayed in frame with the signal peptide xGZein27ss-01, with only the addition of an alanine residue at the cloning junction. Transformants were screened for the presence of the amylase gene using primers ZeinAmy1199F and prGTL-03R. Positive clones produced an amplicon of ~1.6 kB (SY1709:130). Five clones were selected and were digested with SanDI and RsrII to remove prGZein-01:cAmy(SEQ ID NO:70):t35s-08. Construct 15468 was linearized with RsrII. The binary backbone and digested cassette from one of the positive clones (SanDI/RsrII) were ligated together at the RsrII restriction site. Following transformation into Top10 cells, transformants were screened for the presence of the cassette using primers ZeinAmy1199F and Mubi-5 (SY1709:146, 150).

Three positive transformants were selected and checked via a BamHI diagnostic digest. These clones were sequenced (SY1709:162; both cloning junctions as well as the entire cAmy(SEQ ID NO:70) coding sequence), it was confirmed that all three were correct in sequence.

The exemplary vector designated "15750", is a binary vector containing a glucoamylase, the exemplary SEQ ID NO:18, minus its native leader. The native leader was replaced with the Gamma Zein signal sequence for targeting to the apoplast. The Gamma Zein-SEQ ID NO:18 fusion is expressed using the Gamma Zein promoter. The binary vector also contains an Ubi-PMI-Nos cassette for mannose selection.

A fragment of cAmy(SEQ ID NO:18)-01, containing amino acids 88-712 (plus stop codon), was PCR amplified from plasmid 15652. The PCR amplification introduced an AfeI site at the 5' end and a BglII site at the 3' end of the fragment. The addition of the AfeI site resulted in amino acid 88 changing from a serine to an alanine (SY1709: 113-114, 116). This PCR amplicon was cloned into pCR2.1-TOPO and sequenced to verify the presence of the new restriction enzyme sites (SY1709:116, 131). Once verified, the cAmy (SEQ ID NO:18) fragment was digested out of the TOPO backbone via AfeI/BglII. Similarly, construct 15460Zein-AmyVN was digested with AfeI/BglII. This backbone and the cAmy(SEQ ID NO:18) fragment were ligated together. When ligated, cAmy(SEQ ID NO:18) stayed in frame with the signal peptide xGZein27ss-01, with the addition of an alanine residue at the cloning junction. Six clones were selected and were digested with SanDI and RsrII to remove prGZein-01:cAmy(SEQ ID NO:18):t35s-08. Construct 15468 was linearized with RsrII. The binary backbone and digested cassette from one of the positive clones (SanDI/RsrII) were ligated together at the RsrII restriction site. Following transformation into Top10 cells, transformants were screened for the presence of the cassette using primers ZeinAmy1199F and Mubi-5 (SY1709:181). Additionally, all 6 transformants were selected and checked via a SacI diagnostic digest. Three of the positive clones were sequenced (SY1709:189-190) (both cloning junctions as well as the entire cAmy(SEQ ID NO:18) coding sequence), it was confirmed that all three were correct in sequence.

The exemplary vector designated "15751", is a binary vector containing a glucoamylase, the exemplary SEQ ID NO:48, minus its native leader. The native leader was replaced with the Gamma Zein signal sequence for targeting to the apoplast. The Gamma Zein-SEQ ID NO:48 fusion is expressed using the Gamma Zein promoter. The binary vector also contains a Ubi-PMI-Nos cassette for mannose selection.

Using 15651 as a template, mutagenesis primers were used in a multi-site mutagenesis reaction (QUICKCHANGE™, Stratagene) to remove an internal AfeI site, introduce an AfeI site at the 5' end (mutation was in signal sequence, no peptide change), and introduce an external 3' BglII site for cloning. Restriction enzyme analysis was performed and clones that were positive for having the internal AfeI site removed and the BglII site introduced were selected. A positive clone was sent for sequence analysis which was confirmed. This clone DNA was then used as template for PCR amplification to introduce an AfeI site at the 5' end of the glucoamylase domain. The mutation was in the native signal sequence and did not change the glucoamylase peptide sequence. The PCR product was digested sequentially with AfeI and then with BglII. The digested product was gel purified and ligated to the 15460AmyZeinVN backbone, creating cAmy(SEQ ID NO:48) with a gamma zein signal sequence targeting to the apoplast. This intermediate vector was sequence verified and then digested with SanDI and RsrII sequentially. This fragment was gel purified and then ligated into 15468 binary cut with RsrII and CIP treated. The positive clones were PCR size screened and then one of the positive clones was sent off for sequence analysis of the entire fragment ligated into the binary. Sequence was confirmed.

The exemplary vector designated "15761", is a binary vector containing an alpha amylase, the exemplary SEQ ID NO:66, minus its native leader. The native leader was replaced with the Gamma Zein signal sequence for targeting to the apoplast. The Gamma Zein-SEQ ID NO:66 fusion is expressed using the Gamma Zein promoter. The binary vector also contains a Ubi-PMI-Nos cassette for mannose selection.

A fragment of cAmy(SEQ ID NO:66)-01, containing amino acids 86-521 was mutagenized using site directed mutagenesis according to the Stratagene Quick Change protocol. The mutagenesis required 3 individual primers (all amplifying in the forward direction) and introduced three mutations: an AfeI site at the 5' end, a BglII site at the 3' end (external to the gene), and the removal of an internal AfeI site (SY1709:174). The mutagenized construct was transformed into Top 10 cells for screening to determine if any/all of the desired mutations were present. 15 transformants were selected for screening and were digested separately with AfeI and BglII (SY1709:185-186). It was determined from the restriction digests that there were 6 possible clones with all three of the desired mutations; three of these clones were sent for sequencing (SY1709:190; SY1777:11). For all three clones, an AfeI site had been introduced at the 5' end and the internal site had been removed. In addition, the 3' BglII site had been introduced. Following confirmation, the alpha amylase was digested out of the mutagenized construct with AfeI/BglII and ligated into the 15460ZeinAmyVN backbone which had also been digested with AfeI and BglII. When ligated, cAmy(SEQ ID NO:66) stayed in frame with the signal peptide xGZein27ss with no amino acid changes at the cloning junction. Transformants were screened for the presence of the amylase gene using primers ZeinAmy1199F and prGTL-03R. Positive clones produced an amplicon of ~1.6 kB (SY1777:24). Three clones were selected and digested with SanDI/RsrII to remove prGZein-01:cAmy(SEQ ID NO:66):t35s-08. Construct 15468 was linearized with RsrII. The binary backbone and digested cassette from one of the positive clones (SanDI/RsrII) were ligated together at the RsrII restriction site. Following transformation into Top10 cells, transformants were screened for the presence of the cassette using primers ZeinAmy1199F and prGTL-03R (SY1777:47-48). Six positive transformants were selected and checked via a HindIII diagnostic digest. Three of these clones were sequenced (SY1777:56, 62) at both cloning junctions as well as the entire coding sequence; it was confirmed that all three were correct in sequence.

The exemplary vector designated "15756", is a binary vector containing a glucoamylase, the exemplary SEQ ID NO:26, minus its native leader. The native leader was replaced with the Gamma Zein signal sequence for targeting to the apoplast. The Gamma Zein-SEQ ID NO:26 fusion is expressed using the Gamma Zein promoter. The binary vector also contains a Ubi-PMI-Nos cassette for mannose selection.

Using exemplary vector 15653 as a template, mutagenesis primers were used in a multi-site mutagenesis reaction (QUICKCHANGE™, Stratagene) to remove an internal AfeI site, introduce an AfeI site at the 5' end (mutation was in signal sequence, no peptide change), and introduce an external 3' SacI site for cloning. The reaction was transformed into Top10 competent cells. Colonies were picked and screened via restriction enzyme analysis. Clones that were positive for having the internal AfeI site removed, the 5' Afe site inserted and the SacI site introduced were selected. A positive clone was sent off for sequence analysis which was confirmed. This clone DNA was then digested with SacI and AfeI. The digest was then gel purified and ligated to the 15460AmyZeinVN backbone creating cAmy(SEQ ID NO:26) with a gamma zein signal sequence targeting to apoplast. This intermediate vector was sequence verified then digested with SanDI and RsrII. This fragment was gel purified and ligated into 15468 binary vector cut with RsrII and CIP treated. The positive clones were PCR size screened and then one of the positive clones was sent off for sequence analysis of the entire fragment ligated into the binary. Sequence was confirmed.

The exemplary vector designated "15742", is a binary vector harboring (comprising) the C-terminal 616 amino acids of a glucoamylase, the exemplary SEQ ID NO:28 (cAmy(SEQ ID NO:28)-01) fused in-frame with the Gamma Zein signal sequence (xGZein27ss-01), targeting the glucoamylase to the apoplast to create (cAmy(SEQ ID NO:28)-02). Expression is driven by the 5' region from Gamma Zein A (prGZein-01), which is a seed specific promoter.

Vector 15654 harboring cAmy(SEQ ID NO:28)-01 served as PCR DNA template modified by the addition of an NcoI site (5-prime end) and a BglII site (3-prime end). The PCR product was TOPO-cloned and Clone #1 was sequenced for validation (SY1533:181). The new component alias "cAmy (SEQ ID NO:28)" was digested with NcoI/BglII and gel purified. The fragment was ligated in-frame to the NcoI/BglII site of a cloning vector alias "15460ZeinAmyVN" thereby generating a cassette harboring prGZein-01:xGZein27ss-01:cAmy(SEQ ID NO:28):iPEPC9-01:t35s-08 (SY1533:183). The gene cassette was digested sequentially with SanDI/RsrII, gel purified and ligated into the RsrII site of binary vector 15468. Successful ligation was confirmed by PCR and DNA sequence (SY1533:185-187).

The exemplary vector designated "15749", is a binary vector containing an alpha amylase, the exemplary SEQ ID NO:52, minus its native leader. The native leader was replaced with the Gamma Zein signal sequence for targeting to the apoplast (cAmy(SEQ ID NO:52)-02). The Gamma Zein-SEQ ID NO:52 fusion is expressed using the Gamma Zein promoter. The binary vector also contains a Ubi-PMI-Nos cassette for mannose selection.

A fragment of cAmy(SEQ ID NO:52)-01, containing amino acids 88-674 (plus stop codon), was PCR amplified from plasmid 15648. The PCR amplification introduced an AfeI site at the 5' end and a SacI site at the 3' end of the fragment. The addition of the AfeI site resulted in amino acid 88 changing from a serine to an alanine (SY1709:95-96). The PCR amplicon was cloned into pCR2.1TOPO and sequenced to verify the presence of the new restriction enzyme sites (SY1709:103, 111-112). Once verified, cAmy(SEQ ID NO:52) was digested out of the TOPO backbone via AfeI/SacI. Similarly, construct 15460ZeinAmyVN was digested with AfeI/SacI. This backbone and cAmy(SEQ ID NO:52) were ligated together. When ligated, cAmy(SEQ ID NO:52) stayed in frame with the signal peptide xGZein27ss-01 with only the first amino acid residue changed from a leucine to an alanine. Transformants were screened for the presence of the amylase gene using primers ZeinAmy1199F and prGTL-03R. Positive clones produced an amplicon of ~2.1 kB (SY1709:130). Five clones were selected and were digested with SanDI and RsrII to remove prGZein-01:cAmy(SEQ ID NO:52):t35s08. Construct 15468 was linearized with RsrII. The binary backbone and digested cassette from one of the positive clones (SanDI/RsrII) were ligated together at the RsrII restriction site. Following transformation into Top10 cells, transformants were screened for the presence of the cassette using primers ZeinAmy1199F and Mubi-5 (SY1709:146, 150). Three positive transformants were selected and checked via a BamHI diagnostic digest. These clones were sequenced (SY1709:162; both cloning junctions as well as entire cAmy(SEQ ID NO:52) coding sequence) and it was determined that there was a point mutation within the prG-Zein sequence. This mutation is a single base pair change-T to C- at nucleotide 340. The promoter within the original 15460ZeinAmy backbone was sequenced again to check for the mutation and it was not present in the backbone source. However, it was present when the positive clones were sequenced a second time (SY1709:182, 189). This mutation may have occurred during bacterial replication.

The exemplary vector designated "15718", is a binary vector containing an alpha amylase, the exemplary SEQ ID NO:76, minus its native leader. The native leader was replaced with the Gamma Zein signal sequence for targeting to the apoplast. The Gamma Zein-SEQ ID NO:76 fusion (cAmy(SEQ ID NO:76)-02) is expressed using the Gamma Zein promoter. The binary vector also contains a Ubi-PMI-Nos cassette for mannose selection.

A fragment of cAmy(SEQ ID NO:76)-01, containing amino acids 87-508 (plus stop codon), was PCR amplified from plasmid 15650. The PCR amplification introduced an AfeI site at the 5' end and a BglII site at the 3' end of the fragment. The addition of the AfeI site changed a glycine amino acid to alanine. The PCR product was digested with AfeI and BglII and cloned into the 15460AmyZeinVN backbone cut with AfeI and BglII, creating cAmy(SEQ ID NO:76) fused to the gamma zein signal sequence. This intermediate vector was then digested with SanDI and RsrII sequentially. This fragment was gel purified and then ligated into 15468 binary vector cut with RsrII and CIP treated. The positive clones were PCR size screened and then one of the positive clones was sent for sequence analysis of the entire insert. Sequence was confirmed.

Enzymatic Activity Analysis

Twenty seeds from selected events were randomly selected and pooled. The seeds were then ground and assayed using the Megazyme CERALPHA HR™ assay for alpha-amylases or Megazyme's glucoamylase assay for glucoamylases.

Activity Calculations

One CERALPHA™ Unit of α-amylase activity is defined as the amount of enzyme, in the presence of excess thermostable α-glucosidase, required to release one micromole of p-nitrophenol in one minute under the defined assay conditions. Our assay condition is at pH 5.5 (100 mM NaOAc, pH 5.5 buffer with 1 mg/ml BSA), 60° C. Note that the activity calculated is a CERALPHA™ unit.

According to Megazyme, 1 mM PNP in 1% tri-sodium phosphate gives absorbance 18.1 at 400 nm. So 1M of PNP in tri-sodium phosphate gives absorbance 18,100 at 400 nm.

$\Delta A_{400}/18,100 = $ [PNP] (mol/l or M) in the final plate.

[PNP] in plate (mol/l×8×100×$10^{-6}$1×1×$10^6$ (umol/mol)= PNP (μmol/rxn)

PNP (μmol/rxn)/(0.05 ml×20 min)=units/ml of diluted α-Amylase units/ml in diluted enzyme×dilution=Ceralpha Units/ml in α-Amylase sample or $\Delta A_{400} \times 0.0442 \times$ dilution of enzyme=Ceralpha U/ml in α-amylase sample.

This SOP is adapted from a CERALPHA HR™ assay method SOP and a Megazyme α-amylase assay procedure (CERALPHA™ method) using amylase HM™ Reagent, ICC Standard No. 303.

Figure 27:
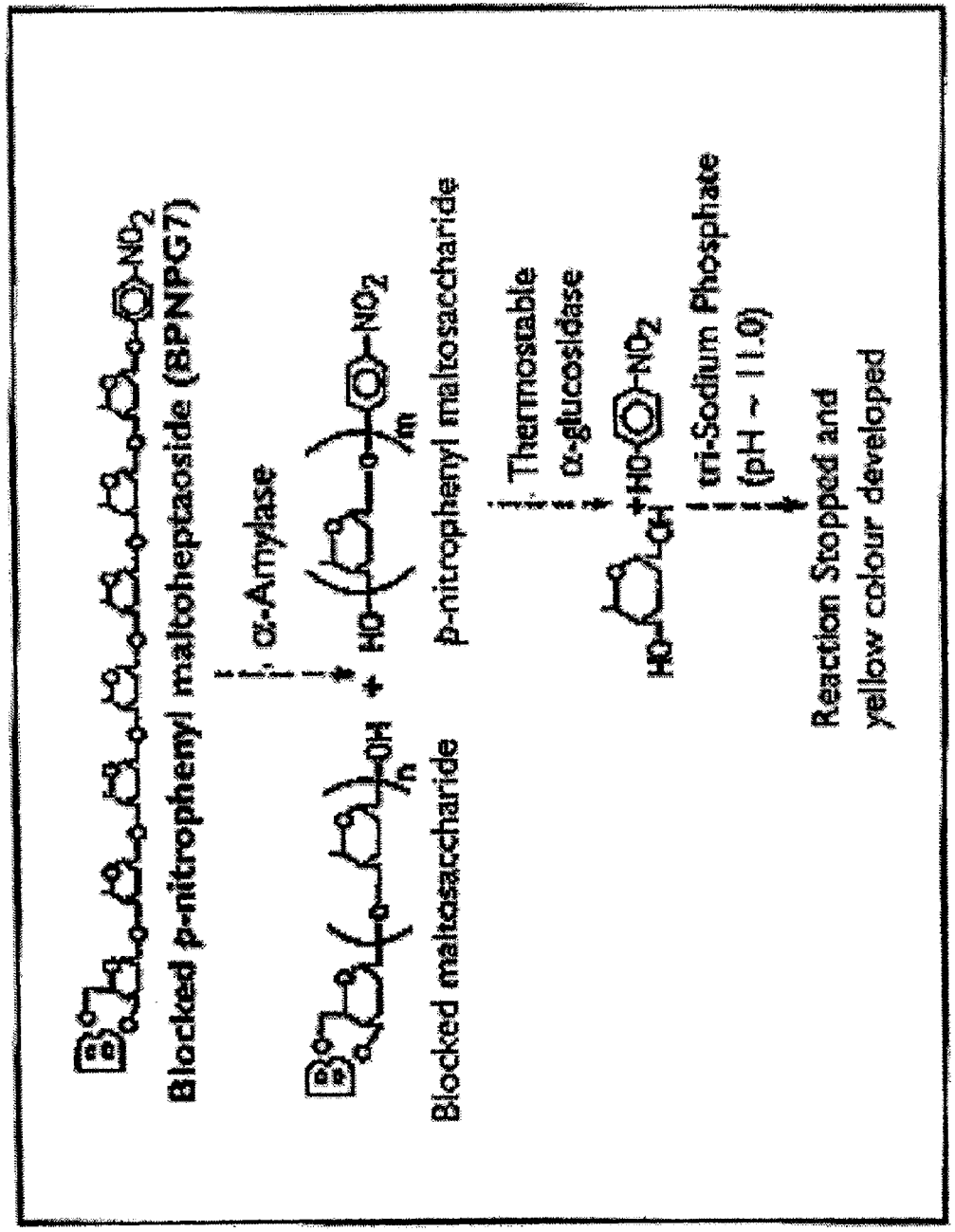
FIG. 27 illustrates the theoretical basis of the CERALPHA™ α-amylase assay procedure, as discussed in detail in Example 27, below.

FIG. 27 illustrates the theoretical basis of the CERALPHA™ α-amylase assay procedure; from Megazyme's alpha-amylase assay procedure (CERALPHA™ Method)

using amylase HR™ reagent: the figure illustrates the overall reaction scheme: that after alpha-amylase cleaves a bond within the blocked p-nitrophenyl malto-saccharide substrate, the non-blocked reaction product containing the p-nitrophenyl constituent is instantly cleaved to glucose and free p-nitrophenyl by the excess quantities of thermostable alpha-glucosidase, which are integral parts of the substrate mixture, and free p-nitrophenyl is released. The reaction is terminated and the phenolate color is developed on addition of tri-sodium phosphate, pH at about 11.0.

Glucoamylase Extraction from Corn Flour and Activity Assay For Starch Hydrolysis: Glucoamylase Extraction and Assay from Single Corn Seed To describe the procedure for glucoamylase extraction and assay from corn flour:

Preparation of Extraction Buffer:
25 mM Sodium borate, 0.01% Tween 20, pH 10 buffer
Procedure:
Pooled seed grinding:
Pool 20 seeds. Add the seeds to a Kelco grinding vessel. Place a steel ball in each vessel on top of the seed. Place a rubber ring around the vessel and place the cap on top. Grind in the Kelco for 45 seconds. Using a scupula transfer the flour from the vessel to a weigh boat and then pour into a 15 mL conical tube. Wash the vessel, ring, and steel ball with soap and water.

Extraction
1. Add 3 ml of extraction buffer to the samples.
2. Seal the tubes with caps using a hammer
3. Shake vigorously until the flour is suspended in the buffer.
4. Rotate at room temperature on a Rugged rotor at 70% for 5 minutes.
5. Incubate at 45° C. in a water bath for 30 minutes
6. Rotate the samples for another 5 minutes at room temperature after incubation.
7. Centrifuge the samples at 3000 rpm for 5 minutes.

GA Assay (Reagent Information is after the Assay Procedure)
1. Dilute samples in the dilution buffer to get an assay in the range of 0.5 to 1.5 $OD_{400}$.
2. Turn on the PCR machine. Set the program to incubate at 40° C. for 10 min and then ramp down to 4° C.
3. On ice, add 50 µl of each diluted Glucoamylase sample to a PCR plate
4. Add 150 µl of Stop solution to each well of a microtiter plate. There should be two wells of Stop solution for each sample assayed.
5. Mix 50 µl of substrate reagent with the sample. Pipette 2 times. Prepare substrate as indicated in the instructions from Megazyme (10 ml water/bottle).
6. Immediately, remove 20 µl of the mixture and mix with 150 µl of Stop solution. Pipette 3 times with swirling. This is the O-time point.
7. Place plate in the incubator and press Start. Make sure the samples are in the machine as it ramps up. Incubate the PCR plate for 10 min at 40° C.
8. Allow the machine to ramp down to 4° C. while the samples are in the machine.
9. Wait 2 minutes.
10. Remove 20 µl of product and mix with 150 µl of Stop in a microtiter plate. This is the 10 min time point.
11. Let the plate sit for 15 min
12. Read $OD_{400}$ in the plate reader. Set Pathcheck to ON (this will normalize the sample absorbance reading as pathlength 1 cm).
13. Calculate $\Delta AL_{400}$, the change in $A_{400}$ between the 0 and 10 min point.

Preparation of Stock Solutions:
Substrate (Megazyme catalog #: R-AMGR3)
p-nitrophenyl-α-maltoside (4 mM)
Thermostable α-glucosidase (5 U/ml)
Dissolve the entire contents of one vial in 10.0 ml of MilliQ water. Divide into aliquots and store frozen. Store on ice during use.
Stop solution: 2% trizma base solution
2.0 g of trizma base (Sigma T-1503)
MilliQ water added to final volume of 100 ml
Dilution buffer: 200 mM Sodium acetate buffer (pH 4.5)
Activity Calculations One Unit of α-glucoamylase activity is defined as the amount of enzyme, in the presence of excess thermostable α-glucosidase, required to release one micromole of p-nitrophenol in one minute under the defined assay conditions.

According to Megazyme, 1 mM PNP in 2% trizma base gives absorbance of 18.1 at 400 nm.

$$GA \text{ activity in samples } (U/\text{ml}) = (A400/10) \times (170/10) \times$$
$$(1/18.1) \times \text{Dilution}$$
$$= A400 \times 0.0939 \times \text{Dilution}$$

This SOP is adapted from Megazyme's assay of amyloglucosidase using p-nitrophenyl-α-maltoside plus thermostable α-glucosidase Raw Starch Fermentation: carried out as described above.
Results
TAQMAN™ Assay and Enzymatic Activity Assay Copy numbers of the transgenes were determined by primary and secondary TAQMAN™ assays. Primers specific for the selectable marker gene used in all the maize transformation vectors described above, pmi, were used in the primary TAQMAN™ assays. Primers specific for both pmi gene and the bacterial selectable marker gene, spec, were used in secondary TAQMAN™ assays.

Expression of alpha-amylases or glucoamylases in mature dried-down T1 transgenic seeds of selected constructs were also analyzed by enzymatic activity assays. Results of gene copy numbers in events generated from construct 15749 and expression of the exemplary alpha-amylase SEQ ID NO:52 in these events were summarized in Table 2.2.

TABLE 2.2

Transgene copy numbers and α-amylase activity in events generated from construct 15749

| Plant Number | α-amylase Activity in Pooled Seed (U/g) |
|---|---|
| 1 | 25.6 |
| 2 | 23.5 |
| 3 | 21.3 |
| 4 | 21.2 |
| 5 | 20.2 |
| 6 | 18.4 |
| 7 | 15.0 |
| 8 | 14.3 |
| 9 | 14.0 |
| 10 | 12.7 |
| 11 | 12.2 |
| 12 | 11.1 |
| 13 | 10.2 |
| 14 | 9.9 |
| 15 | 9.6 |
| 16 | 7.6 |

TABLE 2.2-continued

Transgene copy numbers and α-amylase activity in events generated from construct 15749

| Plant Number | α-amylase Activity in Pooled Seed (U/g) |
|---|---|
| 17 | 6.9 |
| 18 | 6.8 |
| 19 | 6.4 |
| 20 | 6.4 |
| 21 | 6.0 |
| 22 | 5.4 |
| 23 | 5.3 |
| 24 | 5.3 |
| 25 | 4.7 |
| 26 | 4.7 |
| 27 | 4.5 |
| 28 | 4.2 |
| 29 | 4.0 |
| 30 | 3.9 |
| 31 | 3.7 |
| 32 | 3.6 |
| 34 | 3.1 |
| 35 | 3.0 |
| 36 | 2.8 |
| 37 | 2.5 |
| 38 | 2.4 |
| 39 | 2.0 |
| 40 | 1.5 |
| 41 | 0.4 |
| 42 | 0.4 |
| 43 | 0.3 |
| 44 | 0.2 |
| 45 | 0.1 |

Results of gene copy numbers in events generated from construct 15751 and expression of glucoamylase SEQ ID NO:48 in these events are summarized in Table 2.3:

TABLE 2.3

Transgene copy numbers and glucoamylase activity in events generated from construct 15751

| Plant | Gluco-amylase Activity in Pooled Seed (U/g) |
|---|---|
| 1 | 4.86 |
| 2 | 4.48 |
| 3 | 4.47 |
| 4 | 4.22 |
| 5 | 4.20 |
| 6 | 4.08 |
| 7 | 4.05 |
| 8 | 3.94 |
| 9 | 3.88 |
| 10 | 3.84 |
| 11 | 3.82 |
| 12 | 3.68 |
| 13 | 3.65 |
| 14 | 3.57 |
| 15 | 3.50 |
| 16 | 3.47 |
| 17 | 3.43 |
| 18 | 3.33 |
| 19 | 2.91 |
| 20 | 1.13 |
| 21 | 0.73 |

Table 2.4 summarizes results of gene copy numbers in events generated from construct 15756 and expression of glucoamylase SEQ ID NO:26 in these events. Seeds from multiple events of constructs 15761 and 15718 expressing alpha-amylases SEQ ID NO:66 and SEQ ID NO:76, respectively, were pooled and ground to make composite samples. The two composite samples were assayed for □-amylase activities. Similarly, seeds from multiple events of constructs 15742 and 15750 expressing glucoamylases SEQ ID NO:28 and SEQ ID NO:18, respectively, were also pooled and ground to make composite samples. The two composite samples were assayed for glucoamylase activities. The results were summarized in Table 2.5.

TABLE 2.4

Transgene copy numbers and glucoamylase activity in events generated from construct 15756

| Plant number | Gluco-amylase Activity in Pooled Seed (U/g) |
|---|---|
| 1 | 4.41 |
| 2 | 4.31 |
| 3 | 4.18 |
| 4 | 4.15 |
| 5 | 3.95 |
| 6 | 3.94 |
| 7 | 3.88 |
| 8 | 3.83 |
| 9 | 3.78 |
| 10 | 3.68 |
| 11 | 3.67 |
| 12 | 3.64 |
| 13 | 3.60 |
| 14 | 3.58 |
| 15 | 3.45 |
| 16 | 3.27 |
| 17 | 3.18 |
| 18 | 3.16 |
| 19 | 3.14 |
| 20 | 3.10 |
| 21 | 3.07 |
| 22 | 3.00 |
| 23 | 2.75 |

TABLE 2.5

α-amylase or glucoamylase activity in seeds generated from constructs 15718, 15761, 15742, and 15750

| Construct | Variety | Enzyme Expressed | Enzyme Type | Pooled Seed Activity (U/g) |
|---|---|---|---|---|
| 15718 | JHAX707 | SEQ ID NO: 76 | α-amylase | 0.033 |
| 15761 | JHAX708 | SEQ ID NO: 66 | α-amylase | 0.085 |
| 15742 | JHAX709 | SEQ ID NO: 28 | Glucoamylase | 3.399 |
| 15750 | JHAX710 | SEQ ID NO: 18 | Glucoamylase | 3.55 |

Raw Starch Fermentation Using Maize Expressed Enzymes

Seeds from multiple events of selected constructs expressing α-amylases or glucoamylases were pooled and ground to make composite samples for raw starch fermentations. In all experiments, corn flour containing α-amylases was used at the inclusion rate of 20% (w/w) and corn flour containing glucoamylases at the inclusion rate of 50% (w/w). Yellow dent II commodity corn flour made up the rest of the 30% (w/w) of the corn flour. Raw starch fermentations were carried out by following the standard SOP described above (Section I). The ability of these maize expressed α-amylase and glucoamylase combinations to produce ethanol in raw starch fermentation was summarized in Table 2.6.

TABLE 2.6

Ethanol yield after 72 hours of raw starch fermentation using "lead" exemplary enzymes expressed in maize without codon optimization*

| Construct (α-amylase) | Construct (Gluco-amylase) | Inclusion Rate (α-amylase) (% w/w) | Inclusion Rate (Gluco-amylase) (% w/w) | Inclusion Rate (Commodity) (% w/w) | Ethanol Yield (% v/v) |
|---|---|---|---|---|---|
| 15749 (SEQ ID NO: 52) | 15756 (SEQ ID NO: 26) | 20 | 50 | 30 | 6.96 |
| 15749 (SEQ ID NO: 52) | 15742 (SEQ ID NO: 28) | 20 | 50 | 30 | 8.90 |
| 15761 (SEQ ID NO: 66) | 15751 (SEQ ID NO: 48) | 20 | 50 | 30 | 7.30 |
| 15718 (SEQ ID NO: 76) | 15750 (SEQ ID NO: 18) | 20 | 50 | 30 | 8.33 |
| N/A | N/A | 0 | 0 | 100 | 2.25 |

Example 28

Plant Expression of Exemplary Enzymes using Synthetic Maize Codon Optimized Genes and Raw Starch Fermentation Using Plant Material Synthetic genes with codons optimized for maize expression were generated for 2 α-amylases, SEQ ID NO:52 (encoded, e.g., by SEQ ID NO:51) and SEQ ID NO:4 (encoded, e.g., by SEQ ID NO:3), and 2 glucoamylases, SEQ ID NO:48 (encoded, e.g., by SEQ ID NO:47) and SEQ ID NO:26 (encoded, e.g., by SEQ ID NO:25). The table below correlates the wild-type SEQ ID NO: with the SEQ ID NO: assigned to the codon-optimized sequence. The enzymes chosen for codon optimization were selected based on giving the highest ethanol yield in raw starch fermentation. The objectives of this study were to generate commercial events for product development and to generate enough material to evaluate the raw starch fermentation performance of the maize expressed enzymes.

| Enzyme | Wild-type SEQ ID NO: | Codon-optimized SEQ ID NO: |
|---|---|---|
| Amylase | 51 | 79 |
| Amylase | 3 | 80 |
| Glucoamylase | 47 | 81 |
| Glucoamylase | 25 | 82 |

Experimental Methods
Synthetic Genes

The synthetic genes were made by GENEART™. The sequences were codon optimized using GENEART™'s proprietary GENEOPTIMIZER™ technology. Sequences of the synthetic genes are listed below. The codon usage was adapted to the codon bias of *Zea mays* genes.

Vector Construction

Table 3.1 summarized the abbreviations used for the DNA elements in the maps shown below.

TABLE 3.1

Abbreviations used in the commercial construct maps

| Name | Function | Description |
|---|---|---|
| cAmy(SEQ ID NO: 79)Apo-01 | CDS | Apoplast targeted maize codon optimized synthetic alpha-amylase gene encoding enzyme SEQ ID NO: 52 |
| cAmy(SEQ ID NO: 79)ER-01 | CDS | ER targeted synthetic maize codon-optimized alpha-amylase gene with Gamma Zein signal sequence and KDEL sequence encoding enzyme SEQ ID NO: 52 |
| cAmy(SEQ ID NO: 80)Apo-01 | CDS | Apoplast targeted synthetic maize codon optimized alpha-amylase gene encoding enzyme SEQ ID NO: 4 |
| cAmy(SEQ ID NO: 80)ER-01 | CDS | ER targeted synthetic maize codon-optimized alpha-amylase gene with Gamma Zein signal sequence and KDEL sequence encoding enzyme SEQ ID NO: 4 |
| cGAmy(SEQ ID NO: 82)Apo-01 | CDS | Apoplast targeted synthetic maize codon optimized glucoamylase gene encoding enzyme SEQ ID NO: 26 |
| cGAmy(SEQ ID NO: 82)ER-01 | CDS | ER targeted synthetic maize codon optimized glucoamylase gene with gamma zein signal sequence and KDEL sequence encoding enzyme SEQ ID NO: 26 |
| cGAmy(SEQ ID NO: 81)Apo-01 | CDS | Apoplast targeted synthetic maize codon optimized gluco-amylase gene encoding enzyme SEQ ID NO: 48 |
| cGAmy(SEQ ID NO: 81)ER-01 | CDS | ER targeted (with addition of KDEL ER-retention signal) synthetic maize codon optimized glucoamylase gene encoding enzyme SEQ ID NO: 48 |

The exemplary vector designated "15740", below, is a binary vector for maize transformation harboring seed specific promoter prGTL-03 driving the apoplast targeted synthetic maize optimized version of the exemplary alpha-amylase SEQ ID NO:51, the optimized version is the exemplary SEQ ID NO:79 or, cAmy(SEQ ID NO:79)Apo-01. This binary also contains a Ubi-PMI-Nos cassette for selection.

Cloning Vector: Construct alias15460ZeinAmyVN was digested with SacI and RsrII to remove iPEPC9-01 and t35s-08. Likewise, construct 15460 was digested with SacI and RsrII to remove tNOS-03-01. Terminator t35s-08/iPEPC9-01 was ligated into 15460 using these sites (SY1709:6). The ligation reaction was transformed into DH5-alpha cells; transformants were screened with colony PCR. Four positive clones were sequenced, and from these sequences both cloning junctions and restriction enzyme sites were determined to be correct (SY1709:15-16). To insert promoter prGTL-03, 15460 containing t35s08/iPEPC9-01 was digested with BamHI and HindIII and gel purified (SY1709:14). Construct 11267 containing prGTL-03 was also digested with BamHI and HindIII and the promoter was gel purified (SY1710:3-4). It was then ligated into the 15460 backbone using these sites and transformed into competent DH5-alpha cells. Ten transformants were screened using HindIII and BamHI to determine if prGTL-03 was present in vector; all ten had correct banding pattern (SY1709:25). Two clones were sequenced to confirm cloning junctions and restriction enzyme sites, and both were correct without any sequence differences (SY1709:34-35). Glycerol stocks were prepared from clone #1 and stored at −80 degrees Celsius. Cloning vector was digested with BamHI/SacI and CIP treated. The synthetic maize codon optimized version of alpha amylase SEQ ID NO:51, known as SEQ ID NO:79 (also known as cAmy(SEQ ID NO:79)) was digested with BamHI and SacI and ligated into the BamHI/SacI site of prGTL-03 cloning vector to create alias GTL+SYN(SEQ ID NO:79) (Sy1773:48). Binary Vector: An AscI/BamHI fragment from vector 15468 was ligated into the AscI/BamHI site of binary vector 12678 to create alias "12678 RsrII" (SY1533:189). This clone was then digested with RsrII and CIP treated. Cloning vector "GTL+SYN(SEQ ID NO:79)" was digested with SanDI/RsrII and ligated into the RsrII site to create B-prGTL:(SEQ ID NO:79):t35S:PMI (SY1773:56). Positive clones were identified by PCR and confirmed by DNA sequencing.

The exemplary vector designated "15741", is a binary vector for maize transformation harboring seed specific promoter prGTL-03 driving the apoplast targeted synthetic maize optimized version of the exemplary glucoamylase SEQ ID NO:25, the optimized version is the exemplary SEQ ID NO:82 or cGAmy(SEQ ID NO:82)Apo-01. This binary also contains a Ubi-PMI-Nos cassette for selection.

Cloning Vector Construct alias15460ZeinAmyVN was digested with SacI and RsrII to remove iPEPC9-01 and t35s-08 Likewise, construct 15460 was digested with SacI and RsrII to remove tNOS-03-01. Terminator t35s-08/iPEPC9-01 was ligated into 15460 using these sites (SY1709:6). The ligation reaction was transformed into DH5-alpha cells; transformants were screened with colony PCR. Four positive clones were sequenced, and from these sequences both cloning junctions and restriction enzyme sites were determined to be correct (SY1709:15-16). To insert promoter prGTL-03, 15460 containing t35s08/iPEPC9-01 was digested with BamHI and HindIII and gel purified (SY1709:14). Construct 11267 containing prGTL-03 was also digested with BamHI and HindIII and the promoter was gel purified (SY1710:3-4). It was then ligated into the 15460 backbone using these sites and transformed into competent DH5-alpha cells. Ten transformants were screened using HindIII and BamHI to determine if prGTL-03 was present in vector; all ten had correct banding pattern (SY1709:25). Two clones were sequenced to confirm cloning junctions and restriction enzyme sites, and both were correct without any sequence differences (SY1709:34-35). Glycerol stocks were prepared from clone #1 and stored at −80 degrees Celsius. Cloning vector was digested with BamHI/SacI and CIP treated. The synthetic maize codon optimized version of glucoamylase SEQ ID NO:25, known as SEQ ID NO:82 (also known as cAmy(SEQ ID NO:82 or SYN(SEQ ID NO:82) was digested with BamHI and SacI and ligated into the BamHI/SacI site of prGTL-03 cloning vector to create alias GTL+SYN(SEQ ID NO:82) (SY1773:48). Binary Vector: An AscI/BamHI fragment from vector 15468 was ligated into the AscI/BamHI site of binary vector 12678 to create alias "12678 RsrII" (SY1533:189). This clone was then digested with RsrII and CIP treated. Cloning vector "GTL+SYN(SEQ ID NO:82)" was digested with SanDI/RsrII and ligated into the RsrII site to create B-prGTL:(SEQ ID NO:82):t35S:PMI (SY1773:66). Positive clones were identified by PCR and confirmed by DNA sequencing.

The exemplary vector designated "15742", is a binary vector harboring (comprising) the seed specific promoter prGTL-03 driving the apoplast targeted synthetic maize optimized version of the exemplary glucoamylase SEQ ID NO:47, the optimized version is the exemplary SEQ ID NO:81. This binary also contains a Ubi:PMI:NOS cassette for selection.

Cloning Vector: Construct alias15460ZeinAmyVN was digested with SacI and RsrII to remove iPEPC9-01 and t35s-08. Likewise, construct 15460 was digested with SacI and RsrII to remove tNOS-03-01. Terminator t35s-08/iPEPC9-01 was ligated into 15460 using these sites (SY1709:6). The ligation reaction was transformed into DH5-alpha cells; transformants were screened with colony PCR. Four positive clones were sequenced, and from these sequences both cloning junctions and restriction enzyme sites were determined to be correct (SY1709:15-16). To insert promoter prGTL-03, 15460 containing t35s08/iPEPC9-01 was digested with BamHI and HindIII and gel purified (SY1709:14). Construct 11267 containing prGTL-03 was also digested with BamHI and HindIII and the promoter was gel purified (SY1710:3-4). It was then ligated into the 15460 backbone using these sites and transformed into competent DH5-alpha cells. Ten transformants were screened using HindIII and BamHI to determine if prGTL-03 was present in vector; all ten had correct banding pattern (SY1709:25). Two clones were sequenced to confirm cloning junctions and restriction enzyme sites, and both were correct without any sequence differences (SY1709:34-35). Glycerol stocks were prepared from clone #1 and stored at −80 degrees Celsius. Cloning vector was digested with BamHI/SacI and CIP treated. The synthetic maize codon optimized version of glucoamylase SEQ ID NO:47, known as SEQ ID NO:81 (also known as cAmy(SEQ ID NO:81) was digested with BamHI and SacI and ligated into the BamHI/SacI site of prGTL-03 cloning vector to create alias GTL+SYN(SEQ ID NO:81)) (SY1773:48). Binary Vector An AscI/BamHI fragment from vector 15468 was ligated into the AscI/BamHI site of binary vector 12678 to create alias "12678 RsrII" (SY1533:189). This clone was then digested with RsrII and CIP treated. Cloning vector "GTL+SYN(SEQ ID NO:81)" was digested with SanDI/RsrII and ligated into the RsrII site to create B-prGTL:(SEQ ID NO:81):t35S:PMI (SY1773:56). Positive clones were identified by PCR and confirmed by DNA sequencing (SY1773:58).

The exemplary vector designated "15743", is a binary vector harboring (comprising) the seed specific promoter prGTL-03 driving the apoplast targeted synthetic maize optimized version of the exemplary alpha-amylase SEQ ID NO:3, the optimized version is SEQ ID NO:80. This binary also contains a Ubi:PMI:NOS cassette for selection.

Cloning Vector: Construct alias15460ZeinAmyVN was digested with SacI and RsrII to remove iPEPC9-01 and t35s-08. Likewise, construct 15460 was digested with SacI and RsrII to remove tNOS-03-01. Terminator t35s-08/iPEPC9-01 was ligated into 15460 using these sites (SY1709:6). The ligation reaction was transformed into DH5-alpha cells; transformants were screened with colony PCR. Four positive clones were sequenced, and from these sequences both cloning junctions and restriction enzyme sites were determined to be correct (SY1709:15-16). To insert promoter prGTL-03, 15460 containing t35s08/iPEPC9-01 was digested with BamHI and HindIII and gel purified (SY1709:14). Construct 11267 containing prGTL-03 was also digested with BamHI and HindIII and the promoter was gel purified (SY1710:3-4). It was then ligated into the 15460 backbone using these sites and transformed into competent DH5-alpha cells. Ten transformants were screened using HindIII and BamHI to determine if prGTL-03 was present in vector; all ten had correct banding pattern (SY1709:25). Two clones were sequenced to confirm cloning junctions and restriction enzyme sites, and both were correct without any sequence differences (SY1709:34-35). Glycerol stocks were prepared from clone #1 and stored at −80 degrees Celsius. Cloning vector was digested with BamHI/SacI and CIP treated. The synthetic maize codon optimized version of alpha-amylase SEQ ID NO:3, known as SEQ ID NO:80 (also known as cAmy(SEQ ID NO:80) was digested with BamHI and SacI and ligated into the BamHI/SacI site of prGTL-03 cloning vector to create alias GTL+SYN(SEQ ID NO:80) (SY1773:48). Binary Vector: An AscI/BamHI fragment from vector 15468 was ligated into the AscI/BamHI site of binary vector 12678 to create alias "12678 RsrII" (SY1533:189). This clone was then digested with RsrII and CIP treated. Cloning vector "GTL+SYN(SEQ ID NO:80)" was digested with SanDI/RsrII and ligated into the RsrII site to create B-prGTL:(SEQ ID NO:80):t35S:PMI (SY1773:56). Positive clones were identified by PCR and confirmed by DNA sequencing.

The exemplary vector designated "15862", is a binary vector for maize transformation harboring (comprising) the seed specific promoter prGTL-03 driving the synthetic maize optimized version of the exemplary glucoamylase SEQ ID NO:47, the optimized version is the exemplary SEQ ID NO:81 or cGAmy(SEQ ID NO:81)ER-01 that is targeted to the ER by the KDEL ER-retention signal. This binary also contains a Ubi-PMI-Nos cassette for selection.

The maize codon optimized version of SEQ ID NO:47, known as SYN(SEQ ID NO:81) (cAMY(SEQ ID NO:81)-03) was PCR replicated and TOPO cloned with primers such that an ER-retention signal KDEL was added to the 3-prime end (SY1773:53). The presence of the KDEL was confirmed by DNA sequencing (SY1773:54 & 60). DNA sequence data confirmed no discrepancies (SY1773:63). Clone #1 was digested with BamHI/BglII, purified by agarose gel and ligated into a cloning vector harboring the prGTL-03 promoter and t35S-08 to create alias "GTL+SYN(SEQ ID NO:81) kdel v2" (SY1773:66). A gene cassette prGTL-03:cAmy(SEQ ID NO:81)kdel:t35s-08 was ligated as a SanDI/RsrII fragment into the RsrII site of a modified version of binary vector 12678 to create B-prGTL-(SEQ ID NO:81) KDEL:PMI (SY1773:83). Integrity of the binary vector was confirmed by PCR and DNA sequencing (SY1773:88).

The exemplary vector designated "15880", is a binary vector containing (comprising) the maize codon-optimized version of the exemplary alpha amylase SEQ ID NO:51, the codon-optimized version is the exemplary SEQ ID NO:79, was expressed using the rice glutelin promoter (prGTL-03). The alpha amylase also contains a Gamma Zein signal sequence and KDEL sequence for ER retention. This vector contains an Ubi-PMI-Nos cassette for mannose selection.

The maize codon optimized alpha amylase SEQ ID NO:51, known as SEQ ID NO:79 or cAmy(SEQ ID NO:79) was PCR replicated with primers such that an ER-retention signal (KDEL) was added to the 3-prime end (SY1777:180). The PCR product was then gel purified, TOPO cloned, and transformed into TOP10 competent cells. Presence of the KDEL without any discrepancies was confirmed via sequencing (SY1773:73). TOPO clones were digested with BamHI and BglII to obtain the modified amylase gene which was then gel purified. The gel purified product was ligated into 15460 containing prGTL-03 (rice glutelin promoter) and t35s-08 to create alias "GTL+syn(SEQ ID NO:79) KDEL v2" (SY1773:80; SY1777:180). Following transformation into DH5a competent cells, clones were screened for insert orientation via PCR. In addition, the entire CDS as well as cloning junctions were sequenced prior to construction of binary vector (SY1777:189, 191). The gene cassette prGTL:cAmy(SEQ ID NO:79):t35s08 was digested with SanDI/RsrII and ligated into a modified version of construct 12678 at the RsrII site (SY1818:12). This construct was modified by ligating an AscI/BamHI fragment from vector 15468 into the AscI/BamHI site of binary vector 12678 to create alias "12678 RsrII" (SY1533:189). The ligation reaction was transformed into TOP10 competent cells, and transformants were subsequently screened via colony PCR. Two of the screened transformants were positive for the gene cassette and were digested with BamHI to confirm its presence. Following the digest confirmation, the entire cassette from clone #5 was sequenced (SY1818:34). Data confirmed that the entire cassette, including all junctions, is present without any sequence discrepancies (SY1818:37-38).

The exemplary vector designated "15884", is a binary vector containing (comprising) the maize codon-optimized version of the exemplary SEQ ID NO:25, the maize codon-optimized version is the exemplary SEQ ID NO:82, was expressed using the rice glutelin promoter (prGTL-03). The glucoamylase also contains a Gamma Zein signal sequence and ER retention signal (KDEL). This vector contains an Ubi-PMI-Nos cassette for mannose selection.

The maize codon optimized version glucoamylase SEQ ID NO:25, known as SEQ ID NO:82 or cAmy(SEQ ID NO:82) was PCR replicated with primers such that an ER-retention signal (KDEL) was added to the 3-prime end (SY1777:184). The PCR product was then gel purified, TOPO cloned, and transformed into TOP10 competent cells. Presence of the KDEL without any discrepancies was confirmed via sequencing (SY1777:190). TOPO clones were digested with BamHI and BglII to obtain the modified amylase gene which was then gel purified. The gel purified product was ligated into 15460 containing prGTL-03 (rice glutelin promoter) and t35s-08 to create alias "GTL+syn(SEQ ID NO:82) KDEL v2" (SY1818; 1-3). Following transformation into Top10 competent cells, clones were screened for insert orientation via PCR. In addition, the entire CDS as well as cloning junctions were sequenced prior to construction of binary vector (SY1818: 29-30). It was determined from sequencing that there is a single base pair change within the coding sequence of cAmy (SEQ ID NO:82) at base pair 156. It is a T to C change that does not change the amino acid sequence of the protein (SY1818: 39-40). The gene cassette prGTL: syn(SEQ ID NO:82) KDEL: t35s08 was digested with SanDI/RsrII and ligated into a modified version of construct 12678 at the RsrII site (SY1818:31). This construct was modified by ligating an AscI/BamHI fragment from vector 15468 into the AscI/BamHI site of binary vector 12678 to create alias "12678 RsrII" (SY1533:189). The ligation reaction was transformed into TOP10 competent cells, and transformants were subsequently screened using restriction enzyme digests. Two of the transformants were digested with various combinations of restriction enzymes including NotI, SacI, EcoRV, and PstI to confirm the presence of the gene cassette (SY1818:45). Following the digest confirmation, the entire cassette from clone #7 was sequenced (SY1818:46-47). Data confirmed that the entire cassette, including all junctions, is present and only contains the single base pair change described earlier (SY1818:50).

The exemplary vector designated "15890", is a binary vector for maize transformation containing the maize codon-optimized version of the exemplary alpha-amylase SEQ ID NO:3, the maize codon-optimized version is the exemplary SEQ ID NO:80 or cAmy(SEQ ID NO:80) was expressed using the rice glutelin promoter (prGTL-03). The glucoamylase also contains a Gamma Zein signal sequence and ER retention signal (KDEL). This vector contains an Ubi-PMI-Nos cassette for mannose selection.

The maize codon optimized version of the exemplary alpha-amylase SEQ ID NO:3, known as cAmy(SEQ ID NO:80) was PCR replicated with primers such that an ER-retention signal (KDEL) was added to the 3-prime end (SY1777:184). The PCR product was then gel purified, TOPO cloned, and transformed into TOP10 competent cells. Presence of the KDEL without any discrepancies was confirmed via sequencing (SY1777:190). TOPO clones were digested with BamHI and BglII to obtain the modified amylase gene which was then gel purified. The gel purified product was ligated into 15460 containing prGTL-03 (rice glutelin promoter) and t35s-08 to create alias "GTL+syn(SEQ ID NO:80) KDEL v2" (SY1818; 1-3). Following transformation into TOP10 competent cells, clones were screened for insert orientation via PCR. In addition, the entire CDS as well as cloning junctions were sequenced prior to construction of binary vector (SY1818:51). The gene cassette prGTL: syn (SEQ ID NO:80) KDEL: t35s08 was digested with SanDI/RsrII and ligated into a modified version of construct 12678 at the RsrII site (SY1818:52). This construct was modified by ligating an AscI/BamHI fragment from vector 15468 into the AscI/BamHI site of binary vector 12678 to create alias "12678 RsrII" (SY1533:189). The ligation reaction was transformed into TOP10 competent cells, and transformants were subsequently screened using PCR and restriction enzyme digests. Two of the transformants that had positive PCR results were digested with various combinations of restriction enzymes including NcoI, KpnI, EcoRV, XbaI, and BglII to confirm the presence of the gene cassette (SY1818: 65-66). Following the digest confirmation, the entire cassette from clone #2 was sequenced (SY1818:67). Data confirmed that the entire cassette, including all junctions, is present without any sequence differences (SY1818:69-70).

The exemplary vector designated "15889", is a binary vector for maize transformation containing a molecular stack of the codon optimized version of the exemplary glucoamylase SEQ ID NO:25, the codon optimized version is the exemplary SEQ ID NO:82 or cGAmy(SEQ ID NO:82) was expressed by two different promoters. In the first cassette, cAmy(SEQ ID NO:82) is driven by the rice glutelin promoter and has a Gamma Zein signal sequence and KDEL signal for retention in the ER. In the second cassette, the gluco-amylase is driven by the alpha trypsin inhibitor promoter and is targeted to the apoplast with the Gamma Zein signal sequence. This construct also contains a Ubi-PMI-Nos cassette for mannose selection.

The rice promoter, prATI-01 was mutagenized through site-directed mutagenesis to remove an internal RsrII site, and was submitted as a new component in construct #15882. Following sequence confirmation of the removal of this site, the cloning vector "15460+prATI+t35s08" was digested with BamHI/SacI, CIP treated, and gel extracted (SY1777:162). The synthetic, codon optimized gluco-amylase Syn(SEQ ID NO:82) (BamHI/SacI) was ligated into the digested backbone and the resulting construct is known as "15460prATIm.syn (SEQ ID NO:82)" (SY1777:170). Transformants were screened for the presence of the gene, using both colony PCR and a diagnostic NcoI/BglII digest. Three positive clones were sequenced; cloning junctions were confirmed for the three clones (SY1777:177-179). Following sequence confirmation, "15460prATIm.syn(SEQ ID NO:82)" was digested with SanDI/RsrII and the ATI: syn(SEQ ID NO:82):t35s08 cassette was gel purified (SY1773:52). Binary vector #15884 was linearized with RsrII, CIP treated, and gel extracted. Following purification, the ATI: syn(SEQ ID NO:82):t35s08 cassette was ligated into the binary backbone and transformed into TOP10 competent cells (SY1818:53). Ten transformants were selected for screening, via PCR, one of which was confirmed to have the cassette containing the ATI promoter (SY1818:56). The positive clone was then screened with diagnostic restriction enzyme digests using the following enzymes: EcoRI, BglII, NcoI, and HindIII (SY1818:60, 66). Clone #9 was determined to be correct by analyzing the banding pattern from the various digests. In addition, the cloning junctions of clone #9 were sequenced and also confirmed to be correct (SY1818:65).

The exemplary vector designated "15934", is a binary vector for plant transformation containing a molecular stack of the codon optimized version of the exemplary glucoamylase SEQ ID NO:47, the codon optimized version is the exemplary SEQ ID NO:81 or cGAmy(SEQ ID NO:81) was expressed by two different promoters. In the first cassette, GAmy(SEQ ID NO:81) is driven by the rice glutelin promoter and has a KDEL signal for retention in the ER (component is cGAmy (SEQ ID NO:81)ER-01). In the second cassette, the GAmy (SEQ ID NO:81) is driven by the alpha trypsin inhibitor promoter and is targeted to the apoplast (component is cGAmy(SEQ ID NO:81)Apo-01). This construct also contains an Ubi-PMI-Nos cassette for mannose selection. NOTE: IT was determined by restriction digest and sequencing that one of the left border insertions was missing. The project elected to proceed with the vector.

The cloning vector "15460+prATI+t35s08" was digested with BamHI/SacI, CIP treated, and gel extracted (SY1777: 162). The synthetic, codon optimized gluco-amylase cGAmy (SEQ ID NO:81)Apo-01 (BamHI/SacI) was ligated into the digested backbone and the resulting construct is known as "15460prATIm.syn(SEQ ID NO:81)" (SY1777:170). Transformants were screened for the presence of the gene, using both colony PCR and a diagnostic NcoI/BglII digest. Three positive clones were sequenced; cloning junctions were confirmed for the three clones (SY1777:177-179). Following sequence confirmation, "15460prATIm.syn(SEQ ID NO:81)" was digested with SanDI/RsrII and the ATI: cGAmy (SEQ ID NO:81)Apo-01:t35s08 cassette was gel purified (SY1773:72). Binary vector "B-prGTL: (SEQ ID NO:81) KDEL: PMI" was constructed and labeled as construct #15862 (SY17773:92). It was linearized with RsrII, CIP treated, and gel extracted. Following purification, the ATI: cGAmy(SEQ ID NO:81)Apo-01:t35s08 cassette was ligated into the binary backbone and transformed into TOP10 competent cells (SY1818:22-23). Transformants were initially screened with colony PCR using primers which only annealed in the ATI promoter. Ten transformants were selected and confirmed to have the cassette containing the ATI promoter. Clone #8 was selected for restriction analyses to further confirm the presence of the cassette within the binary vector. Two enzymes which specifically cut in the ATI promoter as well as the backbone were selected to rule out the possibility of a double cassette. When clone #8 was digested with AvrII and NcoI, it was determined that there was only one copy of each cassette present (SY1818: 93-94).

Enzymatic Activity Analysis

Single seed analysis or pooled seed analysis was used to measure alpha-amylase or glucoamylase activity in transgenic seeds. For single seed analysis, 12 seeds from each event were randomly selected and ground individually. For pooled seed analysis, twenty seeds from selected events were randomly selected, pooled, and ground. The flours were then assayed using the Megazyme CERALPHA HR™ assay for alpha-amylases or Megazyme's glucoamylase assay for glucoamylases. The assay's standard operating procedures (SOPs) are described above, including the "enzymatic activity analysis", the alpha-amylase extraction from corn flour and activity assay, the glucoamylase extraction from corn flour and activity assay, and the raw starch fermentation protocol.

Results

Taqman Assay and Enzymatic Activity Assay

Copy numbers of the transgenes were determined by primary and secondary Taqman assays. Primers specific for the selectable marker gene used in all the maize transformation vectors described above, pmi, were used in the primary Taqman assays. Primers specific for pmi gene, the bacterial selectable marker gene, spec, and genes encoding the alpha-amylases or glucoamylases were used in secondary Taqman assays.

Expression of alpha-amylases or glucoamylases in mature dried-down T1 transgenic seeds of selected constructs were also analyzed by enzymatic activity assays. Results of gene copy numbers in selected events generated from construct 15840 were summarized in Table 3.2. Expression of the exemplary codon-optimized alpha-amylase SEQ ID NO:79 in these events were measured by analysis of enzymatic activity in 12 randomly selected seeds individually. The average activity of the 12 seeds for each event is also shown in Table 3.2, below.

Similarly, Table 3.3 shows gene copy numbers of selected events generated from construct 15841. Expression of the exemplary codon-optimized glucoamylase SEQ ID NO:82 in these events were also measured by analysis of enzymatic activity in 12 randomly selected seeds individually and average activity of the 12 seeds for each event is summarized in Table 3.3, below.

Twenty (20) seeds from each selected events generated from constructs 15842 and 15843, on the other hand, were pooled for enzymatic assays to determine expression levels of the codon-optimized glucoamylase SEQ ID NO:81 and the exemplary codon-optimized alpha-amylase SEQ ID NO:80 in these events, respectively. Results were summarized in Tables 3.4 and 3.5, respectively, below. Transgene copy numbers are also shown.

TABLE 3.2

Transgene copy numbers and alpha-amylase activity in selected events generated from construct 15840

| Plant number | Average Activity of 12 Seeds (U/g) |
|---|---|
| 1 | 377.3 |
| 2 | 291.9 |
| 3 | 95.1 |
| 4 | 119.4 |
| 5 | 155.4 |
| 6 | 129.4 |
| 7 | 125.3 |
| 8 | 539.4 |
| 9 | 1362.4 |
| 10 | 195.1 |
| 11 | 88.4 |
| 12 | 458.2 |
| 13 | 722.9 |
| 14 | 151.7 |
| 15 | 164.8 |

TABLE 3.3

Transgene copy numbers and glucoamylase activity in selected events generated from construct 15841

| Plant Number | Average Activity of 12 Seeds (U/g) |
|---|---|
| 1 | 2.5 |
| 2 | 3.5 |
| 3 | 2.6 |
| 4 | 2.8 |
| 5 | 2.4 |
| 6 | 3.0 |
| 7 | 2.6 |
| 8 | 2.5 |
| 9 | 2.6 |
| 10 | 2.8 |
| 11 | 3.0 |
| 12 | 3.0 |
| 13 | 2.9 |
| 14 | 3.4 |
| 15 | 2.3 |
| 16 | 2.5 |
| 17 | 2.6 |
| 18 | 3.3 |
| 19 | 2.4 |
| 20 | 2.9 |
| 21 | 3.5 |
| 22 | 2.3 |
| 23 | 2.5 |
| 24 | 2.3 |

TABLE 3.4

Transgene copy numbers and glucoamylase activity in selected events generated from construct 15842

| Plant Number | Pooled Seed Activity (U/g) |
|---|---|
| 1 | 1.5 |
| 2 | 1.3 |
| 3 | 1.3 |
| 4 | 1.2 |
| 5 | 1.3 |
| 6 | 1.6 |
| 7 | 1.4 |
| 8 | 1.4 |
| 9 | 1.3 |
| 10 | 1.2 |
| 11 | 1.4 |
| 12 | 1.6 |
| 13 | 1.7 |
| 14 | 1.2 |
| 15 | 1.3 |
| 16 | 1.6 |
| 17 | 1.4 |
| 18 | 1.6 |
| 19 | 1.6 |
| 20 | 1.6 |

TABLE 3.5

Transgene copy numbers and alpha-amylase activity in selected events generated from construct 15843

| Plant Number | Pooled Seed Activity (U/g) |
|---|---|
| 1 | 116.14 |
| 2 | 107.07 |
| 3 | 105.02 |
| 4 | 277.65 |
| 5 | 240.90 |
| 6 | 165.25 |
| 7 | 425.17 |
| 8 | 151.02 |
| 9 | 139.74 |
| 10 | 245.27 |
| 11 | 197.68 |
| 12 | 179.77 |
| 13 | 368.59 |
| 14 | 350.91 |
| 15 | 225.03 |
| 16 | 233.18 |
| 17 | 366.24 |
| 18 | 220.36 |

TABLE 3.6

Ethanol yield after 72 hours of raw starch fermentation using "lead" exemplary enzymes expressed in maize using maize codon optimized synthetic genes

| Construct (alpha-amylase) | Construct (Glucoamylase) | Inclusion Rate (alpha-amylase) (% w/w) | Inclusion Rate (Glucoamylase) (% w/w) | Inclusion Rate (Commidity) (% w/w) | Ethanol Yield (% v/v) |
|---|---|---|---|---|---|
| 15840 (SEQ ID NO: 79) | 15841 (SEQ ID NO: 82) | 20 | 50 | 30 | 16.77 |
| 15840 (SEQ ID NO: 79) | 15842 (SEQ ID NO: 81) | 20 | 50 | 30 | 17.08 |
| 15843 (SEQ ID NO: 80) | 15841 (SEQ ID NO: 82) | 20 | 50 | 30 | 7.30 |
| 15843 (SEQ ID NO: 80) | 15842 (SEQ ID NO: 81) | 20 | 50 | 30 | 10.60 |
| N/A | N/A | 0 | 0 | 100 | 2.25 |

Raw Starch Fermentation Using Maize Expressed Enzymes

Seeds from events shown above expressing alpha-amylases or glucoamylases were pooled and ground to make composite samples for raw starch fermentations. In all experiments, corn flour containing alpha-amylases was used at the inclusion rate of 20% (w/w) and corn flour containing glucoamylases at the inclusion rate of 50% (w/w). Yellow dent II commodity corn flour made up the rest of the 30% (w/w) of the corn flour. Raw starch fermentations were carried out by following the standard SOP described above (Section I). The ability of these maize expressed alpha-amylase and glucoamylase combinations using maize codon optimized synthetic genes to produce ethanol in raw starch fermentation is summarized in Table 3.6, below.

Example 29

Pichia pastoris Expression Constructs

This example described the expression of enzymes in yeast using, e.g., exemplary Pichia expression systems.

For construction of expression constructs in pPICZalpha and pAO815 vectors (both from Invitrogen, Carlsbad, Calif.), Xi-cloning technology was used. pPICZalpha was digested with EcoRI, then treated with Xi-cloning cocktails (according to manufacture protocol by Genlantis, a division of Gene Therapy Systems, Inc., San Diego, Calif.). The genes were amplified by PCR reactions with end matching to the vector sequences. The PCR products were mixed with the vectors and transformed into E. coli host TOP10 (Invitrogen) and selected under zeocin 25 (pPICZalpha) or carbenicillin 100 (pAO815). The final constructs were verified by sequencing. For transformation into Pichia hosts, the verified plasmid DNA was digested to make linear DNA and transform in to Pichia hosts. The transformants were selected under Zeocin (pPICZalpha) or histine deficient plates.

All enzymes were obtained by expression in Pichia pastoris, except for SEQ ID NO:78 (encoded by SEQ ID NO:77), which was expressed in Pseudomonas fluorescens (see JBC, 2002, 277(29):26501-26507).

I. Characterization of Glucoamylases and Amylases.
Methods:
6. Determination of Protein Concentration Lyophilized supernatants of P. pastoris cultures expressing glucoamylases and α-amylases were suspended in water at a concentration of ~10 mg of powder/ml. After protein content determination by the Bradford protocol, 5 µg of protein sample and standardized BSA solution were run on a 4-20% Tris-Glycine gradient gel. The gel was scanned on the BioRad GS800 gel scanner following Coomassie blue staining. The Bio-Rad Quantity One software was used for the quantification of the BSA and glucoamylase (or α-amylases) bands, and the actual enzyme concentration was then calculated. Protein concentration was adjusted accordingly and confirmed by additional SDS PAGE.

7. Determination of Initial Reaction Rates.

Unless mentioned otherwise, assays were performed in triplicate at 37° C. and pH 5.0 in buffer (50 mM $NaCH_3CO_2$, 10 mM $CaCl_2$; 10 mM $NaN_3$ and 0.01% Triton X-100) containing 1% raw corn starch, or 0.5% dextrin or 1% "soluble corn starch" (see note below on the "soluble starch" preparation). Assays were performed at 0.5 ml scale for glucoamylase and 0.25 ml scale for α-amylase in an Eppendorf tabletop incubator with constant shaking (800 rpm).

For glucoamylases, reactions were started by adding the enzyme (final concentration 0.25 µg/ml) to the reaction mix. At 0, 2.5, 5, 7.5, 10, 15, 20 and 30 min, 50 µA aliquots of the reactions were withdrawn and quenched by addition to 100 µl of 1M Tris buffer, pH 7.5.

For α-amylases, reactions were started by adding the enzyme (final concentration 0.4 µg total protein/ml for SEQ ID NO:56, SEQ ID NO:2 and SEQ ID NO:52; 2 µg/ml for SEQ ID NO:62; 4 µg/ml for SEQ ID NO:70 and SEQ ID NO:66) to the reaction mix, and 10 µA aliquots of reactions were withdrawn and quenched in BCA reagent at 2, 5, 10, 15, 20, 25, 30, and 40 min.

For determination of temperature profiles, assays were performed at 30, 34, 37 and 40° C.

The effect of pH on glucoamylase and amylase activities was evaluated at pH 3.5, 4, 5, 6 and 7, using the broad pH range Britton—Robinson buffer (50 mM $CH_3COOH$; $H_3PO_4$; $H_3BO_3$). Parallel reactions at pH 4, 5 and 6 were also performed in the presence of 50 mM acetate buffer to ensure that the buffer used did not influence the results. For the determination of pH profile of two calcium-dependent α-amylases (SEQ ID NO:56 and SEQ ID NO:62), malic acid/acetate/MES buffers were used instead of Britton-Robinson.

Preparation of "soluble corn starch" for reaction with α-amylases. Dextrin (Sigma D2006) could not be used as a substrate in the BCA α-amylase reactions due to the high reducing ends background. Therefore a heated corn starch was employed as a substrate. Specifically, 2% corn starch was dissolved in deionized water and heated with mixing in a boiling water bath for 30-40 minutes, until the starch had dissolved and the solution appeared milky, but translucent. The solution of heated starch was used for 2 days, after which time some signs of retrogradation were observed (appearance of starch clumps), and the solution was discarded.

8. Glucose Oxidase/Peroxidase (go) Assay for the Quantification of Glucose Released During Starch Hydrolysis A coupled glucose oxidase/peroxidase (GO) assay was used to determine the amount of glucose released by glucoamylase during starch hydrolysis. GO reactions were started by adding 10 μA of the quenched starch hydrolysis reaction to 90 μA of PBS containing glucose oxidase (0.1 U/ml), peroxidase (0.25 U/ml) and 0.05 mM Amplex Red, in black Nunc 96-well plates. Plates were kept at room temperature in the dark for 30 min prior to reading on a fluorescent plate reader with Ex/Em 545/590 nm. A standard curve with glucose concentrations of 0 to 100 μM was used to assess the amount of glucose produced in the hydrolysis reactions. Initial rates of starch hydrolysis (nmols of glucose released from 1% granular starch/min/μg glucoamylase) were determined by plotting the amount of glucose released over time, and calculating the slope of the best linear fit through the data points.

9. BCA Assay for Determining the Increase in Concentration of Reducing Ends During Starch Hydrolysis.

A 10 μl aliquot of amylase starch hydrolysis reaction was quenched into 100 μl of BCA reagent (consisting of 64 mg/mL sodium carbonate monohydrate, 24 mg/mL sodium bicarbonate, 1.95 mg/mL BCA, 1.24 mg/mL cupric sulfate pentahydrate, 1.26 mg/mL L-serine). Color development occurred during incubation of the quenched reaction at 80° C. for 35 minutes and was followed by absorbance determination at 560 nm Initial rates were calculated over a 40 min reaction time. A standard curve using maltose (0-54 μM) was constructed to correlate $A_{560nm}$ with the concentration of generated reducing sugars (nmoles). Specific activity was expressed as nmoles/min/μg enzyme.

10. Bond-type Specificity of Glucoamylases with Maltose and Isomaltose as Substrates.

Reactions were started by adding the enzyme (final concentration 5 μg/ml for maltose, and 30 μg/ml for isomaltose) to the reaction mix. At 2, 5, 10, 15, 20, 25, 30 and 40 min, 5 μA aliquots of the reactions were withdrawn and quenched by addition to 10 μl of 1M Tris buffer, pH 7.5. Nine substrate concentrations were used in the studies, ranging from 0 to 12 mM for maltose and 2.5 to 120 mM for isomaltose. The reactions were performed in triplicate at 37° C. and pH 5.0 in buffer (50 mM $NaCH_3CO_2$, 10 mM $CaCl_2$), at 50 ul scale in an Eppendorf tabletop incubator with constant shaking (800 rpm). Glucose production was measured at the end of the reaction using the glucose oxidase/peroxidase (GO) assay.

Results

2. Characterization of Glucoamylases 1.1 Initial Reaction Rates:

Initial rates for granular and soluble starch hydrolysis are presented in Table 1.

As can be seen from Table 1, exemplary glucoamylases of this invention displayed up to 3× better activity (SEQ ID NO:48) against granular starch, with similar or slightly better activity on soluble starch when compared to the benchmark *A. niger* enzyme. SEQ ID NO:48 was also expressed in *E. coli* (see above section on Picha expression constructs)—this *E. coli* expressed enzyme is labeled SEQ ID NO:48 (Ec) in the table below. SEQ ID NO:48(Ec) did not display any activity against granular starch under the conditions tested (probably due to the lack of a Starch Binding Domain).

TABLE 1

Comparison of initial rates of granular corn starch and soluble starch (dextrin) hydrolysis by "lead" exemplary amylases and/or glucoamylases and a benchmark enzyme *A. niger* glucoamylase (Sigma A7095) at 37° C., pH 5.0:

| Enzyme | Initial rate* ± SD Granular starch | Initial rate* ± SD Soluble starch |
|---|---|---|
| SEQ ID NO: 48 | 35.6 ± 3.8 | 60.7 ± 5.1 |
| SEQ ID NO: 26 | 28.8 ± 3.4 | 51.8 ± 7.4 |
| SEQ ID NO: 74 | 25.1 ± 2.5 | 84.3 ± 3.5 |
| SEQ ID NO: 18 | 24.3 ± 4.3 | 58.3 ± 3.0 |
| SEQ ID NO: 28 | 17.8 ± 4.3 | 33.8 ± 4.0 |
| SEQ ID NO: 14 | 6.6 ± 1.2 | 53.9 ± 4.1 |
| SEQ ID NO: 48(Ec) | 0 | 59.3 ± 8.5 |
| *A. niger* glucoamylase (Sigma A7095) | 11.3 ± 2.7 | 43.3 ± 7.4 |

*Initial rates are expressed as nmols of glucose/min/μg of glucoamylase protein released from 1% granular starch or from 0.5% dextrin. Each number is the average value from 6-10 data points.

1.2 Temperature profile: The effect of temperature (30° C.-40° C.) on starch hydrolysis by the characterized glucoamylases is presented in FIGS. 1A and 1B. Activities of glucoamylases increased with temperature; they were most active at 40° C. but retained ~50% of peak activity at 30° C.

FIG. 28A: Effect of Temperature on the Activity of exemplary amylases and/or glucoamylases and the glucoamylase *A. niger* glucoamylase with Granular Starch as substrate (Benchmark *A. niger* glucoamylase (Sigma A7095). Glucose release was measured at the indicated temperature at pH 5.0. The exemplary SEQ ID NO:20 is not included in the plot because it did not display any activity against granular starch under these particular conditions as tested.

FIG. 28B: Effect of Temperature on the Activity of the exemplary glucoamylase SEQ ID NO:20 and the glucoamylase *A. niger* glucoamylase (Sigma A7095) with Soluble Starch (Dextrin) as a substrate. Glucose release was measured at the indicated temperature at pH 5.0.

1.3 pH profile: The influence of pH on starch hydrolysis was tested with both granular and soluble starch and the results are presented in FIG. 2A and FIG. 2B, respectively. All glucoamylases hydrolyzed both substrates best at lower pH with SEQ ID NO:26 being the most acidic in character.

FIG. 29A: Effect of pH on the Activity of Glucoamylases with Granular Starch as substrate. Glucose release was measured at the indicated pH at 37° C. Initial rates were calculated over 20 min and converted to a percentage of the maximum rate. The exemplary SEQ ID NO:20 is not included in the plot because it did not display any activity against granular starch, under the particular conditions tested here.

FIG. 29B: Effect of pH on the Activity of Glucoamylases with Soluble Starch as substrate. Glucose released was measured at the indicated pH at 37° C. Initial rates were calculated over 20 min and converted to a percentage of the maximum rate.

1.4 Bond-type cleavage specificity: The kinetic parameters for the hydrolysis of maltose (alpha-1,4-linkage) (maltose is two alpha-D-glucoses) and isomaltose (alpha-1,6-linkage) were determined for 7 selected glucoamylases and the benchmark (*A. niger* glucoamylase (Sigma A7095). The experiments were conducted with lyophilized *P. pastoris* lysates and the proteins were not purified; therefore only data independent of protein concentration are reported in this document. Table 2, below, summarizes values of $K_M$ for maltose and isomaltose and the ratio of $k_{cat}/K_M$ for maltose compared to $k_{cat}/K_M$ for isomaltose. These parameters determined for *A. niger* glucoamylase (Sigma A7095) are in good agreement with published data ($K_M$ for maltose is reported to be 1.2-2.1 mM; $K_M$ for isomaltose is reported to be 19.8-42.0 and $k_{cat}/K_M$ for maltose over $k_{cat}/K_M$ for isomaltose is reported to be between 300-600 according to Frandesen at al. 1995; Sierks and Svensson; 1996; Fagerstrom and Kalkkinen; 1995).

As can be seen from Table 2, the exemplary glucoamylase SEQ ID NO:20 was most strongly selective for maltose and had nearly 900-fold higher specificity towards alpha-1,4-linkages relative to alpha-1,6-bonds. The least selective glucoamylase was SEQ ID NO:14 with ~100-fold higher specificity towards alpha-1,4-bonds relative to alpha-1,6-bonds.

TABLE 2

Kinetic parameters for hydrolysis of Maltose and Isomaltose by 7 exemplary glucoamylases of this invention and a benchmark (*A. niger* glucoamylase (Sigma A7095)).

| Enzyme | Maltose $K_M$ (mM) | Isomaltose $K_M$ (mM) | $k_{cat}/K_M$ (maltose)/ $k_{cat}/K_M$ (isomaltose) |
|---|---|---|---|
| SEQ ID NO: 28 | 0.61 ± 0.06 | 11.94 ± 4.99 | 750 |
| SEQ ID NO: 74 | 1.87 ± 0.17 | 11.55 ± 2.92 | 481 |
| SEQ ID NO: 20 | 2.62 ± 0.19 | 53.97 ± 23.17 | 897 |
| SEQ ID NO: 14 | 2.67 ± 0.15 | 41.5 ± 5.05 | 116 |
| SEQ ID NO: 26 | 0.98 ± 0.33 | 12.18 ± 0.64 | 456 |
| SEQ ID NO: 48 | 2.26 ± 0.12 | 21.69 ± 3 | 565 |
| SEQ ID NO: 18 | 1.01 ± 0.09 | 11.74 ± 7.74 | 415 |
| *A. niger* glucoamylase (Sigma A7095) | 0.93 ± 0.1 | 18.72 ± 3.95 | 249 |

Each number is the average value from 5 different experiments.

References
1. Frandsen T P, Christensen T, Stoffer B, Lehmbeck J, Dupont C, Honzatko R B, Svensson B (1995) Biochemistry. 34:10162-9.
2. Sierks M R and Svensson B. (1996) Biochemistry; 35:1865-71.
3. Fagerstrom R and Kalkkinen N. (1995) Biotechnol Appl Biochem. 21:223-31.

Characterization of Amylases

Initial reaction rates: The initial rates of hydrolysis of granular and soluble starch are presented in Table 3. Eight exemplary alpha-amylases were compared with a benchmark alpha-amylase from *A. oryzae*. As can be seen from Table 3, below all amylases tested displayed significantly higher activity against soluble starch when compared with granular starch. However, this difference was less marked for Amylases and/or glucoamylases than for the benchmark enzyme.

TABLE 3

Comparison of initial rates of hydrolysis of granular corn starch and soluble corn starch by 8 α-amylases and a benchmark alpha-amylase from *A. oryzae* at 37° C. and pH 5:

| Exemplary Enzyme | Initial rate* ± SD Granular starch | Initial rate* ± SD Soluble starch |
|---|---|---|
| SEQ ID NO: 56 | 15.7 ± 1.67 | 1607.9 ± 518.22 |
| SEQ ID NO: 70** | 20.5 | 109.1 |
| SEQ ID NO: 62 | 3.5 ± 0.37 | 139.6 ± 55.96 |
| SEQ ID NO: 66** | 2.1 | 70.8 |
| SEQ ID NO: 2 | 7 ± 0.75 | 381.2 ± 74.15 |
| SEQ ID NO: 52 | 10.3 ± 1.75 | 248.2 ± 28.46 |
| SEQ ID NO: 78 | 0.4 ± 0.06 | 232 ± 52.63 |
| SEQ ID NO: 76** | 25.2 | 809.1 |

TABLE 3-continued

Comparison of initial rates of hydrolysis of granular corn starch and soluble corn starch by 8 α-amylases and a benchmark alpha-amylase from *A. oryzae* at 37° C. and pH 5:

| Exemplary Enzyme | Initial rate* ± SD Granular starch | Initial rate* ± SD Soluble starch |
|---|---|---|
| *A. oryzae* amylase (MegazymeE-ANAAM) | 0.4 ± 0.07 | 498.7 ± 64.78 |

*Initial rates are expressed as nmole of reducing ends released from 1% starch/min/µg of alpha-amylase protein.
**Data obtained using purified enzyme.
Each number is an average value from 5 data points.

Temperature profile: The effect of temperature on starch hydrolysis by the characterized α-amylases is presented in FIG. 30. Activities of amylases were affected by temperature to a different degree. Five of the exemplary amylases of this invention (SEQ ID NO:56, SEQ ID NO:70, SEQ ID NO:78, SEQ ID NO:76 and SEQ ID NO:66) were most active at 40° C. and retained ~30% of activity at 30° C. Activities of the exemplary SEQ ID NO:2, SEQ ID NO:52 and SEQ ID NO:62 were only marginally affected by changes in temperature over the range investigated.

FIG. 30 illustrates: the Influence of Temperature on Starch Hydrolysis by 9 α-amylases. Activity was measured at pH 5.0 during 40 min incubation at the indicated temperature, and initial rates were calculated and plotted against time. In FIG. 30:

Rates for the exemplary SEQ ID NO:56, SEQ ID NO:2 and SEQ ID NO:52 are presented on the left axis; rates for the rest of enzymes are presented on the right axis.

Initial rates are expressed as nmoles of reducing ends released from 1% granular corn starch/mining of enzyme in 250 µl reaction.

Activities of the exemplary SEQ ID NO:70, SEQ ID NO:66 and SEQ ID NO:76 are expressed in nmoles/min/µg of total protein in *Pichia pastoris* supernatant.

pH profile: The influence of pH on starch hydrolysis was tested with both granular and soluble starch substrates and the results are presented in FIG. 31A and FIG. 31B, respectively. The exemplary SEQ ID NO:52 (of fungal origin) had the lowest pH optimum (~pH 4). Another exemplary enzyme (SEQ ID NO:2) (of fungal origin) also displayed preference for acidic pH, with an apparent optimum at ~pH 4.5-5. The exemplary amylase SEQ ID NO:66 (of Archaeal origin) had an apparent optimum of ~pH 5.0, retaining ~70% of peak activity at pH 4.0. The remaining enzymes had apparent optima between pH 5.0 and 6.0, and were almost inactive at pH 4.0 and 3.5.

FIG. 31A: Effect of pH on the activities of α-amylases with Granular Starch as substrate. The increase in reducing ends was measured at the indicated pH at 37° C. Initial rates were calculated over 40 min and converted to a percentage of the maximum rate.

FIG. 31B: Effect of pH on the activities of α-amylases with Soluble Starch as substrate. The increase in reducing ends was measured at the indicated pH at 37° C. Initial rates were calculated over 40 min and converted to a percentage of the maximum rate.

A number of embodiments have been described. Nevertheless, it will be understood that various modifications may be made without departing from the spirit and scope. Accordingly, other embodiments are within the scope of the following claims.

What is claimed is:

1. An isolated, synthetic, or recombinant nucleic acid encoding a polypeptide having glucoamylase activity, selected from the group consisting of:
   (a) a nucleic acid encoding a polypeptide having glucoamylase activity comprising a nucleic acid sequence having at least 95% sequence identity to SEQ ID NO:25;
   (b) a nucleic acid encoding a polypeptide having glucoamylase activity comprising a nucleic acid sequence having at least 95% sequence identity to SEQ ID NO:25, or a fragment thereof, wherein the fragment encodes a polypeptide having glucoamylase activity;
   (c) a nucleic acid encoding a polypeptide having glucoamylase activity that hybridizes under at least high stringency conditions to the full length nucleic acid sequence of SEQ ID NO:25, wherein high stringency conditions are defined as prehybridization and hybridization at 42° C. in 5×SSPE, 0.3% SDS, 200 μg/ml sheared and denatured salmon sperm DNA, and 50% formamide and washing using 6×SSC, 0.5% SDS at 50° C.;
   (d) a nucleic acid sequence encoding a polypeptide having glucoamylase activity comprising an amino acid sequence having at least 90% sequence identity to SEQ ID NO:26;
   (e) a nucleic acid sequence encoding a polypeptide having glucoamylase activity comprising an amino acid sequence having at least 90% sequence identity to SEQ ID NO:26, or a fragment thereof, wherein the fragment has glucoamylase activity;
   (f) the nucleic acid of (a), (b), (c), (d), or (e) encoding a polypeptide having glucoamylase activity but lacking a signal sequence or a carbohydrate binding module;
   (g) the nucleic acid of (a), (b), (c), (d), (e) or (f) encoding a polypeptide having glucoamylase activity, and further comprising a heterologous sequence;
   (h) the nucleic acid sequence of (g), wherein the heterologous sequence comprises a sequence encoding a heterologous signal sequence, carbohydrate binding module, catalytic domain (CD), or a combination thereof, or the heterologous signal sequence, carbohydrate binding module, or catalytic domain (CD) is derived from another amylase enzyme, or a non-amylase enzyme; or
   (i) a nucleic acid sequence fully complementary to (a), (b), (c), (d), (e), (f), (g), or (h).

2. The isolated, synthetic, or recombinant nucleic acid of claim 1, wherein the glucoamylase activity comprises hydrolyzing glucosidic bonds, or hydrolyzing glucosidic bonds in a polysaccharide, an oligosaccharide, or a starch, or optionally wherein the glucoamylase activity comprises cleaving a maltose or a D-glucose unit from non-reducing end of a polysaccharide, an oligosaccharide, or a starch, or optionally wherein the glucosidic bonds comprise an α-1,4-glucosidic bond or an α-1,6-glucosidic bond.

3. The isolated, synthetic, or recombinant nucleic acid of claim 1, wherein the glucoamylase activity is thermostable or thermotolerant.

4. A vector, an expression cassette, or a cloning vehicle comprising:
   (a) a nucleic acid comprising the nucleic acid sequence of claim 1;
   (b) the vector, expression cassette, or cloning vehicle of (a), wherein the nucleic acid is operably linked to a promoter;
   (c) the vector, expression cassette, or cloning vehicle of (b), wherein the promoter is a plant promoter or a viral promoter;
   (d) the vector, expression cassette or cloning vehicle of (c), wherein the plant promoter is a corn seed embryo-specific promoter; a corn seed endosperm-specific promoter; or a rice seed endosperm-specific promoter.

5. A plant cell or an isolated host cell comprising a nucleic acid comprising the nucleic acid sequence of claim 1.

6. A method of producing a recombinant polypeptide comprising the steps of: (a) providing a nucleic acid, wherein the nucleic acid comprises the nucleic acid sequence of claim 1; and (b) expressing the nucleic acid of step (a) under conditions that allow expression of a polypeptide, thereby producing a recombinant polypeptide.

* * * * *